United States Patent
Shandler et al.

(10) Patent No.: US 10,772,934 B2
(45) Date of Patent: Sep. 15, 2020

(54) HIGHLY ACTIVE POLYPEPTIDES AND METHODS OF MAKING AND USING THE SAME

(71) Applicant: Longevity Biotech, Inc., Philadelphia, PA (US)

(72) Inventors: Scott J. Shandler, Philadelphia, PA (US); Samuel H. Gellman, Madison, WI (US)

(73) Assignee: LONGEVITY BIOTECH, INC., Philadelphia, PA (US)

( * ) Notice: Subject to any disclaimer, the term of this patent is extended or adjusted under 35 U.S.C. 154(b) by 0 days.

(21) Appl. No.: 15/691,811

(22) Filed: Aug. 31, 2017

(65) Prior Publication Data

US 2018/0193422 A1    Jul. 12, 2018

Related U.S. Application Data

(63) Continuation of application No. 13/642,757, filed as application No. PCT/US2011/033684 on Apr. 22, 2011, now Pat. No. 9,782,454.

(60) Provisional application No. 61/445,468, filed on Feb. 22, 2011, provisional application No. 61/405,560, filed on Oct. 21, 2010, provisional application No. 61/364,659, filed on Jul. 14, 2010, provisional application No. 61/327,098, filed on Apr. 22, 2010.

(51) Int. Cl.
*A61K 38/22* (2006.01)
*C07K 14/575* (2006.01)

(52) U.S. Cl.
CPC .... *A61K 38/2278* (2013.01); *C07K 14/57563* (2013.01)

(58) Field of Classification Search
None
See application file for complete search history.

(56) References Cited

U.S. PATENT DOCUMENTS

| | | |
|---|---|---|
| 3,989,816 A | 11/1976 | Rajadhyaksha |
| 4,316,893 A | 2/1982 | Rajadhyaksha |
| 4,405,616 A | 9/1983 | Rajadhyaksha |
| 4,414,148 A | 11/1983 | Jansen et al. |
| 4,557,934 A | 12/1985 | Cooper |
| 4,568,343 A | 2/1986 | Leeper et al. |
| 4,569,789 A | 2/1986 | Blattler et al. |
| 4,589,071 A | 5/1986 | Yamamuro et al. |
| 4,659,839 A | 4/1987 | Nicolotti et al. |
| 4,671,958 A | 6/1987 | Rodwell et al. |
| 4,680,338 A | 7/1987 | Sundoro |
| 4,699,784 A | 10/1987 | Shih et al. |
| 4,783,450 A | 11/1988 | Fawzi et al. |
| 4,904,584 A | 2/1990 | Shaw |
| 5,120,712 A | 6/1992 | Habener |
| 5,188,835 A | 2/1993 | Lindskog et al. |
| 5,218,092 A | 6/1993 | Sasaki et al. |
| 5,464,933 A | 11/1995 | Bolognesi et al. |
| 5,565,486 A | 10/1996 | Renno et al. |
| 5,595,760 A | 1/1997 | Cherif-Cheikh |
| 5,656,480 A | 8/1997 | Wild et al. |
| 5,672,659 A | 9/1997 | Shalaby et al. |
| 5,677,419 A | 10/1997 | Bolin et al. |
| 5,686,511 A | 11/1997 | Bobo |
| 5,739,106 A | 4/1998 | Rink et al. |
| 5,990,077 A | 11/1999 | Drucker |
| 5,998,367 A | 12/1999 | Gaeta et al. |
| 6,007,792 A | 12/1999 | Dean et al. |
| 6,051,555 A | 4/2000 | Hadley |
| 6,051,557 A | 4/2000 | Drucker |
| 6,060,585 A | 5/2000 | Gellman et al. |
| 6,133,418 A | 10/2000 | Bolognesi et al. |
| 6,136,828 A | 10/2000 | Elliott |
| 6,184,201 B1 | 2/2001 | Drucker et al. |
| 6,218,410 B1 | 4/2001 | Uehata et al. |
| 6,258,782 B1 | 7/2001 | Barney et al. |
| 6,348,568 B1 | 2/2002 | Barney et al. |
| 6,462,016 B1 | 10/2002 | Wakita et al. |
| 6,562,787 B1 | 5/2003 | Barney et al. |
| 6,608,174 B1 | 8/2003 | Burman et al. |
| 6,656,906 B1 | 12/2003 | Barney et al. |

(Continued)

FOREIGN PATENT DOCUMENTS

| EP | 0188256 A2 | 7/1986 |
|---|---|---|
| EP | 0699686 A2 | 3/1996 |

(Continued)

OTHER PUBLICATIONS

Inagaki et al. (Proc. Natl. Acad. Sci. USA vol. 91, pp. 2679-2683, Mar. 1994) (Year: 1994).*
Batterham et al., Gut hormone PYY(3-36) physiologically inhibits food intake, Nature 2002 418(6898):650-654.
Brenneman, Neuroprotection: a comparative view of vasoactive intestinal peptide and pituitary adenylate cyclase-activating polypeptide, Peptides 2007 28(9):1720-1726.
Deacon et al., Both subcutaneously and intravenously . . . from the NH2-terminus in type II diabetic patients and in healthy subjects, Diabetes 1995 44(9):1126-1131.

(Continued)

*Primary Examiner* — Sergio Coffa
(74) *Attorney, Agent, or Firm* — Troutman Pepper Hamilton Sanders LLP

(57) ABSTRACT

This invention relates to novel compositions comprising analogs of naturally occurring polypeptides, wherein the analog comprises an α-amino acid and at least one β-amino acid. Administration of the compositions may be used for effecting treatment or prevention of a plurality of disease states caused by dysfunctional biochemical or biological pathways. The compositions and methods of this invention are particularly useful to identify novel therapeutic modulators of in-vivo receptor activity with extended half-lives and relevant bioactivity as compared to the naturally translated polypeptides upon which the analogs are derived.

17 Claims, 7 Drawing Sheets

Specification includes a Sequence Listing.

(56) References Cited

U.S. PATENT DOCUMENTS

| | | | |
|---|---|---|---|
| 6,683,154 | B1 | 1/2004 | Gellman et al. |
| 6,710,186 | B2 | 3/2004 | Gellman et al. |
| 6,727,368 | B1 | 4/2004 | Gellman et al. |
| 6,750,008 | B1 | 6/2004 | Jeffs et al. |
| 6,824,783 | B1 | 11/2004 | Bolognesi et al. |
| 6,849,714 | B1 | 2/2005 | Bridon et al. |
| 6,858,580 | B2 | 2/2005 | Ekwuribe et al. |
| 6,861,059 | B2 | 3/2005 | Johnson et al. |
| 6,958,384 | B2 | 10/2005 | Gellman et al. |
| 7,186,692 | B2 | 3/2007 | Quay et al. |
| 7,504,409 | B2 | 3/2009 | Zhou et al. |
| 7,723,288 | B2 | 5/2010 | During et al. |
| 8,273,713 | B2 | 9/2012 | Pittner et al. |
| 9,782,454 | B2 * | 10/2017 | Shandler .......... C07K 14/57563 |
| 2002/0037997 | A1 | 3/2002 | Gellman et al. |
| 2002/0132766 | A1 | 9/2002 | DeGrado et al. |
| 2005/0288228 | A1 | 12/2005 | Cundy et al. |
| 2007/0224273 | A1 | 9/2007 | Xu et al. |
| 2009/0143283 | A1 | 6/2009 | Clairmont et al. |
| 2010/0048871 | A1 | 2/2010 | Cho et al. |

FOREIGN PATENT DOCUMENTS

| | | |
|---|---|---|
| EP | 0708179 A2 | 4/1996 |
| WO | 87/06941 A1 | 11/1987 |
| WO | 90/11296 A1 | 10/1990 |
| WO | 91/11457 A1 | 8/1991 |
| WO | 97/39031 A1 | 10/1997 |
| WO | 99/03887 A1 | 1/1999 |
| WO | 99/07404 A1 | 2/1999 |
| WO | 99/25727 A2 | 5/1999 |
| WO | 99/25728 A1 | 5/1999 |
| WO | 99/67291 A2 | 12/1999 |
| WO | 00/26354 A1 | 5/2000 |
| WO | 01/00224 A1 | 1/2001 |
| WO | 02/47712 A2 | 6/2002 |
| WO | 2011/133948 A2 | 10/2011 |

OTHER PUBLICATIONS

Deacon et al., Degradation of glucagon-like peptide-1 by . . . N-terminally truncated peptide that is a major endogenous metabolite in vivo, J Clin Endocrinol Metab 1995 80(3):952-957.

Delgado el. al., Anti-inflammatory neuropeptides: a new class of endogenous immunoregulatory agents, Brain Behav Immun 2008 22(8):1146-1151.

Dickson et al., VPAC and PAC receptors: From ligands to function, Pharmacology & Therapeutics 2009 121 (3):294-316.

Eberlein et al., A new molecular form of PYY: structural characterization of human PYY(3-36) and PYY(1-36), Peptides 1989 10(4):797-803.

Gaudin et al, The human vasoactive intestinal Peptide/Pituitary adenylate cyclase activating peptide receptor 1 (VPAC1):constitutive activation by mutations at threonine 343, Biochem Biophys Res Commun 1999 254(1):15-20.

Gonzalez-Rey el. al., Anti-inflammatory neuropeptide receptors: new therapeutic targets for immune disorders?, TRENDS Pharmacal Sci 2007 28(9):482-491.

Gozes el. al., VIP and drug design, Current Pharmaceutical Design 2003 9(6):483-494.

Grandt et al., Two molecular forms of peptide YY (PYY) are abundant in human blood: characterization . recognizing PYY 1-36 and PYY 3-36, Regul Pept 1994 51(2):151-159.

Higuchi and Stella, Pro-Drugs as Novel Delivery Systems, Am Chem Soc 1975.

Knudsen et al., Potent derivatives of glucagon-like peptide-1 with pharmacokinetic properties suitable for once daily administration, J Med Chem 2000 43(9):1664-1669.

Larsen et al., One-week continuous infusion of GLP-1 (7-37) improves the glycaemic control in NIDDM, Diabetes 45 (2):233A.

Lesma et al, An efficient enantioselective approach to cyclic b-amino acid derivatives via olefin metathesis reactions, J Org Chem 2006 71:3317-3320.

Miller, The Enantioselective Synthesis of Conformationally Constrained Cyclic beta-amino Acids, Mini Reviews in Organic Chemistry, vol. 2, No. 1, Jan. 2005.

Onoue et al., Structure-activity relationship . . . (VIP): potent agonists and potential clinical applications, Naunyn Schmiedebergs Arch Pharmacal 2008 377(4-6):579-590.

Rampelbergh et al., Characterization of a novel VPAC1 selective agonist and identifacation of the receptor domains implicated in the carboxyl-terminal peptide recognition, British Journal of Pharmacology 2000 130:819-826.

Ritzel et al., Pharmacokinetic, insulinotropic, and glucagonostatic properties of . . . in healthy volunteers. Dose-response-relationships, Diabetologia 1995 38(6):720-725.

Stark et al., Liposomal vasoactive intestinal peptide for lung application: Protection from proteolytic degradation, Eur J Pharm Biopharm 2008 70(1):153-64.

Tatemoto, Isolation and characterization of peptide YY (PYY), a candidate gut hormone that inhibits pancreatic exocrine secretion, PNAS 79(8):2514-2518.

Varela el al., Tuning inflammation with anti-inflammatory neuropeptides, Expert Opin Biol Ther 2007 7(4):461-478.

AAA59172.1.
AAB59397.1.
AAH55093.1.
AAN87347.1.
AAS83395.1.
NP_0011 08.2.
NP_003372.1.
NP_919416.1.
NP_000030.1.
NP_000896.1.
NP_001093203.1.
NP_002045.1.
NP_002512.1.
NP_004151.2.
NP_005535.1.
NP_006163.1.
NP_077720.1.
P01275.3

De Serres et al., Immunogenicity of thrombopoietin mimetic peptide GW395058 in BALC/c mice and New Zealand white rabbits: evaluation of the potential for thrombopoietin neutralizing antibody production in man, Stem Cells 1999 17(4)203-209.

Dewit et al., The vasoactive intestinal peptide analogue RO25-1553 inhibits the production of TNF and IL-12 by LPS-activated monocytes, Immunol Lett 1998 60(1):57-60.

O'Donnell et al., RO25-1553: a novel long-acting vasoactive intestinal peptide agonist. Part 1: In vitro and in vivo bronchodilator studies, J Pharmacol Exp Ther 1994 270(3):1282-1288.

Tams et al., Creation of a selective antagonist and agonist of the rat VPAC 1 receptor using a combinatorial approach with vasoactive intestinal peptide 6 -23 as template, Molecular Pharmacology 2000 58:1035-1041.

* cited by examiner

PANEL A

CHO VIPR1 Gs
Agonist Mode
Normalized data

PANEL B

CHO VIPR2 Gs
Agonist Mode
Normalized data

PANEL A

PANEL B

FIGURE 7

HSDAV FTDNY ARLRK QMAVK KALNS ILA  (SEQ ID NO: 435)

HSDAV FTDNY ARLRK QMAVK KALNS ILA  (SEQ ID NO: 435)

HSDAV FTDNY ARLRK QMAVK KALNS ILA  (SEQ ID NO: 435)

HSDAV FTDNY ARLRK QMAVK KALNS ILA  (SEQ ID NO: 435)

HSDAV FTDNY ARLRK QMAVK KALNS ILA  (SEQ ID NO: 435)

HSDAV FTDNY ARLRK QMAVK KALNS ILA  (SEQ ID NO: 435)

HSDAV FTDNY ARLRK QMAVK KALNS ILA  (SEQ ID NO: 435)

HIGHLY ACTIVE POLYPEPTIDES AND METHODS OF MAKING AND USING THE SAME

CROSS-REFERENCE TO RELATED APPLICATIONS

This application is a continuation of U.S. patent application Ser. No. 13/642,757, filed Jan. 2, 2013, now issued as U.S. Pat. No. 9,782,454, which is a National Stage entry of International Application No. PCT/US 11/33684, filed on Apr. 22, 2011, which claims priority to U.S. Provisional Ser. No. 61/364,098, filed on Apr. 22, 2010; U.S. Provisional Ser. No. 61/364,359, filed on Jul. 14, 2010; U.S. Provisional Ser. No. 61/405,560, filed on Oct. 21, 2010; and U.S. Provisional Ser. No. 61/445,468, filed on Feb. 22, 2011, all of which are herein incorporated by reference in their entirety.

FIELD OF THE INVENTION

The invention relates generally to compositions comprising modified polypeptide sequences with greater resistance to degradation and equivalent and/or increased bioactivity as compared to naturally encoded, unmodified polypeptide sequences, and to methods of making the compositions and methods of using the compositions as pharmaceutically active agents to treat disease in animals, including humans.

BACKGROUND OF THE INVENTION

The secretin family is a family of well-conserved animal proteins with a variety of biological functions. Biologically active members of the secretin family are generally from about 26 to about 65 amino acids in length and are thought to have relatively simple alpha-helical secondary structures. Many members are originally produced in vivo as larger pro-peptides, which are eventually converted in the active forms. Members of the secretin family include the following proteins: GHRF, GIP, GLP-1, Glucagon, PACAP-27, PACAP-38, PHM, PrP, and secretin. The q25 region of chromosome 6 on the human genome encodes another secretin family member that is 170 amino acids long which becomes post-translationally cleaved to form vasoactive intestinal peptide (VIP). The active form of the VIP polypeptide is a 28 amino acid protein that functions, among other ways, to reduce arterial blood pressure, to increase vasodilation of blood vessel walls, to relax smooth muscle in the respiratory system and gastrointestinal tissues, reduce inflammatory responses through both promotion of Th2 differentiation as well as the reduction of Th1 responses, modulate both the innate and adaptive immune response, and to stimulate secretion of electrolytes in the gut. VIP has also been shown to be active in the central nervous system as a neurotransmitter and in communication with lymphocytes. Bioactivity of VIP is transmuted through three known receptor subtypes: $VIP_1R$, $VIP_2R$, and $PAC_1R$. These receptors are known to induce cAMP concentration as well as stimulate the production of intracellular calcium. Their affinities for secretins such as VIP vary depending upon the subtype and the amino acid sequence of the ligand.

Secretin family members have short half-lives. For instance, VIP has a half-life of about two minutes in the blood stream. It is desirable to identify polypeptides that mimic the function of secretins such as VIP, but have increased half-life and equivalent or more bioactivity than the naturally occurring VIP amino acid sequence. It is also desirable to identify another peptidomimetic of VIP to have association to one receptor subtype over another secretin receptor.

HDL cholesterol level is inversely related to the incidence of coronary heart disease and recently received increasing attention as a novel target in lipid management of treating atherosclerotic vascular disease. Direct vascular protective effects of HDL have been attributed to apolipoprotein (apo) A-I or apoA-I-associated molecules in HDL using direct intravenous injections of homologous HDL,3 recombinant mutant apoA-Imilano or apoA-I gene therapy, or use of transgenic animals overexpressing apoA-I or apoAl-related molecules such as paraoxonase. A recent phase II randomized trial showed that 5 weekly intravenous injections of recombinant apoA-1milano induced rapid regression of coronary atherosclerotic lesions in humans. It is desirable to identify polypeptides that mimic the function of apoA-1 such as paraoxonase, but have increased half-life and equivalent or more bioactivity than the naturally occurring paraoxonase amino acid sequence. It is also desirable to identify another peptidomimetic of apoA-1 to have association to a natural ligand for apoA-1 as compared to wild-type sequences.

Cytokines mediate cellular activities in a number of ways. Cytokines support the proliferation, growth, and differentiation of pluripotential hematopoietic stem cells into vast numbers of progenitors comprising diverse cellular lineages making up a complex immune system. Proper and balanced interactions between the cellular components are necessary for a healthy immune response. The different cellular lineages often respond in a different manner when cytokines are administered in conjunction with other agents.

Cytokines mediate communication between cells of the immune system, e.g., antigen presenting cells (APCs) and T lymphocytes. Dendritic cells (DCs) are the most potent of antigen presenting cells. See, e.g., Paul (ed.) (1993) Fundamental Immunology 3d ed., Raven Press, NY. Antigen presentation refers to the cellular events in which a proteinaceous antigen is taken up, processed by antigen presenting cells (APC), and then recognized to initiate an immune response. The most active antigen presenting cells have been characterized as the macrophages (which are direct developmental products from monocytes), dendritic cells, and certain B cells. DCs are highly responsive to inflammatory stimuli such as bacterial lipopolysaccharides (LPS), and cytokines such as tumor necrosis factor alpha (TNFalpha). Cytokines or stimuli, such as LPS, can induce a series of phenotypic and functional changes in DC that are collectively referred to as maturation. See, e.g., Banchereau and Schmitt (eds.) (1995) Dendritic Cells in Fundamental and Clinical Immunoloy, Plenum Press, NY. It is desirable to identify polypeptides that mimic the function of cytokine families such as IL-10, IL-2, IL-4, IL-12, and IL-17, but have increased half-life and equivalent or more bioactivity than the naturally occurring IL-10, IL-2, IL-4, IL-12, and IL-17 representative amino acid sequences. It is also desirable to identify another peptidomimetic of a cytokine such as IL-17 to have association to a natural receptor for IL-17 as compared to wild-type sequences.

Chemists have long sought to extrapolate the power of biological catalysis and recognition to synthetic systems. These efforts have focused largely on low-molecular weight catalysts and receptors. Most biological systems, however, rely almost exclusively on large polymers such as proteins and RNA to perform complex biochemical and/or biological functions. There is a long-felt need to identify synthetic polymers of amino acids which display discrete and predictable folding propensities to mimic natural biological systems. Such polypeptides are designed to provide a molecular equivalent or improved functionality as compared to naturally occurring protein-protein interactions specifically because of their ability to mimic natural interactions in addition to their resistance to natural degradative enzymes in a subject. Whereas a naturally occurring probe, comprised entirely of α-amino acid residues, will be readily degraded by any number of proteases and peptidases, the secretin analogs of the present invention comprising a mixture of α- and β-amino acid residues are not degraded in the same manner.

There is a need for secretin analogs that exhibit increased conformational constraints or increased conformational flexibility and greater half-lives. Increased conformational constraints may lock the active domain of the polypeptides into their active state. Increased conformational flexibility of the polypeptide may yield a high affinity selectivity for the naturally occurring polypeptide's natural biological target. There is a need for use of such analogs, compositions comprising such analogs, and methods of using the compositions as pharmaceutically active agents to treat disease in animals. New polypeptide analogs are disclosed that may provide one or more increased half-life, reduced degradation upon administration, reduced degradation upon solubilization, increased conformational constraints and that produce the same or greater biological effect as compared to naturally occurring secretin family members. The present invention addresses these and other needs associated with treatment and prevention of disease that implicate dysfunction of biological systems involving naturally occurring polypeptides.

SUMMARY OF THE INVENTION

In some embodiments, the invention relates to compositions comprising a helical polypeptide synthesized with a repeated pattern of β-amino acids at positions along the entire length of a polypeptide chain. For any of the peptides described herein, there may embodiments in which there are no β-amino acids within the peptide. The selected pattern of synthetic amino acids along the helical polypeptide decreases the rate at which the polypeptide may degrade when administered to a subject or when reconstituted or placed in solution. Selected side chains of the amino acids increase the conformational rigidity of the polypeptide in order to constrain the polypeptide in its active state. The selected pattern of synthetic amino acids along the helical polypeptide increases the half-life of the polypeptide as compared to naturally encoded polypeptides with the same α-amino acid sequence. In some embodiments, the polypeptide comprises β-amino acids that spatially aligned along a longitudinal axis of the analog in order to confer degradation resistance to the composition while preserving the native binding interface. In some embodiments, the composition comprises a secretin analog. In some embodiments, the composition comprises a vasoactive intestinal peptide (VIP) analog, wherein said analog comprises an α-amino acid and at least one β-amino acid.

In some embodiments, the composition comprises a secretin analog wherein the total number of β-amino acids in the analog is from about 10 percent to about 60 percent of the total number of amino acids of the analog. In some embodiments, the composition comprises a secretin analog wherein the total number of β-amino acids in the analog is from about 12 percent to about 50 percent of the total number of amino acids of the analog. In some embodiments, the composition comprises a secretin analog wherein the total number of β-amino acids in the analog is from about 14 percent to about 50 percent of the total number of amino acids of the analog. In some embodiments, the composition comprises a secretin analog wherein the total number of β-amino acids in the analog is from about 16 percent to about 50 percent of the total number of amino acids of the analog. In some embodiments, the composition comprises a secretin analog wherein the total number of β-amino acids in the analog is from about 18 percent to about 50 percent of the total number of amino acids of the analog. In some embodiments, the composition comprises a secretin analog wherein the total number of β-amino acids in the analog is from about 20 percent to about 50 percent of the total number of amino acids of the analog. In some embodiments, the composition comprises a secretin analog wherein the total number of β-amino acids in the analog is from about 30 percent to about 50 percent of the total number of amino acids of the analog.

In some embodiments, the composition comprises a secretin analog wherein the total number of β-amino acids in the analog is from about 40 percent to about 50 percent of the total number of amino acids of the analog. In some embodiments, the composition comprises a secretin analog wherein the total number of β-amino acids in the analog is from about 45 percent to about 50 percent of the total number of amino acids of the analog. In some embodiments, the composition comprises a secretin analog wherein the total number of β-amino acids in the analog is from about 40 percent to about 45 percent of the total number of amino acids of the analog.

In some embodiments, the composition comprises a secretin analog wherein the total number of β-amino acids in the analog is from about 30 percent to about 40 percent of the total number of amino acids of the analog. In some embodiments, the composition comprises a secretin analog wherein the total number of β-amino acids in the analog is from about 35 percent to about 40 percent of the total number of amino acids of the analog. In some embodiments, the composition comprises a secretin analog wherein the total number of β-amino acids in the analog is from about 20 percent to about 30 percent of the total number of amino acids of the analog.

In some embodiments, the composition comprises a secretin analog wherein the total number of β-amino acids in the analog is from about 10 percent to about 20 percent of the total number of amino acids of the analog. In some embodiments, the composition comprises a secretin analog wherein the total number of β-amino acids in the analog is from about 15 percent to about 20 percent of the total number of amino acids of the analog. In some embodiments, the composition comprises a secretin analog wherein the total number of β-amino acids in the analog is from about 20 percent to about 25 percent of the total number of amino acids of the analog. In some embodiments, the composition comprises a secretin analog wherein the total number of β-amino acids in the analog is from about 25 percent to about 30 percent of the total number of amino acids of the analog. In some embodiments, the composition comprises a secretin analog wherein the total number of β-amino acids in the analog is from about 30 percent to about 35 percent of the total number of amino acids of the analog.

In some embodiments, the invention relates to analogs of various protein targets. In some embodiments, the amino acid sequences upon which the analogs are based or derived include biologically active polypeptides chosen from the group of transcription factors, ligands for cellular receptors, hormones and extracellular binding peptides. In some embodiments, the invention comprises analogs of derived from amino acid sequences chosen from human and non-human enkephlin, LHRH, neuropeptides, glycoincretins, integrin, glucagons and glucagon-like peptides, antithrombotic peptides, cytokines and interleukins, transferrins, interferons, endothelins, natriuretic hormones, extracellular kinase ligands, angiotensin enzyme inhibitors, peptide antiviral compounds, thrombin, substance P, substance G, somatotropin, somatostatin, GnRH, bradykinin, vasopressin, insulin, and growth factors. The amino acid sequences of these proteins or peptides are known to the skilled artisan and can be obtained by numerous means. The amino acid sequences are incorporated herein by reference from databases such as, for example, GenBank.

As used herein, "glucagon-like peptide-1" or "GLP-1" shall include those polypeptides and proteins that have at least one biological activity of human GLP-1, including but not limited to those described in U.S. Patent Publication No. 20040127412, EP 0699686-A2 and EP0733,644, U.S. Pat. Nos. 5,545,618; 5,118,666; 5,512,549; WO 91/11457; WO 90/11296; WO 87/06941 which are incorporated by reference herein, as well as GLP-1 analogs, GLP-1 isoforms, GLP-1 mimetics, GLP-1 fragments, hybrid GLP-1 proteins, fusion proteins, oligomers and multimers, homologues, glycosylation pattern variants, and muteins, thereof, regardless of the biological activity of same, and further regardless of the method of synthesis or manufacture thereof including synthetic, transgenic, and gene activated methods. Numerous GLP-1 analogs and derivatives are known and are referred to herein as "GLP-1 compounds." These GLP-1 analogs include the Exendins which are peptides found in the venom of the GILA-monster. Specific examples of GLP-1 include, but are not limited to, GLP-1(3-36), GLP-1(3-37), GLP-1(1-45), and Exendins 1 through 4. Further, it is possible to obtain GLP-1 through the use of recombinant DNA technology, as disclosed by Maniatis, T., et al., Molecular Biology: A Laboratory Manual, Cold Spring Harbor, N.Y. (1982), and produce GLP-1 in host cells by methods known to one of ordinary skill in the art.

The term "human GLP-1 (GLP-1)" or "GLP-1 polypeptide" refers to GLP-1 as described herein, as well as a polypeptide that retains at least one biological activity of a naturally-occurring GLP-1. GLP-1 polypeptides also include the pharmaceutically acceptable salts and prodrugs, and prodrugs of the salts, polymorphs, hydrates, solvates, biologically-active fragments, biologically active variants and stereoisomers of the naturally-occurring human GLP-1 as well as agonist, mimetic, and antagonist variants of the naturally-occurring human GLP-1, the family of exendins including exendins 1 through 4, and polypeptide fusions thereof. Examples of GLP-1 polypeptides include, but are not limited to, those described in U.S. Pat. No. 5,118,666; which is incorporated by reference herein. Fusions comprising additional amino acids at the amino terminus, carboxyl terminus, or both, are encompassed by the term "GLP-1 polypeptide." Exemplary fusions include, but are not limited to, e.g., fusions for the purpose of purification (including, but not limited to, to poly-histidine or affinity epitopes), fusions with serum albumin binding peptides; fusions with serum proteins such as serum albumin; fusions with constant regions of immunoglobulin molecules such as Fc; and fusions with fatty acids. The naturally-occurring GLP-1 nucleic acid and amino acid sequences for various forms are known, as are variants such as single amino acid variants or splice variants.

The term "GLP-1 polypeptide" encompasses GLP-1 polypeptides comprising one or more amino acid substitutions, additions or deletions. Exemplary substitutions in a wide variety of amino acid positions in naturally-occurring GLP-1 have been described, including but not limited to, substitutions that modulate one or more of the biological activities of GLP-1, such as but not limited to, increase agonist activity, increase solubility of the polypeptide, convert the polypeptide into an antagonist, decrease peptidase or protease susceptibility, etc. and are encompassed by the term "GLP-1 polypeptide."

Human GLP-1 antagonists include, but are not limited to, those with a substitutions at: 7, 8, 9, 22, 18, 29, 25, 32, 21, 28, 17, 24, 31, and 20 (other GLP-1 sequence of U.S. Patent Application Publication 2010-0048871). In some embodiments, the GLP-1 antagonist comprises a non-naturally encoded amino acid linked to a water soluble polymer that is present in a receptor binding region of the GLP-1 molecule. In some embodiments the water soluble polymer is coupled to the GLP-1 polypeptide at one or more of the amino acid positions: 7, 8, 9, 22, 18, 29, 25, 32, 21, 28, 17, 24, 31, and 20 (U.S. Patent Application Publication 2010-0048871).

For the GLP-1 amino acid sequence as well as the exendin-4 and exendin-3 amino acid sequence, (His Ala Glu Gly Thr Phe Thr Ser Asp Val Ser Ser Tyr Leu Glu Gly Gln Ala Ala Lys Glu Phe Ile Ala Trp Leu Val Lys Gly Arg) (GLP-1(7-36), SEQ ID NO: 1330); {His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly} (GLP-1(7-37), SEQ ID NO:1331); {His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser) (exendin-4, SEQ ID NO:1332); and (His Ser Asp Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser}(exendin-3, SEQ ID NO:724). In some embodiments, GLP-1 polypeptides of the invention are substantially identical to the sequences above, or any other sequence of a GLP-1 polypeptide (see, U.S. Patent Application Publication 2010-0048871). Nucleic acid molecules encoding GLP-1 mutants and mutant GLP-1 polypeptides are well known. Examples of GLP-1 mutants include those disclosed in U.S. Patent Publication No. 20040127412A1; which is incorporated by reference herein.

A number of GLP-1 products are in preclinical and clinical development, including GLP-1 peptide analogs, conjugates, fusion proteins, and drug delivery or combination therapies. Some of the products in development are Exenatide (AC2993, Amylin/Eli Lilly), AVE-0010 (ZP10, Zealand Pharm/Aventis), BIM-51077 (Ipsen/Roche), Liraglutide (NN2211, Novo Nordisk), CJC-1131 (Conjuchem), Albugon (Human Genome Sciences/Glaxo Smith Kline), GLP-1 transferrin (Biorexis), AC2993 LAR (Amylin/Alkermes), GLP-1 nasal (Suntory) and GLP-1-INT (Transition Therapeutics).

The biological activities of GLP-1 have been disclosed and are known in the art, and can be found, for example, in U.S. Patent Publication No: 20040082507A1 and 20040232754A1 which are incorporated by reference herein.

Variants of GLP-1(7-37) and analogs thereof, also have been disclosed. These variants and analogs include, for example, $Gln^9$-GLP-1(7-37), $D-Gln^9$-GLP-1(7-37), acetyl-$Lys^9$-GLP-1(7-37), $Thr^{16}$-$Lys^{18}$-GLP-1(7-37), $Lys^{18}$-GLP-1(7-37) and the like, and derivatives thereof including, for example, acid addition salts, carboxylate salts, lower alkyl esters, and amides (see, e.g., WO 91/11457; EP0733,644 (1996); and U.S. Pat. No. 5,512,549 (1996), which are incorporated by reference). Generally, the various disclosed forms of GLP-1 are known to stimulate insulin secretion (insulinotropic action) and cAMP formation (see, e.g., Mojsov, S., Int. J. Peptide Protein Research, 40:333-343 (1992)).

As used herein, "T-20" or "DP-178" shall include those polypeptides and proteins that have at least one biological activity of human DP-178, as well as DP-178 analogs, DP-178 isoforms, DP-178 mimetics, DP-178 fragments, hybrid DP-178 proteins, fusion proteins, oligomers and multimers, homologues, glycosylation pattern variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), synthetic, transgenic, and gene activated methods. Hyphenated and non-hyphenated forms (T20, DP178) of the terms are equivalent.

The term "human DP-178" or "DP-178 polypeptide" refers to DP-178 or T-20 as described herein, as well as a polypeptide that retains at least one biological activity of a naturally-occurring DP-178. "DP-178" includes portions, analogs, and homologs of DP-178, all of which exhibit antiviral activity. Antiviral activity includes, but is not limited to, the inhibition of HIV transmission to uninfected CD-4+ cells. Further, the invention relates to the use of DP-178 and DP-178 fragments and/or analogs or homologs as inhibitors of retroviral transmission, in particular HIV, to uninfected cells, in both humans and non-humans. Non retroviral viruses whose transmission may be inhibited by the peptides of the invention include, but are not limited to enveloped viruses, human respiratory syncytial virus, canine distemper virus, Newcastle disease virus, human parainfluenza virus, and influenza viruses.

DP-178 polypeptides also include the pharmaceutically acceptable salts and prodrugs, and prodrugs of the salts, polymorphs, hydrates, solvates, biologically-active fragments, biologically active variants and stereoisomers of the naturally-occurring human DP-178 as well as agonist, mimetic, and antagonist variants of the naturally-occurring human DP-178, and polypeptide fusions thereof. Fusions comprising additional amino acids at the amino terminus, carboxyl terminus, or both, are encompassed by the term "DP-178 polypeptide." Exemplary fusions include, but are not limited to, e.g., methionyl DP-178 in which a methionine is linked to the N-terminus of DP-178 resulting from the recombinant expression of DP-178, fusions for the purpose of purification (including, but not limited to, to poly-histidine or affinity epitopes), T-20 extended at the N-terminus, fusions with serum albumin binding peptides; fusions with serum proteins such as serum albumin; fusions with constant regions of immunoglobulin molecules such as Fc; and fusions with fatty acids. The naturally-occurring DP-178 nucleic acid and amino acid sequences are known, as are variants such as single amino acid variants or splice variants.

The term "DP-178 polypeptide" encompasses DP-178 polypeptides comprising one or more amino acid substitutions, additions or deletions. Exemplary substitutions in a wide variety of amino acid positions in naturally-occurring DP-178 have been described, including but not limited to, substitutions that modulate one or more of the biological activities of DP-178, such as but not limited to, increase agonist activity, increase solubility of the polypeptide, convert the polypeptide into an antagonist, decrease peptidase or protease susceptibility, etc. and are encompassed by the term "DP-178 polypeptide," the DP-178 amino acid sequence, (Tyr Thr Ser Leu He His Ser Leu lie Glu Glu Ser Gln Asn Gln Gln Glu Lys Asn Glu Gln Glu Leu Leu Glu Leu Asp Lys Trp Ala Ser Leu Trp Asn Trp Phe) (SEQ ID NO:1333). In some embodiments, DP-178 polypeptides of the invention are substantially identical to the following sequences or functional fragments thereof: (Tyr Thr Ser Leu He His Ser Leu Ile Glu Glu Ser Gln Asn Gln Gln Glu Lys Asn Glu Gln Glu Leu Leu Glu Leu Asp Lys Trp Ala Ser Leu Trp Asn Trp Phe); Glu Trp Asp Arg Glu Ile Asn Asn Tyr Thr Ser Leu Ile His Ser Leu Ile Glu Glu Ser Gln Asn Gln Gln Glu Lys Asn Glu Gln Glu Leu Leu Glu Leu Asp Lys Trp Ala Ser Leu Trp Asn Trp Phe (SEQ ID NO: 1334); or any other sequence of a DP-178 polypeptide. Nucleic acid molecules encoding DP-178 mutants and mutant DP-178 polypeptides are well known.

A commercially available form of DP-178 is Fuzeon®. (enfuvirtide. Roche Laboratories Inc. and Trimeris, Inc.). Fuzeon® has an acetylated N terminus and a carboxamide as the C-terminus. It is used in combination with other antivirals in HIV-1 patients that show HIV-1 replication despite ongoing antiretroviral therapy.

As used herein, "PYY" and "peptide YY" shall include those polypeptides and proteins that have at least one biological activity of human PYY, as well as PYY analogs, PYY isoforms, PYY mimetics, PYY fragments, hybrid PYY proteins, fusion proteins, oligomers and multimers, homologues, glycosylation pattern variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), synthetic, transgenic, and gene activated methods.

The term "PYY" or "PYY polypeptide" refers to PYY as described herein, as well as a polypeptide that retains at least one biological activity of a naturally-occurring PYY. "PYY" includes portions, analogs, and homologs of PYY including, but not limited to, PYY(3-36), full-length PYY, PYY(22-36), and DPPIV resistant variants of PYY. The term "PYY" includes the human full length: Tyr Pro Ile Lys Pro Glu Ala Pro Gly Glu ASp Ala Ser Pro Glu Glu Leu Asn Arg Tyr Tyr Ala Ser Leu Arg His Tyr Leu Asn Leu Val Thr Arg Gln Arg Tyr (SEQ ID NO: 561), which is disclosed in International Publication No. WO 02/47712 (which is the PCT counterpart to U.S. patent Publication No. 2002/0141985, which is hereby incorporated by reference) and the following amino acid sequences from Tatemoto, Proc Natl Acad Sci U.S.A. 79:2514-8, 1982, which are incorporated by reference herein:

(SEQ ID NO: 1375)
1. Tyr-Pro-Ala-Lys-Pro-Glu-Ala-Pro-Gly (SEQ ID NO: 1376)
2. Tyr-Pro-Ala-Lys-Pro-Glu-Ala-Pro-Gly-Glu-Asp-Ala-Ser-Pro-Glu-Glu-Leu-Ser-Arg (SEQ ID NO: 1377)
3. Tyr-Tyr-Ala-Ser-Leu-Arg (SEQ ID NO: 1378)
4. His-Tyr-Leu-Asn-Leu-Val-Thr-Arg

-continued (SEQ ID NO: 1379)
5. Tyr-Pro-Ala-Lys-Pro-Glu-Ala-Pro-Gly-Glu-Asp-
Ala-Ser-Pro-Glu-Glu-Leu-Ser-Arg-Tyr-Tyr-Ala-Ser-
Leu-Arg-His-Tyr-Leu-Asn-Leu-Val-Thr-Arg-Gln-
Arg-Tyr-NH$_2$ PYY agonists are also included in the term "PYY". PYY agonists include any compound which elicits an effect of PYY to reduce nutrient availability, for example a compound (1) having activity in the food intake, gastric emptying, pancreatic secretion, or weight loss assays described in Examples 1, 2, 5, or 6 of WO 02/47712 and U.S. patent Publication No. 2002/0141985, and (2) which binds specifically in a Y receptor assay (Example 10 of WO 02/47712 and U.S. patent Publication No. 2002/0141985) or in a competitive binding assay with labeled PYY or PYY {3-36} from certain tissues having an abundance of Y receptors, including e.g., area postrema (Example 9 of WO 02/47712 and U.S. patent Publication No. 2002/0141985), wherein the PYY agonist is not pancreatic polypeptide. In some embodiments, PYY agonists would bind in such assays with an affinity of greater than about 1 µM, or with an affinity of greater than about 1 nM to about 5 nM.

Such agonists can comprise a polypeptide having a functional PYY domain, an active fragment of PYY, or a chemical or small molecule. PYY agonists may be peptide or peptide-nonpeptide hybrid molecules, and include "PYY agonist analogs," which refer to any compound structurally similar to a PYY that have PYY activity typically by virtue of binding to or otherwise directly or indirectly interacting with a PYY receptor or other receptor or receptors with which PYY itself may interact to elicit a biological response. Such compounds include derivatives of PYY, fragments of PYY, extended PYY molecules having more than 36 amino acids, truncated PYY molecules having less than 36 amino acids, and substituted PYY molecules having one or more different amino acids as compared to the wild-type or consensus sequence, or any combination of the above. Such compounds may also be modified by processes such as pegylation, amidation, glycosylation, acylation, sulfation, phosphorylation, acetylation and cyclization.

One such PYY agonist analog is PYY (3-36), identified as Ile Lys Pro Glu Ala Pro Gly Glu Asp Ala Ser Pro Glu Glu Leu Asn Arg Tyr Tyr Ala Ser Leu Arg His Tyr Leu Asn Leu Ile Lys pro Glu Ala Pro Gly Glu ASp Ala Ser Pro Glu Glu Leu Asn Arg Tyr Tyr Ala Ser Leu Arg His Tyr Leu Asn Leu Val Thr Arg Gln Arg Tyr Val Thr Arg Gln Arg Tyr (SEQ ID NO:559); Eberlein, Eysselein et al., Peptides 10:797-803 (1989); and Grandy, Schimiczek et al., Regul Pept 51:151-9 (1994). Additional PYY fragments and derivatives are described in U.S. Patent Publication 20050002927 whose sequences follow. All of the above referenced patent publications are incorporated by reference herein.

PYY polypeptides also include the pharmaceutically acceptable salts and prodrugs, and prodrugs of the salts, polymorphs, hydrates, solvates, biologically-active fragments, biologically active variants and stereoisomers of the naturally-occurring human PYY as well as agonist, mimetic, and antagonist variants of the naturally-occurring human PYY, and polypeptide fusions thereof. Fusions comprising additional amino acids at the amino terminus, carboxyl terminus, or both, are encompassed by the term "PYY polypeptide." Exemplary fusions include, but are not limited to, e.g., fusions with serum albumin binding peptides; fusions with serum proteins such as serum albumin; fusions with constant regions of immunoglobulin molecules such as Fc; and fusions with fatty acids. The naturally-occurring PYY nucleic acid and amino acid sequences are known, as are variants such as single amino acid variants or splice variants.

The term "PYY polypeptide" encompasses PYY polypeptides comprising one or more amino acid substitutions, additions or deletions. Exemplary substitutions in a wide variety of amino acid positions in naturally-occurring PYY have been described, including but not limited to, substitutions that modulate one or more of the biological activities of PYY, such as but not limited to, increase agonist activity, increase solubility of the polypeptide, convert the polypeptide into an antagonist, decrease peptidase or protease susceptibility, etc. and are encompassed by the term "PYY polypeptide."

In some embodiments, PYY polypeptides of the invention are substantially identical to Ile Lys Pro Glu Ala Pro Gly Glu Asp Ala Ser Pro Glu Glu Leu Asn Arg Tyr Tyr Ala Ser Leu Arg His Tyr Leu Asn Leu Val Thr Arg Gln Arg Tyr (SEQ ID NO: 559) or any other sequence of a PYY polypeptide (see, U.S. Patent Application Publication 2010-0048871). Nucleic acid molecules encoding PYY mutants and mutant PYY polypeptides are well known.

Various references disclose modification of polypeptides by polymer conjugation or glycosylation. The term analog includes polypeptides conjugated to a polymer such as PEG and may be comprised of one or more additional deriviti-zations of cysteine, lysine, or other residues. In addition, analogs of the instant invention may comprise a linker or polymer, wherein the amino acid to which the linker or polymer is conjugated may be a non-natural amino acid, or may be conjugated to a naturally encoded amino acid utilizing techniques known in the art such as coupling to lysine or cysteine.

Polymer modification of polypeptides has been reported. U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been substituted with a non-essential amino acid residue located in a specified region of the polypeptide. WO 00/26354 discloses a method of producing a glycosylated polypeptide variant with reduced allergenicity, which as compared to a corresponding parent polypeptide comprises at least one additional glycosylation site. U.S. Pat. No. 5,218,092 discloses modification of granulocyte colony stimulating factor (G-CSF) and other polypeptides so as to introduce at least one additional carbohydrate chain as compared to the native polypeptide. Examples of PEGylated peptides include GW395058, a PEGylated peptide thrombopoietin receptor (TPOr) agonist (de Serres M., et al., Stem Cells. 1999; 17(4):203-9), and a PEGylated analogue of growth hormone releasing factor (PEG-GRP; D'Antonio M, et al. Growth Horm IGF Res. 2004 June; 14(3):226-34).

The term analog also includes glycosylated analogs, such as but not limited to, analogs glycosylated at any amino acid position, N-linked or O-linked glycosylated forms of the polypeptide. In addition, splice variants are also included. The term analog also includes heterodimers, homodimers, heteromultimers, or homomultimers of any one or more polypeptide, protein, carbohydrate, polymer, small molecule, linker, ligand, or other biologically active molecule of any type, linked by chemical means or expressed as a fusion protein, as well as polypeptide analogs containing, for example, specific deletions or other modifications yet maintain biological activity.

Various references disclose additional variants of GLP-1 and acylation of GLP-1, including, but not limited to, the GLP-1 parent analogs and acylation sites described in J. of Med. Chem. (2000) 43:1664-1669, which is incorporated herein by reference.

Those of skill in the art will appreciate that aminoacid positions corresponding to positions in analogs can be readily identified in any other molecule such as analog fusions, variants, fragments, etc. For example, sequence alignment by visual means or computer programs such as BLAST can be used to align and identify a particular position in a protein that corresponds with a position in the analog of polypeptide sequences identified in this application or other GLP-1, VIP, PYY, IL-10, PACAP, Ghrelin, ANP/BNP/CNP, Maxadilan/M65, Apolipoprotein mimetic polypeptides and any other analog sequences are intended to also refer to substitutions, deletions or additions in corresponding positions in GLP-1, VIP, PYY, IL-10, PACAP, Ghrelin, ANP/BNP/CNP, Maxadilan/M65, Apolipoprotein mimetic polypeptides fusions, variants, fragments, etc. described herein or known in the art and are expressly encompassed by the present invention.

The term analog encompasses polypeptides comprising one or more amino acid substitutions, additions or deletions. Analogs of the present invention may be comprised of modifications with one or more natural amino acids in conjunction with one or more non-natural amino acid modification. Exemplary substitutions in a wide variety of amino acid positions in naturally-occurring analogs have been described, including but not limited to substitutions that modulate one or more of the biological activities of the analogs, such as but not limited to, increase agonist activity, increase solubility of the polypeptide, convert the polypeptide into an antagonist, decrease peptidase or protease susceptibility, etc. and are encompassed by the term analog.

Human GLP-1 antagonists include, but are not limited to, those with a substitutions at: 19, 23, 26, 27, 28, 29, 30, and 33 of the consensus sequence identified in Table 4. In some embodiments, the GLP-1 antagonist comprises a non-naturally encoded amino acid linked to a water soluble polymer that is present in a receptor binding region of the GLP-1 molecule. In some embodiments, the water soluble polymer is coupled to the GLP-1 polypeptide at one or more of the amino acid positions: 19, 23, 26, 27, 30, and 33 of the consensus sequence identified in Table 4.

In some embodiments, the analogs further comprise an addition, substitution or deletion that modulates biological activity of the analogs. For example, the additions, substitution or deletions may modulate one or more properties or activities of the analog. For example, the additions, substitutions or deletions may modulate affinity for the analog receptor or binding partner, modulate (including but not limited to, increases or decreases) receptor dimerization, stabilize receptor dimers, modulate the conformation or one or more biological activities of a binding partner, modulate circulating half-life, modulate therapeutic half-life, modulate stability of the polypeptide, modulate cleavage by peptidases or proteases, modulate dose, modulate release or bio-availability, facilitate purification, or improve or alter a particular route of administration. Similarly, analogs of the present invention may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

A "non-naturally encoded amino acid" refers to an amino acid that is not one of the 20 common amino acids or pyrolysine or seienocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, peptides or proteins such as serum albumin, immunoglobulin constant region portions such as Fc, or other moieties that increase serum half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, hard drugs, soft drugs, carbohydrates, inorganic atoms or molecules, dyes, lipids, nucleosides, radionuclides, oligonucleotides, toxins, cells, viruses, liposomes, microparticles and micelles. Classes of biologically active agents that are suitable for use with the invention include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No 188,256; U.S. Pat. Nos. 4,671,958, 4,659,839, 4,414,148, 4,699,784; 4,680,338; 4,569,789; and 4,589,071 which are incorporated by reference herein. A "multi-functional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired molecular length or molecular weight, and may be selected to provide a particular desired spacing or conformation between one or more molecules linked to the analog and its binding partner or the analog.

Representative non-limiting classes of polypeptides useful in the present invention include those falling into the following therapeutic categories: adrenocorticotropic hormone peptides, adrenomedullin peptides, allatostatin peptides, amylin peptides, amyloid beta-protein fragment peptides, angiotensin peptides, antibiotic peptides, antigenic polypeptides, anti-microbial peptides, apoptosis related peptides, atrial natriuretic peptides, bag cell peptides, bombesin peptides, bone GLA peptides, bradykinin peptides, brain natriuretic peptides, C-peptides, C-type natriuretic peptides, calcitonin peptides, calcitonin gene related peptides, CART peptides, casomorphin peptides, chemotactic peptides, cholecystokinin peptides, colony-stimulating factor peptides, corticortropin releasing factor peptides, cortistatin peptides, cytokine peptides, dermorphin peptides, dynorphin peptides, endorphin peptides, endothelin peptides, ETa receptor antagonist peptides, ETh receptor antagonist peptides, enkephalin peptides, fibronectin peptides, galanin peptides, gastrin peptides, glucagon peptides, Gn-RH associated peptides, growth factor peptides, growth hormone peptides, GTP-binding protein fragment peptides, guanylin peptides, inhibin peptides, insulin peptides, interleukin peptides, laminin peptides, leptin peptides, leucokinin peptides, luteinizing hormone-releasing hormone peptides, mastoparan peptides, mast cell degranulating peptides, melanocyte stimulating hormone peptides, morphiceptin peptides, motilin peptides, neuro-peptides, neuropeptide Y peptides, neurotropic factor peptides, orexin peptides, opioid peptides, oxytocin peptides, PACAP peptides, pancreastatin peptides, pancreatic polypeptides, parathyroid hormone peptides, parathyroid hormone-related peptides, peptide T peptides, prolactin-releasing peptides, peptide YY peptides, renin substrate peptides, secretin peptides, somatostatin peptides, substance P peptides, tachykinin peptides, thyrotropin-releasing hormone peptides, toxin peptides, vasoactive intestinal peptides, vasopressin peptides, and virus related peptides. (see U.S. Pat. No. 6,858,580).

Examples of polypeptides include, but are not limited to, pituitary hormones such as vasopressin, oxytocin, melanocyte stimulating hormones, adrenocorticotropic hormones, growth hormones; hypothalamic hormones such as growth hormone releasing factor, corticotropin releasing factor, prolactin releasing peptides, gonadotropin releasing hormone and its associated peptides, luteinizing hormone release hormones, thyrotropin releasing hormone, orexins, and somatostatin; thyroid hormones such as calcitonins, calcitonin precursors, and calcitonin gene related peptides; parathyroid hormones and their related proteins; pancreatic hormones such as insulin and insulin-like peptides, glucagon, somatostatin, pancreatic polypeptides, amylin, peptide YY, and neuropeptide Y; digestive hormones such as gastrin, gastrin releasing peptides, gastrin inhibitory peptides, cholecystokinin, secretin, motilin, and vasoactive intestinal peptide; natriuretic peptides such as atrial natriuretic peptides, brain natriuretic peptides, and C-type natriuretic peptides; neurokinins such as neurokinin A, neurokinin B, and substance P; renin related peptides such as renin substrates and inhibitors and angiotensins; endothelins, including big endothelin, endothelin A receptor antagonists, and sarafotoxin peptides; and other peptides such as adrenomedullin peptides, allatostatin peptides, amyloid beta protein fragments, antibiotic and antimicrobial peptides, apoptosis related peptides, bag cell peptides, bombesin, bone Gla protein peptides, CART peptides, chemotactic peptides, cortistatin peptides, fibronectin fragments and fibrin related peptides. FMRF and analog peptides, galanin and related peptides, growth factors and related peptides, G therapeutic peptide-binding protein fragments, guanylin and uroguanylin, inhibin peptides, interleukin and interleukin receptor proteins, laminin fragments, leptin fragment peptides, leucokinins, mast cell degranulating peptides, pituitary adenylate cyclase activating polypeptides, pancreastatin, peptide T, polypeptides, virus related peptides, signal transduction reagents, toxins, and miscellaneous peptides such as adjuvant peptide analogs, alpha mating factor, antiarrhythmic peptide, antifreeze polypeptide, anorexigenic peptide, bovine pineal antireproductive peptide, bursin, C3 peptide P16, tumor necrosis factor, cadherin peptide, chromogranin A fragment, contraceptive tetrapeptide, conantokin G, conantokin T, crustacean cardioactive peptide, C-telopeptide, cytochrome b588 peptide, decorsin, delicious peptide, delta-sleep-inducing peptide, diazempam-binding inhibitor fragment, nitric oxide synthase blocking peptide, OVA peptide, platelet calpain inhibitor (P1), plasminogen activator inhibitor 1, rigin, schizophrenia related peptide, serum thymic factor, sodium potassium A therapeutic peptidease inhibitor-1, speract, sperm activating peptide, systemin, thrombin receptor agonists, thymic humoral gamma2 factor, thymopentin, thymosin alpha 1, thymus factor, tuftsin, adipokinetic hormone, uremic pentapeptide, glucose-dependent insulinotropic polypeptide (GIP), glucagon-like peptide-1 (GLP-1), glucagon-like peptide-2 (GLP-1), exendin-3, exendin-4, and other therapeutic peptides or fragments thereof. Additional examples of peptides include ghrelin, opioid peptides (casomorphin peptides, demorphins, endorphins, enkephalins, deltorphins, dynorphins, and analogs and derivatives of these), thymic peptides (thymopoietin, thymulin, thymopentin, thymosin, Thymic Humoral Factor (THF)), cell adhesion peptides, complement inhibitors, thrombin inhibitors, trypsin inhibitors, alpha-1 antitrypsin. Sea Urchin Sperm Activating Peptide, Asterosap, SHU-9119 MC3-R & MC4-R Antagonist, glaspimod (immunostimulant, useful against bacterial infections, fungal infections, immune deficiency immune disorder, leukopenia), HP-228 (melanocortin, useful against chemotherapy induced emesis, toxicity, pain, diabetes mellitus, inflammation, rheumatoid arthritis, obesity), alpha 2-plasmin inhibitor (plasmin inhibitor), APC tumor suppressor (tumor suppressor, useful against neoplasm), early pregnancy factor (immunosuppressor), endozepine diazepam binding inhibitor (receptor peptide), gamma interferon (useful against leukemia), glandular kallikrein-1 (immunostimulant), placental ribonuclease inhibitor, sarcolecin binding protein, surfactant protein D, Wilms' tumor suppressor, GABAB 1b receptor peptide, prion related peptide (iPrP13), choline binding protein fragment (bacterial related peptide), telomerase inhibitor, cardiostatin peptide, endostatin derived peptide (angiogenesis inhibitor), prion inhibiting peptide, N-methyl D-aspartate receptor antagonist, C-peptide analog (useful against diabetic complications), RANTES, NTY receptors, NPY2-R (neuropeptide Y type 2-receptor) ligands, NC4R peptides, or fragments thereof. Other analogs and polypeptides upon which the analogs of the instant invention are derived are found in U.S. Pat. No. 6,849,714 which is incorporated by reference herein.

The hormones regulating insulin secretion belong to the so-called enteroinsular axis, designating a group of hormones released from the gastrointestinal mucosa in response to the presence and absorption of nutrients in the gut, which promote an early and potentiated release of insulin. The enhancing effect on insulin secretion, the so-called incretin effect, is probably essential for a normal glucose tolerance. Many of the gastrointestinal hormones, including gastrin and secretin (cholecystokinin is not insulinotropic in man), are insulinotropic, but the only physiologically important ones, those that are responsible for the incretin effect, are the glucose-dependent insulinotropic polypeptide, GIP, and glucagon-like peptide-1 (GLP-1).

GIP is composed of 42 amino acids, processed from a 153 amino acid precursor (Takeda et al., PNAS USA (1987) 84:7005-7008). GIP is secreted by K cells present in the duodenum and in the small intestinal mucosa in response to carbohydrate and lipid containing meals (Mortensen et al. Ann. NY Acad. Sci. (2000) 921:469-472). Expression of the GIP receptor has been shown in pancreatic islets, the adrenal cortex, gut, heart, adipose tissue, several regions of the brain, and the pituitary gland (Usdin et al. (1993) Endocrinology 133:2861-2870).

Because of its insulinotropic effect, GIP, isolated in 1973 (Pederson R A. Gastric Inhibitory Polypeptide. In Walsh J H, Dockray G J (eds.) Gut peptides: Biochemistry and Physiology. Raven Press, New York 1994, pp. 217-259) immediately attracted considerable interest among diabetologists. However, numerous investigations carried out during the following years clearly indicated that a defective secretion of GIP was not involved in the pathogenesis of insulin dependent diabetes mellitus (IDDM) or non insulin-dependent diabetes mellitus (NIDDM) (Krarup T., Endocr Rev 1988; 9: 122-134). Furthermore, as an insulinotropic hormone, GIP was found to be almost ineffective in NIDDM (Krarup T., Endocr Rev 1988; 9: 122-134). The other incretin hormone, GLP-1 is the most potent insulinotropic substance known (O'rskov C., Diabetologia 1992; 35:701-711). Unlike GIP, it is surprisingly effective in stimulating insulin secretion in NIDDM patients. In addition, and in contrast to the other insulinotropic hormones (perhaps with the exception of secretin), it also potently inhibits glucagon secretion. Because of these actions, it has pronounced blood glucose lowering effects particularly in patients with NIDDM.

GLP-1, a product of the proglucagon gene (Bell G I, et al., Nature 1983; 304: 368-371), is one of the members of the secretin-VIP family of peptides, and is established as an important gut hormone with regulatory function in glucose metabolism and gastrointestinal secretion and metabolism (Hoist J J., 1994; Gastroenterology. 1994 December; 107 (6):1848-55). The glucagon gene is processed differently in the pancreas and in the intestine. In the pancreas (Hoist J J, et al., J Biol Chem, 1994; 269: 18827-18833), the processing leads to the formation and parallel secretion of 1) glucagon itself, occupying positions 33-61 of proglucagon (PG); 2) an N-terminal peptide of 30 amino acids (PG (1-30)) often called glicentin-related pancreatic peptide, GRPP (Moody A J, et al., Nature 1981; 289: 514-516; Thim L, et al., Biochim Biophys Acta 1982; 703:134-141); 3) a hexapeptide corresponding to PG (64-69); 4) and, finally, the so-called major proglucagon fragment (PG (72-158)), in which the two glucagon-like sequences are buried (Hoist J J, et al., J Biol Chem, 1994; 269: 18827-18833). Glucagon seems to be the only biologically active product. In contrast, in the intestinal mucosa, it is glucagon that is buried in a larger molecule, while the two glucagon-like peptides are formed separately (O'rskov C, et al., Endocrinology 1986; 119:1467-1475). The following products are formed and secreted in parallel: 1) glicentin, corresponding to PG (1-69), with the glucagon sequence occupying residues Nos. 33-61 (Thim L, et al., Regul Pept 1981; 2:139-151); 2) GLP-1(7-36)amide (PG (78-107))amide (O'rskov C, et al., J. Biol. Chem. 1989; 264:12826-12829), not as originally believed PG (72-107) amide or 108, which is inactive). Small amounts of C-terminally glycine-extended but equally bioactive GLP-1(7-37), (PG (78-108)) are also formed (Orskov C, et al., Diabetes 1991; 43: 535-539); 3) intervening peptide-2 (PG (111-122)amide) (Buhl T, et al., J. Biol. Chem. 1988; 263:8621-8624); and 4) GLP-2 (PG (126-158)) (Buhl T, et al., J. Biol. Chem. 1988; 263:8621-8624; O'rskov C, et al., FEBS letters, 1989; 247:193-106). A fraction of glicentin is cleaved further into GRPP (PG (1-30)) and oxyntomodulin (PG (33-69)) (Hoist J J. Biochem J. 1980; 187:337-343; Bataille D, et al., FEBS Lett 1982; 146:79-86).

Being secreted in parallel with glicentin/enteroglucagon, it follows that the many studies of enteroglucagon secretion (Hoist J J., Gastroenterology 1983; 84:1602-1613; Hoist J J, et al., Glucagon and other proglucagon-derived peptides. In Walsh J H, Dockray G J, eds. Gut peptides: Biochemistry and Physiology. Raven Press, New York, pp. 305-340, 1993) to some extent also apply to GLP-1 secretion, but GLP-1 is metabolized more quickly with a plasma half-life in humans of 2 minutes (O'rskov C, et al., Diabetes 1993; 42:658-661). Carbohydrate or fat-rich meals stimulate secretion (Elliott R M, et al., J Endocrinol 1993; 138: 159-166), presumably as a result of direct interaction of yet unabsorbed nutrients with the microvilli of the open-type L-cells of the gut mucosa.

The incretin function of GLP-1(29-31) has been clearly illustrated in experiments with the GLP-1 receptor antagonist, exendin 9-39, which dramatically reduces the incretin effect elicited by oral glucose in rats (Kolligs F, et al., Diabetes 1995 44: 16-19; Wang Z, et al., J. Clin. Invest. 1995 95: 417-421). The hormone interacts directly with the 3-cells via the GLP-1 receptor (Thorens B., Proc Natl Acad Sci 1992; 89:8641-4645, U.S. Pat. Nos. 5,670,360 and 6,051,689, which are incorporated by reference herein) which belongs to the glucagon/VIP/calcitonin family of G-protein-coupled 7-transmembrane spanning receptors. The importance of the GLP-1 receptor in regulating insulin secretion was illustrated in recent experiments in which a targeted disruption of the GLP-1 receptor gene was carried out in mice. Animals homozygous for the disruption had greatly deteriorated glucose tolerance and fasting hyperglycaemia, and even heterozygous animals were glucose intolerant (Scrocchi L, et al., Diabetes 1996; 45: 21A). The signal transduction mechanism (Fehmann H C, et al., Endocrine Reviews, 1995; 16: 390-410) primarily involves activation of adenylate cyclase, but elevations of intracellular $Ca^{2+}$ are also essential (Fehmann H C, et al., Endocrine Reviews, 1995; 16: 390-410; Gromada J, et al., Diabetes 1995; 44: 767-774). A model of GLP-1 receptor-ligand interaction is shown in Lopez de Maturana, R. et al. (2003) J. Biol. Chem. 278, 10195-10200. Lopez de Maturana et al. indicate that the N-terminal domain of the receptor binds to the conserved face of the central helix of exendin-4, GLP-1, and exendin (9-39). The N-terminal regions of exendin-4 and GLP-1 interact with the extracellular loops and/or the transmembrane regions of the GLP-1R. Also the N-terminal domain of the receptor interacts with the Trp-cage portion of the exendin-4 and exendin (9-39). Neidigh et al. Nature Structural Biology (2002) 9(6):425-430 describe the Trp-cage structure of Exendin-4 and mutants thereof.

The action of the hormone is best described as a potentiation of glucose stimulated insulin release (Fehmann H C, et al., Endocrine Reviews, 1995; 16: 390-410), but the mechanism that couples glucose and GLP-1 stimulation is not known. It may involve a calcium-induced calcium release (Gromada J, et al., Diabetes 1995; 44: 767-774; Holz G G. et al., J Biol Chem, 1996; 270: 17749-17759). As already mentioned, the insulinotropic action of GLP-1 is preserved in diabetic P-cells. The relation of the latter to its ability to convey "glucose competence" to isolated insulin-secreting cells (Gromada J, et al., Diabetes 1995, 44: 767-774; Holz G G, et al., Nature 1993, 361:362-365), which respond poorly to glucose or GLP-1 alone, but fully to a combination of the two, is also not known. Equally importantly, however, the hormone also potently inhibits glucagon secretion (O'rskov C, et al., Endocrinology 1988; 123:2009-2013). The mechanism is not known, but seems to be paracrine, via neighbouring insulin or somatostatin cells (Fehmann H C, et al., Endocrine Reviews, 1995; 16: 390-410). Also the glucagonostatic action is glucose-dependent, so that the inhibitory effect decreases as blood glucose decreases. Because of this dual effect, if the plasma GLP-1 concentrations increase either by increased secretion or by exogenous infusion, the molar ratio of insulin to glucagon in the blood that reaches the liver via the portal circulation is greatly increased, whereby hepatic glucose production decreases (Hvidberg A, et al., Metabolism 1994; 43:104-108). As a result blood glucose concentrations decrease. Because of the glucose dependency of the insulinotropic and glucagonostatic actions, the glucose lowering effect is self-limiting, and the hormone, therefore, does not cause hypoglycaemia regardless of dose (Qualmann C, et al., Acta Diabetologica, 1995; 32: 13-16). The effects are preserved in patients with diabetes mellitus (Nauck M A, et al., J Clin Invest 1993; 91:301-307), in whom infusions of slightly supraphysiological doses of GLP-1 may completely normalise blood glucose values in spite of poor metabolic control and secondary failure to sulphonylurea (Nauck M A, et al., Diabetologia 1993; 36:741-744). The importance of the glucagonostatic effect is illustrated by the finding that GLP-1 also lowers blood glucose in type-I diabetic patients without residual P-cell secretory capacity (Creutzfeldt W, et al., Diabetes Care 1996; 19: 580-586).

GLP-1 is involved in increasing beta-cell mass as well as regulating beta-cell differentiation, beta-cell proliferation and beta-cell survival (Stoffers D A, Horm Metab Res. 2004 November-December; 36(11-12):811-21), and has a role in increasing proinsulin gene transcription and biosynthesis.

In addition to its effects on the pancreatic islets, GLP-1 has powerful actions on the gastrointestinal tract. Infused in physiological amounts, GLP-1 potently inhibits pentagastrin-induced as well as meal-induced gastric acid secretion (Schjoldager B T G, et al., Dig. Dis. Sci. 1989; 35:703-708; Wettergren A, et al., Dig Dis Sci 1993; 38:665-673). It also inhibits gastric emntying rate and pancreatic enzyme secretion (Wettergren A., et al., Dig Dis Sci 1993; 38:665-673). Similar inhibitory effects on gastric and pancreatic secretion and motility may be elicited in humans upon perfusion of the ileum with carbohydrate- or lipid-containing solutions (Layer P, et al., Dig Dis Sci 1995; 40: 1074-1082; Layer P, et al., Digestion 1993; 54: 385-386). Concomitantly, GLP-1 secretion is greatly stimulated, and it has been speculated that GLP-1 may be at least partly responsible for this so-called "ileal-brake" effect (Layer P, et al., Digestion 1993; 54: 385-386). In fact, recent studies suggest that, physiologically, the ileal-brake effects of GLP-1 may be more important than its effects on the pancreatic islets. Thus, in dose response studies GLP-1 influences gastric emptying rate at infusion rates at least as low as those required to influence islet secretion (Nauck M, et al., Gut 1995; 37 (suppl. 2): A124).

GLP-1 seems to have an effect on food intake. Intraventricular administration of GLP-1 profoundly inhibits food intake in rats (Schick R R, vorm Walde T, Zimmermann J P, Schusdziarra V, Classen M. Glucagon-like peptide 1—a novel brain peptide involved in feeding regulation. in Ditschuneit H, Gries F A, Hauner H, Schusdziarra V, Wechsler J G (eds.) Obesity in Europe. John Libbey & Company Ltd., 1994; pp. 363-367; 42). This effect seems to be highly specific. Thus, N-terminally extended GLP-1 (PG 72-107) amide is inactive and appropriate doses of the GLP-1 antagonist, exendin 9-39, abolish the effects of GLP-1. Acute, peripheral administration of GLP-1 does not inhibit food intake acutely in rats (Turton M D, et al., Nature 1996;

379: 69-72). However, it remains possible that GLP-1 secreted from the intestinal L-cells may also act as a satiety signal.

Not only the insulinotropic effects but also the effects of GLP-1 on the gastrointestinal tract are preserved in diabetic patients (Willms B, et al., Diabetologia 1994; 37, suppl. 1: A118), and may help curtailing meal-induced glucose excursions, but, more importantly, may also influence food intake. Administered intravenously, continuously for one week, GLP-1 at 4 ng/kg/min has been demonstrated to dramatically improve glycaemic control in NIDDM patients without significant side effects (Larsen J, et al., Diabetes 1996; 45, suppl. 2: 233A). The peptide is fully active after subcutaneous administration (Ritzel R, et al., Diabetologia 1995; 38: 720-725), but is rapidly degraded mainly due to degradation by dipeptidyl peptidase IV-like enzymes (Deacon C F, et al., J Clin Endocrinol Metab 1995; 80: 952-957; Deacon C F, et al., Diabetes 44: 1126-1131).

The amino acid sequence of GLP-1 is disclosed in Schmidt et al. (Diabetologia 28 704-707 (1985). Human GLP-1 is a 30-31 amino acid residue peptide originating from preproglucagon which is synthesized, i.a. in the L-cells in the distal ileum, in the pancreas and in the brain. Processing of preproglucagon to GLP-1 (7-36)amide, GLP-1 (7-37) and GLP-2 occurs mainly in the L-cells. Although the interesting pharmacological properties of GLP-1(7-37) and analogues thereof have attracted much attention in recent years only little is known about the structure of these molecules. The secondary structure of GLP-1 in micelles has been described by Thornton et al. (Biochemistry 33: 3532-3539 (1994)), but in normal solution, GLP-1 is considered a very flexible molecule. Derivatisation of this relatively small and very flexible molecule resulted in compounds whose plasma profile were highly protracted and still had retained activity.

GLP-1 and analogues of GLP-1 and fragments thereof are useful i.e. in the treatment of Type 1 and Type 2 diabetes and obesity.

WO 87/06941 discloses GLP-1 fragments, including GLP-1(7-37), and functional derivatives thereof and to their use as an insulinotropic agent. GLP-1(7-37), certain derivatives thereof and the use thereof to treat Diabetes mellitus in a mammal are disclosed in U.S. Pat. No. 5,120,712, which is incorporated by reference herein.

WO 90/11296 discloses GLP-1 fragments, including GLP-1(7-36), and functional derivatives thereof which have an insulinotropic activity which exceeds the insulinotropic activity of GLP-1(1-36) or GLP-1(1-37) and to their use as insulinotropic agents.

The amino acid sequence of GLP-1(7-36) and GLP-1(7-37) is: His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-X, wherein X is $NH_2$ for GLP-1(7-36) (SEQ ID NO: 1330) and X is Gly for GLP-1(7-37) (SEQ ID NO: 1331).

WO 91/11457 discloses analogues of the active GLP-1 peptides 7-34, 7-35, 7-36, and 7-37 which can also be useful as GLP-1 moieties.

EP 0708179-A2 discloses GLP-1-like polypeptides and derivatives that include an N-terminal imidazole group and optionally an unbranched $C_6$-$C_{10}$ acyl group in attached to the lysine residue in position 34.

EP 0699686-A2 discloses certain N-terminal truncated fragments of GLP-1 that are reported to be biologically active.

In some embodiments the compositions, pharmaceutical compositions comprise analogs, wherein the analog amino acid sequence is based upon the GLP-1 fragments, polypeptides, and functional deriviatives disclosed above.

Another example of a peptide is T-20 (DP-178) which is a peptide corresponding to amino acids 638 to 673 of the HIV-1$_{LAI}$ transmembrane protein (TM) gp41, the carboxyl-terminal helical segment of the extracellular portion of gp41. The extracellular portion of gp41 has another .alpha.-helical region which is the amino-terminal proposed zipper domain, DP-107, DP-107 exhibits potent antiviral activity by inhibiting viral fusion. It is a 38 amino acid peptide, corresponding to residues 558 to 595 of the HIV-1$_{LAI}$ transmembrane gp41 protein. Studies with DP-107 have proven both are non-toxic in in vitro studies and in animals. U.S. Pat. No. 5,656,480, which is incorporated by reference herein, describes DP-107 and its antiviral activity. In some embodiments the compositions, pharmaceutical compositions comprise analogs, wherein the analog amino acid sequence is based upon the DP-107 fragments, polypeptides, and functional deriviatives disclosed.

T-20 inhibits entry of HIV into cells by acting as a viral fusion inhibitor. The fusion process of HIV is well characterized. HIV binds to CD4 receptor via gp120, and upon binding to its receptor, gp120 goes through a series of conformational changes that allows it to bind to its coreceptors, CCR5 or CXCR4. After binding to both receptor and coreceptor, gp120 exposes gp41 to begin the fusion process. gp41 has two regions named heptad repeat 1 and 2 (HR1 and 2). The extracellular domain identified as HR1 is an 3.-helical region which is the amino-terminal of a proposed zipper domain. HR1 comes together with HR2 of gp41 to form a hairpin. The structure that it is formed is a α-helix bundle that places the HIV envelope in the proximity of the cellular membrane causing fusion between the two membranes. T-20 prevents the conformational changes necessary for viral fusion by binding the first heptad-repeat (HR1) of the gp41 transmembrane glycoprotein. Thus, the formation of the 6-helix bundle is blocked by T-20's binding to the HR1 region of gp41. The DP107 and DP178 domains (i.e., the HR1 and HR2 domains) of the HIV gp41 protein non-covalently complex with each other, and their interaction is required for the normal infectivity of the virus. Compounds that disrupt the interaction between DP107 and DP178, and/or between DP107-like and DP178-like peptides are antifusogenic, including antiviral.

DP-178 acts as a potent inhibitor of HIV-1 mediated CD-4$^+$ cell-cell fusion (i.e., syncytial formation) and infection of CD-4+ cells by cell-free virus. Such anti-retroviral activity includes, but is not limited to, the inhibition of HIV transmission to uninfected CD-4$^+$ cells. DP-178 act at low concentrations, and it has been proven that it is non-toxic in in vitro studies and in animals. The amino acid conservation within the DP-178—corresponding regions of HIV-1 and HIV-2 has been described.

Potential uses for DP-178 peptides are described in U.S. Pat. Nos. 5,464,933 and 6,133,418, as well as U.S. Pat. Nos. 6,750,008 and 6,824,783, all of which are incorporated by reference herein, for use in inhibition of fusion events associated with HIV transmission.

Portions and homologs of DP178 and DP-107 as well as modulators of DP178/DP107, DP178-like/DP107-like or HR1/HR2 interactions have been investigated that show antiviral activity, and/or show anti-membrane fusion capability, or an ability to modulate intracellular processes involving coiled-coil peptide structures in retroviruses other than HIV-1 and nonretroviral viruses. Viruses in such studies include, simian immunodeficiency virus (U.S. Pat. No. 6,017,536), respiratory synctial virus (U.S. Pat. Nos. 6,228, 983; 6,440,656; 6,479,055; 6,623,741), Epstein-Barr virus (U.S. Pat. Nos. 6,093,794; 6,518,013), parainfluenza virus (U.S. Pat. No. 6,333,395), influenza virus (U.S. Pat. Nos. 6,068,973; 6,060,065), and measles virus (U.S. Pat. No. 6,013,263). All of which are incorporated by reference herein.

A commercially available form of DP-178 is Fuzeon® (enfuvirtide, Roche Laboratories Inc. and Trimeris, Inc.). Fuzeon® has an acetylated N terminus and a carboxamide as the C-terminus, and is described by the following primary amino acid sequence: $CH_3CO$-YTSLIHSLIEESQN-QQEKNEQELLELDKWASLWNWF-$NH_2$ (SEQ ID NO: 784). It is used in combination with other antivirals in HIV-1 patients that show HIV-1 replication despite ongoing antiretroviral therapy.

U.S. Pat. Nos. 5,464,933 and 6,824,783, which are incorporated by reference herein, describes DP-178, DP-178 fragments and homologs, including, but not limited to, molecules with amino and carboxy terminal truncations, substitutions, insertions, deletions, additions, or macromolecular carrier groups as well as DP-178 molecules with chemical groups such as hydrophobic groups present at their amino and/or carboxy termini. Additional variants, include but are not limited to, those described in U.S. Pat. No. 6,830,893 and the derivatives of DP-178 disclosed in U.S. Pat. No. 6,861,059. A set of T-20 hybrid polypeptides are described in U.S. Pat. Nos. 6,656,906, 6,562,787, 6,348,568 and 6,258,782, and a DP-178-toxin fusion is described in U.S. Pat. No. 6,627,197. In some embodiments the compositions, pharmaceutical compositions comprise analogs, wherein the analog amino acid sequence is based upon the T-20 and DP-178 fragments, polypeptides, and functional deriviatives disclosed above.

HAART (Highly Active Anti-Retroviral Therapy) is the standard of therapy for HIV which combines drugs from a few classes of antiretroviral agents to reduce viral loads. U.S. Pat. No. 6,861,059, which is incorporated by reference herein, discloses methods of treating HIV-1 infection or inhibiting HIV-1 replication employing DP-178 or DP-107 or derivatives thereof, in combination with at least one other antiviral therapeutic agent such as a reverse transcriptase inhibitor (e.g. AZT, ddI, ddC, ddA, d4T, 3TC, or other dideoxynucleotides or dideoxyfluoronucleosides) or an inhibitor of HIV-1 protease (e.g. indinavir; ritonavir). Other antivirals include cytokines (e.g., rIFN.alpha., rIFN.beta., rIFN.gamma.), inhibitors of viral mRNA capping (e.g. ribavirin), inhibitors of HIV protease (e.g. ABT-538 and MK-639), amphotericin B as a lipid-binding molecule with anti-HIV activity, and castanospermine as an inhibitor of glycoprotein processing. In some embodiments, the pharmaceutical compositions comprises an analog of T20, wherein the analog amino acid sequence is based upon the T20 fragments, polypeptides, and functional deriviatives disclosed above. In some embodiments, the pharmaceutical composition comprises an analog of T20, wherein the analog amino acid sequence is based upon the T20 fragments, polypeptides, and functional deriviatives disclosed above and one other anti-viral agent. In some embodiments the pharmaceutical composition of the claimed invention comprises one another anti-viral agent chosen from the following: reverse transcriptase inhibitors, integrase inhibitors, protease inhibitors, cytokine antagonists, and chemokine receptor modulators described U.S. Pat. Nos. 6,855,724; 6,844,340; 6,841,558; 6,833,457; 6,825,210; 6,811,780; 6,809,109; 6,806,265; 6,768,007; 6,750,230; 6,706,706; 6,696,494; 6,673,821; 6,673,791; 6,667,314; 6,642,237; 6,599,911; 6,596,729; 6,593,346; 6,589,962; 6,586,430; 6,541,515; 6,538,002; 6,531,484; 6,511,994; 6,506,777; 6,500,844; 6,498,161; 6,472,410; 6,432,981; 6,410,726; 6,399,619; 6,395,743; 6,358,979; 6,265,434; 6,248,755; 6,245,806; and 6,172,110, which are incorporated by reference.

Potential delivery systems for DP-178 include, but are not limited to those described in U.S. Pat. Nos. 6,844,324 and 6,706,892. In addition, a process for producing T-20 in inclusion bodies was described in U.S. Pat. No. 6,858,410.

T20/DP178, T21/DP107, and fragments thereof have also been found to interact with N-formyl peptide receptor (FPR members). T-20 activates the N-formyl peptide receptor present in human phagocytes (Su et al. (1999) Blood 93(11): 3885-3892) and is a chemoattractant and activator of monocytes and neutrophils (see U.S. Pat. No. 6,830,893). The FPR class receptors are G-protein-coupled, STM receptors that bind the chemoattractant fMLP (N-formyl-methionyl-leucyl-phenylalanine) and are involved in monocyte chemotaxis and the induction of a host immune response to a pathogen. The prototype FPR class receptor, FPR, binds fMLP with high affinity and is activated by low concentrations of fMLP. The binding of FPR by fMLP induces a cascade of G protein-mediated signaling events leading to phagocytic cell adhesion, chemotaxis, release of oxygen intermediates, enhanced phagocytosis and bacterial killing, as well as MAP kinase activation and gene transcription. (Krump et al., J Biol Chem 272:937 (1997); Prossnitz et al., Pharmacol Ther 74:73 (1997); Murphy, Annu. Rev. Immuno. 12: 593 (1994); and Murphy, The N-formyl peptide chemotactic receptors, Chemoattractant ligands and their receptors. CRC Press, Boca Raton, p. 269 (1996)). Another FPR class receptor is the highly homologous variant of FPR, named FPRL1 (also referred to as FPRH2 and LXA4R). FPRL1 was originally cloned as an orphan receptor (Murphy et al., J. Biol. Chem., 267:7637-7643 (1992); Ye et al., Biochem. Biophys. Res. Commun., 184:582-589 (1992); Bao et al., Genomics, 13:437-440 (1992); Gao, J. L. and P. M. Murphy, J. Biol. Chem., 268:25395-25401 (1993); and Nomura et al., Int. Immunol., 5:1239-1249 (1993)) but was subsequently found to mediate $Ca^{2+}$ mobilization in response to high concentrations of fMLP. (Ye et al., Biochem. Biophys. Res. Commun., 184:582-589 (1992); and Gao, J. L. and P. M. Murphy, J. Biol. Chem. 268:25395-25401 (1993)). In some embodiments, the invention relates to a method of modulating an FPR member or CCR5 by:

a) contacting the FPR member or CCR5 molecule with a T20 analog, wherein said analog comprises an α-amino acid and at least one β-amino acid;

b) measuring the association of the T20 analog to the FPR member or CCR5 in the presence and absence of an unknown compound; and c) comparing the rate of association of the T20 analog to the FPR member or CCR5 in the presence of an unknown compound to the rate of association of the T20 analog to the FPR member or CCR5 in the absence of an unknown compound.

The chemokine receptor CCR5 is another G-protein-coupled, STM receptor and is a major fusion-cofactor exploited by most primary isolates of the human immunodeficiency virus type 1 (HIV-1). (Al Khatib et al., Science 1996, 272:1955; Doranz et al., Cell 1996, 85:1149; Deng et al., Nature 1996, 381:661; Dragic et al., Nature 1996; 381:667; Horuk, Immunol Today, 20:89 (1999); Dimitrov and Broder, "HIV and Membrane Receptors," HIV and membrane fusion: Medical Intelligence Unit, Landes Bioscience, Austin, Tex., 1997:99; and Berger, AIDS 11, Suppl A:S3 (1997)). Individuals that fail to express CCR5 are largely resistant to HIV-1 infection. (Liu et al., Cell 1996, 86:367-77; Huang, Y, Nat Med 1996, 2:1240; Dean, et al., Science, 273:1856 (1996)). Due to its prominent role in HIV-1 fusion and entry, investigators have focused considerable research on developing molecules that interrupt the interaction between the HIV-1 envelope and CCR5. Chemokine ligands and antibodies specific for CCR5, for example, have been shown to inhibit HIV-1 entry and replication. (Cocchi et al., Science, 270:1811 (1995); Wu et al., J Exp Med, 186: 373 (1997); Proudfoot et al., J Biol Chem, 271:2599 (1996); Arenzana-Seisdedos et al., Nature, 383:400 (1996); Gong et al., J Biol Chem, 273:4289 (1998)). U.S. Pat. No. 6,808,877 discusses DP-178 and its role in phosphorylation and downregulation of CCR5 and/or the inhibition of HIV infection by acting as a ligand to the N-formyl peptide receptor.

Peptide YY (PYY) is a thirty six amino acid long peptide, first isolated from porcine intestinal tissue and mainly localized in intestinal endocrine cells. PYY is secreted postprandially by endocrine cells of the distal gastrointestinal tract and acts at the hypothalamus signaling satiety. See Batterham, R. L. et al., Nature 418:650-654 (2002), which is incorporated by reference herein. It has many biological activities, including a range of activities within the digestive system and potent inhibition of intestinal electrolyte and fluid secretion. Like its relatives, neuropeptide Y (NPY) and pancreatic polypeptide (PP), peptide YY (PYY) is bent into hairpin configuration that is important in bringing the free ends of the molecule together for binding to the receptors.

Recent studies have shown that fasting and postprandial PYY levels are low in obese subjects, which may account for their high appetite and food consumption. When administered intravenously, it suppresses appetite and food intake in both lean and obese subjects (Batterham, R. L. et al., N Engl J Med 349:941-948 (2003)). Other peptides from the pancreatic peptide (PP) family, like peptide YY fragments (e.g. PYY{3-36}), and PYY agonists (including those not in the PP family) also suppress appetite. Its oral activity, however, is negligible due to its low absorption and rapid degradation in the gastrointestinal tract. PYY (3-36) is identified as Ile Lys pro Glu Ala Pro Gly Glu ASp Ala Ser Pro Glu Glu Leu Asn Arg Tyr Tyr Ala Ser Leu Arg His Tyr Leu Asn Leu val Thr Arg Gln Arg Tyr; Eberlein, Eysselein et al., Peptides 10:797-803 (1989); and Grandy, Schimiczek et al., Regul Pept 51:151-9 (1994), which are incorporated by reference herein.

PYY {3-36} has a sequence identical to PYY over amino acids 3 to 36. PYY{3-36} contains approximately 40% of total peptide YY-like immunoreactivity in human and canine intestinal extracts and about 36% of total plasma peptide YY immunoreactivity in a fasting state to slightly over 50% following a meal. It is apparently a dipeptidyl peptidase-IV (DPP4) cleavage product of peptide YY. Peptide YY{3-36} is reportedly a selective ligand at the Y2 and Y5 receptors, which appear pharmacologically unique in preferring N-terminally truncated (i.e. C terminal fragments of) neuropeptide Y analogs. A PYY agonist may bind to a PYY receptor with higher or lower affinity, demonstrate a longer or shorter half-life in vivo or in vitro, or be more or less effective than native PYY. In some embodiments a functional fragment of PYY{3-36} is a fragment of the above sequence that shares the immunoreactivity in human and canine intestinal extracts.

Current antiobesity drugs have limited efficacy and numerous side effects. Crowley, V. E., Yeo, G. S. & O'Rahilly, S., Nat. Rev. Drug Discov 1, 276-86 (2002). With obesity reaching epidemic proportions worldwide, there is a pressing need for the development of adequate therapeutics in this area. In recent years, hormones and neuropeptides involved in the regulation of appetite, body energy expenditure, and fat mass accumulation such as PYY have emerged as potential antiobesity drugs. See McMinn, J. E., Baskin, D. G. & Schwartz, M. W., Obes Rev 1:37-46 (2000), Drazen, D. L. & Woods, S. C., Curr Opin Clin Nutr Metab Care 6:621-629 (2003), which are incorporated by reference herein.

According to Batterham et al., Nature 418:650-654 (2002), which is hereby incorporated by reference, the peptide YY {3-36} system may provide a therapeutic target for the treatment of obesity. International Publication No. WO 02/47712 and U.S. Patent Application Publication No. 2002/0141985 disclose methods for treating obesity and diabetes with peptide YY and peptide YY agonists, such as peptide YY{3-36}. U.S. Patent Application Publication No. 20050002927 describes the use of at least one Y2 receptor-binding peptide, such as peptide YY, Neuropeptide Y (NPY) or Pancreatic Peptide (PP) for treating a variety of diseases and conditions in mammalian subjects such as obesity and epilepsy. In some embodiments the compositions, pharmaceutical compositions comprise analogs, wherein the analog amino acid sequence is based upon the PPY or the peptide YY {3-36} fragments, polypeptides, and functional derivatives disclosed above. In some embodiments, the invention relates to a pharmaceutical composition that comprise a PPY or peptide YY {3-36} analog, wherein the analog amino acid sequence is based upon the fragments, polypeptides, and functional deriviatives disclosed above for treatment of obesity, diabetes, seizures associated with temporal lobe epilepsy, ulcers, irritable bowel disease and inflammatory bowel disease according to the dosing regimens disclosed below.

In some embodiments, the compositions of the claimed invention comprise analog of PYY(3-36), AC162352, Neuropeptide Y (NPY) (U.S. Pat. No US 2005/0136036 A1).

In addition, treatment with DPP-IV inhibitors prevents degradation of Peptide YY which has been linked to gastrointestinal conditions such as ulcers, irritable bowel disease and inflammatory bowel disease. Peptide YY and its analogs or agonists have been used to manipulate endocrine regulation of cell proliferation, nutrient transport, and intestinal water and electrolyte secretion. (U.S. Pat. No. 5,604,203; WO9820885A1; EP692971A1; U.S. Pat. No. 5,912,227, which are incorporated by reference herein). A role for peptide YY in the regulation of intestinal motility, secretion, and blood flow has also been suggested, as well as its use in a treatment of malabsorptive disorders. Analogs of PYY have been reported that emulate and enhance the duration, effect, biological activity and selectivity of the natural peptide in the treatment of pancreatic tumors (See U.S. Pat. No. 5,574,010, incorporated herein by reference).

Other suitable PYY agonists include those described in International Publication No. WO 98/20885, which is hereby incorporated by reference.

In one aspect, the invention provides a method of treating obesity in an obese or overweight animal by administering a therapeutically effective amount of PYY analog, a PYY agonist analog, or a mixture thereof with at least one delivery agent compound and to a subject in need thereof. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from this method.

In other aspects, the invention features methods of reducing food intake, treating diabetes mellitus, and improving lipid profile (including reducing LDL cholesterol and triglyceride levels and/or changing HDL cholesterol levels) comprising administering to a subject in need thereof a therapeutically effective amount of a PYY analog, a PYY agonist analog, or a mixture thereof with at least one delivery agent compound. In some embodiments, the methods of the invention are used to treat conditions or disorders which can be alleviated by reducing nutrient availability in a subject in need thereof, comprising administering to said subject in need thereof a therapeutically effective amount of a PYY analog, a PYY agonist analog, or a mixture thereof with at least one delivery agent compound. Such conditions and disorders include, but are not limited to, hypertension, dyslipidemia, cardiovascular disease, eating disorders, insulin-resistance, obesity, and diabetes mellitus of any kind.

Suitable PYY agonist analogs may be derived or based upon the amino acid sequence of PYY agonists that have a potency in one of the assays described in WO 02/47712 and U.S. patent Publication No. 2002/0141985 (which is herein incorporated by reference and discloses the activity of food intake, gastric emptying, pancreatic secretion, or weight reduction assays) which is greater than the potency of NPY in that same assay. A PYY analog and/or a PYY agonist analog with the delivery agent compound may be administered separately or together with one or more other compounds and compositions that exhibit a long term or short-term action to reduce nutrient availability, including, but not limited to other compounds and compositions that comprise an amylin or amylin agonist, a cholecystokinin (CCK) or CCK agonist, a leptin (OB protein) or leptin agonist, an exendin or exendin agonist, or a GLP-1 or GLP-1 agonist as described in U.S. Patent Publication 20050009748. Suitable amylin agonists include, for example, (25,28,29Pro-)-human amylin (also known as "pramlintide", and described in U.S. Pat. Nos. 5,686,511 and 5,998,367), calcitonin (e.g., salmon calcitonin), including those described in U.S. Pat. No. 5,739,106, which is hereby incorporated by reference. The CCK used is preferably CCK octapeptide (CCK-8). Leptin is discussed in, for example, Pelleymounter, C. et al., Science 269: 540-543 (1995), Halaas, G. et al., Science 269: 543-6 (1995) and Campfield, S. et al., Science 269: 546-549 (1995). Suitable CCK agonist includes those described in U.S. Pat. No. 5,739,106, which is hereby incorporated by reference. Suitable exendins include exendin-3 and exendin-4, and exendin agonist compounds include, for example, those described in PCT Publications WO 99/07404, WO 99/25727, and WO 99/25728, all of which are hereby incorporated by reference. According to one embodiment, the composition of the present invention includes at least one delivery agent compound, PYY, a PYY agonist, or a mixture thereof, at least one amylin agonist, and a CCK agonist. Suitable combinations of amylin agonist and CCK agonist include, but are not limited to, those described in U.S. Pat. No. 5,739,106, which is hereby incorporated by reference.

In some embodiments, the pharmaceutical compositions comprises an analog of the polypeptides disclosed below, wherein the analog amino acid sequence is based upon fragments, polypeptides, and functional derivatives with 70%, 75%, 85%, 90%, 95%, 98%, or 99% sequence homology to the following polypeptides disclosed below:

Adrenocorticotropic hormone (ACTH) peptides including, but not limited to, ACTH, human; ACTH 1-10; ACTH 1-13, human; ACTH 1-16, human; ACTH 1-17; ACTH 1-24, human; ACTH 4-10; ACTH 4-11; ACTH 6-24; ACTH 7-38, human; ACTH 18-39, human; ACTH, rat; ACTH 12-39, rat; beta-cell tropin (ACTH 22-39); biotinyl-ACTH 1-24, human; biotinyl-ACTH 7-38, human; corticostatin, human; corticostatin, rabbit; {Met(02)$^4$, DLys$^8$, Phe$^9$} ACTH 4-9, human; {Met(0)$^4$,DLys$^8$, Phe$^9$} ACTH 4-9, human; N-acetyl, ACTH 1-17, human; and ebiratide.

Adrenomedullin peptides including, but not limited to, adrenomedullin, adrenomedullin 1-52, human; adrenomedullin 1-12, human; adrenomedullin 13-52, human; adrenomedullin 22-52, human; pro-adrenomedullin 45-92, human; pro-adrenomedullin 153-185, human; adrenomedullin 1-52, porcine; pro-adrenomedullin (N-20), porcine; adrenomedullin 1-50, rat; adrenomedullin 11-50, rat; and proAM-N20 (proadrenomedullin N-terminal 20 peptide), rat.

Allatostatin peptides including, but not limited to, allatostatin I; allatostatin II; allatostatin III; and allatostatin IV.

Amylin peptides including, but not limited to, acetyl-amylin 8-37, human; acetylated amylin 8-37, rat; AC187 amylin antagonist; AC253 amylin antagonist; AC625 amylin antagonist; amylin 8-37, human; amylin (IAPP), cat; amylin (insulinoma or islet amyloid polypeptide(IAPP)); amylin amide, human; amylin 1-13 (diabetes-associated peptide 1-13), human; amylin 20-29 (IAPP 20-29), human; AC625 amylin antagonist; amylin 8-37, human; amylin (IAPP), cat; amylin, rat; amylin 8-37, rat; biotinyl-amylin, rat; and biotinyl-amylin amide, human.

Amyloid beta-protein fragment peptides including, but not limited to, Alzheimer's disease beta-protein 12-28 (SP17); amyloid beta-protein 25-35; amyloid beta/A4-protein precursor 328-332; amyloid beta/A4 protein precursor (APP) 319-335; amyloid beta-protein 1-43; amyloid beta-protein 1-42; amyloid beta-protein 1-40; amyloid beta-protein 10-20; amyloid beta-protein 22-35; Alzheimer's disease beta-protein (SP28); beta-amyloid peptide 1-42, rat; beta-amyloid peptide 1-40, rat; beta-amyloid 1-11; beta-amyloid 31-35; beta-amyloid 32-35; beta-amyloid 35-25; beta-amyloid/A4 protein precursor 96-110; beta-amyloid precursor protein 657-676; beta-amyloid 1-38; (Gln$^{11}$)-Alzheimer's disease beta-protein; (Gln$^{11}$)-beta-amyloid 1-40; (Gln$^{22}$)-beta-amyloid 6-40; non-A beta component of Alzheimer's disease amyloid (NAC); P3, (A beta 17-40) Alzheimer's disease amyloid .beta.-peptide; and SAP (serum amyloid P component) 194-204.

Angiotensin peptides including, but not limited to, A-779; Ala-Pro-Gly-angiotensin II; (Ile$^3$,Val$^5$)-angiotensin II; angiotensin III antipeptide; angiogenin fragment 108-122; angiogenin fragment 108-123; angiotensin I converting enzyme inhibitor; angiotensin I, human; angiotensin I converting enzyme substrate; angiotensin I 1-7, human; angiopeptin; angiotensin II, human; angiotensin II antipeptide; angiotensin II 1-4, human; angiotensin II 3-8, human; angiotensin II 4-8, human; angiotensin II 5-8, human; angiotensin III ({Des-Asp$^1$}-angiotensin II), human; angiotensin III inhibitor ({Ile$^7$}-angiotensin III); angiotensin-converting enzyme inhibitor (*Neothunnus macropterus*); {Asn$^1$, Val$^5$}-angiotensin I, goosefish; {Asn$^1$, Val$^5$, Asn$^9$}-angiotensin I, salmon; {Asn$^1$, Val$^5$, Gly$^9$}-angiotensin I, eel; {Asn$^1$, Val$^5$}-angiotensin I 1-7, eel, goosefish, salmon; {Asn$^1$,Val$^5$}-angiotensin II; biotinyl-angiotensin I, human; biotinyl-angiotensin II, human; biotinyl-Ala-Ala-Ala-angiotensin II; {Des-Asp$^1$}-angiotensin I, human; {β-aminophenylalanine$^6$}-angiotensin II; renin substrate (angiotensinogen 1-13), human; preangiotensinogen 1-14 (renin substrate tetradecapeptide), human; renin substrate tetradecapeptide (angiotensinogen 1-14), porcine; {Sar$^1$}-angiotensin II; {Sar$^1$}-angiotensin II 1-7 amide; {Sar$^1$, Ala$^8$}-angiotensin II; {Sar$^1$, Ile$^8$}-angiotensin II; {Sar$^1$, Thr}-angiotensin II; {Sar$^1$, Tyr (Me)$^4$}-angiotensin II (Sarmesin); {Sar$^1$, Val$^5$, Ala$^8$}-angiotensin II; {Sar$^1$, Ile$^7$}-angiotensin III; synthetic tetradecapeptide renin substrate (No. 2); {Val$^4$}-angiotensin III; {Val$^5$}-angiotensin II; {Val$^5$}-angiotensin I, human; {Val$^5$}-angiotensin I; {Val$^5$, Asn$^9$}-angiotensin I, bullfrog; and {Val$^5$, Ser$^9$}-angiotensin I, fowl.

Antibiotic peptides including, but not limited to, Ac-SQNY; bactenecin, bovine; CAP 37 (20-44); carbormethoxycarbonyl-DPro-DPhe-OBzl; CD36 peptide P 139-155; CD36 peptide P 93-110; cecropin A-melittin hybrid peptide {CA(1-7)M(2-9)NH$_2$}; cecropin B, free acid; CYS(Bzl)84 CD fragment 81-92; defensin (human) HNP-2; dermaseptin; immunostimulating peptide, human; lactoferricin, bovine (BLFC); and magainin spacer.

Antigenic polypeptides, which can elicit an enhanced immune response, enhance an immune response and or cause an immunizingly effective response to diseases and/or disease causing agents including, but not limited to, adenoviruses; anthrax; *Bordetella pertussus*; botulism; bovine rhinotracheitis; *Branhamella catarrhalis*; canine hepatitis; canine distemper; Chlamydiae; cholera; coccidiomycosis; cowpox; cytomegalovirus; Dengue fever; dengue toxoplasmosis; diphtheria; encephalitis; enterotoxigenic *E. coli*; Epstein Barr virus; equine encephalitis; equine infectious anemia; equine influenza; equine pneumonia; equine rhinovirus; *Escherichia coli*; feline leukemia; flavivirus; globulin; haemophilus influenza type b; *Haemophilus influenzae*; *Haemophilus pertussis*; *Helicobacter pylori*; hemophilus; hepatitis; hepatitis A; hepatitis B; Hepatitis C; herpes viruses; HIV; HIV-1 viruses; HIV-2 viruses; HTLV; influenza; Japanese encephalitis; Klebsiellae species; *Legionella pneumophila; leishmania*; leprosy; lyme disease; malaria immunogen; measles; meningitis; meningococcal; Meningococcal polysaccharide group A; Meningococcal polysaccharide group C; mumps; mumps virus; mycobacteria; *Mycobacterium tuberculosis; Neisseria; Neisseria gonorrhea; Neisseria meningitidis*; ovine blue tongue; ovine encephalitis; papilloma; parainfluenza; paramyxoviruses; Pertussis; plague; pneumococcus; *Pneumocystis carinii*; pneumonia; poiiovirus; *proteus* species; *Pseudomonas aeruginosa*; rabies; respiratory syncytial virus; rotavirus; rubella; salmonellae; schistosomiasis; shigellae; simian immunodeficiency virus; smallpox; *Staphylococcus aureus; Staphylococcus* species; *Streptococcus pneumoniae; Streptococcus pyogenes; Streptococcus* species; swine influenza; tetanus; *Treponema pallidum*; typhoid; vaccinia; varicella-zoster virus; and *Vibrio cholerae*.

Anti-microbial peptides including, but not limited to, buforin I; buforin II; cecropin A; cecropin B; cecropin P1, porcine; gaegurin 2 (*Rana rugosa*); gaegurin 5 (Rana rugosa); indolicidin; protegrin-(PG)-I; magainin 1; and magainin 2; and T-22 {Tyr$^{5,12}$, Lys$^7$}-poly-phemusin II peptide.

Apoptosis related peptides including, but not limited to, Alzheimer's disease beta-protein (SP28); calpain inhibitor peptide; capsase-1 inhibitor V; capsase-3, substrate IV; caspase-1 inhibitor I, cell-permeable; caspase-1 inhibitor VI; caspase-3 substrate III, fluorogenic; caspase-1 substrate V, fluorogenic; caspase-3 inhibitor I, cell-permeable; caspase-6 ICE inhibitor III; {Des-Ac, biotin}-ICE inhibitor III; IL-1B converting enzyme (ICE) inhibitor II; IL-1 B converting enzyme (ICE) substrate IV; MDL 28170; and MG-132.

Atrial natriuretic peptides including, but not limited to, alpha-ANP (alpha-chANP), chicken; anantin; ANP 1-11, rat; ANP 8-30, frog; ANP 11-30, frog; ANP-21 (fANP-21), frog; ANP-24 (fANP-24), frog; ANP-30, frog; ANP fragment 5-28, human, canine; ANP-7-23, human; ANP fragment 7-28, human, canine; alpha-atrial natriuretic polypeptide 1-28, human, canine; A71915, rat; atrial natriuretic factor 8-33, rat; atrial natriuretic polypeptide 3-28, human; atrial natriuretic polypeptide 4-28, human, canine; atrial natriuretic polypeptide 5-27; human; atrial natriuretic aeptide (ANP), eel; atriopeptin I, rat, rabbit, mouse; atriopeptin II, rat, rabbit, mouse; atriopeptin III, rat, rabbit, mouse; atrial natriuretic factor (rANF), rat, auriculin A (rat ANF 126-149); auriculin B (rat ANF 126-150); beta-ANP (1-28, dimer, antiparallel); beta-rANF 17-48; biotinyl-alpha-ANP 1-28, human, canine; biotinyl-atrial natriuretic factor (biotinyl-rANF), rat; cardiodilatin 1-16, human; C-ANF 4-23, rat; Des-{Cys$^{105}$, Cys$^{121}$}-atrial natriuretic factor 104-126, rat; {Met(O)$^{12}$} ANP 1-28, human; {Mpr$^7$,DAla$^9$}ANP 7-28, amide, rat; prepro-ANF 104-116, human; prepro-ANF 26-55 (proANF 1-30), human; prepro-ANF 56-92 (proANF 31-67), human; prepro-ANF 104-123, human; {Tyr$^0$}-atriopeptin I, rat, rabbit, mouse; {Tyr}-atriopeptin II, rat, rabbit, mouse; {Tyr$^0$-prepro ANF 104-123, human; urodilatin (CDD/ANP 95-126); ventricular natriuretic peptide (VNP), eel; and ventricular natriuretic peptide (VNP), rainbow trout.

Bag cell peptides including, but not limited to, alpha bag cell peptide; alpha-bag cell peptide 1-9; alpha-bag cell peptide 1-8; alpha-bag cell peptide 1-7; beta-bag cell factor, and gamma-bag cell factor.

Bombesin peptides including, but not limited to, alpha-s1 casein 101-123 (bovine milk); biotinyl-bombesin; bombesin 8-14; bombesin; {Leu$^{13}$-psi (CH$_2$NH)Leu$^{14}$}-bombesin; {D-Phe$^6$, Des-Met$^{14}$}-bombesin 6-14 ethylamide; {DPhe$^{12}$} bombesin; {DPhe$^{12}$,Leu$^{14}$}-bombesin; {Tyr$^4$}-bombesin; and {Tyr$^4$,DPhe$^{12}$}-bombesin.

Bone GLA peptides (BGP) including, but not limited to, bone GLA protein; bone GLA protein 45-49; {Glu$^{17}$, Gla$^{21,24}$}-osteocalcin 1-49, human; myclopeptide-2 (MP-2); osteocalcin 1-49 human; osteocalcin 37-49, human; and {Tyr$^{38}$, Phe$^{42,46}$} bone GLA protein 38-49, human.

Bradykinin peptides including, but not limited to, {Ala$^{2,6}$, des-Pro$^3$}-bradykinin; bradykinin; bradykinin (Bowfin. Gar); bradykinin potentiating peptide; bradykinin 1-3; bradykinin 1-5; bradykinin 1-6; bradykinin 1-7; bradykinin 2-7; bradykinin 2-9; {DPhe$^7$} bradykinin; {Des-Arg$^9$}-bradykinin; {Des-Arg$^{10}$}-Lys-bradykinin ({Des-Arg$^{10}$}-kallidin); {D-N-Me-Phe$^7$}-bradykinin; {Des-Arg$^9$, Leu$^8$}-bradykinin; Lys-bradykinin (kallidin); Lys-(Des-Arg$^9$, Leu$^8$}-bradykinin ({Des-Arg$^{10}$, Leu$^9$}-kallidin); {Lys-Hyp$^3$}-bradykinin; ovokinin; {Lys, Ala$^3$}-bradykinin; Met-Lys-bradykinin; peptide K12 bradykinin potentiating peptide; {(pCl)Phe$^{5,8}$}-bradykinin; T-kinin (Ile-Ser-bradykinin); {Thi.$^{5,8}$, D-Phe$^7$}-bradykinin; {Tyr$^0$}-bradykinin; {Tyr$^5$}-bradykinin; {Tyr$^8$}-bradykinin; and kallikrein.

Brain natriuretic peptides (BNP) including, but not limited to, BNP 32, canine; BNP-like Peptide, eel; BNP-32, human; BNP-45, mouse; BNP-26, porcine; BNP-32, porcine; biotinyl-BNP-32, porcine; BNP-32, rat; biotinyl-BNP-32, rat; BNP45 (BNP 51-95, 5K cardiac natriuretic peptide), rat; and {Tyr$^0$}-BNP 1-32, human.

C-peptides including, but not limited to, C-peptide; and {Tyr$^0$}-C-peptide, human.

C-type natriuretic peptides (CNP) including, but not limited to, C-type natriuretic peptide, chicken; C-type natriuretic peptide-22 (CNP-22), porcine, rat, human; C-type natriuretic peptide-53 (CNP-53), human; C-type natriuretic peptide-53 (CNP-53), porcine, rat; C-type natriuretic peptide-53 (porcine, rat) 1-29 (CNP-531-29); prepro-CNP 1-27, rat; prepro-CNP 30-50, porcine, rat; vasonatrin peptide (VNP); and {Tyr⁰}-C-type natriuretic peptide-22 ({Tyr⁰}-CNP-22).

Calcitonin peptides including, but not limited to, biotinyl-calcitonin, human; biotinyl-calcitonin, rat; biotinyl-calcitonin, salmon; calcitonin, chicken; calcitonin, eel; calcitonin, human; calcitonin, porcine; calcitonin, rat; calcitonin, salmon; calcitonin 1-7, human; calcitonin 8-32, salmon; katacalcin (PDN-21) (C-procalcitonin); and N-proCT (amino-terminal procalcitonin cleavage peptide), human.

Calcitonin gene related peptides (CGRP) including, but not limited to, acetyl-alpha-CGRP 19-37, human; alpha-CGRP 19-37, human; alpha-CGRP 23-37, human; biotinyl-CGRP, human; biotinyl-CGRP II, human; biotinyl-CGRP, rat; beta-CGRP, rat; biotinyl-beta-CGRP, rat; CGRP, rat; CGRP, human; calcitonin C-terminal adjacent peptide; CGRP 1-19, human; CGRP 20-37, human; CGRP 8-37, human; CGRP II, human; CGRP, rat; CGRP 8-37, rat; CGRP 29-37, rat; CGRP 30-37, rat; CGRP 31-37, rat; CGRP 32-37, rat; CGRP 33-37, rat; CGRP 31-37, rat; ({Cys(Acm)$^{2,7}$}-CGRP; elcatonin; {Tyr}-CGRP, human; {Tyr⁰}-CGRP II, human; {Tyr}-CGRP 28-37, rat; {Tyr⁰}-CGRP, rat; and {Tyr$^{22}$}-CGRP 22-37, rat.

CART peptides including, but not limited to, CART, human; CART 55-102, human; CART, rat; and CART 55-102, rat.

Casomorphin peptides including, but not limited to, beta-casomorphin, human; beta-casomorphin 1-3; beta-casomorphin 1-3, amide; beta-casomorphin, bovine; beta-casomorphin 1-4, bovine; beta-casomorphin 1-5, bovine; beta-casomorphin 1-5, amide, bovine; beta-casomorphin 1-6, bovine; {DAla²}-beta-casomorphin 1-3, amide, bovine; {DAla², Hyp⁴, Tyr⁵}-beta-casomorphin 1-5 amide; {DAla², DPro⁴, Tyr⁵}-beta-casomorphin 1-5, amide; {DAla², Tyr⁵}-beta-casomorphin 1-5, amide, bovine; {DAla$^{2,4}$, Tyr⁵}-beta-casomorphin 1-5, amide, bovine; {DAla², (pCl)Phe³}-beta-casomorphin, amide, bovine; {DAla²}-beta-casomorphin 1-4, amide, bovine; {DAla²}-beta-casomorphin 1-5, bovine; {DAla²}-beta-casomorphin 1-5, amide, bovine; {DAla², Met⁵}-beta-casomorphin 1-5, bovine; {DPro²}-beta-casomorphin 1-5, amide, bovine; {DAla²}-beta-casomorphin 1-6, bovine; {DPro²}-beta-casomorphin 1-4, amide; {Des-Tyr¹}-beta-casomorphin, bovine; {DAla$^{2,4}$, Tyr⁵}-beta-casomorphin 1-5, amide, bovine; {DAla², (pCl)Phe³}-beta-casomorphin, amide, bovine; {DAla²}-beta-casomorphin 1-4, amide, bovine; {DAla²}-beta-casomorphin 1-5, bovine; {DAla²}-beta-casomorphin 1-5, amide, bovine; {DAla², Met⁵}-beta-casomorphin 1-5, bovine; {DPro²}-beta-casomorphin 1-5, amide, bovine; {DAla²}-beta-casomorphin 1-6, bovine; {DPro²}-beta-casomorphin 14, amide; {Des-Tyr¹}-beta-casomorphin, bovine; and {Val³}-beta-casomorphin 1-4, amide, bovine.

Chemotactic peptides including, but not limited to, defensin 1 (human) HNP-1 (human neutrophil peptide-1); and N-formyl-Met-Leu-Phe.

Cholecystokinin (CCK) peptides including, but not limited to, caerulein; cholecystokinin; cholecystokinin-pancreozymin; CCK-33, human; cholecystokinin octapeptide 14 (non-sulfated) (CCK 26-29, unsulfated); cholecystokinin octapeptide (CCK 26-33); cholecystokinin octapeptide (non-sulfated) (CCK 26-33, unsulfated); cholecystokinin heptapeptide (CCK 27-33); cholecystokinin tetrapeptide (CCK 30-33); CCK-33, porcine; CR 1409, cholecystokinin antagonist; CCK flanking peptide (unsulfated); N-acetyl cholecystokinin, CCK 26-30, sulfated; N-acetyl cholecystokinin, CCK 26-31, sulfated; N-acetyl cholecystokinin, CCK 26-31, non-sulfated; prepro CCK fragment V-9-M; and proglumide.

Colony-stimulating factor peptides including, but not limited to, colony-stimulating factor (CSF); GMCSF; MCSF; and G-CSF.

Corticortropin releasing factor (CRF) peptides including, but not limited to, astressin; alpha-helical CRF 12-41; biotinyl-CRF, ovine; biotinyl-CRF, human, rat; CRF, bovine; CRF, human, rat; CRF, ovine; CRF, porcine; {Cys$^{21}$}-CRF, human, rat; CRF antagonist (alpha-helical CRF 9-41); CRF 6-33, human, rat; {DPro⁵}-CRF, human, rat; {D-Phe$^{12}$, Nle$^{21,38}$}-CRF 12-41, human, rat; eosinophilotactic peptide; {Met(0)$^{21}$}-CRF, ovine; {Nle$^{21}$, Tyr$^{32}$}-CRF, ovine; prepro CRF 125-151, human; sauvagine, frog; {Tyr⁰}-CRF, human, rat; {Tyr⁰}-CRF, ovine; {Tyr⁰}-CRF 34-41, ovine; {Tyr⁰}-urocortin; urocortin amide, human; urocortin, rat; urotensin I (Catostomus commersoni); urotensin II; and urotensin II (Rana ridibunda).

Cortistatin peptides including, but not limited to, cortistatin 29; cortistatin 29 (1-13); {Tyr⁰}-cortistatin 29; pro-cortistatin 28-47; and pro-cortistatin 51-81.

Cytokine peptides including, but not limited to, tumor necrosis factor; and tumor necrosis factor-.beta. (TNF-.beta.).

Dermorphin peptides including, but not limited to, dermorphin and dermorphin analog 1-4.

Dynorphin peptides including, but not limited to, big dynorphin (prodynorphin 209-240), porcine; biotinyl-dynorphin A (biotinyl-prodynorphin 209-225); {DAla², DArg⁶} dynorphin A 1-13, porcine; {D-Ala²}-dynorphin A, porcine; {D-Ala²}-dynorphin A amide, porcine; {D-Ala²}-dynorphin A 1-13, amide, porcine; {D-Ala²}-dynorphin A 1-9, porcine; {DArg⁶}-dynorphin A 1-13, porcine; {DArg⁸}-dynorphin A 1-13, porcine; {Des-Tyr¹}-dynorphin A 1-8; {D-Pro¹⁰}-dynorphin A 1-11, porcine; dynorphin A amide, porcine; dynorphin A 1-6, porcine; dynorphin A 1-7, porcine; dynorphin A 1-8, porcine; dynorphin A 1-9, porcine; dynorphin A 1-10, porcine; dynorphin A 1-10 amide, porcine; dynorphin A 1-11, porcine; dynorphin A 1-12, porcine; dynorphin A 1-13, porcine; dynorphin A 1-13 amide, porcine; DAKLI (dynorphin A-analogue kappa ligand); DAKLI-biotin ({Arg$^{11,13}$}-dynorphin A (1-13)-Gly-NH(CH₂)₅NH-biotin); dynorphin A 2-17, porcine; dynorphin 2-17, amide, porcine; dynorphin A 2-12, porcine; dynorphin A 3-17, amide, porcine; dynorphin A 3-8, porcine; dynorphin A 3-13, porcine; dynorphin A 3-17, porcine; dynorphin A 7-17, porcine; dynorphin A 8-17, porcine; dynorphin A 6-17, porcine; dynorphin A 13-17, porcine; dynorphin A (prodynorphin 209-225), porcine; dynorphin B 1-9; {MeTyr¹, MeArg⁷, D-Leu⁸}-dynorphin 1-8 ethyl amide; {(nMe)Tyr¹} dynorphin A 1-13, amide, porcine; {Phe⁷}-dynorphin A 1-7, porcine; {Phe⁷}-dynorphin A 1-7, amide, porcine; and pro-dynorphin 228-256 (dynorphin B 29) (leumorphin), porcine.

Endorphin peptides including, but not limited to, alpha-neo-endorphin, porcine; beta-neoendorphin; Ac-beta-endorphin, camel, bovine, ovine; Ac-beta-endorphin 1-27, camel, bovine, ovine; Ac-beta-endorphin, human; Ac-beta-endorphin 1-26, human; Ac-beta-endorphin 1-27, human; Ac-gamma-endorphin (Ac-beta-lipotropin 61-77); acetyl-alpha-endorphin; alpha-endorphin (beta-lipotropin 61-76); alpha-neo-endorphin analog; alpha-neo-endorphin 1-7; {Arg⁸}-alpha-neoendorphin 1-8; beta-endorphin (beta-lipotropin 61-91), camel, bovine, ovine; beta-endorphin 1-27, camel, bovine, ovine; beta-endorphin, equine; beta-endorphin (beta-lipotropin 61-91), human; beta-endorphin (1-5)+(16-31), human; beta-endorphin 1-26, human; beta-endorphin 1-27, human; beta-endorphin 6-31, human; beta-endorphin 18-31, human; beta-endorphin, porcine; beta-endorphin, rat; beta-lipotropin 1-10, porcine; beta-lipotropin 60-65; beta-lipotropin 61-64; beta-lipotropin 61-69; beta-lipotropin 88-91; biotinyl-beta-endorphin (biotinyl-bets-lipotropin 61-91); biocytin-beta-endorphin, human; gamma-endorphin (beta-lipotropin 61-77); {DAla$^2$}-alpha-neo-endorphin 1-2, amide; {DAla$^2$}-beta-lipotropin 61-69; {DAla$^2$}-gamma-endorphin; {Des-Tyr$^1$}-beta-endorphin, human; {Des-Tyr$^1$}-gamma-endorphin (beta-lipotropin 62-77); {Leu$^5$}-beta-endorphin, camel, bovine, ovine; {Met$^5$, Lys$^6$}-alpha-neo-endorphin 1-6; {Met$^5$, Lys$^{6,7}$}-alpha-neo-endorphin 1-7; and {Met$^5$, Lys$^6$, Arg$^7$}-alpha-neo-endorphin 1-7.

Endothelin peptides including, but not limited to, endothelin-1 (ET-1); endothelin-1 {Biotin-Lys$^9$}; endothelin-1 (1-15), human; endothelin-1 (1-15), amide, human; Ac-endothelin-1 (16-21), human; Ac-{DTrp$^{16}$}-endothelin-1 (16-21), human; {Ala$^{3,11}$}endothelin-1; {Dpr1, Asp$^{15}$}-endothelin-1; {Ala$^2$)}-endothelin-3, human; {Ala$^{18}$}-endothelin-1, human; {Asn$^{18}$}-endothelin-1, human; {Res-701-1}-endothelin B receptor antagonist; Suc-{Glu$^9$, Ala$^{11,15}$}-endothelin-1 (8-21), IRL-1620; endothelin-C-terminal hexapeptide; {D-Val$^{22}$}-big endothelin-1 (16-38), human; endothelin-2 (ET-2), human, canine; endothelin-3 (ET-3), human, rat, porcine, rabbit; biotinyl-endothelin-3 (biotinyl-ET-3); prepro-endothelin-1 (94-109), porcine; BQ-518; BQ-610; BQ-788; endothelium-dependent relaxation antagonist; FR139317; IRL-1038; JKC-30 1; JKC-302; PD-145065; PD-142893; sarafotoxin S6a (atractaspis *engaddensis*); sarafotoxin S6b (atractaspis *engaddensis*); sarafotoxin S6c (atractaspis *engaddensis*); {Lys$^4$}-sarafotoxin S6c; sarafotoxin S6d; big endothelin-1, human; biotinyl-big endothelin-1, human; big endothelin-1 (1-39), porcine; big endothelin-3 (22-41), amide, human; big endothelin-1 (22-39), rat; big endothelin-1 (1-39), bovine; big endothelin-1 (22-39), bovine; big endothelin-1 (19-38), human; big endothelin-1 (22-38), human; big endothelin-2, human; big endothelin-2 (22-37), human; big endothelin-3, human; big endothelin-1, porcine; big endothelin-1 (22-39) (prepro-endothelin-1 (74-91)); big endothelin-1, rat; big endothelin-2 (1-38), human; big endothelin-2 (22-38), human; big endothelin-3, rat; biotinyl-big endothelin-1, human; and {Tyr$^{123}$}-prepro-endothelin (110-130), amide, human.

ETa receptor antagonist peptides including, but not limited to, {BQ-123}; {BE18257B}; {BE-18257A}/{W-7338A}; {BQ-485}; FR139317; PD-151242; and TTA-386.

ETh receptor antagonist peptides including, but not limited to, {BQ-3020}; {RES-701-3}; and {IRL-1720}

Enkephalin peptides including, but not limited to, adrenorphin, free acid; amidorphin (proenkephalin A (104-129)-NII2), bovine; BAM-12P (bovine adrenal medulla enkephalin; {D-Ala$^2$, D-Leu$^5$}-enkephalin; {D-Ala$^2$, D-Met$^5$}-enkephalin; {DAla$^2$}-Leu-enkephalin, amide; {DAla$^2$, Leu$^5$, Arg$^6$}-enkephalin; {Des-Tyr$^1$,DPen$^{2,5}$}-enkephalin; {Des-Tyr$^1$,DPen$^2$,Pen$^5$}-enkephalin; {Des-Tyr$^1$}-Leu-enkephalin; {D-Pen$^{2,5}$}-enkephalin; {DPen$^2$, Pen$^5$}-enkephalin; enkephalinase substrate; {D-Pen$^2$, pCI-Phe$^4$, D-Pen$^5$}-enkephalin; Leu-enkephalin; Leu-enkephalin, amide; biotinyl-Leu-enkephalin; {D-Ala$^2$}-Leu-enkephalin; {D-Ser$^2$}-Leu-enkephalin-Thr (delta-receptor peptide) (DSLET); {D-Thr$^2$}-Leu-enkephalin-Thr (DTLET); {Lys$^6$}-Leu-enkephalin; {Met$^5$,Arg$^6$}-enkephalin; {Met$^5$,Arg$^6$}-enkephalin-Arg; {Met$^5$,Arg$^6$,Phe$^7$}-enkephalin, amide; Met-enkephalin; biotinyl-Met-enkephalin; {D-Ala$^2$}-Met-enkephalin; {D-Ala$^2$}-Met-enkephalin, amide; Met-enkephalin-Arg-Phe; Met-enkephalin, amide; {Ala$^2$}-Met-enkephalin, amide; {DMet$^2$,Pro$^5$}-enkephalin, amide; {DTrp$^2$}-Met-enkephalin, amide, metorphinamide (adrenorphin); peptide B, bovine; 3200-Dalton adrenal peptide E, bovine; peptide F, bovine; preproenkephalin B 186-204, human; spinorphin, bovine; and thiorphan (D,L,3-mercapto-2-benzylpropanoyl-glycine).

Fibronectin peptides including, but not limited to platelet factor-4 (58-70), human; echistatin (*Echis carinatus*); E, P, L selectin conserved region; fibronectin analog; fibronectin-binding protein; fibrinopeptide A, human; {Tyr$^0$}-fibrinopeptide A, human; fibrinopeptide B, human; {Glu$^1$}-fibrinopeptide B, human; {Tyr$^{15}$}-fibrinopeptide B, human; fibrinogen beta-chain fragment of 24-42; fibrinogen binding inhibitor peptide; fibronectin related peptide (collagen binding fragment); fibrinolysis inhibiting factor; FN—C/H-1 (fibronectin heparin-binding fragment); FN—C/H—V (fibronectin heparin-binding fragment); heparin-binding peptide; laminin penta peptide, amide; Leu-Asp-Val-NH$_2$ (LDV-NH$_2$), human, bovine, rat, chicken; necrofibrin, human; necrofibrin, rat; and platelet membrane glycoprotein IIB peptide 296-306.

Galanin peptides including, but not limited to, galanin, human; galanin 1-19, human; preprogalanin 1-30, human; preprogalanin 65-88, human; preprogalanin 89-123, human; galanin, porcine; galanin 1-16, porcine, rat; galanin, rat; biotinyl-galanin, rat; preprogalanin 28-67, rat; galanin 1-13-bradykinin 2-9, amide; M40, galanin 1-13-Pro-Pro-(Ala-Leu) 2-Ala-amide; C7, galanin 1-13-spantide-amide; GMAP 1-41, amide; GMAP 16-41, amide; GMAP 25-41, amide; galantide; and entero-kassinin.

Gastrin peptides including, but not limited to, gastrin, chicken; gastric inhibitory peptide (GIP), human; gastrin I, human; biotinyl-gastrin I, human; big gastrin-1, human; gastrin releasing peptide, human; gastrin releasing peptide 1-16, human; gastric inhibitory polypeptide (GIP), porcine; gastrin releasing peptide, porcine; biotinyl-gastrin releasing peptide, porcine; gastrin releasing peptide 14-27, porcine, human; little gastrin, rat; pentagastrin; gastric inhibitory peptide 1-30, porcine; gastric inhibitory peptide 1-30, amide, porcine; {Tyr$^0$-gastric inhibitory peptide 23-42, human; and gastric inhibitory peptide, rat.

Glucagon peptides including, but not limited to, {Des-His$^9$}-glucagon, exendin-4, glucagon, human; biotinyl-glucagon, human; glucagon 19-29, human; glucagon 22-29, human; }Des-His$^1$-Glu$^9$}-glucagon, amide; glucagon-like peptide 1, amide; glucagon-like peptide 1, human; glucagon-like peptide 1 (7-36); glucagon-like peptide 2, rat; biotinyl-glucagon-like peptide-1 (7-36) (biofinyl-preproglucagon 78-107, amide); glucagon-like peptide 2, human; intervening peptide-2; oxyntomodulin/glucagon 37; and valosin (peptide VQY), porcine.

Gn-RH associated peptides (GAP) including, but not limited to, Gn-RH associated peptide 25-53, human; Gn-RH associated peptide 1-24, human; Gn-RH associated peptide 1-13, human; Gn-RH associated peptide 1-13, rat; gonadotropin releasing peptide, follicular, human; {Tyr$^0$}-GAP ({Tyr$^0$}-Gn-RH Precursor Peptide 14-69), human; and proopiomelanocortin (POMC) precursor 27-52, porcine.

Growth factor peptides including, but not limited to, cell growth factors; epidermal growth factors; tumor growth factor; alpha-TGF; beta-TF; alpha-TGF 34-43, rat; EGF, human; acidic fibroblast growth factor; basic fibroblast growth factor; basic fibroblast growth factor 13-18; basic fibroblast growth factor 120-125; brain derived acidic fibroblast growth factor 1-11; brain derived basic fibroblast growth factor 1-24; brain derived acidic fibroblast growth factor 102-111; {Cys(Acm$^{20,31}$)}-epidermal growth factor 20-31; epidermal growth factor receptor peptide 985-996; insulin-like growth factor (IGF)-I, chicken; IGF-I, rat; IGF-I, human; Des (1-3) IGF-I, human; R3 IGF-I, human; R3 IGF-I, human; long R3 IGF-I, human; adjuvant peptide analog; anorexigenic peptide; Des (1-6) IGF-II, human; R6 IGF-II, human; IGF-I analogue; IGF 1 (24-41); IGF 1 (57-70); IGF 1(30-41); IGF II; IGF II (33-40); {Tyr$^0$}-IGF II (33-40); liver cell growth factor; midkine; midkine 60-121, human; N-acetyl, alpha-TGF 34-43, methyl ester, rat; nerve growth factor (NGF), mouse; platelet-derived growth factor; platelet-derived growth factor antagonist; transforming growth factor-alpha, human; and transforming growth factor-I, rat.

Growth hormone peptides including, but not limited to, growth hormone (hGH), human; growth hormone 1-43, human; growth hormone 6-13, human; growth hormone releasing factor, human; growth hormone releasing factor, bovine; growth hormone releasing factor, porcine; growth hormone releasing factor 1-29, amide, rat; growth hormone pro-releasing factor, human; biotinyl-growth hormone releasing factor, human; growth hormone releasing factor 1-29, amide, human; {D-Ala$^2$}-growth hormone releasing factor 1-29, amide, human; {N-Ac-Tyr$^1$, D-Arg$^2$}-GRF 1-29, amide; {His$^1$, Nle$^{27}$}-growth hormone releasing factor 1-32, amide; growth hormone releasing factor 1-37, human; growth hormone releasing factor 140, human; growth hormone releasing factor 1-40, amide, human; growth hormone releasing factor 30-44, amide, human; growth hormone releasing factor, mouse; growth hormone releasing factor, ovine; growth hormone releasing factor, rat; biotinyl-growth hormone releasing factor, rat; GHRP-6 ({His$^1$, Lys$^6$}-GHRP); hexarelin (growth hormone releasing hexapeptide); and {D-Lys$^3$}-GHRP-6.

GTP-binding protein fragment peptides including, but not limited to, {Arg}-GTP-binding protein fragment, Gs alpha; GTP-binding protein fragment, G beta; GTP-binding protein fragment, GAlpha; GTP-binding protein fragment, Go Alpha; GTP-binding protein fragment, Gs Alpha; and GTP-binding protein fragment, G Alpha i2.

Guanylin peptides including, but not limited to, guanylin, human; guanylin, rat; and uroguanylin.

Inhibin peptides including, but not limited to, inhibin, bovine; inhibin, alpha-subunit 1-32, human; {Tyr$^0$}-inhibin, alpha-subunit 1-32, human; seminal plasma inhibin-like peptide, human; {Tyr$^0$}-seminal plasma inhibin-like peptide, human; inhibin, alpha-subunit 1-32, porcine; and {Tyr$^0$}-inhibin, alpha-subunit 1-32, porcine.

Insulin peptides including, but not limited to, insulin, human; insulin, porcine; IGF-I, human; insulin-like growth factor II (69-84); pro-insulin-like growth factor 11 (68-102), human; pro-insulin-like growth factor 11(105-128), human; {Asp$^{B28}$}-insulin, human; {Lys$^{B28}$}-insulin, human; {Leu$^{B28}$}-insulin, human; {Val$^{B28}$}-insulin, human; {Ala$^{B28}$}-insulin, human; {Asp$^{B28}$, Pro$^{B29}$}-insulin, human; {Lys$^{B28}$, Pro$^{B29}$}-insulin, human; {Leu$^{B28}$Pro$^{B29}$}-insulin, human; {Val$^{B28}$, Pro$^{B29}$}-insulin, human; {Ala$^{B28}$, Pro$^{B29}$}-insulin, human; {Gly$^{A21}$}-insulin, human; {Gly$^{A21}$ Gln$^{B30}$}-insulin, human; {Ala$^{A21}$}-insulin, human; {Ala$^{A21}$ Gln$^{B30}$} insulin, human; {Gln$^{B30}$}-insulin, human; {Gln$^{B30}$}-insulin, human; {Gly$^{A21}$ Glu$^{B30}$}-insulin, human; {Gly$^{A21}$ Gln$^{B3}$ Glu$^{B30}$}-insulin, human; {Gln$^{B3}$ Glu$^{B30}$}-insulin, human; B22-B30 insulin, human; B23-B30 insulin, human; B25-B30 insulin, human; B26-B30 insulin, human; B27-B30 insulin, human; B29-B30 insulin, human; the A chain of human insulin, and the B chain of human insulin.

Interleukin peptides including, but not limited to, interleukin-1 beta 165-181, rat; and interleukin-8 (IL-8, CINC/gro), rat.

Lamimin peptides including, but not limited to, laminin; alpha1 (I)-CB3 435-438, rat; and laminin binding inhibitor.

Leptin peptides including, but not limited to, leptin 93-105, human; leptin 22-56, rat; Tyr-leptin 26-39, human; and leptin 116-130, amide, mouse.

Leucokinin peptides including, but not limited to, leucomyosuppressin (LMS); leucopyrokinin (LPK); leucokinin I; leucokinin II; leucokinin III; leucokinin IV; leucokinin VI; leucokinin VII; and leucokinin VIII.

Luteinizing hormone-releasing hormone peptides including, but not limited to, antide; Gn-RH II, chicken; luteinizing hormone-releasing hormone (LH-RH) (GnRH); biotinyl-LH-RH; cetrorelix (D-20761); {D-Ala$^6$}-LH-RH; {Gln$^8$}-LH-RH (Chicken LH-RH); {DLeu$^6$, Val$^7$} LH-RH 1-9, ethyl amide; {D-Lys$^6$}-LH-RH; {D-Phe$^2$, Pro$^3$, D-Phe$^6$}-LH-RH; {DPhe$^2$, DAla$^6$} LH-RH; {Des-Gly$^{10}$}-LH-RH, ethyl amide; {D-Ala$^6$, Des-Gly$^{10}$}-LH-RH, ethyl amide; {DTrp$^6$}-LH-RH, ethyl amide; {D-Trp$^6$, Des-Gly$^{10}$}-LH-RH, ethyl amide (Deslorelin); {DSer(But)$_6$, Des-Gly$^{10}$}-LH-RH, ethyl amide; ethyl amide; leuprolide; LH-RH 4-10; LH-RH 7-10; LH-RH, free acid; LH-RH, lanprey; LH-RH, salmon; {Lys$^8$}-LH-RH; {Trp$^7$,Leu$^8$} LH-RH, free acid; and {(t-Bu)DSer$^6$, (Aza)Glyo$^{10}$}-LH-RH.

Mastoparan peptides including, but not limited to, mastoparan; mas7; mas8; mas17; and mastoparan X.

Mast cell degranulating peptides including, but not limited to, mast cell degranulating peptide HR-1; and mast cell degranulating peptide HR-2.

Melanocyte stimulating hormone (MSH) peptides including, but not limited to, {Ac-Cys$^4$,DPhe$^7$, Cys$^{10}$} alpha-MSH 4-13, amide; alpha-melanocyte stimulating hormone; alpha-MSH, free acid; beta-MSH, porcine; biotinyl-alpha-melanocyte stimulating hormone; biotinyl-{Nle$^4$, D-Phe$^7$} alpha-melanocyte stimulating hormone; {Des-Acetyl}-alpha-MSH; {DPhe$^7$}-alpha-MSH, amide; gamma-1-MSH, amide; {Lys}-gamma-1-MSH, amide; MSH release inhibiting factor, amide; {Nle$^4$}-alpha-MSH, amide; {Nle$^4$, D-Phe$^7$}-alpha-MSH; N-Acetyl, {Nle$^4$,DPhe$^7$} alpha-MSH 4-10, amide; beta-MSH, human; and gamma-MSH.

Morphiceptin peptides including, but not limited to, morphiceptin (beta-casomorphin 14 amide); {D-Pro$^4$}-morphiceptin; and {N-MePhe$^3$,D-Pro$^4$}-morphiceptin.

Motilin peptides including, but not limited to, motilin, canine; motilin, porcine; biotinyl-motilin, porcine; and {Leu$^{13}$}-motilin, porcine.

Neuro-peptides including, but not limited to, Ac-Asp-Glu; achatina cardio-excitatory peptide-1 (ACEP-1) (*Achatina fulica*); adipokinetic hormone (AKH) (Locust); adipokinetic hormone (*Heliothis zea* and *Manduca sexta*); alytesin; *Tabanus atratus* adipokinetic hormone (Taa-AKH); adipokinetic hormone II (*Locusta migratoria*); adipokinetic hormone II (*Schistocera gregaria*); adipokinetic hormone III (AKH-3); adipokinetic hormone G (AKH-G) (*Gryllus bimaculatus*); allatotropin (AT) (*Manduca sexta*); allatotropin 6-13 (*Manduca sexta*); APGW amide (*Lymnaea stagnalis*); buccalin; cerebellin; {Des-Ser$^1$}-cerebellin; corazonin (American Cockroach *Periplaneta americana*); crustacean cardioactive peptide (CCAP); crustacean erythrophore; DF2 (*Procambarus clarkii*); diazepam-binding inhibitor fragment, human; diazepam binding inhibitor fragment (ODN); eledoisin related peptide; FMRF amide (molluscan cardioexcitatory neuropeptide); Gly-Pro-Glu (GPE), human; granuliberin R; head activator neuropeptide; {His$^7$}-corazonin; stick insect hypertrehalosaemic factor II;

Tabanus atratus hypotrehalosemic hormone (Taa-HoTH); isoguvacine hydrochloride; bicuculline methiodide; piperidine-4-sulphonic acid; joining peptide of proopiomelanocortin (POMC), bovine; joining peptide, rat; KSAYMRF amide (P. redivivus); kassinin; kinetensin; levitide; litorin; LUQ 81-91 (*Aplysia californica*); LUQ 83-91 (*Aplysia californica*); myoactive peptide I (Periplanetin CC-1) (Neuro-homone D); myoactive peptide II (Periplanetin CC-2); myomodulin; neuron specific peptide; neuron specific enolase 404-443, rat; neuropeptide FF; neuropeptide K, porcine; NEI (prepro-MCH 131-143) neuropeptide, rat; NGE (prepro-MCH 110-128) neuropeptide, rat; NFI (Procambarus clarkii); PBAN-1 (*Bombyx mori*); Hez-PBAN (*Heliothis zea*); SCPB (cardioactive peptide from aplysia); secretoneurin, rat; uperolein; urechistachykinin I; urechistachykinin II; xenopsin-related peptide I; xenopsin-related peptide II; pedal peptide (Pep), aplysia; peptide F1, lobster, phyllomedusin; polistes mastoparan; proctolin; ranatensin; Ro I (Lubber Grasshopper, Romalea microptera); Ro II (Lubber Grasshopper, *Romalea microptera*); SALMF amide 1 (S1); SALMF amide 2 (S2); and SCPA.

Neuropeptide Y (NPY) peptides including, but not limited to, $\{Leu^{31}, Pro^{34}\}$ neuropeptide Y, human; neuropeptide F (*Moniezia expansa*); B1BP3226 NPY antagonist; Bis (31/31') $\{\{Cys^{31}, Trp^{32}, Nva^{34}\}$ NPY 31-36$\}$; neuropeptide Y, human, rat; neuropeptide Y 1-24 amide, human; biotinyl-neuropeptide Y; $\{D-Tyr^{27,36}, D-Thr^{32}\}$-NPY 27-36; Des 10-17 (cyclo 7-21) $\{Cys^{7,21}, Pro^{34}\}$-NPY; C2-NPY; $\{Leu^{31}, Pro^{34}\}$ neuropeptide Y, human neuropeptide Y, free acid, human; neuropeptide Y, free acid, porcine; prepro NPY 68-97, human; N-acetyl-$\{Leu^{28}, Leu^{31}\}$ NPY 24-36; neuropeptide Y, porcine; $\{D-Trp^{32}\}$-neuropeptide Y, porcine; $\{D-Trp^{32}\}$ NPY 1-36, human; $\{Leu^{17}, DTrp^{32}\}$ neuropeptide Y, human; $\{Leu^{31}, Pro^{34}\}$-NPY, porcine; NPY 2-36, porcine; NPY 3-36, human; NPY 3-36, porcine; NPY 13-36, human; NPY 13-36, porcine; NPY 16-36, porcine; NPY 18-36, porcine; NPY 20-36; NFY 22-36; NPY 26-36; $\{Pro^{34}\}$-NPY 1-36, human; $\{Pro^{34}\}$-neuropeptide Y, porcine; PYX-1; PYX-2; T4-$\{NPY(33-36)\}$4; and Tyr(OMe)$^{21}$-neuropeptide Y, human.

Neurotropic factor peptides including, but not limited to, glial derived neurotropic factor (GDNF); brain derived neurotropic factor (BDNF); and ciliary neurotropic factor (CNTF).

Orexin peptides including, but not limited to, orexin A; orexin B, human; orexin B, rat, mouse.

Opioid peptides including, but not limited to, alpha-casein fragment 90-95; BAM-18P; casomokinin L; casoxin D; crystalline; DALDA; dermenkephalin (deltorphin) (*Phylomedusa sauvagei*); $\{D-Ala^2\}$-deltorphin I; $\{D-Ala2\}$-deltorphin II; endomorphin-1; endomorphin-2; kyotorphin; $\{DArg^2\}$-kyotorphin; morphine tolerance peptide; morphine modulating peptide, C-terminal fragment; morphine modulating neuropeptide (A-18-F—NH$_2$); nociceptin $\{$orphanin FQ$\}$ (ORL1 agonist); TIPP; Tyr-MIF-1; Tyr-W-MIF-1; valorphin; LW-hemorphin-6, human; Leu-valorphin-Arg; and Z-Pro-D-Leu.

Oxytocin peptides including, but not limited to, $\{Asu^6\}$-oxytocin; oxytocin; biotinyl-oxytocin; $\{Thr^4, Gly^7\}$-oxytocin; and tocinoic acid ($\{Ile^3\}$-pressinoic acid).

PACAP (pituitary adenylating cyclase activating peptide) peptides including, but not limited to, PACAP 1-27, human, ovine, rat; PACAP (1-27)-Gly-Lys-Arg-NH$_2$, human; $\{$Des-Gln$^{16}\}$-PACAP 6-27, human, ovine, rat; PACAP38, frog; PACAP27-NH$_2$, human, ovine, rat; biotinyl-PACAP27-NH$_2$, human, ovine, rat; PACAP 6-27, human, ovine, rat; PACAP38, human, ovine, rat; biotinyl-PACAP38, human, ovine, rat; PACAP 6-38, human, ovine, rat; PACAP27-NH$_2$, human, ovine, rat; biotinyl-PACAP27-NH$_2$, human, ovine, rat; PACAP 6-27, human, ovine, rat; PACAP38, human, ovine, rat; biotinyl-PACAP38, human, ovine, rat; PACAP 6-38, human, ovine, rat; PACAP38 16-38, human, ovine, rat; PACAP38 31-38, human, ovine, rat; PACAP38 31-38, human, ovine, rat; PACAP-related peptide (PRP), human; and PACAP-related peptide (PRP), rat.

Pancreastatin peptides including, but not limited to, chromostatin, bovine; pancreastatin (hPST-52) (chromogranin A 250-301, amide); pancreastatin 24-52 (hPST-29), human; chromogranin A 286-301, amide, human; pancreastatin, porcine; biotinyl-pancreastatin, porcine; $\{Nle^8\}$-pancreastatin, porcine; $\{Tyr^0, Nle^8\}$-pancreastatin, porcine; $\{Tyr^0\}$-pancreastatin, porcine; parastatin 1-19 (chromogranin A 347-365), porcine; pancreastatin (chromogranin A 264-314-amide, rat; biotinyl-pancreastatin (biotinyl-chromogranin A 264-314-amide; $\{Tyr^0\}$-pancreastatin, rat; pancreastatin 26-51, rat; and pancreastatin 33-49, porcine.

Pancreatic polypeptides including, but not limited to, pancreatic polypeptide, avian; pancreatic polypeptide, human; C-fragment pancreatic polypeptide acid, human; C-fragment pancreatic polypeptide amide, human; pancreatic polypeptide (*Rana temporaria*); pancreatic polypeptide, rat; and pancreatic polypeptide, salmon.

Parathyroid hormone peptides including, but not limited to, $\{Asp^{76}$-parathyroid hormone 39-84, human; $\{Asp^{76}\}$-parathyroid hormone 53-84, human; $\{Asn^{76}\}$-parathyroid hormone 1-84, hormone; $\{Asn^{76}\}$-parathyroid hormone 64-84, human; $\{Asn^8, Leu^{18}\}$-parathyroid hormone 1-34, human; $\{Cys^{5,28}\}$-parathyroid hormone 1-34, human; hypercalcemia malignancy factor 1-40; $\{Leu^{18}\}$-parathyroid hormone 1-34, human; (Lys(biotinyl) 13, Nle$^{8,18}$, Tyr$^{34}$}-parathyroid hormone 1-34 amide; $\{Nle^{8,18}, Tyr^{34}\}$-parathyroid hormone 1-34 amide; $\{Nle^{8,18}, Tyr^{34}\}$-parathyroid hormone 3-34 amide, bovine; $\{Nle^{8,18}, Tyr^{34}\}$-parathyroid hormone 1-34, human; $\{Nle^{8,18}, Tyr^{34}\}$-parathyroid hormone 1-34 amide human; $\{Nle^{8,18}, Tyr^{34}\}$-parathyroid hormone 3-34 amide, human; $\{Nle^{8,18}, Tyr^{34}\}$-parathyroid hormone 7-34 amide, bovine; $\{Nle^{8,21}, Tyr^{34}\}$-parathyroid hormone 1-34 amide, rat; parathyroid hormone 44-68, human; parathyroid hormone 1-34, bovine; parathyroid hormone 3-34, bovine; parathyroid hormone 1-31 amide, human; parathyroid hormone 1-34, human; parathyroid hormone 13-34, human; parathyroid hormone 1-34, rat; parathyroid hormone 1-38, human; parathyroid hormone 1-44, human; parathyroid hormone 28-48, human; parathyroid hormone 39-68, human; parathyroid hormone 39-84, human; parathyroid hormone 53-84, human; parathyroid hormone 69-84, human; parathyroid hormone 70-84, human; $\{Pro^{34}\}$-peptide YY (PYY), human; $\{Tyr^0\}$-hypercalcemia malignancy factor 1-40; $\{Tyr^0\}$-parathyroid hormone 1-44, human; $\{Tyr^0\}$-parathyroid hormone 1-34, human; $\{Tyr^1\}$-parathyroid hormone 1-34, human; $\{Tyr^{27}\}$-parathyroid hormone 27-48, human; $\{Tyr^{34}\}$-parathyroid hormone 7-34 amide, bovine; $\{Tyr^{43}\}$-parathyroid hormone 43-68, human; $\{Tyr^{52}, Asn^{76}\}$-parathyroid hormone 52-84, human; and $\{Tyr^{63}\}$-parathyroid hormone 63-84, human.

Parathyroid hormone (PTH)-related peptides including, but not limited to, PTHrP ($\{Tyr^{36}\}$-PTHrP 1-36 amide), chicken; hHCF-(1-34)-NH$_2$ (humoral hypercalcemic factor), human; PTH-related protein 1-34, human; biotinyl-PTH-related protein 1-34, human; $\{Tyr^0\}$-PTH-related protein 1-34, human; $\{Tyr^{34}\}$-PTH-related protein 1-34 amide, human; PTH-related protein 1-37, human; PTH-related protein 7-34 amide, human; PTH-related protein 38-64 amide, human; PTH-related protein 67-86 amide, human; PTH-related protein 107-111, human, rat, mouse; PTH-related protein 107-111 free acid; PTH-related protein 107-138, human; and PTH-related protein 109-111, human.

Peptide T peptides including, but not limited to, peptide T; {D-Ala$^1$}-peptide T; and {D-Ala$^1$}-peptide T amide.

Prolactin-releasing peptides including, but not limited to, prolactin-releasing peptide 31, human; prolactin-releasing peptide 20, human; prolactin-releasing peptide 31, rat; prolactin-releasing peptide 20, rat; prolactin-releasing peptide 31, bovine; and prolactin-releasing peptide 20, bovine.

Peptide YY (PYY) peptides including, but not limited to, PYY, human; PYY 3-36, human; biotinyl-PYY, human; PYY, porcine, rat; and {Leu$^{31}$, Pro$^{34}$}-PYY, human.

Renin substrate peptides including, but not limited to, acetyl, angiotensinogen 1-14, human; angiotensinogen 1-14, porcine; renin substrate tetradecapeptide, rat; {Cys$^8$}-renin substrate tetradecapeptide, rat; {Leu$^8$}-renin substrate tetradecapeptide, rat; and {Val$^8$}-renin substrate tetradecapeptide, rat.

Secretin peptides including, but not limited to, secretin, canine; secretin, chicken; secretin, human; biotinyl-secretin, human; secretin, porcine; and secretin, rat.

Somatostatin (GIF) peptides including, but not limited to, BIM-23027; biotinyl-somatostatin; biotinylated cortistatin 17, human; cortistatin 14, rat; cortistatin 17, human; {Tyr$^0$}-cortistatin 17, human; cortistatin 29, rat; {D-Trp$^8$}-somatostatin; {DTrp$^8$,DCys$^{14}$}-somatostatin; {DTrp$^8$,Tyr$^{11}$}-somatostatin; {D-Trp$^{11}$}-somatostatin; NTB (Naltriben); {Nle$^8$}-somatostatin 1-28; octreotide (SMS 201-995); prosomatostatin 1-32, porcine; {Tyr$^0$}-somatostatin: {Tyr$^0$}-somatostatin; {Tyr$^1$}-somatostatin 28 (1-14); {Tyr$^{11}$}-somatostatin; {Tyr$^0$}, D-Trp$^8$}-somatostatin; somatostatin; somatostatin antagonist; somatostatin-25; somatostatin-28; somatostatin 28 (1-12); biotinyl-somatostatin-28; {Tyr$^0$}-somatostatin-28; {Leu$^8$, D-Trp$^{22}$, Tyr$^{25}$}-somatostatin-28; biotinyl-{Leu$^8$, D-Trp$^{22}$, Tyr$^{25}$}-somatostatin-28; somatostatin-28 (1-14); and somatostatin analog, RC-160.

Substance P peptides including, but not limited to, G protein antagonist-2; Ac-{Arg$^6$, Sar$^9$, Met(02)$^{11}$}-substance P 6-11; {Arg$^3$}-substance P; Ac-Trp-3,5-bis(trifluoromethyl)benzyl ester; Ac-{Arg$^6$, Sar$^9$, Met(O2)$^{11}$}-substance P 6-11; {D-Ala$^4$}-substance P 4-11; {Tyr$^6$, D-Phe$^7$, D-His$^9$}-substance P 6-11 (sendide); biotinyl-substance P; biotinyl-NTE{Arg$^3$}-substance P; {Tyr$^8$}-substance P; {Sar$^9$, Met (02)$^1$}-substance P; {D-Pro$^2$, DTrp$^{7,9}$-substance P; {D-Pro$^4$, O-Trp$^{7,9}$}-substance P 4-11; substance P 4-11; {DTrp$^{2,7,9}$}-substance P; {(Dehydro)Pro$^{2,4}$, Pro$^9$}-substance P; {Dehydro-Pro$^4$}-substance P 4-11; {Glp$^5$,(Me)Phe$^8$,Sar$^9$}-substance P 5-11; Glp$^5$,Sar$^9$}-substance P 5-11; {Glp$^5$}-substance P 5-11; hepta-substance P (substance P 5-11); hexa-substance P(substance P 6-11); {MePhe$^8$,Sar$^9$}-substance P; {Nle$^1$}-substance P; Octa-substance P(substance P 4-11); {pGlu$^1$}-hexa-substance P ({pGlu$^6$}-substance P 6-11); {pGlu$^6$, D-Pro$^9$}-substance P 6-11; {(pNO$_2$)Phe$^7$ Nle$^{11}$}-substance P; penta-substance P (substance P 7-11); {Pro$^9$}-substance P; GR73632, substance P 7-11; {Sar$^4$}-substance P 4-11; {Sar$^9$}-substance P; septide ({pGlu$^6$, Pro$^9$}-substance P 6-11); spantide I; spantide II; substance P; substance P, cod; substance P, trout; substance P antagonist; substance P-Gly-Lys-Arg; substance P 1-4; substance P 1-6; substance P 1-7; substance P 1-9; deca-substance P (substance P 2-11); nona-substance P (substance P 3-11); substance P tetrapeptide (substance P 8-11); substance P tripeptide (substance P 9-11); substance P, free acid; substance P methyl ester, and {Tyr$^8$,Nle$^{11}$}substance P.

Tachykinin peptides including, but not limited to, {Ala$^5$, beta-Ala$^8$} neurokinin A 4-10; eledoisin; locustatachykinin I (Lom-TK-I) (*Locusta migratoria*); locustatachykinin II (Lom-TK-II) (*Locusta migratoria*); neurokinin A 4-10; neurokinin A (neuromedin L, substance K); neurokinin A, cod and trout; biotinyl-neurokinin A (biotinryl-neuromedin L, biotinyl-substance K); {Tyr$^0$}-neurokinin A; {Tyr$^6$}-substance K; FR64349; {Lys$^3$, Gly$^8$-(R)-gamma-lactam-Leu$^9$}-neurokinin A 3-10; GR83074; GR87389; GR94800; {Beta-Ala$^8$}-neurokinin A 4-10; {Nle$^{10}$}-neurokinin A 4-10; {Trp$^7$, beta-Ala$^8$}-neurokinin A 4-10; neurokinin B (neuromedin K); biotinyl-neurokinin B (biotinyl-neuromedin K); {MePhe$^7$}-neurokinin B; {Pro$^7$}-neurokinin B; {Tyr$^0$}-neurokinin B; neuromedin B, porcine; biotinyl-neuromedin B, porcine; neuromedin B-30, porcine; neuromedin B-32, porcine; neuromedin B receptor antagonist; neuromedin C, porcine; neuromedin N, porcine; neuromedin (U-8), porcine; neuromedin (U-25), porcine; neuromedin U, rat; neuropeptide-gamma (gamma-preprotachykinin 72-92); PG-KII; phyllolitorin; {Leu$^8$}-phyllolitorin (Phyllomedusa sauvagei); physalaemin; physalaemin 1-11; scyliorhinin II, amide, dogfish; senktide, selective neurokinin B receptor peptide; {Ser$^2$}-neuromedin C; beta-preprotachykinin 69-91, human; beta-preprotachykinin 111-129, human; tachyplesin I; xenopsin; and xenopsin 25 (xenin 25), human.

Thyrotropin-releasing hormone (TRH) peptides including, but not limited to, biotinyl-thyrotropin-releasing hormone; {Glu$^1$}-TRH; His-Pro-diketopiperazine; {3-Me-His$^2$}-TRH; pGlu-Gln-Pro-amide; pGlu-His; {Phe$^2$}-TRH; prepro TRH 53-74; prepro TRH 83-106; prepro-TRH 160-169 (Ps4, TRH-potentiating peptide); prepro-TRH 178-199, thyrotropin-releasing hormone (TRH); TRH, free acid; TRH-SH Pro; and TRH precursor peptide.

Toxin peptides including, but not limited to, omega-agatoxin TK; agelenin, (spider, *Agelena opulenta*); apamin (honeybee, *Apis mellifera*); calcicudine (CaC) (green mamba, *Dedroaspis angusticeps*); calciseptine (black mamba, *Dendroaspis polylepis polylepis*); charybdotoxin (ChTX) (scorpion, *Leiurus quinquestriatus* var. *hebraeus*); chlorotoxin; conotoxin GI (marine snail, *Conus geographus*); conotoxin GS (marine snail, *Conus geographus*); conotoxin MI (Marine *Conus magus*); alpha-conotoxin EI, *Conus ermineus*; alpha-conotoxin SIA; alpha-conotoxin ImI; alpha-conotoxin SI (cone snail, *Conus striatus*); microconotoxin GIIIB (marine snail, *Conus geographus*); omega-conotoxin GVIA (marine snail, *Conus geographus*); omega-conotoxin MVIIA (*Conus magus*); omega-conotoxin MVIIC (*Conus magus*); omega-conotoxin SVIB, (cone snail, *Conus striatus*); endotoxin inhibitor; geographutoxin I (GTX-I) (.mu.-Conotoxin GIIIA); iberiotoxin (IbTX) (scorpion, *Buthus tamulus*); kaliotoxin 1-37; kaliotoxin (scorpion, *Androctonus mauretanicus mauretanicus*); mast cell-degranulating peptide (MCD-peptide, peptide 401); margatoxin (MgTX) (scorpion, Centruriodes Margaritatus); neurotoxin NSTX-3 (Papua New Guinean spider, *Nephilia maculata*); PLTX-II (spider, *Plectreurys tristes*); scyllatoxin (leiurotoxin I); and stichodactyla toxin (ShK).

Vasoactive intestinal peptides (VIP/PHI) including, but not limited to, VIP, human, porcine, rat, ovine; VIP-Gly-Lys-Arg-NH$_2$; biotinyl-PHI (biotinyl-PHI-27), porcine; {Glp$^{16}$}VIP 16-28, porcine; PHI (PHI-27), porcine; PHI (PHI-27), rat; PHM-27 (PHI), human; prepro VIP 81-122, human; preproVIP/PHM 111-122; prepro VIP/PHM 156-170; biotinyl-PHM-27 (biotinyl-PHI), human; vasoactive intestinal contractor (endothelin-beta); vasoactive intestinal octacosa-peptide, chicken; vasoactive intestinal peptide, guinea pig; biotinyl-VIP, human, porcine, rat; vasoactive intestinal peptide 1-12, human, porcine, rat; vasoactive intestinal peptide 10-28, human, porcine, rat; vasoactive intestinal peptide 11-28, human, porcine, rat, ovine; vasoactive intestinal peptide (cod, *Gadus morhua*); vasoactive intestinal peptide 6-28; vasoactive intestinal peptide antagonist; vasoactive intestinal peptide antagonist ({Ac-Tyr$^1$, D-Phe$^2$}-GHRF 1-29 amide); vasoactive intestinal peptide receptor antagonist (4-Cl-D-Phe$^6$, Leu$^{17}$}-VIP); and vasoactive intestinal peptide receptor binding inhibitor, L-8-K. Additional constructs include but are not limited to, Ala{$^{11,22,28}$}VIP, Ala{$^{2,8,9,11,19,22,24,25,27,28}$}VIP, {K$^{15}$, R$^{16}$, L$^{27}$}-VIP(1-7)/GRF(8-27), Ro25-1553, Ro25-1392, BAY55-9837, R3P65, Maxadilan, PG97-269, PG99-465, Max.d.4., and M65 (Dickson & Finlayson, Pharmacology & Therapeutics, Volume 121, Issue 3, March 2009, Pages 294-316).

Vasopressin (ADH) peptides including, but not limited to, vasopressin; {Asu$^{1,6}$,Arg$^8$}-vasopressin; vasotocin; {Asu$^{1,6}$,Arg$^8$}-vasotocin; {Lys$^8$}-vasopressin; pressinoic acid; {Arg$^8$}-desamino vasopressin desglycinamide; {Arg$^8$}-vasopressin (AVP); {Arg$^8$}-vasopressin desglycinamide; biotinyl-{Arg$^8$}-vasopressin (biotinyl-AVP); {D-Arg$^8$}-vasopressin; desamino-{Arg$^8$}-vasopressin; desamino-{D-Arg$^8$}-vasopressin (DDAVP); {deamino-{D-3-(3'-pyridyl-Ala)}-{Arg$^8$}-vasopressin; {1-(beta-Mercapto-beta, beta-cyclopentamethylene propionic acid), 2-(O-methyl)tyrosine}-{Arg$^8$}-vasopressin; vasopressin metabolite neuropeptide {pGlu$^4$, Cys$^6$}; vasopressin metabolite neuropeptide {pGlu$^4$, Cys$^6$}; {Lys$^8$}-deamino vasopressin desglycinamide; {Lys$^8$}-vasopressin; {Mpr$^1$, Val$^4$,DArg$^8$}-vasopressin; {Phe$^2$, Ile$^3$, Orn$^8$}-vasopressin ({Phe$^2$, Orn$^8$}-vasotocin); {Arg$^8$}-vasotocin; and {d(CH$_2$)$_5$, Tyr(Me)$_2$, Orn$^8$}-vasotocin.

Virus related peptides including, but not limited to, viral membrane fusion proteins, fluorogenic human CMV protease substrate; HCV core protein 59-68; HCV NS4A protein 1840 (JT strain); HCV NS4A protein 21-34 (JT strain); hepatitis B virus receptor binding fragment; hepatitis B virus pre-S region 120-145; {Ala$^{127}$}-hepatitis B virus pre-S region 120-131; herpes virus inhibitor 2; HIV envelope protein fragment 254-274; HIV gag fragment 129-135; HIV substrate; P 18 peptide; peptide T; {3,5 diiodo-Tyr$^7$} peptide T; R15K HIV-1 inhibitory peptide; T20; T21; V3 decapeptide P 18-110; and virus replication inhibiting peptide.

The human hormone glucagon is a 29-amino acid peptide hormone produced in the A-cells of the pancreas. The hormone belongs to a multi-gene family of structurally related peptides that include secretin, gastric inhibitory peptide, vasoactive intestinal peptide and glicentin. These peptides variously regulate carbohydrate metabolism, gastrointestinal mobility and secretory processing. The principal recognized actions of pancreatic glucagon, however, are to promote hepatic glycogenolysis and glyconeogenesis, resulting in an elevation of blood sugar levels. In this regard, the actions of glucagon are counter regulatory to those of insulin and may contribute to the hyperglycemia that accompanies Diabetes mellitus {(Lund, P. K., et al., Proc. Natl. Acad. Sci. U.S.A., 79:345-349 (1982)}.

Glucagon has been found to be capable of binding to specific receptors which lie on the surface of insulin producing cells. Glucagon, when bound to these receptors, stimulates the rapid synthesis of cAMP by these cells. cAMP, in turn, has been found to stimulate insulin expression {Korman, L. Y., et al., Diabetes, 34:717-722 (1985)}. Insulin acts to inhibit glucagon synthesis (Ganong, W. F., Review of Medical Physiology, Lange Publications, Los Altos, Calif., p. 273 (1979)). Thus, the expression of glucagon is carefully regulated by insulin, and ultimately by the serum glucose level.

The glucagon gene is initially translated from a 360 base pair precursor to form the polypeptide, preproglucagon {Lund, et al., Proc. Natl. Acad. Sci. U.S.A. 79:345-349 (1982)}. This polypeptide is subsequently processed to form proglucagon. Patzelt, C., et al., Nature, 282:260-266 (1979) demonstrated that proglucagon was subsequently cleaved into glucagon and a second polypeptide. Subsequent work by Lund, P. K., et al. supra, Lopez L. C., et al., Proc. Natl. Acad. Sci. U.S.A., 80:5485-5489 (1983), and Bell, G. I., et al., Nature 302:716-718 (1983), demonstrated that the proglucagon molecule was cleaved immediately after lysine-arginine dipeptide residues. Studies of proglucagon produced by channel catfish (*Ictalurus punctata*) indicated that glucagon from this animal was also proteolytically cleaved after adjacent lysine-arginine dipeptide residues {Andrews P. C., et al., J. Biol. Chem., 260:3910-3914 (1985), Lopez, L. C., et al., Proc. Natl. Acad. Sci. U.S.A., 80:5485-5489 (1983)}. Bell, G. I., et al., supra, discovered that mammalian proglucagon was cleaved at lysine-arginine or arginine-arginine dipeptides, and demonstrated that the proglucagon molecule contained three discrete and highly homologous peptide molecules which were designated glucagon, glucagon-like peptide 1 (GLP-1) and glucagon-like peptide 2 (GLP-2). Lopez, et al., concluded that glucagon-like peptide 1 was 37 amino acid residues long and that glucagon-like peptide 2 was 34 amino acid residues long. Analogous studies on the structure of rat preproglucagon revealed a similar pattern of proteolytic cleavage between adjacent lysine-arginine or arginine-arginine dipeptide residues, resulting in the formation of glucagon, GLP-1 and GLP-2 {Heinrich, G., et al., Endocrinol., 115:2176-2181 (1984)}.

Glucagon-like peptide-2 (GLP-2) is a 33 amino acid peptide expressed in a tissue-specific manner from the pleiotropic glucagon gene. GLP-2 shows remarkable homology in terms of amino acid sequence to glucagon and Glucagon-like peptide-1 (GLP-1). Further, different mammalian forms of GLP-2 are highly conserved. The sequence of human GLP-2, is as follows: His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp. Further, a large number of agonist GLP-2 peptides that are described in PCT Application PCT/CA97/00252, filed Apr. 11, 1997. Analogs are described in U.S. Pat. No. 6,051,557, and examples of GLP-2 variants are found in U.S. Pat. Nos. 5,990,077 and 6,184,201.

Recently it was demonstrated that GLP-2 is an intestinotrophic peptide hormone (Drucker et al., (1996) PNAS, 93:7911-7916). When given exogenously, GLP-2 can produce a marked increase in the proliferation of small intestinal epithelium of the test mice, apparently with no undesirable side effects. Subsequently it was shown that peptide analogs of native GLP-2 with certain modifications to the peptide sequence possess enhanced intestinotrophic activity (U.S. patent application Ser. No. 08/669,791). Moreover, GLP-2 has also been shown to increase D-Glucose maximal transport rate across the intestinal basolateral membrane (Cheeseman and Tseng (1996) American Journal of Physiology 271:G477-G482).

A number of peptide hormones (IGF-2, IGF-1, GH), structurally unrelated to GLP-2, have been demonstrated to have varying degrees of intestinotrophic activity. (U.S. Pat. No. 5,482,926, WO 91/12018, U.S. Pat. No. 5,288,703). However, none of the above peptide hormones possess the efficacy or specificity of GLP-2 in promoting proliferation of the intestine epithelium. GLP-2 acts synergistically with the peptide hormones IGF-1 and/or GH to promote the proliferation of cells in the large intestine. Furthermore, the intestinotrophic effects on the small and large intestines of this combination therapy are greater than that seen with any one of alone. Coadministration of GLP-2 with IGF-2 to promote growth of small and/or large intestine tissue is discussed in U.S. Pat. No. 5,952,301.

Nucleic acid encoding the GLP-2 receptor has been isolated and methods to identify GLP-2 receptor agonists are described (U.S. patent application Ser. No. 08/767,224 and U.S. Ser. No. 08/845,546). GLP-2's role in diseases involving the esophagus and the stomach, in assisting patients at risk of developing a malfunctioning of the upper gastrointestinal tract, and in increasing tissue growth in the upper gastrointestinal tract have been discussed (see U.S. Pat. No. 6,051,557). GLP-2 receptor agonists act to enhance functioning of the large intestine. (U.S. Pat. No. 6,297,214). GLP-2 and peptidic agonists of GLP-2 can cause proliferation of the tissue of large intestine. GLP-2 may also be useful to treat or prevent inflammatory conditions of the large intestine, including inflammatory bowel diseases (U.S. Pat. No. 6,586,399).

A very wide variety of non-naturally encoded amino acids are suitable for use in the present invention. Any number of non-naturally encoded amino acids can be introduced into an analog. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, an analog that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen {3+2} cycloaddition product.

In some embodiments, the composition or pharmaceutical compositions of the claimed invention comprises an analog of a polypeptide, wherein the analog amino acid sequence is based upon the fragments, polypeptides, and functional deriviatives disclosed herein and wherein the analog compruises at least one or a plurality of non-natural amino acids and at least one or a plurality of β-amino acid residues. A non-natural amino acid typically possesses an R group that is any substituent other than one component of the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-natural amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-natural amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of skill in the art. In some embodiments, the invention relates to a method of manufacturing a polypeptide analog wherein the polypeptide analog is manufactured using a synthesis technique disclosed in the following references, which are incorporated herein by reference: For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). See, also, U.S. Patent Application Publications 2003/0082575 and 2003/0108885, which is incorporated by reference herein. In addition to unnatural (or non-natural) amino acids that contain novel side chains, unnatural amino acids that may be suitable for use in the present invention also optionally comprise modified backbone structures, including but not limited to, as illustrated by the structures of Formula II and III of U.S. Patent Application Publication 2010-0048871, wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, 3 amino acids such as substituted β-alanine.

In some embodiments, the composition or pharmaceutical compositions of the claimed invention comprises an analog of a polypeptide, wherein the analog amino acid sequence is based upon the fragments, polypeptides, and functional deriviatives disclosed herein and wherein the analog comprises at least one or a plurality of unnatural amino acid or non-natural amino acid and at least one or a plurality of β-amino acid residues, wherein the unnatural amino acids based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated.

Glutamine analogs that may be suitable for use in the present invention include, but are not limited to, α.-hydroxy derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an 0-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a β-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002). Incorporation of azides into recombinant proteins for chemoselective modification by the Staudinger ligation, PNAS 99:19-24, for additional methionine analogs.

The chemical moieties via unnatural amino acids that can be incorporated into analogs offer a variety of advantages and manipulations of the protein. For example, the unique reactivity of a keto functional group allows selective modification of proteins with any of a number of hydrazine- or hydroxylamine-containing reagents in vitro and in vivo. A heavy atom unnatural amino acid, for example, can be useful for phasing X-ray structure data. The site-specific introduction of heavy atoms using unnatural amino acids also provides selectivity and flexibility in choosing positions for heavy atoms. In some embodiments, the composition or pharmaceutical compositions of the claimed invention comprises an analog of a polypeptide, wherein the analog amino acid sequence is based upon the fragments, polypeptides, and functional deriviatives disclosed herein and wherein the analog comprises at least one or a plurality of unnatural amino acid or non-natural amino acid and at least one or a plurality of β-amino acid residues, wherein the unnatural amino is a photoreactive unnatural amino acid chosen from (including but not limited to, amino acids with benzophenone and arylazides (including but not limited to, phenylazide) side chains), for example, allow for efficient in vivo and in vitro photocrosslinking of protein. Examples of photoreactive unnatural amino acids include, but are not limited to, p-azido-phenylalanine and p-benzoyl-phenylalanine. The protein with the photoreactive unnatural amino acids can then be crosslinked at will by excitation of the photoreactive group-providing temporal control. In one example, the methyl group of an unnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a {3+2} cycloaddition reaction.

A non-natural amino acid incorporated into a polypeptide at the amino terminus can be composed of an R group that is any substituent other than one used in the twenty natural amino acids and a second reactive group different from the $NH_2$ group normally present in α-amino acids. A similar non-natural amino acid can be incorporated at the carboxyl terminus with a second reactive group different from the COOH group normally present in α-amino acids.

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) J. Med. Chem., 38, 4660-4669; King, F. E. & Kidd, D. A. A. (1949) A New Synthesis of Glutamine and of γ-Dipeptides of Glutamic Acid from Phthylated Intermediates. J. Chem. Soc., 3315-3319; Friedman, O. M. & Chattenji, R. (1959) Synthesis of Derivatives of Glutamine as Model Substrates for Anti-Tumor Agents. J. Am. Chem. Soc. 81, 3750-3752; Craig, J. C. et al. (1988) Absolute Configuration of the Enantiomers of 7-Chloro-4 {{4-(diethylamino)-}-methylbutyl}amino}quinoline (Chloroquine). J. Org. Chem. 53, 1167-1170; Azoulay, M., Vilmont, M. & Frappier, F. (1991) Glutamine analogues as Potential Antimalarials, Eur. J. Med. Chem. 26, 201-5; Koskinen, A. M. P. & Rapoport, H. (1989) Synthesis of 4-Substituted Prolines as Conformationally Constrained Amino Acid Analogues. J. Org. Chem. 54, 1859-1866; Christie, B. D. & Rapoport, H. (1985) Synthesis of Optically Pure Pipecolates from L-Asparagine. Application to the Total Synthesis of (+)-Apovincamine through Amino Acid Decarbonylation and Iminium Ion Cyclization. J. Org. Chem. 50:1239-1246; Barton et al., (1987) Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives. Tetrahedron 43:4297-4308; and, Subasinghe et al., (1992) Quisqualic acid analogues: synthesis of beta-heterocyclic 2-aminopropanoic acid derivatives and their activity at a novel quisqualate-sensitized site. J. Med. Chem. 35:4602-7. See also, patent applications entitled "Protein Arrays," filed Dec. 22, 2003, Ser. No. 10/744,899 and Ser. No. 60/435,821 filed on Dec. 22, 2002.

In some embodiments, the composition comprises a transcription factor analog wherein the total number of β-amino acids in the analog is from about 10 percent to about 60 percent of the total number of amino acids of the analog. In some embodiments, the composition comprises an enkephlin analog wherein the total number of β-amino acids in the analog is from about 10 percent to about 60 percent of the total number of amino acids of the analog. In some embodiments, the composition comprises an LHRH analog wherein the total number of β-amino acids in the analog is from about 10 percent to about 60 percent of the total number of amino acids of the analog. In some embodiments, the composition comprises a neuropeptide analog wherein the total number of β-amino acids in the analog is from about 10 percent to about 60 percent of the total number of amino acids of the analog. In some embodiments, the composition comprises an glycointegrin analog wherein the total number of β-amino acids in the analog is from about 10 percent to about 60 percent of the total number of amino acids of the analog. In some embodiments, the composition comprises an integrin analog wherein the total number of β-amino acids in the analog is from about 10 percent to about 60 percent of the total number of amino acids of the analog. In some embodiments, the composition comprises a glucagon or glucagon-like peptide analog wherein the total number of β-amino acids in the analog is from about 10 percent to about 60 percent of the total number of amino acids of the analog. In some embodiments, the composition comprises an antithrombotic peptides analog wherein the total number of β-amino acids in the analog is from about 10 percent to about 60 percent of the total number of amino acids of the analog. In some embodiments, the composition comprises a vassopressin analog wherein the total number of β-amino acids in the analog is from about 10 percent to about 60 percent of the total number of amino acids of the analog. In some embodiments, the composition comprises a cytokine or interleukin analog wherein the total number of β-amino acids in the analog is from about 10 percent to about 60 percent of the total number of amino acids of the analog. In some embodiments, the composition comprises an interferon analog wherein the total number of β-amino acids in the analog is from about 10 percent to about 60 percent of the total number of amino acids of the analog. In some embodiments, the composition comprises an endothlin analog wherein the total number of β-amino acids in the analog is from about 10 percent to about 60 percent of the total number of amino acids of the analog. In some embodiments, the composition comprises an natriuretic hormone analog wherein the total number of β-amino acids in the analog is from about 10 percent to about 60 percent of the total number of amino acids of the analog. In some embodiments, the composition comprises an extracellular kinase ligand analog wherein the total number of β-amino acids in the analog is from about 10 percent to about 60 percent of the total number of amino acids of the analog. In some embodiments, the composition comprises an angiotensin enzyme inhibitor analog wherein the total number of β-amino acids in the analog is from about 10 percent to about 60 percent of the total number of amino acids of the analog. In some embodiments, the composition comprises an antiviral peptide analog wherein the total number of β-amino acids in the analog is from about 10 percent to about 60 percent of the total number of amino acids of the analog. In some embodiments, the composition comprises a thrombin analog wherein the total number of β-amino acids in the analog is from about 10 percent to about 60 percent of the total number of amino acids of the analog. In some embodiments, the composition comprises a substance P analog wherein the total number of β-amino acids in the analog is from about 10 percent to about 60 percent of the total number of amino acids of the analog. In some embodiments, the composition comprises a substance G analog wherein the total number of β-amino acids in the analog is from about 10 percent to about 60 percent of the total number of amino acids of the analog. In some embodiments, the composition comprises a somatotropin analog wherein the total number of β-amino acids in the analog is from about 10 percent to about 60 percent of the total number of amino acids of the analog. In some embodiments, the composition comprises a somatostatin analog wherein the total number of β-amino acids in the analog is from about 10 percent to about 60 percent of the total number of amino acids of the analog. In some embodiments, the composition comprises a GnRH analog wherein the total number of β-amino acids in the analog is from about 10 percent to about 60 percent of the total number of amino acids of the analog. In some embodiments, the composition comprises a bradykinin analog wherein the total number of β-amino acids in the analog is from about 10 percent to about 60 percent of the total number of amino acids of the analog. In some embodiments, the composition comprises an insulin analog wherein the total number of β-amino acids in the analog is from about 10 percent to about 60 percent of the total number of amino acids of the analog. In some embodiments, the composition comprises a growth factor analog wherein the total number of β-amino acids in the analog is from about 10 percent to about 60 percent of the total number of amino acids of the analog. Any of the compositions above may be used in the methods disclosed in this instant specification.

In some embodiments, the composition comprises a VIP analog wherein the total number of β-amino acids in the analog is from about 10 percent to about 60 percent of the total number of amino acids of the analog. In some embodiments, the composition comprises a VIP analog wherein the total number of β-amino acids in the analog is from about 12 percent to about 50 percent of the total number of amino acids of the analog. In some embodiments, the composition comprises a VIP analog wherein the total number of β-amino acids in the analog is from about 14 percent to about 50 percent of the total number of amino acids of the analog. In some embodiments, the composition comprises a VIP analog wherein the total number of β-amino acids in the analog is from about 16 percent to about 50 percent of the total number of amino acids of the analog. In some embodiments, the composition comprises a VIP analog wherein the total number of β-amino acids in the analog is from about 18 percent to about 50 percent of the total number of amino acids of the analog. In some embodiments, the composition comprises a VIP analog wherein the total number of β-amino acids in the analog is from about 20 percent to about 50 percent of the total number of amino acids of the analog. In some embodiments, the composition comprises a VIP analog wherein the total number of β-amino acids in the analog is from about 30 percent to about 50 percent of the total number of amino acids of the analog. In some embodiments, the composition comprises a VIP analog wherein the total number of β-amino acids in the analog is from about 40 percent to about 50 percent of the total number of amino acids of the analog. In some embodiments, the composition comprises a VIP analog wherein the total number of β-amino acids in the analog is from about 45 percent to about 50 percent of the total number of amino acids of the analog. In some embodiments, the composition comprises a VIP analog wherein the total number of β-amino acids in the analog is from about 40 percent to about 45 percent of the total number of amino acids of the analog. In some embodiments, the composition comprises a VIP analog wherein the total number of β-amino acids in the analog is from about 30 percent to about 40 percent of the total number of amino acids of the analog. In some embodiments, the composition comprises a VIP analog wherein the total number of β-amino acids in the analog is from about 35 percent to about 40 percent of the total number of amino acids of the analog. In some embodiments, the composition comprises a VIP analog wherein the total number of β-amino acids in the analog is from about 20 percent to about 30 percent of the total number of amino acids of the analog. In some embodiments, the composition comprises a VIP analog wherein the total number of β-amino acids in the analog is from about 10 percent to about 20 percent of the total number of amino acids of the analog. In some embodiments, the composition comprises a VIP analog wherein the total number of β-amino acids in the analog is from about 15 percent to about 20 percent of the total number of amino acids of the analog. In some embodiments, the composition comprises a VIP analog wherein the total number of β-amino acids in the analog is from about 20 percent to about 25 percent of the total number of amino acids of the analog. In some embodiments, the composition comprises a VIP analog wherein the total number of β-amino acids in the analog is from about 25 percent to about 30 percent of the total number of amino acids of the analog.

In some embodiments, the composition comprises a VIP analog wherein the total number of β-amino acids in the analog is from about 30 percent to about 35 percent of the total number of amino acids of the analog.

In some embodiments, the composition comprises a VIP analog, wherein the ratio of total β-amino acids in the analog is from 1 to 3 β-amino acids for every 7 amino acids of the analog. In some embodiments, the composition comprises a VIP analog, wherein the ratio of total β-amino acids in the analog is from 2 to 4 β-amino acids for every 7 amino acids of the analog. In some embodiments, the composition comprises a VIP analog, wherein the ratio of total β-amino acids to amino acids in the analog is from 3 to 5 β-amino acids for every 7 amino acids of the analog. In some embodiments, the composition comprises a VIP analog, wherein the ratio of total β-amino acids to amino acids in the analog is from 4 to 6 β-amino acids for every 7 amino acids of the analog. In some embodiments, the composition comprises a VIP analog, wherein the ratio of total β-amino acids to amino acids in the analog is from 5 to 7 β-amino acids for every 7 amino acids of the analog. In some embodiments, the composition comprises a VIP analog, wherein the ratio of total β-amino acids to amino acids in the analog is 1 β-amino acid for every 7 amino acids of the analog. In some embodiments, the composition comprises a VIP analog, wherein the ratio of total β-amino acids to amino acids in the analog is 2 β-amino acids for every 7 amino acids of the analog.

In some embodiments, the composition comprises a VIP analog, wherein the ratio of total β-amino acids to amino acids in the analog is 3 β-amino acids for every 7 amino acids of the analog. In some embodiments, the composition comprises a VIP analog, wherein the ratio of total β-amino acids to amino acids in the analog is 4 β-amino acids for every 7 amino acids of the analog. In some embodiments, the composition comprises a VIP analog, wherein the ratio of total β-amino acids to amino acids in the analog is 5 β-amino acids for every 7 amino acids of the analog. In some embodiments, the composition comprises a VIP analog, wherein the ratio of total β-amino acids to amino acids in the analog is 6 β-amino acids for every 7 amino acids of the analog.

In another embodiment of the invention, the composition comprises a VIP analog, wherein the analog comprises a repetitive pattern of β-amino acids from the amino-terminus to the carboxy-terminus selected from the following: ααααααβ, αααααβα, ααααβαα, αααβααα, ααβαααα, αβααααα, βαααααα, ααααββ, αααββα, αααββαα, ααββααα, αββαααα, ββαααααα, βααααβ, βααααβα, βαααβαα, βααβααα, βαβαααα, αβαααβ, αβαα+βα, αβααβαα, αβαβααα, ααβααβ, ααβααβα, ααβαβαα, ααβαααβ, αααβαβα, and αααβαβ.

Some embodiments of the claimed invention include pharmaceutical compositions. In some embodiments, the pharmaceutical composition comprises any of the aforementioned compositions in combination with a pharmaceutically acceptable carrier. In another embodiment of the invention, the pharmaceutical composition comprises a secretin analog and one other active agent, wherein the secretin analog comprises at least one α-amino acid and at least one β-amino acid.

In another embodiment of the invention, the pharmaceutical composition comprises a VIP analog and one other active agent, wherein the VIP analog comprises at least one α-amino acid and at least one β-amino acid.

The invention further relates to uses of a composition comprising a secretin analog in the preparation of a medicament for treating or preventing pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction. The invention further relates to use of a composition comprising a VIP analog in the preparation of a medicament for treating or preventing pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction.

In some embodiments, the invention relates to methods of manufacturing any one of the aforementioned compositions, pharmaceutical compositions, or a pharmaceutical salt derived therefrom comprising catalyzing a reaction between at least one α-amino acid with at least one β-amino acid.

The invention also relates to methods of treating or preventing pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction comprising administrating any one of the compositions or pharmaceutical compositions comprising a secretin family analog, or a pharmaceutical salt derived therefrom, to a subject in need thereof.

The present invention also relates to methods of inhibiting secretion of TNF-α in a subject comprising administering a composition comprising a vasoactive intestinal peptide (VIP) analog to a subject, wherein said analog comprises an α-amino acid and at least one β-amino acid. In some embodiments, the method comprises administering the composition comprising any of the percentages of β-amino acids.

The present invention is also directed towards kits comprising any of the aforementioned compositions or pharmaceutical compositions comprising a secretin analog, wherein the secretin analog comprises an α-amino acid and at least one β-amino. The present invention is directed toward kits comprising any of the aforementioned compositions or pharmaceutical compositions comprising a VIP analog, wherein the VIP analog comprises an α-amino acid and at least on β-amino acid. In some embodiments, the kit further comprises a vehicle for administration of the composition.

The present invention also relates to methods of identifying a modulator of human receptor activity comprising:
a) contacting a human receptor with a secretin analog, wherein the analog comprises an α-amino acid and at least one β-amino acid;
b) measuring the association of the secretin analog to the human receptor in the presence and absence of an unknown compound; and
c) comparing the rate of association of the secretin analog to the human receptor in the presence of an unknown compound to the rate of association of the secretin analog to the human receptor in the absence of an unknown compound.

The present invention also relates to methods of identifying a modulator of animal receptor activity comprising:
a) contacting an animal receptor with a secretin analog, wherein the analog comprises an α-amino acid and at least one β-amino acid;
b) measuring the association of the secretin analog to the animal receptor in the presence and absence of an unknown compound; and
c) comparing the rate of association of the secretin analog to the animal receptor in the presence of an unknown compound to the rate of association of the secretin analog to the animal receptor in the absence of an unknown compound.

The present invention also relates to methods of identifying a modulator of human secretin receptor activity comprising:
a) contacting a human secretin receptor with a secretin analog, wherein the analog comprises an α-amino acid and at least one β-amino acid;
b) measuring the association of the secretin analog to the human secretin receptor in the presence and absence of an unknown compound; and
c) comparing the rate of association of the secretin analog to the human secretin receptor in the presence of an unknown compound to the rate of association of the secretin analog to the human secretin receptor in the absence of an unknown compound.

The present invention also relates to methods of identifying a modulator of human VIP receptor activity comprising:
a) contacting a human VIP receptor with the VIP analog, wherein the analog comprises an α-amino acid and at least one β-amino acid;
b) measuring the association of the VIP analog to the human VIP receptor in the presence and absence of an unknown compound; and
c) comparing the rate of association of the VIP analog to the human VIP receptor in the presence of an unknown compound to the rate of association of the VIP analog to the human VIP receptor in the absence of an unknown compound.

BRIEF DESCRIPTION OF DRAWINGS

FIG. 7 illustrates multiple VIP analog sequences and their corresponding helical wheel diagrams, where the position of β-amino acids are represented by solid dots.

DETAILED DESCRIPTION OF ILLUSTRATIVE EMBODIMENTS

Figure 1:
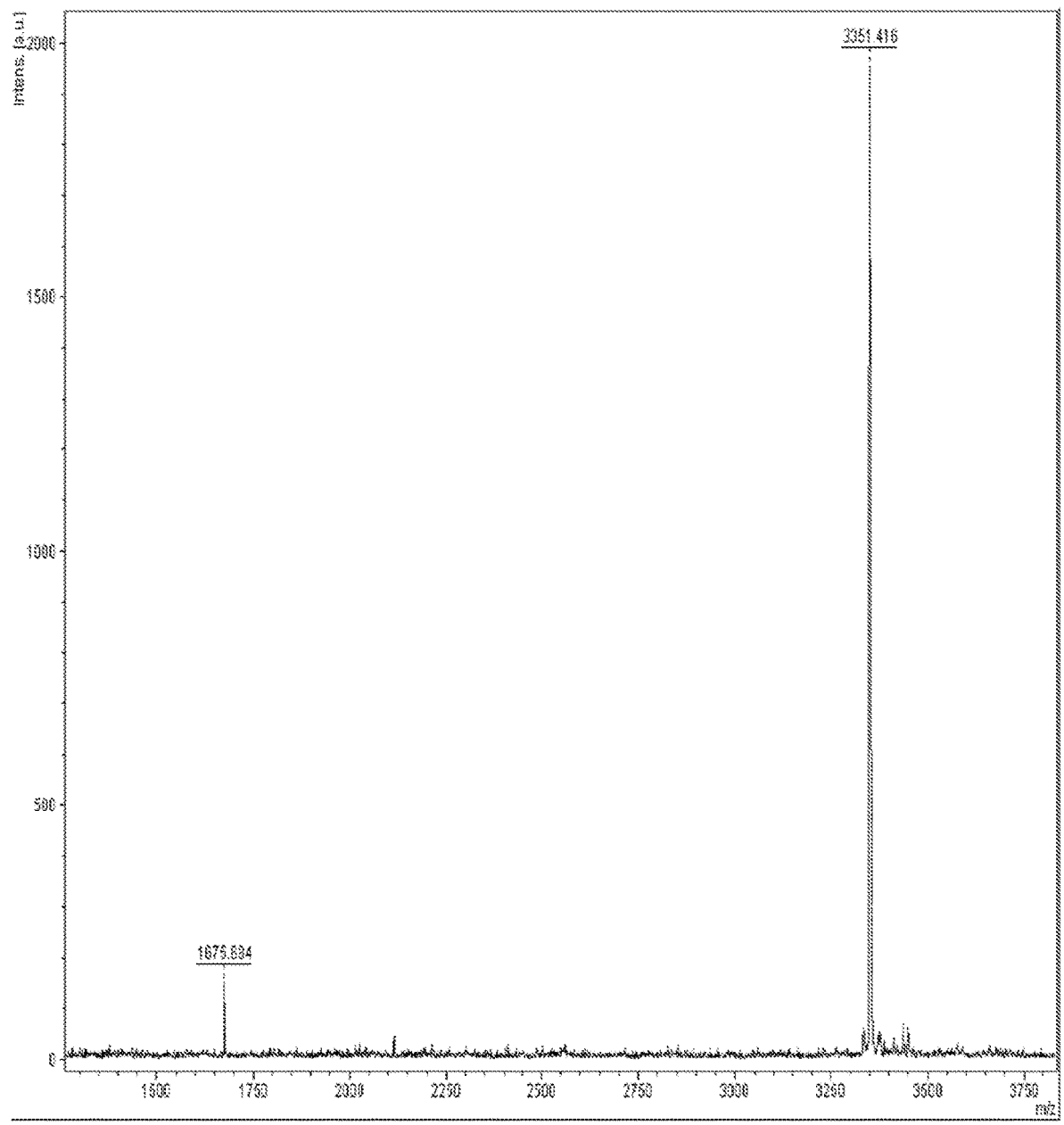
FIG. 1 shows MALDI-TOF data of a purified VIP analogue which illustrates the expected mass (within a reasonable tolerance) of both singly charged and doubly charged species of the analogue after chemical synthesis, cleavage from resin, and subsequent purification of the analogue through a C18 HPLC column.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise.

The term "about" as used herein when referring to a measurable value such as an amount, a temporal duration, and the like, is meant to encompass variations of ±20%, ±10%, ±5%, +1%, or ±0.1% from the specified value, as such variations are appropriate to perform the disclosed methods.

The term "active state" refers to the conformation or set of conformations of a polypeptide that allows functional domain or domains of the polypeptide to associate or disassociate with another compound, macromolecule, or ligand. In some embodiments, the association or disassociation of the polypeptide with another compound, macromolecule, or ligand may propagate or inhibit a biologic signal.

The terms "amino acid" refer to a molecule containing both an amino group and a carboxyl group bound to a carbon which is designated the α-carbon. Suitable amino acids include, without limitation, both the D- and L-isomers of the naturally-occurring amino acids, as well as non-naturally occurring amino acids prepared by organic synthesis or other metabolic routes. in some embodiments, a single "amino acid" might have multiple sidechain moieties, as available per an extended aliphatic or aromatic backbone scaffold. Unless the context specifically indicates otherwise, the term amino acid, as used herein, is intended to include amino acid analogs.

The term "analog" refers to any polypeptide comprising at least one α-amino acid and at least one β-amino acid residue, wherein the polypeptide is structurally similar to a naturally occurring full-length protein and shares the biochemical or biological activity of the naturally occurring full-length protein upon which the analog is based. In some embodiments, an analog is any polypeptide comprising at least one β-amino acid residue, wherein the polypeptide is structurally similar to a naturally occurring full-length protein and shares the biochemical or biological activity of the naturally occurring full-length protein upon which the analog is based and wherein the addition of one or more β-amino acid residues constrains an alpha helical structure in the polypeptide. In some embodiments, an analog is any polypeptide comprising at least one β-amino acid residue, wherein the polypeptide is structurally similar to a naturally occurring full-length protein and shares the biochemical or biological activity of the naturally occurring full-length protein upon which the analog is based. In some embodiments, the non-natural amino acid residue is a monomer of an aliphatic polypeptide. In some embodiments the aliphatic analogs are chosen from oligoureas, azapeptides, pyrrolinones, α-aminoxy-peptides, and sugar-based peptides. In some embodiments, the composition comprises a non-natural β-amino acid. In some embodiments, the analog is a fragment of the full-length protein upon which the analog is based. In some embodiments, fragments are from about 5 to about 75 amino acids in length as compared to the naturally occurring, fully translated and fully processed protein sequences. In some embodiments, the analogs comprise a fragment of a naturally translated full-length protein that induces the biochemical or biological activity of a biological pathway of a subject at a level equivalent to or increased as compared to the activity induced by a naturally occurring full-length protein upon which the analog is derived. In some embodiments, the analog is a truncated polypeptide as compared to the full-length, naturally translated or naturally occurring polypeptide upon which the truncated polypeptide is derived. In some embodiments, the analog is a synthetic polypeptide, wherein at least one of the amino acid residues of the polypeptide comprises at least one non-natural side chain. In some embodiments, the analogs of the invention comprise at least one non-natural amino acid chosen from one of the following structures: aminoisobutyric acid, 3-Aminobutyric acid, and 2-hydroxy-4-(4-nitrophenyl)butyric acid. In some embodiments, the analog has a polypeptide backbone of identical length and similar homology to the polypeptides disclosed in Tables 1, 2, 3, and/or 4. In some embodiments, the analog is about 70%, 75%, 80%, 85%, 90%, 95%, 98%, or 99% homolgous to at least one of the polypeptides disclosed in Tables 1, 2, 3, and/or 4. In some embodiments, the analog is an agonist or antagonist of one or more of the following receptors: VPAC1, VPAC2, or PAC1. In some embodiments, the analog is a fragment of one of the polypeptides disclosed in Tables 1, 2, 3, and 4 and shares the same or improved biological or biochemical activity as compared to the biological or biochemical activity of the polypeptides disclosed in Tables 1, 2, 3, and/or 4 upon which the analog amino acid sequence is derived. In some embodiments, the analog is an agonist or antagonist of the receptor of the the full-length, naturally translated or naturally occurring polypeptide upon which the amino acid sequence of the agonist or antagonist is derived. In some embodiments, the analog is an agonist or antagonist of the receptor of the polypeptides disclosed in Tables 1, 2, 3, and/or 4. In such embodiments, the amino acid sequence of the agonists or antagonists are derived from the amino acid sequence of the the polypeptides disclosed in Tables 1, 2, 3, and/or 4. In some embodiments the analog of the present invention is modified by a bioactive lipid moiety on at least one amino acid residue of the analog. In such embodiments, the lipid moieties may be chosen from the following lipid molecules: LPA, progesterone, prostanoids, S1P, LPA, cannabinoids, 2-arachidonylglycerol. In some embodiments, the side chain or terminal end of the amino acid residues of the polypeptides disclosed in Tables 1, 2, 3, and/or 4 may be modified with the bioreactive lipid moieties. In some embodiments, the analogs of the present invention are derived from one of the following sequences:

```
                                             (SEQ ID NO: 6)
HSDGIFTDSYSRYRKQMAVKKYLAAVLGKRYKQRVKNK-NH2;

(SEQ ID NO: 5)
HSDGIFTDSYSRYRKQMAVKKYLAAVL-NH2;

(SEQ ID NO: 9)
HSDGTFTSELSRLRDSARLQRLLQGLV-NH2;

(SEQ ID NO: 1335)
HSDGTFTSDYSKYLDSRRAQDFVQWLMNT-NH2;

(SEQ ID NO: 7)
HADGVFTSDFSKLLGQLSAKKYLESLM-NH2
```

The term "α-amino acid" refers to any and all natural and unnatural α-amino acids and their respective residues (i.e., the form of the amino acid when incorporated into a polypeptide molecule), without limitation. In some embodiments, "α-amino acid" explicitly encompasses the conventional and well-known naturally occurring amino acids, as well as all synthetic variations, derivatives, and analogs thereof. In some embodiments, "α-amino acid" means alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and/or valine. In some embodiments, α-amino acids also include analogs such as N-methylated α-amino acids, hydroxylated α-amino acids, and aminoxy acids. In some embodiments, α-amino refers to include N-alkyl α-amino acids (such as N-methyl glycine), hydroxylysine, 3-hydroxyproline, 4-hydroxyproline, nor-valine, nor-leucine, and ornithine.

The terms "β-amino acid" and "β-amino acid residue" refer to any and all β-amino acids and their respective residues (i.e., the form of the amino acid when incorporated into a polypeptide molecule), without limitation. In some embodiments, the terms "β-amino acid" refers to those β-amino acids described in U.S. Pat. No. 6,060,585, issued May 9, 2000, incorporated herein by reference, and those described in allowed U.S. Pat. No. 6,683,154, issued Jan. 27, 2004; U.S. Pat. No. 6,710,186, issued Mar. 23, 2004; and U.S. Pat. No. 6,727,368, issued Apr. 27, 2004, all of which are incorporated herein by reference. Further still, cyclic imino carboxylic acids and gem-di-substituted cyclic imino carboxylic acids (both of which are a type of cyclically-constrained β-amino acid) may also be used in the invention. In some embodiments, the term "β-amino acid" refers to residues disclosed in U.S. Pat. No. 6,958,384, issued Oct. 25, 2005, incorporated herein by reference. Further still, these β-residues may also take the form of the gem-di-substituted cyclic amino acids disclosed in U.S. Pat. No. 6,710,186, incorporated herein by reference. In some embodiments, the terms "β-amino acid" refers to β-homo amino acids. In some embodiments the β-amino acids refers to the selection of an amino acid chosen from the following:

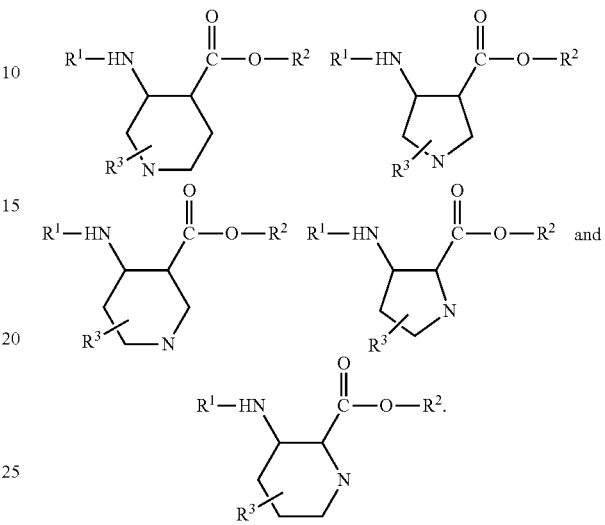

$R^1$ is selected from the group consisting hydrogen and an amino protecting group; $R^2$ is selected from the group consisting of hydrogen and a carboxy protecting group; and when $R^3$ is bonded to a carbon atom, $R^3$ is selected from the group consisting of hydrogen, hydroxy, linear or branched $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —$(CH_2)_{n+1}$, —$OR^4$, —$(CH_2)_{n+1}$—$SR^4$, —$(CH_2)_{n+1}$—S(=O)—$CH_2$—$R^4$, —$(CH_2)_{n+1}$—S(=O)$_2$—$CH_2$—$R^4$, —$(CH_2)_{n+1}$—$NR^4R^4$, —$(CH_2)_{n+1}$—NHC(=O)$R^4$, —$(CH_2)_{n+1}$—NHS(=O)$_2$—$CH_2$—$R^4$, —$(CH_2)_{n+1}$—O—$(CH_2)_m$—$R^5$, —$(CH_2)_{n+1}$—S—$(CH_2)_m R^5$, —$(CH_2)_{n+1}$—S(=O)—$(CH_2)_m$—$R^5$, —$(CH_2)_{n+1}$—S(=O)$_2$—$(CH_2)_m$—$R^5$, —$(CH_2)_{n+1}$—NH—$(CH_2)_m$—$R^5$, —$(CH_2)_{n+1}$—N((CH_2)_m—$R^5$}$_2$, —$(CH_2)_{n+1}$—NHC(=O)—$(CH_2)_{n+1}$—$R^5$, and —$(CH_2)_{n+1}$—NHS(=O)$_2$—$(CH_2)_m$—$R^5$; wherein each $R^4$ is independently selected from the group consisting of hydrogen, $C_1$-$C_6$alkyl, alkenyl, or alkynyl; mono- or bicyclic aryl, mono- or bicyclic heteroaryl having up to S heteroatoms selected from N, O, and S; mono- or bicyclic aryl-$C_1$-$C_6$alkyl, mono- or bicyclic heteroaryl-$C_1$-$C_6$alkyl; and wherein $R^5$ is selected from the group consisting of hydroxy, $C_1$-$C_6$alkyloxy, aryloxy, heteroaryloxy, thio, $C_1$-$C_6$alkylthio, $C_1$-$C_6$alkylsulfinyl, $C_1$-$C_6$alkylsulfonyl, arylthio, arylsulfinyl, arylsulfonyl, heteroarylthio, heteroarylsulfinyl, heteroarylsulfonyl, amino, mono- or di-$C_1$-$C_6$alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$alkylamino, carboxylic acid, carboxamide, mono- or di-$C_1$-$C_6$alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$alkyl, aryl, heteroaryl; O-alkylurethane, O-arylurethane, and O-heteroarylurethane; and m is an integer of from 2-6 and n is an integer of from 0-6; and when $R^3$ is bonded to a nitrogen atom, $R^3$ is independently selected from the group consisting of those listed above for when $R^3$ is attached to a carbon atom, and further selected from the group consisting of —S(=O)$_2$—CH$_2$—R$^4$, —C(=O)—R$^4$—S(=O)$_2$—(CH$_2$)$_m$R$^5$, and —C(=O)—(CH$_2$)$_{n+1}$—R$^5$; wherein $R^4$ and $R^5$ are as defined hereinabove, and m is an integer of from 2-6 and n is an integer of from 0-6; provided that when the β-amino acid is of formula $R^3$ is not hydrogen; racemic mixtures thereof, isolated or enriched enantiomers thereof; isolated or enriched diastereomers thereof; and salts thereof. In some embodiments the β-amino acids refers to the selection of an amino acid chosen from the following:

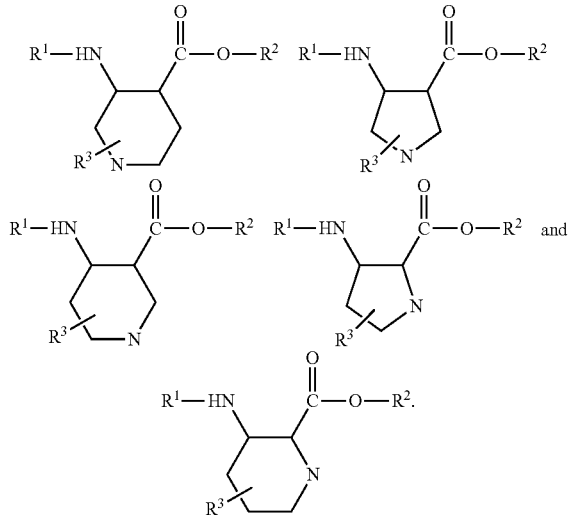

In some embodiments the β-amino acids refers to the following formula:

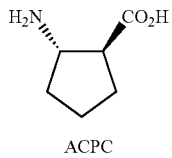

ACPC

In some embodiments the β-amino acids refers to the following formula:

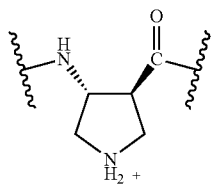

An APC residue within an underlined peptide chain, under neutral aqueous conditions (the ring N is protonated).

wherein the NH$_2$ and/or COOH groups are replaced with functional peptide bonds.

In some embodiments the term "β-amino acid" refers to:

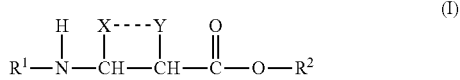

(I)

wherein X and Y combined, together with the carbon atoms to which they are bonded, define a substituted or unsubstituted $C_4$-$C_8$ cycloalkyl, cycloalkenyl or heterocyclic ring having one or more nitrogen atoms as the sole heteroatom;

the substituents on carbon atoms of the rings being independently selected from the group consisting of linear or branched $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —(CH$_2$)$_{n+1}$—OR$^4$, —(CH$_2$)$_{n+1}$—SR$^4$, —(CH$_2$)$_{n+1}$—S(=O)—CH$_2$—R$^4$, —(CH$_2$)$_{n+1}$—S(=O)$_2$—CH$_2$—R$^4$, —(CH$_2$)$_{n+1}$—NR$^4$R$^4$, —(CH$_2$)$_{n+1}$—NHC(=O)R$^4$, —(CH$_2$)$_{n+1}$—NHS(=O)$_2$—CH$_2$—R$^4$, —(CH$_2$)$_{n+1}$—O—(CH$_2$)$_m$—R$^5$, —(CH$_2$)$_{n+1}$—S—(CH$_2$)$_m$—R$^5$, —(CH$_2$)$_{n+1}$—S(=O)—(CH$_2$)$_m$—R, —(CH$_2$)$_{n+1}$—S(=O)$_2$—(CH$_2$)$_m$—R$^5$, —(CH$_2$)$_{n+1}$—NH—(CH$_2$)$_m$—R$^5$, —(CH$_2$)$_{n+1}$—N—{(CH$_2$)$_m$—R$^5$ }2, —(CH$_2$)$_{n+1}$—NHC(=O)—(CH$_2$)$_{n+1}$ R$^5$, and —(CH$_2$)$_{n+1}$—NHS(=O)$_2$—(CH$_2$)$_m$—R$^5$;

wherein $R^4$ is independently selected from the group consisting of hydrogen. $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and wherein $R^5$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino. N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteruarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, hetcroaryl; O-alkylurethane, O-arylurethane, and O-heteroarylurethane; and m is an integer of from 2-6 and n is an integer of from 0-6;

the substituents on heteroatoms of the ring being independently selected from the group consisting of —S(=O)$^2$—CH$_2$—R$^4$—C(=O)—R$^4$—S(=O)$_2$—(CH$_2$)$_m$—R$^5$, and —C(=O)—(CH$_2$)$_{n+1}$—R$^5$; wherein $R^4$ and $R^5$ are as defined hereinabove, and m is an integer of from 2-6 and n is an integer of from 0-6;

provided that when X & Y together with the carbons to which they are bonded define a five- or six-membered cycloalkyl or a five-membered heterocyclic ring having one nitrogen as the sole heteroatom, and the nitrogen is bonded to a carbon atom adjacent to the carboxy carbon of Formula I, the cycloalkyl or heterocyclic ring is substituted;

$R^1$ is selected from the group consisting hydrogen and an amino protecting group;

$R^2$ is selected from the group consisting of hydrogen and a carboxy protecting group;

racemic mixtures thereof, isolated or enriched enantiomers thereof; isolated or enriched diastereomers thereof; and salts thereof.

In some embodiments the term "β-amino acid" refers to selection of an amino acid chosen from the following: $β^3$ or $β^2$. In some embodiments the term "β-amino acid" refers to selection of an amino acid chosen from the following:

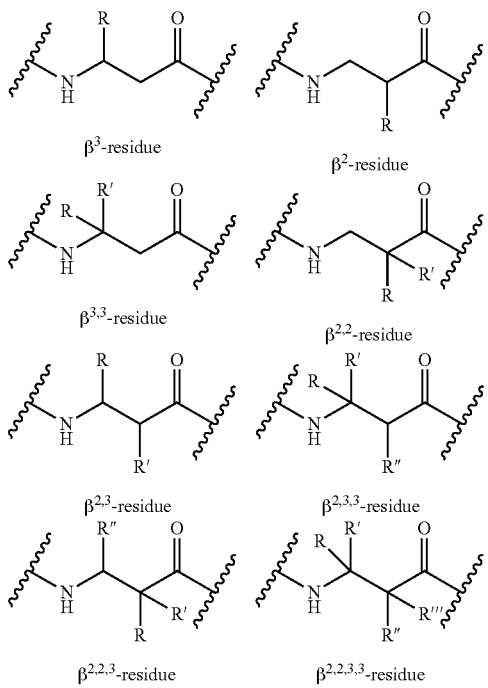

wherein R, R', R", and R''' are any substituent.

In some embodiments the term "β-amino acid" refers to selection of an amino acid chosen from the following:

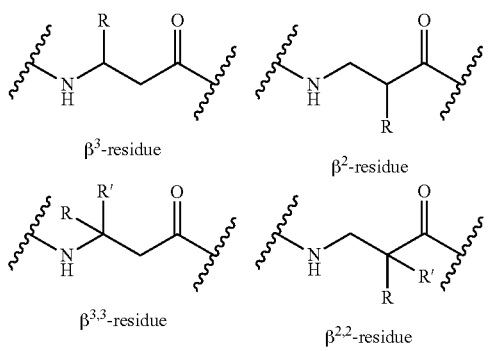

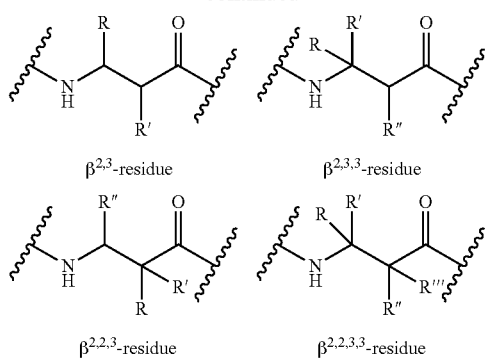

wherein R, R', R", and R''' is an amine, hydroxy, hydroxyl, carbonyl, H, =O, —OH, —COOH, —N, —CH$_3$, —CH$_2$—X, halo, aryl, arylalkoxy, arylalkyl, alkynyl, alkenyl, alkylene, alkyl, akyl-halo, arylamido, alkylheterocycle, alkylamino, alkylguanidino, alkanol, alkylcarboxy, cycloalkyl, heteroaryl, heteroarylalkyl, heteroarylalkoxy, or heterocyclyl; wherein X is any substituent.

In some embodiments the term "β-amino acid" refers to selection of an amino acid chosen from the following:

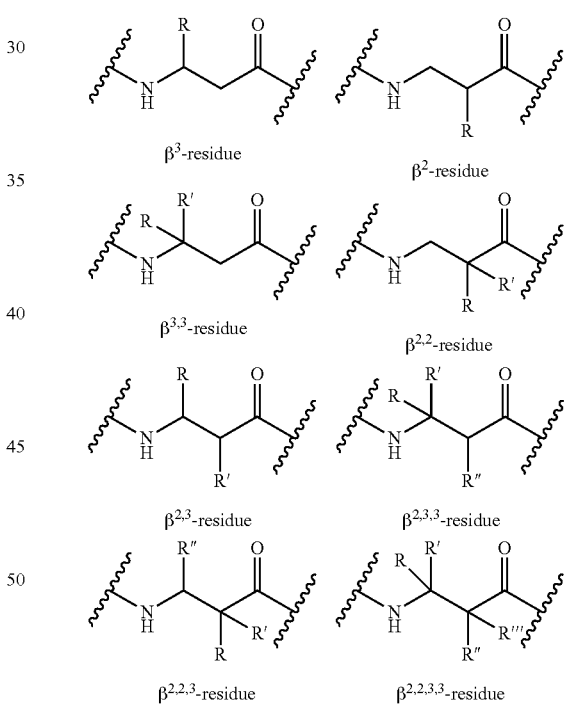

wherein R, R', R", and R''' are any substituent, provided that: (i) R is not O, N, or halo when the R is in a $β^3$-residue, (ii) R and R' are not O, N, or halo when the R and R' are in a $β^{3,3}$-residue; (iii) R is not O, N, or halo when the R is in a $β^{2,3}$-residue; (iv) R and R' are not O, N, or halo when the R and R' are in a $β^{2,3,3}$-residue; (v) R" is not O, N, or halo when the R" is in a $β^{2,2,3}$-residue; (vi) R and R' are not O, N, or halo when the R and R' are in a $β^{2,2,3,3}$-residue.

In some embodiments the term "β-amino acid" refers to selection of an amino acid chosen from the following:

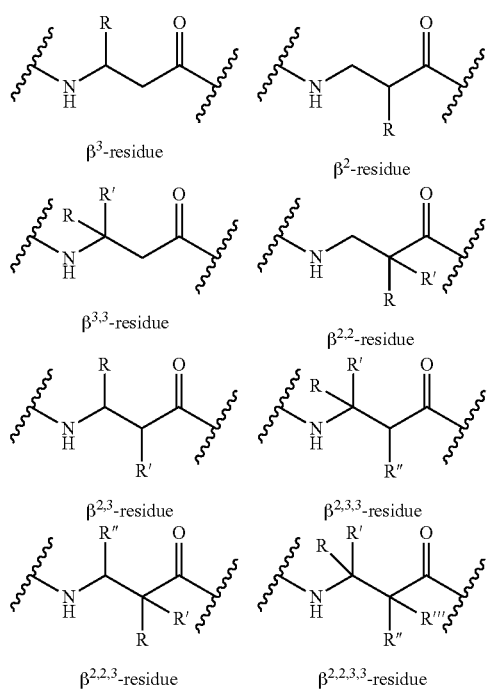

β³-residue  β²-residue  β³,³-residue  β²,²-residue  β²,³-residue  β²,³,³-residue  β²,²,³-residue  β²,²,³,³-residue wherein R, R', R", and R'" is an amine, hydroxy, hydroxyl, carbonyl, H, =O, —OH, —COOH, —N, —CH₃, —CH₂—X, halo, aryl, arylalkoxy, arylalkyl, alkynyl, alkenyl, alkylene, alkyl, akyl-halo, arylamido, alkylheterocycle, alkylamino, alkylguanidino, alkanol, alkylcarboxy, cycloalkyl, heteroaryl, heteroarylalkyl, heteroarylalkoxy, or heterocyclyl; wherein X is any substituent; provided that: (i) R is not O, N, or halo when the R is in a β³-residue, (ii) R and R' are not O, N, or halo when the R and R' are in a β³,³-residue; (iii) R is not O, N, or halo when the R is in a β²,³-residue; (iv) R and R' are not O, N, or halo when the R and R' are in a β3²,³,³-residue; (v) R" is not O, N, or halo when the R" is in a β²,²,³-residue; (vi) R and R' are not O, N, or halo when the R and R' are in a β²,²,³,³-residue.

A "cyclic" beta-amino acid is acid is an amino acid of the following formula I:

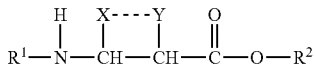

wherein X and Y combined, together with the carbon atoms to which they are bonded, define a substituted or unsubstituted $C_4$-$C_8$ cycloalkyl or cycloalkenyl group; wherein substituents on carbon atoms of the rings being independently selected from the group consisting of linear or branched $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —(CH 2)$_{n+1}$—OR$_4$, —(CH 2)$_{n+1}$—SR$_4$, —(CH 2)$_{n+1}$—S(=O)—CH$_2$—R$_4$, —(CH$_2$)$_{n+1}$—S(=O)$_2$—CH$_2$—R$_4$, —(CH$_2$)$_{n+1}$—NR$_4$R$_4$, —(CH$_2$)$_{n+1}$—NHC(=O)R$_4$, —(CH$_2$)$_{n+1}$—NHS(=O)$_2$—CH$_2$—R$_4$, —(CH$_2$)$_{n+1}$—O—(CH$_2$)$_m$—R$_5$, —(CH$_2$)$_{n+1}$—S—(CH$_2$)$_m$—R$_5$, —(CH$_2$)$_{n+1}$—S(=O)—(CH$_2$)$_m$—R$_5$, —(CH$_2$)$_{n+1}$—S(=O)$_2$—(CH$_2$)$_m$—R$_5$, —(CH$_2$)$_{n+1}$—NH—(CH$_2$)$_m$—R$_5$, —(CH$_2$)$_{n+1}$—N—{(CH$_2$)$_m$—R$_5$}$_2$, —(CH$_2$)$_{n+1}$—NHC(=O)—(CH$_2$)$_{n+1}$—R$_5$, and —(CH$_2$)$_{n+1}$—NHS(=O)$_2$—(CH$_2$)$_m$—R$_5$; wherein R$_4$ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and wherein R$_5$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane; and m is an integer of from 2-6 and n is an integer of from 0-6; the substituents on heteroatoms of the ring being independently selected from the group consisting of —S(=O)$_2$—CH$_2$—R$_4$—C(=O)—R$_4$—S(=O)$_2$—(CH$_2$)$_m$—R$_5$, and —C(O)—(CH$_2$)$_{n+1}$—R$_5$; wherein R$_4$ and R$_5$ are as defined hereinabove, and m is an integer of from 2-6 and n is an integer between 0 and 6; provided that when X and Y together with the carbons to which they are bonded define a five- or six-membered cycloalkyl or a five-membered heterocyclic ring having one nitrogen as the sole heteroatom, and the nitrogen is bonded to a carbon atom adjacent to the carboxy carbon of Formula I, the cycloalkyl or heterocyclic ring is substituted; R$_1$ is selected from the group consisting hydrogen and an amino protecting group; R$_2$ is selected from the group consisting of hydrogen and a carboxy protecting group; racemic mixtures thereof, isolated or enriched enantiomers thereof; isolated or enriched diastereomers thereof; and salts thereof.

A "heterocyclic" beta-amino acid is an amino acid of formula I, wherein X and Y combined, together with the carbon atoms to which they are bonded, define a substituted or unsubstituted $C_4$-$C_8$ cyclically or cycloalkenyl group having one or more nitrogen, oxygen or sulfur atoms as a heteroatom(s) within the cycloakyl or cycloalkenyl group; wherein substituents on carbon atoms of the cycloakyl or cycloalkenyl rings being independently selected from the group consisting of linear or branched $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —(CH 2)$_{n+1}$—OR$_4$, —(CH 2)$_{n+1}$—SR$_4$, —(CH$_2$)$_{n+1}$—S(=O)—CH$_2$—R$_4$, —(CH$_2$)$_{n+1}$—S(=O)$_2$—CH$_2$—R$_4$, —(CH$_2$)$_{n+1}$—NR$_4$R$_4$, —(CH$_2$)$_{n+1}$—NHC(O)R$_4$, —(CH$_2$)$_{n+1}$—NHS(=O)$_2$—CH$_2$—R$_4$, —(CH$_2$)$_{n+1}$—O—(CH$_2$)$_m$—R$_5$, —(CH$_2$)$_{n+1}$—S—(CH$_2$)$_m$—R$_5$, —(CH$_2$)$_{n+1}$—S(=O)—(CH$_2$)$_m$—R$_5$, —(CH$_2$)$_{n+1}$—S(=O)$_2$—(CH$_2$)$_m$—R$_5$, —(CH$_2$)$_{n+1}$—NH—(CH$_2$)$_m$—R$_5$, —(CH$_2$)$_{n+1}$—N—{(CH$_2$)$_m$—R$_5$}$_2$, —(CH$_2$)$_{n+1}$—NHC(=O)—(CH$_2$)$_{n+1}$—R$_5$, and —(CH$_2$)$_{n+1}$—NHS(=O)$_2$—(CH$_2$)$_m$—R$_5$; wherein R$_4$ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and wherein $R_5$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane; and m is an integer of from 2-6 and n is an integer of from 0-6; the substituents on heteroatoms of the ring being independently selected from the group consisting of —S(=O)$_2$—CH$_2$—R$_4$—C(=O)—R$_4$—S(=O)$_2$—(CH$_2$)$_m$—R$_5$, and —C(=O)—(CH$_2$)$_{n+1}$—R$_5$; wherein R$_4$ and R$_5$ are as defined hereinabove, and m is an integer of from 2-6 and n is an integer between 0 and 6; provided that when X and Y together with the carbons to which they are bonded define a five- or six-membered cycloalkyl or a five-membered heterocyclic ring having one nitrogen as the sole heteroatom, and the nitrogen is bonded to a carbon atom adjacent to the carboxy carbon of Formula I, the cycloalkyl or heterocyclic ring is substituted; R$_1$ is selected from the group consisting hydrogen and an amino protecting group; R$_2$ is selected from the group consisting of hydrogen and a carboxy protecting group; racemic mixtures thereof, isolated or enriched enantiomers thereof; isolated or enriched diastereomers thereof; and salts thereof.

In some embodiments, at least one of the β-amino acid residues in the analog is replaced with at least one β-amino acid residue that is cyclically constrained via a ring encompassing its $β^2$ and $β^3$ carbon atoms. In another embodiment of the invention, most or all of the inserted β-amino acid residues are cyclically constrained. In another version of the invention, at least one of the β-amino acid residues is unsubstituted at its $β^2$ and $β^3$ carbon atoms. Alternatively, all of the β-amino acid residues may be substituted at their $β^2$ and $β^3$ carbon atoms (with linear, branched or cyclic substituents). In some embodiments, the cyclic substituents of the claimed invention comprise side chains that are covalently bonded to the side chains of other contiguous amino acids. In some embodiments, the cyclic substituents of the claimed invention comprise side chains that are covalently bonded to the side chains of other non-contiguous amino acids. In some embodiments the cyclic substituents of the claimed invention do not include side chains that are covalently bonded to the side chains of other contiguous or non-contiguous amino acids. In some embodiments the terms beta-3 or beta-2 amino acid refers to β3-homo β2-homo amino acids.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C, H), nonpolar side chains (e.g., G, A, V, L, I, P, F, M, W), beta-branched side chains (e.g., T, V, I) and aromatic side chains (e.g., Y, F, W, H). Thus, a predicted nonessential amino acid residue in a VIP analog, for example, replaced with another amino acid residue from the same side chain family. Other examples of acceptable substitutions are substitutions based on isosteric considerations (e.g. norleucine for methionine) or other properties (e.g. 2-thienylalanine for phenylalanine).

As used herein, the term "derived from" in the context of the relationship between a chemical structure or amino acid sequence and a related chemical structure or related amino acid sequence describes a chemical structure or amino acid sequence that may be homologous to or structurally similar to the related chemical structure or related amino acid sequence.

As used herein, the term "inflammatory disease" refers to any disease, condition, or ailment that results from an immune response or a pathogen infection, which in some instances may be characterized by one or more of pain, swelling, and redness of a tissue types. In some embodiments, inflammatory disease refers to rheumatoid arthritis, Crohn's disease, sepsis, ulcerative colitis, irritable bowel disease, chronic irritable bowel syndrome, and allergies such as allergic rhinitis.

A "non-essential" amino acid residue is a residue that can be altered from the wild-type sequence of a polypeptide (e.g., a short domain of VIP) without abolishing or substantially altering its essential biological or biochemical activity (e.g., receptor binding or activation). An "essential" amino acid residue is a residue that, when altered from the wild-type sequence of the polypeptide, results in abolishing or substantially abolishing the polypeptide's essential biological or biochemical activity.

A "non-natural side chain" is a modified or synthetic chain of atoms joined by covalent bond to the α-carbon atom, β-carbon atom, or γ-carbon atom which does not make up the backbone of the polypeptide chain of amino acids. The natural side chain, or R group, of of alanine is a methyl group. In some embodiments, the non-natural side chain of the composition is a methyl group in which on e or more of the hydrogen atoms is replaced by a deuterium atom.

The term "polypeptide" encompasses two or more naturally or non-naturally-occurring amino acids joined by a covalent bond (e.g., an amide bond). Polypeptides as described herein include full-length proteins (e.g., fully processed pro-proteins or full-length synthetic polypeptides) as well as shorter amino acid sequences (e.g., fragments of naturally-occurring proteins or synthetic polypeptide fragments).

The term "salt" refers to acidic salts formed with inorganic and/or organic acids, as well as basic salts formed with inorganic and/or organic bases. Examples of these acids and bases are well known to those of ordinary skill in the art. Such acid addition salts will normally be pharmaceutically acceptable although salts of non-pharmaceutically acceptable acids may be of utility in the preparation and purification of the compound in question. Salts include those formed from hydrochloric, hydrobromic, sulphuric, phosphoric, citric, tartaric, lactic, pyruvic, acetic, succinic, fumaric, maleic, methanesulphonic and benzenesulphonic acids.

In some embodiments, salts of the compositions comprising either a secretin or VIP analog may be formed by reacting the free base, or a salt, enantiomer or racemate thereof, with one or more equivalents of the appropriate acid. In some embodiments, pharmaceutical acceptable salts of the present invention refer to analogs having at least one basic group or at least one basic radical. In some embodiments, pharmaceutical acceptable salts of the present invention comprise a free amino group, a free guanidino group, a pyrazinyl radical, or a pyridyl radical that forms acid addition salts. In some embodiments, the pharmaceutical acceptable salts of the present invention refer to analogs that are acid addition salts of the subject compounds with (for example) inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin. In some embodiments, the salts may be those that are physiologically tolerated by a patient. Salts according to the present invention may be found in their anhydrous form or as in hydrated crystalline form (i.e., complexed or crystallized with one or more molecules of water).

The term "subject" is used throughout the specification to describe an animal to whom treatment with the compositions according to the present invention is provided or administered. For treatment of those conditions which are specific for a specific subject, such as a human being, the term "patient" may be interchangeably used. In some instances in the description of the present invention, the term "patient" will refer to human patients. In some embodiments, the subject may be a mammal to whom the present invention is provided or administered. In some embodiments, the subject may be a non-human animal to whom the present invention is provided or administered.

The term "soluble" or "water soluble" refers to solubility that is higher than 1/100,000 (mg/ml). The solubility of a substance, or solute, is the maximum mass of that substance that can be dissolved completely in a specified mass of the solvent, such as water. "Practically insoluble" or "insoluble," on the other hand, refers to an aqueous solubility that is 1/10,000 (mg/ml) or less. Water soluble or soluble substances include, for example, polyethylene glycol. In some embodiments, the polypeptide of the claimed invention may be bound by polyethylene glycol to better solubilize the composition comprising the peptide.

The terms "treating" and "to treat", mean to alleviate symptoms, eliminate the causation either on a temporary or permanent basis, or to prevent or slow the appearance of symptoms. The term "treatment" includes alleviation, elimination of causation (temporary or permanent) of, or prevention of symptoms and disorders associated with any condition. The treatment may be a pre-treatment as well as a treatment at the onset of symptoms.

"Effective amount" refers to an amount of a compound, material, or composition, as described herein effective to achieve a particular biological result such as, but not limited to, biological results disclosed, described, or exemplified herein. Such results may include, but are not limited to, the effective reduction of symptoms associated with any of the disease states mentioned herein, as determined by any means suitable in the art. The effective amount of the composition may be dependent on any number of variables, including without limitation, the species, breed, size, height, weight, age, overall health of the subject, the type of formulation, the mode or manner or administration, the type and/or severity of the particular condition being treated, or the need to modulate the activity of the molecular pathway induced by association of the analog to its receptor. The appropriate effective amount can be routinely determined by those of skill in the art using routine optimization techniques and the skilled and informed judgment of the practitioner and other factors evident to those skilled in the art. A therapeutically effective dose of the analogs described herein may provide partial or complete biological activity as compared to the biological activity induced by the wild-type or naturally occurring polypeptides upon which the analogs are derived. A therapeutically effective dose of the analogs described herein may provide a sustained biochemical or biological affect and/or an increased resistance to degradation when placed in solution as compared with the normal affect observed when the naturally occurring and fully processed translated protein is administered to the same subject.

The term "fragment" refers to any analog of a naturally occurring polypeptide disclosed herein that comprises at least 4 amino acids identical to the naturally occurring polypeptide upon which the analog is based. The term "functional fragment" refers to any fragment of any analog of a naturally occurring polypeptide disclosed herein that comprises at least 4 amino acids identical to the naturally occurring polypeptide upon which the analog is based and shares the function of the naturally occurring polypeptide upon which the analog is based. In some embodiments, the compositions or pharmaceutical composition comprises an analog comprising at least one β-amino acid, wherein the analog is a fragment of VIP, a secretin family member, an interleukin, or any of the polypeptides disclosed in the instant application. In some embodiments, the compositions or pharmaceutical composition comprises an analog comprising at least one β-amino acid, wherein the analog is a fragment of VIP, a secretin family member, an interleukin, or any of the polypeptides disclosed in the instant application and wherein the fragment shares at least 4 contiguous amino acid residues with the naturally occurring polypeptide upon which the analog is based and wherein the fragment retains the biological activity of the naturally occurring polypeptide upon which the analog is based. In some embodiments, the VIP analog is a fragment that comprises between about 1 to about 27 amino acids of the naturally occurring VIP sequence. In some embodiments, the VIP analog is a fragment that comprises between about 1 to about 26 amino acids of the naturally occurring VIP sequence. In some embodiments, the VIP analog is a fragment that comprises between about 1 to about 25 amino acids of the naturally occurring VIP sequence. In some embodiments, the VIP analog is a fragment that comprises between about 1 to about 24 amino acids of the naturally occurring VIP sequence. In some embodiments, the VIP analog is a fragment that comprises between about 1 to about 23 amino acids of the naturally occurring VIP sequence. In some embodiments, the VIP analog is a fragment that comprises between about 1 to about 22 amino acids of the naturally occurring VIP sequence. In some embodiments, the VIP analog is a fragment that comprises between about 1 to about 21 amino acids of the naturally occurring VIP sequence. In some embodiments, the VIP analog is a fragment that comprises between about 1 to about 20 amino acids of the naturally occurring VIP sequence. In some embodiments, the VIP analog is a fragment that comprises between about 1 to about 19 amino acids of the naturally occurring VIP sequence. In some embodiments, the VIP analog is a fragment that comprises between about 1 to about 18 amino acids of the naturally occurring VIP sequence. In some embodiments, the VIP analog is a fragment that comprises between about 1 to about 19 amino acids of the naturally occurring VIP sequence. In some embodiments, the VIP analog is a fragment that comprises between about 1 to about 17 amino acids of the naturally occurring VIP sequence. In some embodiments, the VIP analog is a fragment that comprises between about 1 to about 16 amino acids of the naturally occurring VIP sequence. In some embodiments, the VIP analog is a fragment that comprises between about 1 to about 15 amino acids of the naturally occurring VIP sequence. In some embodiments, the VIP analog is a fragment that comprises between about 1 to about 14 amino acids of the naturally occurring VIP sequence. In some embodiments, the VIP analog is a fragment that comprises between about 1 to about 13 amino acids of the naturally occurring VIP sequence. In some embodiments, the VIP analog is a fragment that comprises between about 1 to about 12 amino acids of the naturally occurring VIP sequence. In some embodiments, the VIP analog is a fragment that comprises between about 1 to about 11 amino acids of the naturally occurring VIP sequence. In some embodiments, the VIP analog is a fragment that comprises between about 1 to about 10 amino acids of the naturally occurring VIP sequence. In some embodiments, the VIP analog is a fragment that comprises between about 1 to about 9 amino acids of the naturally occurring VIP sequence. In some embodiments, the VIP analog is a fragment of VIP that comprises between about 1 to about 8 amino acids of the naturally occurring VIP sequence. In some embodiments, the VIP analog is a fragment that comprises between about 1 to about 7 amino acids of the naturally occurring VIP sequence. In some embodiments, the VIP analog is a fragment that comprises between about 1 to about 6 amino acids of the naturally occurring VIP sequence. In some embodiments, the VIP analog is a fragment that comprises between about 1 to about 5 amino acids of the naturally occurring VIP sequence. In some embodiments, the VIP analog is a fragment that comprises between about 1 to about 4 amino acids of the naturally occurring VIP sequence. In some embodiments, the analog is modified with at least one PEG molecule on at least one of the non-natural amino acids.

The term "halo" or "halogen" refers to fluorine, chlorine, bromine or iodine or a radical thereof.

The term "alkyl" refers to a hydrocarbon chain that is a straight chain or branched chain, containing the indicated number of carbon atoms. For example, $C_1$-$C_{10}$ indicates that the group has from 1 to 10 (inclusive) carbon atoms in it. In the absence of any numerical designation, "alkyl" is a chain (straight or branched) having 1 to 20 (inclusive) carbon atoms in it. In some embodiments the alkyl group is chosen from: $C_1$-$C_{10}$, $C_2$-$C_{10}$, $C_3$-$C_{10}$, $C_4$-$C_{10}$, $C_5$-$C_{10}$, $C_6$-$C_{10}$, $C_7$-$C_{10}$, $C_8$-$C_{10}$, $C_9$-$C_{10}$, $C_1$-$C_{10}$, $C_1$-$C_2$, $C_1$-$C_3$, $C_1$-$C_4$, $C_1$-$C_5$, $C_1$-$C_6$, $C_1$-$C_7$, $C_1$-$C_8$, or $C_1$-$C_9$.

The term "alkylene" refers to a divalent alkyl (i.e., —R—).

The term "alkenyl" refers to a hydrocarbon chain that is a straight chain or branched chain having one or more carbon-carbon double bonds. The alkenyl moiety contains the indicated number of carbon atoms. For example, $C_2$-$C_{10}$ indicates that the group has from 2 to 10 (inclusive) carbon atoms in it. The term "lower alkenyl" refers to a $C_2$-$C_6$ alkenyl chain. In the absence of any numerical designation, "alkenyl" is a chain (straight or branched) having 2 to 20 (inclusive) carbon atoms in it.

The term "alkynyl" refers to a hydrocarbon chain that is a straight chain or branched chain having one or more carbon-carbon triple bonds. The alkynyl moiety contains the indicated number of carbon atoms. For example, $C_2$-$C_{10}$ indicates that the group has from 2 to 10 (inclusive) carbon atoms in it. The term "lower alkynyl" refers to a $C_2$-$C_6$ alkynyl chain. In the absence of any numerical designation, "alkynyl" is a chain (straight or branched) having about 2 to about 20 (inclusive) carbon atoms in it.

The term "aryl" refers to an aromatic ring system. In some embodiments, the aryl group of the analog include substituents, wherein 0, 1, 2, 3, 4, 5, 6, 7, 8, 9, or 10 atoms of each ring are substituted by a substituent. In some embodiments, the aryl group refers to a 6-carbon monocyclic or 10-carbon bicyclic aromatic ring system wherein 0, 1, 2, 3, or 4 atoms of each ring are substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl. "Arylalkyl" refers to an aryl group, as defined above, wherein one of the aryl group's hydrogen atoms has been replaced with an alkyl group, as defined above. Representative examples of an arylalkyl group include, but are not limited to, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-pentylphenyl, 3-pentylphenyl, 4-pentylphenyl, 2-isopropylphenyl, 3-isopropylphenyl, 4-isopropylphenyl, 2-isobutylphenyl, 3-isobutylphenyl, 4-isobutylphenyl, 2-sec-butylphenyl, 3-sec-butylphenyl, 4-sec-butylphenyl, 2-t-butylphenyl, 3-t-butylphenyl and 4-t-butylphenyl.

"Arylamido" refers to an aryl group, as defined above, wherein one of the aryl group's hydrogen atoms has been replaced with one or more —C(O)NH$_2$ groups. Representative examples of an arylamido group include 2-C(O)NH$_2$-phenyl, 3-C(O)NH$_2$-phenyl, 4-C(O)NH$_2$-phenyl, 2-C(O)NH$_2$-pyridyl, 3-C(O)NH$_2$-pyridyl, and 4-C(O)NH$_2$-pyridyl.

"Alkylheterocycle" refers to an alkyl group, as defined above, wherein one of the alkyl group's hydrogen atoms has been replaced with a heterocycle. Representative examples of an alkylheterocyclo group include, but are not limited to, —CH$_2$CH$_2$-morpholine, —CH$_2$CH$_2$piperidine, —CH$_2$CH$_2$CH$_2$-morpholine, and —CH$_2$CH$_2$CH$_2$-imidazole.

"Alkylamido" refers to an alkyl group, as defined above, wherein one of the alkyl group's hydrogen atoms has been replaced with a —C(O)NH$_2$ group. Representative examples of an alkylamido group include, but are not limited to, —CH$_2$C(O)NH$_2$, —CH$_2$CH$_2$C(O)NH$_2$, —CH$_2$CH$_2$CH$_2$C(O)NH$_2$, —CH$_2$CH$_2$CH$_2$C(O)NH$_2$, —CH$_2$CH$_2$CH$_2$CH$_2$C(O)NH$_2$, —CH$_2$CH(C(O)NH$_2$)CH$_3$, —CH$_2$CH(C(O)NH$_2$)CH$_2$CH$_3$, —CH(C(O)NH$_2$)

$CH_2CH_3$, —$C(CH_3)_2CH_2C(O)NH_2$, —$CH_2CH_2NHC(O)CH_3$, —$CH_2CH_2NHC(O)CH_2CH_3$, and —$CH_2CH_2NHC(O)CH=CH_2$.

"Alkylamino" refers to an alkyl group, as defined above, wherein one of the alkyl group's hydrogen atoms has been replaced with a —$NH_2$ group. Representative examples of an alkylamido group include, but are not limited to —$CH_2NH_2$, $CH_2CH_2NH_2$, $CH_2CH_2CH_2NH_2$, —$CH_2CH_2CH_2CH_2NH_2$, —$CH_2CH_2CH_2CH_2CH_2NH_2$.

"Alkylguanidino" refers to an alkyl group, as defined above, wherein one of the alkyl group's hydrogen atoms has been replaced with a —$NH_2(C=NH)NH_2$ group. Representative examples of an alkylamido group include, but are not limited to —$CH_2$ $NH_2(C=NH)NH_2$, $CH_2CH_2$ $NH_2(C=NH)NH_2$, $CH_2CH_2CH_2NH_2(C=NH)NH_2$, —$CH_2CH_2CH_2CH_2$ $NH_2(C=NH)NH_2$, —$CH_2CH_2CH_2CH_2CH_2$ $NH_2(C=NH)NH_2$. In some embodiments alkyl units can be found on the N atom(s) of the alkylamino or alkylguanidino groups (for example, —$CH_2NH(CH_3)$, $CH_2N(CH_3)_2$).

"Alkanol" refers to an alkyl group, as defined above, wherein one of the alkyl group's hydrogen atoms has been replaced with a hydroxyl group. Representative examples of an alkanol group include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH(OH)CH_3$, —$CH_2CH(OH)CH_2CH_3$, —$CH(OH)CH_3$ and —$C(CH_3)_2CH_2OH$.

"Alkylcarboxy" refers to an alkyl group, as defined above, wherein one of the alkyl group's hydrogen atoms has been replaced with a —COOH group. Representative examples of an alkylcarboxy group include, but are not limited to, —$CH_2COOH$, —$CH_2CH_2COOH$, —$CH_2CH_2CH_2COOH$, —$CH_2CH_2CH_2CH_2COOH$, —$CH_2CH(COOH)CH_3$, —$CH_2CH_2CH_2CH_2CH_2COOH$, —$CH_2CH(COOH)CH_2CH_3$, —$CH(COOH)CH_2CH_3$ and —$C(CH_3)_2CH_2COOH$.

The term "cycloalkyl" as employed herein includes saturated and partially unsaturated cyclic hydrocarbon groups having 3 to 12 carbons, 3 to 8 carbons, or 3 to 6 carbons, wherein the cycloalkyl group additionally is optionally substituted. Some cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2, 3, or 4 atoms of each ring are substituted by a substituent. Examples of heteroaryl groups include, but are not limited to, pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2 or 3 atoms of each ring are substituted by a substituent. Examples of heterocyclyl groups include, but are not limited to, piperazinyl, pyrrolidinyl, dioxanyl, morpholinyl, tetrahydrofuranyl, and the like.

The term "substituent" refers to a group replacing a second atom or group such as a hydrogen atom on any molecule, compound or moiety. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

In some embodiments, the composition comprises an analog comprises one or more asymmetric centers and thus occur as racemates and racemic mixtures, single enantiomers, individual diastereomers and diastereomeric mixtures. Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

All tautomeric forms and isomeric forms and mixtures, whether individual geometric isomers or stereoisomers or racemic or non-racemic mixtures, of a chemical structure or entire analog is intended, unless the specific stereochemistry or isomeric form is specifically indicated in the analog name, chemical name or structure. All such isomeric forms of these compositions are included in the present invention unless expressly provided otherwise. In some embodiments, the analogs of this invention are also represented in multiple tautomeric forms, in such instances, the invention includes all tautomeric forms of the analogs described herein (e.g., if alkylation of a ring system results in alkylation at multiple sites, the invention includes all such reaction products). All such isomeric forms of such analogs are included in the present invention unless expressly provided otherwise. All crystal forms of the analogs described herein are included in the present invention unless expressly provided otherwise. All deuterated form of the analogs described herein are included in the present invention. In some embodiments as least one hydrogen atom of the analog is replace with a deuterium atom. In some embodiments at least one hydrogen atom that is involved with a hydrogen-bond is replaced with a deuterium atom. In some embodiments at least one solvent exchangeable hydrogen atom is replaced with a deuterium atom. In some embodiments, the compositions, pharmaceutical compositions, and analogs contained therein comprise from about 1% to about 100% of their hydrogen replaced with deuterium atoms. In some embodiments, the compositions, pharmaceutical compositions, and analogs contained therein comprise from about 90% to about 100% of their hydrogen replaced with deuterium atoms. In some embodiments, the compositions, pharmaceutical compositions, and analogs contained therein comprise from about 80% to about 90% of their hydrogen replaced with deuterium atoms. In some embodiments, the compositions, pharmaceutical compositions, and analogs contained therein comprise from about 70% to about 80% of their hydrogen replaced with deuterium atoms. In some embodiments, the compositions, pharmaceutical compositions, and analogs contained therein comprise from about 60% to about 70% of their hydrogen replaced with deuterium atoms. In some embodiments, the compositions, pharmaceutical compositions, and analogs contained therein comprise from about 50% to about 60% of their hydrogen replaced with deuterium atoms. In some embodiments, the compositions, pharmaceutical compositions, and analogs contained therein comprise from about 40% to about 50% of their hydrogen replaced with deuterium atoms. In some embodiments, the compositions, pharmaceutical compositions, and analogs contained therein comprise from about 30% to about 40% of their hydrogen replaced with deuterium atoms. In some embodiments, the compositions, pharmaceutical compositions, and analogs contained therein comprise from about 20% to about 30% of their hydrogen replaced with deuterium atoms. In some embodiments, the compositions, pharmaceutical compositions, and analogs contained therein comprise from about 10% to about 20% of their hydrogen replaced with deuterium atoms. In some embodiments, the compositions, pharmaceutical compositions, and analogs contained therein comprise from about 5% to about 10% of their hydrogen replaced with deuterium atoms. If the analog of the claimed invention includes a methyl group, a deutrated analog may have one, two, or three of the hydrogens replaced by deuterium atoms. In some embodiments, the analog may contain one or more radioisotopes. In some embodiments, as least one hydrogen atom of the analog is replace with a tritium atom. In some embodiments, the compositions, pharmaceutical compositions, and analogs contained therein comprise from about 1% to about 5% of their hydrogens are replaced with tritium atoms.

As used herein, the terms "increase" and "decrease" mean, respectively, to cause a statistically significantly (i.e., p<0.15) increase or decrease of at least 1%, 2%, or 5%.

As used herein, the recitation of a numerical range for a variable is intended to convey that the invention may be practiced with the variable equal to any of the values within that range. Thus, for a variable which is inherently discrete, the variable is equal to any integer value within the numerical range, including the end-points of the range. Similarly, for a variable which is inherently continuous, the variable is equal to any real value within the numerical range, including the end-points of the range. As an example, and without limitation, a variable which is described as having values between 0 and 2 takes the values 0, 1 or 2 if the variable is inherently discrete, and takes the values 0.0, 0.1, 0.01, 0.001, $10^{-12}, 10^{-11}, 10^{-10}, 10^{-9}, 10^{-8}, 10^{-7}, 10^{-6}, 10^{-5}, 10^{-4}$ or any other real values $\geq 0$ and $\leq 2$ if the variable is inherently continuous.

As used herein, unless specifically indicated otherwise, the word "or" is used in the inclusive sense of "and/or" and not the exclusive sense of "either/or."

The term "biological activity" encompasses structural and functional properties of a macrocycle of the invention. Biological activity is, for example, structural stability, alpha-helicity, affinity for a target, resistance to proteolytic degradation, cell penetrability, intracellular stability, in vivo stability, or any combination thereof.

The terms "prodrug" or "prodrug derivative" mean a covalently-bonded derivative or carrier of the analog of the claimed invention or active drug substance which undergoes at least some biotransformation prior to exhibiting its pharmacological effect(s). In general, such prodrugs have metabolically cleavable groups and are rapidly transformed in vivo to yield the analog of the claimed invention, for example, by hydrolysis in blood, and generally include esters and amide analogs of the analogs. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the analogs using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987, each of which is incorporated herein by reference in their entireties. In some embodiments, the analog may be a prodrug that, when administered to the subject becomes biologically active.

In some embodiments, the invention relates to a composition or pharmaceutical composition comprising a pharmaceutically acceptable prodrug that, when administered to the subject becomes biologically active. The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

In some embodiments, the analog of the claimed invention is a pharmaceutically-acceptable acid addition salt. The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

In some embodiments, the analog of the claimed invention is a pharmaceutically-acceptable base addition salt. The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Suitable salts include the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. In some embodiments, the composition of the claimed invention comprises at least one organic nontoxic bases chosen from isopropylamine, diethylamine, ethanolamine, trimethylamine, dicyclohexylamine, choline, and caffeine.

The term "solvate" means a physical association of a compound with one or more solvent molecules or a complex of variable stoichiometry formed by a solute (the analog of the claimed invention) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, ethanolates, and methanolates.

The invention relates to compositions comprising an analog of a naturally occurring polypeptide sequence. In some embodiments the invention relates to a composition comprising an analog of a naturally occurring polypeptide sequence wherein the analog is from about 80% to 99% homologous to a naturally occurring polypeptide sequence. In some embodiments the invention relates to a composition comprising an analog of a naturally occurring polypeptide sequence wherein the analog is from about 80% to 85% homologous to a naturally occurring polypeptide sequence. In some embodiments the invention relates to a composition comprising an analog of a naturally occurring polypeptide sequence wherein the analog is from about 85% to 90% homologous to a naturally occurring polypeptide sequence. In some embodiments the invention relates to a composition comprising an analog of a naturally occurring polypeptide sequence wherein the analog is from about 90% to 95% homologous to a naturally occurring polypeptide sequence. In some embodiments the invention relates to a composition comprising an analog of a naturally occurring polypeptide sequence wherein the analog is from about 95% to 99% homologous to a naturally occurring polypeptide sequence. In some embodiments the invention relates to a composition comprising an analog of a naturally occurring polypeptide sequence wherein the analog is about 95%, 96%, 97%, 98%, or 99% homologous to a naturally occurring polypeptide sequence. In some embodiments the analog is derived from the naturally occurring polypeptide of the secretin family. In some embodiments, the analog is derived from the naturally occurring polypeptide of the secretin family and has at least one β-amino acid residue and/or at least one modified amino acid residue comprising APC or ACPC. Table 1 below illustrates the known wild-type sequences of each naturally occurring human secretin family members:

TABLE 1

Amino Acid Sequences for Peptides of the Secretin Family

GHRF
YADAIFTNSYRKVLGQLSARKLLQDIMSRQQGESNQERGARARL
(SEQ ID NO: 1)

GIP
YAEGTFISDYSIAMDKIHQQDFVNWLLAQKGKKNDWKHNITQ
(SEQ ID NO: 2)

GLP-1
HDEFERHAEGTFTSDVSSYLEGQAAQGFIAWLVKGRG (SEQ ID NO: 3)

Glucagon
HSQGTFTSDYSKYLDSRRAQDFVQWLMNT (SEQ ID NO: 4)

PACAP-27
HSDGIFTDSYSRYRKQMAVKKYLAAVL (SEQ ID NO: 5)

PACAP-38
HSDGIFTDSYSRYRKQMAVKKYLAAVLGKRYKQRVKNK (SEQ ID NO: 6)

PHM
HADGVFTSDFSKLLGQLSAKKYLESLM (SEQ ID NO: 7)

PrP
DVAHGILNEAYRKVLGQLSAGKHLQSLVA (SEQ ID NO: 8)

Secretin
HSDGTFTSELSRLREGARLQRLLQGLV (SEQ ID NO: 9)

VIP
HSDAVFTDNYTRLRKQMAVKKYLNSILN (SEQ ID NO: 10)

TABLE 2

Amino Acid Sequences for Interleukins

IL-10
>gi|10835141|ref|NP_000563.1|interleukin-10 precursor {Homo sapiens}
(SEQ ID NO: 11)
MHSSALLCCLVLLTGVRASPGQGTQSENSCTHFPGNLPNMLRDLRDAFSRVKTFFQMKDQL
DNLLLKESLLEDFKGYLGCQALSEMIQFYLEEVMPQAENQDPDIKAHVNSLGENLKTLRLRL
RRCHRFLPCENKSKAVEQVKNAFNKLQEKGIYKAMSEFDIFINYIEAYMTMKIRN TABLE 2-continued Amino Acid Sequences for Interleukins IL-4
>gi|4504669|ref|NP_000580.1|interleukin-4 isoform 1 precursor {Homo sapiens}
(SEQ ID NO: 12)
MGLTSQLLPPLFFLLACAGNFVHGHKCDITLQEIIKTLNSLTEQKTLCTELTVTDIFAASKNTT
EKETFCRAATVLRQFYSHHEKDTRCLGATAQQFHRHKQLIRFLKRLDRNLWGLAGLNSCPV
KEANQSTLENFLERLKTIMREKYSKCSS >gi|27477092|ref|NP_758858.1|interleukin-4 isoform 2 precursor {Homo sapiens}
(SEQ ID NO: 13)
MGLTSQLLPPLFFLLACAGNFVHGHKCDITLQEIIKTLNSLTEQKNTTEKETFCRAATVLRQF
YSHHEKDTRCLGATAQQFHRHKQLIRFLKRLDRNLWGLAGLNSCPVKEANQSTLENFLERL
KMREKYSKCSS IL-5
>gi|4504671|ref|NP_000870.1|interleukin 5 precursor {Homo sapiens}
(SEQ ID NO: 14)
MRMLLHLSLLALGAAYVYAIPTEIPTSALVKETLALLSTHRTLLIANETLRIPVPVHKNHQLCT
EEIFQGIGTLESQTVQGGTVERLFKNLSLIKKYIDGQKKKCGEERRRVNQFLDYLQEFLGVMN
TEWIIES IL-8
>gi|10834978|ref|NP_000575.1|interleukin-8 precursor {Homo sapiens}
(SEQ ID NO: 15)
MTSKLAVALLAAFLISAALCEGAVLPRSAKELRCQCIKTYSKPFHPKFIKELRVIESGPHCANT
EIIVKLSDGRELCLDPKENWVQRVVEKFLKRAENS IL-12A
>gi|24430219|ref|NP_000873.2|interleukin-12 subunit alpha precursor {Homo sapiens}
(SEQ ID NO: 16)
MWPPGSASQPPPSPAAATGLHPAARPVSLQCRLSMCPARSLLLVATLVLLDHLSLARNLPVA
TPDPGMFPCLHHSQNLLRAVSNMLQKARQTLEFYPCTSEEIDHEDITKDKTSTVEACLPLELT
KNESCLNSRETSFITNGSCLASRKTSFMMALCLSSIYEDLKMYQVEFKTMNAKLLMDPKRQI
FLDQNMLAVIDELMQALNFNSETVPQKSSLEEPDFYKTKIKLCILLHAFRIRAVTIDRVMSYL
NAS IL-12B
>gi|24497438|ref|NP_002178.2|interleukin-12 subunit beta precursor {Homo sapiens}
(SEQ ID NO: 17)
MCHQQLVISWFSLVFLASPLVAIWELKKDVYVVELDWYPDAPGEMVVLTCDTPEEDGITWT
LDQSSEVLGSGKTLTIQVKEFGDAGQYTCHKGGEVLSHSLLLLHKKEDGIWSTDILKDQKEP
KNKTFLRCEAKNYSGRFTCWWLTTISTDLTFSVKSSRGSSDPQGVTCGAATLSAERVRGDNK
EYEYSVECQEDSACPAAEESLPIEVMVDAVHKLKYENYTSSFFIRDIIKPDPPKNLQKPLKNS
RQVEVSWEYPDTWSTPHSYFSLTFCVQVQGKSKREKKDRVFTDKTSATVICRKNASISVRAQ
DRYYSSSWSEWASVPCS IL-2
>gi|28178861|ref|NP_000577.2|interleukin 2 precursor {Homo sapiens}
(SEQ ID NO: 18)
MYRMQLLSCIALSLALVTNSAPTSSSTKKTQLQLEHLLLDLQMILNGINNYKNPKLTRMLTF
KFYMPKKATELKHLQCLEEELKPLEEVLNLAQSKNFHLRPRDLISNINVIVLELKGSETTFMC
EYADETATIVEFLNRWITFCQSIISTLT IL-15
gi|26787984|ref|NP_751914.1|interleukin 15 preproprotein {Homo sapiens}
(SEQ ID NO: 19)
MRISKPHLRSISIQCYLCLLLNSHFLTEAGIHVFILGCFSAGLPKTEANWVNVISDLKKIEDLIQ
SMHIDATLYTESDVHPSCKVTAMKCFLLELQVISLESGDASIHDTVENLIILANNSLSSNGNVT
ESGCKECEELEEKNIKEFLQSFVHIVQMFINTS gi|10835153|ref|NP_000576.1|interleukin 15 preproprotein {Homo sapiens}
(SEQ ID NO: 20)
MRISKPHLRSISIQCYLCLLLNSHFLTEAGIHVFILGCFSAGLPKTEANWVNVISDLKKIEDLIQ
SMHIDATLYTESDVHPSCKVTAMKCFLLELQVISLESGDASIHDTVENLIILANNSLSSNGNVT
ESGCKECEELEEKNIKEFLQSFVHIVQMFINTS IL-17
>gi|4504651|ref|NP_002181.1|interleukin 17A precursor {Homo sapiens}
(SEQ ID NO: 21)
MTPGKTSLVSLLLLLSLEAIVKAGITIPRNPGCPNSEDKNFPRTVMVNLNIHNRNTNTNPKRSS
DYYNRSTSPWNLHRNEDPERYPSVIWEAKCRHLGCINADGNVDYHMNSVPIQQEILVLRREP
PHCPNSFRLEKILVSVGCTCVTPIVHHVA IL-18
>gi|4504653|ref|NP_001553.1|interleukin-18 proprotein {Homo sapiens}
(SEQ ID NO: 22)
MAAEPVEDNCINFVAMKFIDNTLYFIAEDDENLESDYFGKLESKLSVIRNLNDQVLFIDQGNR
PLFEDMTDSDCRDNAPRTIFIISMYKDSQPRGMAVTISVKCEKISTLSCENKIISFKEMNPPDNI TABLE 2-continued Amino Acid Sequences for Interleukins

KDTKSDIIFFQRSVPGHDNKMQFESSSYEGYFLACEKERDLFKLILKKEDELGDRSIMFTVQN
ED

Interleukin-18-binding protein isoform a precursor {Homo sapiens}
>gi|89111125|ref|NP_001034748.1|interleukin-18-binding protein isoform a precursor {Homo
sapiens}
(SEQ ID NO: 23)
MTMRHNWTPDLSPLWVLLLCAHVVTLLVRATPVSQTTTAATASVRSTKDPCPSQPPVFPAA
KQCPALEVTWPEVEVPLNGTLSLSCVACSRFPNFSILYWLGNGSFIEHLPGRLWEGSTSRERG
STGTQLCKALVLEQLTPALHSTNFSCVLVDPEQVVQRHVVLAQLWAGLRATLPPTQEALPSS
HSSPQQQ IL-21
>gi|11141875|ref|NP_068575.1|interleukin-21 {Homo sapiens}
(SEQ ID NO: 24)
MRSSPGNMERIVICLMVIFLGTLVHKSSSQGQDRHMIRMRQLIDIVDQLKNYVNDLVPEFLPA
PEDVETNCEWSAFSCFQKAQLKSANTGNNERIINVSIKKLKRKPPSTNAGRRQKHRLTCPSCD
SYEKKPPKEFLERFKSLLQKMIHQHLSSRTHGSEDS IL-22
>gi|10092625|ref|NP_065386.1|interleukin-22 precursor {Homo sapiens}
(SEQ ID NO: 25)
MAALQKSVSSFLMGTLATSCLLLLALLVQGGAAAPISSHCRLDKSNFQQPYITNRTFMLAKE
ASLADNNTDVRLIGEKLFHGVSMSERCYLMKQVLNFTLEEVLFPQSDRFQPYMQEVVPFLAR
LSNRLSTCHIEGDDLHIQRNVQKLKDTVKKLGESGEIKAIGELDLLFMSLRNACI IL-24
>gi|5803086|ref|NP_006841.1|interleukin 24 isoform 1 precursor {Homo sapiens}
(SEQ ID NO: 26)
MNFQQRLQSLWTLARPFCPPLLATASQMQMVVLPCLGFTLLLWSQVSGAQGQEFHFGPCQV
KGVVPQKLWEAFWAVKDTMQAQDNITSARLLQQEVLQNVSDAESCYLVHTLLEFYLKTVF
KNYHNRTVEVRTLKSFSTLANNFVLIVSQLQPSQENEMFSIRDSAHRRFLLFRRAFKQLDVEA
ALTKALGEVDILLTWMQKFYKL >gi|31317246|ref|NP_851936.1|interleukin-24 isoform 2 {Homo sapiens}
(SEQ ID NO: 27)
MFSIRDSAHRRFLLFRRAFKQLDVEAALTKALGEVDILLTWMQKFYKL IL-26
>gi|8923756|ref|NP_060872.1|interleukin-26 precursor {Homo sapiens}
(SEQ ID NO: 28)
MLVNFILRCGLLLVTLSLAIAKHKQSSFTKSCYPRGTLSQAVDALYIKAAWLKATIPEDRIKNI
RLLKKKTKKQFMKNCQFQEQLLSFFMEDVFGQLQLQGCKKIRFVEDFHSLRQKLSHCISCAS
SAREMKSITRMKRIFYRIGNKGIYKAISELDILLSWIKKLLESSQ

TABLE 3

Amino Acid Sequences for Anti-inflammatory Neuropeptides pro-opiomelanocortin preproprotein {Homo sapiens}
>gi|4505949|ref|NP_000930.1|pro-opiomelanocortin preproprotein {Homo sapiens}
(SEQ ID NO: 29)
MPRSCCSRSGALLLALLLQASMEVRGWCLESSQCQDLTTESNLLECIRACKPDLSAE
TPMFPGNGDEQPLTENPRKYVMGHFRWDRFGRRNSSSSGSSGAGQKREDVSAGEDC
GPLPEGGPEPRSDGAKPGPREGKRSYSMEHFRWGKPVGKKRRPVKVYPNGAEDESA
EAFPLEFKRELTGQRLREGDGPDGPADDGAGAQADLEHSLLVAAEKKDEGPYRMEH
FRWGSPPKDKRYGGFMTSEKSQTPLVTLFKNAIIKNAYKKGE Active form:
α-MSH SYSMEHFRWGKPV-NH2 (SEQ ID NO: 581)

>gi|490074|emb|CAA00890.1|ACTH {Homo sapiens}
GPSYSMEHFRWGKPVGKKRRPVKVYPNGAEDESAEAFPLEF urocortin preproprotein {Homo sapiens}
>gi|4507803|ref|NP_003344.1|urocortin preproprotein {Homo sapiens}
(SEQ ID NO: 30)
MRQAGRAALLAALLLLVQLCPGSSQRSPEAAGVQDPSLRWSPGARNQGGGARALL
LLLAERFPRRAGPGRLGLGTAGERPRRDNPSLSIDLTFHLLRTLLELARTQSQRERA
EQNRIIFDSVGK Active form:
Urocortin DNPSLSIDLTFHLLRTLLELADTQSQRERAQNRIIFDSV- (SEQ ID NO: 1336)
NH2

TABLE 3-continued

Amino Acid Sequences for Anti-inflammatory Neuropeptides urocortin-2 preproprotein {Homo sapiens}
>gi|15082240|ref|NP_149976.1|urocortin-2 preproprotein {Homo sapiens}
(SEQ ID NO: 31)
MTRCALLLLMVLMLGRVLVVPVTPIPTFQLRPQNSPQTTPRPAASESPSAAPTWPWA
AQSHCSPTRHPGSRIVLSLDVPIGLLQILLEQARARAAREQATTNARILARVGHC urocortin-3 preproprotein {Homo sapiens}
>gi|45238845|ref|NP_444277.2|urocortin-3 preproprotein {Homo sapiens}
(SEQ ID NO: 32)
MLMPVHFLLLLLLLLGGPRTGLPHKFYKAKPIFSCLNTALSEAEKGQWEDASLLSKR
SFPHYLRSRDASSGEEEEGKEKKTFPISGARGGARGTRYRYVSQAQPRGKPRQDTAKS
PHRTKFTLSLDVPTNIMNLLFNIAKAKNLRAQAAANAHLMAQIGRKK adrenomedullin precursor {Homo sapiens}
>gi|4501945|ref|NP_001115.1|adrenomedullin precursor {Homo sapiens}
(SEQ ID NO: 33)
MKLVSVALMYLGSLAFLGADTARLDVASEFRKKWNKWALSRGKRELRMSSSYPTG
LADVKAGPAQTLIRPQDMKGASRSPEDSSPDAARIRVKRYRQSMNNFQGLRSFGCRF
GTCTVQKLAHQIYQFTDKDKDNVAPRSKISPQGYGRRRRRSLPEAGPGRTLVSSKPQ
AHGAPAPPSGSAPHFL gi|41152110|ref|NP_079142.2|adrenomedullin 2 precursor {Homo sapiens}
(SEQ ID NO: 1337)
MARIPTAALGCISLLCLQLPGSLSRSLGGDPRPVKPREPPARSPSSSLQPRHPAPRPVV
WKLHRALQAQRGAGLAPVMGQPLRDGGRQHSGPRRHSGPRRTQAQLLRVGCVLGT
CQVQNLSHRLWQLMGPAGRQDSAPVDSSPHSYG Active portion:
Adrenomedullin YRQSMNNFQGLRFG{CRFGTC}TVQKLAHQIYQFTDKDKDNVAPRNKISPQ (SEQ ID NO: 1338)
GY-NH2 cortistatin preproprotein {Homo sapiens}
>gi|41327683|ref|NP_001293.2|cortistatin preproprotein {Homo sapiens}
(SEQ ID NO: 34)
MYRHKNSWRLGLKYPPSSKEETQVPKTLISGLPGRKSSSRVGEKLQSAHKMPLSPGL
LLLLLSGATATAALPLEGGPTGRDSEHMQEAAGIRKSSLLTFLAWWFEWTSQASAGP
LIGEEAREVARRQEGAPPQQSARRDRMPCRNFFWKTFSSCK Active form:
Cortistatin DRMP{CKNFFWKTFSSC}K-NH2 (SEQ ID NO: 1339)

somatostatin preproprotein {Homo sapiens}
>gi|4507243|ref|NP_001039.1|somatostatin preproprotein {Homo sapiens}
(SEQ ID NO: 35)
MLSCRLQCALAALSIVLALGCVTGAPSDPRLRQFLQKSLAAAAGKQELAKYFLAELL
SEPNQTENDALEPEDLSQAAEQDEMRLELQRSANSNPAMAPRERKAGCKNFFWKTF
TSC appetite-regulating hormone isoform 1 preproprotein {Homo sapiens}
>gi|7706519|ref|NP_057446.1|appetite-regulating hormone isoform 1 preproprotein {Homo sapiens}
(SEQ ID NO: 36)
MPSPGTVCSLLLLGMLWLDLAMAGSSFLSPEHQRVQQRKESKKPPAKLQPRALAGW
LRPEDGGQAEGAEDELEVRFNAPFDVGIKLSGVQYQQHSQALGKFLQDILWEEAKE
APADK appetite-regulating hormone isoform 2 preproprotein {Homo sapiens}
>gi|201860279|ref|NP_001128413.1|appetite-regulating hormone isoform 2 preproprotein
{Homo sapiens}
(SEQ ID NO: 37)
MPSPGTVCSLLLLGMLWLDLAMAGSSFLSPEHQRVQRKESKKPPAKLQPRALAGWL
RPEDGGQAEGAEDELEVRFNAPFDVGIKLSGVQYQQHSQALGKFLQDILWEEAKEA
PADK appetite-regulating hormone isoform 3 preproprotein {Homo sapiens}
>gi|201860281|ref|NP_001128416.1|appetite-regulating hormone isoform 3 preproprotein
{Homo sapiens}
(SEQ ID NO: 38)
MFTCWWSYLRSTLAAVPGEASRVQQRKESKKPPAKLQPRALAGWLRPEDGGQAEG
AEDELEVRFNAPFDVGIKLSGVQYQQHSQALGKFLQDILWEEAKEAPADK appetite-regulating hormone isoform 4 preproprotein {Homo sapiens}
>gi|201860283|ref|NP_001128417.1|appetite-regulating hormone isoform 4 preproprotein
{Homo sapiens}
(SEQ ID NO: 39)
MFTCWWSYLRSTLAAVPGEASRVQRKESKKPPAKLQPRALAGWLRPEDGGQAEGA
EDELEVRFNAPFDVGIKLSGVQYQQHSQALGKFLQDILWEEAKEAPADK TABLE 3-continued Amino Acid Sequences for Anti-inflammatory Neuropeptides appetite-regulating hormone isoform 5 preproprotein {Homo sapiens}
>gi|201860285|ref|NP_001128418.1|appetite-regulating hormone isoform 5 preproprotein
{Homo sapiens}
(SEQ ID NO: 40)
MFTCWWSYLRSTLAAVPGEASRVQFNAPFDVGIKLSGVQYQQHSQALGKFLQDILW
EEAKEAPADK ghrelin {Homo sapiens}
>gi|53794041|gb|AAU93610.1|ghrelin {Homo sapiens}
(SEQ ID NO: 41)
MPSPGTVCSLLLLGMLWLDLAMAGSSFLSPEHQRVQ Active form: Ghrelin GSSFLSPEHQRVQQRKESKKPPAKLPQR-NH2 (SEQ ID NO: 567)
(Expert Opin. Biol. Ther. (2007) 7(4): 461-478)

In some embodiments, the composition comprises a VIP analog. In some embodiments, the composition comprises a Secretin analog. In some embodiments, the composition comprises a PrP analog. In some embodiments, the composition comprises a PrP analog. In some embodiments, the composition comprises a PHM analog. In some embodiments, the composition comprises a PACAP-27 analog. In some embodiments, the composition comprises a PACAP-38 analog. In some embodiments, the composition comprises a Glucagon analog. In some embodiments, the composition comprises a GLP-1 analog. In some embodiments, the composition comprises a GIP analog. In some embodiments, the composition comprises a GHRF analog. In some embodiments, the composition comprises a secretin family analog that is derived from mammalian amino acid sequences of secretin family polypeptides other than humans. In some embodiments, the secretin family analog may be selective for one particular receptor versus another. In some embodiments, the composition comprises a secretin analog wherein the secretin analog is selective for, or preferentially binds to, VPAC1, VPAC2, PAC1, VIPR1, or VIPR2. In some embodiments, the composition comprises a secretin analog wherein the secretin analog is selective for, or preferentially binds, VPAC1. In some embodiments, the composition comprises a secretin analog wherein the secretin analog is selective for, or preferentially binds, VPAC2. In some embodiments, the composition comprises a secretin analog wherein the secretin analog is selective for, or preferentially binds, PAC1. In some embodiments, the composition comprises a secretin analog wherein the secretin analog is selective for, or preferentially binds, VIPR1. In some embodiments, the composition comprises a secretin analog wherein the secretin analog is selective for, or preferentially binds, VIPR2. In some embodiments, the secretin analog is an agonist of at least one of the following: VPAC1, VPAC2, PAC1, VIPR1, or VIPR2. In some embodiments, the the secretin analog is an antagonist of at least one of the following: VPAC1, VPAC2, PAC1, VIPR1, or VIPR2.

In some embodiments, the composition comprises a apolipoprotein A-1 analog. In some embodiments the apoA-1 analog is from about 80% to about 99% homologous to the human sequence of apolipoprotein A-1. In some embodiments the apoA-1 analog is from about 80% to about 85% homologous to the human sequence of apolipoprotein A-1. In some embodiments the apoA-1 analog is from about 85% to about 90% homologous to the human sequence of apolipoprotein A-1. In some embodiments the apoA-1 analog is from about 90% to about 95% homologous to the human sequence of apolipoprotein A-1. In some embodiments the apoA-1 analog is from about 95% to about 99% homologous to the human sequence of apolipoprotein A-1. In some embodiments the apoA-1 analog is about 95%, 96%, 97%, 98%, or 99% homologous to the human sequence of apolipoprotein A-1. In some embodiments the apoA-1 analog is from about 80% to about 85% homologous to the following of apolipoprotein A-1 analog: DWFKAFYDKVAEK-FKEAF (SEQ ID NO:533).

In some embodiments, the composition comprises a cytokine or interleukin analog. In some embodiments the cytokine or interleukin analog is from about 80% to about 99% homologous to the human sequence of cytokine or interleukin. In some embodiments the cytokine or interleukin analog is from about 80% to about 85% homologous to the human sequence of a cytokine or interleukin. In some embodiments the cytokine or interleukin analog is from about 85% to about 90% homologous to the human sequence of a cytokine or interleukin. In some embodiments the cytokine or interleukin analog is from about 90% to about 95% homologous to the human sequence of a cytokine or interleukin. In some embodiments the cytokine or interleukin analog is from about 95% to about 99% homologous to the human sequence of a cytokine or interleukin. In some embodiments the cytokine or interleukin analog is about 95%, 96%, 97%, 98%, or 99% homologous to the human sequence of a cytokine or interleukin. In some embodiments the cytokine or interleukin analog is from about 80% to about 99% homologous to a cytokine or interleukin chosen from IL-2, IL-4, IL-5, IL-6, IL-7, IL-10, IL-12, IL-15, IL-17, IL-18, IL-21, IL-22, IL-23, IL-24, IL-26, IFN-γ, TNF-α, and TNF-β. In some embodiments, the cytokine or interleukin analog comprises at least one non-natural amino acid within the structure that corresponds to helix F in the naturally occurring polypeptide sequence upon which the analog is based or derived. In some embodiments, the cytokine or interleukin analog comprises at least one non-natural amino acid within the structure that corresponds to AB loop in the naturally occurring polypeptide sequence upon which the analog is based or derived.

The invention relates to the manufacturing of a synthetic polypeptide which is an amino acid sequence that corresponds to the sequence of a biologically active polypeptide or fragment thereof. In the synthetic polypeptide, from about 14% to about 50% of the α-amino acid residues found in the biologically active polypeptide or fragment are replaced with β-amino acid residues. In another embodiment of the invention, the α-amino acid residues and the β-amino acid residues are distributed in a repeating pattern. Human cells are then contacted with the synthetic polypeptide to induce the biochemical pathway or biological activity ordinarily induced by the naturally occurring polypeptide upon which the analog is based.

The compositions of the invention may be prepared by the synthetic chemical procedures described herein, as well as other procedures similar to those which may be used for making β-amino acid peptides. Such procedures include both solution and solid phase procedures, e.g., using either Boc and Fmoc methodologies. The compounds of the invention may be synthesized using solid phase synthesis techniques. Fmoc-N-Protected β-amino acids can be used to synthesize poly-α/β-peptides by conventional manual solid-phase synthesis procedures under standard conditions on any number of solid supports, including ortho-chloro-trityl chloride resin. Esterification of Fmoc-β-amino acids with the ortho-chloro-trityl resin can be performed according to the method of Barlos et. al., Tetrahedron Lett., 1989, 30, 3943. The resin (150 mg, 1.05 mmol Cl) is swelled in 2 ml $CH_2Cl_2$ for 10 min. A solution of the Fmoc-protected β-amino acid in $CH_2Cl_2$ and $iPr_2EtN$ are then added successively and the suspension is mixed under argon for 4 h. Subsequently, the resin is filtered and washed with $CH_2Cl_2/MeOH/iPr_2EtN$ (17:2:1, 3×3 min), $CH_2Cl_2$ (3×3 min), DMF (2×3 min), $CH_2Cl_2$ (3×3 min), and MeOH (2×3 min). The substitution of the resin is determined on a 3 mg sample by measuring the absorbance of the dibenzofulvene adduct at 300 nm. The Fmoc group is removed using 20% piperidine in DMF (4 ml, 2×20 min) under Ar bubbling. The resin is then filtered and washed with DMF (6×3 min). For each coupling step, a solution of the β-amino acid (3 equiv.), BOP (3 equiv.) and HOBT (3 equiv.) in DMF (2 ml) and $iPr_2EtN$ (9 eq) are added successively to the resin and the suspension is mixed for 1 h under Ar. Monitoring of the coupling reaction is performed with 2,4,6-trinitrobenzene-sulfonic acid (TNBS) (W. S. Hancock and J. E. Battersby, Anal. Biochem. (1976), 71, 260). In the case of a positive TNBS test (indicating incomplete coupling), the suspension is allowed to react for a further 1 h. The resin is then filtered and washed with DMF (3×3 min) prior to the following Fmoc deprotection step. After the removal of the last Fmoc protecting group, the resin is washed with DMF (6×3 min), $CH_2Cl_2$ (3×3 min), $Et_2O$ (3×3 min) and dried under vacuum for 3 h. Finally the peptides are cleaved from the resin using 2% TFA in $CH_2Cl_2$ (2 ml, 5×15 min) under Ar. The solvent is removed and the oily residues are triturated in ether to give the crude α-/β-polypeptides. The compounds are further purified by HPLC.

The compositions of the invention may be prepared by the synthetic chemical procedures described herein, as well as other procedures similar to those which may be used for making β-amino acid peptides. Such procedures include both solution and solid phase procedures, e.g., using either Boc or Fmoc methodologies. The compounds of the invention may be synthesized using solid phase synthesis techniques. Fmoc-N-Protected β-amino acids can be used to synthesize poly-α/β-peptides by conventional manual solid-phase synthesis procedures under standard conditions on any number of solid supports, including ortho-chloro-trityl chloride resin, Wang resin (NovaBiochem 0.75 mmol substitution) and Rink amid resin (NovaBiochem 0.55 mmol substitution). Resin is typically swelled in 100% DMF for 30 minutes then deprotected using 20% piperidine in DMF for 2 minutes at 800 (3×). Fmoc protected amino acids (natural or non-natural) can then be coupled to the resin using a cocktail of AA:HATU:DIEA:Resin (3:2.5:4:1, LiCL 0.8M final concentration) in DMF for 2 minutes at 70° (3×). The resin is then washed (3×) with DMF, DCM (dichloromethane) (3×) and again with DMF (3×) between deprotection and coupling steps. Monitoring of the coupling reaction is performed with 2,4,6-trinitrobenzene-sulfonic acid (TNBS) (W. S. Hancock and J. E. Battersby, Anal. Biochem. (1976), 71, 260). In the case of a positive TNBS test (indicating incomplete coupling), the suspension is allowed to react for another three times. This process is repeated until the desired product has been achieved. After the removal of the last Fmoc protecting group, the resin is washed with DMF (3×), $CH_2Cl_2$ (3×) and DMF again (3×). The remaining free-amine group is then acetylated using a cocktail of DIEA:$Ac_2O$ (1:1) for 5 minutes at room temperature. Full-length peptides were then cleaved from solid support using TFA:TIS:$H_2O$ (95:2.5:2.5) for 150 minutes, precipitated in cold ethyl ether and lyophilized. The polymer was reconstituted in a 1:1 solution of A:B (A: $H_2O$, 0.1% TFA) (B: 90:10:0.1 acetonitrile/$H_2O$/TFA).

The compositions described herein may be prepared by successive amide bond-forming procedures in which amide bonds are formed between the β-amino group of a first β-amino acid residue or a precursor thereof and the α-carboxyl group of a second β-amino acid residue or α-amino acid residue or a precursor thereof. The amide bond-forming step may be repeated as many times, and with specific α-amino acid residues and/or β-amino acid residues and/or precursors thereof, as required to give the desired α/β-polypeptide. Also analogs comprising two, three, or more amino acid residues (α- or β-) may be joined together to yield larger analogs comprising any combination of α-, or β-amino acids. Cyclic compounds may be prepared by forming peptide bonds between the N-terminal and C-terminal ends of a previously synthesized linear polypeptide or through the disulfide crosslinking of sidechains of non-adjacent residues. $β^3$-amino acids may be produced enantioselectively from corresponding β-amino acids. For instance, by Arndt-Eisert homologation of N-protected α-amino acids. Homologation may be followed by coupling of the reactive diazoketone intermediate of the Wolff rearrangement with a R-amino acid residue.

Figure 5:
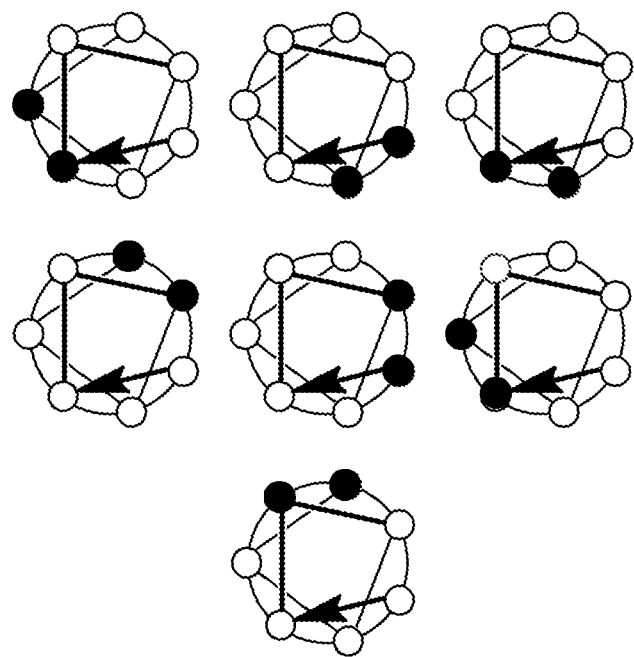
FIG. 5 illustrates helical wheel diagrams of repeating patterns of α- or β-amino acids residues in alignment along one longitudinal axis of a folded molecular structure from N-terminus to C-terminus when the unnatural polypeptides adopt a helical conformation, where the position of β-amino acids are represented by solid dots.

In some embodiments, the analog of the invention comprises a repeating pattern of the β-amino acid residues in alignment on a longitudinal axis of the analog in order to constrain the conformation of the analog in an active state or to avoid disruption of the active site. That is, in the folded structure adopted by the analogs of the present invention, the repeating pattern of α- or β-amino acids residues disposes the synthetic non-natural amino acid residues in alignment along one longitudinal axis of the folded molecular structure from N-terminus to C-terminus when the unnatural polypeptides adopt a helical conformation. In some embodiments, the analog of the invention comprises the alignment of β-amino acids or ACPC or APC along a longitudinal axis of the folded molecular structure from N-terminus to C-terminus when the polypeptide adopts a helical conformation chosen from any of the conformations shown in FIG. 5, wherein the residue positions in a solid dot represent non-natural amino acid residues. In some embodiments, the analog of the invention comprises the alignment along a longitudinal axis of the folded molecular structure from N-terminus to C-terminus when the polypeptide adopts a helical conformation chosen from any of the conformations shown in FIG. 5, wherein the positions with solid dots represent $β^3$-amino acid residues. In some embodiments, the analog of the invention comprises the alignment along a longitudinal axis of the folded molecular structure from N-terminus to C-terminus when the polypeptide adopts a helical conformation chosen from any of the conformations shown in FIG. 5, wherein the positions with solid dots represent β-amino acid residues.

The repeating pattern of β-amino acid residues and α-amino acid residues may be a pattern of from about two to about seven residues in length, such as (βαααααα), (βαααβαα), (ααααααβ), (ααααβ), (αααβ), (ααβ), (ααβαααβ), (ααβαβαβ), and (αβ). All unique patterns of α- or β-amino acids residues from about two to about fourteen residues in length are explicitly within the scope of the invention. All unique patterns of α- or β-amino acids residues from about two to about seven residues in length are explicitly within the scope of the invention. In some embodiments, the composition comprises an analog, wherein the analog wherein the analog comprises a repetitive pattern of sequential β-amino acids from the amino-terminus to the carboxy-terminus, and wherein the analog is an agonist or antagonist of the receptor to which it selectively binds or associates. For instance, in some embodiments, the analog is a VIP analog or a functional fragment thereof that selectivity binds to VPAC1, VPAC2, or PAC1 and wherein the VIP analog of functional fragment thereof is an agonist or antagonist of at least one receptor chosen from: VPAC1, VPAC2, and PAC1. In some embodiments, the methods of treatment or prevention include administration of VIP analogs, wherein the VIP analog is an an agonist or antagonist of at least one receptor chosen from: VPAC1, VPAC2, and PAC1. In some embodiments, the composition comprises an analog, wherein the analog wherein the analog comprises a repetitive pattern of sequential β-amino acids from the amino-terminus to the carboxy-terminus chosen from the following: ααααααβ, αααααβα, ααααβαα, αααβααα, ααβαααα, αβααααα, βααααααα, ααααα ββ, αααα ββα, αααββαα, ααββααα, αββαααα, ββαααααα, βαααααβ, βαααα βα, βααα βαα, βααβααα, βαβαααα, αβααααβ, αβαααβα, αβααβαα, αβαβααα, ααβαααβ, ααβααβα, ααβαβαα, αααβααβ, αααβαβα, and αααα βββ. In some embodiments, the composition comprises an analog, wherein the analog comprises a repetitive pattern of sequential β-amino acids from the amino-terminus to the carboxy-terminus chosen from the following: ββααβαααβαααβααα, βααβαααβααβαααββαα, βααβαααβααβαααβββα, and βααβαααβααβαααββββ. In some embodiments, the composition comprises an analog, wherein the analog comprises a repetitive pattern of sequential β-amino acids from the amino-terminus to the carboxy-terminus chosen from the following: ββααβααυβααβαααβααβ; βαββαααβααβαααβααβ; βααββααβααβαααβααβ; βααβαβαβααβαααβααβ; βααβααβαβααβαααβααβ; βααβαααββααβαααβααβ; βααβαααβαββααβαααβααβ; βααβαααβαβαβααβ; βααβαααβααβαααβ ββαβ; and βααβαααβααβαααβαββ. In some embodiments, the composition comprises an analog, wherein the analog comprises a repetitive pattern of sequential β-amino acids from the amino-terminus to the carboxy-terminus chosen from the following: ββααβααβαααβααβααα; βαβαβααβαααβααβααα; βααββααβαααβααβααα; βαααββαααβααβααα; βαααβαββααβαααβααα; βαααβααββααβααα; βαααβααβαβαβααα; βαααβααββααβαααα; βαααβααβααββαβααα; βαααβααβαααβββααα; βαααβααβαααβααβ βαα; βαααβααβαααβααβαβα; and βαααβαααβααβααβ.

In some embodiments, the composition comprises an analog, wherein the analog comprises a repetitive pattern of sequential β-amino acids from the amino-terminus to the carboxy-terminus chosen from the following: ββαβαααβααβαααβααα, βααβαααβααβαααβ βαα, βααβαααβααβαααβββα, and βααβαααβααβαααββββ, wherein any α-amino acid residue may be a non-natural amino acid. In some embodiments, the composition comprises an analog, wherein the analog comprises a repetitive pattern of sequential β-amino acids from the amino-terminus to the carboxy-terminus chosen from the following: βααβαααβααβαααβααα, βααβαααβααβαααββαα, βααβαααβααβαααβββα, and βααβαααβααβαααββββ, wherein at least one α-amino acid residue may be a non-natural amino acid. In some embodiments, the composition comprises an analog, wherein the analog comprises a repetitive pattern of sequential β-amino acids from the amino-terminus to the carboxy-terminus chosen from the following: βααβαααβααβαααβααα, βααβαααβααβαααββαα, βααβαααβααβαααβββα, and βααβαααβααβαααββββ, wherein from about 1 to about 10 α-amino acid residues may be a non-natural amino acid. In any of the above-mentioned patterns one or more of the β-amino acid residues may be replaced or modified with cyclic β-amino acid (cyclically-constrained beta amino acid), such as APC or ACPC.

In some embodiments, the composition comprises a VIP analog, wherein the analog comprises the following repetitive pattern of sequential β-amino acids from the amino-terminus to the carboxy-terminus: βααβαααβααβαααβααβ. In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid, $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta-3, beta-2, cyclic or heterocyclic beta-amino acid; $\alpha_1$=any alpha amino acid; $\alpha_2$=any alpha amino acid; $\beta_2$=any beta-3, beta-2, cyclic or heterocyclic beta-amino acid; $\alpha_3$=any alpha amino acid; $\alpha_4$=any alpha amino acid; $\alpha_5$=any alpha amino acid; $\beta_3$=any beta-3, beta-2, cyclic or heterocyclic beta-amino acid; $\alpha_6$=any alpha amino acid; m=any alpha amino acid; $\beta_4$=any beta-3, beta-2, cyclic or heterocyclic beta-amino acid; $\alpha_8$=any alpha amino acid; $\alpha_9$=any alpha amino acid; $\alpha_{10}$=any alpha amino acid; $\beta_5$=any beta-3, beta-2, cyclic or heterocyclic beta-amino acid; $\alpha_{11}$=any alpha amino acid; $\alpha_{12}$=any alpha amino acid; $\beta_6$=any beta-3, beta-2, cyclic or heterocyclic beta-amino acid.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta-3 amino acid; $\alpha_1$=any alpha amino acid; $\alpha_2$=any alpha amino acid; $\beta_2$=any beta-3 amino acid; $\alpha_3$=any alpha amino acid; $\alpha_4$=any alpha amino acid; $\alpha_5$=any alpha amino acid; $\beta_3$=any beta-3 amino acid; $\alpha_6$=any alpha amino acid; $\alpha_7$=any alpha amino acid; $\beta_4$=any beta-3 amino acid; $\alpha_8$=any alpha amino acid; $\alpha_9$=any alpha amino acid;

$\alpha_{10}$=any alpha amino acid; $\beta_5$=any beta-3 amino acid; $\alpha_{11}$=any alpha amino acid; $\alpha_{12}$=any alpha amino acid; $\beta_6$=any beta-3 amino acid.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\,\alpha_8\alpha_9\alpha_{10}\beta_5\alpha_{11}\alpha_{12}\beta_6$, wherein $\beta_1$=any beta-2 amino acid; $\alpha_1$=any alpha amino acid; $\alpha_2$=any alpha amino acid; $\beta_2$=any beta-2 amino acid; $\alpha_3$=any alpha amino acid; $\alpha_4$=any alpha amino acid; $\alpha_5$=any alpha amino acid; $\beta_3$=any beta-2 amino acid; $\alpha_6$=any alpha amino acid; $\alpha_7$=any alpha amino acid; $\beta_4$=any beta-2 amino acid; $\alpha_8$=any alpha amino acid; $\alpha_9$=any alpha amino acid; $\alpha_{10}$=any alpha amino acid; $\beta_5$=any beta-2 amino acid; $\alpha_{11}$=any alpha amino acid; $\alpha_{12}$=any alpha amino acid; $\beta_6$=any beta-2 amino acid.

In some embodiments, the composition comprises a VIP analog, wherein the analog comprises the following repetitive pattern of sequential β-amino acids from the amino-terminus: $\beta_1\alpha_1\alpha_2\beta_2\alpha_3\beta_4\alpha_5\beta_3\alpha_6\alpha_7\beta_4\,\alpha_8\alpha_9\alpha_{10}\beta_5\alpha_{11}\alpha_{12}\beta_6$, wherein $\beta_1$=any cyclic or heterocyclic beta-amino acid; $\alpha_1$=any alpha amino acid; $\alpha_2$=any alpha amino acid; $\beta_2$=any cyclic or heterocyclic beta-amino acid; $\alpha_3$=any alpha amino acid; $\alpha_4$=any alpha amino acid; $\alpha_5$=any alpha amino acid; $\beta_3$=cyclic or heterocyclic beta-amino acid; $\alpha_6$=any alpha amino acid; $\alpha_7$=any alpha amino acid; $\beta_4$=cyclic or heterocyclic beta-amino acid; $\alpha_8$=any alpha amino acid; $\alpha_9$=any alpha amino acid; $\alpha_{10}$=any alpha amino acid; $\beta_5$=cyclic or heterocyclic beta-amino acid; $\alpha_{11}$=any alpha amino acid; $\alpha_{12}$=any alpha amino acid; $\beta_6$=cyclic or heterocyclic beta-amino acid.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta-3 amino acid; $\alpha_1$=any alpha amino acid; $\alpha_2$=any alpha amino acid; $\beta_2$=any beta-3 amino acid; $\alpha_3$=any alpha amino acid; $\alpha_4$=any alpha amino acid; $\alpha_5$=any alpha amino acid; $\beta_3$=any beta-3 amino acid; $\alpha_6$=any alpha amino acid; $\alpha_7$=any alpha amino acid; $\beta_4$=any beta-3 amino acid; $\alpha_8$=any alpha amino acid; $\alpha_9$=any alpha amino acid; $\alpha_{10}$=any alpha amino acid; $\beta_5$=a beta-3 alanine; $\alpha_{11}$=any alpha amino acid; $\alpha_{12}$=any alpha amino acid; $\beta_6$=any beta-3 amino acid.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta-3 amino acid; $\alpha_1$=any alpha amino acid; $\alpha_2$=any alpha amino acid; $\beta_2$=any beta-3 amino acid; $\alpha_3$=any alpha amino acid; $\alpha_4$=any alpha amino acid; $\alpha_5$=an alpha leucine; $\beta_3$=any beta-3 amino acid; $\alpha_6$=any alpha amino acid; $\alpha_7$=any alpha amino acid; $\beta_4$=any beta-3 amino acid; $\alpha_8$=any alpha amino acid; $\alpha_9$=any alpha amino acid; $\alpha_{10}$=any alpha amino acid; $\beta_5$=a beta-3 alanine; $\alpha_{11}$=any alpha amino acid; $\alpha_{12}$=any alpha amino acid; $\beta_6$=any beta-3 amino acid.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta-3 amino acid; $\alpha_1$=any alpha amino acid; $\alpha_2$=any alpha amino acid; $\beta_2$=any beta-3 amino acid; $\alpha_3$=any alpha amino acid; $\alpha_4$=any alpha amino acid; $\alpha_5$=an alpha leucine; $\beta_3$=any beta-3 amino acid; $\alpha_6$=any alpha amino acid; $\alpha_7$=any alpha amino acid; $\beta_4$=any beta-3 amino acid; $\alpha_8$=any alpha amino acid; $\alpha_9$=any alpha amino acid;

$\alpha_{10}$=any alpha amino acid; $\beta_5$=a beta-3 amino acid; $\alpha_{11}$=any alpha amino acid; $\alpha_{12}$=any alpha amino acid; $\beta_6$=any beta-3 amino acid.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=a beta 3-threonine; $\alpha_1$=any alpha amino acid; $\alpha_2$=any alpha amino acid; $\beta_2$=a beta-3 arginine; $\alpha_3$=any alpha amino acid; $\alpha_4$=any alpha amino acid; $\alpha_5$=any alpha amino acid; $\beta_3$=a beta-3 alanine; $\alpha_6$=any alpha amino acid; $\alpha_7$=any alpha amino acid; $\beta_4$=a beta-3 lysine; $\alpha_8$=any alpha amino acid; $\alpha_9$=any alpha amino acid; $\alpha_{10}$=any alpha amino acid; $\beta_5$=a beta-3 alanine; $\alpha_{11}$=any alpha amino acid; $\alpha_{12}$=any alpha amino acid; $\beta_6$=a beta-3 asparagine.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=a beta 3-threonine; $\alpha_1$=any alpha amino acid; $\alpha_2$=any alpha amino acid; $\beta_2$=a beta-3 arginine; $\alpha_3$=any alpha amino acid; $\alpha_4$=any alpha amino acid; $\beta_5$=an alpha leucine; $\beta_3$=a beta-3 alanine; $\alpha_6$=any alpha amino acid; $\alpha_7$=any alpha amino acid; $\beta_4$=a beta-3 lysine; $\alpha_8$=any alpha amino acid; $\alpha_9$=any alpha amino acid; $\alpha_{10}$=any alpha amino acid; $\beta_5$=a beta-3 alanine; $\alpha_{11}$=any alpha amino acid; $\alpha_{12}$=any alpha amino acid; $\beta_6$=a beta-3 asparagine.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=an alpha arginine; $\alpha_2$=an alpha leucine; $\beta_2$=any beta amino acid; $\alpha_3$=an alpha lysine; $\alpha_4$=an alpha glutamine; $\alpha_5$=an alpha-leucine; $\beta_3$=any beta amino acid; $\alpha_6$=an alpha valine; $\alpha_7$=an alpha lysine; $\beta_4$=any beta amino acid; $\alpha_8$=an alpha tyrosine; $\alpha_9$=an alpha leucine; $\alpha_{10}$=an alpha asparagine; $\beta_5$=a beta-3 alanine; $\alpha_{11}$=an alpha isoleucine; $\alpha_{12}$=an alpha leucine; $\beta_6$=any beta amino acid.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta-3 amino acid; $\alpha_1$=an alpha arginine; $\alpha_2$=an alpha leucine; $\beta_2$=any beta-3 amino acid; $\alpha_3$=an alpha lysine; $\alpha_4$=an alpha glutamine; $\alpha_5$=an alpha leucine; $\beta_3$=any beta-3 amino acid; $\alpha_6$=an alpha valine; $\alpha_7$=an alpha lysine; $\beta_4$=any beta-3 amino acid; $\alpha_8$=an alpha tyrosine; $\alpha_9$=an alpha leucine; $\alpha_{10}$=an alpha asparagine; $\beta_5$=any beta-3 amino acid; $\alpha_{11}$=an alpha isoleucine; $\alpha_{12}$=an alpha leucine; $\beta_6$=any beta amino acid.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=a beta-2 threonine; $\alpha_1$=an alpha arginine; $\alpha_2$=an alpha leucine; $\beta_2$=a beta-2 arginine; $\alpha_3$=an alpha lysine; $\alpha_4$=an alpha glutamine; $\alpha_5$=an alpha leucine; $\beta_3$=a beta-2 alanine; $\alpha_6$=an alpha valine; $\alpha_7$=an alpha lysine; $\beta_4$=a beta-2 lysine; $\alpha_8$=an alpha tyrosine; $\alpha_9$=an alpha leucine; $\alpha_{10}$=an alpha asparagine; $\beta_5$=a beta-2 alanine; $\alpha_{11}$=an alpha isoleucine; $\alpha_{12}$=an alpha leucine; $\beta_6$=a beta-2 asparagine.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=a beta-3 threonine or ACPC; $\alpha_1$=an alpha arginine; $\alpha_2$=an alpha leucine; $\beta_2$=a beta-3 arginine or ARC; $\alpha_3$=an alpha lysine; $\alpha_4$=an alpha glutamine; $\alpha_5$=an alpha-leucine; $\beta_3$=a beta-3 alanine or ACPC; $\alpha_6$=an alpha valine; $\alpha_7$=an alpha lysine; $\beta_4$=a beta-3 lysine or APC; $\alpha_8$=an alpha tyrosine; $\alpha_9$=an alpha leucine; $\alpha_{10}$=an alpha asparagine; $\beta_5$=a beta-3 alanine or ACPC; $\alpha_{11}$=an alpha isoleucine; $\alpha_{12}$=an alpha leucine; $\beta_5$=a beta-3 asparagine.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; $\alpha6$=any alpha amino acid; $\alpha7$=any alpha amino acid; $\alpha8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta-3, beta-2, cyclic or heterocyclic beta-amino acid; m=any alpha amino acid; $\alpha_2$=any alpha amino acid; $\alpha_3$=any alpha amino acid; $\beta_2$=any beta-3, beta-2, cyclic or heterocyclic beta-amino acid; $\alpha_4$=any alpha amino acid; $\alpha_5$=any alpha amino acid; $\beta_3$=any beta-3, beta-2, cyclic or heterocyclic beta-amino acid; $\alpha_6$=any alpha amino acid; $\alpha_7$=any alpha amino acid; $\alpha_8$=any alpha amino acid; $\beta_4$=any beta-3, beta-2, cyclic or heterocyclic beta-amino acid; $\alpha_9$=any alpha amino acid; $\alpha_{10}$=any alpha amino acid; $\beta_5$=any beta-3, beta-2, cyclic or heterocyclic beta-amino acid; $\alpha_{11}$=any alpha amino acid; $\alpha_{12}$=any alpha amino acid; $\alpha_{13}$=any alpha amino acid.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta-3 amino acid; $\alpha_1$=any alpha amino acid; $\alpha_2$=any alpha amino acid; $\alpha_3$=any alpha amino acid; $\beta_2$=any beta-3 amino acid; $\alpha_4$=any alpha amino acid; $\alpha_5$=any alpha amino acid; $\beta_3$=any beta-3 amino acid; $\alpha6$=any alpha amino acid; $\alpha7$=any alpha amino acid; $\alpha8$=any alpha amino acid; $\beta_4$=any beta-3 amino acid; $\alpha_9$=any alpha amino acid; $\alpha_{10}$=any alpha amino acid; $\beta_5$=any beta-3 amino acid; $\alpha_{11}$=any alpha amino acid; $\alpha_{12}$=any alpha amino acid; $\alpha_{11}$=any alpha amino acid.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta-2 amino acid; $\alpha_1$=any alpha amino acid; $\alpha_2$=any alpha amino acid; $\alpha_3$=any alpha amino acid; $\beta_2$=any beta-2 amino acid; $\alpha_4$=any alpha amino acid; $\alpha_5$=any alpha amino acid; $\beta_3$=any beta-2 amino acid; $\alpha6$=any alpha amino acid; $\alpha7$=any alpha amino acid; $\alpha8$=any alpha amino acid; $\beta_4$=any beta-2 amino acid; $\alpha_9$=any alpha amino acid; $\alpha_{10}$=any alpha amino acid; $\beta_5$=any beta-2 amino acid; $\alpha_{11}$=any alpha amino acid; $\alpha_{12}$=any alpha amino acid; $\alpha_{13}$=any alpha amino acid.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any cyclic or heterocyclic beta-amino acid; $\alpha_1$=any alpha amino acid; $\alpha_2$=any alpha amino acid; $\alpha_3$=any alpha amino acid; $\beta_2$=any cyclic or heterocyclic beta-amino acid; $\alpha_4$=any alpha amino acid; $\alpha_5$=any alpha amino acid; $\beta_3$=any cyclic or heterocyclic beta-amino acid; $\alpha6$=any alpha amino acid; $\alpha7$=any alpha amino acid; $\alpha8$=any alpha amino acid; $\beta_4$=any cyclic or heterocyclic beta-amino acid; $\alpha_9$=any alpha amino acid; $\alpha_{10}$=any alpha amino acid; $\beta_5$=any cyclic or heterocyclic beta-amino acid; $\alpha_{11}$=any alpha amino acid; $\alpha_{12}$=any alpha amino acid; $\alpha_{13}$=any alpha amino acid.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=a beta-3 threonine; $\alpha_1$=any alpha amino acid; $\alpha_2$=any alpha amino acid; $\alpha_1$=any alpha amino acid; $\beta_2$=a beta-3 lysine; $\alpha_4$=any alpha amino acid; $\alpha_5$=any alpha amino acid; $\beta_1$=a beta-3 alanine; $\alpha_6$=any alpha amino acid; $\alpha_7$=any alpha amino acid; $\alpha_8$=any alpha amino acid; $\beta_4$=a beta-3 tyrosine; $\alpha_9$=any alpha amino acid; $\alpha_{10}$=any alpha amino acid; $\beta_5$=a beta-3 alanine; $\alpha_{11}$=any alpha amino acid; $\alpha_{12}$=any alpha amino acid; $\alpha_{13}$=any alpha amino acid.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\beta_{12}\alpha_{13}$; wherein $\beta_1$=any beta amino acid; $\alpha_1$=an alpha arginine; $\alpha_2$=an alpha leucine; $\alpha_3$=an alpha arginine; $\beta_2$=any beta amino acid; $\alpha_4$=an alpha glutamine; $\alpha_5$=an alpha leucine; $\beta_3$=any beta amino acid; $\alpha_6$=an alpha valine acid; $\alpha_7$=an alpha lysine; $\alpha_8$=an alpha lysine; $\beta_4$=any beta amino acid; $\alpha_9$=an alpha leucine; $\alpha_{10}$=an alpha asparagine; $\beta_5$=any beta amino acid; $\alpha_{11}$=an alpha isoleucine; $\alpha_{12}$=an alpha leucine; $\alpha_{13}$=an alpha asparagine.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$; wherein $\beta_1$=any beta-3 amino acid; $\alpha_1$=an alpha arginine; $\alpha_2$=an alpha leucine; $\alpha_3$=an alpha arginine; $\beta_2$=any beta-3 amino acid; $\alpha_4$=an alpha glutamine; $\alpha_5$=an alpha leucine; $\beta_3$=any beta-3 amino acid; $\alpha_6$=an alpha valine acid; $\alpha_7$=an alpha lysine; $\alpha_8$=an alpha lysine; $\beta_4$=any beta-3 amino acid; $\alpha_9$=an alpha leucine; $\alpha_{10}$=an alpha asparagine; $\beta_5$=any beta-3 amino acid; $\alpha_{11}$=an alpha isokucine; $\alpha_{12}$=an alpha leucine; $\alpha_{13}$=an alpha asparagine.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$; wherein $\beta_1$=any beta-2 amino acid; $\alpha_1$=an alpha arginine; $\alpha_2$=an alpha leucine; $\alpha_3$=an alpha arginine; $\beta_2$=any beta-2 amino acid; $\alpha_4$=an alpha glutamine; $\alpha_5$=an alpha leucine; $\beta_3$=any beta-2 amino acid; $\alpha_6$=an alpha valine acid; $\alpha_7$=an alpha lysine; $\alpha_8$=an alpha lysine; $\beta_4$=any beta-2 amino acid; $\alpha_9$=an alpha leucine; $\alpha_{10}$=an alpha asparagine; $\beta_5$=any beta-2 amino acid; $\alpha_{11}$=an alpha isoleucine; $\alpha_{12}$=an alpha leucine; $\alpha_{13}$=an alpha asparagine.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$; wherein $\beta_1$=any cyclic and heterocyclic beta amino acid; $\alpha_1$=an alpha arginine; $\alpha_2$=an alpha leucine; $\alpha_3$=an alpha arginine; $\beta_2$=any cyclic and heterocyclic beta amino acid; $\alpha_4$=an alpha glutamine; $\alpha_5$=an alpha leucine; $\beta_3$=any cyclic and heterocyclic beta amino acid; $\alpha_6$=an alpha valine acid;

$\alpha_7$=an alpha lysine; $\alpha_8$=an alpha lysine; $\beta_4$=any cyclic and heterocyclic beta amino acid; $\alpha_9$=an alpha leucine; $\alpha_{10}$=an alpha asparagine; $\beta_5$=any cyclic and heterocyclic beta amino acid; $\alpha_{11}$=an alpha isoleucine; $\alpha_{12}$=an alpha leucine; $\alpha_{13}$=an alpha asparagine.

In some embodiments, the composition comprises a VIP analog, wherein the analog comprises the following repetitive pattern of sequential $\beta$-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=a beta-3 threonine or an ACPC; $\alpha_1$=an alpha arginine; $\alpha_2$=an alpha leucine; $\alpha_3$=an alpha arginine; $\beta_2$=a beta-3 lysine or APC; $\alpha_4$=an alpha glutamine; $\alpha_5$=an alpha leucine; $\beta_3$=a beta-3 alanine or ACPC; $\alpha_6$=an alpha valine acid; $\alpha_7$=an alpha lysine; $\alpha_8$=an alpha lysine; $\beta_4$=a beta-3 tyrosine or; $\alpha_9$=an alpha leucine; $\alpha_{10}$=an alpha asparagine; $\beta_5$=a beta-3 alanine or ACPC; $\alpha_{11}$=an alpha isoleucine; $\alpha_{12}$=an alpha leucine; $\alpha_{13}$=an alpha asparagine.

In some embodiments, the composition comprises a VIP analog, wherein the analog comprises the following repetitive pattern of sequential $\beta$-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid.

In some embodiments, the composition comprises a VIP analog, wherein the analog comprises the following repetitive pattern of sequential $\beta$-amino acids from the amino-terminus:

$\beta_1\alpha_1\alpha_2\alpha_3\beta_2\alpha_4\alpha_8\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=any beta-3, beta-2, cyclic or heterocyclic beta-amino acid; $\alpha_1$=any alpha amino acid; $\alpha_2$=any alpha amino acid; $\alpha_3$=an alpha amino acid; $\beta_2$=any beta-3, beta-2, cyclic or heterocyclic beta-amino acid; $\alpha_4$=an alpha alpha amino acid; $\alpha_5$=any alpha amino acid; $\beta_3$=any beta-3, beta-2, cyclic or heterocyclic beta-amino acid; $\alpha_6$=any alpha amino acid; $\alpha_7$=any alpha amino acid; $\alpha_8$=any alpha amino acid; $\beta_4$=any beta-3, beta-2, cyclic or heterocyclic beta-amino acid; $\alpha_9$=any alpha amino acid; $\alpha_{10}$=any alpha amino acid; $\beta_5$=any beta-3, beta-2, cyclic or heterocyclic beta-amino acid; $\alpha_{11}$=any alpha amino acid; $\alpha_{12}$=any alpha amino acid; $\alpha_{11}$=any alpha amino acid; and $\beta_6$=any beta-3, beta-2, cyclic or heterocyclic beta-amino acid.

In some embodiments, the composition comprises a VIP analog, wherein the analog comprises the following repetitive pattern of sequential $\beta$-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=any beta-3 amino acid; $\alpha_1$=any alpha amino acid; $\alpha_2$=any alpha amino acid; $\alpha_3$=an alpha amino acid; $\beta_2$=any beta-3 amino acid; $\alpha_4$=an alpha alpha amino acid; $\alpha_5$=any alpha amino acid; $\beta_3$=any beta-3 amino acid; $\beta_6$=any alpha amino acid; $\alpha_7$=any alpha amino acid; $\alpha_8$=any alpha amino acid; $\beta_4$=any beta-3 amino acid; $\alpha_9$=any alpha amino acid; $\alpha_{10}$=any alpha amino acid; $\beta_5$=any beta-3 amino acid; $\alpha_{11}$=any alpha amino acid; $\alpha_{12}$=any alpha amino acid; $\alpha_{13}$=any alpha amino acid; and $\beta_6$=any beta-3 amino acid.

In some embodiments, the composition comprises a VIP analog, wherein the analog comprises the following repetitive pattern of sequential $\beta$-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=any beta-2 amino acid; $\alpha_1$=any alpha amino acid; $\alpha_2$=any alpha amino acid; $\alpha_3$=an alpha amino acid; $\beta_2$=any beta-2 amino acid; $\alpha_4$=an alpha alpha amino acid; $\alpha_5$=any alpha amino acid; $\beta_3$=any beta-2 amino acid; $\alpha_6$=any alpha amino acid; $\alpha_7$=any alpha amino acid; $\alpha_8$=any alpha amino acid; $\beta_4$=any beta-2 amino acid; $\alpha_9$=any alpha amino acid; $\alpha_{10}$=any alpha amino acid; $\beta_5$=any beta-2 amino acid; $\alpha_{11}$=any alpha amino acid; $\alpha_{12}$=any alpha amino acid, $\alpha_{11}$=any alpha amino acid; and $\beta_6$=any beta-2 amino acid.

In some embodiments, the composition comprises a VIP analog, wherein the analog comprises the following repetitive pattern of sequential $\beta$-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=any cyclic or heterocyclic beta-amino acid; $\alpha_1$=any alpha amino acid; $\alpha_2$=any alpha amino acid; $\alpha_3$=an alpha amino acid; $\beta_2$=any cyclic or heterocyclic beta-amino acid; $\alpha_4$=an alpha alpha amino acid; $\beta_5$=any alpha amino acid; $\beta_3$=any cyclic or heterocyclic beta-amino acid; $\alpha_6$=any alpha amino acid; $\alpha_7$=any alpha amino acid; $\alpha_8$=any alpha amino acid; $\beta_4$=any cyclic or heterocyclic beta-amino acid; $\alpha_9$=any alpha amino acid; $\alpha_{10}$=any alpha amino acid; $\beta_5$=any cyclic or heterocyclic beta-amino acid; $\alpha_{11}$=any alpha amino acid; $\alpha_{12}$=any alpha amino acid; $\alpha_{11}$=any alpha amino acid; and $\beta_6$=any cyclic or heterocyclic beta-amino acid.

In some embodiments, the composition comprises a VIP analog, wherein the analog comprises the following repetitive pattern of sequential $\beta$-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=a beta-2 tyrosine; $\alpha_1$=any alpha amino acid; $\alpha_2$=any alpha amino acid; $\alpha_3$=an alpha amino acid; $\beta_2$=a beta-2 arginine; $\alpha_4$=an alpha alpha amino acid; $\alpha_5$=any alpha amino acid; $\beta_3$=a beta-2 leucine; $\alpha_6$=any alpha amino acid; $\alpha_7$=any alpha amino acid; $\alpha_8$=any alpha amino acid; $\beta_4$=a beta-2 lysine; $\alpha_9$=any alpha amino acid; $\alpha_{10}$=any alpha amino acid; $\beta_5$=a beta-2 asparagine; $\alpha_{11}$=any alpha amino acid; $\alpha_{12}$=any alpha amino acid; $\alpha_{13}$=any alpha amino acid; and $\beta_6$=a beta-2 asparagine.

In some embodiments, the composition comprises a VIP analog, wherein the analog comprises the following repetitive pattern of sequential $\beta$-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=a beta-3 tyrosine; $\alpha_1$=any alpha amino acid; $\alpha_2$=any alpha amino acid; $\alpha_3$=an alpha amino acid; $\beta_2$=a beta-3 arginine; $\alpha_4$=an alpha alpha amino acid; $\alpha_5$=any alpha amino acid; $\beta_3$=a beta-3 leucine; $\alpha_6$=any alpha amino acid; $\alpha_7$=any alpha amino acid; $\alpha_8$=any alpha amino acid; $\beta_4$=a beta-3 lysine; $\alpha_9$=any alpha amino acid; $\alpha_{10}$=any alpha amino acid; $\beta_5$=a beta-3 asparagine; $\alpha_{11}$=any alpha amino acid; $\alpha_{12}$=any alpha amino acid; $\alpha_{13}$=any alpha amino acid; and $\beta_6$=a beta-3 asparagine.

In some embodiments, the composition comprises a VIP analog, wherein the analog comprises the following repetitive pattern of sequential $\beta$-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=any beta amino acid; $\alpha_1$=an alpha threonine; $\alpha_2$=an alpha arginine; $\alpha_3$=an alpha leucine; $\beta_2$=any beta amino acid; $\alpha_4$=an alpha lysine; $\alpha_5$=an alpha glutamine; $\beta_3$=any beta amino acid; $\alpha_6$=an alpha alanine; $\alpha_7$=an alpha valine; $\alpha_8$=an alpha lysine; $\beta_4$=any beta amino acid; $\alpha_9$=an alpha tyrosine; $\alpha_{10}$=an alpha leucine; $\beta_5$=any beta amino acid; $\alpha_{11}$=an alpha alanine; $\alpha_{12}$=an alpha isoleucine; $\alpha_{11}$=an alpha leucine; and $\beta_6$=any beta amino acid.

In some embodiments, the composition comprises a VIP analog, wherein the analog comprises the following repetitive pattern of sequential β-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta-3 amino acid; $\alpha_1$=an alpha threonine; $\alpha_2$=an alpha arginine; $\alpha_3$=an alpha leucine; $\beta_2$=any beta-3 amino acid; $\alpha_4$=an alpha lysine; $\alpha_5$=an alpha glutamine; $\beta_3$=any beta-3 amino acid; $\alpha_6$=an alpha alanine; $\alpha_7$=an alpha valine; $\alpha_8$=an alpha lysine; $\beta_4$=any beta-3 amino acid; $\alpha_9$=an alpha tyrosine; $\alpha_{10}$=an alpha leucine; $\beta_5$=any beta-3 amino acid; $\alpha_{11}$=an alpha alanine; $\alpha_{12}$=an alpha isoleucine; $\alpha_{13}$=an alpha leucine; and $\beta_6$=any beta-3 amino acid.

In some embodiments, the composition comprises a VIP analog, wherein the analog comprises the following repetitive pattern of sequential β-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta-2 amino acid; $\alpha_1$=an alpha threonine; $\alpha_2$=an alpha arginine; $\alpha_3$=an alpha leucine; $\beta_2$=any beta-2 amino acid; $\alpha_4$=an alpha lysine; $\alpha_5$=an alpha glutamine; $\beta_3$=any beta-2 amino acid; $\alpha_6$=an alpha alanine; $\alpha_7$=an alpha valine; $\alpha_8$=an alpha lysine; $\beta_4$=any beta-2 amino acid; $\alpha_9$=an alpha tyrosine; $\alpha_{10}$=an alpha leucine; $\beta_5$=any beta-2 amino acid; $\alpha_{11}$=an alpha alanine; $\alpha_{12}$=an alpha isoleucine; $\alpha_{13}$=an alpha leucine; and $\beta_6$=any beta-2 amino acid.

In some embodiments, the composition comprises a VIP analog, wherein the analog comprises the following repetitive pattern of sequential β-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any cyclic or heterocyclic beta amino acid; $\alpha_1$=an alpha threonine; $\alpha_2$=an alpha arginine; $\alpha_3$=an alpha leucine; $\beta_2$=any cyclic or heterocyclic beta amino acid; $\alpha_4$=an alpha lysine; $\alpha_5$=an alpha glutamine; $\beta_3$=any cyclic or heterocyclic beta amino acid; $\alpha_6$=an alpha alanine; $\alpha_7$=an alpha valine; $\alpha_8$=an alpha lysine; $\beta_4$=any cyclic or heterocyclic beta amino acid; $\alpha_9$=an alpha tyrosine; $\alpha_{10}$=an alpha leucine; $\beta_5$=any cyclic or heterocyclic beta amino acid; $\alpha_{11}$=an alpha alanine; $\alpha_{12}$=an alpha isoleucine; $\alpha_{13}$=an alpha leucine; and $\beta_6$=any cyclic or heterocyclic beta amino acid.

In some embodiments, the composition comprises a VIP analog, wherein the analog comprises the following repetitive pattern of sequential β-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta amino acid; $\alpha_1$=an alpha threonine; $\alpha_2$=an alpha arginine; $\alpha_3$=an alpha leucine; $\beta_2$=a beta-2 arginine or APC; $\alpha_4$=an alpha lysine; $\alpha_5$=an alpha glutamine; $\beta_3$=any beta-2 amino acid; $\alpha_6$=an alpha alanine; $\alpha_7$=an alpha valine; $\alpha_8$=an alpha lysine; $\beta_4$=any beta-2 amino acid; $\alpha_9$=an alpha tyrosine; $\alpha_{10}$=an alpha leucine; $\beta_5$=any beta-2 amino acid; $\alpha_{11}$=an alpha alanine; $\alpha_{12}$=an alpha isoleucine, $\alpha_{13}$=an alpha leucine; and $\beta_6$=any beta-2 amino acid.

In some embodiments, the composition comprises a VIP analog, wherein the analog comprises the following repetitive pattern of sequential β-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=a beta-3 tyrosine; $\alpha_1$=an alpha threonine; $\alpha_2$=an alpha arginine; $\alpha_3$=an alpha leucine; $\beta_2$=a beta-3 arginine or APC; $\alpha_4$=an alpha lysine; $\alpha_5$=an alpha glutamine; $\beta_3$=a beta-3 leucine or ACPC; $\alpha_6$=an alpha alanine; $\alpha_7$=an alpha valine; $\alpha_8$=an alpha lysine; $\beta_4$=a beta-3 lysine or APC; $\alpha_9$=an alpha tyrosine; $\alpha_{10}$=an alpha leucine; $\beta_5$=a beta-3 asparagine or ACPC; $\alpha_{11}$=an alpha alanine; $\alpha_{12}$=an alpha isoleucine; $\alpha_{13}$=an alpha leucine; and $\beta_6$=a beta-3 asparagine.

In some embodiments, the composition comprises a VIP analog, wherein the analog comprises the following repetitive pattern of sequential β-amino acids from the amino-terminus selected from the following:
$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid, $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid; and wherein the repetitive pattern is, optionally, preceded by:
HSDAVFTDNY (SEQ ID NO: 1340) if the composition comprises $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$; or HSDAVFTDN (SEQ ID NO: 1341) if the composition comprises
$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; and wherein the C-terminus is optionally amidated; and wherein the N-terminus is optionally acylated; or functional fragments thereof.

In some embodiments, the composition comprises a VIP analog, wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$,
wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; α6=any alpha amino acid; α7=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{11}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any alpha amino acid; $\alpha_3$=any alpha amino acid; $\alpha_4$=any alpha amino acid; $\alpha_5$=any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{11}$=any alpha amino acid; and $\beta_6$=any beta amino acid; and wherein the repetitive pattern is, optionally, preceded by:
HSDAVFTDNY (SEQ ID NO: 1340) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$ or $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$; or HSDAVFTDN (SEQ ID NO: 1341) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; and wherein the C-terminus is optionally amidated; and
wherein the N-terminus is optionally acylated;
or functional fragments thereof.

In some embodiments, the composition comprises a VIP analog, wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; $\alpha6$=any alpha amino acid; $\alpha7$=any alpha amino acid; $\alpha8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=an alpha leucine; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=a beta-3 alanine or an ACPC; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid; and wherein the repetitive pattern is, optionally, preceded by.
HSDAVFTDNY (SEQ ID NO: 1340) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$ or $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$; or HSDAVFTDN (SEQ ID NO: 1341) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; and wherein the C-terminus is optionally amidated; and
wherein the N-terminus is optionally acylated;
or functional fragments thereof.

In some embodiments, the composition comprises a VIP analog, wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; $\alpha6$=any alpha amino acid; $\alpha7$=any alpha amino acid; $\alpha8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=an alpha leucine; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid;

wherein the repetitive pattern is, optionally, preceded by:
HSDAVFTDNY (SEQ ID NO: 1340) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$ or $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$; or HSDAVFTDN (SEQ ID NO: 1341) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; or a fragment thereof; and wherein at least one or more of the amino acids HSDAVFTDNY (SEQ ID NO: 1340) or HSDAVFTDN (SEQ ID NO: 1341) is substituted with a non-natural amino acid.

In some embodiments, the composition comprises a VIP analog, wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; $\alpha6$=any alpha amino acid; $\alpha7$=any alpha amino acid; $\alpha8$=any alpha amino acid; $\beta_4$=any beta amino acid; $\alpha_8$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=an alpha leucine; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=a beta-3 alanine or an ACPC; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid;

wherein the repetitive pattern is, optionally, preceded by: HSDAVFTDNY (SEQ ID NO: 1340) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$ or $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$; or HSDAVFTDN (SEQ ID NO: 1341) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; or a fragment thereof; and wherein at least one or more of the amino acids HSDAVFTDNY (SEQ ID NO: 1340) or HSDAVFTDN (SEQ ID NO: 1341) is substituted with a non-natural amino acid.

In some embodiments, the composition comprises a VIP analog, wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$,
wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; $\alpha 6$=any alpha amino acid; $\alpha 7$=any alpha amino acid; $\alpha 8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=an alpha leucine; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid;

wherein the repetitive pattern is, optionally, preceded by: HSDAVFTDNY (SEQ ID NO: 1340) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$ or $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$; or HSDAVFTDN (SEQ ID NO: 1341) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}P\$\alpha_{11}\alpha_{12}\alpha_{13}\beta_6$; and wherein at least one or more of the amino acids HSDAVFTDNY (SEQ ID NO: 1340) or HSDAVFTDN (SEQ ID NO: 1341) is substituted with a beta amino acid selected from the group chosen from: a beta-3 homolog of the wild-type amino acid sequence.

In some embodiments, the composition comprises a VIP analog, wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\alpha_8\beta_4\alpha_9\alpha_{10}\beta_4\alpha_{11}\alpha_{12}\alpha_{13}$,
wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; $\alpha 6$=any alpha amino acid; $\alpha_7$=any alpha amino acid; $\alpha 8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid, $\alpha_{12}$=any alpha amino acid; $\alpha_{13}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=an alpha leucine; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid;

wherein the repetitive pattern is, optionally, preceded by: HSDAVFTDNY (SEQ ID NO: 1340) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$ or $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$; or HSDAVFTDN (SEQ ID NO: 1341) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; and wherein at least one or more of the amino acids HSDAVFTDNY (SEQ ID NO: 1340) or HSDAVFTDN (SEQ ID NO: 1341) is substituted with a beta amino acid selected from the group chosen from: ARC, ACPC, a beta-2 homolog of a wild-type amino acid, or a beta-3 homolog of a wild-type amino acid.

In some embodiments, the composition comprises a VIP analog, wherein the analog comprises the following repetitive pattern of sequential β-amino acids from the amino-terminus selected from the following:

$\beta_1\alpha_1\alpha_2\alpha_3\beta_2\alpha_4\beta_5\alpha_3\alpha_6\alpha_7\alpha_8\beta_4\alpha_9\alpha_{10}\beta_5\alpha_{11}\alpha_{12}\alpha_{13}$,
wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; $\alpha 6$=any alpha amino acid; $\alpha 7$=any alpha amino acid; $\alpha 8$=any alpha amino acid; $\beta_4$=any beta amino acid; $\alpha_9$=any alpha amino acid; $\alpha_{10}$=any alpha amino acid; $\beta_5$=any beta amino acid; $\beta_{11}$=any alpha amino acid; $\alpha_{12}$=any alpha amino acid; $\alpha_{13}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid; $\beta_3$=any beta amino acid; $\alpha_6$=any alpha amino acid;

$\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$:

wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid;

wherein the repetitive pattern is, optionally, preceded by:
HSDAVFTDNY (SEQ ID NO: 1340) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$ or $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$; or HSDAVFTDN (SEQ ID NO: 1341) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; and wherein at least one or more of the amino acids HSDAVFTDNY (SEQ ID NO: 1340) or HSDAVFTDN (SEQ ID NO: 1341) is substituted with a beta amino acid selected from the group chosen from: a beta-3 homolog of the wild-type amino acid sequence, a beta-2 homolog of the wild-type amino acid sequence, ACPC, or APC.

In some embodiments, the composition comprises a VIP analog, wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; α6=any alpha amino acid: α7=any alpha amino acid; α8=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=an alpha amino acid; $\beta_3$=any beta amino acid; $\alpha_6$=any alpha amino acid; $\alpha_7$=any alpha amino acid; $\beta_4$=any beta amino acid; $\beta_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid;

wherein the repetitive pattern is, optionally, preceded by:
HSDAVFTDNY (SEQ ID NO: 1340) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$ or $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$; or HSDAVFTDN (SEQ ID NO: 1341) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; and wherein the D at position 8 of HSDAVFTDNY (SEQ ID NO: 1340) is substituted with a beta amino acid selected from the group chosen from: a beta-3 homolog of the wild-type amino acid sequence, a beta-2 homolog of the wild-type amino acid sequence, ACPC, or APC.

In some embodiments, the composition comprises a VIP analog, wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; α6=any alpha amino acid; α7=any alpha amino acid; α8=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{11}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=an alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid;

wherein the repetitive pattern is, optionally, preceded by:
HSDAVFTDNY (SEQ ID NO: 1340) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$ or $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$; or HSDAVFTDN (SEQ ID NO: 1341) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; and wherein the T at position 7 of HSDAVFTDNY (SEQ ID NO: 1340) is substituted with a beta amino acid selected from the group chosen from: a beta-3 homolog of the wild-type amino acid sequence, a beta-2 homolog of the wild-type amino acid sequence, ACPC, or APC.

In some embodiments, the composition comprises a VIP analog, wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_1$=any beta amino acid; α6=any alpha amino acid; α7=any alpha amino acid; α8=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=an alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid;

wherein the repetitive pattern is, optionally, preceded by:

HSDAVFTDNY (SEQ ID NO: 1340) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$ or $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$; or HSDAVFTDN (SEQ ID NO: 1341) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; and wherein the D at position 8 of HSDAVFTDNY (SEQ ID NO: 1340) and, optionally, the T at position 7 of HSDAVFTDNY (SEQ ID NO: 1340) is substituted with a beta amino acid selected from the group chosen from: a beta-3 homolog of the wild-type amino acid sequence, a beta-2 homolog of the wild-type amino acid sequence, ACPC, or APC.

In some embodiments, the composition comprises a VIP analog, wherein the analog comprises the following repetitive pattern of sequential β-amino acids from the amino-terminus selected from the following:

$\beta_1\alpha_1\alpha_2\alpha_3\beta_2\alpha_4\alpha_5\beta_3\alpha_6\alpha_7\beta_4\alpha_8\alpha_9\alpha_{10}\beta_5\alpha_{11}\alpha_{12}\alpha_{13}$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; $\alpha6$=any alpha amino acid; $\alpha7$=any alpha amino acid; $\alpha8$=any alpha amino acid; $\beta_4$=any beta amino acid; $\alpha_9$=any alpha amino acid; $\alpha_{10}$=any alpha amino acid, $\beta_5$=any beta amino acid; $\alpha_{11}$=any alpha amino acid; $\alpha_{12}$=any alpha amino acid; $\alpha_{13}$=any alpha amino acid;

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=an alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid, $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid;

wherein the repetitive pattern is, optionally, preceded by:

HSDAVFTDNY (SEQ ID NO: 1340) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$ or $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$; or HSDAVFTDN (SEQ ID NO: 1341) if the composition comprises $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$; and wherein the T at position 7 of HSDAVFTDNY (SEQ ID NO: 1340) and, optionally, the D at position 8 of HSDAVFTDNY (SEQ ID NO: 1340) is substituted with a beta amino acid selected from the group chosen from: a beta-3 homolog of the wild-type amino acid sequence, a beta-2 homolog of the wild-type amino acid sequence ACPC, or APC.

In some embodiments, the composition comprises a VIP analog, wherein the analog comprises the following repetitive pattern of sequential β-amino acids from the amino-terminus to the carboxy-terminus: βααβαααβααβαααβααβ. In some embodiments, the composition comprises a VIP analog, wherein the analog comprises the following repetitive pattern of sequential β-amino acids from the amino-terminus: p i$\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid, $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; wherein the repetitive pattern is, optionally, preceded by: HSDAVFTDNY (SEQ ID NO: 1340) if the composition comprises; and wherein the C-terminus is, optionally, amidated; and wherein the N-terminus is, optionally, acylated;

or functional fragments thereof.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=a beta 3-threonine; $\alpha_1$=any alpha amino acid; $\alpha_2$=any alpha amino acid; $\beta_2$=a beta-3 arginine; $\alpha_3$=any alpha amino acid; $\alpha_4$=any alpha amino acid; $\alpha_5$=any alpha amino acid; $\beta_3$=a beta-3 alanine; $\beta_6$=any alpha amino acid; $\alpha_7$=any alpha amino acid; $\beta_4$=a beta-3 lysine; $\alpha_8$=any alpha amino acid, $\alpha_9$=any alpha amino acid; $\alpha_{10}$=any alpha amino acid; $\beta_5$=a beta-3 asparagine; $\alpha_{11}$=any alpha amino acid; $\alpha_{12}$=any alpha amino acid; $\beta_6$=any beta amino acid; wherein the repetitive pattern is, optionally, preceded by: HSDAVFTDNY (SEQ ID NO: 1340) if the composition comprises; and wherein the C-terminus is, optionally, amidated; and wherein the N-terminus is, optionally, acylated;

or functional fragments thereof.

In some embodiments, the composition comprises a VIP analog, wherein the analog comprises the following repetitive pattern of sequential β-amino acids from the armno-terminus:

$\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=a beta 3-threonine; $\alpha_1$=any alpha amino acid; $\alpha_2$=any alpha amino acid; $\beta_2$=a beta-3 arginine; $\alpha_3$=any alpha amino acid; $\alpha_4$=any alpha amino acid; $\alpha_5$=any alpha amino acid; $\beta_3$=a beta-3 alanine; $\alpha_6$=any alpha amino acid; $\alpha_7$=any alpha amino acid; $\beta_4$=a beta-3 lysine; $\alpha_8$=any alpha amino acid; $\alpha_9$=any alpha amino acid; $\alpha_{10}$=any alpha amino acid; $\beta_5$=a beta-3 alanine; $\alpha_{11}$=any alpha amino acid; $\alpha_{12}$=any alpha amino acid; $\beta_6$=a beta-3 asparagine; wherein the repetitive pattern is, optionally, preceded by: HSDAVFTDNY (SEQ ID NO: 1340) if the composition comprises; and
  wherein the C-terminus is, optionally, amidated; and
  wherein the N-terminus is, optionally, acylated;
  or functional fragments thereof.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=a beta 3-threonine; $\alpha_1$=any alpha amino acid; $\alpha_2$=any alpha amino acid; $\beta_2$=a beta-3 arginine; $\alpha_3$=any alpha amino acid; $\alpha_4$=any alpha amino acid; $\alpha_5$=an alpha leucine; $\beta_3$=a beta-3 alanine; $\alpha_6$=any alpha amino acid; $\alpha_7$=any alpha amino acid; $\beta_4$=a beta-3 lysine; $\alpha_8$=any alpha amino acid; $\alpha_9$=any alpha amino acid; $\alpha_{10}$=any alpha amino acid; $\beta_5$=a beta-3 alanine; $\alpha_{11}$=any alpha amino acid; $\alpha_{12}$=any alpha amino acid; $\beta_6$=a beta-3 asparagine; wherein the repetitive pattern is, optionally, preceded by: HSDAVFTDNY (SEQ ID NO: 1340) if the composition comprises; and wherein the C-terminus is, optionally, amidated; and
  wherein the N-terminus is, optionally, acylated;
  or functional fragments thereof.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=a beta-3 alanine; $\alpha_{11}$=any alpha amino acid; $\alpha_{12}$=any alpha amino acid; $\beta_6$=a beta-3 asparagine; wherein the repetitive pattern is, optionally, preceded by: HSDAVFTDNY (SEQ ID NO: 1340) if the composition comprises; and
  wherein the C-terminus is, optionally, amidated; and
  wherein the N-terminus is, optionally, acylated;
  or functional fragments thereof.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=an alpha arginine; $\alpha_2$=an alpha leucine; $\beta_2$=any beta amino acid, $\alpha_3$=an alpha lysine; $\alpha_4$=an alpha glutamine; $\alpha_5$=an alpha leucine; $\beta_3$=any beta amino acid; $\alpha_6$=an alpha valine; $\alpha_7$=an alpha lysine; $\beta_4$=any beta amino acid; $\alpha_8$=an alpha tyrosine; $\alpha_9$=an alpha leucine; $\alpha_{10}$=an alpha asparagine; $\beta_5$=any beta amino acid; $\alpha_{11}$=an alpha isoleucine; $\alpha_{12}$=an alpha leucine; $\beta_6$=any beta amino acid; wherein the repetitive pattern is, optionally, preceded by: HSDAVFTDNY (SEQ ID NO: 1340) if the composition comprises; and
  wherein the C-terminus is, optionally, amidated; and
  wherein the N-terminus is, optionally, acylated;
  or functional fragments thereof.

In some embodiments, the composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=a beta-3 threonine or ACPC; $\alpha_1$=an alpha arginine; $\alpha_2$=an alpha leucine; $\beta_2$=a beta-3 arginine or APC; $\alpha_3$=an alpha lysine; $\alpha_4$=an alpha glutamine; $\alpha_5$=an alpha leucine; $\beta_3$=a beta-3 alanine or ACPC; $\alpha_6$=an alpha valine; $\alpha_7$=an alpha lysine; $\beta_4$=a beta-3 lysine or APC; $\alpha_8$=an alpha tyrosine; $\alpha_9$=an alpha leucine; $\alpha_{10}$=an alpha asparagine; $\beta_5$=a beta-3 alanine or ACPC; $\alpha_{11}$=an alpha isoleucine; $\alpha_{12}$=an alpha leucine; $\beta_6$=a beta-3 asparagine; wherein the repetitive pattern is, optionally, preceded by: HSDAVFTDNY (SEQ ID NO: 1340) if the composition comprises; and
  wherein the C-terminus is, optionally, amidated; and
  wherein the N-terminus is, optionally, acylated;
  or functional fragments thereof.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; α6=any alpha amino acid; α7=any alpha amino acid; β8=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; wherein the repetitive pattern is, optionally, preceded by: HSDAVFTDNY (SEQ ID NO: 1340) if the composition comprises; and
  wherein the C-terminus is, optionally, amidated; and
  wherein the N-terminus is, optionally, acylated;
  or functional fragments thereof.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=a beta-3 threonine; $\alpha_1$=any alpha amino acid; $\alpha_2$=any alpha amino acid; $\alpha_3$=any alpha amino acid; $\beta_2$=a beta-3 lysine; $\alpha_4$=any alpha amino acid; $\alpha_5$=any alpha amino acid; $\beta_3$=a beta-3 alanine; α6=any alpha amino acid; α7=any alpha amino acid; α8=any alpha amino acid; $\beta_4$=a beta-3 tyrosine; $\alpha_9$=any alpha amino acid; $\alpha_{10}$=any alpha amino acid; $\beta_5$=a beta-3 alanine; $\alpha_{11}$=any alpha amino acid; $\alpha_{12}$=any alpha amino acid; $\alpha_{13}$=any alpha amino acid; wherein the repetitive pattern is, optionally, preceded by: HSDAVFTDNY (SEQ ID NO: 1340) if the composition comprises; and
  wherein the C-terminus is, optionally, amidated; and
  wherein the N-terminus is, optionally, acylated;
  or functional fragments thereof.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$; wherein $\beta_1$=any beta amino acid; $\alpha_1$=an alpha arginine; $\alpha_2$=an alpha leucine; $\alpha_3$=an alpha arginine; $\beta_2$=any beta amino acid; $\alpha_4$=an alpha glutamine; $\alpha_5$=an alpha leucine; $\beta_3$=any beta amino acid; $\alpha_6$=an alpha valine acid; $\alpha_7$=an alpha lysine; $\alpha_8$=an alpha lysine; $\beta_4$=any beta amino acid; $\alpha_9$=an alpha leucine; $\alpha_{10}$=an alpha asparagine; $\beta_5$=any beta amino acid; $\alpha_{11}$=an alpha isoleucine; $\alpha_{12}$=an alpha leucine; $\alpha_{13}$=an alpha asparagine; wherein the repetitive pattern is, optionally, preceded by:
  HSDAVFTDNY (SEQ ID NO: 1340) if the composition comprises; and
  wherein the C-terminus is, optionally, amidated; and
  wherein the N-terminus is, optionally, acylated;
  or functional fragments thereof.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=a beta-3 threonine or an ACPC; $\alpha_1$=an alpha arginine; $\alpha_2$=an alpha leucine; $\alpha_3$=an alpha arginine; $\beta_2$=a beta-3 lysine or APC; $\alpha_4$=an alpha glutamine; $\alpha_5$=an alpha leucine; $\beta_3$=a beta-3 alanine or ACPC; $\alpha_6$=an alpha valine acid; $\alpha_7$=an alpha lysine; $\alpha_8$=an alpha lysine; $\beta_4$=a beta-3 tyrosine or; $\alpha_9$=an alpha leucine; $\alpha_{10}$=an alpha asparagine; $\beta_5$=a beta-3 alanine or ACPC; $\alpha_{11}$=an alpha isoleucine; $\alpha_{12}$=an alpha leucine; $\alpha_{13}$=an alpha asparagine; wherein the repetitive pattern is, optionally, preceded by: HSDAVFTDNY (SEQ ID NO: 1340) if the composition comprises; and wherein the C-terminus is, optionally, amidated; and
wherein the N-terminus is, optionally, acylated;
or functional fragments thereof.

In some embodiments, the composition comprises a VIP analog, wherein the analog comprises the following repetitive pattern of sequential β-amino acids from the amino-terminus:
$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; and $\beta_6$=any beta amino acid; wherein the repetitive pattern is, optionally, preceded by: HSDAVFTDN (SEQ ID NO: 1341); and wherein the C-terminus is, optionally, amidated; and
wherein the N-terminus is, optionally, acylated;
or functional fragments thereof.

In some embodiments, the composition comprises a VIP analog, wherein the analog comprises the following repetitive pattern of sequential β-amino acids from the amino-terminus:
$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=a beta-3 tyrosine; $\alpha_1$=any alpha amino acid; $\alpha_2$=any alpha amino acid; $\alpha_3$=an alpha amino acid; $\beta_2$=a beta-3 arginine; $\alpha_4$=an alpha alpha amino acid; $\alpha_5$=any alpha amino acid; $\beta_3$=a beta-3 leucine; $\alpha_6$=any alpha amino acid; $\alpha_7$=any alpha amino acid; $\alpha_8$=any alpha amino acid; $\beta_4$=a beta-3 lysine; $\alpha_9$=any alpha amino acid; $\alpha_{10}$=any alpha amino acid; $\beta_5$=a beta-3 asparagine; $\alpha_{11}$=any alpha amino acid; $\alpha_{12}$=any alpha amino acid; $\alpha_{11}$=any alpha amino acid; and $\beta_6$=a beta-3 asparagine; wherein the repetitive pattern is, optionally, preceded by: HSDAVFTDN (SEQ ID NO: 1341); and wherein the C-terminus is, optionally, amidated; and
wherein the N-terminus is, optionally, acylated;
or functional fragments thereof.

In some embodiments, the composition comprises a VIP analog, wherein the analog comprises the following repetitive pattern of sequential β-amino acids from the amino-terminus:
$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=a beta-3 tyrosine; $\alpha_1$=an alpha threonine; $\alpha_2$=an alpha arginine; $\alpha_3$=an alpha leucine; $\beta_2$=a beta-3 arginine or APC; $\alpha_4$=an alpha lysine; $\alpha_5$=an alpha glutamine; $\beta_3$=a beta-3 leucine or ACPC; $\alpha_6$=an alpha alanine; $\alpha_7$=an alpha valine; $\alpha_8$=an alpha lysine; $\beta_4$=a beta-3 lysine or APC; $\alpha_9$=an alpha tyrosine; $\alpha_{10}$=an alpha leucine; $\beta_5$=a beta-3 asparagine or ACPC; $\alpha_{11}$=an alpha alanine; $\alpha_{12}$=an alpha isoleucine; $\alpha_{13}$=an alpha leucine; and $\beta_6$=a beta-3 asparagine; wherein the repetitive pattern is, optionally, preceded by: HSDAVFTDN (SEQ ID NO: 1341); and wherein the C-terminus is, optionally, amidated; and
wherein the N-terminus is, optionally, acylated;
or functional fragments thereof.

In some embodiments, the composition comprises a VIP analog, wherein the analog comprises the following repetitive pattern of sequential β-amino acids from the amino-terminus:
$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=a beta-3 tyrosine; $\alpha_1$=an alpha threonine; $\alpha_2$=an alpha arginine; $\alpha_3$=an alpha leucine; $\beta_2$=a beta-3 arginine or APC; $\alpha_4$=an alpha lysine; $\alpha_5$=an alpha glutamine; $\beta_3$=a beta-3 leucine or ACPC; $\alpha_6$=an alpha alanine; $\alpha_7$=an alpha valine; $\alpha_8$=an alpha lysine; $\beta_4$=a beta-3 lysine or APC; $\alpha_9$=an alpha tyrosine; $\alpha_{10}$=an alpha leucine; $\beta_5$=a beta-3 asparagine or ACPC; $\alpha_{11}$=an alpha alanine; $\alpha_{12}$=an alpha isoleucine; $\alpha_{13}$=an alpha leucine; and $\beta_6$=a beta-3 asparagine; wherein the repetitive pattern is, optionally, preceded by: HSDAVFTDN (SEQ ID NO: 1341); and wherein the C-terminus is, optionally, amidated; and
wherein the N-terminus is, optionally, acylated;
or functional fragments thereof.

In some embodiments, the composition comprises HSDAVFTDN (SEQ ID NO: 1341) or HSDAVFTDNY (SEQ ID NO: 1340), wherein at least one of the amino acids from HSDAVFTDN (SEQ ID NO: 1341) or HSDAVFTDNY (SEQ ID NO: 1340) are non-natural or beta amino acids. In some embodiments, the composition comprises HSDAVFTDN (SEQ ID NO: 1341) or HSDAVFTDNY (SEQ ID NO: 1340), wherein at least one of the amino acids from HSDAVFTDN (SEQ ID NO: 1341) or HSDAVFTDNY (SEQ ID NO: 1340) is a beta-3, beta-2, cyclic, or heterocyclic beta amino acids. In some embodiments, the C-terminus is not amidated. In some embodiments, the N-terminus is not acylated. In some embodiments, the composition comprises HSDAVFTDN (SEQ ID NO: 1341) or HSDAVFTDNY (SEQ ID NO: 1340), wherein the the amino acids from HSDAVFTDN or HSDAVFTDNY (SEQ ID NO: 1340) are alpha amino acids. In some embodiments, the composition comprises HSDAVFTDN (SEQ ID NO: 1341) or HSDAVFTDNY (SEQ ID NO: 1340), wherein the the amino acids from HSDAVFTDN (SEQ ID NO: 1341) or HSDAVFTDNY (SEQ ID NO: 1340) are not alpha amino acids. In some embodiments, the composition comprises HSDAVFTDN (SEQ ID NO: 1341) or HSDAVFTDNY (SEQ ID NO: 1340), wherein none of the amino acids from HSDAVFTDN (SEQ ID NO: 1341) or HSDAVFTDNY (SEQ ID NO: 1340) are beta-3 amino acids. In some embodiments, the composition comprises HSDAVFTDN (SEQ ID NO: 1341) or HSDAVFTDNY (SEQ ID NO: 1340), wherein none of the amino acids from HSDAVFTDN or HSDAVFTDNY (SEQ ID NO: 1340) are beta-2 amino acids. In some embodiments, the composition comprises HSDAVFTDN (SEQ ID NO: 1341) or HSDAVFTDNY (SEQ ID NO: 1340), wherein none of the amino acids from HSDAVFTDN (SEQ ID NO: 1341) or HSDAVFTDNY (SEQ ID NO: 1340) are ACPC or APC. In some embodiments, the composition comprises HSDAVFTDN (SEQ ID NO: 1341) or HSDAVFTDNY (SEQ ID NO: 1340), wherein none of the amino acids from HSDAVFTDN (SEQ ID NO: 1341) or HSDAVFTDNY (SEQ ID NO: 1340) are cyclic. In some embodiments, the composition comprises HSDAVFTDN (SEQ ID NO: 1341) or HSDAVFTDNY (SEQ ID NO: 1340), wherein none of the amino acids from HSDAVFTDN (SEQ ID NO: 1341) or HSDAVFTDNY (SEQ ID NO: 1340) are heterocyclic.

"Selective" or "Selectivity" means that the analog of the present invention has a binding preference for one protein as compared to another protein. In some embodiments, the binding preference may be measured as an affinity for a protein in terms of half maximal inhibitory concentration (IC50). In some embodiments, the binding preference may be measured as an affinity for a protein in terms of half maximal effective concentration (EC50). For example, an analog selective to VPAC2 receptor with a selectivity to VPAC2 means that the analog may bind to VPAC1 receptor but has a higher binding affinity for a domain of the VPAC2 receptor if the analog is exposed to both VPAC1 and VPAC2 at similar or equivalent concentrations. As used herein, an analog that selectively binds to VPAC2 refers to an analog with increased selectivity for the VPAC2 receptor compared to other known receptors or proteins to which the peptide may bind. In some embodiments, the analog selective for VPAC2 may be an agonist of the VPAC2 receptor peptide. In some embodiments, the analog selective for VPAC2 may be an antagonist of VPAC2 receptor. In some embodiments, an analog selective to VPAC2 receptor means that the analog may bind to VPAC1 receptor but has a higher binding affinity for a domain of the VPAC2 receptor if the analog is exposed to PAC1, VPAC1 receptor and VPAC2 receptors at similar or equivalent concentrations. In some embodiments, an analog selective to VPAC1 receptor means that the analog may bind to a domain of VPAC2 or PAC1 receptor but has a higher binding affinity for a domain of the VPAC1 receptor if the analog is exposed to to PAC1, VPAC1 receptor and VPAC2 receptors at similar or equivalent concentrations. As used herein, an analog that selectively binds to VPAC1 refers to an analog with increased selectivity for the VPAC1 receptor compared to other known receptors or proteins to which the peptide may bind. In some embodiments, the analog selective for VPAC1 may be an agonist of the VPAC1 receptor peptide. In some embodiments, the analog selective for VPAC1 may be an antagonist of VPAC1 receptor. In some embodiments, an analog selective to VPAC1 receptor means that the analog may bind to VPAC2 receptor but has a higher binding affinity for a domain of the VPAC1 receptor if the analog is exposed to both VPAC1 receptor and VPAC2 receptor at similar or equivalent concentrations. As used herein, an analog that selectively binds to PAC1 refers to an analog with increased selectivity for the PAC1 receptor as compared to other known receptors or proteins to which the peptide may bind. In some embodiments, the analog selective for PAC1 may be an agonist of the PAC1 receptor peptide. In some embodiments, the analog selective for PAC1 may be an antagonist of PAC1 receptor. In some embodiments, an analog selective to PAC1 receptor means that the analog may bind to VPAC2 or VPAC1 receptors but has a higher binding affinity for a domain of the PAC1 receptor if the analog is exposed to to PAC1, VPAC1 receptor and VPAC2 receptors at similar or equivalent concentrations. The degree of selectivity may be determined by a ratio of VPAC2 receptor binding affinity to VPAC1 receptor binding affinity or by a ratio of VPAC2 receptor binding affinity to PAC1 receptor binding affinity. Binding affinity is determined as described below in Example 1.

In any of the embodiments described below wherein the polypeptide comprises a residue designated f, the residue designated f is D-Phe or L-Phe or S. In some embodiments, the invention relates to compositions or pharmaceutical compositions comprising a VIP analog, wherein the analog comprises an α-amino acid and at least one β-amino acid, and wherein the analog is between 75% and 99% homologous to HfDA VFTNSYRKVLKRLSARKLLQDIL; where residue designated f (position 2) is D-Phe, and wherein the analog interferes with the VPAC1 receptor signaling pathway. In some embodiments, the invention relates to compositions or pharmaceutical compositions comprising a VIP analog, wherein the analog comprises an α-amino acid and at least one β-amino acid, and wherein the analog is between 75% and 99% homologous to HfDA VFTNSYRKVLKRLSARKLLQDIL, where residue designated f (position 2) is D-Phe, and wherein the analog is an antagonist of the VPAC1 receptor. In some embodiments, the composition comprises a VIP analog is from about 80% to about 99% homologous to HfDA VFTNSYRKVLKRLSARKLLQDIL, where residue designated f (position 2) is D-Phe. In some embodiments the VIP analog is from about 80% to about 85% homologous to HfDA VFTNSYRKVLKRLSARKLLQDIL, where residue designated f (position 2) is D-Phe. In some embodiments the VIP analog is from about 85% to about 90% homologous to HfDA VFTNSYRKVLKRLSARKLLQDIL, where residue designated f (position 2) is D-Phe. In some embodiments the VIP analog is from about 90% to about 95% homologous to HfDA VFTNSYRKVLKRLSARKLLQDIL, where residue designated f (position 2) is D-Phe. In some embodiments the VIP analog is from about 95% to about 99% homologous to HfDA VFTNSYRKVLKRLSARKLLQDIL, where residue designated f (position 2) is D-Phe. In some embodiments the VIP analog is about 95%, 96%, 97%, 98%, or 99% homologous to HfDA VFTNSYRKVLKRLSARKLLQDIL, where residue designated f (position 2) is D-Phe. In some embodiments, the composition or pharmaceutical compositions comprise a VIP analog, wherein the analog is either: (a) an antagonist of VPAC1 receptor; or (b) interferes with VPAC1 receptor signaling pathway and comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; $\alpha_5$=any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; wherein the repetitive pattern is, optionally, preceded by: HfDAV FTNSY; and wherein residue designated f (position 2) is D-Phe
wherein the C-terminus is, optionally, amidated; and
wherein the N-terminus is, optionally, acylated;
or functional fragments thereof.

In some embodiments, the composition or pharmaceutical compositions comprise a VIP analog, wherein the analog is either: (a) an antagonist of VPAC1 receptor; or (b) interferes with VPAC1 receptor signaling pathway and comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5$, wherein $\gamma_1$=any beta 3 amino acid; $\alpha_1$=any alpha amino acid; $\alpha_2$=any alpha amino acid; $\beta_2$=any beta 3 amino acid; $\alpha_3$=any alpha amino acid; $\alpha_4$=any alpha amino acid; $\alpha_5$=any alpha amino acid; $\beta_3$=any beta 3 amino acid; $\alpha_6$=any alpha amino acid; $\alpha_7$=any alpha amino acid; $\beta_4$=any beta 3 amino acid; $\alpha_8$=any alpha amino acid; $\alpha_9$=any alpha amino acid; $\alpha_{10}$=any alpha amino acid; $\beta_5$=any beta 3 amino acid; wherein the repetitive pattern is, optionally, preceded by: HfDAV FTNSY; and wherein residue designated f (position 2) is D-Phe
wherein the C-terminus is, optionally, amidated; and
wherein the N-terminus is, optionally, acylated;
or functional fragments thereof.

In some embodiments, the composition or pharmaceutical compositions comprise a VIP analog, wherein the analog is either: (a) an antagonist of VPAC1 receptor; or (b) interferes with VPAC1 receptor signaling pathway and comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5$, wherein $\beta_1$=a beta-3 arginine; $\alpha_1$=any alpha amino acid; $\alpha_2$=any alpha amino acid; $\beta_2$=a beta-3 leucine; $\alpha_3$=any alpha amino acid; $\alpha_4$=any alpha amino acid; $\alpha_5$=any alpha amino acid; $\beta_3$=a beta-3 serine; $\alpha_6$=any alpha amino acid; $\alpha_7$=any alpha amino acid; $\beta_4$=a beta-3 lysine; $\alpha_8$=any alpha amino acid; $\alpha_9$=any alpha amino acid; $\alpha_{10}$=any alpha amino acid; $\beta_5$=a beta-3 aspartic acid; wherein the repetitive pattern is, optionally, preceded by: HfDAV FTNSY; and wherein residue designated/(position 2) is D-Phe
wherein the C-terminus is, optionally, amidated; and
wherein the N-terminus is, optionally, acylated;
or functional fragments thereof.

In some embodiments, the composition comprises HfDA VFTDN or HfDA VFTDNY, wherein at least one of the amino acids from HfDA VFTDN or HfDA VFTDNY are non-natural or beta amino acids, wherein residue designated/(position 2) is D-Phe. In some embodiments, the composition comprises HfDA VFTDN or HfDA VFTDNY, wherein at least one of the amino acids from HfDA VFTDN or HfDA VFTDNY is a beta-3, beta-2, cyclic, or heterocyclic beta amino acids, and wherein residue designated/(position 2) is D-Phe. In some embodiments, the C-terminus is not amidated. In some embodiments, the N-terminus is not acylated. In some embodiments, the composition comprises HfDA VFTDN or HfDA VFTDNY, wherein the the amino acids from HfDA VFTDN or HfDA VFTDNY are alpha amino acids, and wherein residue designated/(position 2) is D-Phe. In some embodiments, the composition comprises HfDA VFTDN or HfDA VFTDNY, wherein the the amino acids from HfDA VFTDN or HfDA VFTDNY are not alpha amino acids, and wherein residue designated/(position 2) is D-Phe. In some embodiments, the composition comprises HfDA VFTDN or HfDA VFTDNY, wherein none of the amino acids from HfDA VFTDN or HfDA VFTDNY are beta-3 amino acids, and wherein residue designated/(position 2) is D-Phe. In some embodiments, the composition comprises HfDA VFTDN or HfDA VFTDNY, wherein none of the amino acids from HfDA VFTDN or HfDA VFTDNY are beta-2 amino acids, and wherein residue designated/(position 2) is D-Phe. In some embodiments, the composition comprises HfDA VFTDN or HfDA VFTDNY, wherein none of the amino acids from HfDA VFTDN or HfDA VFTDNY are ACPC or APC, and wherein residue designated/(position 2) is D-Phe. In some embodiments, the composition comprises HfDA VFTDN or HfDA VFTDNY, wherein none of the amino acids from HfDA VFTDN or HfDA VFTDNY are cyclic, wherein residue designated/(position 2) is D-Phe. In some embodiments, the composition comprises HfDA VFTDN or HfDA VFTDNY, wherein none of the amino acids from HfDA VFTDN or HfDA VFTDNY are heterocyclic, and wherein residue designated/(position 2) is D-Phe.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5$; wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; wherein the repetitive pattern is, optionally, preceded by: HfDAV FTNSY or HfDAV FTNS; and wherein the C-terminus is, optionally, amidated; and
wherein the N-terminus is, optionally, acylated;
or functional fragments thereof; and wherein residue designated/(position 2) is D-Phe.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5$; wherein $\beta_1$=a beta-3 arginine or beta-3 tyrosine; $\alpha_1$=any alpha amino acid; $\alpha_2$=any alpha amino acid; $\alpha_3$=an alpha amino acid; $\beta_2$=a beta-3 lysine or beta-3 leucine; $\alpha_4$=an alpha alpha amino acid; $\alpha_5$=any alpha amino acid; $\beta_1$=a beta-3 serine or a beta-3 leucine; $\alpha_6$=any alpha amino acid; $\alpha_7$=any alpha amino acid; $\alpha_8$=any alpha amino acid; $\beta_4$=a beta-3 leucine or beta-3 lysine; $\alpha_9$=any alpha amino acid; $\alpha_{10}$=any alpha amino acid; $\beta_5$=a beta-3 aspartic acid or beta-3 glutamine; wherein the repetitive pattern is, optionally, preceded by: HfDAV FTNSY or HfDAV FTNS; and wherein the C-terminus is, optionally, amidated; and
wherein the N-terminus is, optionally, acylated;
or functional fragments thereof, and wherein residue designated/(position 2) is D-Phe.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5$; wherein $\beta_1$=a beta-3 arginine, beta-3 tyrosine, or APC; $\alpha_1$=any alpha amino acid; $\alpha_2$=any alpha amino acid; $\alpha_3$=an alpha amino acid, $\alpha_3$=ACPC or APC; $\alpha_4$=an alpha alpha amino acid; $\alpha_5$=any alpha amino acid; $\beta_3$=ACPC or a beta-3 leucine; $\alpha_6$=any alpha amino acid; $\alpha_7$=any alpha amino acid; $\alpha_8$=any alpha amino acid; $\beta_4$=a beta-3 leucine, beta-3 lysine, or APC; $\alpha_9$=any alpha amino acid; $\alpha_{10}$=any alpha amino acid; $\beta_5$=a beta-3 aspartic acid or ACPC; wherein the repetitive pattern is, optionally, preceded by. HfDAV FTNSY or HfDAV FI NS; and wherein the C-terminus is, optionally, amidated; and
wherein the N-terminus is, optionally, acylated;
or functional fragments thereof, and wherein residue designated/(position 2) is D-Phe.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

```
HfDAV FTNSY ZKVXK RLXAR KLLQD IL

HfDAV FTNSY RKVXK RLXAR ZLLQD IL

HfDAV FTNSY RKVXK RLXAR KLLQX IL

HfDAV FTNSY ZKVXK RLXAR ZLLQX IL

HfDAV FTNSY RKVLZ RLXAR KLLQX IL

HfDAV FTNSY ZKVLZ RLXAR KLLQX IL
```

-continued

```
HfDAV FTNSY RKVXK RLSAR ZLLXD IL

HfDAV FTNSY RKVXK RXSAR KLLXD IL

HfDAV FTNSY RKVXK RXSAR ZLLXD IL
``` wherein residue designated/(position 2) is D-Phe, wherein each underlined residue is a beta amino acid, wherein X is a ACPC, wherein Z is APC, and wherein the analog interferes with the VPAC1 receptor signaling pathway. In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

```
HfDAV FTNSY ZKVXK RLXAR KLLQD IL

HfDAV FTNSY RKVXK RLXAR ZLLQD IL

HfDAV FTNSY RKVXK RLXAR KLLQX IL

HfDAV FTNSY ZKVXK RLXAR ZLLQX IL

HfDAV FTNSY RKVLZ RLXAR KLLQX IL

HfDAV FTNSY ZKVLZ RLXAR KLLQX IL

HfDAV FTNSY RKVXK RLSAR ZLLXD IL

HfDAV FTNSY RKVXK RXSAR KLLXD IL

HfDAV FTNSY RKVXK RXSAR ZLLXD IL
``` wherein residue designated/(position 2) is D-Phe, wherein each underlined residue is a beta amino acid, wherein X is a ACPC, wherein Z is APC, and wherein the analog is an antagonist of the VPAC1 receptor; or functional fragments thereof.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

```
                                          (SEQ ID NO: 1342)
HSDAV FTDNY TRLRK QlAVK KYLNa ILN (SEQ ID NO: 1342)
HSDAV FTDNY tRLrK QLaVK kYLNa Iln (SEQ ID NO: 1342)
HSDAV FTDNY tRLRk QLaVK KyLNa ILN (SEQ ID NO: 1342)
HSDAV FTDNy TRLrK QlAVK kYLnA Iln (SEQ ID NO: 1343)
HSDAV FTDNY tRLzK QLxVK kYLNx ILn (SEQ ID NO: 1344)
HSDAV FTDNY tRLzK QLxVK zYLNx Iln (SEQ ID NO: 1345)
HSDAV FTDNY xRLzK QLxVK kYLNx Iln (SEQ ID NO: 1346)
HSDAV FTDNY xRLzK QLxVK zYLNx Iln (SEQ ID NO: 1347)
HSDAV FTDNY tRLRz QLxVK KyLNx ILN (SEQ ID NO: 1348)
HSDAV FTDNY xRLRz QLxVK KyLNx ILN (SEQ ID NO: 1349)
HSDAV FTDNy TRLzK QlAVK zYLxA Iln (SEQ ID NO: 1350)
HSDAV FTDNy TRLzK QxAVK kYLxA Iln (SEQ ID NO: 1351)
HSDAV FTDNy TRLzK QxAVK zYLxA Iln
``` wherein each underlined residue is a beta amino acid corresponding to the single code amino acid upon which it is based, wherein X is a ACPC, and wherein Z is APC; or functional fragments thereof.

In some embodiments, the invention relates to compositions or pharmaceutical compositions comprising a VIP analog, wherein the analog comprises an α-amino acid and at least one β-amino acid, and wherein the analog is between 75% and 99% homologous to HSDAVFTDNYTRL-RKQVAAKKYLQSIKNKRY (SEQ ID NO:433), and wherein the analog stimulates the VPAC2 receptor signaling pathway. In some embodiments, the invention relates to compositions or pharmaceutical compositions comprising a VIP analog, wherein the analog comprises an α-amino acid and at least one β-amino acid, and wherein the analog is between 75% and 99% homologous to HSDAVFTDNY-TRLRKQVAAKKYLQSIKNKRY (SEQ ID NO:433), wherein the analog is an agonist of the VPAC2 receptor. In some embodiments, the composition comprises a VIP analog is from about 80% to about 99% homologous to HSDAVFTDNYTRLRKQVAAKKYLQSIKNKRY (SEQ ID NO:433). In some embodiments the VIP analog is from about 80% to about 85% homologous to HSDAVFTDNY-TRLRKQVAAKKYLQSIKNKRY (SEQ ID NO:433). In some embodiments the VIP analog is from about 85% to about 90% homologous to HSDAVFTDNYTRL-RKQVAAKKYLQSIKNKRY (SEQ ID NO:433). In some embodiments the VIP analog is from about 90% to about 95% homologous to HSDAVFTDNYTRLRKQVAAKKY-LQSIKNKRY (SEQ ID NO:433). In some embodiments the VIP analog is from about 95% to about 99% homologous to HSDAVFTDNYTRLRKQVAAKKYLQSIKNKRY (SEQ ID NO:433). In some embodiments the VIP analog is about 95%, 96%, 97%, 98%, or 99% homologous to HSDAVFTD-NYTRLRKQVAAKKYLQSIKNKRY (SEQ ID NO:433). In some embodiments the VIP analog is HSDAVFTDNY-TRLRKQVAAKKYLQSIKNKRY (SEQ ID NO:433).

In some embodiments, the composition or pharmaceutical composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid, $\alpha_4$=any alpha amino acid; $\alpha_5$=any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\beta_6$=any beta amino acid; and wherein the repetitive pattern is, optionally, preceded by: HSDAV FTDNY (SEQ ID NO: 1340) or HSDAV FTDN (SEQ ID NO: 1341); and wherein the repetitive pattern is, optionally, succeeded by: K, KR, or KRY wherein the C-terminus is, optionally, amidated; and
wherein the N-terminus is unmodified or modified; or functional fragments thereof.

In some embodiments, the composition or pharmaceutical composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1=$ a beta-3 threonine; $\alpha_1=$ any alpha amino acid; $\alpha_2=$ any alpha amino acid; $\beta_2=$ a beta-3 arginine; $\alpha_3=$ any alpha amino acid, $\alpha_4=$ any alpha amino acid; $\alpha_5=$ an alpha leucine. $\beta_3=$ a beta-3 alanine, $\alpha_6=$ any alpha amino acid; $\alpha_7=$ any alpha amino acid; $\beta_4=$ a beta-3 lysine; $\alpha_8=$ any alpha amino acid; $\alpha_9=$ any alpha amino acid; $\alpha_{10}=$ any alpha amino acid; $\beta_3=$ a beta-3 serine; $\alpha_{11}=$ any alpha amino acid; $\alpha_{12}=$ any alpha amino acid; $\beta_6=$ a beta-3 asparagine; and
wherein the repetitive pattern is, optionally, preceded by: HSDAV FTDNY (SEQ ID NO: 1340) or HSDAV FTDN (SEQ ID NO: 1341); and wherein the repetitive pattern is, optionally, succeeded by: K, KR, or KRY
wherein the C-terminus is, optionally, amidated; and
wherein the N-terminus is unmodified or modified; or functional fragments thereof,
wherein the VIP analog or functional fragment thereof is a VPAC2 agonist.

In some embodiments, the composition or pharmaceutical composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1=$ any beta amino acid; $\alpha_1=$ any alpha amino acid; $\alpha_2=$ any alpha amino acid; $\beta_2=$ any beta amino acid; $\alpha_3=$ any alpha amino acid; $\alpha_4=$ any alpha amino acid; $\alpha_5=$ any alpha amino acid; $\beta_3=$ any beta amino acid; $\alpha_6=$ any alpha amino acid; $\alpha_7=$ any alpha amino acid; $\beta_4=$ any beta amino acid; $\alpha_8=$ any alpha amino acid; $\alpha_9=$ any alpha amino acid; $\alpha_{10}=$ any alpha amino acid; $\beta_5=$ any beta amino acid; $\alpha_{11}=$ any alpha amino acid; $\alpha_{12}=$ any alpha amino acid; $\beta_6=$ any beta amino acid; and wherein the repetitive pattern is, optionally, preceded by: HSDAV FTDNY (SEQ ID NO: 1340) or HSDAV FTDN (SEQ ID NO: 1341); and wherein the repetitive pattern is, optionally, succeeded by: K, KR, or KRY
wherein the C-terminus is, optionally, amidated; and
wherein the N-terminus is unmodified or modified; or functional fragments thereof; and wherein the analog or functional fragment thereof is a VPAC2 agonist.

In some embodiments, the composition or pharmaceutical composition comprises a VIP analog, wherein the analog comprises the following repetitive pattern of sequential β-amino acids from the amino-terminus: $\beta_1\alpha_1\alpha_2\beta_2\alpha_3\alpha_4\alpha_5\beta_3\alpha_6\alpha_7\beta_4\alpha_8\alpha_9\alpha_{10}\beta_5\alpha_{11}\alpha_{12}\beta_6$, wherein $\beta_1=$ a beta-3 threonine; $\alpha_1=$ any alpha amino acid; $\alpha_2=$ any alpha amino acid; $\beta_2=$ a beta-3 arginine; $\alpha_3=$ any alpha amino acid; $\alpha_4=$ any alpha amino acid; $\alpha_5=$ any alpha amino acid; $\beta_3=$ a beta-3 alanine; $\alpha_6=$ any alpha amino acid; $\alpha_7=$ any alpha amino acid; $\beta_4=$ a beta-3 lysine; as =any alpha amino acid; $\alpha_9=$ any alpha amino acid; $\alpha_{10}=$ any alpha amino acid; $\beta_5=$ a beta-3 serine; $\alpha_{11}=$ any alpha amino acid; $\alpha_{12}=$ any alpha amino acid; $\beta_6=$ a beta-3 asparagine; and
wherein the repetitive pattern is, optionally, preceded by: HSDAVFTDNY (SEQ ID NO: 1340), and wherein the repetitive pattern is, optionally, succeeded by: K, KR, or KRY
wherein the C-terminus is, optionally, amidated; and
wherein the N-terminus is unmodified or modified; or functional fragments thereof.

In some embodiments, the composition comprises a VIP analog, wherein the analog comprises the following repetitive pattern of sequential β-amino acids from the amino-terminus:
$\beta_1\alpha_1\alpha_2\alpha_3\beta_2\alpha_4\alpha_5\beta_3\alpha_6\alpha_7\alpha_8\beta_4\alpha_9\alpha_{10}\beta_3\alpha_{11}\alpha_{12}\alpha_{13}\beta_6$;
wherein $\beta_1=$ any beta amino acid; $\alpha_1=$ any alpha amino acid; $\alpha_2=$ any alpha amino acid; $\alpha_3=$ an alpha amino acid; $\beta_2=$ any beta amino acid; $\alpha_4=$ an alpha alpha amino acid; $\alpha_5=$ any alpha amino acid; $\beta_3=$ any beta amino acid; $\alpha_6=$ any alpha amino acid; $\alpha_7=$ any alpha amino acid; $\alpha_8=$ any alpha amino acid; $\beta_4=$ any beta amino acid; $\alpha_9=$ any alpha amino acid; $\alpha_{10}=$ any alpha amino acid; $\beta_5=$ any beta amino acid; $\alpha_{11}=$ any alpha amino acid; $\alpha_{12}=$ any alpha amino acid; $\alpha_{13}=$ any alpha amino acid; and $\beta_6=$ any beta amino acid; and
wherein the repetitive pattern is, optionally, preceded by: HSDAV FTDNY (SEQ ID NO: 1340) or HSDAV FTDN (SEQ ID NO: 1341); and
wherein the repetitive pattern is, optionally, succeeded by: K, KR, or KRY
wherein the C-terminus is, optionally, amidated; and
wherein the N-terminus is unmodified or modified; or functional fragments thereof.

In some embodiments, the composition comprises a VIP analog, wherein the analog comprises the following repetitive pattern of sequential β-amino acids from the amino-terminus:
$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1=$ a beta-3 threonine or a beta-3 tyrosine; $\alpha_1=$ any alpha amino acid; $\alpha_2=$ any alpha amino acid; $\alpha_3=$ an alpha amino acid; $\beta_2=$ a beta-3 lysine or a beta-3 arginine; $\alpha_4=$ an alpha alpha amino acid; $\alpha_5=$ any alpha amino acid; $\beta_3=$ a beta-3 alanine or a beta-3 valine; $\alpha_6=$ any alpha amino acid, $\alpha_7=$ any alpha amino acid; $\alpha_8=$ any alpha amino acid; $\beta_4=$ a beta-3 tyrosine or a beta-3 lysine; $\alpha_9=$ any alpha amino acid; $\alpha_{10}=$ any alpha amino acid; $\beta_5=$ a beta-3 serine or a beta-3 glutamine; $\alpha_{11}=$ any alpha amino acid; $\alpha_{12}=$ any alpha amino acid; $\alpha_{13}=$ any alpha amino acid; and $\beta_6=$ a beta-3 lysine or a beta-3 asparagine; and wherein the repetitive pattern is, optionally, preceded by: HSDAV FTDNY (SEQ ID NO: 1340) or HSDAV FTDN (SEQ ID NO: 1341); and wherein the repetitive pattern is, optionally, succeeded by: K, KR, or KRY
wherein the C-terminus is, optionally, amidated; and
wherein the N-terminus is unmodified or modified; or functional fragments thereof.

In some embodiments, the composition comprises a VIP analog, wherein the analog comprises the following repetitive pattern of sequential β-amino acids from the amino-terminus:
$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1=$ a beta-3 threonine or a beta-3 tyrosine; $\alpha_1=$ any alpha amino acid; $\alpha_2=$ any alpha amino acid; $\alpha_3=$ an alpha amino acid; $\beta_2=$ a beta-3 lysine or a beta-3 arginine; $\alpha_4=$ air alpha alpha amino acid; $\alpha_5=$ any alpha amino acid; $\beta_3=$ a beta-3 alanine or a beta-3 valine; $\alpha_6=$ any alpha amino acid; $\alpha_7=$ any alpha amino acid; $\alpha_8=$ any alpha amino acid; $\beta_4=$ a beta-3 tyrosine or a beta-3 lysine; $\alpha_9=$ any alpha amino acid; $\alpha_{10}=$ any alpha amino acid; $\beta_5=$ a beta-3 serine or a beta-3 glutamine; $\alpha_{11}=$ any alpha amino acid; $\alpha_{12}=$ any alpha amino acid; $\alpha_{13}=$ any alpha amino acid; and $\beta_6=$ a beta-3 lysine or a beta-3 asparagine; and wherein the repetitive pattern is, optionally, preceded by: HSDAV FTDNY (SEQ ID NO: 1340) or HSDAV FTDN (SEQ ID NO: 1341); and wherein the repetitive pattern is, optionally, succeeded by: K, KR, or KRY.
wherein the C-terminus is, optionally, amidated; and
wherein the N-terminus is unmodified or modified; or functional fragments thereof;

and wherein the analog or functional fragment thereof is a VPAC2 agonist.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

HSDAVFTDNY<u>X</u>RL<u>Z</u>KQV<u>X</u>AK<u>K</u>YLQ<u>S</u>IK<u>N</u>KRY (SEQ ID NO: 1353)

HSDAVFTDNY<u>T</u>RL<u>Z</u>KQV<u>X</u>AK<u>Z</u>YLQ<u>S</u>IK<u>N</u>KRY (SEQ ID NO: 1354)

HSDAVFTDNY<u>T</u>RL<u>Z</u>KQV<u>X</u>AK<u>K</u>YLQ<u>X</u>IK<u>N</u>KRY (SEQ ID NO: 1355)

HSDAVFTDNY<u>X</u>RL<u>Z</u>KQV<u>X</u>AK<u>Z</u>YLQ<u>X</u>IK<u>X</u>KRY (SEQ ID NO: 1356)

HSDAVFTDNY<u>T</u>RLR<u>Z</u>QV<u>X</u>AK<u>K</u>YLQ<u>X</u>IKNKRY (SEQ ID NO: 1357)

HSDAVFTDNY<u>X</u>RLR<u>Z</u>QV<u>X</u>AK<u>K</u>YLQ<u>X</u>IKNKRY (SEQ ID NO: 1358)

HSDAVFTDN<u>Y</u>TRL<u>Z</u>KQ<u>V</u>SAK<u>Z</u>YL<u>X</u>SIK<u>N</u>KRY (SEQ ID NO: 1359)

HSDAVFTDN<u>Y</u>TRL<u>Z</u>KQ<u>X</u>SAK<u>K</u>YL<u>X</u>SIK<u>N</u>KRY (SEQ ID NO: 1360)

HSDAVFTDN<u>Y</u>TRL<u>Z</u>KQ<u>X</u>SAK<u>Z</u>YL<u>X</u>SIK<u>N</u>KRY (SEQ ID NO: 1361)

wherein each underlined residue is a beta amino acid corresponding to the single code amino acid upon which it is based, wherein X is a ACPC, and wherein Z is APC; or functional fragments thereof; wherein the C-terminus is, optionally, amidated; and wherein the N-terminus is unmodified.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

HSDAVFTDNY<u>X</u>RL<u>Z</u>KQV<u>X</u>AK<u>K</u>YLQ<u>S</u>IK<u>N</u>KRY (SEQ ID NO: 1353)

HSDAVFTDNY<u>T</u>RL<u>Z</u>KQV<u>X</u>AK<u>Z</u>YLQ<u>S</u>IK<u>N</u>KRY (SEQ ID NO: 1354)

HSDAVFTDNY<u>T</u>RL<u>Z</u>KQV<u>X</u>AK<u>K</u>YLQ<u>X</u>IK<u>N</u>KRY (SEQ ID NO: 1355)

HSDAVFTDNY<u>X</u>RL<u>Z</u>KQV<u>X</u>AK<u>Z</u>YLQ<u>X</u>IK<u>X</u>KRY (SEQ ID NO: 1356)

HSDAVFTDNY<u>T</u>RLR<u>Z</u>QV<u>X</u>AK<u>K</u>YLQ<u>X</u>IKNKRY (SEQ ID NO: 1357)

HSDAVFTDNY<u>X</u>RLR<u>Z</u>QV<u>X</u>AK<u>K</u>YLQ<u>X</u>IKNKRY (SEQ ID NO: 1358)

HSDAVFTDN<u>Y</u>TRL<u>Z</u>KQ<u>V</u>SAK<u>Z</u>YL<u>X</u>SIK<u>N</u>KRY (SEQ ID NO: 1359)

HSDAVFTDN<u>Y</u>TRL<u>Z</u>KQ<u>X</u>SAK<u>K</u>YL<u>X</u>SIK<u>N</u>KRY (SEQ ID NO: 1360)

HSDAVFTDN<u>Y</u>TRL<u>Z</u>KQ<u>X</u>SAK<u>Z</u>YL<u>X</u>SIK<u>N</u>KRY (SEQ ID NO: 1361)

wherein each underlined residue is a beta amino acid corresponding to the single code amino acid upon which it is based, wherein X is a ACPC, and wherein Z is APC: or functional fragments thereof; wherein the C-terminus is, optionally, amidated; and wherein the N-terminus is, optionally, modified.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

HSDAVFTDNY<u>X</u>RL<u>Z</u>KQV<u>X</u>AK<u>K</u>YLQ<u>S</u>IK<u>N</u>KRY (SEQ ID NO: 1353)

HSDAVFTDNY<u>T</u>RL<u>Z</u>KQV<u>X</u>AK<u>Z</u>YLQ<u>S</u>IK<u>N</u>KRY (SEQ ID NO: 1354)

HSDAVFTDNY<u>T</u>RL<u>Z</u>KQV<u>X</u>AK<u>K</u>YLQ<u>X</u>IK<u>N</u>KRY (SEQ ID NO: 1355)

HSDAVFTDNY<u>X</u>RL<u>Z</u>KQV<u>X</u>AK<u>Z</u>YLQ<u>X</u>IK<u>X</u>KRY (SEQ ID NO: 1356)

HSDAVFTDNY<u>T</u>RLR<u>Z</u>QV<u>X</u>AK<u>K</u>YLQ<u>X</u>IKNKRY (SEQ ID NO: 1357)

HSDAVFTDNY<u>X</u>RLR<u>Z</u>QV<u>X</u>AK<u>K</u>YLQ<u>X</u>IKN<u>K</u>RY (SEQ ID NO: 1358)

HSDAVFTDN<u>Y</u>TRL<u>Z</u>KQ<u>V</u>SAK<u>Z</u>YL<u>X</u>SIK<u>N</u>KRY (SEQ ID NO: 1359)

HSDAVFTDN<u>Y</u>TRL<u>Z</u>KQ<u>X</u>SAK<u>K</u>YL<u>X</u>SIK<u>N</u>KRY (SEQ ID NO: 1360)

HSDAVFTDN<u>Y</u>TRL<u>Z</u>KQ<u>X</u>SAK<u>Z</u>YL<u>X</u>SIK<u>N</u>KRY (SEQ ID NO: 1361)

wherein each underlined residue is a beta amino acid corresponding to the single code amino acid upon which it is based, wherein X is a ACPC, and wherein Z is APC: or functional fragments thereof; wherein the C-terminus is, optionally, amidated; wherein the N-terminus is, optionally, modified; and wherein the VIP analog or functional fragment thereof is a VPAC2 agonist.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

HSDAVFTDNY<u>T</u>RL<u>R</u>KQV<u>A</u>AK<u>K</u>YLQ<u>S</u>IK<u>N</u>KR Y (SEQ ID NO: 433)

HSDAVFTDNY<u>T</u>RLRKQV<u>A</u>AK<u>K</u>YLQ<u>S</u>IK<u>N</u>KR Y (SEQ ID NO: 433)

HSDAVFTDN<u>Y</u>TRL<u>R</u>KQ<u>V</u>AAK<u>K</u>YL<u>Q</u>SIK<u>N</u>KR Y (SEQ ID NO: 433)

HSDAVFTDNY<u>X</u>RL<u>Z</u>KQV<u>X</u>AK<u>K</u>YLQ<u>S</u>IK<u>N</u>KRY (SEQ ID NO: 1353)

HSDAVFTDNY<u>T</u>RL<u>Z</u>KQV<u>X</u>AK<u>Z</u>YLQ<u>S</u>IK<u>N</u>KRY (SEQ ID NO: 1354)

HSDAVFTDNY<u>T</u>RL<u>Z</u>KQV<u>X</u>AK<u>K</u>YLQ<u>X</u>IK<u>N</u>KRY (SEQ ID NO: 1355)

HSDAVFTDNY<u>X</u>RL<u>Z</u>KQV<u>X</u>AK<u>Z</u>YLQ<u>X</u>IK<u>X</u>KRY (SEQ ID NO: 1356)

```
                                              (SEQ ID NO: 1357)
HSDAVFTDNYTRLRZQVXAKKYLQXIKNKRY (SEQ ID NO: 1358)
HSDAVFTDNYXRLRZQVXAKKYLQXIKNKRY (SEQ ID NO: 1359)
HSDAVFTDNYTRLZKQVSAKZYLXSIKNKRY (SEQ ID NO: 1360)
HSDAVFTDNYTRLZKQXSAKKYLXSIKNKRY (SEQ ID NO: 1361)
HSDAVFTDNYTRLZKQXSAKZYLXSIKNKRY
``` wherein each underlined residue is an unnatural amino acid corresponding to the single code amino acid upon which it is based, wherein X is a ACPC, and wherein Z is APC; or functional fragments thereof; wherein the C-terminus is, optionally, amidated; wherein the N-terminus is, optionally, modified; and wherein the VIP analog or functional fragment thereof is a VPAC1 agonist.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

```
                                              (SEQ ID NO: 433)
HSDAVFTDNYTRLRKQVAAKKYLQSIKNKR Y (SEQ ID NO: 433)
HSDAVFTDNYTRLRKQVAAKKYLQSIKNKR Y (SEQ ID NO: 433)
HSDAVFTDNYTRLRKQVAAKKYLQSIKNKR Y (SEQ ID NO: 1353)
HSDAVFTDNYXRLZKQVXAKKYLQSIKNKRY (SEQ ID NO: 1354)
HSDAVFTDNYTRLZKQVXAKZYLQSIKNKRY (SEQ ID NO: 1355)
HSDAVFTDNYTRLZKQVXAKKYLQXIKNKRY (SEQ ID NO: 1356)
HSDAVFTDNYXRLZKQVXAKZYLQXIKXKRY (SEQ ID NO: 1357)
HSDAVFTDNYTRLRZQVXAKKYLQXIKNKRY (SEQ ID NO: 1358)
HSDAVFTDNYXRLRZQVXAKKYLQXIKNKRY (SEQ ID NO: 1359)
HSDAVFTDNYTRLZKQVSAKZYLXSIKNKRY (SEQ ID NO: 1360)
HSDAVFTDNYTRLZKQXSAKKYLXSIKNKRY (SEQ ID NO: 1361)
HSDAVFTDNYTRLZKQXSAKZYLXSIKNKRY
``` wherein each underlined residue is a beta amino acid corresponding to the single code amino acid upon which it is based, wherein X is a ACPC, and wherein Z is APC; or functional fragments thereof; wherein the C-terminus is, optionally, amidated; wherein the N-terminus is, optionally, modified; and wherein the VIP analog or functional fragment thereof is a VPAC1 agonist.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

```
                                              (SEQ ID NO: 433)
HSDAVFTDNYTRLRKQVAAKKYLQSIKNKR Y (SEQ ID NO: 433)
HSDAVFTDNYTRLRKQVAAKKYLQSIKNKR Y (SEQ ID NO: 433)
HSDAVFTDNYTRLRKQVAAKKYLQSIKNKR Y (SEQ ID NO: 1353)
HSDAVFTDNYXRLZKQVXAKKYLQSIKNKRY (SEQ ID NO: 1354)
HSDAVFTDNYTRLZKQVXAKZYLQSIKNKRY (SEQ ID NO: 1355)
HSDAVFTDNYTRLZKQVXAKKYLQXIKNKRY (SEQ ID NO: 1356)
HSDAVFTDNYXRLZKQVXAKZYLQXIKXKRY (SEQ ID NO: 1357)
HSDAVFTDNYTRLRZQVXAKKYLQXIKNKRY (SEQ ID NO: 1358)
HSDAVFTDNYXRLRZQVXAKKYLQXIKNKRY (SEQ ID NO: 1359)
HSDAVFTDNYTRLZKQVSAKZYLXSIKNKRY (SEQ ID NO: 1360)
HSDAVFTDNYTRLZKQXSAKKYLXSIKNKRY (SEQ ID NO: 1361)
HSDAVFTDNYTRLZKQXSAKZYLXSIKNKRY
``` wherein each underlined residue is a beta-3 homo amino acid corresponding to the single code amino acid upon which it is based, wherein X is a ACPC, and wherein Z is APC; or functional fragments thereof; wherein the C-terminus is, optionally, amidated; wherein the N-terminus is, optionally, modified; and wherein the VIP analog or functional fragment thereof is a VPAC1 agonist.

In some embodiments, the invention relates to compositions or pharmaceutical compositions comprising a VIP analog, wherein the analog comprises an α-amino acid and at least one R-amino acid, and wherein the analog comprises an amino acid sequence that is between 75% and 100% homologous to one or more of the following sequences:

```
                                              (SEQ ID NO: 433)
HSDAVFTDNYTRLRKQVAAKKYLQSIKNKR Y (SEQ ID NO: 433)
HSDAVFTDNYTRLRKQVAAKKYLQSIKNKR Y (SEQ ID NO: 433)
HSDAVFTDNYTRLRKQVAAKKYLQSIKNKR Y (SEQ ID NO: 1353)
HSDAVFTDNYXRLZKQVXAKKYLQSIKNKRY (SEQ ID NO: 1354)
HSDAVFTDNYTRLZKQVXAKZYLQSIKNKRY (SEQ ID NO: 1355)
HSDAVFTDNYTRLZKQVXAKKYLQXIKNKRY (SEQ ID NO: 1356)
HSDAVFTDNYXRLZKQVXAKZYLQXIKXKRY
```

-continued (SEQ ID NO: 1357)
HSDAVFTDNYTRLRZQVXAKKYLQXIKNKRY (SEQ ID NO: 1358)
HSDAVFTDNYXRLRZQVXAKKYLQXIKNKRY (SEQ ID NO: 1359)
HSDAVFTDNYTRLZKQVSAKZYLXSIKNKRY (SEQ ID NO: 1360)
HSDAVFTDNYTRLZKQXSAKKYLXSIKNKRY (SEQ ID NO: 1361)
HSDAVFTDNYTRLZKQXSAKZYLXSIKNKRY wherein each underlined residue is any unnatural amino acid; any beta-2 amino acid; any beta-3 amino acid; or a beta-3 homo amino acid corresponding to the single code amino acid upon which it is based; wherein X is a ACPC, and wherein Z is APC; or functional fragments thereof; wherein the C-terminus is, optionally, amidated; wherein the N-terminus is, optionally, modified; and wherein the VIP analog or functional fragment thereof is a VPAC1 or VPAC2 agonist.

In some embodiments, the invention relates to compositions or pharmaceutical compositions comprising a VIP analog, wherein the analog comprises an α-amino acid and at least one β-amino acid, and wherein the analog comprises an amino acid sequence that is between 75% and 100% homologous to:

(SEQ ID NO: 433)
HSDAVFTDNYTRLRKQVAAKKYLQSIKNKRY or functional fragments thereof; and wherein the VIP analog or functional fragment thereof is a VPAC2 agonist.

In some embodiments, the invention relates to compositions or pharmaceutical compositions comprising a VIP analog, wherein the analog comprises an α-amino acid and at least one β-amino acid, and wherein the analog comprises an amino acid sequence that is between 75% and 100% homologous to any of the amino acid sequence provided in this application.

The invention relates to methods of manufacturing a composition comprising an analog, wherein the analog comprises an α-amino acid and at least one β-amino acid. In some embodiments, the invention relates to methods of manufacturing a composition comprising an analog, wherein the analog comprises an α-amino acid, at least one β-amino acid, and at least one modified amino acid residue comprising ACPC or APC. The invention relates to methods of manufacturing a composition comprising a secretin family analog, wherein the secretin family analog comprises an α-amino acid and at least one β-amino acid. The invention relates to methods of manufacturing a composition comprising a VIP analog, wherein the VIP analog comprises an α-amino acid and at least one β-amino acid. The method used to fabricate polypeptide compounds may be any means of polypeptide synthesis. Using methods of peptide synthesis, polypeptides fabricated according to the present method are generally less than about 100 residues long. In some embodiments, the invention relates to a method of manufacturing an analog (or fragments herein) comprising non-natural amino acids from from about 5 total residues to about 50 total residues, from about 10 total residues to about 20 total residues, from about 20 total residues to about 30 total residues, from about 30 total residues to about 40 total residues, from about 40 total residues to about 50 total residues, from about 50 to about 60 total residues, from about 60 to about 70 total residues from about 70 to about 80 total residues, from about 80 to about 90 total residues, and from about 90 to about 100 total residues. Ranges above and below these stated ranges are within the scope of the invention. Many commercial services, such as Abgent (San Diego, Calif., USA) offer peptide synthesis services up to about 100 residues. In some embodiments, the invention relates to a method of manufacturing an analog comprising no more than 100 non-natural amino acids. In some embodiments, the invention relates to a method of manufacturing an analog comprising no more than 90 non-natural amino acids. In some embodiments, the invention relates to a method of manufacturing an analog comprising no more than 80 non-natural amino acids. In some embodiments, the invention relates to a method of manufacturing an analog comprising no more than 70 non-natural amino acids. In some embodiments, the invention relates to a method of manufacturing an analog comprising no more than 60 non-natural amino acids. In some embodiments, the invention relates to a method of manufacturing an analog comprising no more than 50 non-natural amino acids. In some embodiments, the invention relates to a method of manufacturing an analog comprising no more than 40 non-natural amino acids. In some embodiments, the invention relates to a method of manufacturing an analog comprising no more than 30 non-natural amino acids. In some embodiments, the invention relates to a method of manufacturing an analog comprising no more than 20 non-natural amino acids. In some embodiments, the invention relates to a method of manufacturing an analog comprising no more than 10 non-natural amino acids. In some embodiments, the method of manufacturing the analog comprises synthesizing the analog using at least one, and, in some embodiments, a plurality of the following non-naturally occurring amino acid residues: (2S,3R)-3-(amino)-2-hydroxy-4-(4-nitrophenyl)butyric acid, (2R,3R)-3-(amino)-2-hydroxy-4-phenylbutyric acid, (R)-3-(amino)-5-phenylpentanoic acid, (R)-3-(amino)-4-(2-naphthyl)butyric acid, (R)-2-methyl-β-Phe-OH, (R)-3,4-dimethoxy-β-Phe-OH, (R)-(3-pyridyl)-β-Ala-OH, (R)-3-(trifluoromethyl)-β-Phe-OH, (R)-3-cyano-β-Phe-OH, (R)-3-methoxy-β-Phe-OH, (R)-3-methyl-β-Phe-OH, (R)-4-(4-pyridyl)-β-HomoAla-OH, (R)-4-(trifluoromethyl)-β-HomoPhe-OH, (R)-4-(trifluoromethyl)-β-Phe-OH, (R)-4-bromo-β-Phe-OH, (R)-4-chloro-β-HomoPhe-OH, (R)-4-chloro-β-Phe-OH, (R)-4-cyano-β-HomoPhe-OH, (R)-4-cyano-β-Phe-OH, (R)-4-fluoro-β-Phe-OH, (R)-4-methoxy-β-Phe-OH, (R)-4-methyl-β-Phe-OH, (R)-β-Tyr-OH, (R)-4-(3-pyridyl)-β-HomoAla-OH, (R)-4-fluoro-β-HomoPhe-OH, (S)-5-phenylpentanoic acid, (S)-5-hexenoic acid, (S)-5-phenyl-pentanoic acid, (S)-6-phenyl-5-hexenoic acid, (S)-2-(trifluoromethyl)-β-HomoPhe-OH, (S)-2-(trifluoromethyl)-β-Phe-OH, (S)-2-cyano-β-HomoPhe-OH, (S)-2-methyl-β-Phe-OH, (S)-3,4-dimethoxy-β-Phe-OH, (S)-3-(trifluoromethyl)-β-HomoPhe-OH, (S)-3-(trifluoromethyl)-β-Phe-OH, (S)-3-cyano-β-Phe-OH, (S)-3-methoxy-β-Phe-OH, (S)-3-methyl-β-Phe-OH, (S)-4-(4-pyridyl)-β-HomoAla-OH, (S)-4-(trifluoromethyl)-β-Phe-OH, (S)-4-bromo-β-Phe-OH, (S)-4-chloro-β-HomoPhe-OH, (S)-4-chloro-β-Phe-OH, (S)-4-cyano-β-HomoPhe-OH, (S)-4-cyano-β-Phe-OH, (S)-4-fluoro-β-Phe-OH, (S)-4-iodo-β-HomoPhe-OH, (S)-4-methyl-β-HomoPhe-OH, (S)-4-methyl-β-Phe-OH, (S)-β-Tyr-OH, (S)-γ,γ-diphenyl-β-HomoAla-OH, (S)-2-methyl-β-Homophe-OH, (S)-3,4-difluoro-β-HomoPhe-OH, (S)-3-(trifluoromethyl)-β-HomoPhe-OH, (S)-3-cyano-β-HomoPhe-OH, (S)-3-methyl-β-HomoPhe-OH, (S)-γ,γ- diphenyl-β-HomoAla-OH, 3-Amino-3-(3-bromophenyl)propionic acid, and 3-Amino-4,4,4-trifluorobutyric acid.

In some embodiments, the fragment comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 30, 31, 32, 33, 34, 35, 36, 37, 38, 39, or 40 amino acids of the wild type protein sequence.

In some embodiments, the fragment comprises any of the above-mentioned numbers of amino acids located anywhere within the peptide. Thus, one skilled in the art understands that a fragment of any of these lengths can be walked along the length of the peptide, thus providing any fragment of the peptide with the same or similar function as the native or wild-type amino acid sequence.

One of ordinary skill in the art would readily appreciate that the protecting groups would be removed from the final chemical structure of the analog which becomes administered to a subject. One of ordinary skill would be able to predict the final chemical structure of the analog by using the protecting groups selectively to create a polypeptide with a desirable chirality or secondary structure. For instance, if the analog of the composition is manufactured using (S)-Fmoc-3-methyl-3-HomoPhe-OH, the final yielded product should comprise at least one β-amino acid residue of a 3-methyl-β-homophenylalanine.

In some embodiments, the method of manufacturing the analog comprises synthesizing the analog using at least one, and in some embodiments, a plurality of cyclic amino acid residues. In some embodiments, the VIP analog of the claimed invention comprises the cyclic amino acid residues. In some embodiments, the VIP analog of the claimed invention comprises at least one disulfide bridge that forms a cyclic chain of atoms along a side chain of two amino acid residues.

In some embodiments, the VIP analog of the claimed invention comprises the following sequence:

(SEQ ID NO: 10)
HSDAVFTDNYTRLRKQMAVKKYLNSILN;

wherein at least one of the amino acid residues is a β-amino acid residue, and at least one of the amino acid residues is an α-amino acid residue. In some embodiments, the at least one α-amino acid residue is a non-natural amino acid residue. In some embodiments, the amino acid residues at positions 1, 3, 6, 7, 10, and 23 of the VIP analog are not alanine, glycine, or any β amino acid residue with a methyl side chain.

In some embodiments, the VIP analog of the claimed invention comprises the following sequence:

(SEQ ID NO: 1362)
HSDAVF$\underline{X_1X_2}$NYTRLR $\underline{X_3}$Q$\underline{X_4}$A$\underline{X_5X_6X_7}$YLN$\underline{X_8}$I$\underline{X_9X_{10}}$ wherein any of $X_1$, $X_2$, $X_3$, $X_4$, $X_5$, $X_6$, $X_7$, $X_8$, $X_9$, or $X_{10}$ may be a beta-amino acid. In some embodiments, the VIP analog of the claimed invention comprises the following sequence:

(SEQ ID NO: 1362)
HSDAVF$\underline{X_1X_2}$NYTRLR $\underline{X_3}$Q$\underline{X_4}$A$\underline{X_5X_6X_7}$YLN$\underline{X_8}$I$\underline{X_9X_{10}}$ wherein any of $X_1$, $X_2$, $X_3$, $X_4$, $X_5$, $X_6$, $X_7$, $X_8$, $X_9$, or $X_{10}$ are a β³-amino acid residue. In some embodiments, at least one of the β³-amino acid residues is substituted with a residue chosen from the following: (S,S)-trans-2-aminocyclopentanecarboxylic acid ((S,S)-ACPC), (S,R)-trans-2-aminocyclopentanecarboxylic acid ((S,R)-ACPC), (R,S)-trans-2-aminocyclopentanecarboxylic acid ((R,S)-ACPC), or (R,R)-trans-2-aminocyclopentanecarboxylic acid ((R,R)-ACPC) if the amino acid is non-polar; or pyrrolidine analogue of (S,S)-ACPC, (R,S)-ACPC, (S,R)-ACPC, (R,R)-ACPC), which is designated APC, if the amino acid is basic. In some embodiments, at least one of the β³-amino acid residues is substituted with a residue chosen from the following: (S,S)-trans-2-aminocyclopentanecarboxylic acid ((S,S)-ACPC) if the amino acid is non-polar; or pyrrolidine analogue of (S,S)-ACPC if the residue is basic.

In some embodiments, the VIP analog of the claimed invention comprises the following sequence:

(SEQ ID NO: 1362)
HSDAVF$\underline{X_1X_2}$NYTRLR $\underline{X_3}$Q$\underline{X_4}$A$\underline{X_5X_6X_7}$YLN$\underline{X_8}$I$\underline{X_9X_{10}}$ wherein any one or more of $X_1$, $X_2$, $X_3$, $X_4$, $X_5$, $X_6$, $X_7$, $X_8$, $X_9$, or $X_{10}$ is a beta-amino acid, and wherein $X_1$=T; $X_2$=D; $X_3$=R or K; $X_4$=M or L; $X_5$=A or V; $X_6$=R or K; $X_7$=R or K; $X_8$=S or A; $X_9$=L or K; and $X_{10}$=N or K. In some embodiments, the VIP analog of the claimed invention comprises the following sequence:

(SEQ ID NO: 1362)
HSDAVF$\underline{X_1X_2}$NYTRLR $\underline{X_3}$Q$\underline{X_4}$A$\underline{X_5X_6X_7}$YLN$\underline{X_8}$I$\underline{X_9X_{10}}$ wherein any one of $X_1$, $X_2$, $X_3$, $X_4$, $X_5$, $X_6$, $X_7$, $X_8$, $X_9$, or $X_{10}$ is a β³-amino acid residue. In some embodiments, at least one of the β³-amino acid residues is substituted with a residue chosen from the following: (S,S)-trans-2-aminocyclopentanecarboxylic acid ((S,S)-ACPC), (S,R)-trans-2-aminocyclopentanecarboxylic acid ((S,R)-ACPC), (R,S)-trans-2-aminocyclopentanecarboxylic acid ((R,S)-ACPC), or (R,R)-trans-2-aminocyclopentanecarboxylic acid ((R,R)-ACPC) if the amino acid is non-polar; or pyrrolidine analogue of (S,S)-ACPC, (R,S)-ACPC, (S,R)-ACPC, (R,R)-ACPC), which is designated APC, if the amino acid is basic. In some embodiments, at least one of the β³-amino acid residues is substituted with a residue chosen from the following: (S,S)-trans-2-aminocyclopentanecarboxylic acid ((S,S)-ACPC) if the amino acid is non-polar; or pyrrolidine analogue of (S,S)-ACPC if the residue is basic.

In some embodiments, the VIP analog of the claimed invention comprises the following sequence:

(SEQ ID NO: 1362)
HSDAVF$\underline{X_1X_2}$NYTRLR $\underline{X_3}$Q$\underline{X_4}$A$\underline{X_5X_6X_7}$YLN$\underline{X_8}$I$\underline{X_9X_{10}}$ wherein any one or more of $X_1$, $X_2$, $X_3$, $X_4$, $X_5$, $X_6$, $X_7$, $X_8$, $X_9$, or $X_{10}$ is a beta-amino acid, and wherein $X_1$=T; $X_2$=D; $X_3$=R or K; $X_4$=M or L; $X_5$=A or V; $X_6$=R or K; $X_7$=R or K; $X_8$=S or A; $X_9$=L or K; and $X_{10}$=N or K. In some embodiments, the VIP analog of the claimed invention comprises the following sequence:

(SEQ ID NO: 1362)
HSDAVF$\underline{X_1X_2}$NYTRLR $\underline{X_3}$Q$\underline{X_4}$A$\underline{X_5X_6X_7}$YLN$\underline{X_8}$I$\underline{X_9X_{10}}$ wherein any one or more of $X_1$, $X_2$, $X_3$, $X_4$, $X_5$, $X_6$, $X_7$, $X_8$, $X_9$, or $X_{10}$ is a β³-amino acid residue. In some embodiments, at least one of the β³-amino acid residues is substituted with a residue chosen from the following: (S,S)-trans-2-aminocyclopentanecarboxylic acid ((S,S)-ACPC), (S,R)-trans-2-aminocyclopentanecarboxylic acid ((S,R)-ACPC), (R,S)- trans-2-aminocyclopentanecarboxylic acid ((R,S)-ACPC), or (R,R)-trans-2-aminocyclopentanecarboxylic acid ((R,R)-ACPC) if the amino acid is non-polar; or pyrrolidine analogue of (S,S)-ACPC, (R,S)-ACPC, (S,R)-ACPC, (R,R)-ACPC), which is designated APC, if the amino acid is basic. In some embodiments, at least one of the $\beta^3$ amino acid residues is substituted with a residue chosen from the following: (S,S)-trans-2-aminocyclopentanecarboxylic acid ((S,S)-ACPC) if the amino acid is non-polar; or pyrrolidine analogue of (S,S)-ACPC if the residue is basic.

In some embodiments, the VIP analog of the claimed invention comprises the following sequence:

(SEQ ID NO: 1363)
HSDAVF$\underline{X_1X_2}$NY$\underline{X_3}$RL$X_4$ $X_5$Q$\underline{X_6X_7X_8X_9}X_{10}$YLN$X_{11}$I$\underline{X_{12}X_{13}}$ wherein $X_3$, $X_4$, $X_7$, $X_{10}$, and $X_{11}$ are beta-amino acid residues derived from the naturally occurring α-amino acid residue at that position, and wherein $X_1$=T; $X_2$=D; $X_5$=R or K; $X_6$=M or L; $X_8$=A or V; $X_9$=R or K; $X_{10}$=R or K; $X_{11}$=S or A; $X_{12}$=L or K; and $X_{13}$=N or K.

(SEQ ID NO: 1363)
HSDAVF$\underline{X_1X_2}$NY$\underline{X_3}$RL$X_4$ $X_5$Q$\underline{X_6X_7X_8X_9}X_{10}$YLN$X_{11}$I$\underline{X_{12}X_{13}}$ wherein $X_3$, $X_4$, $X_7$, $X_{10}$, and $X_{11}$ are $\beta^3$-amino acid residues derived from the naturally occurring α-amino acid residue at that position. In some embodiments, at least one of the $\beta^3$-amino acid residues is substituted with a residue chosen from the following: (S,S)-trans-2-aminocyclopentanecarboxylic acid ((S,S)-ACPC), (S,R)-trans-2-aminocyclopentanecarboxylic acid ((S,R)-ACPC), (R,S)-trans-2-aminocyclopentanecarboxylic acid ((R,S)-ACPC), or (R,R)-trans-2-aminocyclopentanecarboxylic acid ((R,R)-ACPC) if the amino acid is non-polar; or pyrrolidine analogue of (S,S)-ACPC, (R,S)-ACPC, (S,R)-ACPC, (R,R)-ACPC), which is designated APC, if the amino acid is basic. In some embodiments, at least one of the $\beta^3$-amino acid residues is substituted with a residue chosen from the following: (S,S)-trans-2-aminocyclopentanecarboxylic acid ((S,S)-ACPC) if the amino acid is non-polar; or pyrrolidine analogue of (S,S)-ACPC if the residue is basic.

In some embodiments, the VIP analog of the claimed invention comprises the following sequence:

(SEQ ID NO: 1363)
HSDAVF$\underline{X_1X_2}$NY$\underline{X_3}$RL$X_4$ $X_5$Q$\underline{X_6X_7X_8X_9}X_{10}$YLN$X_{11}$I$\underline{X_{12}X_{13}}$ wherein at least one of $X_1$, $X_2$, $X_3$, $X_4$, $X_5$, $X_6$, $X_7$, $X_8$, $X_9$, $X_{10}$, $X_{11}$, $X_{12}$, or $X_{13}$ is a beta-amino acid, and wherein $X_1$=T; $X_2$=D; $X_5$=R or K; $X_6$=M or L; $X_8$=A or V; $X_9$=R or K; $X_{10}$=R or K; $X_{11}$=S or A; $X_{12}$=L or K; and $X_{13}$=N or K. In some embodiments, the VIP analog of the claimed invention comprises the following sequence:

(SEQ ID NO: 1363)
HSDAVF$\underline{X_1X_2}$NY$\underline{X_3}$RL$X_4$ $X_5$Q$\underline{X_6X_7X_8X_9}X_{10}$YLN$X_{11}$I$\underline{X_{12}X_{13}}$ wherein at least one of $X_1$, $X_2$, $X_3$, $X_4$, $X_5$, $X_6$, $X_7$, $X_8$, $X_9$, $X_{10}$, $X_{11}$, $X_{12}$, or $X_{13}$ is a $\beta^3$-amino acid residue, and wherein $X_1$=T; $X_2$=D; $X_5$=R or K; $X_6$=M or L; $X_8$=A or V; $X_9$=R or K; $X_{10}$=R or K; $X_{11}$=S or A; $X_{12}$=L or K; and $X_{13}$=N or K. In some embodiments, at least one of the $\beta^3$-amino acid residues is substituted with a residue chosen from the following: (S,S)-trans-2-aminocyclopentanecarboxylic acid ((S,S)-ACPC), (S,R)-trans-2-aminocyclopentanecarboxylic acid ((S,R)-ACPC), (R,S)-trans-2-aminocyclopentanecarboxylic acid ((R,S)-ACPC), or (R,R)-trans-2-aminocyclopentanecarboxylic acid ((R,R)-ACPC) if the amino acid is non-polar; or pyrrolidine analogue of (S,S)-ACPC, (R,S)-ACPC, (S,R)-ACPC, (R,R)-ACPC), which is designated APC, if the amino acid is basic. In some embodiments, at least one of the $\beta^3$-amino acid residues is substituted with a residue chosen from the following: (S,S)-trans-2-aminocyclopentanecarboxylic acid ((S,S)-ACPC) if the amino acid is non-polar; or pyrrolidine analogue of (S,S)-ACPC if the residue is basic.

In some embodiments, the VIP analog of the claimed invention comprises the following sequence:

(SEQ ID NO: 1364)
$X_1\underline{T}$ $X_2$L$\underline{R}$ $X_3$QL $\underline{X_4}$A $X_5$ $\underline{X_6}$YLQ$\underline{S}$ I $X_7X_8$;

wherein $X_1$, $X_2$, $X_3$, $X_4$, $X_5$, $X_6$, $X_7$, $X_8$ are non-natural amino acids and wherein the underlined residues are β-amino acid residues. In some embodiments, the VIP analog of the claimed invention comprises the following sequence:

(SEQ ID NO: 1364)
$X_1\underline{T}$ $X_2$L$\underline{R}$ $X_3$QL $\underline{X_4}$A $X_5$ $\underline{X_6}$YLQ$\underline{S}$ I $X_7X_8$;

wherein $X_1$, $X_2$, $X_3$, $X_4$, $X_5$, $X_6$, $X_7$, $X_8$ are non-natural amino acids and wherein the underlined residues are $\beta^3$-amino acid residues. In some embodiments, at least one of the $\beta^3$-amino acid residues is substituted with a residue chosen from the following: (S,S)-trans-2-aminocyclopentanecarboxylic acid ((S,S)-ACPC), (S,R)-trans-2-aminocyclopentanecarboxylic acid ((S,R)-ACPC), (R,S)-trans-2-aminocyclopentanecarboxylic acid ((R,S)-ACPC), or (R,R)-trans-2-aminocyclopentanecarboxylic acid ((R,R)-ACPC) if the amino acid is non-polar; or pyrrolidine analogue of (S,S)-ACPC, (R,S)-ACPC, (S,R)-ACPC, (R,R)-ACPC), which is designated APC, if the amino acid is basic. In some embodiments, at least one of the $\beta^3$-amino acid residues is substituted with a residue chosen from the following: (S,S)-trans-2-aminocyclopentanecarboxylic acid ((S,S)-ACPC) if the amino acid is non-polar; or pyrrolidine analogue of (S,S)-ACPC if the residue is basic.

In some embodiments, the VIP analog of the claimed invention comprises the following sequence:

(SEQ ID NO: 1365)
Y(OMe)$\underline{T}$OrnL$\underline{R}$Aib QL$\underline{U}$AAib $\underline{Orn}$YLQ$\underline{S}$ IOrnOrn, wherein Orn=ornithine, Y(OMe)=O-methylated Tyrosine, Aib=α-aminoisobutyric acid, U=amino butyric acid (i.e., side chain=ethyl), and wherein each underlined position is a β-amino acid residue. In some embodiments at least one of the β-amino acid residue are $\beta^3$-amino acid residues. In some embodiments, at least one of the $\beta^3$-amino acid residues is substituted with a residue chosen from the following: (S,S)-trans-2-aminocyclopentanecarboxylic acid ((S,S)-ACPC), (S,R)-trans-2-aminocyclopentanecarboxylic acid ((S,R)-ACPC), (R,S)-trans-2-aminocyclopentanecarboxylic acid ((R,S)-ACPC), or (R,R)-trans-2-aminocyclopentanecarboxylic acid ((R,R)-ACPC) if the amino acid is non-polar; or pyrrolidine analogue of (S,S)-ACPC, (R,S)-ACPC, (S,R)-ACPC, (R,R)-ACPC), which is designated APC, if the amino acid is basic. In some embodiments, at least one of the $\beta^3$-amino acid residues is substituted with a residue chosen from the following: (S,S)-trans-2-aminocyclopentanecarboxylic acid ((S,S)-ACPC) if the amino acid is non-polar; or pyrrolidine analogue of (S,S)-ACPC if the residue is basic.

In some embodiments, the VIP analog of the claimed invention comprises at least 17% β-amino acid residues. In some embodiments, the VIP analog of the claimed invention comprises from about 15% to about 30% β-amino acid residues. In some embodiments, the VIP analog of the claimed invention comprises from about 15% to about 30% β-amino acid residues wherein the first ten amino acids of the amino acid sequence are alpha amino acids. In some embodiments, the VIP analog of the claimed invention comprises from about 16% to about 29% β-amino acid residues. In some embodiments, the VIP analog of the claimed invention comprises from about 17% to about 29% β-amino acid residues. In some embodiments, the VIP analog of the claimed invention comprises from about 18% to about 29% β-amino acid residues. In some embodiments, the VIP analog of the claimed invention comprises from about 19% to about 29% β-amino acid residues. In some embodiments, the VIP analog of the claimed invention comprises from about 20% to about 29% β-amino acid residues.

In some embodiments, the VIP analog of the claimed invention comprises β-amino acid residues at residue positions 11, 14, 18, 21, and 25 of HSDAVFTDNYTRLRKQ-MAVKKYLNSILN (SEQ ID NO: 10). In some embodiments, the VIP analog of the claimed invention comprises β-amino acid residues at positions 11, 14, 18, 21, and 25 of HSDAVFTDNYTRLRKQMAVKKYLNSILN (SEQ ID NO: 10), wherein the position 11 is $β^3$-homothreonine, position 14 is $β^3$-homoarginine, position 18 is $β^3$-homoalanine, position 21 is $β^3$-homolysine, and position 25 is $β^3$-homoserine. In some embodiments, at least one of the $β^3$-amino acid residues is substituted with a residue chosen from the following: (S,S)-trans-2-aminocyclopentanecarboxylic acid ((S,S)-ACPC), (S,R)-trans-2-aminocyclopentanecarboxylic acid ((S,R)-ACPC), (R,S)-trans-2-aminocyclopentanecarboxylic acid ((R,S)-ACPC), or (R,R)-trans-2-aminocyclopentanecarboxylic acid ((R,R)-ACPC) if the amino acid is non-polar; or pyrrolidine analogue of (S,S)-ACPC, (R,S)-ACPC, (S,R)-ACPC, (R,R)-ACPC, which is designated APC, if the amino acid is basic. In some embodiments, at least one of the $β^3$-amino acid residues is substituted with a residue chosen from the following: (S,S)-trans-2-aminocyclopentanecarboxylic acid ((S,S)-ACPC) if the amino acid is non-polar; or pyrrolidine analogue of (S,S)-ACPC if the residue is basic.

In some embodiments, the VIP analog of the claimed invention comprises the following sequence:

```
                                      (SEQ ID NO: 1352)
HSDAVFTDNY X₁RL X₂KQL X₃VK X₄YLN X₅ILN
``` wherein $X_1$, $X_2$, $X_3$, $X_4$, and $X_5$ are β-amino acid residues and wherein all other α-amino residues are naturally-occurring or non-naturally occurring amino acid residues. In some embodiments, the VIP analog comprises a cyclic amino acid residue covalently bonded to one or more contiguous or non-contiguous amino acid sidechain residues via a lactam ring. In some embodiments, the VIP analog comprises a cyclic amino acid residue covalently bonded to one or more contiguous or non-contiguous amino acid sidechain residues via an amide bond. In some embodiments, the VIP analog of the claimed invention comprises one of the following sequences:

```
                                      (SEQ ID NO: 435)
HSDAV FTDNY ARLRK QMAVK KALNS ILA (SEQ ID NO: 435)
HSDAV FTDNY ARLRK QMAVK KALNS ILA (SEQ ID NO: 435)
HSDAV FTDNY ARLRK QMAVK KALNS ILA (SEQ ID NO: 435)
HSDAV FTDNY ARLRK QMAVK KALNS ILA (SEQ ID NO: 435)
HSDAV FTDNY ARLRKQ MAVK KALNS ILA (SEQ ID NO: 435)
HSDAV FTDNY ARLRKQ MAVK KALNS ILA (SEQ ID NO: 435)
HSDAV FTDNY ARLRKQ MAVK KALNS ILA (SEQ ID NO: 434)
HADAV FTAAY ARLRK QMAAK KALAA IAA (SEQ ID NO: 434)
HADAV FTAAY ARLRK QMAAK KALAA IAA (SEQ ID NO: 434)
HADAV FTAAY ARLRK QMAAK KALAA IAA (SEQ ID NO: 434)
HADAV FTAAY ARLRK QMAAK KALAA IAA (SEQ ID NO: 434)
HADAV FTAAY ARLRKQ MAAK KALAA IAA (SEQ ID NO: 434)
HADAV FTAAY ARLRKQ MAAK KALAA IAA (SEQ ID NO: 434)
HADAV FTAAY ARLRKQ MAAK KALAA IAA
``` wherein each underlined residue is: a $β^3$-homoamino acid residue; or, if a non-polar (e.g., A, V), the underlined residues is/are (S,S)-trans-2-aminocyclopentanecarboxylic acid ((S,S)-ACPC); or, if the underlined position is basic, (such as Lys or Arg), the underlined residue is a pyrrolidine analogue of (S,S)-ACPC, which is designated APC. (Note: Ac=acetyl; $N^{le}$=norleucine; K*-D* indicates that the side chains of these two residues are linked via an amide bond.) In some embodiments, the sidechains of K and D are not linked via any bond.

a/b-Peptide analogues will be synthesized:

```
                                              (SEQ ID NO: 1373)
Ac-HSDAV FTENY TKLRK QN^{le}AVK K*YLND* LKKGG T (SEQ ID NO: 1373)
Ac-HSDAV FTENY TKLRK QN^{le}AVK K*YLND* LKKGG T (SEQ ID NO: 1373)
Ac-HSDAV FTENY TKLRK QN^{le}AVK K*YLND* LKKGG T (SEQ ID NO: 1373)
Ac-HSDAV FTENY TKLRK QN^{le}AVK K*YLND* LKKGG T (SEQ ID NO: 1373)
Ac-HSDAV FTENY TKLRK QN^{le}AVK K*YLND* LKKGG T (SEQ ID NO: 1373)
Ac-HSDAV FTENY TKLRK QN^{le}AVK K*YLND* LKKGG T (SEQ ID NO: 1373)
Ac-HSDAV FTENY TKLRK QN^{le}AVKK*YLND* LKKGG T (SEQ ID NO: 1374)
Ac-HSDAV FTENY TKLRK RN^{le}AAK N^{le}YLNN LKKGG T
```

```
                                          (SEQ ID NO: 1374)
Ac-HSDAV FTENY TKLRK RN^le AAK N^le YLNN LKKGG T (SEQ ID NO: 1374)
Ac-HSDAV FTENY TKLRK RN^le AAK N^le YLNN LKKGG T (SEQ ID NO: 1374)
Ac-HSDAV FTENY TKLRK RN^le AAK N^le YLNN LKKGG T (SEQ ID NO: 1374)
Ac-HSDAV FTENY TKLRK RN^le AAK N^le YLNN LKKGG T (SEQ ID NO: 1374)
Ac-HSDAV FTENY TKLRK RN^le AAK N^le YLNN LKKGG T (SEQ ID NO: 1374)
Ac-HSDAV FTENY TKLRK RN^le AAKN^le YLNN LKKGG T
``` wherein each underlined residue is: a β³-homoamino acid residue; or, if a non-polar (e.g., A, V), the underlined positions will be replaced by (S,S)-trans-2-aminocyclopentanecarboxylic acid ((S,S)-ACPC); or if the underlined residue is basic, (such as Lys or Arg), the underlined residue is/are the pyrrolidine analogue of (S,S)-ACPC, which is designated APC; and wherein Ac=acetyl; N^le=norleucine; K*-D* indicates that the side chains of these two residues are linked via an amide bond. In some embodiments, the sidechains of K and D are not linked via any bond. In some embodiments, the VIP analog comprises a cyclic amino acid residue covalently bonded to one or more contiguous or non-contiguous amino acid sidechain residues via the following synthetic linking structures:

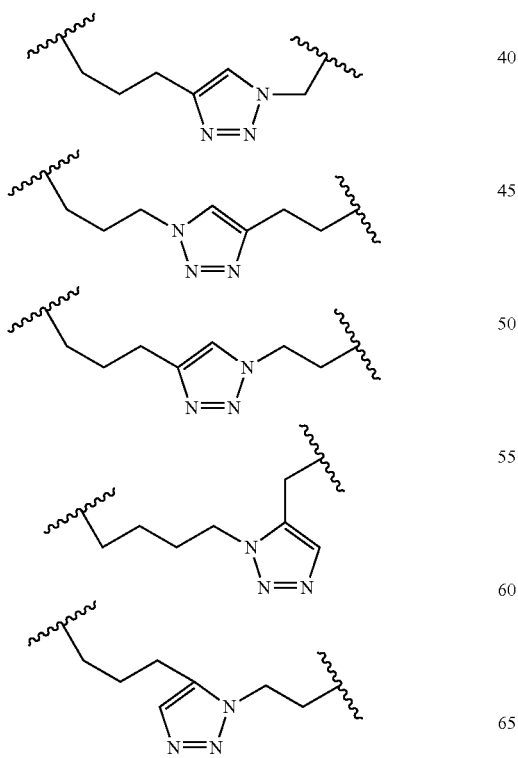

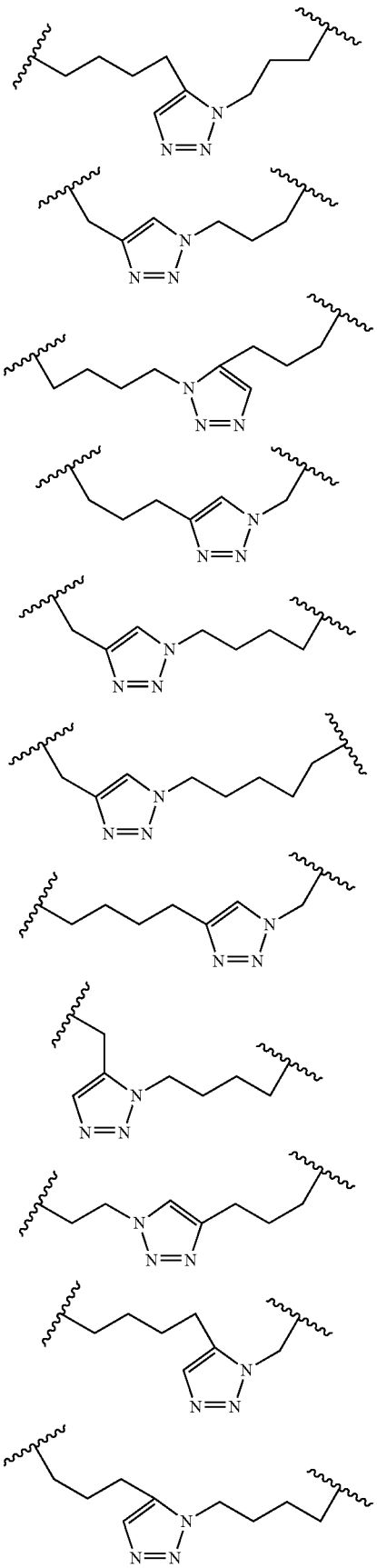

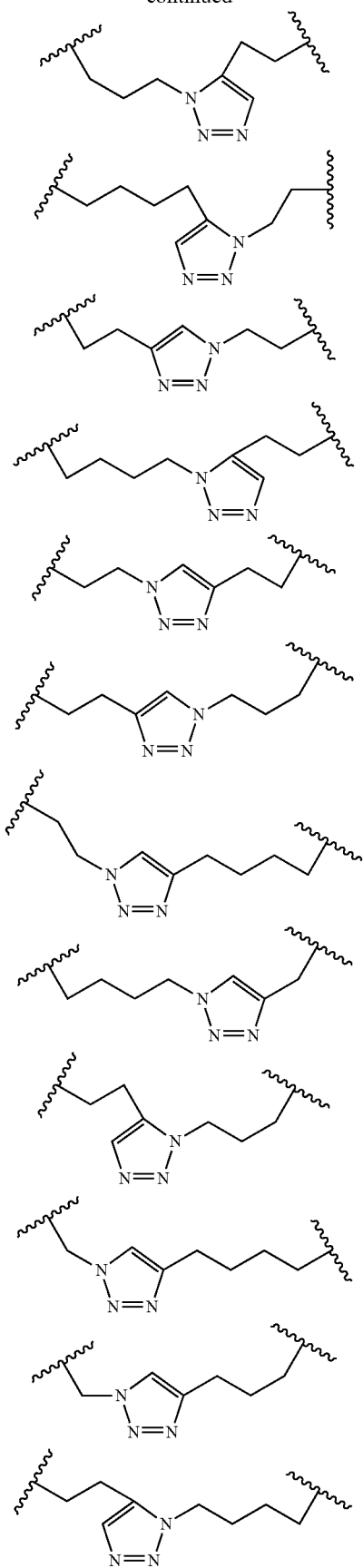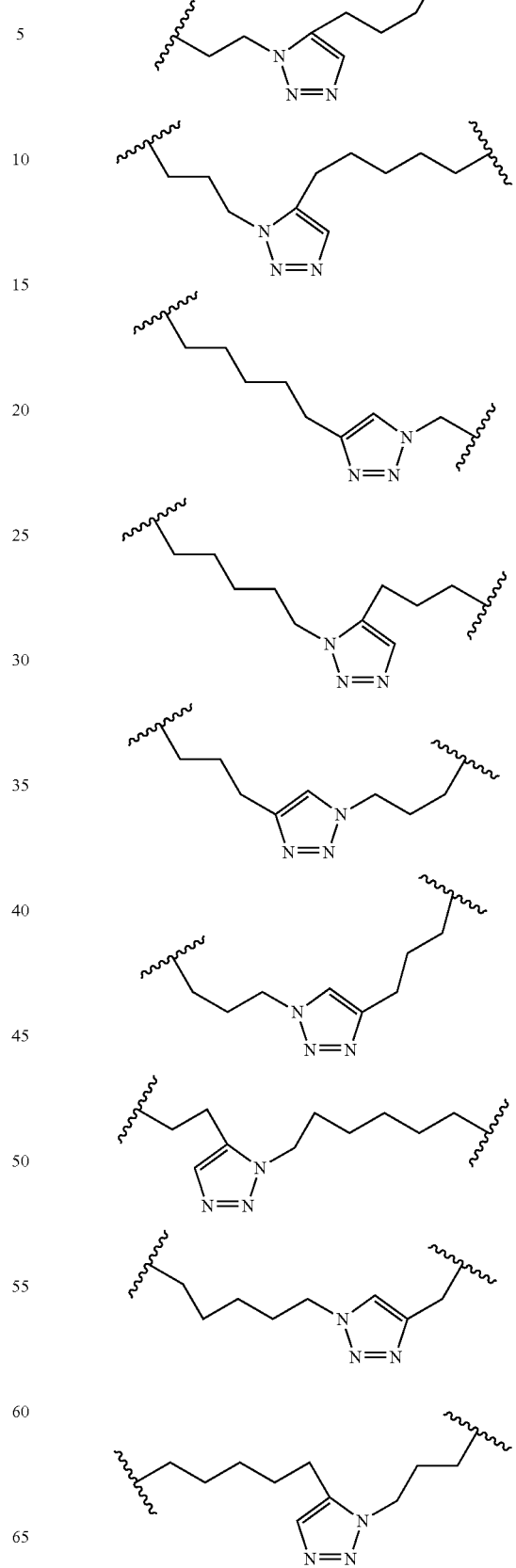

129
-continued
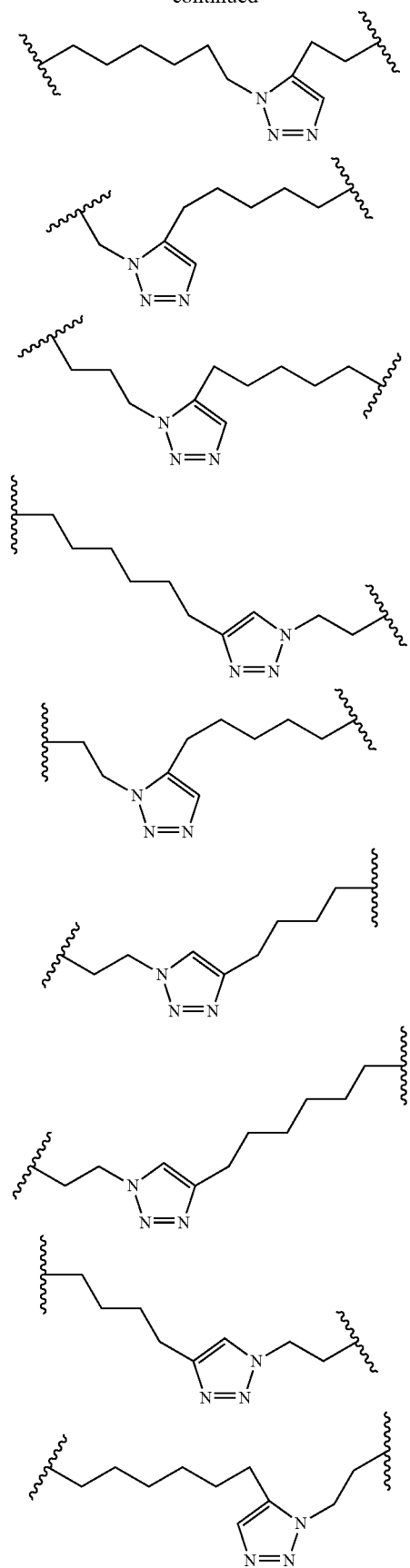
130
-continued
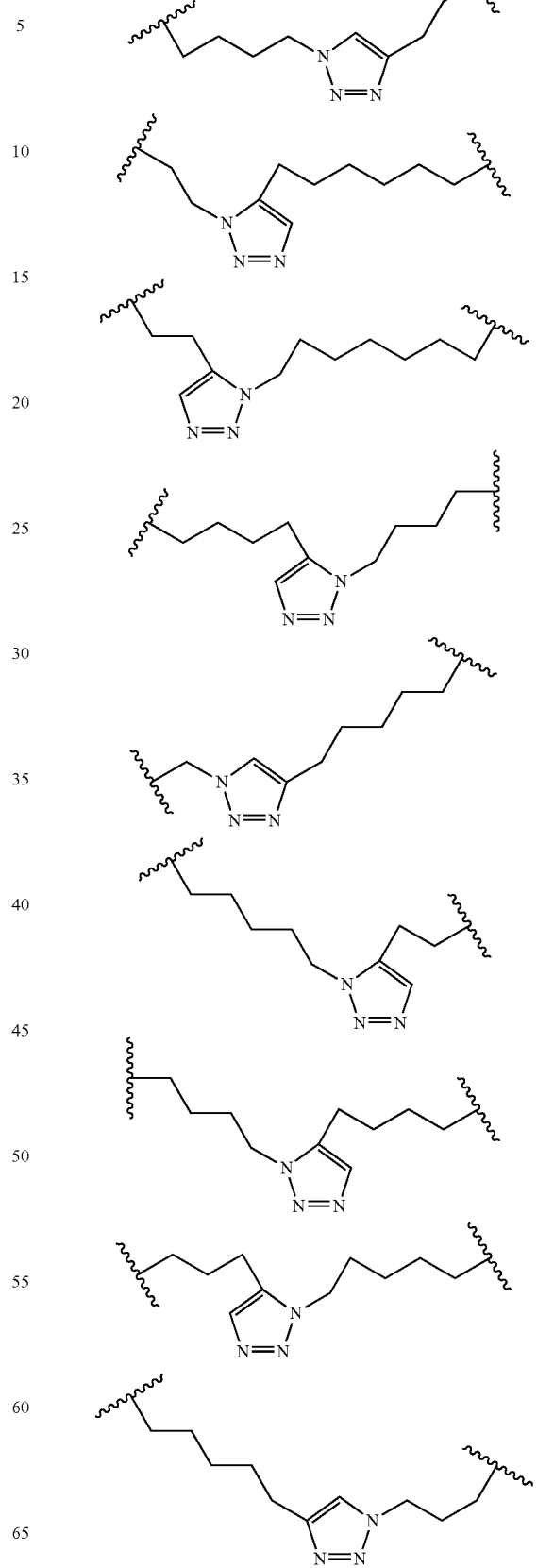

131
-continued
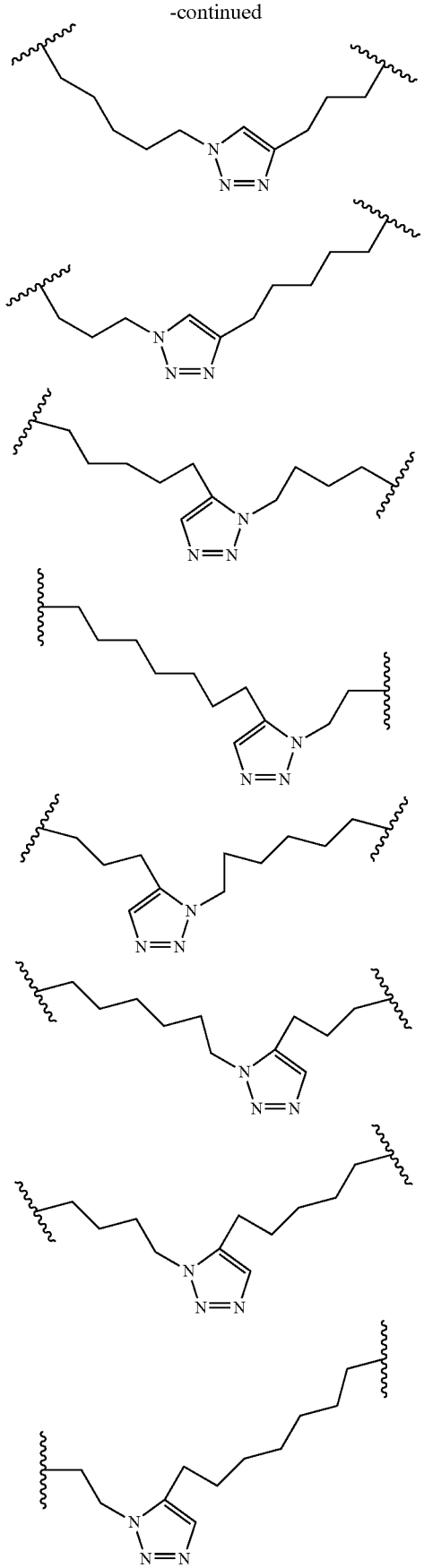
132
-continued
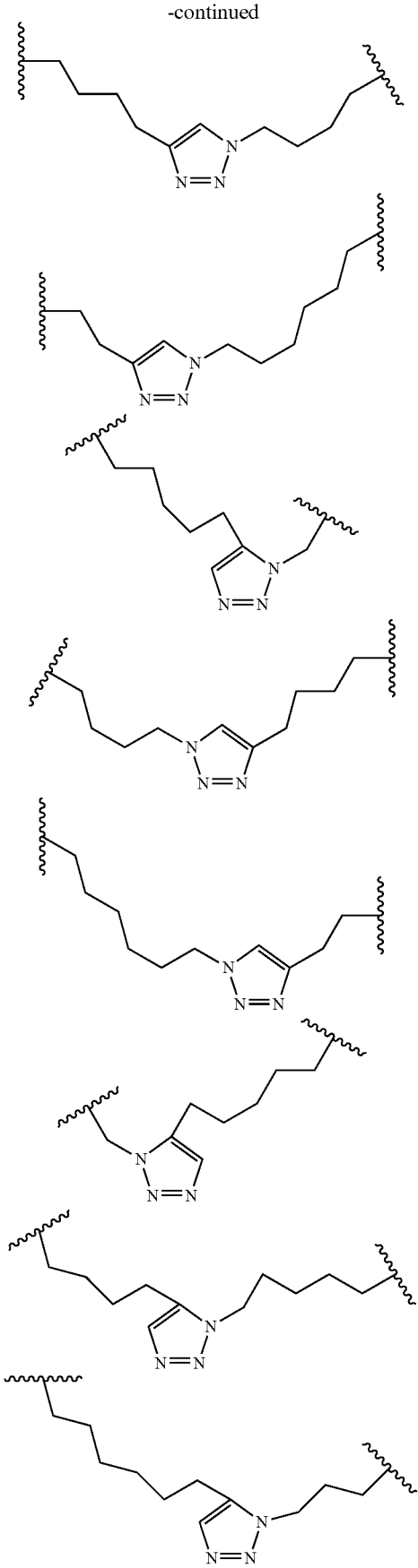

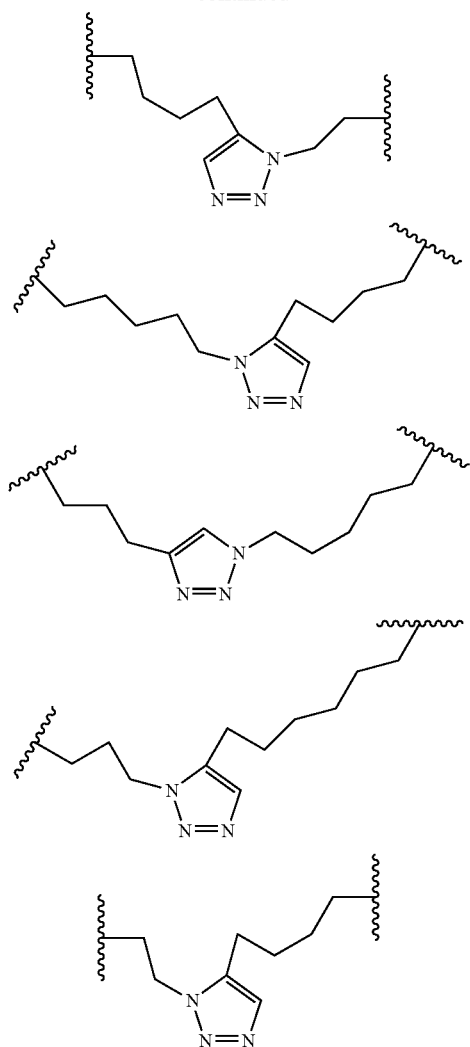
In some embodiments, the analog does not comprise a cyclic substituent in its side chain. In some embodiments, the cyclic amino acid residues are not covalently bonded to one or more contiguous or non-contiguous amino acid sidechain residues via the following synthetic linking structures:
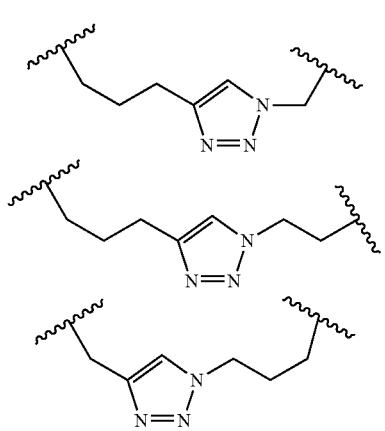
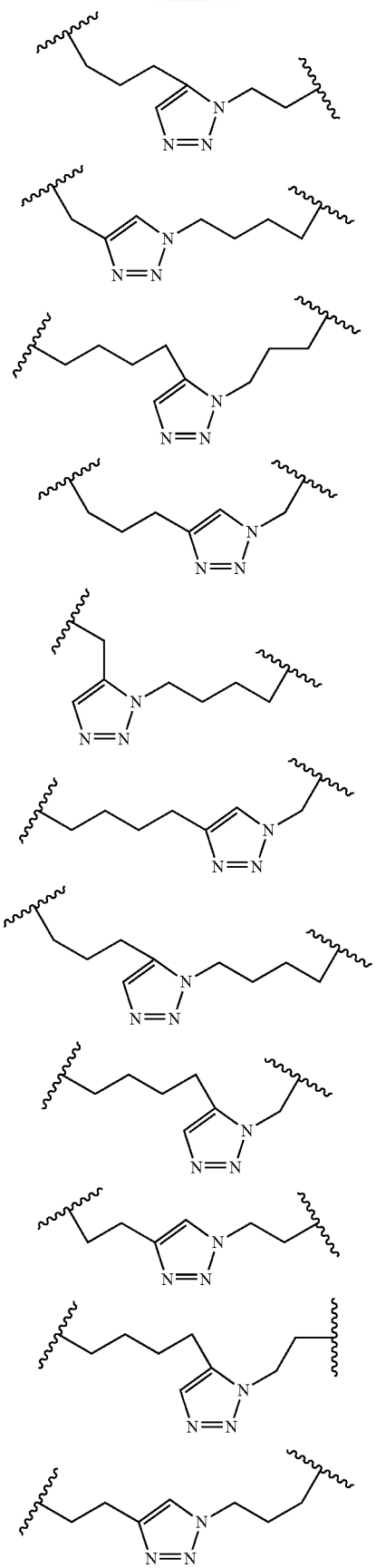

135
-continued
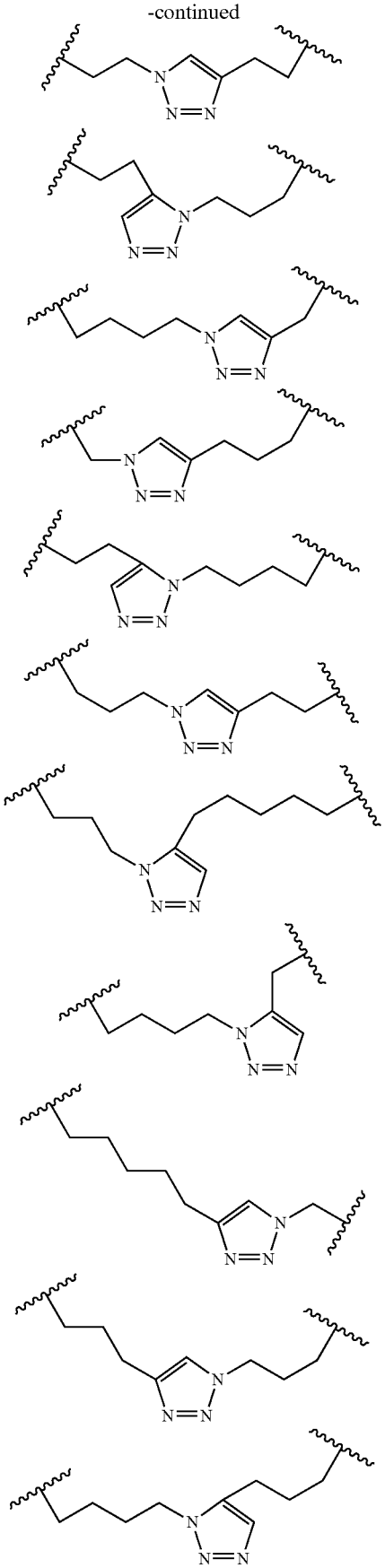
136
-continued
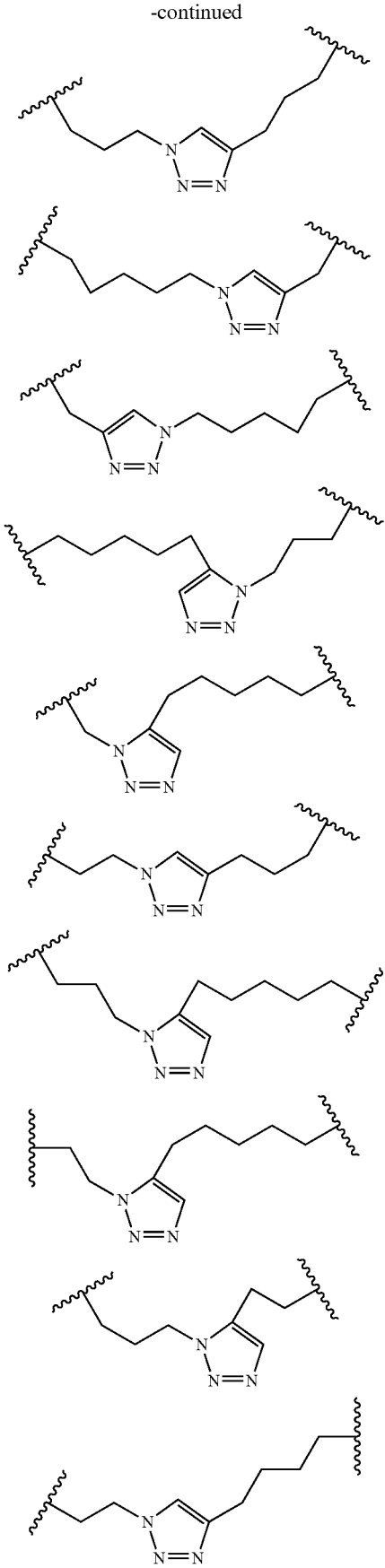

137
-continued
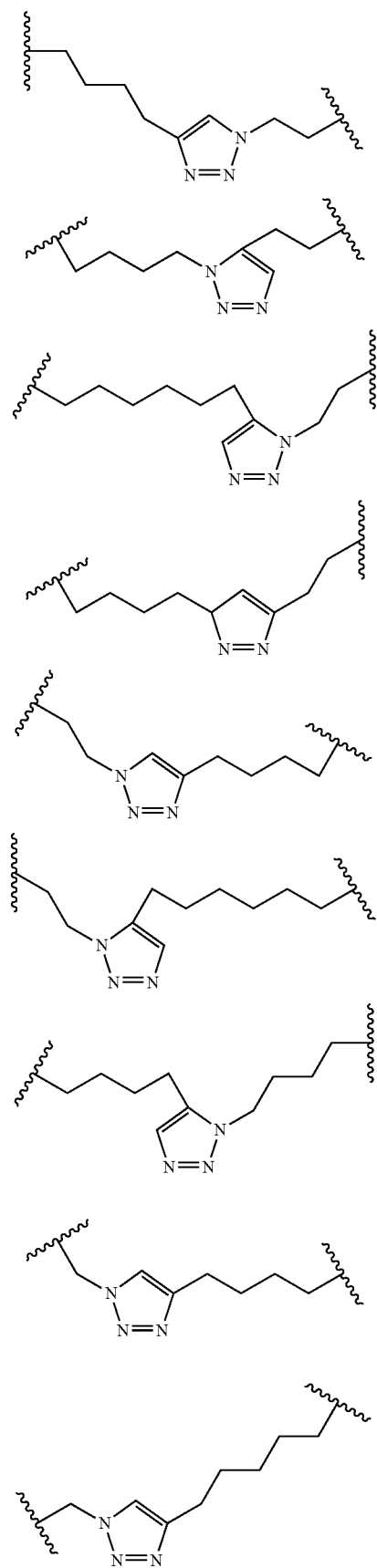
138
-continued
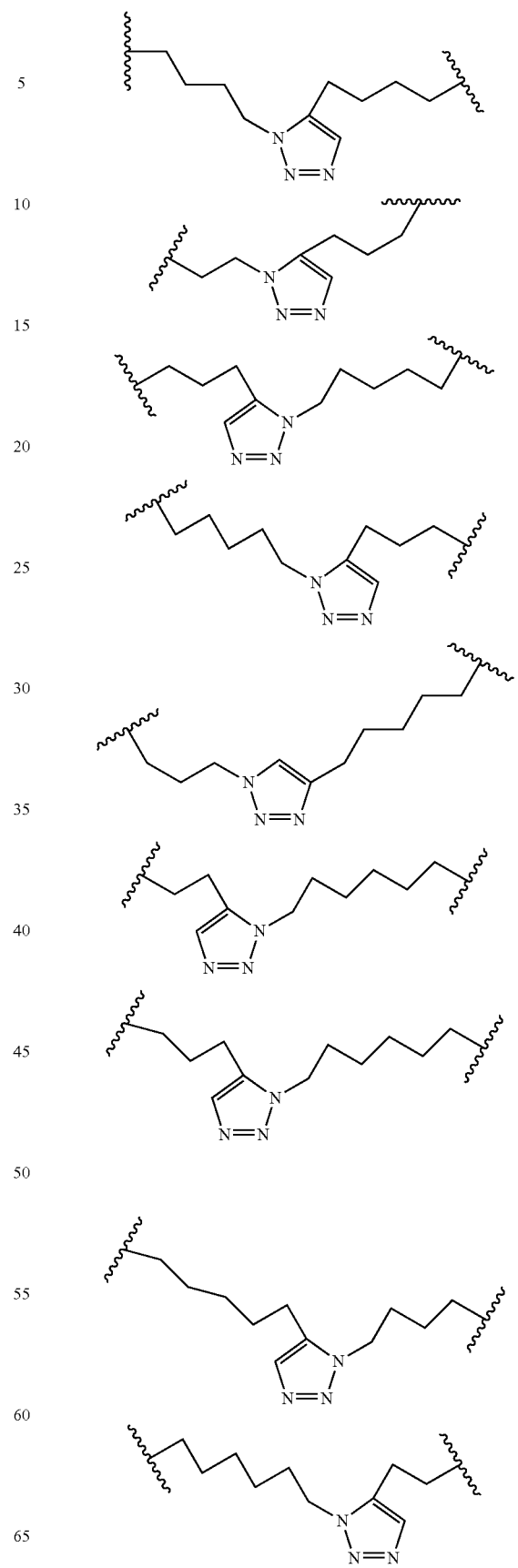

139 140
-continued -continued
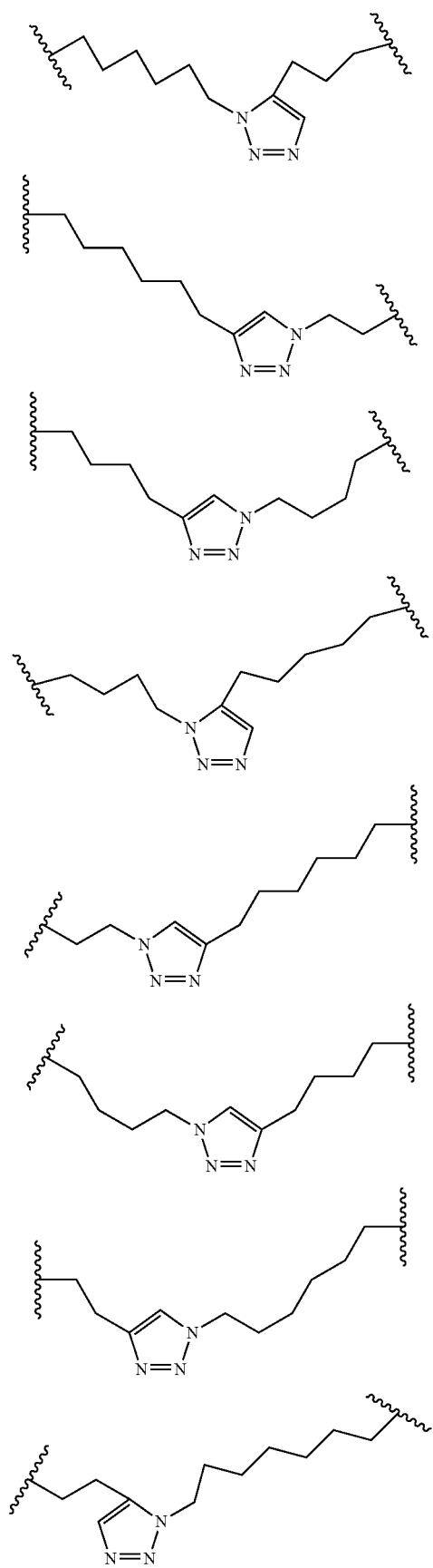
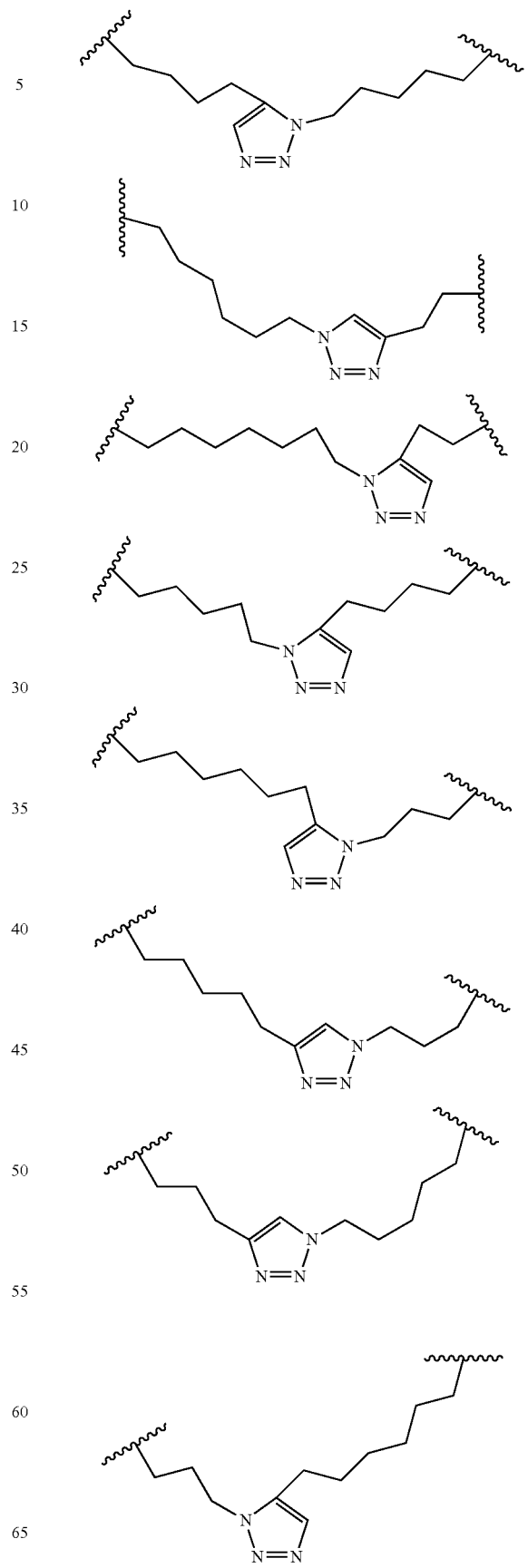

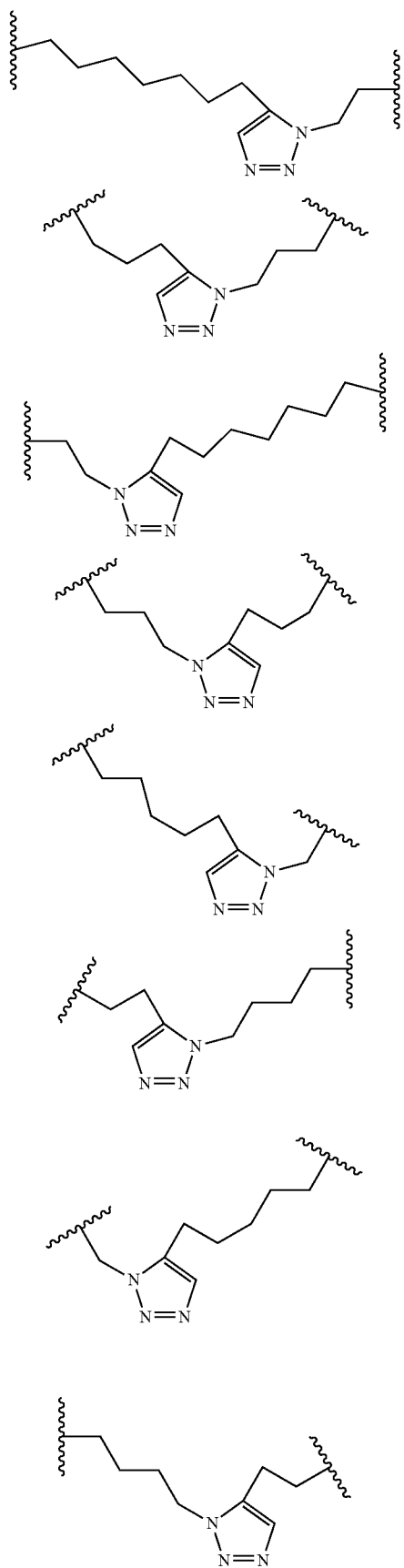
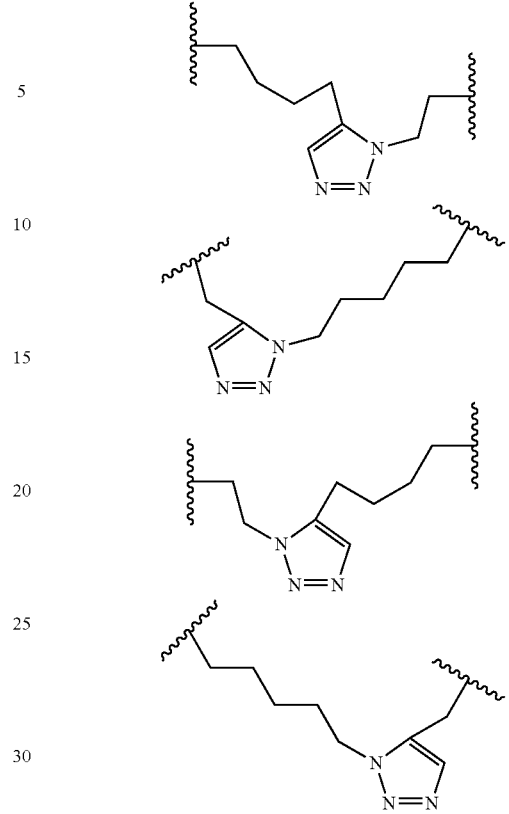

In some embodiments, the analogs of the present invention comprise at least one or a plurality of the following cyclic amino acid residues, some of which being described with a protecting group that becomes eliminated from the analog either during synthesis or when the analog is purified after synthesis:

L-β-HomohydroxyProline hydrochloride
(1R,2R)-Boc-2-aminocyclohexane carboxylic acid {(1R,2R)-ACHC}
(1R,2R)-Fmoc-2-aminocyclohexane carboxylic acid {(1R,2R)-ACHC}
(1R,2S)-Boc-2-aminocyclohexane carboxylic acid {(1R,2S)-ACHC}
(1R,2S)-Fmoc-2-aminocyclohexane carboxylic acid {(1R,2S)-ACHC}
(1S,2R)-Boc-2-aminocyclohexane carboxylic acid {(1S,2R)-ACHC}
(1S,2R)-Fmoc-2-aminocyclohexane carboxylic acid {(1S,2R)-ACHC}
(1S,2S)-Boc-2-aminocyclohexane carboxylic acid {(1S,2S)-ACHC}
(1S,2S)-Fmoc-2-aminocyclohexane carboxylic acid {(1S,2S)-ACHC}
(1R,2R)-Boc-2-aminocyclopentane carboxylic acid {(1R,2R)-ACPC}
(1R,2R)-Fmoc-2-aminocyclopentane carboxylic acid {(1R,2R)-ACPC}
(1S,2S)-Boc-2-aminocyclopentane carboxylic acid {(1S,2S)-ACPC}
(1S,2S)-Fmoc-2-aminocyclopentane carboxylic acid {(1S,2S)-ACPC}
Boc-cis-2-aminocyclopentane carboxylic acid, cis-Acpc
Fmoc-cis-2-aminocyclopentane carboxylic acid, cis-Acpc (R)-Boc-(2-carboxymethyl)-piperidine, (R)-(1-piperidin-2-yl)-acetic acid
(R)-Fmoc-(2-carboxymethyl)-piperidine, (R)-(1-Fmoc-piperidin-2-yl)-acetic acid
(S)-Boc-(2-carboxymethyl)-piperidine (S)-1-Boc-piperidin-2-yl)-acetic acid
(S)-Fmoc-(2-carboxymethyl)-piperidine (S)-(1-Fmoc-piperidin-2-yl)-acetic acid
(R,S)-Boc-2-carboxymorpholine Boc-Cop
(R,S)-Boc-2-carboxymorpholine Fmoc-Cop
(R,S)-Boc-nipecotic acid Boc-Nip
(R,S)-Boc-nipecotic acid Fmoc-Nip
(R)-Fmoc-nipecotic acid (R)-Fmoc-Nip
(R)-Fmoc-nipecotic acid (R)-Boc-Nip
(3S)-Boc-1-pyrrolidine-3-carboxylic acid (3S)-Boc-beta-Pro-OH
(3S)-Fmoc-1-pyrrolidine-3-carboxylic acid (3S)-Fmoc-beta-Pro-OH In some embodiments, the analogs of the present invention comprise at least one or a plurality of non-natural amino acid residues that can modified by PEGylation. In some embodiments the analogs or fragments of the polypeptides related to this invention comprise PEG molecules which are covalently bound to the side chain of the a, or P amino acids in the polypeptide. In some embodiments, the polypeptides of this invention comprise the PEGylated cyclic amino acid residues or cyclic amino acid side chains. PEG molecule(s) may be covalently attached to any Lys, Cys, K(W) or K(CO(CH$_2$)$_2$SH) residue at any position in the analog or fragment of analog. In some embodiments, the analog or a fragment thereof comprises a C-terminal extension may comprise one or more Cys residues which may be PEGylated. In some embodiment of the invention the polypeptides or fragments thereof may comprise one or more PEGylated residues in either or both sequences.

In some embodiments, the analog or fragment thereof comprises a PEG molecule covalently attached to one or all of the β-residue within the analog. In some embodiments, the analog is at least one PEG molecule covalently attached to a residue in the C-terminal extension of the analog or fragment thereof. In some embodiments, the analog comprises more than one PEG molecule, there may be a combination of Lys, Cys, K(CO(CH$_2$)$_2$SH), K(W) and carboxy-terminal amino acid PEGylation. For example, if there are two PEG molecules, one may be attached to a Lys residue and one may be attached to a Cys residue. In some embodiments, the polypeptide comprises one or more covalently bound PEG molecules, wherein at least one of the PEG molecules is branched. In some embodiments, one or more of the PEG molecules are linear. In some embodiments, the composition comprises one or more PEG molecule, wherein the PEG molecule is between about 200 daltons and about 100,000 daltons in molecular weight. In some embodiments, the PEG molecule is chosen from 10,000, 20,000, 30,000, 40,000, 50,000 and 60,000 daltons. In some embodiments, it is chosen from 20,000, 30,000, 40,000, or 60,000 daltons. Where there are two PEG molecules covalently attached to the analog or fragment thereof, each is 1,000 to 40,000 daltons and, they have molecular weights of 20,000 and 20,000 daltons, 10,000 and 30,000 daltons, 30,000 and 30,000 daltons, or 20,000 and 40,000 daltons. In some embodiments mini-PEG s™ are covalently bound to at least one residue or side chain of an α, or β-amino acid. In some embodiments, the mini-PEG™ is chosen from the following list of products: 8-Amino-3,6-Dioxaoctanoic Acid, 11-Amino-3,6,9-Trioxaundecanoic Acid, 8-Amino-3,6-Dioxaoctanoic Acid•DCHA, 11-Amino-3,6,9-Trioxaundecanoic Acid•DCHA.

In some embodiments the method of treatment or prevention of a human disorder depends upon the analog being synthesized. For instance: Peptides for triggering B and T cell activity can be used to treat autoimmune disease, including uveitis, collagen-induced, adjuvant and rheumatoid arthritis, thyroiditis, myasthenia gravis, multiple sclerosis and diabetes. Examples of these peptides are interleukins (referenced in Aulitzky, W E; Schuler, M; Peschel, C.; Huber, C.; Interleukins. Clinical pharmacology and therapeutic use. Drugs. 48(5):667-77, November 1994) and cytokines (referenced in Peters, M.; Actions of cytokines on the immune response and viral interactions: an overview. Hepatology. 23(4):909-16, April 1996).

Enkephlin analogs, agonist analogs and antagonist analogs can be used to treat AIDS, ARC, and cancer, pain modulation, Huntington's, Parkinson's diseases.

LHRH and analogs, agonists and antagonists can be used to treat prostatic tumors and reproductive physiopathology, including breast cancer, and infertility.

Peptides and peptidomimetics that target crucial enzymes, oncogenes or oncogene products, tumor-suppressor genes and their products, growth factors and their corresponding receptors can be used to treat cancer. Examples of these peptides are described in Unger, C.

Current concepts of treatment in medical oncology: new anticancer drugs. Journal of Cancer Research & Clinical Oncology. 122(4):189-98, 1996.

Neuropeptide Y and other pancreatic polypeptides, and analogs, agonists and antagonists can be used to treat stress, anxiety, neurodegernative diseases, depression and associated vasoconstrictive activities.

Gluco-incretins, including gastric inhibitory polypeptide, glucose-dependent insulinotropic polypeptide, PACAP/Glucagon and glucagon-like polypeptide-1 and 2 and analogs, agonists and antagonists can be used to treat Type II diabetic hyperglycaemia. Atrial natriuretic factor and analogs, agonists and antagonists can be used to treat congestive heart failure.

Integrin and analogs, agonists and antagonists can be used to treat osteoporosis, scar formation, bone synthesis, inhibition of vascular occlusion, and inhibition of tumor invasion and metastasis.

Glucagon, glucagon-like peptide 1, PACAP/Glucagon, and analogs, agonists and antagonists can be used to treat diabetes cardiovascular emergencies.

Antithrombotic peptides and analogs, agonists and antagonists can be used to treat cardiovascular and cerebrovascular diseases. Examples of these peptides RGD, D-Phe-Pro-Arg and others named are described in Ojima I.; Chakravarty S.; Dong Q. Antithrombotic agents: from RGD to peptide mimetics. Bioorganic & Medicinal Chemistry. 3(4):337-60, 1995.

Cytokines/interleukins and analogs, agonists and antagonists can be used to treat inflammatory disease, immune response dysfunction, hematopoiesis, mycosis fungoides, aplastic anemia, thrombocytopenia, and malignant melanoma. Examples of these peptides are Interleukins, referenced in Aulitzky et al. and Peters et al., which is herein incorporated by reference.

Endothelin and analogs, agonists and antagonists can be used to treat arterial hypertension, myocardial infarction, congestive heart failure, atherosclerosis, shock conditions, renal failure, asthma and vasospasm Natriuretic hormones and analogs, agonists and antagonists can be used to treat cardiovasicular disease and acute renal failure. Examples of these peptides are named and described in Espiner, E. A;. Richards, A. M.; Yandle, T. G.; Nicholls, M. G.; Natriuretic hormones. Endocrinology & Metabolism Clinics of North America. 24(3):481-509, 1995.

Peptides that activate or inhibit tyrosine kinase, or bind to TK-activating or inhibiting peptides and analogs, agonists and antagonists can be used to treat chronic myelogenous and acute lymphocytic leukemias, breast and ovarian cancers and other tyrosine kinase associated diseases. Examples of these peptides are described in Smithgall, T E.; SH2 and SH3 domains: potential targets for anti-cancer drug design. Journal of Pharmacological & Toxicological Methods. 34(3): 125-32, 1995.

Renin inhibitors analogs, agonists and antagonists can be used to treat cardiovascular disease, including hypertension and congestive heart failure. Examples of these peptides are described in Rosenberg, S. H.; Renin inhibition. Cardiovascular Drugs & Therapy. 9(5):645-55, 1995.

Angiotensin-converting enzyme inhibitors, analogs, agonists and antagonists can be used to treat cardiovascular disease, including hypertension and congestive heart failure.

Peptides that activate or inhibit tyrosine phosphorylases can be used to treat cardiovascular diseases. Examples of these peptides are described in Srivastava, A. K.; Protein tyrosine phosphorylation in cardiovascular system. Molecular & Cellular Biochemistry. 149-150:87-94, 1995.

Peptide based antivirals can be used to treat viral diseases. Examples of these peptides are described in Toes, R. E.; Feltkamp, M. C.; Ressing, M. E.; Vierboom, M. P.; Blom, R. J.; Brandt, R. M; Hartman, M.; Offringa, R.; Melief, C. J.; Kast, W. M.; Cellular immunity against DNA tumour viruses: possibilities for peptide-based vaccines and immune escape. Biochemical Society Transactions. 23(3):692-6, 1995.

Corticotropin releasing factor and peptide analogs, agonist analogs and antagonist analogs can be used to treat disease associated with high CRF, i.e Alzheimer's disease, anorexia nervosa, depressive disorders, arthritis, and multiple sclerosis.

Peptide agonist analogs and antagonist analogs of platelet-derived wound-healing formula (PDWHF) can be used as a therapy for donor tissue limitations and wound-healing constraints in surgery. Examples of these peptides are described in Rudkin, G. H.; Miller, T. A.; Growth factors in surgery. Plastic & Reconstructive Surgery. 97(2):469-76, 1996. Fibronectin, fibrinopeptide inhibitors and analogs, agonists and antagonists can be used to treat metastasis (i.e. enzyme inhibition, tumor cell migration, invasion, and metastasis).

Chemokine (types of cytokine, including interleukin-8, RANTES, and monocyte chemotactic peptide) analogs, agonist analogs and antagonist analogs can be used to treat arthritis, hypersensitivity, angiogenesis, renal disease, glomerulonephritis, inflammation, and hematopoiesis.

Neutral endopeptidase inhibitors analogs, agonist analogs and antagonist analogs can be used to treat hypertension and inflammation. Examples of these peptides are described in Gregoire, J. R; Sheps, S. G; Newer antihypertensive drugs. Current Opinion in Cardiology. 10(5):445-9, 1995.

Substance P analogs, agonist analogs and antagonist analogs can be used to treat immune system dysfunction, pain transmission/perception and in autonomic reflexes and behaviors. Alpha-melanocyte-stimulating hormone analogs, agonist analogs and antagonist analogs can be used to treat AIDS, rheumatoid arthritis, and myocardial infarction.

Bradykinin (BK) analogs, agonist analogs and antagonist analogs can be used to treat inflammatory diseases (edema, etc), asthma, allergic reactions (rhinitis, etc), anesthetic uses, and septic shock.

Secretin analogs can be used to treat cardiovascular emergencies.

GnRH analogs, agonist analogs and antagonist analogs can be used to treat hormone-dependent breast and prostate tumors.

Somatostatin analogs, agonist analogs and antagonist analogs can be used to treat gut neuroendocrine tumors.

Gastrin, Gastrin Releasing Peptide analogs, agonist analogs and antagonist analogs can be used as an adjuvant to chemotherapy or surgery in small cell lung cancer and other malignancies, or to treat allergic respiratory diseases, asthma and allergic rhinitis.

Laminin analogs, agonist analogs and antagonist analogs, the Laminin derivative antimetastatic drug YIGSR analogs, Laminin-derived synthetic peptides analogs, agonist analogs and antagonist analogs can be used to treat tumor cell growth, angiogenesis, regeneration studies, vascularization of the eye with diabetes, and ischemia. The peptides of this category can inhibit the tumor growth and metastasis of leukemic cells and may be useful as a potential therapeutic reagent for leukaemic infiltrations. Peptides containing this sequence also inhibit experimental metastasis. Exemplary references include McGowan K A. Marinkovich M P. Laminins and human disease. Microscopy Research & Technique. 51(3):262-79, Nov. 1, 2000; Yoshida N. Ishii E. Nomizu M. Yamada Y. Mohri S. Kinukawa N. Matsuzaki A. Oshima K. Hara T. Miyazaki S. The laminin-derived peptide YIGSR (Tyr-Ile-Gly-Ser-Arg) inhibits human pre-B leukaemic cell growth and dissemination to organs in SCID mice. British Journal of Cancer. 80(12): 1898-904, 1999. Examples of these peptides are also described in Kleinman, H. K.; Weeks, B. S.; Schnaper, H. W.; Kibbey, M. C.; Yamamura, K.; Grant, D. S; The laminins: a family of basement membrane glycoproteins important in cell differentiation and tumor metastases. Vitamins & Hormones. 47:161-86, 1993.

Defensins, corticostatins, dermaseptins, mangainins, and other antibiotic (antibacterial and antimicrobial) peptides analogs, agonist analogs and antagonist analogs can be used to treat infections, tissue inflammation and endocrine regulation.

Vasopressin analogs, agonist analogs and antagonist analogs can be used to treat neurological disorders, stress and Diabetes insipidus.

Oxytocin analogs, agonist analogs and antagonist analogs can be used to treat neurological disorders and to induce labor.

ACTH-related peptides and analogs, agonist analogs and antagonist analogs can be used as neurotrophic, neuroprotective, and peripheral demyelinating neuropathy agents.

Amyloid-beta peptide analogs, agonist analogs and antagonist analogs can be used to treat Alzheimer's disease.

Epidermal growth factor, receptor analogs, agonist analogs and antagonist analogs can be used to treat necrotizing enterocolitis, Zollinger-Ellison syndrome, gastrointestinal ulceration, colitis, and congenital microvillus atrophycarcinomas.

Leukocyte adhesion molecule analogs, agonist analogs and antagonist analogs can be used to treat atherosclerosis, inflammation. Examples of these peptides are described in Barker, J. N.; Adhesion molecules in cutaneous inflammation. Ciba Foundation Symposium. 189:91-101.

Major histocompatibility complex (MHC) analogs, agonist analogs and antagonist analogs can be used to treat autoimmune, immunodysfunctional, immuno modulatory diseases and as well as used for their corresponding therapies. Examples of these peptides are described in Appella, E.; Padlan, E. A.; Hunt, D. F; Analysis of the structure of naturally processed peptides bound by class I and class II major histocompatibility complex molecules. EXS. 73:105-19, 1995.

Corticotropin releasing factor analogs can be used to treat neurological disorders.

Neurotrophins (including brain-derived neurotrophic factor (BDNF), nerve growth factor, and neurotrophin 3) analogs, agonist analogs and antagonist analogs can be used to treat neurological disorders.

Cytotoxic T-cell activating peptide analogs, agonist analogs and antagonist analogs can be used to treat infectious diseases and cancer. Examples of these peptides are described in: Chesnut R. W.; Sette, A.; Celis, E.; Wentworth, P.; Kubo, R. T.; Alexander, J.; Ishioka, G.; Vitiello, A.; Grey, H. M; Design and testing of peptide-based cytotoxic T-cell-mediated immunotherapeutics to treat infectious diseases and cancer. Pharmaceutical Biotechnology. 6:847-74, 1995.

Peptide immunogens for prevention of HIV-1 and HTLV-I retroviral infections can be used to treat AIDS. Examples of these peptides are described in Hart, M. K.; Palker, T. J.; Haynes, B F; Design of experimental synthetic peptide immunogens for prevention of HIV-1 and HTLV-I retroviral infections. Pharmaceutical Biotechnology. 6:821-45, 1995.

Galanin analogs, agonist analogs and antagonist analogs can be used to treat Alzheimer's disease, depression, eating disorders, chronic pain, prevention of ischemic damage, and growth hormone modulation.

Tachykinins (neurokinin A and neurokinin B) analogs, agonist analogs and antagonist analogs can be used to treat pain transmission/perception and in autonomic reflexes and behaviors.

RGD containing peptide analogs can be used to treat various diseases involved with cell adhesion, antithrombotics, and acute renal failure.

Osteogenic growth peptide analogs, agonist analogs and antagonist analogs can be used as treatment of systemic bone loss. Examples of these peptides are described in Bab IA. Regulatory role of osteogenic growth peptide in proliferation, osteogenesis, and hemopoiesis. Clinical Orthopaedics & Related Research. (313):64-8, 1995.

Parathyroid hormone, parathyroid hormone related-peptide analogs, agonist analogs and antagonist analogs can be used to treat diseases affecting calcium homeostasis (hypercalcemia), bone metabolism, vascular disease, and atherosclerosis.

Kallidin analogs, agonist analogs and antagonist analogs can be used to treat tissue injury or inflammation and pain signaling pathological conditions of the CNS.

T cell receptor peptide analogs, agonist analogs and antagonist analogs can be used in immunotherapy. Examples of these peptides are described in Brostoff, S W; T cell receptor peptide vaccines as immunotherapy. Agents & Actions-Supplements. 47:53-8, 1995.

Platelet-derived growth factor (PDGF) analogs, agonist analogs and antagonist analogs can be used to treat nonneoplastic hyperproliferative disorders, therapy for donor tissue limitations and wound-healing constraints in surgery.

Amylin, calcitonin gene related peptides (CGRP) analogs, agonist analogs and antagonist analogs can be used to treat insulin-dependent diabetes.

VIP analogs, agonist analogs and antagonist analogs can be used to treat allergic respiratory diseases, asthma and allergic rhinitis, and nervous control of reproductive functions.

Growth hormone-releasing hormone (GHRH) analogs, agonist analogs and antagonist analogs can be used to treat growth hormone deficiency and immunomodulation.

HIV protease inhibiting peptide analogs, agonist analogs and antagonist analogs can be used to treat AIDS. Examples of these peptides are described in Bugelski, P. J.; Kirsh, R.; Hart, T. K; HIV protease inhibitors: effects on viral maturation and physiologic function in macrophages. Journal of Leukocyte Biology. 56(3):374-80, 1994.

Thymopoietin active fragment peptides analogs, agonist analogs and antagonist analogs can be used to treat rheumatoid arthritis and virus infections.

Cecropins analogs, agonist analogs and antagonist analogs can be used as antibacterials.

Thyroid releasing hormone (TRH) analogs, agonist analogs and antagonist analogs can be used to treat spinal cord injury and shock.

Erythropoietin (EPO) analogs, agonist analogs and antagonist analogs can be used to treat anemia.

Fibroblast growth factor (FGF), receptor analogs, agonist analogs and antagonist analogs can be as stimulation of bone formation, as well as used as a treatment for Kaposi's sarcoma, neuron regeneration, prostate growth, tumor growth inhibition, and angiogenesis.

Stem cell factor analogs, agonist analogs and antagonist analogs can be used to treat anemias. GP120, GP160, CD4 fragment peptides analogs, agonist analogs and antagonist analogs can be used to treat HIV and AIDS.

Insulin-like growth factor (IGF) analogs, agonist analogs and antagonist analogs, and IGF receptor analogs, agonist analogs and antagonist analogs can be used to treat breast and other cancers, noninsulin-dependent diabetest mellitus, cell proliferation, apoptosis, hematopoiesis, HIV, AIDS, growth disorders, osteoporosis, and insulin resistance.

Colony stimulating factors (granulocyte-macrophage colony-stimulating factor (GMCSF), granulocyte colony-stimulating factor (GCSF), and macrophage colony-stimulating factor (MCSF) analogs, agonist analogs and antagonist analogs can be used to treat anemias.

Kentsin analogs, agonist analogs and antagonist analogs can be used for immunomodulation.

Lymphocyte activating peptide (LAP) analogs, agonist analogs and antagonist analogs can be used for immunomodulation. Examples of these peptides are described in Loleit, M.; Deres, K.; Wiesmuller, K. H.; Jung, G.; Eckert, M.; Bessler, W. G; Biological activity of the *Escherichia coli* lipoprotein: detection of novel lymphocyte activating peptide segments of the molecule and their conformational characterization. Biological Chemistry Hoppe-Seyler. 375 (6):407-12, June 1994.

Tuftsin analogs, agonist analogs and antagonist analogs can be used for immunomodulation.

Prolactin analogs, agonist analogs and antagonist analogs can be used to treat rheumatic diseases, systemic lupus erythematosus, and hyperprolactemia.

Angiotensin II analogs, agonist analogs and antagonist analogs and Angiotensin II receptor(s) analogs, agonist analogs and antagonist analogs can be used to treat hypertension, hemodynamic regulation, neurological disorders, diabetic nephropathies, aortoarterities induced RVH, hyperaldosteronism, heavy metal induced cardiovascular effects, diabetes mellitus and thyroid dysfunction.

Dynorphin analogs, agonist analogs and antagonist analogs can be used to treat neurological disorders, pain management, algesia, spinal cord injury and epilepsy.

Calcitonin analogs, agonist analogs and antagonist analogs can be used to treat neurological disorders, immune system dysfunction, calcium homeostasis, and osteoporosis.

Pituitary adenylate cyclase activating polypeptide analogs, agonist analogs and antagonist analogs may modulate growth, signal transduction vasoactivity roles.

Cholecystokinin analogs, agonist analogs and antagonist analogs can be used to treat feeding disorders, panic disorders, and anti-opioid properties.

Pepstatin analogs, agonist analogs and antagonist analogs can be used as pepsin and HIV protease inhibitors (AIDS).

Bestatin analogs, agonist analogs and antagonist analogs can be used to treat muscular dystrophy, anticancer, antileukemia, immune response modulator, and acute non-lymphocytic leukemia.

Leupeptin analogs, agonist analogs and antagonist analogs can be used as a protease inhibitor, exact role in diseases not determined yet.

Luteinizing hormone and releasing hormone analogs, agonist analogs and antagonist analogs can be used as a infertility male contraceptive.

Neurotensin analogs, agonist analogs and antagonist analogs can be used, e.g., as antipsychotic, analgesic, anticancer, and/or neuroprotective agents, e.g., for treating stroke victims, e.g., by inducing hypothermia so as to provide neuroprotection.

Motilin analogs, agonist analogs and antagonist analogs can be used for the control of gastric emptying.

Insulin analogs, agonist analogs and antagonist analogs can be used to treat diabetes.

Transforming growth factor (TGF) analogs, agonist analogs and antagonist analogs can be used for cell proliferation and differentiation, cancer treatment, immunoregulation, therapy for donor tissue limitations, and wound-healing constraints in surgery.

Bone morphogenetic proteins (BMPs) analogs, agonist analogs and antagonist analogs can be used as therapy for donor tissue limitations, osteogenesis, and wound-healing constraints in surgery.

Bombesin and Enterostatin analogs, agonist analogs and antagonist analogs can be used to prevent the proliferation of tumor cells, modulation of feeding, and neuroendocrine functions. These peptides fall within a supercategory of the neuromedins described above. These peptides are described in such exemplary references as Yamada K. Wada E. Wada K. Bombesin-like peptides: studies on food intake and social behaviour with receptor knock-out mice. Annals of Medicine. 32(8):519-29, November 2000; Ohki-Hamazaki H. Neuromedin B. Progress in Neurobiology. 62(3):297-312, October 2000; Still CD. Future trends in weight management. Journal of the American Osteopathic Association. 99(10 Su Pt 2):S 18-9, 1999; Martinez V. Tache Y. Bombesin and the brain-gut axis. Peptides. 21(11):1617-25, 2000; Afferent signals regulating food intake. Proceedings of the Nutrition Society. 59(3):373-84, 2000; Takenaka Y. Nakamura F. Jinsmaa Y. Lipkowski A W. Yoshikawa M. Enterostatin (VPDPR) has anti-analgesic and anti-amnesic activities. Bioscience Biotechnology & Biochemistry. 65(1): 236-8, 2001 J.

Glucagon, glucagon-like peptide 1 analogs, agonist analogs and antagonist analogs can be used to treat diabetes cardiovascular emergencies.

Pancreastatin, chromogranins A, B and C analogs, agonist analogs and antagonist analogs—conditions associated with inhibition of insulin secretion, exocrine pancreatic secretion and gastric acid secretion, and stimulation of secretion.

Endorphins analogs, agonist analogs and antagonist analogs can be used to treat neurological disorders, alleviating pain, treatment of opioid abuse, obesity, and diabetes.

Examples of these peptides are named and described in Dalayeun, J. F.; Nores, J. M.; Bergal, S.; Physiology of beta-endorphins. A close-up view and a review of the literature. Biomedicine & Pharmacotherapy. 47(8):311-20, 1993.

Miscellaneous opioid peptides analogs, agonist analogs and antagonist analogs, including (but not limited to) adrenal peptide E analogs, alpha casein fragment analogs, beta casomorphin analogs, dermorphin analogs, kyotorphin analogs, metophamide neuropeptide FF (NPFF) analogs, melanocyte inhibiting factor analogs, agonist analogs and antagonist analogs can be used to treat neurological disorders, alleviating pain, as well as for the treatment of opioid abuse.

Vasotocin analogs, agonist analogs and antagonist analogs can be used for sleep disorders including but not limited to insomnia.

Protein kinase C and inhibitors analogs, agonist analogs and antagonist analogs can be used to treat cancer, apoptosis, smooth muscle function, and Alzheimer's disease.

Examples of these peptides are named and described in Philip, P. A.; Harris, A. L; Potential for protein kinase C inhibitors in cancer therapy. Cancer Treatment & Research. 78:3-27, 1995.

Amyloid, amyloid fibrin, analogs, agonist analogs and antagonist analogs can be used to treat neurodegenerative diseases and diabetes.

Calpain and other calmodulin-inhibitory protein analogs, agonist analogs and antagonist analogs can be used to treat neurodegenerative disorders, cerebral ischaemia, cataracts, myocardial ischaemia, muscular dystrophy and platelet aggregation.

Charybdotoxin and Apamin analogs, agonist analogs and antagonist analogs can be used for treatment of neurodegenerative diseases and pain and cerebral ischemia.

Phospholipase A2 analogs, agonist analogs and antagonist analogs and Phospholipase A2 receptor inhibiting/activating peptides analogs, agonist analogs and antagonist analogs can be used to treat acute pancreatitis, pancreatic cancer, abdominal trauma, and inflammation, e.g., sepsis, infections, acute pancreatitis, various forms of arthritis, cancer, complications of pregnancy, and postoperative states.

Potassium channel activating and inhibiting analogs, agonist analogs and antagonist analogs can be used to treat various diseases. Examples of these peptides are described in Edwards, G.; Weston, A. H; Pharmacology of the potassium channel openers. Cardiovascular Drugs & Therapy. 9 Suppl 2:185-93, March 1995.

IgG activators, inhibitors analogs, agonist analogs and antagonist analogs can be used to treat autoimmune diseases and immune dysfunctions. Examples of these peptides are described in Mouthon, L.; Kaveri, S. V.; Spalter, S. H.; Lacroix-Desmazes, S.; Lefranc, C.; Desai, R.; Kazatchkine, M. D; Mechanisms of action of intravenous immune globulin in immune-mediated diseases. Clinical & Experimental Immunology. 104 Suppl 1:3-9, 1996.

Endotoxin and inhibitor analogs, agonist analogs and antagonist analogs can be used for decreasing cardiac output, systemic hypotension, decreased blood flow and $O_2$ delivery to tissues, intense pulmonary vasoconstriction and hypertension, bronchoconstriction, increased permeability, pulmonary oedema, ventilation-to-perfusion inequalities, hypoxaemia, and haemoconcentration. Examples of these peptides are named and described in Burrell, R; Human responses to bacterial endotoxin. Circulatory Shock. 43(3): 137-53, July 1994.

Orphan receptor ligand analogs, agonist analogs and antagonist analogs (including but not limited to ADNF, Adrenomedullin, Apelin, Ghrelin, Mastoparan (MCD peptides), Melanin concentrating hormone, Nociceptin/Nocistatin, Orexin, Receptor activity modulating protein, Urotensin) can be used to treat obesity, weight problems, neuropathy, sleep deprivation, sleep disorder inclusing insomnia, and lung cell repair. These orphan receptor ligands are described in such references as In DS. Orphan G protein-coupled receptor s and beyond. Japanese Journal of Pharmacology. 90(2): 101-6, 2002; Maguire J J. Discovering orphan receptor function using human in vitro pharmacology. Current Opinion in Pharmacology. 3(2):135-9, 2003; Szekeres P G. Functional assays for identifying ligands at orphan G protein-coupled receptor s. Receptor s & Channels. 8(5-6):297-308, 2002; Shiau A K. Coward P. Schwarz M. Lehmann J M. Orphan nuclear receptor s: from new ligand discovery technologies to novel signaling pathways. Current Opinion in Drug Discovery & Development. 4(5): 575-90, 2001; Civelli O. Nothacker H P. Saito Y. Wang Z. Lin S H. Reinscheid R K. Novel neurotransmitters as natural ligands of orphan G-protein-coupled receptor s. Trends in Neurosciences. 24(4):230-7, 2001; Darland T. Heinricher M M. Grandy D K. Orphan in F Q/nociceptin: a role in pain and analgesia, but so much more. Trends in Neurosciences. 21(5):215-21, 1998, the disclosures of which are incorporated herein by reference.

Another embodiment of the invention includes analogs of Glycoprotein IIb/IIIa inhibitors. The central role of platelet-rich thrombus in the pathogenesis of acute coronary syndromes (ACSs) is well-known. Glycoprotein IIb/IIIa (Gp IIb/IIa) receptor analogs, agonist analogs and antagonist analogs can be used as potent modulators of platelet function that may be expected to affect favorably the natural history of ACSs. Exemplary references for this category include Bhatt D L. Topol E J. Current role of platelet glycoprotein IIb/IIIa inhibitors in acute coronary syndromes. JAMA. 284(12):1549-58, 2000; Kereiakes D J. Oral blockade of the platelet glycoprotein IIb/IIIa receptor: fact or fancy?. American Heart Journal. 138(1 Pt 2):S39-46, 1999; Bassand J P. Low-molecular-weight heparin and other antithrombotic agents in the setting of a fast-track revascularization in unstable coronary artery disease. Haemostasis. 30 Suppl 2:114-21; discussion 106-7, 2000.

Apo-lipoprotein A-I analogs, agonist analogs and antagonist analogs may increase the HDL levels of subjects upon administration. Analogs of the present invention that are homologous to Apo-lipoprotein A-I may be useful to treat or prevent liver disease and inflammatory diseases including but not limited to artherosclerosis. Analogs of the present invention that are homologous to Apo-lipoprotein A-I may be useful to increase the amount of formation of pre-β1 HDL in human plasma.

The cytokine analogs of the present invention may treat or prevent autoimmune disease, inflammatory disease, and dysfunctional growth or differentiation of cells such as cellular proliferative disorders, the development of neoplasia, tumors, and cancer.

The present invention provides for the use of an antibody or binding composition which specifically binds to a specified analog, in some embodiments the antibody specifically binds the analog derived from a mammalian polypeptide, e.g., a polypeptide derived from a primate, human, cat, dog, rat, or mouse. Antibodies can be raised to various analogs, including individual, polymorphic, allelic, strain, or species variants, and fragments thereof, both in their naturally occurring (full-length) forms or in their synthetic forms. Additionally, antibodies can be raised to the analogs in their inactive state or active state. Anti-idiotypic antibodies may also be used.

A number of immunogens may be selected to produce antibodies specifically reactive with ligand or receptor proteins. Synthetic analogs may serve as an immunogen for the production of monoclonal or polyclonal antibodies. Such antibodies may be used as antagonists or agonists for their targets modulating the disease state associated with the naturally occurring proteins and analogs listed above. Synthetic polypeptides of the claimed invention may also be used either in pure or impure form. Synthetic peptides, made using the appropriate protein sequences, may also be used as an immunogen for the production of antibodies. Naturally folded or denatured material can be used, as appropriate, for producing antibodies. Either monoclonal or polyclonal antibodies may be generated, e.g., for subsequent use in immunoassays to measure the protein, or for immunopurification methods. Methods of producing polyclonal antibodies are well known to those of skill in the art.

Typically, an immunogen, such as a purified analog of the invention, is mixed with an adjuvant and animals are immunized with the mixture. The animal's immune response to the immunogen preparation is monitored by taking test bleeds and determining the titer of reactivity to the protein of interest. For example, when appropriately high titers of antibody to the immunogen are obtained, usually after repeated immunizations, blood is collected from the animal and antisera are prepared. Further fractionation of the antisera to enrich for antibodies reactive to the protein can be performed if desired. See, e.g., Harlow and Lane; or Coligan. Immunization can also be performed through other methods, e.g. DNA vector immunization. See, e.g., Wang, et al. (1997) Virology 228:278-284.

Monoclonal antibodies may be obtained by various techniques familiar to researchers skilled in the art. Typically, spleen cells from an animal immunized with a desired analog are immortalized, commonly by fusion with a myeloma cell. See, Kohler and Milstein (1976) Eur. J. Immunol. 6:511-519. Alternative methods of immortalization include transformation with Epstein Barr Virus, oncogenes, or retroviruses, or other methods known in the art. See, e.g., Doyle, et al. (eds. 1994 and periodic supplements) Cell and Tissue Culture: Laboratory Procedures, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) Science 246:1275-1281.

Antibodies or binding compositions, including binding fragments, single chain antibodies, $F_v$, $F_{ab}$, single domain $V_H$, disulfide-bridged $F_v$, single-chain $F_v$ or $F(_{ab}')_2$ fragments of antibodies, diabodies, and triabodies against predetermined fragments of the analogs can be raised by immunization of animals with analogs or conjugates of analogs or receptor proteins with carrier proteins. Monoclonal antibodies are prepared from cells secreting the desired antibody. These antibodies can be screened for binding to analogs described herein. These monoclonal antibodies will usually bind with at least a $K_D$ of about 1 mM, usually at least about 300 µM, typically at least about 10 µM, at least about 30 µM, at least about 10 µM, and at least about 3 µM or more. These antibodies can be screened for binding to the naturally occurring polypeptides upon which the analogs are derived.

In some instances, it is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) Basic and Clinical Immunology, 4th ed., Lange Medical Publications, Los Altos, Calif., and references cited therein; Harlow and Lane (1988) Antibodies: A Laboratory Manual CSH Press; Goding (1986) Monoclonal Antibodies: Principles and Practice, 2nd ed., Academic Press, New York, N.Y.; and particularly in Kohler and Milstein (1975) Nature 256:495-497, which discusses one method of generating monoclonal antibodies. Summarized briefly, this method involves injecting an animal with an analog described herein. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the analog. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) Science 246:1275-1281; and Ward, et al. (1989) Nature 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see, Cabilly, U.S. Pat. No. 4,816,567; and Queen, et al. (1989) Proc. Nat'l Acad. Sci. USA 86:10029-10033; or made in transgenic mice, see Mendez, et al. (1997) Nature Genetics 15:146-156; also see Abgenix and Medarex technologies.

The instant invention is related to pharmaceutical compositions of the instant invention or the pharmaceutical acceptable salts derived therefrom that comprise analogs that comprise isotopes. In some embodiments, the compositions of the claimed invention may contain any isotope described in Cyr and Pearson (Stabilization of radiopharmaceutical compositions using hydrophilic thioethers and hydrophilic 6-hydroxy chromans. Cyr, John E.; Pearson, Daniel A. (Diatide, Inc., USA). PCT Int. Appl. (2002), WO 200260491 A2 20020808), which is herein incorporated by reference. In some embodiments the compositions of the invention comprise analog that comprise one or more of the following isotopes: $^{125}I$, $^{131}I$, $^{211}At$, $^{47}Sc$, $^{67}CU$, $^{72}Ga$, $^{90}Y$, $^{153}Sm$, $^{159}Gd$, $^{165}Dy$, $^{166}Ho$, $^{175}Yb$, $^{177}Lu$, $^{212}Bi$, $^{213}Bi$, $^{68}Ga$, $^{99}Tc$, $^{111}In$, $^{123}I$, and $^{3}H$.

The pharmaceutical compositions of the instant invention or the pharmaceutical acceptable salts derived therefrom may be in a liquid or solid dosage form. Such compositions may include any type of dosage form such as tablets, capsules, powders, liquid formulations, delayed or sustained release, patches, snuffs, nasal sprays and the like. The formulations may additionally include other ingredients such as dyes, preservatives, buffers and anti-oxidants, for example. The physical form and content of the pharmaceutical formulations contemplated are conventional preparations that can be formulated by those skilled in the pharmaceutical formulation field and are based on well established principles and compositions described in, for example, *Remington: The Science and Practice of Pharmacy*, 19th Edition, 1995; British Pharmacopoeia 2000, each of which is incorporated herein by reference. The compositions of the present invention may also include other active agents useful in the treatment of cardiovascular conditions. Solid forms can be prepared according to any means suitable in the art. For example, capsules are prepared by mixing the analog composition with a suitable diluent and filling the proper amount of the mixture in capsules. Tablets are prepared by direct compression, by wet granulation, or by dry granulation. Their formulations usually incorporate diluents, binders, lubricants and disintegrators as well as the compound. Diluents, but are not limited to, include various types of starch, cellulose, crystalline cellulose, microcrystalline cellulose, lactose, fructose, sucrose, mannitol or other sugar alcohols, kaolin, calcium phosphate or sulfate, inorganic salts such as sodium chloride and powdered sugar. Powdered cellulose derivatives are also useful. Non-limiting examples of tablet binders include, but are not limited to, starches, gelatin and sugars such as lactose, fructose, glucose and the like. Natural and synthetic gums are also convenient, including, but are not limited to, acacia, alginates, methylcellulose, polyvinylpyrrolidone and the like. Polyethylene glycol, ethylcellulose and waxes can also serve as binders.

A lubricant can be used in a tablet formulation to prevent the tablet and punches from sticking in the die. The lubricant include, but are not limited to, such slippery solids as talc, magnesium and calcium stearate, stearic acid and hydrogenated vegetable oils.

Tablets can be coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

Also contemplated are liquid formulations and solid form preparations which are intended to be converted, shortly before use, to liquid form preparations. Such liquid forms include, but are not limited to, solutions, suspensions, syrups, slurries, and emulsions. Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder form for constitution with a suitable vehicle such as sterile water, saline solution, or alcohol, before use. Preparations may also contain mucosal enhancers.

In some embodiments, the oral transmucosal solid dosage form further comprises a permeation enhancer. In some embodiments, the permeation enhancer is chosen from: a bile salt, sodium dodecyl sulfate, dimethyl sulfoxide, sodium lauryl sulfate, a derivative of a saturated or a unsaturated fatty acid, a surfactant, a bile salt analog, and a derivative of a bile salt. In some embodiments the oral transmucosal dosage form is chosen from: a chewing gum, a patch, a lozenge, a lozenge-on-a-handle, a tablet, a troche, a pastille, a sachet, a sublingual tablet, and a rapid disintegrating tablet. In some embodiments, the oral transmucosal solid dosage form of wherein the composition further comprises at least one flavoring agent, artificial coloring, sweetener, lubricating agent, disintegration agent, lubricating agent, diluent, base, or buffering agent. In some embodiments, the oral transmucosal solid dosage form further comprises a sustained release agent. The invention is directed to an oral transmucosal solid dosage form comprising from wherein the concentration of analog is from about 0.01% to about 90% of the dry matter weight of the composition.

Solid dosage forms such as lozenges and tablets may also be used for oral transmucosal delivery of pharmaceuticals. For example, nitroglycerin sublingual tablets have been on the market for many years. The sublingual tablets are designed to deliver small amounts of the potent nitroglycerin, which is almost immediately dissolved and absorbed. On the other hand, most lozenges or tablets are typically designed to dissolve in the mouth over a period of at least several minutes which allows extended dissolution of the lozenge and absorption of the drug.

Administration of lozenges or sublingual tablets generally utilize an "open" delivery system, in which the drug delivery conditions are influenced by the conditions of the surrounding environment, such as rate of saliva secretion, pH of the saliva, or other conditions beyond the control of the formulation.

A lozenge-on-a-handle (similar to a lollipop) is another dosage form suitable for transmucosal drug delivery. In addition to being non-invasive and providing a particularly easy method of delivery, the lozenge-on-a-handle (or lozenge with an integrated oral transmucosal applicator) dosage form allows a patient or caregiver to move the dosage form in and out of the mouth to titrate the dose. This practice is called dose-to-effect, in which a patient or caregiver controls the administration of the dose until the expected therapeutic effect is achieved. This is particularly important for certain symptoms, such as pain, nausea, motion sickness, and premedication prior to anesthesia because each patient needs a different amount of medication to treat these symptoms. For these types of treatments, the patient is the only one who knows how much medication is enough. Once the appropriate amount of drug is delivered, the patient or caregiver can remove the lozenge-on-a-handle, thus, stopping delivery of the drug. This feature is especially important for particularly potent drugs, which may present a significant advantage of terminating drug administration once the desired effect is achieved.

As used herein, the term "oral transmucosal delivery" (OTD) refers to the delivery of a pharmaceutical agent across a mucous membrane in the oral cavity, pharyngeal cavity, or esophagus, and may be contrasted, for example, with traditional oral delivery, in which absorption of the drug occurs in the intestines. Accordingly, routes of administration in which the pharmaceutical agent is absorbed through the buccal, sublingual, gingival, pharyngeal, and/or esophageal mucosa are all encompassed within "oral transmucosal delivery," as that term is used herein. Oral transmucosal delivery involves the administration of an oral transmucosal solid dosage form to the oral cavity of a patient, which is held in the oral cavity and dissolved, thereby releasing the pharmaceutical agent for oral transmucosal delivery. Of course, as the solid dosage form dissolves in the oral cavity, some of the saliva containing the pharmaceutical agent may be swallowed, and a portion of the drug may ultimately be absorbed from the intestines.

The compositions of the invention can be administered in a sustained release composition, such as those described in, for example, U.S. Pat. Nos. 5,672,659 and 5,595,760, and herein incorporate by reference. The use of immediate or sustained release compositions depends on the type of condition being treated.

The pharmaceutical compositions of the instant invention or the pharmaceutical acceptable salts derived therefrom may be in a dosage amount in an effective amount for inducing or increasing the naturally occurring biological activity of the wild-type polypeptide upon which the analog is derived. The pharmaceutical compositions of the instant invention or the pharmaceutical acceptable salts derived therefrom may be in a dosage amount in an effective amount for inducing or increasing the naturally occurring biological activity of the wild-type secretin polypeptide upon which the analog is derived. The pharmaceutical compositions of the instant invention or the pharmaceutical acceptable salts derived therefrom may be in a dosage amount in an effective amount for increasing the half-life of the composition when administered to a human being or other subject. In some embodiments the secretin analog is VIP.

The present invention also encompasses methods of using the compositions comprising a VIP analog. Any of these methods may involve the administration of a pharmaceutical composition comprising a VIP analog wherein the VIP analog is in a therapeutically effective dose. Any of these methods may involve the administration of a pharmaceutical composition comprising a VIP analog wherein the VIP analog is selective for VPAC1, VPAC2, PAC1, VIPR1, or VIPR2. The composition comprising an analog of the invention produces a broad range of activities, depending on the dosage administered. The present invention encompasses methods of treating or preventing pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction comprising administering to at least one patient in need thereof, mammal in need thereof or human in need thereof a composition or pharmaceutical composition comprising a secretin family analog in a therapeutically effective amount. The compositions of the invention may also be used at lower doses in order to prevent pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject in need thereof. The compositions of the invention may also be used to prevent pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject susceptible to those indications. In some embodiments, the method of prevention comprising administering the composition or pharmaceutical compositions of the invention after the subject is tested for susceptibility or genetic propensity for developing the disease, indication or disorder.

The pharmaceutical composition comprising a pharmaceutically acceptable carrier/diluent and an analog comprising an α-amino acid and at least one β-amino acid may be formulated by one having ordinary skill in the art with compositions selected depending upon the chosen mode of administration. Suitable pharmaceutical carriers are described in the most recent edition of *Remington's Pharmaceutical Sciences*, A. Osol, a standard reference text in this field, which is incorporated herein in its entirety.

For parenteral administration, analog can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of analog in 0.9% sodium chloride solution.

The present invention relates to routes of administration include intramuscular, sublingual, intravenous, intraperitoneal, intrathecal, intravaginal, intraurethral, intradermal, intrabuccal, via inhalation, via nebulizer and via subcutaneous injection. Alternatively, the pharmaceutical composition may be introduced by various means into cells that are removed from the individual. Such means include, for example, microprojectile bombardment and liposome or other nanoparticle device.

Solid dosage forms for oral administration include capsules, tablets, pills, powders and granules. In solid dosage forms, the analogs are generally admixed with at least one inert pharmaceutically acceptable carrier such as sucrose, lactose, starch, or other generally regarded as safe (GRAS) additives. Such dosage forms can also comprise, as is normal practice, an additional substance other than an inert diluent, e.g., lubricating agent such as magnesium state. With capsules, tablets, and pills, the dosage forms may also comprise a buffering agent. Tablets and pills can additionally be prepared with enteric coatings, or in a controlled release form, using techniques know in the art.

Liquid dosage forms for oral administration include pharmaceutically acceptable emulsions, solutions, suspensions and syrups, with the elixirs containing an inert diluent commonly used in the art, such as water. These compositions can also include one or more adjuvants, such as wetting agent, an emulsifying agent, a suspending agent, a sweetening agent, a flavoring agent or a perfuming agent.

In another embodiment of the invention the composition of the invention is used to treat a patient suffering from, or susceptible to, pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction due to administration of a medication that causes onset of or exacerbates symptoms of pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject. In some embodiments, the invention relates to compositions comprising a secretin family analog for treatment or prevention of pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject in need thereof, wherein said analog comprises an α-amino acid and at least one β-amino acid. In some embodiments, the secretin family analog of the invention comprises an analog of VIP.

One of skill in the art will recognize that the appropriate dosage of the compositions and pharmaceutical compositions may vary depending on the individual being treated and the purpose. For example, the age, body weight, and medical history of the individual patient may affect the therapeutic efficacy of the therapy. Further, a lower dosage of the composition may be needed to produce a transient cessation of symptoms, while a larger dose may be needed to produce a complete cessation of symptoms associated with the disease, disorder, or indication. A competent physician can consider these factors and adjust the dosing regimen to ensure the dose is achieving the desired therapeutic outcome without undue experimentation. It is also noted that the clinician and/or treating physician will know how and when to interrupt, adjust, and/or terminate therapy in conjunction with individual patient response. Dosages may also depend on the strength of the particular analog chosen for the pharmaceutical composition.

The dose of the composition or pharmaceutical compositions may vary. The dose of the composition may be once per day. In some embodiments, multiple doses may be administered to the subject per day. In some embodiments, the total dosage is administered in at least two application periods. In some embodiments, the period can be an hour, a day, a month, a year, a week, or a two-week period. In an additional embodiment of the invention, the total dosage is administered in two or more separate application periods, or separate doses.

In some embodiments, subjects can be administered the composition in which the composition is provided in a daily dose range of about 0.0001 mg/kg to about 5000 mg/kg of the weight of the subject. The dose administered to the subject can also be measured in terms of total amount of analog administered per day. In some embodiments, a subject is administered from about 0.001 to about 3000 milligrams of analog per day. In some embodiments, a subject is administered up to about 2000 milligrams of analog per day. In some embodiments, a subject is administered up to about 1800 milligrams of analog per day. In some embodiments, a subject is administered up to about 1600 milligrams of analog per day. In some embodiments, a subject is administered up to about 1400 milligrams of analog per day. In some embodiments, a subject is administered up to about 1200 milligrams of analog per day. In some embodiments, a subject is administered up to about 1000 milligrams of analog per day. In some embodiments, a subject is administered up to about 800 milligrams of analog per day. In some embodiments, a subject is administered from about 0.001 milligrams to about 700 milligrams of analog per dose. In some embodiments, a subject is administered up to about 700 milligrams of analog per dose. In some embodiments, a subject is administered up to about 600 milligrams of analog per dose. In some embodiments, a subject is administered up to about 500 milligrams of analog per dose. In some embodiments, a subject is administered up to about 400 milligrams of analog per dose. In some embodiments, a subject is administered up to about 300 milligrams of secretin analog per dose. In some embodiments, a subject is administered up to about 200 milligrams of analog per dose. In some embodiments, a subject is administered up to about 100 milligrams of analog per dose. In some embodiments, a subject is administered up to about 50 milligrams of analog per dose.

In some embodiments, subjects can be administered the composition in which the composition comprising a VIP analog or pharmaceutically acceptable salt thereof is administered in a daily dose range of about 0.0001 mg/kg to about 5000 mg/kg of the weight of the subject. In some embodiments, the composition comprising a VIP analog or pharmaceutically acceptable salt thereof is administered in a daily dosage of up about 450 mg/kg of the weight of the subject. In some embodiments, the composition comprising a VIP analog or pharmaceutically acceptable salt thereof is administered in a daily dosage of up about 400 mg/kg of the weight of the subject. In some embodiments, the composition comprising a VIP analog or pharmaceutically acceptable salt thereof is administered in a daily dosage of up about 350 mg/kg of the weight of the subject. In some embodiments, the composition comprising a VIP analog or pharmaceutically acceptable salt thereof is administered in a daily dosage of up about 300 mg/kg of the weight of the subject. In some embodiments, the composition comprising a VIP analog or pharmaceutically acceptable salt thereof is administered in a daily dosage of up about 250 mg/kg of the weight of the subject. In some embodiments, the composition comprising a VIP analog or pharmaceutically acceptable salt thereof is administered in a daily dosage of up about 200 mg/kg of the weight of the subject. In some embodiments, the composition comprising a VIP analog or pharmaceutically acceptable salt thereof is administered in a daily dosage of up about 150 mg/kg of the weight of the subject. In some embodiments, the composition comprising a VIP analog or pharmaceutically acceptable salt thereof is administered in a daily dosage of up about 100 mg/kg of the weight of the subject. In some embodiments, the composition comprising a VIP analog or pharmaceutically acceptable salt thereof is administered in a daily dosage of up about 50 mg/kg of the weight of the subject. In some embodiments, the composition comprising a VIP analog or pharmaceutically acceptable salt thereof is administered in a daily dosage of up about 25 mg/kg of the weight of the subject.

In some embodiments, the composition comprising a VIP analog or pharmaceutically acceptable salt thereof is administered in a daily dosage of up about 10 mg/kg of the weight of the subject. In some embodiments, the composition comprising a VIP analog or pharmaceutically acceptable salt thereof is administered in a daily dosage of up about 5 mg/kg of the weight of the subject. In some embodiments, the composition comprising a VIP analog or pharmaceutically acceptable salt thereof is administered in a daily dosage of up about 1 mg/kg of the weight of the subject. In some embodiments, the composition comprising a VIP analog or pharmaceutically acceptable salt thereof is administered in a daily dosage of up about 0.1 mg/kg of the weight of the subject. In some embodiments, the composition comprising a VIP analog or pharmaceutically acceptable salt thereof is administered in a daily dosage of up about 0.01 mg/kg of the weight of the subject.

In some embodiments, the composition comprising a VIP analog or pharmaceutically acceptable salt thereof is administered in a daily dosage of up about 0.001 mg/kg of the weight of the subject. The dose administered to the subject can also be measured in terms of total amount of VIP analog administered per day.

In some embodiments, a subject in need thereof is administered from about 1 ng to about 500 µg of analog or pharmaceutically salt thereof per day. In some embodiments, a subject in need thereof is administered from about 1 ng to about 10 ng of analog or pharmaceutically salt thereof per day. In some embodiments, a subject in need thereof is administered from about 10 ng to about 20 ng of analog or pharmaceutically salt thereof per day. In some embodiments, a subject in need thereof is administered from about 10 ng to about 100 ng of analog or pharmaceutically salt thereof per day. In some embodiments, a subject in need thereof is administered from about 100 ng to about 200 ng of analog or pharmaceutically salt thereof per day. In some embodiments, a subject in need thereof is administered from about 200 ng to about 300 ng of analog or pharmaceutically salt thereof per day. In some embodiments, a subject in need thereof is administered from about 300 ng to about 400 ng of analog or pharmaceutically salt thereof per day. In some embodiments, a subject in need thereof is administered from about 400 ng to about 500 ng of analog or pharmaceutically salt thereof per day. In some embodiments, a subject in need thereof is administered from about 500 ng to about 600 ng of analog or pharmaceutically salt thereof per day. In some embodiments, a subject in need thereof is administered from about 600 ng to about 700 ng of analog or pharmaceutically salt thereof per day. In some embodiments, a subject in need thereof is administered from about 800 ng to about 900 ng of analog or pharmaceutically salt thereof per day. In some embodiments, a subject in need thereof is administered from about 900 ng to about 1 µg of analog or pharmaceutically salt thereof per day. In some embodiments, a subject in need thereof is administered from about 1 µg to about 100 µg of analog or pharmaceutically salt thereof per day. In some embodiments, a subject in need thereof is administered from about 100 µg to about 200 µg of analog or pharmaceutically salt thereof per day. In some embodiments, a subject in need thereof is administered from about 200 µg to about 300 µg of analog or pharmaceutically salt thereof per day. In some embodiments, a subject in need thereof is administered from about 300 µg to about 400 µg of analog or pharmaceutically salt thereof per day. In some embodiments, a subject in need thereof is administered from about 400 µg to about 500 µg of analog or pharmaceutically salt thereof per day. In some embodiments, a subject in need thereof is administered from about 500 µg to about 600 µg of analog or pharmaceutically salt thereof per day. In some embodiments, a subject in need thereof is administered from about 600 µg to about 700 µg of analog or pharmaceutically salt thereof per day. In some embodiments, a subject in need thereof is administered from about 800 µg to about 900 µg of analog or pharmaceutically salt thereof per day. In some embodiments, a subject in need thereof is administered from about 900 µg to about 1 mg of analog or pharmaceutically salt thereof per day.

In some embodiments, a subject in need thereof is administered from about 0.0001 to about 3000 milligrams of VIP analog or pharmaceutically salt thereof per day. In some embodiments, a subject is administered up to about 2000 milligrams of VIP analog or pharmaceutically salt thereof day. In some embodiments, a subject is administered up to about 1800 milligrams of VIP analog or pharmaceutically salt thereof per day. In some embodiments, a subject is administered up to about 1600 milligrams of VIP analog or pharmaceutically salt thereof per day. In some embodiments, a subject is administered up to about 1400 milligrams of VIP analog or pharmaceutically salt thereof per day. In some embodiments, a subject is administered up to about 1200 milligrams of VIP analog or pharmaceutically salt thereof per day. In some embodiments, a subject is administered up to about 1000 milligrams of VIP analog or pharmaceutically salt thereof per day. In some embodiments, a subject is administered up to about 800 milligrams of VIP analog or pharmaceutically salt thereof per day. In some embodiments, a subject is administered from about 0.0001 milligrams to about 700 milligrams of VIP analog or pharmaceutically salt thereof per dose. In some embodiments, a subject is administered up to about 700 milligrams of VIP analog or pharmaceutically salt thereof per dose. In some embodiments, a subject is administered up to about 600 milligrams of VIP analog or pharmaceutically salt thereof per dose. In some embodiments, a subject is administered up to about 500 milligrams of VIP analog or pharmaceutically salt thereof per dose. In some embodiments, a subject is administered up to about 400 milligrams of VIP analog or pharmaceutically salt thereof per dose. In some embodiments, a subject is administered up to about 300 milligrams of VIP analog or pharmaceutically salt thereof per dose. In some embodiments, a subject is administered up to about 200 milligrams of VIP analog or pharmaceutically salt thereof per dose. In some embodiments, a subject is administered up to about 100 milligrams of VIP analog or pharmaceutically salt thereof per dose. In some embodiments, a subject is administered up to about 50 milligrams of VIP analog or pharmaceutically salt thereof per dose. In some embodiments, a subject is administered up to about 25 milligrams of VIP analog or pharmaceutically salt thereof per dose. In some embodiments, a subject is administered up to about 15 milligrams of VIP analog or pharmaceutically salt thereof per dose.

In some embodiments, a subject is administered up to about 10 milligrams of VIP analog or pharmaceutically salt thereof per dose. In some embodiments, a subject is administered up to about 5 milligrams of VIP analog or pharmaceutically salt thereof per dose. In some embodiments, a subject is administered up to about 1 milligram of VIP analog or pharmaceutically salt thereof per dose. In some embodiments, a subject is administered up to about 0.1 milligrams of VIP analog or pharmaceutically salt thereof per dose. In some embodiments, a subject is administered up to about 0.001 milligrams of VIP analog or pharmaceutically salt thereof per dose.

The dose administered to the subject can also be measured in terms of total amount of VIP analog or pharmaceutically salt thereof administered per ounce of liquid prepared. In some embodiments, the VIP analog or pharmaceutically salt thereof is at a concentration of about 2.5 grams per ounce of solution. In some embodiments, the VIP analog or pharmaceutically salt thereof is at a concentration of about 2.25 grams per ounce of solution. In some embodiments, the VIP analog or pharmaceutically salt thereof is at a concentration of about 2.25 grams per ounce of solution. In some embodiments, the VIP analog or pharmaceutically salt thereof is at a concentration of about 2.0 grams per ounce of solution. In some embodiments, the VIP analog or pharmaceutically salt thereof is at a concentration of about 1.9 grams per ounce of solution. In some embodiments, the VIP analog or pharmaceutically salt thereof is at a concentration of about 1.8 grams per ounce of solution. In some embodiments, the VIP analog or pharmaceutically salt thereof is at a concentration of about 1.7 grams per ounce of solution. In some embodiments, the VIP analog or pharmaceutically salt thereof is at a concentration of about 1.6 grams per ounce of solution. In some embodiments, the VIP analog or pharmaceutically salt thereof is at a concentration of about 1.5 grams per ounce of solution. In some embodiments, the VIP analog or pharmaceutically salt thereof is at a concentration of about 1.4 grams per ounce of solution. In some embodiments, the VIP analog or pharmaceutically salt thereof is at a concentration of about 1.3 grams per ounce of solution. In some embodiments, the VIP analog or pharmaceutically salt thereof is at a concentration of about 1.2 grams per ounce of solution. In some embodiments, the VIP analog or pharmaceutically salt thereof is at a concentration of about 1.1 grams per ounce of solution. In some embodiments, the VIP analog or pharmaceutically salt thereof is at a concentration of about 1.0 grams per ounce of solution. In some embodiments, the VIP analog or pharmaceutically salt thereof is at a concentration of about 0.9 grams per ounce of solution. In some embodiments, the VIP analog or pharmaceutically salt thereof is at a concentration of about 0.8 grams per ounce of solution. In some embodiments, the VIP analog or pharmaceutically salt thereof is at a concentration of about 0.7 grams per ounce of solution. In some embodiments, the VIP analog or pharmaceutically salt thereof is at a concentration of about 0.6 grams per ounce of solution. In some embodiments, the VIP analog or pharmaceutically salt thereof is at a concentration of about 0.5 grams per ounce of solution. In some embodiments, the VIP analog or pharmaceutically salt thereof is at a concentration of about 0.4 grams per ounce of solution. In some embodiments, the VIP analog or pharmaceutically salt thereof is at a concentration of about 0.3 grams per ounce of solution. In some embodiments, the VIP analog or pharmaceutically salt thereof is at a concentration of about 0.2 grams per ounce of solution. In some embodiments, the VIP analog or pharmaceutically salt thereof is at a concentration of about 0.1 grams per ounce of solution. In some embodiments, the VIP analog or pharmaceutically salt thereof is at a concentration of about 0.01 grams per ounce of solution. In some embodiments, the VIP analog or pharmaceutically salt thereof is at a concentration of about 0.001 grams per ounce of solution prepared. In some embodiments, the VIP analog or pharmaceutically salt thereof is at a concentration of about 0.0001 grams per ounce of solution prepared. In some embodiments, the VIP analog or pharmaceutically salt thereof is at a concentration of about 0.00001 grams per ounce of solution prepared. In some embodiments, the VIP analog or pharmaceutically salt thereof is at a concentration of about 0.000001 grams per ounce of solution prepared.

Dosage may be measured in terms of mass amount of analog per liter of liquid formulation prepared. One skilled in the art can increase or decrease the concentration of the analog in the dose depending upon the strength of biological activity desired to treat or prevent any above-mentioned disorders associated with the treatment of subjects in need thereof. For instance, one embodiment of the invention can include up to 0.00001 grams of analog per 5 mL of liquid formulation and up to about 10 grams of analog per 5 mL of liquid formulation.

In some embodiments the pharmaceutical compositions of the claimed invention comprise at least one other active agent. in some embodiments, the active agent is a vasoactive agent. In some embodiments the vasoactive agent is chosen from the naturally occurring prostaglandins prostaglandin E0 (PGE0, also referred to 13,14-dihydro-PGE1; hereinafter, the abbreviation "PG" is used for "prostaglandin"), PGE1, 19-hydroxy-PGE1, PGE2, 19-hydroxy-PGE2, PGA1, 19-hydroxy-PGA1, PGA2, 19-hydroxy-PGA2, PGB1, 19-hydroxy-PGB1, PGB2, 19-hydroxy-PGB2, PGB3, PGD2, PGF1α, PGF2α(dinoprost), PGE3, PGF3α, PGI2 (prostacyclin), and combinations thereof. PGE0, PGE1, PGE2, and the hydrolyzable lower alkyl esters thereof (e.g., the methyl, ethyl and isopropyl esters) are, however, particularly suitable. Other suitable prostaglandins are exemplified, without limitation, by arboprostil, carbaprostacyclin, carboprost tromethamine, dinoprost tromethamine, dinoprostone, enprostil, iloprost, lipoprost, gemeprost, metenoprost, sulprostone, tiaprost, viprostil (CL 115,347), viprostil methyl ester, 16,16-dimethyl-Δ2-PGE1 methyl ester, 15-deoxy-16-hydroxy-16-methyl-PGE1 methyl ester (misoprostol), 16,16-dimethyl-PGE1, 11-deoxy-15-methyl-PGE1, 16-methyl-18,18,19,19-tetrahydrocarbacyclin, 16(RS)-15-deoxy-16-hydroxy-16-methyl-PGE1 methyl ester, (+)-4,5-didehydro-16-phenoxy-α-tetranor-PGE2 methyl ester, 1 1-deoxy-11α,16,16-trimethyl-PGE2, (+)-11α,16α,16 β-dihydroxy-1-(hydroxymethyl)-16-methyl-trans-prostene, 9-chloro-16,16-dimethyl-PGE2, 16,16-dimethyl-PGE2, 15(S)-15-methyl-PGE2, 9-deoxy-9-methylene-16,16-dimethyl-PGE2, potassium salt, 19(R)-hydroxy-PGE2, and 11-deoxy-16,16-dimethyl-PGE2. Additional vasoactive agents useful as secondary active agents herein include endothelin-derived relaxation factors ("EDRFs") such as nitric oxide releasing agents, e.g., sodium nitroprusside and diazenium diolates, or "NONOates." NONOates include, but are not limited to, (Z)-1-{N-methyl-N-{6-(N-methyl-ammoniohexyl)amino}}diazen-1-ium-1,2-diolate ("MAHMA/NO"), (Z)-1-{N-(3-ammoniopropyl)-N-(n-propyl)amino}-diazen-1-ium-1,2-diolate ("PAPA/NO"), (Z)-1-{N-{3-aminopropyl}-N-{4-(3-aminopropylammonio)butyl}amino)}diazen-1-ium-1,2-diolate (spermine NONOate or "SPER/NO") and sodium (Z)-1-(N,N-diethylamino)-diazen-1-ium-1,2-diolate (diethylamine NONOate or "DEA/NO") and derivatives thereof). Still other vasoactive agents include vasoactive intestinal polypeptide analogs and derivatives thereof (particularly derivatives in the form of hydrolyzable lower alkyl esters), smooth muscle relaxants, leukotriene inhibitors, calcium channel blockers, P2-adrenergic agonists, angiotensin-converting enzyme ("ACE") inhibitors, angiotensin II receptor antagonists, and phosphodiesterase inhibitors.

Still other suitable vasoactive agents include, but are not limited to: nitrates and like compounds such as nitroglycerin, isosorbide dinitrate, erythrityl tetranitrate, amyl nitrate, molsidomine, linsidomine chlorhydrate ("SIN-1"), S-nitroso-N-acetyl-d,l-penicillamine ("SNAP") and S-nitroso-N-glutathione ("SNO-GLU"); long and short acting α-blockers such as phenoxybenzamine, dibenamine, doxazosin, terazosin, phentolamine, tolazoline, prazosin, trimazosin, alfuzosin, tamsulosin and indoramin; ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; nimodepine; pinacidil; cyclandelate; dipyridamole; isoxsuprine; chlorpromazine; haloperidol; yohimbine; and trazodone.

In some embodiments, the pharmaceutical compositions of the invention comprise an active agent that is an inhibitor of rho kinase, an enzyme belonging to the rhoA/rho associated kinase pathway, which regulates the state of phosphorylation of myosin phosphatase, in turn leading to the control of smooth muscle contraction. One example of a suitable rho kinase inhibitor has the following structural formula and is identified as Y-27632. Other suitable rho kinase inhibitors are disclosed, for example, in U.S. Pat. No. 6,218,410, which is herein incorporated by reference.

In some embodiments, the pharmaceutical compositions of the invention comprise an active agent that are peptide analogs of α-melanocyte-stimulating hormone (α-MSH), also referred to as "melanocortin peptides." Such peptides include the sequence His-Phe-Arg-Trp, His-D-Phe-Arg-Trp, or are homologs thereof, and can be cyclic. A suitable melanocortin peptide is Ac-Nle-cyclo-(-Asp-His-D-Phe-Arg-Trp-Lys)-OH. See U.S. Pat. No. 6,051,555 to Hadley and International Patent Publication No. WO 01/00224 to Blood et al., assigned to Palatin Technologies, Inc. The aforementioned amino acid residues have their conventional meaning as given in Chapter 2422 of the Manual of Patent Examining Procedure (2000). Thus, "Arg" is arginine, "Nle" is norleucine, "His" is histamine, "Phe" is phenylalanine, "D-Phe" is D-phenylalanine, "Trp" is tryptophan, and "Ac" refers to an acetyl moiety, i.e., an acetyl moiety present in a peptide or amino acid sequence that is acetylated.

In some embodiments, the pharmaceutical compositions of the invention comprise an active agent that is an endothelin antagonists, including antagonists of any or all of the three isoforms of endothelin, i.e., ET-1, ET-2, and ET-3, and are exemplified by: phenoxyphenylacetic acids and derivatives thereof, such as N-(4-isopropylbenzene-sulfonyl)-α-(4-carboxy-2-n-propylphenoxy)-3,4-methylenedioxyphenyl acetamide dipotassium salt, 2-{(2,6-dipropyl-4-hydroxymethyl)-phenoxy}-2-(4-phenoxyphenyl)-acetic acid, 2-{(2,6-dipropyl-4-hydroxymethyl)phenoxy}-2-(4-phenylphenyl) acetic acid, 2-{(2,6-dipropyl-4-hydroxymethyl)phenoxy}-2-(3-carboxyphenyl)-acetic acid, 2-{(2,6-dipropyl-4-hydroxymethyl)phenoxy}-2-(3,4-ethylenedioxyphenyl) acetic acid, 2-{(2,6-dipropyl-4-hydroxymethyl)phenoxy}-2-(3,4,5-trimethoxyphenyl)acetic acid, 2-{(2,6-dipropyl-4-hydroxymethyl)phenoxy}-2-(3,4-methylenedioxyphenyl) acetic acid, N-(4-dimethylaminobenzene sulfonyl)-2-(4-methoxycarbonyl-2-propylphenoxy)-2-(3,4-methylenedioxyphenyl) acetamide, N-(2-methylbenzenesulfonyl)-2-(4-methoxycarbonyl-2-propylphenoxy)-2-(3,4-methylenedioxyphenyl)acetamide, N-(2-methoxycarbonyl-benzenesulfonyl)-2-(4-methoxycarbonyl-2-propylphenoxy)-2-(3,4-methylenedioxy-phenyl) acetamide, N-(2-chlorobenzene-sulfonyl)-2-(4-methoxycarbonyl-2-propylphenoxy)-2-(3,4-methylenedioxyphenyl) acetamide, and others, as described in U.S. Pat. No. 5,565,485; and certain isooxazoles, oxazoles, thiazoles, isothiazoles and imidazoles, as described, for example, in U.S. Pat. No. 6,136,828.

In some embodiments, the pharmaceutical compositions of the invention comprise an active agent that is a peptidyl drug including the peptidyl hormones activin, amylin, angiotensin, atrial natriuretic peptide (ANP), calcitonin, calcitonin gene-related peptide, calcitonin N-terminal flanking peptide, ciliary neurotrophic factor (CNTF), corticotropin (adrenocorticotropin hormone, ACTH), corticotropin-releasing factor (CRF or CRH), epidermal growth factor (EGF), follicle-stimulating hormone (FSH), gastrin, gastrin inhibitory peptide (GIP), gastrin-releasing peptide, gonadotropin-releasing factor (GnRF or GNRH), growth hormone releasing factor (GRF, GRH), human chorionic gonadotropin (hCH), inhibin A, inhibin B, insulin, luteinizing hormone (LH), luteinizing hormone-releasing hormone (LHRH), α-melanocyte-stimulating hormone, 1-melanocyte-stimulating hormone, γ-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), secretin, somatotropin (growth hormone, GH), somatostatin (SIF, growth hormone-release inhibiting factor, GIF), thyrotropin (thyroid-stimulating hormone, TSH), thyrotropin-releasing factor (TRH or TRF), thyroxine, and vasopressin. Other peptidyl drugs are the cytokines, e.g., colony stimulating factor 4, heparin binding neurotrophic factor (HBNF), interferon-α, interferon α-2a, interferon α-2b, interferon α-n3, interferon-β, etc., interleukin-1, interleukin-2, interleukin-3, interleukin-4, interleukin-5, interleukin-6, etc., tumor necrosis factor, tumor necrosis factor-α, granuloycte colony-stimulating factor (G-CSF), granulocyte-macrophage colony-stimulating factor (GM-CSF), macrophage colony-stimulating factor, midkine (MD), and thymopoietin.

In some embodiments, the pharmaceutical compositions of the invention comprise an active agent that is a selective androgen receptor modulators (SARMs) include LGD2226 and/or LGD1331, both available from Ligand Pharmaceuticals (San Diego, Calif.). See Negro-Villar et al. J. Clin. Endocrinol. & Metabol. 84(10):3459-62 (1999).

In some embodiments, the pharmaceutical compositions of the invention comprise an active agent that is a suitable neuropeptide including bradykinin, kallidin, des-Arg9-bradykinin, des-Arg 10-kallidin, des-Arg9-{Leu8}-bradykinin, {D-Phe7}-bradykinin, HOE 140, neuropeptide Y, calcitonin gene-related peptide (cGRP), enkaphalins and related opioid peptides such as Met5-enkaphalin, Leu5-enkephalin, α-, β- and γ-endorphin, α- and β-neo-endorphin, and dynorphin, as well as the neurotransmitters GABA (γ-aminobutyric acid), glycine, glutamate, acetylcholine, dopamine, epinephrine, 5-hydroxytryptamine, substance P, serotonin, and catecholamines.

In some embodiments, the pharmaceutical compositions of the invention comprise an active agent that is a suitable serotonin agonists include, but are not limited to 2-methyl serotonin, buspirone, ipsaperone, tiaspirone, gepirone, ergot alkaloids, 8-hydroxy-(2-N,N-dipropyl-amino)-tetraline, 1-(4-bromo-2,5-dimethoxyphenyl)-2-aminopropane, cisapride, sumatriptan, m-chlorophenylpiperazine, trazodone, zacopride, mezacopride, and combinations thereof. Suitable serotonin antagonists include, for example, ondansetron, granisetron, metoclopramide, tropisetron, dolasetron, palonosetron, trimethobenzamide, methysergide, risperidone, ketanserin, ritanserin, clozapine, amitriptyline, MDL 100,907 (R(+)-α-(2,3-dimethoxyphenyl)-1-{2-(4-fluorophenyl)ethyl}-4-piperidine-methanol) (Marion Merrell Dow), azatadine, cyproheptadine, fenclonine, chlorpromazine, mianserin and combinations thereof.

In some embodiments, the pharmaceutical compositions of the invention comprise an active agent that is an ergot alkaloids include ergotamine and ergotamine analogs, e.g., acetergamine, brazergoline, bromerguride, cianergoline, delorgotrile, dihydroergotamine, disulergine, ergonovine, ergonovine maleate, ergotamine tartrate, etisulergine, lergotrile, lysergide, mesulergine, metergoline, metergotamine, nicergoline, pergolide, propisergide, proterguride and terguride.

In some embodiments, the pharmaceutical compositions of the invention comprise an active agent that is a calcium channel blockers that are suitable for use according to the present invention include, without limitation, amlodipine, felodipine, isradipine, nicardipine, nifedipine, nimodipine, nisoldipine, nitrendipine, bepridil, diltiazem, verapamil, and combinations thereof. In some embodiments, the pharmaceutical compositions of the invention comprise an active agent that is a potassium channel openers include, but are not limited to, pinacidil, diazoxide, cromakalim, nicorandil, minoxidil, (N-cyano-N'-(1,1-dimethylpropyl)-N''-3-pyridylguanidine (P-1075), and N-cyano-N'-(2-nitroxyethyl)-3-pridinecarboximidamide monomethanesulfonate (KRN 2391).

In some embodiments, the pharmaceutical compositions of the invention comprise an active agent that is a potassium channel blockers include tedisamil, agitoxin-2, apamin, BDS-I, BDS-II, charybdotoxin, α-dendrotoxin, β-dendrotoxin, γ-dendrotoxin, δ-dendrotoxin, dendrotoxin-I, dendrotoxin-K, E-4031, iberiotoxin, kaliotoxin, MCD-peptide, margatoxin, noxiustoxin, paxilline, penitrem A, stichodactyla, tertiapin, tityustoxin K alpha, verruculogen, and combinations thereof. Although all of the active agents are available commercially, most of the listed potassium channel blockers are available from Alomone Labs (Jerusalem, Israel).

In some embodiments, the pharmaceutical compositions of the invention comprise an active agent that is a dopamine agonist including, for example, levodopa, bromocriptine, pergolide, apomorphine, piribedil, pramipexole, ropinirole, and combinations thereof. Dopamine antagonists include, without limitation, spiroperidol, benperidol, trifluperidol, pimozide, fluphenazine, droperidol, haloperidol, thiothixene, trifluperazine, moperone, prochlorperazine, molindone, thioridazine, clozapine, chlorpromazine, promazine, sulpiride, clebopride, chlorpromazine, spiperone, flupenthixol, and combinations thereof.

In some embodiments, the pharmaceutical compositions of the invention comprise an active agent that is a non-androgenic steroid including progestins and estrogens. Suitable estrogens include synthetic and natural estrogens such as: estradiol (i.e., 1,3,5-estratriene-3,17β-diol, or "17β-estradiol") and its esters, including estradiol benzoate, valerate, cypionate, heptanoate, decanoate, acetate and diacetate; 17α-estradiol; ethinylestradiol (i.e., 17α-ethinylestradiol) and esters and ethers thereof, including ethinylestradiol 3-acetate and ethinylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Suitable progestins include acetoxypregnenolone, allylestrenol, anagestone acetate, chlormadinone acetate, cyproterone, cyproterone acetate, desogestrel, dihydrogesterone, dimethisterone, ethisterone (17α-ethinyltestosterone), ethynodiol diacetate, flurogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone. It is generally desirable to co-administer a progestin along with an estrogen so that the estrogen is not "unopposed." As is well known in the art, estrogen-based therapies are known to increase the risk of endometrial hyperplasia and cancer, as well as the risk of breast cancer, in treated individuals. Co-administration of estrogenic agents with a progestin has been found to decrease the aforementioned risks.

The pharmaceutical compositions of the present invention may also include one or more chemotherapeutic agents. Suitable chemotherapeutic agents include, but are not limited to, platinum coordination compounds, topoisomerase inhibitors, antibiotics, antimitotic alkaloids and difluoronucleosides.

In one embodiment of the present invention, the chemotherapeutic agent is a platinum coordination compound. The term "platinum coordination compound" refers to any tumor cell growth inhibiting platinum coordination compound that provides the platinum in the form of an ion. Suitable platinum coordination compounds include, but are not limited to, cis-diamminediaquoplatinum (II)-ion; chloro (diethylenetriamine)-platinum (II) chloride; dichloro (ethylenediamine)-platinum (II); diammine (1,1-cyclobutanedicarboxylato) platinum (II) (carboplatin); spiroplatin; iproplatin; diammine (2-ethylmalonato)-platinum (II); ethylenediaminemalonatoplatinum (II); aqua (1,2-diaminodyclohexane)-sulfatoplatinum (II); (1,2-diaminocyclohexane) malonatoplatinum (II); (4-caroxyphthalato) (1,2-diaminocyclohexane) platinum (II); (1,2-diaminocyclohexane)-(isocitrato) platinum (II); (1,2-diaminocyclohexane) cis (pyruvato) platinum (II); (1,2-diaminocyclohexane) oxalatoplatinum (II); ormaplatin; and tetraplatin In some embodiments, the secretin analog and the additional active agent or agents may be incorporated into a single formulation, or they may be administered separately, either simultaneously or sequentially. In one embodiment, an androgenic agent is administered prior to administration of VIP or a VIP agonist, i.e., the androgenic agent is administered as a pretreatment. In some embodiments, such a method involves administration of an androgenic agent, e.g., via oral or topical (vulvar and/or vaginal) administration, followed by topical (again, vulvar and/or vaginal) administration of VIP or a VIP agonist.

In some embodiments, the formulations herein are administered by topical application to the vulvar region and/or by vaginal drug administration. These pharmaceutical formulations may typically contain one or more pharmaceutically acceptable carriers suited to the particular type of formulation, i.e., gel, ointment, suppository, or the like. The vehicles are comprised of materials of naturally occurring or synthetic origin that do not adversely affect the active agent or other components of the formulation. Suitable carriers for use herein include water, silicone, waxes, petroleum jelly, polyethylene glycol, propylene glycol, liposomes, sugars such as mannitol and lactose, and a variety of other materials, again depending, on the specific type of formulation used. As described in Section IV, infra, dosage forms used for administration to the vulvar region and/or vagina may be used to deliver drug on an as-needed, on-demand basis, and/or throughout an extended, sustained release profile.

The pharmaceutical compositions may also include a chemical compound to enhance permeation of the active agent through the mucosal tissue, i.e., a "permeation enhancer." Suitable permeation enhancers include those generally useful in conjunction with topical, transdermal or transmucosal drug delivery. Examples of suitable permeation enhancers include the following: sulfoxides such as dimethylsulfoxide (DMSO) and decylmethylsulfoxide (C10MSO); ethers such as diethylene glycol monoethyl ether (available commercially as TRANSCUTOL® (Gattefosse S. A., Saint-Priest, France) and diethylene glycol monomethyl ether; surfactants such as sodium laurate, sodium lauryl sulfate, cetyltrimethylammonium bromide, benzalkonium chloride, Poloxamer (231, 182, 184), TWEEN® (20, 40, 60, 80) (ICI Chemicals, Bridgewater, N.J.), and lecithin (U.S. Pat. No. 4,783,450); the 1-substituted azacycloheptan-2-ones, particularly 1-n-dodecylcyclaza-cycloheptan-2-one (available under the trademark AZONE® (Durham Pharmaceuticals, LLC, Durham, N.C.); see U.S. Pat. Nos. 3,989,816, 4,316,893, 4,405,616 and 4,557,934); alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid. Mixtures of two or more enhancers may also be used.

In some embodiments, the pharmaceutical compositions may include an enzyme inhibitor, i.e., a compound effective to inhibit enzymes present in the vagina or vulvar area that could degrade or metabolize the active agent. That is, inhibitors of enzymes that decrease or eliminate the activity of the active agent may be included in the formulation so as to effectively inhibit the action of those enzymes. Such compounds include, for example, fatty acids, fatty acid esters, and NAD inhibitors.

In some embodiments, the pharmaceutical composition may be in the form of an ointment, cream, emulsion, lotion, gel, solid, solution, suspension, foam or liposomal formulation. Alternatively, the formulations may be contained within avaginal ring (e.g., as disclosed in U.S. Pat. No. 5,188,835 to Lindskoget al., assigned to Kabi Pharmacia AB), or within a tampon, suppository, sponge, pillow, puff, or osmotic pump system; these platforms are useful solely for vaginal delivery. Ointments are semisolid preparations that are typically based on petrolatum or other petroleum derivatives. The specific ointment base to be used, as will be appreciated by those skilled in the art, is one that will provide for optimum drug delivery. As with other carriers or vehicles, an ointment base should be inert, stable, non irritating and nonsensitizing. As explained in *Remington: The Science and Practice of Pharmacy*, supra, at pages 1034-1038, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Suitable water-soluble ointment bases are prepared from polyethylene glycols of varying molecular weight; again, reference may be had to *Remington: The Science and Practice of Pharmacy* for further information.

In one aspect of the invention, a method is provided for treating sexual dysfunction in a female individual comprising administering to the vagina and/or vulvar area a pharmaceutical formulation comprising a secretin family analog. In some embodiments, the secretin family analog is a vasodilator, with vasodilators selected from the group consisting of VIP and vasoactive intestinal polypeptide analogs and combinations of any of the foregoing. Any number of drug delivery platforms may be used, e.g., suppositories, ointments, creams, gels, solutions and the like. Also, one or more additional types of drugs, i.e., pharmacologically active agents may be incorporated into the pharmaceutical formulations. In other aspects of the invention, vaginal administration of a vasoactive agent as just described is used to improve vaginal muscle tone and tissue health, to enhance vaginal lubrication, or to minimize collagen misdeposition resulting from hypoxia as well as the associated lack of elasticity resulting from the collagen misdeposition.

In another embodiment of the invention, a method is provided for improving memory by administering a secretin family analog.

In another aspect of the invention, pharmaceutical compositions and dosage forms are provided for carrying out the aforementioned methods. The compositions and dosage forms contain a vasoactive agent as described above, a pharmaceutically acceptable vehicle, and, optionally, one or more additional pharmacologically active agents. The formulations contain a therapeutically effective amount of the active agent, or a therapeutically effective concentration of the active agent, i.e., a concentration that provides a therapeutically effective amount of active agent upon administration of a selected volume of composition.

The subject can be any animal, including but not necessarily limited to mammals such as a human, mouse, rat, hamster, guinea pig, rabbit, cat, dog, monkey, cow, horse, pig, and the like. In some embodiments, the subject is a human.

According to some embodiments of the invention, the formulation may be supplied as part of a kit. The kit comprise comprising an analog, wherein the analog comprises an α-amino acid and at least one β-amino acid. In another embodiment, the kit comprises a pharmaceutically acceptable salt of an analog with a rehydration mixture. In another embodiment, the pharmaceutically acceptable salt of an analog are in one container while the rehydration mixture is in a second container. The rehydration mixture may be supplied in dry form, to which water or other liquid solvent may be added to form a suspension or solution prior to administration. Rehydration mixtures are mixtures designed to solubilize a lyophilized, insoluble salt of the invention prior to administration of the composition to a subject takes at least one dose of a purgative. In another embodiment, the kit comprises a pharmaceutically acceptable salt in orally available pill form.

The kit may contain two or more containers, packs, or dispensers together with instructions for preparation and administration. In some embodiments, the kit comprises at least one container comprising the pharmaceutical composition or compositions described herein and a second container comprising a means for delivery of the compositions such as a syringe. In some embodiments, the kit comprises a composition comprising an analog in solution or lyophilized or dried and accompanied by a rehydration mixture. In some embodiments, the analog and rehydration mixture may be in one or more additional containers.

The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

In another embodiment, a packaged kit is provided that contains the pharmaceutical formulation to be administered, i.e., a pharmaceutical formulation containing VIP analog or a for enhancing female sexual desire and responsiveness, a container (e.g., a vial, a bottle, a pouch, an envelope, a can, a tube, an atomizer, an aerosol can, etc.), optionally sealed, for housing the formulation during storage and prior to use, and instructions for carrying out drug administration in a manner effective to enhance sexual desire and responsiveness. The instructions will typically be written instructions on a package insert, a label, and/or on other components of the kit.

Depending on the type of formulation and the intended mode of administration, the kit may also include a device for administering the formulation (e.g., a transdermal delivery device). The administration device may be a dropper, a swab, a stick, or the nozzle or outlet of an atomizer or aerosol can. The formulation may be any suitable formulation as described herein. For example, the formulation may be an oral dosage form containing a unit dosage of the active agent, or a gel or ointment contained within a tube. The kit may contain multiple formulations of different dosages of the same agent. The kit may also contain multiple formulations of different active agents.

The present kits will also typically include means for packaging the individual kit components, i.e., the pharmaceutical dosage forms, the administration device (if included), and the written instructions for use. Such packaging means may take the form of a cardboard or paper box, a plastic or foil pouch, etc.

The invention relates to the use of an analog in the preparation of a medicament for treating or preventing chronic obstructive pulmonary disease, pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small cell lung carcinoma, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction due to administration of a medication that causes onset of or exacerbates symptoms of pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small cell lung carcinoma, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject in need thereof. In some embodiments, the invention relates to compositions comprising a secretin family analog for treatment or prevention of chronic obstructive pulmonary disease, pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small cell lung carcinoma, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject in need thereof.

The present invention relates to inhibiting secretion of TNF-α in a subject comprising administering a composition comprising an analog to a subject, wherein said analog comprises an α-amino acid and at least one β-amino acid. In some embodiments the analog is a secretin family analog. In some embodiments the analog is a VIP analog. The present invention relates to inhibiting binding of VIP to a VIP receptor in a subject comprising administering a composition comprising an analog to a subject, wherein said analog comprises an α-amino acid and at least one β-amino acid. In some embodiments the analog is a secretin family analog. In some embodiments the analog is a VIP analog. The present invention relates to inhibiting biological effect of GHRH in a subject comprising administering a composition comprising an analog to a subject, wherein said analog comprises an α-amino acid and at least one β-amino acid. In some embodiments the analog is a secretin family analog. In some embodiments the analog is a VIP analog. The present invention relates to inhibiting chemotaxis of T cells in a subject comprising administering a composition comprising an analog to a subject, wherein said analog comprises an α-amino acid and at least one β-amino acid. In some embodiments the analog is a secretin family analog. In some embodiments the analog is a VIP analog. The present invention relates to inhibiting expression of LPS in a subject comprising administering a composition comprising an analog to a subject, wherein said analog comprises an α-amino acid and at least one β-amino acid. In some embodiments the analog is a secretin family analog. In some embodiments the analog is a VIP analog. The present invention relates to modulating the amount of cyclic cAMP in a subject comprising administering a composition comprising an analog to a subject, wherein said analog comprises an α-amino acid and at least one β-amino acid. In some embodiments the analog is a secretin family analog. In some embodiments the analog is a VIP analog. The present invention relates to increasing the activity or expression of adenylate cyclase in a subject comprising administering a composition comprising an analog to a subject, wherein said analog comprises an α-amino acid and at least one β-amino acid. In some embodiments the analog is a secretin family analog. In some embodiments the analog is a secretin family analog and a VPAC1 antagonist. In some embodiments the analog is a secretin family analog, and a VPAC2 agonist. In some embodiments the analog is a VIP analog. In some embodiments, the composition or pharmaceutical composition of the claimed invention comprises a VIP analog, wherein the VIP analog is a VIPR1 agonist, and has substantially reduced selectivity or no selectivity for VIPR2 or PAC1 receptors. In some embodiments, the composition or pharmaceutical composition of the claimed invention comprises a VIP analog, wherein the VIP analog is a PAC1 agonist, and has substantially reduced selectivity or no selectivity for VIPR2 or VIPR1 receptors. In some embodiments, the composition or pharmaceutical composition of the claimed invention comprises a VIP analog, wherein the VIP analog is a VIPR2 agonist, and has substantially reduced selectivity or no selectivity for VIPR1 or PAC1 receptors. In some embodiments, the composition or pharmaceutical composition of the claimed invention comprises a VIP analog, wherein the VIP analog is a VIPR2 antagonist, but does not antagonize VIPR1 or PAC1 receptors. In some embodiments, the composition or pharmaceutical composition of the claimed invention comprises a VIP analog, wherein the VIP analog is a VIPR1 antagonist, but does not antagonize VIPR2 or PAC1 receptors. In some embodiments, the composition or pharmaceutical composition of the claimed invention comprises a VIP analog, wherein the VIP analog is a PAC1 antagonist, but does not antagonize VIPR2 or VIPR1 receptors. Any of the above-mentioned selective agonist or antagonists may be used in any of the method claims provided herein.

The present invention relates to modulating the amount of PLD in the nervous system of a subject comprising administering a composition comprising an analog to a subject, wherein said analog comprises an α-amino acid and at least one β-amino acid. In some embodiments the analog is a secretin family analog. In some embodiments the analog is a VIP analog.

The present invention relates to modulating the amount of antibody production of a B cell in a subject comprising administering a composition comprising an analog to a subject, wherein said analog comprises an α-amino acid and at least one β-amino acid. In some embodiments the analog is a secretin family analog. In some embodiments the analog is a VIP analog.

The present invention relates to modulating the amount of antibody production of a B cell or a B cell hybridoma cell in vitro comprising treating a culture containing B cells or a hyvridoma with a composition comprising an analog to a subject, wherein said analog comprises an α-amino acid and at least one β-amino acid. In some embodiments the analog is a secretin family analog. In some embodiments the analog is a VIP analog.

The present invention relates to modulating the immune response of a subject comprising administering a subject with a composition comprising an analog to a subject, wherein said analog comprises an α-amino acid and at least one β-amino acid. In some embodiments the analog is a secretin family analog. In some embodiments the analog is a VIP analog.

The present invention relates to modulating the activation of cystic fibrosis transmembrane conductance regulator (CFTR) in a subject comprising administering a subject with a composition comprising an analog to a subject, wherein said analog comprises an α-amino acid and at least one β-amino acid. In some embodiments the analog is a secretin family analog. In some embodiments the analog is a VIP analog.

The present invention also relates measuring the modulation of activity of a secretin receptor molecule by measuring receptor activity comprising:

a) contacting a human secretin family receptor with a secretin family analog, wherein the analog comprises an α-amino acid and at least one β-amino acid;

b) measuring the association of the secretin family analog to the secretin receptor in the presence and absence of an unknown compound; and c) comparing the rate of association of the secretin family analog to the human secretin receptor in the presence of an unknown compound to the rate of association of the secretin analog to the human secretin receptor in the absence of an unknown compound.

The present invention also relates identifying a modulator of activity of a secretin receptor molecule by measuring receptor activity comprising:

a) contacting a human secretin family receptor with a secretin family analog, wherein said analog comprises an α-amino acid and at least one β-amino acid;

b) measuring the association of the secretin family analog to the secretin receptor in the presence and absence of an unknown compound; and c) comparing the rate of association of the secretin family analog to the human secretin receptor in the presence of an unknown compound to the rate of association of the secretin analog to the human secretin receptor in the absence of an unknown compound.

The present invention also relates to a method of measuring the modulation of activity of a human VIP receptor molecule by measuring receptor activity comprising:

a) contacting a human VIP family receptor with a VIP analog, wherein the analog comprises an α-amino acid and at least one β-amino acid;

b) measuring the association of the VIP analog to the VIP receptor in the presence and absence of an unknown compound; and c) comparing the rate of association of the VIP analog to the human VIP receptor in the presence of an unknown compound to the rate of association of the VIP analog to the human VIP receptor in the absence of an unknown compound.

The present invention also relates identifying a modulator of activity of a VIP family receptor molecule by measuring receptor activity comprising:

a) contacting a human VIP family receptor with a VIP analog, wherein said analog comprises an α-amino acid and at least one β-amino acid;

b) measuring the association of the VIP analog to the VIP receptor in the presence and absence of an unknown compound; and c) comparing the rate of association of the VIP analog to the human VIP receptor in the presence of an unknown compound to the rate of association of the VIP analog to the human VIP receptor in the absence of an unknown compound. In some embodiments, the VIP family receptor is chosen from VIPR1, VIPR2, $VPAC_1$, $VPAC_2$ or $PAC_1$.

The present invention also relates identifying a modulator of activity of a VIP family receptor molecule by measuring receptor activity comprising:

a) contacting a VIP family receptor with a VIP analog in a known concentration, wherein said analog comprises an α-amino acid and at least one β-amino acid;

b) measuring the binding affinity of the VIP analog to the VIP family receptor in the presence and absence of a compound that binds to the VIP family receptor; and c) comparing the binding affinity of the VIP analog to the VIP receptor in the presence of a compound that binds to the VIP family receptor to the binding affinity of the VIP analog to the VIP receptor in the absence of a compound that binds to the VIP family receptor. In some embodiments, the VIP family receptor is chosen from VIPR1, VIPR2, $VPAC_1$, $VPAC_2$ or $PAC_1$.

The invention also relates to the use of an analog with selectivity for VPAC1, PAC1, or VPAC2 in the preparation of a medicament for treating or preventing chronic obstructive pulmonary disease, pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small cell lung carcinoma, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood glucose levels, elevated blood pressure, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction due to administration of a medication that causes onset of or exacerbates symptoms of pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small cell lung carcinoma, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject in need thereof. In some embodiments, the invention relates to compositions comprising a secretin family analog with selectivity for VPAC1, PAC1, or VPAC2 for treatment or prevention of chronic obstructive pulmonary disease, pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small cell lung carcinoma, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject in need thereof.

The present invention also relates to a method of treating or preventing cancer in a subject in need thereof comprising administering a VIP analog to the subject, wherein said analog comprises an α-amino acid and at least one β-amino acid and wherein said analog is a VPAC1, VPAC2, or PAC1 receptor antagonist or agonist with increased selectivity for the VPAC1, VPAC2, or PAC1 receptor as compared to the other receptors. In some embodiments, the cancer is chosen from the following: non-small cell lung carcinoma, small cell lung carcinoma, colorectal carcinoma, breast carcinoma, gastric carcinoma, prostate carcinoma, liver carcinoma, ductal pancreatic carcinoma, bladder carcinoma, Non-Hodgkin's lymphoma, maningioma, leiomyoma, endometrial carcinoma, pheochromocytoma, paraganglioma. The present invention also relates to a method of treating or preventing inflammatory disease comprising administering a VIP analog to a subject in need thereof, wherein said analog comprises an α-amino acid and at least one β-amino acid and wherein said analog is a VPAC1, VPAC2, or PAC1 receptor antagonist or agonist with increased selectivity for the VPAC1, VPAC2, or PAC1 receptor as compared to the other receptors. In some embodiments the inflammatory disease is rheumatoid arthritis. In some embodiments, the VIP analog is administered at a therapeutically effective dose.

The present invention also relates to a method of treating or preventing cancer in a subject in need thereof comprising administering a VIP analog to the subject, wherein said analog comprises an α-amino acid and at least one β-amino acid and wherein said analog is a VPAC1 receptor antagonist with increased selectivity for the VPAC1 receptor. The present invention also relates to a method of treating or preventing inflammatory disease comprising administering a VIP analog to a subject in need thereof, wherein said analog comprises an α-amino acid and at least one β-amino acid and wherein said analog is a VPAC1 receptor antagonist with increased selectivity for the VPAC1 receptor. In some embodiments the inflammatory disease is rheumatoid arthritis. In some embodiments, the VIP analog is administered at a therapeutically effective dose.

The present invention also relates to a method of treating or preventing small cell lung carcinoma comprising administering a VIP analog to a subject in need thereof, wherein said analog comprises an α-amino acid and at least one β-amino acid and wherein said analog is a VPAC1, VPAC2, or PAC1 receptor antagonist or agonist with increased selectivity for at least one VPAC1, VPAC2, or PAC1 receptor. The present invention also relates to a method of treating or preventing inflammatory disease comprising administering a VIP analog to a subject in need thereof, wherein said analog comprises an α-amino acid and at least one β-amino acid and wherein said analog is a VPAC1, VPAC2, or PAC1 receptor antagonist or agonist with increased selectivity for at least one of the following: VPAC1, VPAC2, or PAC1 receptors. In some embodiments, the VIP analog is administered at a therapeutically effective dose.

The present invention also relates to a method of treating or preventing primary arterial hypertension (PAH) comprising administering a VIP analog to a subject in need thereof, wherein said analog comprises an α-amino acid and at least one β-amino acid and wherein said analog is a VPAC1, VPAC2, or PAC1 receptor antagonist or agonist with increased selectivity for at least one VPAC1, VPAC2, or PAC1 receptor. The present invention relates to a method of treating or preventing inflammatory disease comprising administering a VIP analog to a subject in need thereof, wherein said analog comprises an α-amino acid and at least one β-amino acid and wherein said analog is a VPAC1, VPAC2, or PAC1 receptor antagonist or agonist with increased selectivity for at least one of the following: VPAC1, VPAC2, or PAC1 receptors as compared to its selectivity for the other receptors. In some embodiments, the VIP analog is administered at a therapeutically effective dose.

The present invention also relates to a method of treating or preventing inflammatory disease comprising administering a VIP analog to a subject in need thereof, wherein said analog comprises an α-amino acid and at least one β-amino acid and wherein said analog is a VPAC1 receptor agonist with increased selectivity for the VPAC1 receptor. The present invention relates to a method of treating or preventing inflammatory disease comprising administering a VIP analog to a subject in need thereof, wherein said analog comprises an α-amino acid and at least one β-amino acid and wherein said analog is a VPAC1 receptor agonist with increased selectivity for the VPAC1 receptor. In some embodiments the inflammatory disease is rheumatoid arthritis. In some embodiments, the VIP analog is administered at a therapeutically effective dose.

The present invention also relates to a method of treating or preventing inflammatory disease comprising administering a VIP analog to a subject in need thereof, wherein said analog comprises an α-amino acid and at least one β-amino acid and wherein said analog is a VPAC2 receptor agonist with increased selectivity for the VPAC2 receptor. The present invention relates to a method of treating or preventing inflammatory disease comprising administering a VIP analog to a subject in need thereof, wherein said analog comprises an α-amino acid and at least one β-amino acid and wherein said analog is a VPAC2 receptor agonist with increased selectivity for the VPAC2 receptor. In some embodiments the inflammatory disease is rheumatoid arthritis. In some embodiments, the VIP analog is administered at a therapeutically effective dose.

The present invention also relates to a method of treating or preventing chronic obstructive pulmonary disease, pulmonary hypertension, primary arterial hypertension, pulmonary hypertension associated to post-ventricular septal defect, idiopathic pulmonary fibrosis, idiopathic pulmonary arterial hypertension comprising administering a VIP analog with selectivity for VPAC2 to a subject in need thereof, wherein said analog comprises an α-amino acid and at least one β-amino acid and wherein said analog is a VPAC2 receptor agonist with increased selectivity to VPAC2 receptor. In all methods of treatment or prevention, analogs of the present invention may be administered in therapeutically effective doses.

The present invention relates to a method of treating or preventing chronic obstructive pulmonary disease (COPD) comprising administering a VIP analog to a subject in need thereof, wherein said analog comprises an α-amino acid and at least one β-amino acid and wherein said analog is a VPAC1 receptor antagonist or agonist with increased selectivity for the VPAC1 receptor. The present invention relates to a method of treating or preventing COPD comprising administering a VIP analog to a subject in need thereof, wherein said analog comprises an α-amino acid and at least one β-amino acid and wherein said analog is a VPAC1 receptor antagonist or agonist with increased selectivity for the VPAC1 receptor. In some embodiments, the VIP analog is administered at a therapeutically effective dose via nebulizer or inhaler.

The invention also relates to a method of preventing or inhibiting activation of alveolar macrophages comprising administering a VIP analog to a subject, wherein said analog comprises an α-amino acid and at least one β-amino acid and wherein said analog is a VPAC1 receptor antagonist or agonist with increased selectivity for the VPAC1 receptor. In some embodiments, the VIP analog is administered at a therapeutically effective dose via nebulizer or inhaler.

The present invention relates to a method of treating or preventing chronic obstructive pulmonary disease (COPD) comprising administering a VIP analog to a subject in need thereof, wherein said analog comprises an α-amino acid and at least one β-amino acid and wherein said analog is a VPAC2 receptor agonist with increased selectivity for the VPAC2 receptor. The present invention relates to a method of treating or preventing COPD comprising administering a VIP analog to a subject in need thereof, wherein said analog comprises an α-amino acid and at least one β-amino acid and wherein said analog is a VPAC2 receptor agonist with increased selectivity for the VPAC2 receptor. In some embodiments, the VIP analog is administered at a therapeutically effective dose via nebulizer or inhaler. The invention relates to a method of preventing or inhibiting activation of alveolar macrophages comprising administering a VIP analog to a subject, wherein said analog comprises an α-amino acid and at least one β-amino acid and wherein said analog is a VPAC2 receptor agonist with increased selectivity for the VPAC2 receptor. In some embodiments, the VIP analog is administered at a therapeutically effective dose via nebulizer or inhaler.

The present invention also relates to methods of identifying a selective modulator of activity of a VIP family receptor molecule by measuring receptor activity comprising:
a) contacting a human VIP family receptor with a VIP analog, wherein said analog comprises an α-amino acid and at least one β-amino acid;

b) measuring the association of the VIP analog to the VIP receptor in the presence and absence of an unknown compound; and c) comparing the rate of association of the VIP analog to the human VIP receptor in the presence of an unknown compound to the rate of association of the VIP analog to the human VIP receptor in the absence of an unknown compound.

The present invention also relates to methods of identifying a selective modulator of activity of a VIP family receptor molecule by measuring receptor activity comprising:

a) contacting a first and a second VIP family receptor with a VIP analog in a known concentration, wherein said analog comprises an ca-amino acid and at least one β-amino acid;

b) measuring the rate association of the VIP analog to the first and second VIP receptors in the presence and absence of an unknown compound; and c) comparing the rate of association of the VIP analog to the first VIP receptor in the presence of an unknown compound to the rate of association of the VIP analog to the the second VIP receptor in the absence of an unknown compound.

The present invention also relates to methods of identifying a selective modulator of activity of a VIP family receptor molecule by measuring receptor activity comprising:

a) contacting a first and a second VIP family receptor with a VIP analog in a known concentration, wherein said analog comprises an α-amino acid and at least one β-amino acid;

b) measuring the binding affinity of the VIP analog to the first and second VIP receptors in the presence and absence of an unknown compound; and c) comparing the binding affinity of the VIP analog to the first VIP receptor in the presence of an unknown compound to the binding affinity of the VIP analog to the the second VIP receptor in the absence of an unknown compound. In some embodiments, the VIP family receptor is chosen from VIPR1, VIPR2, VPAC1, $VPAC_2$ or PAC1.

The present invention also relates to methods of inhibiting the immune response against a transplanted organ in a subject, wherein the subject is an organ donor recipient. in some embodiments, the subject is a mammal. In some embodiments, the subject is a human. In some embodiments, the subject is a human experiencing organ rejection after transplantation.

In another embodiment, the present invention also relates to a method for inhibiting the growth of a tumor cell, the method comprising: contacting the tumor cell with an effective amount of a secretin family analog, wherein the secretin family analog or functional fragment thereof comprises at least one α-amino acid. In some embodiments, the method comprises contacting the tumor cell with an effective amount of a combination of a chemotherapeutic agent and a secretin family analog. In some embodiments, the secretin analog is a VIP analog. Suitable chemotherapeutic agents include, but are not limited to, platinum coordination compounds, topoisomerase inhibitors, antibiotics, antimitotic alkaloids and difluoronucleosides. In some embodiments, the secretin analog is a VPAC1 antagonist with selectivity for VPAC1. In some embodiments, the tumor cell is a tumor cell derived from a breast cancer, a lung cancer, a colon cancer, a prostate cancer, or a pancreatic cancer.

In another embodiment, the present invention also relates to a method of inhibiting the growth of a tumor cell in a mammalian subject in need thereof, the method comprising: administering to the subject an effective amount of a secretin family analog or functional fragment thereof, wherein the secretin family analog or functional fragment thereof comprises at least one β-amino acid. In some embodiments, the method comprises administering to the subject an effective amount of a combination of a chemotherapeutic agent and a secretin family analog. In some embodiments, the secretin analog is a VIP analog. In some embodiments, the tumor cell is a tumor cell derived from a breast cancer, a lung cancer, a colon cancer, a prostate cancer, hepatic cancer (HCC) or a pancreatic cancer. Suitable chemotherapeutic agents include, but are not limited to, platinum coordination compounds, topoisomerase inhibitors, antibiotics, antimitotic alkaloids and difluoronucleosides.

The present invention also relates to a method of treating or preventing cancer cell growth in a subject in need thereof comprising the steps of: administering a VIP analog or functional fragment thereof the subject, wherein the VIP analog or functional fragment comprises at least one β-amino acid, wherein the VIP analog or functional fragment thereof is selective or has increased selectivity to $VPAC_1$; wherein the VIP analog is a $VPAC_1$ antagonist; and wherein the cancer cell is a bladder, breast, colon, liver, lung, prostate, stomach, thyroid or uterine cancer cell. The present invention relates to a method of treating or preventing cancer in a subject in need thereof comprising the steps of: administering a VIP analog or functional fragment thereof the subject, wherein the VIP analog or functional fragment comprises at least one β-amino acid, wherein the VIP analog or functional fragment thereof is selective or has increased selectivity to $VPAC_1$; wherein the VIP analog is a $VPAC_1$ antagonist; and wherein the cancer is a bladder, breast, colon, liver, lung, prostate, stomach, thyroid, hepatocellular, or uterine cancer. In some embodiments, the cancer has been diagnosed as being malignant. In some embodiments, the subject may have an increased risk or increased susceptibility to contracting a malignant cancer.

The present invention also relates to a method of treating or preventing cancer cell growth in a subject in need thereof comprising the steps of: administering a VIP analog or functional fragment thereof the subject, wherein the VIP analog or functional fragment comprises at least one β-amino acid, wherein the VIP analog or functional fragment thereof is selective or has increased selectivity to $VPAC_2$; wherein the VIP analog is a $VPAC_2$ antagonist; and wherein the cancer cell is a lung, breast, stomach cancer cell. In some embodiments the cancer cell is derived from a stomach leiomyoma.

The present invention also relates to a method of treating or preventing cancer in a subject in need thereof comprising the steps of: administering a VIP analog or functional fragment thereof the subject, wherein the VIP analog or functional fragment comprises at least one β-amino acid, wherein the VIP analog or functional fragment thereof is selective or has increased selectivity to $VPAC_2$; wherein the VIP analog is a $VPAC_2$ antagonist; and wherein the cancer a lung, breast, stomach, or heptocellular cancer. In some embodiments, the cancer has been diagnosed as being malignant. In some embodiments, the subject may have an increased risk or increased susceptibility to contracting a malignant cancer.

The present invention also relates to a method of treating or preventing airway constriction comprising administering a VIP analog or functional fragment thereof to a subject in need thereof, wherein said analog comprises an α-amino acid and at least one β-amino acid and wherein said analog is a VPAC2 receptor agonist. In some embodiments, the VIP analog or functional fragment thereof has increased selectivity to VPAC2 receptor. In all methods of treatment or prevention, analogs of the present invention may be administered in therapeutically effective doses.

The present invention also relates to a method of treating or preventing asthma, comprising administering a VIP analog or functional fragment thereof to a subject in need thereof, wherein said analog comprises an α-amino acid and at least one β-amino acid and wherein said analog is a VPAC2 receptor agonist. In some embodiments, the VIP analog or functional fragment thereof has increased selectivity to VPAC2 receptor. In all methods of treatment or prevention, analogs of the present invention may be administered in therapeutically effective doses. In some embodiments, the VIP analog or functional fragment thereof may be administered via an inhaler or nebulizer.

The present invention also relates to a method of treating or preventing cancer cell growth in a subject in need thereof comprising the steps of: administering a VIP analog or functional fragment thereof the subject, wherein the VIP analog or functional fragment comprises at least one β-amino acid, wherein the VIP analog or functional fragment thereof is selective or has increased selectivity to $PAC_1$; wherein the VIP analog is a $PAC_1$ antagonist; and wherein the cancer cell is a nerve cell, adrenal cell, pituitary cell, or breast cell. The present invention also relates to a method of treating or preventing cancer in a subject in need thereof comprising the steps of: administering a VIP analog or functional fragment thereof the subject, wherein the VIP analog or functional fragment comprises at least one β-amino acid, wherein the VIP analog or functional fragment thereof is selective or has increased selectivity to PAC1; wherein the VIP analog is a $PAC_1$ antagonist; and wherein the cancer is a glioblastoma, neuroblastoma, adrenal, pituitary, catecholamine-secreting tumors, pheochromocytomas, paragangliomas, endometrial cancers, or breast cancer. In some embodiments, the cancer has been diagnosed as being malignant. In some embodiments, the subject may have an increased risk or increased susceptibility to contracting a malignant cancer.

The invention also relates to methods of treating or preventing the aforementioned diseases using the analogs of the present invention. Any analog described in the present invention may or may not have preferred selectivity of one of its receptors versus another. The invention relates to analogs based upon the polypeptide sequences identified in Tables 1, 2, 3, and 4. All modified and unmodified variants of the sequences listed in Table 4 are contemplated as being part of the invention. For instance, the sequence of Biotin-Bombesin is listed in Table 4 as Biotin-EQRLGNQ-WAVGHLM-NH$_2$ (SEQ ID NO:67). Not only do analogs of the claimed invention include biotinylated sequence above with an amidated methionine, but the analogs of the present invention also relate to the unmodified or modified polypeptide backbone EQRLGNQWAVGHLM as well as functional fragments thereof. In some embodiments the polypeptide analog is derived from one of the following amino acid sequences of Table 4:

TABLE 4

Targets from which the Analogs are derived

| | |
|---|---|
| 1. Galanin | 2. neurokinin A |
| 3. neurokinin B | 4. RGD |
| 5. Osteogenic growth peptide | 6. Parathyroid hormone |
| 7. Kallidin | 8. T cell receptor peptide |
| 9. PDGF | 10. Amylin |
| 11. Calcitonin | 12. GHRH |
| 13. Thymopoietin | 14. cecropin |
| 15. TRH | 16. EPO |
| 17. FGF | 18. Stem Cell Factor |
| 19. Gp120 | 20. Gp160 |
| 21. CD4 | 22. IGF |
| 23. IGF receptor | 24. Insulin |
| 25. GMCSF | 26. GCSF |
| 27. MCSF | 28. Kentsin |
| 29. LAP | 30. Tuftsin |
| 31. Prolactin | 32. Angiotensin II |
| 33. Angiotensin II receptor | 34. Dynorphin |
| 35. Calcitonin | 36. Cholecystokinin |
| 37. Pepstatin | 38. Bestatin |
| | 39. Leupeptin |
| 40. Luteinizing hormone | 41. Neurotensin |
| 42. Motilin | 43. TGF-alpha |
| 44. TGF-beta | 45. BMP-1 |
| 46. BMP-2 | 47. BMP-3 |
| 48. BMP-4 | 49. BMP-5 |
| 50. BMP-7 | 51. BMP-8 |
| 52. BMP-9 | 53. Bombesin |
| 54. Enterostatin | 55. Glucagon |
| 56. GLP-1 | 57. Beta-Endorphin |
| 58. ACTH | 59. Alpha-MSH |
| 60. γ-MSH | 61. adrenal peptide E |
| 62. alpha casein fragment | 63. beta casomorphin |
| 64. dermorphin | 65. kyotorphin |
| 66. metophamide | 67. neuropeptide FF (NPFF) |
| 68. melanocyte inhibiting factor | 69. vasotocin |
| 70. Protein kinase C | 71. Amyloid |
| 72. Amyloid fibrin | 73. Calpain |
| 74. Charybdotoxin | 75. Apamin |
| 76. Phospholipase A2 | 77. Phospholipase A2 receptor |
| 78. ENaC-alpha | 79. ENaC-beta |
| 80. ENaC-gamma | 81. IgG subunit |

TABLE 4-continued

Targets from which the Analogs are derived

| | |
|---|---|
| 82. Endotoxin | 83. ADNF |
| 84. Adrenomedullin | 85. Apelin |
| 86. Ghrelin | 87. Mastoparan (MCD peptides) |
| 88. Melanin concentrating hormone | 89. Nociceptin |
| 90. Nocistatin | 91. Orexin |
| 92. Receptor activity modulating protein, | 93. Urotensin |
| 94. Glycoprotein IIb/IIIa inhibitors | 95. c7E3 Fab |
| 96. Apo-lipoprotein A-I | 97. IL-1 |
| 98. IL-2 | 99. IL-3 |
| 100. IL-4 | 101. IL-5 |
| 102. IL-6 | 103. IL-7 |
| 104. IL-8 | 105. IL-9 |
| 106. IL-10 | 107. IL-12 |
| 108. IL-15 | 109. IL-18 |
| 110. IL-22 | 111. IL-23 |
| 112. IL-24 | 113. IL-26 |
| 114. IL-27 | 115. IL-28 |
| 116. brain-derived neurotrophic factor (BDNF) | 117. nerve growth factor |
| 118. neurotrophin 3 | 119. Corticotropin releasing factor |
| 120. MHC I bind protei | 121. P-selectin |
| 122. LFA-1 | 123. LFA-3 |
| 124. EPGF | 125. EPGF receptor |
| 126. Oxytocin | 127. Vasopressin |
| 128. Defensin, alpha 1 | 129. Neutrophil defensin 3 |
| 130. Neutrophil defensin 4 | 131. Defensin-5 |
| 132. Defesin-6 | 133. Beta-defensin 1 |
| 134. Beta-defensin-3 | 135. Beta defensin 103 |
| 136. Beta-defensin 107 | 137. Beta-defensin 110 |
| 138. Beta-defensin 136 | 139. RK-1 (MPCSCKKYCDPWEVIDGSCGLFNSKYICCREK) |
| 140. dermaseptin S4 | 141. magainin 1 |
| 142. magainin 2 | 143. magainin A |
| 144. magainin B | 145. magainin G |
| 146. MSI-78 | 147. MSI-99 |
| 148. MSI-130 | 149. MSI-511 |
| 150. Myp30 | 151. Pexiganan |
| 152. Laminin | 153. YIGSR |
| 154. Gastrin | 155. Gastrin releasing peptide |
| 156. GnRH | 157. Secretin |
| 158. Bradykinin | 159. Substance P |
| 160. RANTES | 161. MCP-1 |
| 162. MIP-1alpha | 163. MIP-1beta |
| 164. PDWHF | 165. CRF |
| 166. Endothelin | 167. Integrin |
| 168. Neuropeptide Y | 169. LHRH |
| 170. Enkephilin | 171. alpha-neo-endorphin, porcine |
| 172. beta-neoendorphin | 173. Ac-beta-endorphin, camel, bovine, ovine |
| 174. Ac-beta-endorphin 1-27, camel, bovine, ovine | 175. Ac-beta-endorphin, human |
| 176. Ac-beta-endorphin 1-26, human | 177. Ac-beta-endorphin 1-27, human |
| 178. Ac-gamma-endorphin (Ac-beta-lipotropin 61-77) | 179. acetyl-alpha-endorphin |
| 180. alpha-endorphin (beta-lipotropin 61-76) | 181. alpha-neo-endorphin analog |
| 182. alpha-neo-endorphin 1-7 | 183. {Arg$^8$}-alpha-neoendorphin 1-8 |
| 184. beta-endorphin (beta-lipotropin 61-91), camel, bovine, ovine | 185. beta-endorphin 1-27, camel, bovine, ovine |
| 186. beta-endorphin, equine | 187. beta-endorphin (beta-lipotropin 61-91), human |
| 188. beta-endorphin (1-5) + (16-31), human | 189. beta-endorphin 1-26, human |
| 190. beta-endorphin 1-27, human | 191. beta-endorphin 6-31, human |
| 192. beta-endorphin 18-31, human | 193. beta-endorphin, porcine |
| 194. beta-endorphin, rat | 195. beta-lipotropin 1-10, porcine |
| 196. beta-lipotropin 60-65 | 197. beta-lipotropin 61-64 |
| 198. beta-lipotropin 61-69 | 199. beta-lipotropin 88-91 |
| 200. biotinyl-beta-endorphin (biotinyl-bets-lipotropin 61-91) | 201. biocytin-beta-endorphin, human |
| 202. gamma-endorphin (beta-lipotropin 61-77) | 203. {DAla$^2$}-alpha-neo-endorphin 1-2, amide |
| 204. {DAla$^2$}-beta-lipotropin 61-69 | 205. {DAla$^2$}-gamma-endorphin |
| 206. {Des-Tyr$^1$}-beta-endorphin, human | 207. {Des-Tyr$^1$}-gamma-endorphin (beta-lipotropin 62-77) |
| 208. {Leu$^5$}-beta-endorphin, camel, bovine, ovine | 209. {Met$^5$, Lys$^6$}-alpha-neo-endorphin 1-6 |
| 210. {Met$^5$, Lys$^{6,7}$}-alpha-neo-endorphin 1-7 | 211. {Met$^5$, Lys$^6$, Arg$^7$}-alpha-neo-endorphin 1-7 |
| 212. endothelin-1 (ET-1) | 213. endothelin-1{Biotin-Lys$^9$} |

TABLE 4-continued

| Targets from which the Analogs are derived | |
|---|---|
| 214. endothelin-1 (1-15), human | 215. endothelin-1 (1-15), amide, human |
| 216. Ac-endothelin-1 (16-21), human | 217. Ac-{DTrp$^{16}$}-endothelin-1 (16-21), human |
| 218. {Ala$^{3,11}$}-endothelin-1 | 219. {Dpr1, Asp$^{15}$}-endothelin-1 |
| 220. {Ala$^2$}-endothelin-3, human | 221. {Ala$^{18}$}-endothelin-1, human |
| 222. {Asn$^{18}$}-endothelin-1, human | 223 |
| 224. {Res-701-1}-endothelin B receptor antagonist | 225. Suc-{Glu$^9$, Ala$^{11,15}$}-endothelin-1 (8-21), IRL-1620 |
| 226. endothelin-C-terminal hexapeptide | 227. {D-Val$^{22}$}-big endothelin-1 (16-38), human |
| 228. endothelin-2 (ET-2), human, canine | 229. endothelin-3 (ET-3), human, rat, porcine, rabbit |
| 230. biotinyl-endothelin-3 (biotinyl-ET-3) | 231. prepro-endothelin-1 (94-109), porcine |
| 232. BQ-518 | 233. BQ-610 |
| 234. BQ-788 | 235. endothelium-dependent relaxation antagonist |
| 236. FR139317 | 237. IRL-1038 |
| 238. JKC-301 | 239. JKC-302 |
| 240. PD-145065 | 241. PD-142893 |
| 242. sarafotoxin S6a (atractaspis engaddensis) | 243. sarafotoxin S6b (atractaspis engaddensis) |
| 244. sarafotoxin S6c (atractaspis engaddensis) | 245. {Lys$^4$}-sarafotoxin S6c |
| 246. sarafotoxin S6d | 247. big endothelin-1, human |
| 248. biotinyl-big endothelin-1, human | 249. big endothelin-1 (1-39), porcine |
| 250. big endothelin-3 (22-41), amide, human | 251. big endothelin-1 (22-39), rat |
| 252. big endothelin-1 (1-39), bovine | 253. big endothelin-1 (22-39), bovine |
| 254. big endothelin-1 (19-38), human | 255. big endothelin-1 (22-38), human |
| 256. big endothelin-2, human | 257. big endothelin-2 (22-37), human |
| 258. big endothelin-3, human | 259. big endothelin-1, porcine |
| 260. big endothelin-1 (22-39) (prepro-endothelin-1 (74-91)) | 261. big endothelin-1, rat |
| 262. big endothelin-2 (1-38), human | 263. big endothelin-2 (22-38), human |
| 264. big endothelin-3, rat | 265. biotinyl-big endothelin-1, human |
| 266. {Tyr$^{123}$}-prepro-endothelin (110-130), amide, human | 267. {BQ-123} |
| 268. {BE18257B} | 269. {BE-18257A}/{W-7338A} |
| 270. {BQ-485} | 271. FR139317 |
| 272. PD-151242 and TTA-386 | 273. {BQ-3020} {RES-701-3} and {IRL-1720} |
| 274. adrenorphin | 275. free acid amidorphin (proenkephalin A (104-129)-NII2) |
| 276. bovine BAM-12P | 277. bovine adrenal medulla enkephalin |
| 278. {D-Ala$^2$, D-Leu$^5$}-enkephalin | 279. {D-Ala$^2$, D-Met$^5$}-enkephalin |
| 280. {DAla$^2$}-Leu-enkephalin | 281. amide {DAla$^2$, Leu$^5$, Arg$^6$}-enkephalin |
| 282. {Des-Tyr$^1$,DPen$^{2,5}$}-enkephalin | 283. {Des-Tyr$^1$,DPen$^2$,Pen$^5$}-enkephalin |
| 284. {Des-Tyr$^1$}-Leu-enkephalin | 285. {D-Pen$^{2,5}$}-enkephalin |
| 286. {DPen$^2$, Pen$^5$}-enkephalin | 287. enkephalinase substrate |
| 288. {D-Pen$^2$, pCI-Phe$^4$, D-Pen$^5$}-enkephalin | 289. Leu-enkephalin |
| 290. amide biotinyl-Leu-enkephalin | 291. {D-Ser$^2$}-Leu-enkephalin-Thr (delta-receptor peptide) (DSLET) |
| 292. {D-Thr$^2$}-Leu-enkephalin-Thr (DTLET) | 293. {Lys$^6$}-Leu-enkephalin |
| 294. {Met$^5$,Arg$^6$}-enkephalin | 295. {Met$^5$,Arg$^6$-enkephalin-Arg {Met$^5$,Arg$^6$,Phe$^7$}-enkephalin |
| 296. amide Met-enkephalin biotinyl-Met-enkephalin | 297. {D-Ala$^2$}-Met-enkephalin |
| 298. amide Met-enkephalin-Arg-Phe Met-enkephalin | 299. amide {Ala$^2$}-Met-enkephalin |
| 300. amide {DMet$^2$,Pro$^5$}-enkephalin | 301. amide {DTrp$^2$}-Met-enkephalin, amide, metorphinamide (adrenorphin) peptide B |
| 302. bovine 3200-Dalton adrenal peptide E | 303. bovine peptide F |
| 304. bovine preproenkephalin B 186-204 | 305. human spinorphin |
| 306. bovine and thiorphan (D,L,3-mercapto-2-benzylpropanoyl-glycine) | 307. platelet factor-4 (58-70) |
| 308. human echistatin (Echis carinatus) E | 309. human echistatin (Echis carinatus) P |
| 310. L selectin conserved region fibronectin | 311. fibrinopeptide A |
| 312. human {Tyr$^0$}-fibrinopeptide A | 313. human fibrinopeptide B |
| 314. human {Glu$^1$}-fibrinopeptide B | 315. human {Tyr$^{15}$}-fibrinopeptide B |
| 316. human fibrinogen beta-chain fragment of 24-42 fibrinogen binding inhibitor peptide | 317. fibrinolysis inhibiting factor FN--C/H-1 (fibronectin heparin-binding fragment) |
| 318. FN--C/H--V (fibronectin heparin-binding fragment) | 319. heparin-binding peptide laminin penta peptide, amide Leu-Asp-Val-NH$_2$ (LDV-NH$_2$), |
| 320. human, bovine, rat, | 321. chicken necrofibrin |

TABLE 4-continued

| Targets from which the Analogs are derived | |
|---|---|
| 322. human necrofibrin, rat | 323. platelet membrane glycoprotein IIB peptide 296-306 |
| 324. human galanin 1-19 | 325. human preprogalanin 1-30 |
| 326. human preprogalanin 65-88 | 327. human preprogalanin 89-123 |
| 328. human galanin | 329. porcine galanin 1-16 |
| 330. porcine, rat galanin | 331. rat biotinyl-galanin |
| 332. rat preprogalanin 28-67 | 333. rat galanin 1-13-bradykinin 2-9 |
| 334. amide M40 | 335. galanin 1-13-Pro-Pro-(Ala-Leu) 2-Ala-amide C7 |
| 336. galanin 1-13-spantide-amide GMAP 1-41 | 337. amide GMAP 16-41 |
| 338. amide GMAP 25-41 | 339. amide galantide and entero-kassinin |
| 340. gastrin | 341. chicken gastric inhibitory peptide (GIP) |
| 342. human gastrin I | 343. human biotinyl-gastrin I |
| 344. human big gastrin-1 | 345. human gastrin releasing peptide |
| 346. human gastrin releasing peptide 1-16 | 347. human gastric inhibitory polypeptide (GIP) |
| 348. porcine gastrin releasing peptide | 349. porcine biotinyl-gastrin releasing peptide |
| 350. porcine gastrin releasing peptide 14-27 | 351. porcine, human little gastrin |
| 352. rat pentagastrin gastric inhibitory peptide 1-30 | 353. porcine gastric inhibitory peptide 1-30, amide |
| 354. porcine {Tyr$^0$-gastric inhibitory peptide 23-42 | 355. human and gastric inhibitory peptide, rat |
| 356. {Des-His-Glu$^9$}-glucagon | 357. exendin-4 |
| 358. glucagon | 359. human biotinyl-glucagon |
| 360. human glucagon 19-29 | 361. human glucagon 22-29 |
| 362. human {Des-His$^1$-Glu$^9$}-glucagon | 363. amide glucagon-like peptide 1 |
| 364. amide glucagon-like peptide 1 | 365. human glucagon-like peptide 1 (7-36) glucagon-like peptide 2 |
| 366. rat biotinyl-glucagon-like peptide-1 (7-36) | 367. (biofinyl-preproglucagon 78-107, amide) |
| 368. glucagon-like peptide 2 | 369. human intervening peptide-2 oxyntomodulin/glucagon 37 |
| 370. valosin (peptide VQY), porcine | 371. Gn-RH associated peptide 25-53 |
| 372. human Gn-RH associated peptide 1-24 | 373. human Gn-RH associated peptide 1-13 |
| 374. human Gn-RH associated peptide 1-13 | 375. rat gonadotropin releasing peptide |
| 376. human {Tyr$^0$}-GAP ({Tyr$^0$}-Gn-RH Precursor Peptide 14-69) | 377. proopiomelanocortin (POMC) precursor 27-52, porcine |
| 378. TGF-d | 379. TGF beta |
| 380. TF alpha | 381. TGF 34-43 |
| 382. EGF, any mammalian version | 383. human acidic fibroblast growth factor basic |
| 384. fibroblast growth factor | 385. basic fibroblast growth factor 13-18 |
| 386. basic fibroblast growth factor 120-125 | 387. brain derived acidic fibroblast growth factor 1-11 |
| 388. brain derived basic fibroblast growth factor 1-24 | 389. brain derived acidic fibroblast growth factor 102-111 |
| 390. {Cys(Acm$^{20,31}$)}-epidermal growth factor 20-31 | 391. epidermal growth factor receptor peptide 985-996 |
| 392. insulin-like growth factor (IGF)-I | 393. chicken IGF-I |
| 394. rat IGF-I | 395. human Des (1-3) IGF-I |
| 396. human R3 IGF-I | 397. human R3 IGF-I |
| 398. human long R3 IGF-I | 399. human adjuvant peptide analog |
| 400. anorexigenic peptide Des (1-6) | 401. IGF-II |
| 402. human R6 IGF-II | 403. human IGF-I analogue IGF 1 (24-41) |
| 404. IGF 1 (57-70) | 405. IGF I (30-41) |
| 406. IGF II IGF II (33-40) | 407. {Tyr$^0$}-IGF II (33-40) |
| 408. liver cell growth factor midkine | 409. midkine 60-121 |
| 410. alpha-TGF 34-43 | 411. human alpha-TGF 34-43 |
| 412. human alpha-TGF 34-43 | 413. rat nerve growth factor (NGF) |
| 414. mouse platelet-derived growth factor | 415. platelet-derived growth factor |
| 416. transforming growth factor-α | 417. human and rat transforming growth factor-I |
| 418. growth hormone (hGH) | 419. human growth hormone 1-43 |
| 420. human growth hormone 6-13 | 421. human growth hormone releasing factor |
| 422. murine growth hormone releasing factor | 423. bovine growth hormone releasing factor |
| 424. porcine growth hormone releasing factor 1-29, amide | 425. rat growth hormone pro-releasing factor |
| 426. human biotinyl-growth hormone releasing factor | 427. human growth hormone releasing factor 1-29, amide |
| 428. human {D-Ala$^2$}-growth hormone releasing factor 1-29, amide | 429. human {N-Ac-Tyr$^1$, D-Arg$^2$}-GRF 1-29, amide |
| 430. {His$^1$, Nle$^{27}$}-growth hormone releasing factor 1-32, amide | 431. growth hormone releasing factor 1-37 |
| 432. human growth hormone releasing factor 140 | 433. human growth hormone releasing factor 1-40, amide |

TABLE 4-continued

Targets from which the Analogs are derived 434. human growth hormone releasing factor 30-44, amide
435. human growth hormone releasing factor
436. mouse growth hormone releasing factor
437. ovine growth hormone releasing factor
438. rat biotinyl-growth hormone releasing factor
439. rat GHRP-6 ({His$^1$, Lys$^6$}-GHRP)
440. hexarelin (growth hormone releasing hexapeptide)
441. {D-Lys$^3$}-GHRP-6
442. {Arg$^8$}-GTP-binding protein fragment
443. Gs alpha GTP-binding protein fragment
445. G beta GTP-binding protein fragment
446. GAlpha GTP-binding protein fragment
447. Go Alpha GTP-binding protein fragment
448. Gs Alpha and GTP-binding protein fragment
449. G Alpha i2
450. guanylin
451. human guanylin
452. rat guanylin
453. human uroguanylin
454. inhibin
455. bovine inhibin
456. alpha-subunit 1-32
457. human {Tyr$^0$}-inhibin, alpha-subunit 1-32
458. human seminal plasma inhibin-like peptide
459. human {Tyr$^0$}-seminal plasma inhibin-like peptide
460. human inhibin
461. alpha-subunit 1-32
462. porcine and {Tyr$^0$}-inhibin, alpha-subunit 1-32, porcine
463. human insulin
464. porcine IGF-I
465. human insulin-like growth factor II (69-84)
466. pro-insulin-like growth factor 11 (68-102)
467. human pro-insulin-like growth factor II (105-128)
468. human {Asp$^{B28}$}-insulin
469. human {Lys$^{B28}$}-insulin
470. human {Leu$^{B28}$}-insulin
471. human {Val$^{B28}$}-insulin
472. human {Ala$^{B28}$}-insulin
473. human {Asp$^{B28}$, Pro$^{B29}$}-insulin
474. human {Lys$^{B28}$, Pro$^{B29}$}-insulin
475. human {Leu$^{B28}$ Pro$^{B29}$}-insulin
476. human {Val$^{B28}$, Pro$^{B29}$}-insulin
477. human {Ala$^{B28}$, Pro$^{B29}$}-insulin
478. human {Gly$^{A21}$}-insulin
479. human {Gly$^{A21}$ Gln$^{B30}$}-insulin
480. human {Ala$^{A21}$}-insulin
481. human {Ala$^{A21}$ Gln$^{B30}$} insulin
482. human {Gln$^{B30}$}-insulin
483. human {Gln$^{B30}$}-insulin
484. human {Gly$^{A21}$ Glu$^{B30}$}-insulin
485. human {Gly$^{A21}$ Gln$^{B3}$ Glu$^{B30}$}-insulin
486. human {Gln$^{B3}$ Glu$^{B30}$}-insulin
487. human B22-B30 insulin
488. human B23-B30 insulin
489. human B25-B30 insulin
490. human B26-B30 insulin
491. human B27-B30 insulin
492. human B29-B30 insulin
493. A chain of human insulin
494. B chain of human insulin
495. interleukin-1 beta 165-181, rat
496. rat IL-8
497. laminin alpha1 (I)-CB3 435-438, rat
498. laminin binding inhibitor
499. leptin 93-105
500. human leptin 22-56, rat
501. Tyr-leptin 26-39, human
502. leptin 116-130, amide, mouse
503. leucomyosuppressin (LMS)
504. leucopyrokinin (LPK)
505. leucokinin I
506. leucokinin II
507. leucokinin III
508. leucokinin IV
509. leucokinin VI
510. leucokinin VII
511. leucokinin VIII
512. antide Gn-RH II
513. chicken luteinizing hormone-releasing hormone (LH-RH)
514. (GnRH) biotinyl-LH-RH
515. cetrorelix (D-20761)
516. {D-Ala$^6$}-LH-RH
517. {Gln$^8$}-LH-RH (Chicken LH-RH)
518. {DLeu$^6$, Val$^7$} LH-RH 1-9
519. ethyl amide {D-Lys$^6$}-LH-RH
520. {D-Phe$^2$, Pro$^3$, D-Phe$^6$}-LH-RH
521. {DPhe$^2$, DAla$^6$} LH-RH
522. {Des-Gly$^{10}$}-LH-RH, ethyl amide
523. {D-Ala$^6$, Des-Gly$^{10}$}-LH-RH, ethyl amide
524. {DTrp$^6$}-LH-RH, ethyl amide
525. {D-Trp$^6$, Des-Gly$^{10}$}-LH-RH, ethyl amide (Deslorelin)
526. {DSer(But)$_6$, Des-Gly$^{10}$}-LH-RH, ethyl amide ethyl amide leuprolide
527. LH-RH 4-10
528. LH-RH 7-10 LH-RH
529. free acid LH-RH
530. lanprey LH-RH
531. salmon {Lys$^8$}-LH-RH
532. {Trp$^7$,Leu$^8$} LH-RH, free acid
533. {(t-Bu)DSer$^6$, (Aza)Gly$^{10}$}-LH-RH free acid
534. {(t-Bu)DSer$^6$, (Aza)Gly$^{10}$}-LH-RH
535. mastoparan
536. mas7
537. mas8
538. mas17
539. mastoparan X
540. mast cell degranulating peptide HR-1
541. mast cell degranulating peptide HR-2
542. {Ac-Cys$^4$,DPhe$^7$, Cys$^{10}$} alpha-MSH 4-13
543. amide alpha-melanocyte stimulating hormone alpha-MSH
544. free acid beta-MSH, porcine
545. biotinyl-alpha-melanocyte stimulating hormone
546. biotinyl-{Nle$^4$, D-Phe$^7$}
547. alpha-melanocyte stimulating hormone
548. {Des-Acetyl}-alpha-MSH {DPhe$^7$}-alpha-MSH, amide
549. gamma-1-MSH, amide
550. {Lys$^0$}-gamma-1-MSH, amide
551. MSH release inhibiting factor, amide
552. {Nle$^4$}-alpha-MSH, amide
553. {Nle$^4$, D-Phe$^7$}-alpha-MSH N-Acetyl
554. {Nle$^4$,DPhe$^7$} alpha-MSH 4-10, amide TABLE 4-continued

| Targets from which the Analogs are derived | |
|---|---|
| 555. beta-MSH, human | 556. gamma-MSH |
| 557. morphiceptin (beta-casomorphin 14 amide) | 558. {D-Pro$^4$}-morphiceptin |
| 559. {N-MePhe$^3$,D-Pro$^4$}-morphiceptin | 560. motilin |
| 561. canine motilin | 562. porcine biotinyl-motilin |
| 563. porcine {Leu$^{13}$}-motilin | 564. Ac-Asp-Glu achatina cardio-excitatory peptide-1 (ACEP-1) (Achatina fulica) |
| 565. adipokinetic hormone (AKH) (Locust) | 566. adipokinetic hormone (Heliothis zea and Manduca sexta) |
| 567. alytesin Tabanus atratus | 568. adipokinetic hormone (Taa-AKH) |
| 569. adipokinetic hormone II (Locusta migratoria) | 570. adipokinetic hormone II (Schistocera gregaria) |
| 571. adipokinetic hormone III (AKH-3) | 572. adipokinetic hormone G (AKH-G) (Gryllus bimaculatus) |
| 573. allatotropin (AT) (Manduca sexta) | 574. allatotropin 6-13 (Manduca sexta) |
| 575. APGW amide (Lymnaea stagnalis) | 576. buccalin |
| 577. {Des-Ser$^1$}-cerebellin corazonin (American Cockroach Periplaneta americana) | 578. crustacean cardioactive peptide (CCAP) |
| 579. crustacean erythrophore DF2 (Procambarus clarkii) | 580. diazepam-binding inhibitor fragment |
| 581. human diazepam binding inhibitor fragment (ODN) | 582. eledoisin related peptide FMRF amide (molluscan cardioexcitatory neuropeptide) |
| 583. cerebellin | 584. human granuliberin R head activator neuropeptide {His$^7$}-corazonin |
| 585. stick insect hypertrehalosaemic factor II | 586. Tabanus atratus hypotrehalosemic hormone (Taa-HoTH) |
| 587. rat NGE (prepro-MCH 110-128) neuropeptide | 588. methiodide piperidine-4-sulphonic acid joining peptide of proopiomelanocortin |
| 589. (POMC) | 590. bovine joining peptide |
| 591. rat KSAYMRF amide (P. redivivus) | 592. kassinin kinetensin levitide |
| 593. litorin LUQ 81-91 (Aplysia californica) | 594. LUQ 83-91 (Aplysia californica) |
| 595. myoactive peptide I (Periplanetin CC-1) | 596. myoactive peptide II (Periplanetin CC-2) |
| 597. myomodulin neuron specific peptide | 598. neuron specific enolase 404-443 |
| 599. rat neuropeptide FF neuropeptide K | 600. porcine NEI (prepro-MCH 131-143) neuropeptide |
| 601. rat NGE (prepro-MCH 110-128) neuropeptide | 602. rat NFI (Procambarus clarkii) |
| 603. PBAN-1 (Bombyx mori) | 604. Hez-PBAN (Heliothis zea) |
| 605. SCPB (cardioactive peptide from aplysia) | 606. secretoneurin, rat uperolein |
| 607. urechistachykinin I | 608. urechistachykinin II |
| 609. xenopsin-related peptide I | 610. xenopsin-related peptide II |
| 611. pedal peptide (Pep) | 612. aplysia peptide F1 |
| 613. lobster, phyllomedusin | 614. polistes mastoparan |
| 615. proctolin | 616. ranatensin Ro I (Lubber Grasshopper, Romalea microptera) |
| 617. Ro II (Lubber Grasshopper, Romalea microptera) | 618. SALMF amide 1 (S1) |
| 619. SALMF amide 2 (S2) | 620. SCPA |
| 621. {Leu$^{31}$, Pro$^{34}$} neuropeptide Y, human neuropeptide F (Moniezia expansa) | 622. B1BP3226 NPY antagonist Bis (31/31') {{Cys$^{31}$, Trp$^{32}$, Nva$^{34}$} NPY 31-36} neuropeptide Y, human |
| 623. rat neuropeptide Y 1-24 amide | 624. human biotinyl-neuropeptide Y |
| 625. {D-Tyr$^{27,36}$, D-Thr$^{32}$}-NPY 27-36 | 626. Des 10-17 (cyclo 7-21) {Cys$^{7,21}$, Pro$^{34}$}-NPY C2-NPY |
| 627. {Leu$^{31}$, Pro$^{34}$} neuropeptide Y | 628. human neuropeptide Y |
| 629. porcine prepro NPY 68-97 | 630. human N-acetyl-{Leu$^{28}$, Leu$^{31}$} NPY 24-36 neuropeptide Y |
| 631. porcine {D-Trp$^{32}$}-neuropeptide Y | 632. porcine {D-Trp$^{32}$} NPY 1-36 |
| 633. human {Leu$^{17}$,DTrp$^{32}$} neuropeptide Y | 634. human {Leu$^{31}$, Pro$^{34}$}-NPY |
| 635. porcine NPY 2-36 | 636. porcine NPY 3-36 |
| 637. human NPY 3-36 | 638. porcine NPY 13-36 |
| 639. human NPY 13-36 | 640. porcine NPY 16-36 |
| 641. porcine NPY 18-36 | 642. porcine NPY 20-36 |
| 643. FY 22-36 NPY 26-36 | 644. Pro$^{34}$}-NPY 1-36 |
| 645. human {Pro$^{34}$}-neuropeptide Y | 646. porcine PYX-1 |
| 647. PYX-2 | 648. T4-{NPY(33-36)}4 |
| 649. Tyr(OMe)$^{21}$}-neuropeptide Y, human | 650. glial derived neurotropic factor (GDNF) |
| 651. brain derived neurotropic factor (BDNF) | 652. ciliary neurotropic factor (CNTF) |
| 653. orexin A | 654. human orexin B |
| 655. rat orexin B | 656. mouse orexin B |
| 657. alpha-casein fragment 90-95 | 658. BAM-18P |
| 659. casomokinin L | 660. casoxin D |

TABLE 4-continued

Targets from which the Analogs are derived 661. crystalline DALDA
662. dermenkephalin (deltorphin) (Phylomedusa sauvagei)
663. {D-Ala$^2$}-deltorphin I
664. {D-Ala$^2$}-deltorphin II
665. endomorphin-1
666. endomorphin-2
667. kyotorphin
668. {DArg$^2$}-kyotorphin
669. morphine tolerance peptide
670. morphine modulating peptide
671. C-terminal fragment morphine modulating neuropeptide (A-18-F--NH2)
672. nociceptin {orphanin FQ} (ORL1 agonist)
673. TIPP
674. Tyr-MIF-1
675. Tyr-W-MIF-1
676. valorphin LW-hemorphin-6
677. human Leu-valorphin-Arg
678. Z-Pro-D-Leu
679. {Asu$^6$}-oxytocin
680. oxytocin
681. biotinyl-oxytocin
682. {Thr$^4$, Gly$^7$}-oxytocin
683. tocinoic acid ({Ile$^3$}-pressinoic acid)
684. PACAP 1-27, human, ovine, rat
685. PACAP (1-27)-Gly-Lys-Arg-NH$_2$
686. human {Des-Gln$^{16}$}-PACAP 6-27
687. human, ovine, rat PACAP38
688. frog PACAP27-NH$_2$
689. human, ovine, rat biotinyl-PACAP27-NH2
690. human, ovine, rat PACAP 6-27
691. human, ovine, rat PACAP38
692. human, ovine, rat biotinyl-PACAP38
693. human, ovine, rat PACAP 6-38
694. human, ovine, rat PACAP27-NH$_2$
695. human, ovine, rat biotinyl-PACAP27-NH$_2$
696. human, ovine, rat PACAP 6-27
697. human, ovine, rat PACAP38
698. human, ovine, rat biotinyl-PACAP38
699. human, ovine, rat PACAP 6-38
700. human, ovine, rat PACAP38 16-38
701. human, ovine, rat PACAP38 31-38
702. human, ovine, rat PACAP38 31-38
703. human, ovine, rat PACAP-related peptide (PRP)
704. human
705. PACAP-related peptide (PRP), rat
706. chromostatin
707. bovine pancreastatin (hPST-52) (chromogranin A 250-301, amide)
708. pancreastatin 24-52 (hPST-29)
709. human chromogranin A 286-301, amide
710. human pancreastatin
711. porcine biotinyl-pancreastatin
712. porcine {Nle$^8$}-pancreastatin
713. porcine {Tyr$^0$,Nle$^8$}-pancreastatin
714. porcine {Tyr$^0$}-pancreastatin
715. porcine parastatin 1-19 (chromogranin A 347-365)
716. porcine pancreastatin
717. chromogranin A 264-314-amide
718. rat biotinyl-pancreastatin
719. biotinyl-chromogranin A 264-314-amide
720. {Tyr$^0$}-pancreastatin
721. rat pancreastatin 26-51
722. pancreastatin 33-49, porcine
723. pancreatic polypeptide
724. avian pancreatic polypeptide
725. human C-fragment pancreatic polypeptide acid
726. human C-fragment pancreatic polypeptide amide
727. human pancreatic polypeptide (Rana temporaria)
728. ancreatic polypeptide
729. salmon pancreatic polypeptide
730. {Asp$^{76}$}-parathyroid hormone 39-84
731. human {Asp$^{76}$}-parathyroid hormone 53-84
732. human {Asn$^{76}$}-parathyroid hormone 1-84
733. hormone {Asn$^{76}$}-parathyroid hormone 64-84
734. human {Asn$^8$, Leu$^{18}$}-parathyroid hormone 1-34
735. human {Cys$^{5,28}$}-parathyroid hormone 1-34
736. human hypercalcemia malignancy factor 1-40
737. {Leu$^{18}$}-parathyroid hormone 1-34
738. human {Lys(biotinyl)}$^{13}$
739. {Nle$^{8,18}$, Tyr$^{34}$}-parathyroid hormone 1-34 amide
740. {Nle$^{8,18}$, Tyr$^{34}$}-parathyroid hormone 3-34 amide
741. bovine {Nle$^{8,18}$, Tyr$^{34}$}-parathyroid hormone 1-34
742. human {Nle$^{8,18}$, Tyr$^{34}$}-parathyroid hormone 1-34 amide
743. human {Nle$^{8,18}$, Tyr$^{34}$}-parathyroid hormone 3-34 amide
744. human {Nle$^{8,18}$, Tyr$^{34}$}-parathyroid hormone 7-34 amide
745. bovine {Nle$^{8,21}$, Tyr$^{34}$}-parathyroid hormone 1-34 amide
746. rat parathyroid hormone 44-68
747. human parathyroid hormone 1-34
748. bovine parathyroid hormone 3-34
749. bovine parathyroid hormone 1-31 amide
750. human parathyroid hormone 1-34
751. human parathyroid hormone 13-34
752. human parathyroid hormone 1-34
753. rat parathyroid hormone 1-38
754. human parathyroid hormone 1-44
755. human parathyroid hormone 28-48
756. human parathyroid hormone 39-68
757. human parathyroid hormone 39-84
758. human parathyroid hormone 53-84
759. human parathyroid hormone 69-84
760. human parathyroid hormone 70-84
761. human {Pro$^{34}$}-peptide YY (PYY)
762. human {Tyr$^0$}-hypercalcemia malignancy factor 1-40
763. {Tyr$^0$}-parathyroid hormone 1-44
764. human {Tyr$^0$}-parathyroid hormone 1-34
765. human {Tyr$^1$}-parathyroid hormone 1-34
766. human {Tyr$^{27}$}-parathyroid hormone 27-48
767. human {Tyr$^{34}$}-parathyroid hormone 7-34 amide
768. bovine {Tyr$^{43}$}-parathyroid hormone 43-68
769. human {Tyr$^{52}$, Asn$^{76}$}-parathyroid hormone 52-84
770. {Tyr$^{63}$}-parathyroid hormone 63-84, human TABLE 4-continued

| Targets from which the Analogs are derived | |
|---|---|
| 771. PTHrP ({Tyr$^{36}$}-PTHrP 1-36 amide) | 772. chicken hHCF-(1-34)--NH2 (humoral hypercalcemic factor) |
| 773. human PTH-related protein 1-34 | 774. human biotinyl-PTH-related protein 1-34 |
| 775. human {Tyr$^0$}-PTH-related protein 1-34 | 776. human {Tyr$^{34}$}-PTH-related protein 1-34 amide |
| 777. human PTH-related protein 1-37 | 778. human PTH-related protein 7-34 amide |
| 779. human PTH-related protein 38-64 amide | 780. human PTH-related protein 67-86 amide |
| 781. human PTH-related protein 107-111 | 782. human, rat, mouse PTH-related protein 107-111 free acid |
| 783. PTH-related protein 107-138 | 784. human and PTH-related protein 109-111 |
| 785. peptide T {D-Ala$^1$}-peptide T | 786. {D-Ala$^1$}-peptide T amide |
| 787. prolactin-releasing peptide 31 | 788. human prolactin-releasing peptide 20 |
| 789. human prolactin-releasing peptide 31 | 790. rat prolactin-releasing peptide 20 |
| 791. rat prolactin-releasing peptide 31 | 792. bovine prolactin-releasing peptide 20 |
| 793. human PYY 3-36 | 794. human biotinyl-PYY |
| 795. human PYY | 796. human {Leu$^{31}$, Pro$^{34}$}-PYY |
| 797. porcine PYY | 798. rat PYY |
| 799. acetyl | 800. angiotensinogen 1-14 |
| 801. human angiotensinogen 1-14 | 802. porcine renin substrate tetradecapeptide |
| 803. rat {Cys$^8$}-renin substrate tetradecapeptide | 804. rat {Leu$^8$}-renin substrate tetradecapeptide |
| 805. rat {Val$^8$}-renin substrate tetradecapeptide, rat. | 806. canine secretin |
| 807. chicken secretin | 808. human biotinyl-secretin |
| 809. human secretin | 810. porcine secretin |
| 811. rat secretin | 812. BIM-23027 |
| 813. biotinyl-somatostatin biotinylated cortistatin 17 | 814. human cortistatin 14 |
| 815. rat cortistatin 17 | 816. human {Tyr$^0$}-cortistatin 17 |
| 817. human cortistatin 29 | 818. rat {D-Trp$^8$}-somatostatin |
| 819. {DTrp$^8$,DCys$^{14}$}-somatostatin | 820. {DTrp$^8$,Tyr$^{11}$}-somatostatin |
| 821. {D-Trp$^{11}$}-somatostatin NTB (Naltriben) | 822. {Nle$^8$}-somatostatin 1-28 |
| 823. octreotide (SMS 201-995) | 824. prosomatostatin 1-32 |
| 825. porcine {Tyr$^0$}-somatostatin | 826. {Tyr$^0$}-somatostatin |
| 827. {Tyr$^1$}-somatostatin 28 (1-14) | 828. {Tyr$^{11}$}-somatostatin {Tyr$^0$} |
| 829. {D-Trp$^8$}-somatostatin | 830. somatostatin |
| 831. somatostatin antagonist | 832. somatostatin-25 |
| 833. somatostatin-28 | 834. somatostatin 28 (1-12) |
| 835. biotinyl-somatostatin-28 | 836. {Tyr$^0$}-somatostatin-28 |
| 837. {Leu$^8$, D-Trp$^{22}$, Tyr$^{25}$}-somatostatin-28 | 838. biotinyl-{Leu$^8$, D-Trp$^{22}$, Tyr$^{25}$}-somatostatin-28 |
| 839. somatostatin-28 (1-14) | 840. RC-160 |
| 841. G protein antagonist-2 Ac-{Arg$^6$, Sar$^9$, Met(O2)$^{11}$}-substance P 6-11 {Arg$^3$}-substance P | 842. Ac-Trp-3,5-bis(trifluoromethyl)benzyl ester Ac-{Arg$^6$, Sar$^9$, Met(O2)$^{11}$}-substance P |
| 843. 6-11 {D-Ala$^4$}-substance P | 844. 4-11 {Tyr$^6$, D-Phe$^7$, D-His$^9$}-substance P |
| 845. 6-11 (sendide) biotinyl-substance P biotinyl-NTE{Arg$^3$}-substance P | 846. {Tyr$^8$}-substance P |
| 847. {Sar$^9$, Met(O2)$^{11}$}-substance P | 848. {D-Pro$^2$, DTrp$^{7,9}$}-substance P |
| 849. {D-Pro$^4$, O-Trp$^{7,9}$}-substance P | 850. 4-11 substance P |
| 851. 4-11 {DTrp$^{2,7,9}$}-substance P | 852. {(Dehydro)Pro$^{2,4}$, Pro$^9$}-substance P |
| 853. {Dehydro-Pro$^4$}-substance P | 854. 4-11 {Glp$^5$,(Me)Phe$^8$,Sar$^9$}-substance P |
| 855. 5-11 {Glp$^5$,Sar$^9$}-substance P | 856. 5-11 {Glp$^5$}-substance P |
| 857. 5-11 hepta-substance P (substance P 5-11) hexa-substance P(substance P 6-11) | 858. {MePhe$^8$,Sar$^9$}-substance P |
| 859. {Nle$^{11}$}-substance P | 860. Octa-substance P(substance P 4-11) |
| 861. {pGlu$^1$}-hexa-substance P | 862. ({pGlu$^6$}-substance P 6-11) |
| 863. {pGlu$^6$, D-Pro$^9$}-substance P 6-11 | 864. {(pNO$_2$)Phe$^7$ Nle$^{11}$}-substance P |
| 865. penta-substance P (substance P 7-11) | 866. {Pro$^9$}-substance P GR73632 |
| 867. substance P 7-11 | 868. {Sar$^4$}-substance P 4-11 |
| 869. {Sar$^9$}-substance P septide | 870. ({pGlu$^6$, Pro$^9$}-substance P 6-11) |
| 871. spantide I | 872. spantide II |
| 873. cod substance P | 874. trout substance P |
| 875. antagonist substance P-Gly-Lys-Arg | 876. substance P 1-4 |
| 877. substance P 1-6 | 878. substance P 1-7 |
| 879. substance P 1-9 | 880. deca-substance P (substance P 2-11) |
| 881. nona-substance P (substance P 3-11) | 882. substance P tetrapeptide (substance P 8-11) |
| 883. substance P tripeptide (substance P 9-11) | 884. substance P, free acid |
| 885. substance P methyl ester | 886. {Tyr$^8$,Nle$^{11}$} substance P |
| 887. {Ala$^5$, beta-Ala$^8$} neurokinin A | 888. 4-10 eledoisin |
| 889. locustatachykinin I (Lom-TK-I) (Locusta migratoria) | 890. locustatachykinin II (Lom-TK-II) (Locusta migratoria) |
| 891. neurokinin A 4-10 | 892. neurokinin A (neuromedin L, substance K) |
| 893. cod neurokinin A | 894. biotinyl-neurokinin A (biotinyl-neuromedin L, biotinyl-substance K) |

TABLE 4-continued

| Targets from which the Analogs are derived | |
|---|---|
| 895. {Tyr$^0$}-neurokinin A | 896. {Tyr$^6$}-substance K |
| 897. FR64349 | 898. {Lys$^3$, Gly$^8$-(R)-gamma-lactam-Leu$^9$}-neurokinin A 3-10 |
| 899. GR83074 | 900. GR87389 |
| 901. GR94800 | 902. {Beta-Ala$^8$}-neurokinin A 4-10 |
| 903. {Nle$^{10}$}-neurokinin A 4-10 | 904. {Trp$^7$, beta-Ala$^8$}-neurokinin A 4-10 |
| 905. neurokinin B (neuromedin K) | 906. biotinyl-neurokinin B (biotinyl-neuromedin K) |
| 907. {MePhe$^7$}-neurokinin B | 908. {Pro$^7$}-neurokinin B |
| 909. {Tyr$^0$}-neurokinin B | 910. neuromedin B |
| 911. porcine biotinyl-neuromedin B | 912. porcine neuromedin B-30 |
| 913. porcine neuromedin B-32 | 914. porcine neuromedin B |
| 915. receptor antagonist neuromedin C | 916. porcine neuromedin N |
| 917. porcine neuromedin (U-8) | 918. porcine neuromedin (U-25) |
| 919. porcine neuromedin U | 920. rat neuropeptide-gamma (gamma-preprotachykinin 72-92) |
| 921. PG-KII phyllolitorin | 922. {Leu$^8$}-phyllolitorin (Phyllomedusa sauvagei) |
| 923. physalaemin | 924. physalaemin 1-11 |
| 925. scyliorhinin II, amide | 926. dogfish senktide |
| 927. selective neurokinin B receptor peptide | 928. {Ser$^2$}-neuromedin C |
| 929. beta-preprotachykinin 69-91 | 930. human beta-preprotachykinin 111-129 |
| 931. human tachyplesin I | 932. xenopsin |
| 933. human xenopsin 25 (xenin 25) | 934. biotinyl-thyrotropin-releasing hormone |
| 935. {Glu$^1$}-TRH | 936. His-Pro-diketopiperazine |
| 937. {3-Me-His$^2$}-TRH | 938. pGlu-Gln-Pro-amide pGlu-His {Phe$^2$}-TRH |
| 939. prepro TRH 53-74 | 940. prepro TRH 83-106 |
| 941. prepro-TRH 160-169 | 942. Ps4, TRH-potentiating peptide |
| 943. prepro-TRH 178-199 | 944. thyrotropin-releasing hormone (TRH) |
| 945. TRH, free acid | 946. TRH--SH Pro |
| 947. TRH precursor peptide | 948. omega-agatoxin TK agelenin, (spider, Agelena opulenta) |
| 949. apamin (honeybee, Apis mellifera) | 950. calcicudine (CaC) (green mamba, Dedroaspis angusticeps) |
| 951. calciseptine (black mamba, Dendroaspis polylepis polylepis) | 952. charybdotoxin (ChTX) (scorpion, Leiurus quinquestriatus var. hebraeus) |
| 953. chlorotoxin conotoxin GI (marine snail, Conus geographus) | 954. conotoxin GS (marine snail, Conus geographus) |
| 955. conotoxin MI (Marine Conus magus) | 956. alpha-conotoxin EI, Conus ermineus |
| 957. alpha-conotoxin SIA | 958. alpha-conotoxin ImI alpha-conotoxin SI (cone snail, Conus striatus) |
| 959. micro-conotoxin GIIIB (marine snail, Conus geographus) | 960. omega-conotoxin GVIA (marine snail, Conus geographus) |
| 961. omega-conotoxin MVIIA (Conus magus) | 962. omega-conotoxin MVIIC (Conus magus) |
| 963. omega-conotoxin SVIB, (cone snail, Conus striatus) | 964. endotoxin inhibitor geographutoxin I (GTX-I) (.mu.-Conotoxin GIIIA) |
| 965. iberiotoxin (IbTX) (scorpion, Buthus tamulus) | 967. kaliotoxin 1-37 kaliotoxin (scorpion, Androctonus mauretanicus mauretanicus) |
| 968. mast cell-degranulating peptide (MCD-peptide, peptide 401) | 969. margatoxin (MgTX) (scorpion, Centruriodes Margaritatus) |
| 970. neurotoxin NSTX-3 (Papua New Guinean spider, Nephilia maculata) | 971. PLTX-II (spider, Plectreurys tristes) |
| 972. scyllatoxin (leiurotoxin I) | 973. stichodactyla sheep VIP toxin (ShK) |
| 974. stichodactyla porcine VIP toxin (ShK) | 975. stichodactyla rat VIP toxin (ShK) |
| 976. VIP-Gly-Lys-Arg-NH$_2$ biotinyl-PHI (biotinyl-PHI-27) | 977. porcine {Glp$^{16}$} VIP 16-28 |
| 978. porcine PHI (PHI-27) | 979. porcine PHI (PHI-27) |
| 980. rat PHM-27 (PHI) | 981. human prepro VIP 81-122 |
| 982. human preproVIP/PHM 111-122 | 983. prepro VIP/PHM 156-170 |
| 984. biotinyl-PHM-27 (biotinyl-PHI) | 985. human vasoactive intestinal contractor (endothelin-beta) |
| 986. vasoactive intestinal octacosa-peptide | 987. chicken vasoactive intestinal peptide |
| 988. guinea pig biotinyl-VIP | 989. human VIP peptide 1-12 |
| 990. porcine VIP peptide 1-12 | 991. rat VIP peptide 1-12 |
| 992. sheep VIP peptide 1-12 | 993. human VIP peptide 10-28 |
| 994. porcine VIP peptide 10-28 | 995. rat VIP peptide 10-28 |
| 996. sheep VIP peptide 10-28 | 997. human VIP peptide 11-28 |
| 998. porcine VIP peptide 11-28 | 999. rat VIP peptide 11-28 |
| 1000. sheep VIP peptide 11-28 | 1001. human VIP peptide 6-28 |
| 1002. porcine VIP peptide 6-28 | 1003. rat VIP peptide 6-28 |
| 1004. sheep VIP peptide 6-28 | 1005. vasoactive intestinal peptide antagonist |
| 1006. vasoactive intestinal peptide antagonist ({Ac-Tyr$^1$, D-Phe$^2$}-GHRF 1-29 amide) | 1007. vasoactive intestinal peptide receptor antagonist (4-Cl-D-Phe$^6$, Leu$^{17}$}-VIP) |

TABLE 4-continued

| Targets from which the Analogs are derived | |
|---|---|
| 1008. vasoactive intestinal peptide receptor binding inhibitor, L-8-K | 1009. Ala$\{^{11,22,28}\}$VIP |
| 1010. Ala$\{^{2,8,9,11,19,22,24,25,27,28}\}$VIP | 1011. $\{K^{15,}\ R^{16},\ L^{27}\}$-VIP(1-7)/GRF(8-27) |
| 1012. Ro25-1553 | 1013. Ro25-1392 |
| 1014. BAY55-9837 | 1015. R3P65 |
| 1016. Maxadilan | 1017. PG97-269 |
| 1018. PG99-465 | 1019. Max.d.4. |
| 1020. M65 (Dickson & Finlayson, Pharmacology & Therapeutics, Volume 121, Issue 3, March 2009, Pages 294-316). | 1021. $\{Asu^{1,6},Arg^{8}\}$-vasopressin |
| 1022. vasotocin | 1023. $\{Asu^{1,6},Arg^{8}\}$-vasotocin |
| 1024. $\{Lys^{8}\}$-vasopressin | 1025. $\{Arg^{8}\}$-desamino vasopressin |
| 1026. desglycinamide | 1027. $\{Arg^{8}\}$-vasopressin (AVP) |
| 1028. $\{Arg^{8}\}$-vasopressin desglycinamide | 1029. biotinyl-$\{Arg^{8}\}$-vasopressin (biotinyl-AVP) |
| 1030. $\{D\text{-}Arg^{8}\}$-vasopressin | 1031. desamino-$\{Arg^{8}\}$-vasopressin |
| 1032. desamino-$\{D\text{-}Arg^{8}\}$-vasopressin (DDAVP) | 1033. $\{deamino-\{D\text{-}3\text{-}(3'\text{-}pyridyl\text{-}Ala)\}\}$-$\{Arg^{8}\}$-vasopressin |
| 1034. $\{1\text{-}(beta\text{-}Mercapto\text{-}beta,\ beta\text{-}cyclopentamethylene\ propionic\ acid),\ 2\text{-}(O\text{-}methyl)tyrosine\}$-$\{Arg^{8}\}$-vasopressin | 1035. vasopressin metabolite neuropeptide |
| 1036. $\{pGlu^{4},\ Cys^{6}\}$ vasopressin metabolite neuropeptide | 1037. $\{pGlu^{4},\ Cys^{6}\}\ \{Lys^{8}\}$-deamino vasopressin desglycinamide |
| 1038. $\{Lys^{8}\}$-vasopressin | 1039. $\{Mpr^{1},Val^{4},DArg^{8}\}$-vasopressin |
| 1040. $\{Phe^{2},\ Ile^{3},\ Orn^{8}\}$-vasopressin | 1041. ($\{Phe^{2},\ Orn^{8}\}$-vasotocin) |
| 1042. $\{Arg^{8}\}$-vasotocin | 1043. $\{d(CH_{2})_{5},\ Tyr(Me)_{2},\ Orn^{8}\}$-vasotocin |
| 1044. human CMV protease substrate | 1045. HCV core protein 59-68 |
| 1046. HCV NS4A | 1047. protein 1840 (JT strain) |
| 1048. HCV NS4A protein 21-34 (JT strain) | 1049. hepatitis B virus receptor binding fragment |
| 1050. hepatitis B virus pre-S region 120-145 | 1051. $\{Ala^{127}\}$-hepatitis B virus pre-S region 120-131 |
| 1052. herpes virus inhibitor 2 | 1053. HIV envelope protein fragment 254-274 |
| 1054. HIV gag fragment 129-135 | 1055. HIV substrate P 18 peptide |
| 1056. peptide T | 1057. $\{3,5\ diiodo\text{-}Tyr^{7}\}$ peptide T |
| 1058. R15K | 1059. HIV-1 inhibitory peptide T20 |
| 1060. T21 | 1061. V3 |
| 1062. decapeptide P 18-110 | 1063. virus replication inhibiting peptide |
| 1064. buforin I | 1065. buforin II |
| 1066. cecropin A | 1067. cecropin B |
| 1068. cecropin P1 | 1069. porcine gaegurin 2 (Rana rugosa) |
| 1070. gaegurin 5 (Rana rugosa) | 1071. indolicidin |
| 1072. protegrin-(PG)-I | 1073. magainin 1 |
| 1074. magainin 2 | 1075. T-22 |
| 1076. $\{Tyr^{5,12},\ Lys^{7}\}$-poly-phemusin II peptide | 1077. Alzheimer's disease beta-protein (SP28) |
| 1078. calpain inhibitor peptide | 1079. capsase-1 inhibitor V |
| 1080. capsase-3 | 1081. substrate IV caspase-1 inhibitor I |
| 1082. cell-permeable caspase-1 inhibitor VI | 1083. caspase-3 substrate III |
| 1084. caspase-1 substrate V | 1085. fluorogenic caspase-3 inhibitor I |
| 1086. cell-permeable caspase-6 | 1087. ICE inhibitor III |
| 1088. $\{Des\text{-}Ac,\ biotin\}$-ICE inhibitor III | 1089. IL-1B converting enzyme (ICE) inhibitor II |
| 1090. IL-1 B converting enzyme (ICE) substrate IV | 1091. MDL 28170 |
| 1092. MG-132 | 1093. alpha-ANP (alpha-chANP) |
| 1094. chicken anantin ANP 1-11 | 1095. rat ANP 8-30 |
| 1096. frog ANP 11-30 | 1097. frog ANP-21 (fANP-21) |
| 1098. frog ANP-24 (fANP-24) | 1099. frog ANP-30 |
| 1100. frog ANP fragment 5-28 | 1101. human ANP 7-23 |
| 1102. canine ANP 7-23 | 1103. human ANP fragment 7-28 |
| 1104. human alpha-atrial natriuretic polypeptide 1-28 | 1105. canine alpha-atrial natriuretic polypeptide 1-28 |
| 1106. human A71915 | 1107. canine A71915 |
| 1108. rat atrial natriuretic factor 8-33 | 1109. rat atrial natriuretic polypeptide 3-28 |
| 1110. human atrial natriuretic polypeptide 4-28 | 1111. human atrial natriuretic polypeptide 5-27 |
| 1112. canine atrial natriuretic polypeptide 5-27 | 1113. human atrial natriuretic aeptide (ANP) |
| 1114. eel atriopeptin I | 1115. rat atriopeptin II |
| 1116. rabbit atriopeptin II | 1117. mouse atriopeptin II |
| 1118. rat atriopeptin III | 1119. rabbit atriopeptin III |
| 1120. mouse atriopeptin III | 1121. rat atrial natriuretic factor (rANF), |
| 1122. rabbit atrial natriuretic factor (rANF), | 1123. mouse atrial natriuretic factor (rANF), |

TABLE 4-continued

Targets from which the Analogs are derived 1124. rat, auriculin A (rat ANF 126-149)
1125. auriculin B (rat ANF 126-150)
1126. beta-ANP (1-28, dimer, antiparallel) beta-rANF 17-48
1127. biotinyl-alpha-ANP 1-28
1128. human biotinyl-atrial natriuretic factor (biotinyl-rANF)
1129. canine biotinyl-atrial natriuretic factor (biotinyl-rANF)
1130. rat cardiodilatin 1-16
1131. human C-ANF 4-23
1132. rat Des-{Cys$^{105}$, Cys$^{121}$}-atrial natriuretic factor 104-126
1133. rat {Met(O)$^{12}$} ANP 1-28
1134. human {Mpr$^7$,DAla$^9$}ANP 7-28, amide
1135. rat prepro-ANF 104-116
1136. human prepro-ANF 26-55 (proANF 1-30)
1137. human prepro-ANF 56-92 (proANF 31-67)
1138. human prepro-ANF 104-123
1139. human {Tyr$^0$}-atriopeptin I
1140. rat {Tyr$^0$}-atriopeptin II
1141. rabbit {Tyr$^0$}-atriopeptin II
1142. mouse {Tyr$^0$}-atriopeptin II
1143. rat {Tyr$^0$-prepro ANF 104-123}
1144. rabbit {Tyr$^0$-prepro ANF 104-123}
1145. mouse {Tyr$^0$-prepro ANF 104-123}
1146. human urodilatin (CDD/ANP 95-126)
1147. ventricular natriuretic peptide (VNP), eel
1148. ventricular natriuretic peptide (VNP), rainbow trout
1149. alpha bag cell peptide
1150. alpha-bag cell peptide 1-9
1151. alpha-bag cell peptide 1-8
1152. alpba-bag cell peptide 1-7
1153. beta-bag cell factor
1154. gamma-bag cell factor
1155. alpha-s1
1156. casein 101-123 (bovine milk)
1157. biotinyl-bombesin
1158. bombesin 8-14
1159. {Leu$^{13}$-psi (CH$_2$NH)Leu$^{14}$}-bombesin
1160. {D-Phe$^6$, Des-Met$^{14}$}-bombesin
1161. 6-14 ethylamide {DPhe$^{12}$} bombesin
1162. {DPhe$^{12}$,Leu$^{14}$}-bombesin
1163. {Tyr$^4$}-bombesin
1164. {Tyr$^4$,DPhe$^{12}$}-bombesin
1165. bone GLA protein
1166. bone GLA protein 45-49
1167. {Glu$^{17}$, Gla$^{21,24}$}-osteocalcin 1-49
1168. human myclopeptide-2 (MP-2)
1169. osteocalcin 1-49
1170. human osteocalcin 37-49
1171. {Tyr$^{38}$, Phe$^{42,46}$} bone GLA protein 38-49
1172. {Ala$^{2,6}$, des-Pro$^3$}-bradykinin
1173. bradykinin bradykinin (Bowfin. Gar)
1174. bradykinin potentiating peptide
1175. bradykinin 1-3
1176. bradykinin 1-5
1177. bradykinin 1-6
1178. bradykinin 1-7
1179. bradykinin 2-7
1180. bradykinin 2-9
1181. {DPhe$^7$} bradykinin
1182. {Des-Arg$^9$}-bradykinin
1183. {Des-Arg$^{10}$}-Lys-bradykinin
1184. ({Des-Arg$^{10}$}-kallidin)
1185. {D-N-Me-Phe$^7$}-bradykinin
1186. {Des-Arg$^9$, Leu$^8$}-bradykinin
1187. Lys-bradykinin (kallidin)
1188. Lys-(Des-Arg$^9$, Leu$^8$}-bradykinin
1189. ({Des-Arg$^{10}$, Leu$^9$}-kallidin)
1190. {Lys$^0$-Hyp$^3$}-bradykinin
1191. ovokinin
1192. {Lys$^0$, Ala$^3$}-bradykinin
1193. Met-Lys-bradykinin
1194. peptide K12
1195. bradykinin potentiating peptide
1196. {(pCl)Phe$^{5,8}$}-bradykinin
1197. T-kinin (Ile-Ser-bradykinin)
1198. {Thi.$^{5,8}$, D-Phe$^7$}-bradykinin
1199. {Tyr$^0$}-bradykinin {Tyr$^5$}-bradykinin
1200. {Tyr$^8$}-bradykinin
1201. kallikrein
1202. BNP 32
1203. canine BNP-like Peptide
1204. eel BNP-32
1205. human BNP-45
1206. mouse BNP-26
1207. porcine BNP-32
1208. porcine biotinyl-BNP-32
1209. porcine BNP-32
1210. rat biotinyl-BNP-32
1211. rat BNP45 (BNP 51-95, 5K cardiac natriuretic peptide)
1212. human {Tyr$^0$}-BNP 1-32
1213. C-peptide
1214. human {Tyr$^0$}-C-peptide
1215. C-type natriuretic peptide
1216. chicken C-type natriuretic peptide-22 (CNP-22)
1217. porcine C-type natriuretic peptide-53 (CNP-53)
1218. rat C-type natriuretic peptide-53 (CNP-53)
1219. human C-type natriuretic peptide-53 (CNP-53)
1220. porcine C-type natriuretic peptide-53
1221. rat C-type natriuretic peptide-53
1222. (porcine) 1-29 (CNP-531-29)
1223. (rat) 1-29 (CNP-531-29)
1224. prepro-CNP 1-27
1225. rat prepro-CNP 30-50
1226. porcine vasonatrin peptide (VNP)
1227. rat vasonatrin peptide (VNP)
1228. {Tyr$^0$}-C-type natriuretic peptide-22 ({Tyr$^0$}-CNP-22)
1229. biotinyl-calcitonin
1230. human biotinyl-calcitonin
1231. rat biotinyl-calcitonin
1232. salmon calcitonin
1233. chicken calcitonin
1234. eel calcitonin
1235. human calcitonin
1236. porcine calcitonin
1237. rat calcitonin
1238. salmon calcitonin 1-7
1239. human calcitonin 8-32
1240. salmon katacalcin (PDN-21) (C-procalcitonin)
1241. human N-proCT (amino-terminal procalcitonin cleavage peptide)
1242. acetyl-alpha-CGRP 19-37
1243. human alpha-CGRP 19-37
1244. human alpha-CGRP 23-37
1245. human biotinyl-CGRP
1246. human biotinyl-CGRP II
1247. human biotinyl-CGRP
1248. rat beta-CGRP
1249. rat biotinyl-beta-CGRP
1250. rat CGRP
1251. human calcitonin C-terminal adjacent peptide CGRP 1-19

TABLE 4-continued

| Targets from which the Analogs are derived | |
|---|---|
| 1252. human CGRP 20-37 | 1253. human CGRP 8-37 |
| 1254. human CGRP II | 1255. human CGRP |
| 1256. rat CGRP 8-37 | 1257. rat CGRP 29-37 |
| 1258. rat CGRP 30-37 | 1259. rat CGRP 31-37 |
| 1260. rat CGRP 32-37 | 1261. rat CGRP 33-37 |
| 1262. rat CGRP 31-37 | 1263. rat ({Cys(Acm)$^{2,7}$}-CGRP elcatonin |
| 1264. {Tyr$^0$}-CGRP, human {Tyr$^0$}-CGRP II | 1265. human {Tyr$^0$}-CGRP 28-37 |
| 1266. rat {Tyr$^0$}-CGRP | 1267. {Tyr$^{22}$}-CGRP 22-37, rat |
| 1268. human CART 55-102 | 1269. human CART |
| 1270. rat CART 55-102 | 1271. beta-casomorphin |
| 1272. human beta-casomorphin 1-3 | 1273. beta-casomorphin 1-3, amide |
| 1274. beta-casomorphin, bovine | 1275. beta-casomorphin 1-4 |
| 1276. bovine beta-casomorphin 1-5 | 1277. bovine beta-casomorphin 1-5, amide |
| 1278. bovine beta-casomorphin 1-6 | 1279. bovine {DAla$^2$}-beta-casomorphin 1-3, amide |
| 1280. bovine {DAla$^2$,Hyp$^4$,Tyr$^5$}-beta-casomorphin 1-5 amide | 1281. {DAla$^2$,DPro$^4$,Tyr$^5$}-beta-casomorphin 1-5, amide |
| 1282. {DAla$^2$,Tyr$^5$}-beta-casomorphin 1-5, amide | 1283. bovine {DAla$^{2,4}$,Tyr$^5$}-beta-casomorphin 1-5, amide |
| 1284. bovine {DAla$^2$, (pCl)Phe$^3$}-beta-casomorphin, amide | 1285. bovine {DAla$^2$}-beta-casomorphin 1-4, amide |
| 1286. bovine {DAla$^2$}-beta-casomorphin 1-5 | 1287. bovine {DAla$^2$}-beta-casomorphin 1-5, amide |
| 1288. bovine {DAla$^2$,Met$^5$}-beta-casomorphin 1-5 | 1289. bovine {DPro$^2$}-beta-casomorphin 1-5, amide |
| 1290. bovine {DAla$^2$}-beta-casomorphin 1-6 | 1291. bovine {DPro$^2$}-beta-casomorphin 1-4, amide |
| 1292. {Des-Tyr$^1$}-beta-casomorphin | 1293. bovine {DAla$^{2,4}$,Tyr$^5$}-beta-casomorphin 1-5, amide |
| 1294. bovine {DAla$^2$, (pCl)Phe$^3$}-beta-casomorphin, amide | 1295. bovine {DAla$^2$}-beta-casomorphin 1-4, amide |
| 1296. bovine {DAla$^2$}-beta-casomorphin 1-5 | 1297. bovine {DAla$^2$}-beta-casomorphin 1-5, amide |
| 1298. bovine {DAla$^2$,Met$^5$}-beta-casomorphin 1-5 | 1299. bovine {DPro$^2$}-beta-casomorphin 1-5, amide |
| 1300. bovine {DAla$^2$}-beta-casomorphin 1-6 | 1301. bovine {DPro$^2$}-beta-casomorphin 14, amide |
| 1302. {Des-Tyr$^1$}-beta-casomorphin | 1303. bovine {Val$^3$}-beta-casomorphin 1-4, amide |
| 1304. defensin 1 (human) | 1305. HNP-1 (human neutrophil peptide-1) |
| 1306. N-formyl-Met-Leu-Phe | 1307. caerulein |
| 1308. cholecystokinin | 1309. cholecystokinin-pancreozymin CCK-33 |
| 1310. human cholecystokinin octapeptide 14 (non-sulfated) (CCK 26-29, unsulfated) | 1311. cholecystokinin octapeptide (CCK 26-33) |
| 1312. cholecystokinin octapeptide (non-sulfated) (CCK 26-33, unsulfated) | 1313. cholecystokinin heptapeptide (CCK 27-33) |
| 1314. cholecystokinin tetrapeptide (CCK 30-33) CCK-33 | 1315. porcine CR 1409 |
| 1316. cholecystokinin antagonist CCK flanking peptide (unsulfated) | 1317. N-acetyl cholecystokinin, CCK 26-30 |
| 1318. sulfated N-acetyl cholecystokinin, CCK 26-31 | 1319. sulfated N-acetyl cholecystokinin, CCK 26-31 |
| 1320. non-sulfated prepro CCK fragment V-9-M | 1321. proglumide |
| 1322. colony-stimulating factor (CSF) | 1323. GMCSF |
| 1324. MCSF | 1325. G-CSF |
| 1326. astressin alpha-helical CRF 12-41 | 1327. biotinyl-CRF |
| 1328. ovine biotinyl-CRF | 1329. porcine CRF |
| 1330. human CRF | 1331. rat CRF |
| 1332. bovine CRF | 1333. ovine CRF |
| 1334. porcine {Cys$^{21}$}-CRF | 1335. CRF antagonist human (alpha-helical CRF 9-41) |
| 1336. CRF antagonist rat (alpha-helical CRF 9-41) | 1337. CRF 6-33 |
| 1338. human {DPro$^5$}-CRF | 1339. rat {DPro$^5$}-CRF |
| 1340. human {D-Phe$^{12}$, Nle$^{21,38}$}-CRF 12-41 | 1341. rat {D-Phe$^{12}$, Nle$^{21,38}$}-CRF 12-41 |
| 1342. human eosinophilotactic peptide {Met(0)$^{21}$}-CRF | 1343. rat eosinophilotactic peptide {Met(0)$^{21}$}-CRF |
| 1344. ovine {Nle$^{21}$,Tyr$^{32}$}-CRF | 1345. ovine prepro CRF 125-151 |
| 1346. human sauvagine | 1347. frog {Tyr$^0$}-CRF |
| 1348. human {Tyr$^0$}-CRF | 1349. rat {Tyr$^0$}-CRF |
| 1350. ovine {Tyr$^0$}-CRF 34-41 | 1351. ovine {Tyr$^0$}-urocortin urocortin amide |
| 1352. human urocortin | 1353. rat urotensin I (Catostomus commersoni) |
| 1354. urotensin II | 1355. urotensin II (Rana ridibunda |
| 1356. cortistatin 29 | 1357. cortistatin 29 (1-13) |
| 1358. {Tyr$^0$}-cortistatin 29 | 1359. pro-cortistatin 28-47 |

TABLE 4-continued

Targets from which the Analogs are derived 1360. pro-cortistatin 51-81
1361. tumor necrosis factor
1362. TNF-β
1363. dermorphin
1364. dermorphin analog 1-4
1365. big dynorphin (prodynorphin 209-240)
1366. porcine biotinyl-dynorphin A (biotinyl-prodynorphin 209-225)
1367. {DAla$^2$, DArg$^6$}dynorphin A 1-13
1368. porcine {D-Ala$^2$}-dynorphin A
1369. porcine {D-Ala$^2$}-dynorphin A amide
1370. porcine {D-Ala$^2$}-dynorphin A 1-13, amide
1371. porcine {D-Ala$^2$}-dynorphin A 1-9
1372. porcine {DArg$^6$}-dynorphin A 1-13
1373. porcine {DArg$^8$}-dynorphin A 1-13
1374. porcine {Des-Tyr$^1$}-dynorphin A 1-8
1375. {D-Pro$^{10}$}-dynorphin A 1-11
1376. porcine dynorphin A amide
1377. porcine dynorphin A 1-6
1378. porcine dynorphin A 1-7
1379. porcine dynorphin A 1-8
1380. porcine dynorphin A 1-9
1381. porcine dynorphin A 1-10
1382. porcine dynorphin A 1-10 amide
1383. porcine dynorphin A 1-11
1384. porcine dynorphin A 1-12
1385. porcine dynorphin A 1-13
1386. porcine dynorphin A 1-13 amide
1387. porcine DAKLI (dynorphin A-analogue kappa ligand)
1388. DAKLI-biotin
1389. ({Arg$^{11,13}$}-dynorphin A (1-13)-Gly-NH(CH$_2$)$_5$NH-biotin) dynorphin A 2-17
1390. porcine dynorphin 2-17, amide
1391. porcine dynorphin A 2-12
1392. porcine dynorphin A 3-17, amide
1393. porcine dynorphin A 3-8
1394. porcine dynorphin A 3-13
1395. porcine dynorphin A 3-17
1396. porcine dynorphin A 7-17
1397. porcine dynorphin A 8-17
1398. porcine dynorphin A 6-17
1399. porcine dynorphin A 13-17
1400. porcine dynorphin A (prodynorphin 209-225)
1401. porcine dynorphin B 1-9
1402. {MeTyr$^1$, MeArg$^7$, D-Leu$^8$}-dynorphin 1-8 ethyl amide {(nMe)Tyr$^1$} dynorphin A 1-13, 1403. amide
1404. porcine {Phe$^7$}-dynorphin A 1-7
1405. porcine {Phe$^7$}-dynorphin A 1-7, amide
1406. prodynorphin 228-256 (dynorphin B 29) (leumorphin)
1407. human ACTH 1-10
1408. ACTH 1-13
1409. human ACTH 1-16
1410. human ACTH 1-17
1411. ACTH 1-24
1412. human ACTH 4-10
1413. ACTH 4-11
1414. ACTH 6-24
1415. ACTH 7-38
1416. human ACTH 18-39
1417. human ACTH
1418. rat ACTH 12-39
1419. rat beta-cell tropin (ACTH 22-39)
1420. biotinyl-ACTH 1-24
1421. human biotinyl-ACTH 7-38
1422. human corticostatin
1423. rabbit {Met(02)$^4$,DLys$^8$,Phe$^9$} ACTH 4-9
1424. human {Met(0)$^4$,DLys$^8$,Phe$^9$} ACTH 4-9
1425. human N-acetyl, ACTH 1-17
1426. ebiratide
1427. adrenomedullin
1428. adrenomedullin 1-52
1429. human adrenomedullin 1-12
1430. human adrenomedullin 13-52
1431. human adrenomedullin 22-52
1432. human pro-adrenomedullin 45-92
1433. human pro-adrenomedullin 153-185
1434. human adrenomedullin 1-52
1435. porcine pro-adrenomedullin (N-20)
1436. porcine adrenomedullin 1-50
1437. rat adrenomedullin 11-50
1438. rat proAM-N20 (proadrenomedullin N-terminal 20 peptide
1439. allatostatin I
1440. allatostatin II
1441. allatostatin III
1442. allatostatin IV
1443. acetyl-amylin 8-37
1444. human acetylated amylin 8-37
1445. rat AC187 amylin antagonist AC253
1446. amylin antagonist AC625
1447. amylin antagonist amylin 8-37
1448. human amylin (IAPP)
1449. cat amylin (insulinoma or islet amyloid polypeptide(IAPP)) amylin amide
1450. human amylin 1-13 (diabetes-associated peptide 1-13)
1451. human amylin 20-29 (IAPP 20-29)
1452. human AC625 amylin antagonist
1453. amylin 8-37
1454. human amylin (IAPP)
1455. cat amylin
1456. rat amylin 8-37
1457. rat biotinyl-amylin
1458. rat biotinyl-amylin amide
1459. human biotinyl-amylin amide
1460. Alzheimer's disease beta-protein 12-28 (SP17)
1461. amyloid beta-protein 25-35
1462. amyloid beta/A4-protein precursor 328-332
1463. amyloid beta/A4 protein precursor (APP) 319-335
1464. amyloid beta-protein 1-43 amyloid beta-protein 1-42
1465. amyloid beta-protein 1-40
1466. amyloid beta-protein 10-20
1467. amyloid beta-protein 22-35
1468. Alzheimer's disease beta-protein (SP28)
1469. beta-amyloid peptide 1-42
1470. rat beta-amyloid peptide 1-40
1471. rat beta-amyloid 1-11
1472. beta-amyloid 31-35
1473. beta-amyloid 32-35
1474. beta-amyloid 35-25
1475. beta-amyloid/A4 protein precursor 96-110
1476. beta-amyloid precursor protein 657-676
1477. beta-amyloid 1-38
1478. {Gln$^{11}$}-Alzheimer's disease beta-protein
1479. {Gln$^{11}$}-beta-amyloid 1-40
1480. {Gln$^{22}$}-beta-amyloid 6-40
1481. non-A beta component of Alzheimer's disease amyloid (NAC) P3, (A beta 17-40)
1482. Alzheimer's disease amyloid β-peptide TABLE 4-continued

| Targets from which the Analogs are derived | |
|---|---|
| 1483. SAP (serum amyloid P component) 194-204 | 1484. A-779 Ala-Pro-Gly-angiotensin II |
| 1485. {Ile$^3$,Val$^5$}-angiotensin II | 1486. angiotensin III |
| 1487. antipeptide angiogenin fragment 108-122 | 1488. angiogenin fragment 108-123 |
| 1489. angiotensin I converting enzyme inhibitor angiotensin I | 1490. human angiotensin I converting enzyme substrate angiotensin I 1-7 |
| 1491. human angiopeptin angiotensin II | 1492. human angiotensin II antipeptide angiotensin II 1-4 |
| 1493. human angiotensin II 3-8 | 1494. human angiotensin II 4-8 |
| 1495. human angiotensin II 5-8 | 1496. human angiotensin III ({Des-Asp$^1$}-angiotensin II) |
| 1497. human angiotensin III inhibitor ({Ile$^7$}-angiotensin III) | 1498. angiotensin-converting enzyme inhibitor (Neothunnus macropterus) |
| 1499. {Asn$^1$, Val$^5$}-angiotensin I | 1500. goosefish {Asn$^1$, Val$^5$, Asn$^9$}-angiotensin I |
| 1501. salmon {Asn$^1$, Val$^5$, Gly$^9$}-angiotensin I | 1502. eel {Asn$^1$, Val$^5$}-angiotensin I 1-7 |
| 1503. eel {Asn$^1$,Val$^5$}-angiotensin II | 1504. goosefish {Asn$^1$,Val$^5$}-angiotensin II |
| 1505. salmon {Asn$^1$,Val$^5$}-angiotensin II | 1506. biotinyl-angiotensin I |
| 1507. human biotinyl-angiotensin II | 1508. human biotinyl-Ala-Ala-Ala-angiotensin II |
| 1509. {Des-Asp$^1$}-angiotensin I | 1510. human {p-aminophenylalanine$^6$}-angiotensin II |
| 1511. renin substrate (angiotensinogen 1-13) | 1512. human preangiotensinogen 1-14 (renin substrate tetradecapeptide) |
| 1513. human renin substrate tetradecapeptide (angiotensinogen 1-14) | 1514. porcine {Sar$^1$}-angiotensin II |
| 1515. {Sar$^1$}-angiotensin II 1-7 amide | 1516. {Sar$^1$, Ala$^8$}-angiotensin II |
| 1517. {Sar$^1$, Ile$^8$}-angiotensin II {Sar$^1$, Thr$^8$}-angiotensin II | 1518. {Sar$^1$, Tyr(Me)$^4$}-angiotensin II (Sarmesin) |
| 1519. {Sar$^1$, Val$^5$, Ala$^8$}-angiotensin II | 1520. {Sar$^1$, Ile$^7$}-angiotensin III |
| 1521. synthetic tetradecapeptide renin substrate (No. 2) | 1522. {Val$^4$}-angiotensin III |
| 1523. {Val$^5$}-angiotensin II | 1524. {Val$^5$}-angiotensin I |
| 1525. human {Val$^5$}-angiotensin I | 1526. bullfrog {Val$^5$, Asn$^9$}-angiotensin I |
| 1527. fowl {Val$^5$, Ser$^9$}-angiotensin I | 1528. Ac-SQNY |
| 1529. bovine bactenecin | 1530. CAP 37 (20-44) |
| 1531. carbormethoxycarbonyl-DPro-DPhe-OBzl | 1532. CD36 peptide P 139-155 |
| 1533. CD36 peptide P 93-110 | 1534. cecropin A-melittin hybrid peptide |
| 1535. {CA(1-7)M(2-9)NH$_2$} cecropin B, free acid | 1536. CYS(Bzl)84 CD fragment 81-92 |
| 1537. defensin (human) | 1538. HNP-2 |
| 1539. dermaseptin immunostimulating peptide | 1540. human lactoferricin |
| 1541. bovine lactoferricin | 1542. Hepatocyte Growth Factor (HGF) |
| 1543. HGFR | |

```
α-Bag Cell Peptide (1-9)
                                                                    (SEQ ID NO: 42)
APRLRFYSL γ-Bag Cell Peptide
                                                                    (SEQ ID NO: 43)
RLRFD β-Bag Cell Peptide
                                                                    (SEQ ID NO: 44)
RLRFH BAM 3200 Peptide E
                                                                    (SEQ ID NO: 45)
YGGFMRRVGRPEWWMDYQKRYGGFL BAM-18P
                                                                    (SEQ ID NO: 46)
YGGFMRRVGRPEWWMDYQ BAM-12P, Bovine Adrenal Medulla Docosapeptide
                                                                    (SEQ ID NO: 47)
YGGFMRRVGRPE
```

BAM-12P (7-12)
RVGRPE
(SEQ ID NO: 48)

bFGF (119-126), Basic Fibroblast Growth Factor, human, bovine
KRTGQYKL
(SEQ ID NO: 49)

bFGF Inhibitory Peptide
APSGHYKG
(SEQ ID NO: 50)

bFGF Inhibitory Peptide II
MWYRPDLDERKQQKRE
(SEQ ID NO: 51)

{Glu63} Bax BH3, mutant
STKKLSECEKRIGDELDSNM
(SEQ ID NO: 52)

BAD (103-126), human
NLWAAQRYGRELRRMSDEFVDSFK
(SEQ ID NO: 53)

BAD (103-127), human
NLWAAQRYGRELRRMSDEFVDSFKK
(SEQ ID NO: 54)

BAD (NT-1)
PEFEPSEQEDSSSAERC-NH2
(SEQ ID NO: 55)

Bak-BH3, TAMRA-labeled
GQVGRQLAIIGDDINR-K(TAMRA)-NH2
(SEQ ID NO: 56)

Bax BH3 peptide (55-74), wild type
STKKLSECLKRIGDELDSNM
(SEQ ID NO: 57)

Bcl 9-2
GSEGLSKEQLEHRERSLQTLRDIERLLLRSGETEPFLKGPPGGAG-NH2
(SEQ ID NO: 58)

BMf-BH3
LQHRAEVQIARKLQCIADQFHRLHT
(SEQ ID NO: 59)

Noxa BH3, Peptide 1
PAELEVECATQLRRFGDKLNFRQKLL
(SEQ ID NO: 60)

{D-Phe12, Leu14}-Bombesin
Pyr-QRLGNQWAVGfLL-NH2
(SEQ ID NO: 61)

{D-Phe12}-Bombesin
Pyr-QRLGNQWAVGfLM-NH2
(SEQ ID NO: 62)

{D-Tyr6, β-Ala11, Phe13, Nle14}-Bombesin (6-14)
yQWAV-(β-A)-HF-Nle-NH2
(SEQ ID NO: 63)

{D-Tyr6, β-Ala11, β-Phe13, Nle14}-Bombesin (1-14)
Pyr-QRLGyQWAV-(β-A)-H-(β-F)-Nle-NH2
(SEQ ID NO: 64)

{Lys3}-Bombesin
Pyr-QKLGNQWAVGHLM-NH2
(SEQ ID NO: 65)

{Tyr4, D-Phe12}-Bombesin
Pyr-QRYGNQWAVGfLM-NH2
(SEQ ID NO: 66)

{Tyr4}-Bombesin
Pyr-QRYGNQWAVGHLM-NH2
(SEQ ID NO: 66)

-continued

Biotin-Bombesin
Biotin-EQRLGNQWAVGHLM-NH2
(SEQ ID NO: 68)

Biotin-LC-LC-Bombesin
Biotin-LC-LC-EQRLGNQWAVGHLM-NH2
(SEQ ID NO: 68)

Bombesin
Pyr-QRLGNQWAVGHLM-NH2
(SEQ ID NO: 65)

Bombesin, FAM-labeled
FAM-EQRLGNQWAVGHLM-NH2
(SEQ ID NO: 68)

{D-Phe7}-Bradykinin
RPPGFSfFR
(SEQ ID NO: 69)

{Des-Arg1}-Bradykinin
PPGFSPFR
(SEQ ID NO: 70)

{Des-Arg10}-HOE I40
rRP-Hyp-G-Thi-S-(D-Tic)-Oic

{Ile-Ser}-Bradykinin (T-Kinin)
ISRPPGFSPFR
(SEQ ID NO: 71)

{Leu8, Des-Arg9}-Bradykinin
RPPGFSPL
(SEQ ID NO: 72)

{Lys0}-Bradykinin (Kallidin)
KRPPGFSPFR
(SEQ ID NO: 73)

Angiotensin Converting Enzyme Inhibitor, BPP 9a
Pyr-WPRPQIPP
(SEQ ID NO: 74)

Biotin-Bradykinin
Biotin-RPPGFSPFR
(SEQ ID NO: 75)

Bradykinin
RPPGFSPFR
(SEQ ID NO: 76)

Bradykinin Potentiator B, Angiotensin I Converting Enzyme Inhibitor
Pyr-GLPPRPKIPP
(SEQ ID NO: 77)

Bradykinin Potentiator C, Angiotensin I Converting Enzyme Inhibitor
Pyr-GLPPGPPIPP
(SEQ ID NO: 78)

Hemopressin
PVNFKLLSHHOE I40
(SEQ ID NO: 79)
rRP-(Hyp)-G-(Thi)-S-(D-Tic)-(Oic)-R C-peptide (57-87), human
EAEDLQVGQVELGGGPGAGSLQPLALEGSLQ
(SEQ ID NO: 80)

Proinsulin C-peptide (55-89), human
RREAEDLQVGQVELGGGPGAGSLQPLALEGSLQKR
(SEQ ID NO: 81)

{Trp63, 64}-C3a (63-77)
WWGKKYRASKLGLAR
(SEQ ID NO: 82)

C3a (70-77)
ASHLGLAR
(SEQ ID NO: 83)

C3f fragment, Human c3 (1286-1297)
(SEQ ID NO: 84)
THRIHWESASLL

C3f, Human c3 (1282-1298)
(SEQ ID NO: 85)
SSKITHRIHWESASLLR

Complement anaphylatoxin C5a (37-53), human
(SEQ ID NO: 86)
RAARISLGPRCIKAFTE

α-CGRP (19-37), human
(SEQ ID NO: 87)
SGGVVKNNFVPTNVGSKAF-NH2

{Tyr0}-α-CGRP, human
(SEQ ID NO: 88)
YACDTATCVTHRLAGLLSRSGGVVKNNFVPTNVGSKAF-NH2 (Disulfide bridge: between amino acids 3 and 8)

Biotin-Calcitonin, human
(SEQ ID NO: 89)
Biotin-CGNLSTCMLGTYTQDFNKFHTFPQTAIGVGAP-NH2 (Disulfide bridge: between amino acids 1-7)

Calcitonin Gene Related Peptide, CGRP (8-37), human
(SEQ ID NO: 90)
VTHRLAGLLSRSGGVVKNNFVPTNVGSKAF-NH2

Calcitonin Gene Related Peptide, CGRP (8-37), rat
(SEQ ID NO: 91)
VTHRLAGLLSRSGGVVKDNFVPTNVGSEAF-NH2

Calcitonin Gene Related Peptide, CGRP, chicken
(SEQ ID NO: 92)
ACNTATCVTHRLADFLSRSGGVGKNNFVPTNVGSKAF-NH2 (Disulfide bridge: 2-7)

Calcitonin Gene Related Peptide, CGRP, human
(SEQ ID NO: 93)
ACDTATCVTHRLAGLLSRSGGVVKNNFVPTNVGSKAF-NH2 (Disulfide bridge: 2-7)

Calcitonin N-Terminal Flanking Peptide, human, N-Procalcitonin
(SEQ ID NO: 94)
APFRSALESSPADPATLSEDEARLLLAALVQDYVQMKASELEQEQEREGSSLDSPRS Calcitonin, chicken
(SEQ ID NO: 95)
CASLSTCVLGKLSQELHKLQTYPRTDVGAGTP-NH2 (Disulfide bridge: 1-7)

Calcitonin, eel
(SEQ ID NO: 96)
CSNLSTCVLGKLSQELHKLQTYPRTDVGAGTP-NH2 (Disulfide bridge: 1-7)

Calcitonin, human
(SEQ ID NO: 102)
CGNLSTCMLGTYTQDFNKFHTFPQTAIGVGAP-NH2 (Disulfide bridge: 1-7)

Calcitonin, human, FAM-labeled
(SEQ ID NO: 97)
FAM-CGNLSTCMLGTYTQDFNKFHTFPQTAIGVGAP-NH2 (Disulfide bridge: 1-7)

Calcitonin, porcine
(SEQ ID NO: 98)
CSNLSTCVLSAYWRNLNNFHRFSGMGFGPETP-NH2 (Disulfide bridge: 1-7)

Calcitonin, rat
(SEQ ID NO: 99)
CGNLSTCMLGTYTQDLNKFHTFPQTSIGVGAP-NH2 (Disulfide bridge: 1-7)

Calcitonin, salmon
(SEQ ID NO: 100)
CSNLSTCVLGKLSQELHKLQTYPRTNTGSGTP-NH2 (Disulfide bridge: 1-7)

Calcitonin-Lys(Biotin), human
(SEQ ID NO: 101)
CGNLSTCMLGTYTQDFNKFHTFPQTAIGVGAPK(Biotin) (Disulfide bridge: 1-7)

Calcitonin-Lys(Biotin), human, FAM-labeled
FAM-CGNLSTCMLGTYTQDFNKFHTFPQTAIGVGAPK(Biotin)
(Disulfide bridge: 1-7)

{-2}pPSA, Prostate-Specific Antigen, truncated (SEQ ID NO: 103)

SRIVGGWECEK

{-4}pPSA (SEQ ID NO: 104)

ILSRIVGGWECEK

{A90,95} Bid BH3 (77-100), mouse (SEQ ID NO: 105)

ESQEEIIHNIARHAAQIGAEMDHN

{Ala6, Val15} MUC5AC Analog 2 (SEQ ID NO: 106)

GTTPSAVPTTSTTSVP

{APLILSR}pPSA (SEQ ID NO: 107)

APLILSRIVGGWECEK

{Arg67}Bax H2-H3 (53-86), {R67} Helix 2-3 (53-86), mutant (SEQ ID NO: 108)

DASTKKLSECLKRIRDELDSNMELQRMIAAVDTD

{Asn370} tyrosinase (368-376) (SEQ ID NO: 109)

YMNGTMSQV

{Asp370}-Tyrosinase (368-376) (SEQ ID NO: 110)

YMDGTMSQV

{Cys(Acm)33}-Endostatin (6-49) (SEQ ID NO: 111)

FQPVLHLVALNSPLSGGMRGIRGADFQ-C(Acm)-FQQARAVGLAGTFRAF

{Gln340}-Maspin, Reactive Site Loop (RSL), (330-345) (SEQ ID NO: 112)

GGDSIEVPGAQILQHK

{Glu63} Bax BH3, mutant (SEQ ID NO: 57)

STKKLSECEKRIGDELDSNM

{Ile12, Val15} MUC5AC Analog 3 (SEQ ID NO: 113)

GTTPSPVPTTSITSVP

{Ile161}MAGE-A2 (157-166) (SEQ ID NO: 114)

YLQLIFGIEV

{pSer155}-BAD BH3 (146-159) (SEQ ID NO: 115)

RYGRELRRM-pS-DEFE

{pThr145}-p21 (140-147) (SEQ ID NO: 116)

RKRRQ-pT-SM

{Ser244} Tyrosinase (240-251) (SEQ ID NO: 117)

DAEKSDICTDEY

{Val165}NY-ESO-1(157-165) (SEQ ID NO: 118)

SLLMWITQV

234 CM (SEQ ID NO: 119)

KYICNSSCM

234 CW (SEQ ID NO: 120)

KYMCNSSCM

53BP2 (490-498), p53-Binding Loop (CDB3)

REDEDEIEW (SEQ ID NO: 121)

Adipophilin

SVASTITGV (SEQ ID NO: 122)

Amphoterin (150-183)

KLKEKYEKDIAAYRAKGKPDAAKKGVVKAEKSKK (SEQ ID NO: 123)

Antennapedia Bak BH3 (Ant-BH3) (71-89) Fusion peptide

RQIKIWFQNRRMKWKKMGQVGRQLAIIGDDINRRY (SEQ ID NO: 124)

Anti-Flt1 Peptide

GNQWFI (SEQ ID NO: 1366)

Bad (103-127), human, all d-isomers
nlwaaqrygrelrrmsdefvdsfkk
BAD (CT-1)

KKGLPRPKSAGTATQMRQSSSWTC-NH2 (SEQ ID NO: 126)

BAD BH3 (103-123)

NLWAAQRYGRELRRMSDEFVD (SEQ ID NO: 127)

BAD BH3 (146-159)

RYGRELRRMSDEFE (SEQ ID NO: 128)

BAD Peptide, biotin-labeled

Biotin-LC-AGAGRSRHSSYPAGT (SEQ ID NO: 129)

BAFF-R (160-183)

SVPVPATELGSTELVTTKTAGPEQ (SEQ ID NO: 130)

BAGE (2-10)

AARAVFLAL (SEQ ID NO: 131)

Bak BH3

GQVGRQLAIIGDDINR (SEQ ID NO: 132)

Bak BH3 (67-87)

PSSTMGQVGRQLAIIGDDINR (SEQ ID NO: 133)

Bak BH3 (69-93)

STMGQVGRQLAIIGDDINRRYDSEF (SEQ ID NO: 134)

Bak BH3 (71-89)

MGQVGRQLAIIGDDINRRY (SEQ ID NO: 135)

Bak BH3 (73-87)

QVGRQLAIIGDDINR (SEQ ID NO: 136)

Bak BH3 peptide, Mca labeled
7-methoxycoumarine-4-yl acetyl (Mca)-GQVGRQLAIIGDDINR
Bax BH3

KKLSECLKRIGDELDS (SEQ ID NO: 137)

Bax BH3 (58-71)

KLSECLKRIGDELD (SEQ ID NO: 138)

-continued

Bax BH3 peptide (55-74), wild type
STKKLSECLKRIGDELDSNM
Bax BH3L63A
(SEQ ID NO: 139)
KKLSECAKRIGDELDS Bax H2-H3 (53-86), Helix 2-3
(SEQ ID NO: 140)
DASTKKLSECLKRIGDELDSNMELQRMIAAVDTD Bax H3 (71-86), Helix 3 (71-86)
(SEQ ID NO: 141)
DSNMELQRMIAAVDTD Bax I
(SEQ ID NO: 142)
PQDASTKKLSECLKRIGDELDSNMEL Bcl 9-2
(SEQ ID NO: 58)
GSEGLSKEQLEHRERSLQTLRDIERLLLRSGETEPFLKGPPGGAG-NH2

Bcl-2 BH3 (85-105)
(SEQ ID NO: 143)
ALSPVPVVHLTLRQAGDFSRR

Bcl-2 BH3 Peptide II
(SEQ ID NO: 144)
LSPVPPVVHLALRQAGDDFSRRYRG

Bcl-2 Binding Peptide, Bad BH3 Peptide
(SEQ ID NO: 145)
LWAAQRYGRELRRMSDEFEGSFKGL Bcl-XL BH3 (85-98)
(SEQ ID NO: 146)
AVKQALREAGDEFE Bcl9-2, mutant
(SEQ ID NO: 147)
GSEGLSKEQLEHRERSFQTLRDIERLLLRSGETEPFLKGPPGGAG-NH2

BDC2.5(A)
(SEQ ID NO: 148)
GKKVAAPAWARMG

BH3 BIM Peptide (52-71), human
(SEQ ID NO: 149)
Ac-MRPEIWIAQELRRIGDEFNA

Bid BH3 (77-100), mouse
(SEQ ID NO: 150)
ESQEEIIHNIARHLAQIGDEMDHN

Bid BH3 (79-99)
(SEQ ID NO: 151)
QEDIIRNIARHLAQVGDSMDR

Bid BH3 (85-98)
(SEQ ID NO: 152)
NIARHLAQVGDSMD

Bid BH3 Peptide
(SEQ ID NO: 153)
EDIIRNIARHLAQVGDSMDR

Bid BH3, FAM labeled
(SEQ ID NO: 153)
5-FAM-EDIIRNIARHLAQVGDSMDR

Bid BH3, Peptide II, TAMRA labeled
(SEQ ID NO: 153)
5-TAMRA-EDIIRNIARHLAQVGDSMDR Bid BH3-r8
$_dR_dR_dR_dR_dR_dR_dR_dR$-GEDIIRNIARHLAQVGDSMDR
Bid BH3-R8
(SEQ ID NO: 156)
RRRRRRRRGEDIIRNIARHLAQVGDSMDR -continued Bid BH3-R9 (SEQ ID NO: 157)
RRRRRRRRRGEDIIRNIARHLAQVGDSMDR Bid-BH3 (SEQ ID NO: 158)
RNIARHLAQVGDSMDR Bik BH3 (50-70)
Bik BH3 (56-69) (SEQ ID NO: 159)
ALALRLACIGDEMD BIK BH3 Peptide (SEQ ID NO: 160)
MEGSDALALRLACIGDEMDV Bim BH3 (87-100) (SEQ ID NO: 161)
WIAQELRRIGDEFN Bim BH3 Fragment I, TAMRA labeled (SEQ ID NO: 162)
5-TAMRA-DNRPEIWIAQELRRIGDEFNAYYAR Bim BH3, Fragment II, TAMRA labeled (SEQ ID NO: 163)
5-TAMRA-MRPEIWIAQELRRIGDEFNA Bim BH3, Peptide III (SEQ ID NO: 164)
DMRPEIWIAQELRRIGDEFNAYYAR Bim BH3, Peptide IV (SEQ ID NO: 165)
DMRPEIWIAQELRRIGDEFNAYYARR Bim-23056 (SEQ ID NO: 166)
fFYwKVFnal-NH2

BMF BH3 peptide (SEQ ID NO: 167)
HQAEVQIARKLQLIADQFHR

BNIP3-α BH3 peptide (SEQ ID NO: 168)
VVEGEKEVEALKKSADWVSD

BRCAA1 (610-619) (SEQ ID NO: 169)
SSKKQKRSHK c-Myc peptide epitope (SEQ ID NO: 170)
EQKLISEEDL CEA, CAP-1, Carcinoembryonic Antigen (SEQ ID NO: 171)
YLSGANLNL CEA Related, QYSWFVNGTF (SEQ ID NO: 172)
QYSWFVNGTF CEA Related, TYACFVSNL (SEQ ID NO: 173)
TYACFVSNL CEA, CAP-1-6-D, {Asp6}-Carcinoembryonic Antigen (SEQ ID NO: 174)
YLSGADLNL Cell Penetrating ARF Peptide (26-44) (SEQ ID NO: 175)
dR dR dR dR dR dR dR dR dR KFVRSRRPRTASCALAFVN Cell Penetrating Mutant ARF (37-44) Peptide (SEQ ID NO: 176)
dR dR dR dR dR dR dR dR dR SCALAFVN -continued Cripto-1, CR-1

CPPSFYGRNCEHDVRKE (SEQ ID NO: 177)

CTT, Gelatinase Inhibitor

CTTHWGFTLC (Disulfide Bridge: 1-10) (SEQ ID NO: 178)

Cys-p21 (139-154)

CGRKRRQTSMTDFYHSK (SEQ ID NO: 179)

E7 (43-62), HPV Oncoprotein

GQAEPDRAHYNIVTFCCKCD (SEQ ID NO: 180)

E7 (43-77), HPV Oncoprotein

GQAEPDRAHYNIVTFCCKCDSTLRLCVQSTHVDIR (SEQ ID NO: 181)

EGFR (662-681)

RRELVEPLTPSGEAPNQALLR (SEQ ID NO: 182)

Ep-CAM (263-271)

GLKAGVIAV (SEQ ID NO: 183)

Epidermal Mitosis Inhibiting Pentapeptide

Pyr-EDSG (SEQ ID NO: 184)

F4.2, Gastric Signet Ring Cell Carcinoma Derived Peptide

YSWMDISCWI (SEQ ID NO: 185)

G154, gp100 (154-162)

KTWGQYWQV (SEQ ID NO: 186)

G209, gp100 (209-217)

ITDQVPFSV (SEQ ID NO: 187)

G209-2M, gp100 (209-217)

IMDQVPFSV (SEQ ID NO: 188)

G280-9, gp100 (280-288), Lys (biotin)

YLEPGPVTA-K(Biotin) (SEQ ID NO: 189)

G280-9V, gp100(280-288) Lys(biotin)

YLEPGPVTV-K(Biotin) (SEQ ID NO: 190)

GAD65 (206-220)

TYEIAPVFVLLEYVT (SEQ ID NO: 191)

GAD65 (78-97)

KPCNCPKGDVNYAFLHATDL (SEQ ID NO: 192)

GnT-V (nt38-67)

VLPDVFIRCV (SEQ ID NO: 193)

gp100 (177-186)

AMLGTHTMEV (SEQ ID NO: 194)

gp100 (178-187)

MLGTHTMEV (SEQ ID NO: 195)

gp100 (25-33), human

KVPRNQDWL (SEQ ID NO: 196)

| | |
|---|---|
| gp100 (457-466)<br>LLDGTATLRL | (SEQ ID NO: 197) |
| gp100 (476-485)<br>VLYRYGSFSV | (SEQ ID NO: 198) |
| gp100 (570-579)<br>SLADTNSLAV | (SEQ ID NO: 199) |
| gp100 (614-622)<br>LIYRRRLMK | (SEQ ID NO: 200) |
| gp100 (619-627)<br>RLMKQDFSV | (SEQ ID NO: 201) |
| gp100 (639-647)<br>RLPRIFCSC | (SEQ ID NO: 202) |
| GPC3 (144-152)<br>FVGEFFTDV | (SEQ ID NO: 203) |
| GPC3 (298-306), mouse<br>EYILSLEEL | (SEQ ID NO: 204) |
| GRP78 Binding Chimeric Peptide Motif<br>WIFPWIQL-GG-klaklakklaklak-NH2 | (SEQ ID NO: 205) |
| hACC1 (1258-1271), phosphorylated<br>DSPPQ-pS-PTFPEAGH | (SEQ ID NO: 206) |
| HB-1 (18-41)<br>WKSELVEVDDVYLRHSSSLTYRL | (SEQ ID NO: 207) |
| HB-1 (26-41)<br>EDDVYLRHSSSLTYRL | (SEQ ID NO: 208) |
| HER-2/Neu (654-662), GP2<br>IISAVVGIL | (SEQ ID NO: 209) |
| HIF-1 {alpha} (556-574)<br>DLDLEMLAPYIPMDDDFQL | (SEQ ID NO: 210) |
| HIF-2 (66-84)<br>SLEAQGIKADRETVAVKPT | (SEQ ID NO: 211) |
| HPV16 E7(86-93)<br>TLGIVCPI | (SEQ ID NO: 212) |
| HRK BH3 Peptide<br>SSAAQLTAARLKALGDELHQ | (SEQ ID NO: 213) |
| IL-11R-alpha Binding Peptide II<br>CGRRAGGSC (S—S bonded) | (SEQ ID NO: 214) |
| iLRP1, iLRP, Immature Laminin Receptor Protein (58-66)<br>LLLAARAIV | (SEQ ID NO: 215) |
| iLRP2, iLRP (60-68)<br>LAARAIVAI | (SEQ ID NO: 216) |

-continued iLRP3, iLRP(146-154)
ALCNTDSPL (SEQ ID NO: 217)

iLRP4, iLRP(7-15)
VLQMKEEDV (SEQ ID NO: 218)

IP3 peptide, (Lys)TAMRA labeled
MPRFMDYWEGLN-K(5/6-TMR) (SEQ ID NO: 219)

IP3 peptide, Acetylated and Biotinylated
Ac-MPRFMDYWEGLNK-K(Biotin) (SEQ ID NO: 220)

IP3 Truncated Peptide, Acetylated
Ac-FMDYWEGLN (SEQ ID NO: 221)

Kisspeptin-10, Metastin (45-54)
YNWNSFGLRF-NH2 (SEQ ID NO: 222)

KM-HN-1(107-116)
VFGTRIEKDL (SEQ ID NO: 223)

KM-HN-1(196-204)
NYNNFYRFL (SEQ ID NO: 224)

KM-HN-1(335-343)
HFCRKCKKL (SEQ ID NO: 225)

KM-HN-1(499-508)
EYSKECLKEF (SEQ ID NO: 226)

KM-HN-1(65-74)
SFQALRMQTL (SEQ ID NO: 227)

KM-HN-1(770-778)
EYLSLSDKI (SEQ ID NO: 228)

Laminin Peptide (CDPGYIGSR) NEW
CDPGYIGSR-NH2 (SEQ ID NO: 229)

Livin7, ML-IAP
KWFPSCQFLL (SEQ ID NO: 230)

LyP-1, Peptide 1 NEW
CGNKRTRGC (S—S Bonded) (SEQ ID NO: 231)

LyP-1, Peptide 2
CGNKRTRGC (SEQ ID NO: 232)

MAGE-1 (161-169)
EADPTGHSY (SEQ ID NO: 233)

MAGE-1 (230-238)
STAPPAHGV (SEQ ID NO: 234)

MAGE-3 (112-120)
KVAELVHFL (SEQ ID NO: 235)

MAGE-3 (114-127)
AELVHFLLLKYRAR (SEQ ID NO: 236)

-continued

MAGE-3 (121-134)

LLKYRAREPVTKAE (SEQ ID NO: 237)

MAGE-3 (161-169)

EVDPIGHLY (SEQ ID NO: 238)

MAGE-3 (271-279)

FLWGPRALV (SEQ ID NO: 239)

MAGE-A 1(96-104)

SLFRAVITK (SEQ ID NO: 240)

MAGE-A1 (237-245)

KLLTQDLVQ (SEQ ID NO: 241)

MAGE-A1 Antigen (278-286), human

KVLEYVIKV (SEQ ID NO: 242)

MAGE-A10 (183-191)

MLLVFGIDV (SEQ ID NO: 43)

MAGE-A10 (254-262)

GLYDGMEHL (SEQ ID NO: 244)

MAGE-A2 (112-120)

KMVELVHFL (SEQ ID NO: 245)

MAGE-A2 (157-166)

YLQLVFGIEV (SEQ ID NO: 246)

MAGE-A3 (167-176)

MEVDPIGHLY (SEQ ID NO: 247)

MAGE-A3 (195-203)

IMPKAGLLI (SEQ ID NO: 248)

MAGE-A4 Antigen (230-239), human

GVYDGREHTV (SEQ ID NO: 249)

MAGE-C2 (336-344)

ALKDVEERV (SEQ ID NO: 250)

Malaria CSP (334-342)

YLKKIKNSL (SEQ ID NO: 251)

Maspin Reactive Site Loop (RSL), (330-345)

GGDSIEVPGARILQHK (SEQ ID NO: 252)

Melan-A/MART-1 (24-34)

AEEAAGIGILT (SEQ ID NO: 253)

Melanoma Antigen Family A 3 (196-204); MAGE-3 (196-204)

MPKAGLLII (SEQ ID NO: 254)

Melanoma Antigen Family A 8 (115-123); MAGE-8 (115-123)

KVAELVRFL (SEQ ID NO: 255)

Melanoma Antigen Family A 9B (223-231), MAGE-9B (223-231)

ALSVMGVYV (SEQ ID NO: 256)

-continued

Melanosomal Antigen II  
DAEKCDKTDEY (SEQ ID NO: 257)

MUC-1 (9-17)  
STAPPAHGV (SEQ ID NO: 234)

MUC1, tandem repeat fragment  
PDTRPAPGSTAPPAHGVTSA (SEQ ID NO: 258)

MUC5AC 3  
GT-T*-PSPVPTTSTTSAP (SEQ ID NO: 259)

MUC5AC, Analog 1  
GTTPSPVPTTSTTSAP (SEQ ID NO: 260)

MUC5AC, Analog B  
TTSTTSAPTTS (SEQ ID NO: 261)

MUC5AC-13  
GTTPSPVPTTST-T*-SAP (SEQ ID NO: 262)

MUC5AC-3/13  
GT-T*-PSPVPTTST-T*-SAP (SEQ ID NO: 263)

MUM-1 (261-269)  
EEKLIVVLF (SEQ ID NO: 264)

MycC Peptide  
YEQLRNSRA (SEQ ID NO: 265)

MZ2-F  
YRPRPRRY (SEQ ID NO: 266)

NES Adenoviral E1A  
VMLAVQEGIDL (SEQ ID NO: 267)

NES Nmd3p (491-500)  
INIDELLDEL (SEQ ID NO: 268)

NES p120ctn  
CSLEEELDVLVLDDEGG (SEQ ID NO: 269)

NES Topoisomerase II alpha (1054-1066)  
FILEKIDGKIIIE (SEQ ID NO: 270)

Noxa A BH3 peptide  
AELPPEFAAQLRKIGDKVYC (SEQ ID NO: 271)

Noxa A BH3 peptide, cell permeable  
dR dR dR dR dR dR dR dR GAELPPEFAAQLRKIGDKVYC (SEQ ID NO: 272)

NuBCP-9 A  
FSRSLHSLL (SEQ ID NO: 273)

Nuclear Export Signal, NES HIV Rev  
LQLPPLERLTLD (SEQ ID NO: 274)

Nuclear Export Signal, NES MAPKK  
ALQKKLEELELD (SEQ ID NO: 275)

-continued

Nuclear Export Signal, NES p53

FRELNEALELKD (SEQ ID NO: 276)

NY-ESO-1 (53-62)

ASGPGGGAPR (SEQ ID NO: 277)

ORF5 fragment

PASKKTDPQK (SEQ ID NO: 278)

p21 (140-147)

RKRRQTSM (SEQ ID NO: 279)

p53 (12-20)

PPLSQETFS (SEQ ID NO: 280)

p53 (17-26)

ETFSDLWKLL (SEQ ID NO: 281)

p53 (17-26), FITC labeled

FITC-LC-ETFSDLWKLL-NH2 (SEQ ID NO: 282)

p53 (65-73)

RMPEAAPPV (SEQ ID NO: 283)

p53 Mutant Form (361-371), Pab 421

KKGQSTSRHKK-NH2 (SEQ ID NO: 284)

p53 Tumor Suppressor (361-393), human

GSRAHSSHLKSKKGQSTSRHKKLMFKTEGPDSD (SEQ ID NO: 285)

p53 Tumor Suppressor (361-393), LC-Biotin, human

Biotin-LC-GSRAHSSHLKSKKGQSTSRHKKLMFKTEGPDSD-NH2 (SEQ ID NO: 286)

p53, (12-26)

PPLSQETFSDLWKLL (SEQ ID NO: 287)

Pirh2-Derived Peptide (CDB62) (120-137)

LKCNLCLTTNLRGKHKCI (SEQ ID NO: 288)

PNC-28, MDM Binding Domain

ETFSDLWKLLKKWKMRRNQFWVKVQRG (SEQ ID NO: 289)

PRAME epitope (PRA300-309) Tumor-associated antigen

ALYVDSLFFL (SEQ ID NO: 290)

Pro-TGF-α

HADLLAVVAASQ (SEQ ID NO: 291)

Pro-TGF-α

HADLLAVVAASQ (SEQ ID NO: 292)

Prostate Vasculature Marker, biotin-labeled

SMSIARL-K(epsilon-LC-Biotin) (SEQ ID NO: 293)

Prostate-Specific Antigen, PSA propeptide

APLILSR (SEQ ID NO: 294)

PSA1 (141-150)

FLTPKKLQCV (SEQ ID NO: 295)

-continued

PSA2 (146-154) (SEQ ID NO: 296)
KLQCVDLHV

Rab24 (179-199) (SEQ ID NO: 297)
QVMTEDKGVDLSQKANPYFYS

Rad51 (175-190) (CDB55) (SEQ ID NO: 298)
AERYGLSGSDVLDNVA

Rad51 (179-190) (SEQ ID NO: 299)
GLSGSDVLDNVA

RAGE derived peptide (SEQ ID NO: 300)
SPSSNRIRNT

Shepherdin (79-87) (SEQ ID NO: 301)
KHSSGCAFL

Stromal Target Antigen (SEQ ID NO: 302)
SIYYYRYGL

STT Gelatinase Inhibitor modification, negative control (SEQ ID NO: 303)
STTHWGFTLS Survivin (SEQ ID NO: 304)
ELTLGEFLKL Survivin (85-93) (SEQ ID NO: 305)
AFLSVKKQF Survivin 2B (80-88) (SEQ ID NO: 306)
AYACNTSTL Telomerase Reverse Transcriptase p572Y (TERT572Y) (SEQ ID NO: 307)
RLFFYRKSV TP53 Q9NP68, p53 Mutant Form (361-377), Lys371 (Ac) (SEQ ID NO: 308)
KKGQSTSRHK-K(Ac)-LMFKTEG TRP-1, Fragment (SEQ ID NO: 309)
MSLQRQFL

TRP-2 (180-188) NEW (SEQ ID NO: 310)
SVYDFFVWL

TRP-2 coding region fragment (SEQ ID NO: 311)
LLPGGRPYR

Tumor Necrosis Factor-a Converting Enzyme, TACE (807-823), human (SEQ ID NO: 312)
ASFKLQRQNRVDSKETE Tyrosinase (146-156) (SEQ ID NO: 313)
SSDYVIPIGTY Tyrosinase (192-200) (SEQ ID NO: 314)
SEIWRDIDF Tyrosinase (206-214), T9206 (SEQ ID NO: 315)
AFLPWHRLF -continued Tyrosinase (240-251)

DAEKCDICTDEY (SEQ ID NO: 316)

Tyrosinase (450-462)

SYLQDSDPDSFQD (SEQ ID NO: 317)

Tyrosinase (56-70)

QNILLSNAPLGPQFP (SEQ ID NO: 318)

Tyrosinase (243-251), core nonamer sequence

KCDICTDEY (SEQ ID NO: 319)

VEGFR-2/KDR I, murine

FSNSTNDILI (SEQ ID NO: 320)

VEGFR-2/KDR II, murine

VILTNPISM (SEQ ID NO: 321)

VEGFR2/KDR Antagonist

ATWLPPR (SEQ ID NO: 322)

WP9QY, TNF-alpha Antagonist

YCWSQYLCY (Disulfide bridge: 2-8)

(SEQ ID NO: 323)

Human Cardiac Troponin I (hcTnI) (39-58)

SKISASRKLQLKTLLLQIAK (SEQ ID NO: 324)

CART (55-102), human

VPIYEKKYGQVPMCDAGEQCAVRKGARIGKLCDCPRGTSCNSFLL

KCL (Disulfide bridge: 74-94, 68-86, and 88-101)

(SEQ ID NO: 325)

β-Casomorphin (1-7), human

YPFVEPI (SEQ ID NO: 326)

Caspase Related Peptides
Ac-AEVD-pNA

Ac-AEVD-pNA

Biotin-Caspase 1 Inhibitor II

Biotin-YVAD-CMK

Biotin-Caspase 1 Substrate V

Caspase 1 (ICE) Inhibitor I

Ac-YVAD-CHO (SEQ ID NO: 327)

Caspase 1 (ICE) Substrate 1, chromogenic

Ac-YEVD-pNA (SEQ ID NO: 328)

Caspase 1 (ICE) Substrate 1m, fluorogenic

Ac-YEVD-AMC (SEQ ID NO: 329)

Caspase 1 (ICE) Substrate 2, chromogenic

Ac-YVAD-pNA (SEQ ID NO: 330)

Caspase 1 (ICE) Substrate 2f, fluorogenic
Ac-YVAD-AFC

Caspase 1 (ICE) Substrate 2f, fluorogenic
Ac-YVAD-AFC

Caspase 1 (ICE) Substrate 2m, fluorogenic
Ac-YVAD-AMC

-continued

Caspase 1 (ICE) Substrate 2r, fluorogenic
(Ac-YVAD)2-Rh110

Caspase 1 (ICE) Substrate 3f, fluorogenic
(SEQ ID NO: 331)
Ac-WEHD-AFC

Caspase 1 (ICE) Substrate 3f, fluorogenic
Ac-WEHD-AFC

Caspase 1 (ICE) Substrate 3m, fluorogenic
(SEQ ID NO: 332)
Ac-WEHD-AMC

Caspase 1 (ICE) Substrate 3r, fluorogenic
(Ac-WEHD)2-Rh110

Caspase 1 (ICE) substrate for FRET assays
DABCYL-YVADAPV-EDANS

Caspase 1 Inhibitor

Caspase 1 Inhibitor I

Caspase 1 Inhibitor II
Ac-YVAD-CMK

Caspase 1 Inhibitor IV, Boc-D-CMK
Boc-D(OBzl)-CMK

Caspase 1 Inhibitor VIII
Ac-WEHD-CHO

Caspase 1 Substrate III
(SEQ ID NO: 334)
Ac-WEHD-pNA

Caspase 2 (ICH-1) Substrate 1, chromogenic
(SEQ ID NO: 335)
Ac-VDVAD-pNA

Caspase 2 (ICH-1) Substrate 1, chromogenic
Ac-VDVAD-pNA

Caspase 2 (ICH-1) Substrate 1f, fluorogenic
Ac-VDVAD-AFC

Caspase 2 (ICH-1) Substrate 1m, fluorogenic
Ac-VDVAD-AMC

Caspase 2 (ICH-1) Substrate 2, fluorogenic
(SEQ ID NO: 336)
Mca-VDVADGWK(Dnp)-NH2

Caspase 2 Inhibitor
(SEQ ID NO: 337)
Ac-VDVAD-CHO

Caspase 2 Substrate 3r
(SEQ ID NO: 338)
(D)2-Rh110

Caspase 2 Substrate, chromogenic
Ac-VDQQD-pNA

Caspase 3 (163-175)
(SEQ ID NO: 339)
CRGTELDCGIETD

Caspase 3 (Apopain) Inhibitor 1
(SEQ ID NO: 340)
Ac-DEVD-CHO

Caspase 3 (Apopain) Inhibitor 1b
(SEQ ID NO: 341)
Biotin-DEVD-CHO

Caspase 3 (Apopain) Substrate 1, chromogenic
Ac-DEVD-pNA

-continued

Caspase 3 (Apopain) Substrate 1f, fluorogenic
Ac-DEVD-AFC

Caspase 3 (Apopain) Substrate 1m, fluorogenic
Ac-DEVD-AMC

Caspase 3 (Apopain) Substrate 1m, fluorogenic
Ac-DEVD-AMC

Caspase 3 (Apopain) Substrate 1r-z, fluorogenic
(Z-DEVD)2-Rh110

Caspase 3 (Apopain) Substrate 1z, chromogenic
Z-DEVD-pNA

Caspase 3 (Apopain) Substrate 2, chromogenic
(SEQ ID NO: 342)
Ac-DQMD-pNA

Caspase 3 Inhibitor 1
(SEQ ID NO: 343)
Ac-DMQD-CHO

Caspase 3 Substrate 1, chromogenic
(SEQ ID NO: 344)
Ac-DMQD-pNA

Caspase 3 Substrate 1f, fluorogenic
Ac-DMQD-AFC

Caspase 3 Substrate 1m, fluorogenic
Ac-DMQD-AMC

Caspase 3 Substrate 1r, fluorogenic
(Ac-DMQD)2-Rh110

Caspase 3 Substrate, chromogenic
(SEQ ID NO: 345)
Ac-VQVD-pNA

Caspase 4 (ICH-2) Substrate 1, chromogenic
(SEQ ID NO: 346)
Ac-LEVD-pNA

Caspase 4 (ICH-2) Substrate 1f, fluorogenic
Ac-LEVD-AFC

Caspase 4 (ICH-2) Substrate 1m, fluorogenic
Ac-LEVD-AMC

Caspase 4 (ICH-2) Substrate 1r, fluorogenic
(Ac-LEVD)2-Rh110

Caspase 6 (Mch 2) Inhibitor 1
(SEQ ID NO: 347)
Ac-VEID-CHO

Caspase 6 (Mch2) Substrate 1, chromogenic
(SEQ ID NO: 348)
Ac-VEID-pNA

Caspase 6 (Mch2) Substrate 1f, fluorogenic
Ac-VEID-AFC

Caspase 6 (Mch2) Substrate 1m, fluorogenic
Ac-VEID-AMC

Caspase 6 (Mch2) Substrate 1r, fluorogenic
(Ac-VEID)2-Rh110

Caspase 6 (Mch2) Substrate 2, fluorogenic
Mca-VQVDGW-K(Dnp)-NH2

Caspase 6 Substrate V, fluorogenic
Ac-VEHD-AFC

Caspase 8 Inhibitor 1
Ac-IETD-CHO

Caspase 8 Substrate 1, chromogenic
Ac-IETD-pNA

-continued

Caspase 8 Substrate 1f, fluorogenic
Ac-IETD-AFC

Caspase 8 Substrate 1f-z, fluorogenic
Z-IETD-AFC

Caspase 8 Substrate 1m, fluorogenic
Ac-IETD-AMC

Caspase 8 Substrate 1r-z, fluorogenic
(Z-IEHD)2-Rh110

Caspase 8 Substrate 1r-z, fluorogenic
(Z-IETD)2-Rh110

Caspase 9 Substrate 1, chromogenic
Ac-LEHD-pNA

Caspase 9 Substrate 1f, fluorogenic
Ac-LEHD-AFC

Caspase 9 Substrate 1r, fluorogenic
(Ac-LEHD)2-Rh110

Caspase 9 Substrate 2m, fluorogenic
Ac-LEHD-AMC

Caspase Inhibitor II CHO
Ac-VAD-CHO

Caspase Inhibitor II CMK
Ac-VAD-CMK

Caspase-1 Substrate V, Fluorogenic
Mca-YVADAP-K(Dnp)

Caspase-1/Caspase-4 Substrate II, Fluorogenic
Ac-WVAD-AMC

ICE Inhibitor I, cell permeable
(SEQ ID NO: 349)
Ac-AAVLPAVLLALLAPYVAD-CHO

Smac N7 Protein
AVPIAQK

Z-DEVD-AFC
(SEQ ID NO: 350)
Z-DEVD-AMC 37, 43Gap 27, Connexin Mimetic
(SEQ ID NO: 351)
SRPTEKTIFII 37, 40 GAP26, Connexin Mimetic
(SEQ ID NO: 352)
VCYDQAFPISHIR 40Gap 27, Connexin Mimetic
(SEQ ID NO: 353)
SRPTEKNVFIV 43Gap 26, Connexin Mimetic
(SEQ ID NO: 354)
VCYDKSFPISHVR 43Gap 36, Connexin Mimetic
(SEQ ID NO: 355)
KRDPCHQVDCFLSRPTEK Alpha B-Crystallin (73-92)
(SEQ ID NO: 356)
DRFSVNLDVKHFSPEELKVK Calreticulin (CRT) Binding Peptide 1
(SEQ ID NO: 357)
GQPMYGQPMY -continued Calreticulin (CRT) Binding Peptide 1, biotin-labeled
BIOTIN-GQPMYGQPMY

DAM1 (221-241) (SEQ ID NO: 358)
SFVLNPTNIGMSKSSQGHVTK

Hyaluronan Inhibitor (SEQ ID NO: 359)
GAHWQFNALTVR

L1CD cell adhesion molecule (1144-1163) (SEQ ID NO: 360)
KRSKGGKYSVKDKEDTQVDS

L1FLCD (1173-1185) (SEQ ID NO: 361)
FGEYRSLESDNEE pALA, Polyalanine Peptide (SEQ ID NO: 362)
AAADAAAAL

S1P1 (SEQ ID NO: 363)
VSTSIPEVKALRSSVSDYGNYDIIVRHYNYTGKLNIGAEKDHGIK

Pen2W2F, FAM Labeled (SEQ ID NO: 364)
5-FAM-RQIKIFFQNRRMKFKK-NH2

Hel 11-7 NEW (SEQ ID NO: 365)
KLLKLLLKLWLKLLKLLL

HIV-1 Rev (34-50) (SEQ ID NO: 366)
TRQARRNRRRRWRERQR

HIV-1 Tat (48-60) (SEQ ID NO: 367)
GRKKRRQRRRPPQ

Human T-cell Lymphotrophic Virus (HTLV)-II Rex, (4-16) (SEQ ID NO: 368)
TRRQRTRRARRNR Lipid Membrane Translocating Peptide (SEQ ID NO: 369)
KKAAAVLLPVLLAAP Lipid Membrane Translocating Peptide, D-isomer (SEQ ID NO: 370)
kkaaavllpvllaap Mastoparan (SEQ ID NO: 371)
INLKALAALAKKIL-NH2

Mastoparan 7 (SEQ ID NO: 372)
INLKALAALAKALL-NH2

Mastoparan X (SEQ ID NO: 373)
INWKGIAAMAKKLL-NH2

MEK1 Derived Peptide Inhibitor 1 (SEQ ID NO: 374)
MPKKKPTPIQLNP

Membrane-Permeable Sequence, MPS (SEQ ID NO: 375)
AAVALLPAVLLALLAK

MPGΔNLS, HIV related; (SEQ ID NO: 376)
GALFLGFLGAAGSTMGAWSQPKSKRKV

-continued

MPS-Gαi2  (SEQ ID NO: 377)
AAVALLPAVLLALLAKNNLKDCGLF

MPS-Gαi3  (SEQ ID NO: 378)
AAVALLPAVLLALLAKNNLKECGLY

Myristoyl-MEK1 Derived Peptide Inhibitor 1
Myr-MPKKKPTPIQLNP

NGR Peptide 1  (SEQ ID NO: 379)
CNGRCGGklaklakklaklak-NH2 (Disulfide bridge: 1-5)

NGR Peptide 2  (SEQ ID NO: 380)
CNGRCGGLVTT (Disulfide bridge: 1-5)

NGR Peptide 3  (SEQ ID NO: 381)
CNGRC-NH2 (Disulfide bridge: 1-5)

NGR Peptide 4  (SEQ ID NO: 382)
CNGRCGGkklklllkll (Disulfide bridge: 1-5)

Nuclear Localiation Signal Peptide  (SEQ ID NO: 383)
PKKKRKV

P22 N (14-30)  (SEQ ID NO: 384)
NAKTRRHERRRKLAIER

PenArg, FAM Labeled  (SEQ ID NO: 385)
5-FAM-RQIRIWFQNRRMRWRR-NH2

Pep-1-Cysteamine  (SEQ ID NO: 386)
Ac-KETWWETWWTEWSQPKKKRKV-cysteamine

Pep-1: Chariot (Non-Covalent Delivery of Peptides and Proteins)  (SEQ ID NO: 387)
KETWWETWWTEWSQPKKKRKV phi 21 N Peptide (12-29)  (SEQ ID NO: 388)
TAKTRYKARRAELIAERR Phospho-IkBa-derived peptide, FAM labeled  (SEQ ID NO: 389)
5-FAM-GRHDSGLD-pS-MK-NH2

Rabies Virus Glycoprotein (RVG)  (SEQ ID NO: 390)
YTIWMPENPRPGTPCDIFTNSRGKRASNG

Rabies Virus Matrix Protein Fragment (RV-MAT)  (SEQ ID NO: 391)
MNLLRKIVKNRRDEDTQKSSPASAPLDDG Stearyl-MEK-1 Derived Peptide Inhibitor 1, amide  (SEQ ID NO: 392)
Ste-MPKKKPTPIQLNP-NH2

SV-40 Large T-antigen Nuclear Localization Signal (NLS)  (SEQ ID NO: 393)
CGGGPKKKRKVED SV40 T-Ag-derived Nuclear Localization Signal (NLS) Peptide  (SEQ ID NO: 394)
PKKKRKVEDPYC SynB1  (SEQ ID NO: 395)
RGGRLSYSRRRFSTSTGRA -continued

TAT (47-57)
(SEQ ID NO: 396)
YGRKKRRQRRR

TAT (47-57)
YGRKKRRQRRR

TAT (47-57) GGG-Cys(Npys)
YGRKKRRQRRRGGG-C(Npys)-NH2

TAT (47-57), FAM-labeled
FAM-YGRKKRRQRRR

TAT (47-57), TAMRA-labeled
TAMRA-YGRKKRRQRRR

TAT (47-57)-Lys(TAMRA)
YGRKKRRQRRR-K(TAMRA)

Tat (48-57)
(SEQ ID NO: 397)
GRKKRRQRRR

Tat-C (48-57)
(SEQ ID NO: 398)
CGRKKRRQRRR

Tat-NR2Bct
(SEQ ID NO: 399)
YGRKKRRQRRRKLSSIESDV

TAT-NSF222 Fusion Peptide
(SEQ ID NO: 400)
YGRKKRRQRRR-GGG-LDKEFNSIFRRAFASRVFPPE TAT-NSF700 Fusion Peptide
(SEQ ID NO: 401)
YGRKKRRQRRR-GGG-LLDYVPIGPRFSNLVLQALLVL Transdermal Peptide
(SEQ ID NO: 402)
ACSSSPSKHCG Transportan
(SEQ ID NO: 403)
GWTLNSAGYLLGKINLKALAALAKKIL Yeast PRP6 (129-144)
(SEQ ID NO: 404)
TRRNKRNRIQEQLNRK {Cys58}105Y, Cell Penetrating Peptide, α1-antitrypsin (358-374)
(SEQ ID NO: 405)
CSIPPEVKFNKPFVYLI 105Y, α1-antitrypsin (359-374)
(SEQ ID NO: 406)
SIPPEVKFNKPFVYLI Aminopeptidase N Ligand (CD13), NGR peptide
(SEQ ID NO: 407)
CNGRCG (Disulfide bridge: 1-5)

Antennapedia Leader Peptide (CT)
(SEQ ID NO: 408)
KKWKMRRNQFWVKVQRG

Antennapedia Peptide, acid
(SEQ ID NO: 409)
RQIKIWFQNRRMKWKK

Antennapedia Peptide, amide
(SEQ ID NO: 410)
RQIKIWFQNRRMKWKK-NH2

Antennapedia Peptide, FAM-labeled
(SEQ ID NO: 411)
5-FAM-RQIKIWFQNRRMKWKK-NH2

Anti-BetaGamma (MPS-Phosducin-like protein C terminus)

(SEQ ID NO: 412)

AAVALLPAVLLALLAVTDQLGEDFFAVDLEAFLQEFGLLPEKE

Bcl-2 Binding Peptide, cell permeable (SEQ ID NO: 413)

Decanoyl-KNLWAAQRYGRELRRMSDEFEGSFKGL

Alpha-A-Crystallin (70-88)

(SEQ ID NO: 414)

KFVIFLDVKHFSPEDLTVK

Hsc70-binding Peptide II (SEQ ID NO: 415)

NIVRKKK

Cholecystokinin-Pancreozymin Peptides
{Thr28, Nle31}-Cholecystokinin (25-33), sulfated (SEQ ID NO: 416)

RD-Y(SO3H)-TGW-Nle-DF-NH2

Caerulein (SEQ ID NO: 417)

Pyr-QD-Y(SO3H)-TGWMDF-NH2

Cholecystokinin (1-21)

(SEQ ID NO: 418)

KAPSGRVSMIKNLQSLDPSHR

Cholecystokinin (10-20)

(SEQ ID NO: 419)

IKNLQSLDPSH

Cholecystokinin (26-33), CCK Octapeptide, sulfated (SEQ ID NO: 420)

D-Y(SO3H)-MGWMDF-NH2

Cholecystokinin (26-33), CCK8

(SEQ ID NO: 421)

DYMGWMDF-NH2

Cholecystokinin (26-33), free acid
DYMGWMDF

Cholecystokinin Flanking Peptide, non-sulfated (SEQ ID NO: 422)

SAEEYEYPS

Cholecystokinin, CCK (27-33), CCK7

(SEQ ID NO: 423)

YMGWMDF-NH2

Prepro CCK fragment, V-9-M (SEQ ID NO: 424)

VPVEAVDPM

CRF
{Tyr0}-Corticotropin Releasing Factor, {Tyr0}-CRF, human, rat (SEQ ID NO: 425)

YSEEPPISLDLTFHLLREVLEEMARAEQLAQQAHSNRKLMEII-NH2

{Tyr0}-Corticotropin Releasing Factor, {Tyr0}-CRF, ovine (SEQ ID NO: 426)

YSQEPPISLDLTFHLLREVLEMTKADQLAQQAHSNRKLLDIA-NH2

Biotin-Corticotropin Releasing Factor, Biotin-CRF, human, rat

Biotin-SEEPPISLDLTFHLLREVLEMARAEQLAQQAHSNRKLMEII-NH2

Corticotropin Releasing Factor, CRF, human, rat (SEQ ID NO: 427)

SEEPPISLDLTFHLLREVLEMARAEQLAQQAHSNRKLMEII-NH2

Somatostatin
{Tyr0}-Somatostatin 28

(SEQ ID NO: 428)

YSANSNPAMAPRERKAGCKNFFWKTFTSC (Disulfide bridge: 18-29

-continued

{Tyr1}-Somatostatin 14
(SEQ ID NO: 429)
YGCKNFFWKTFTSC (Disulfide bridge: 3-14)

Big Endothelin-1 (1-38), human
(SEQ ID NO: 430)
CSCSSLMDKECVYFCHLDIIWVNTPEHVVPYGLGSPRS(Disulfide bridge: 1-15 and 3-11)

1: VIP vasoactive intestinal peptide isoform 1 preprotein
>gi|4507897|ref|NP_003372.1|VIP peptides isoform 1 preproprotein {Homo sapiens}
(SEQ ID NO: 431)
MDTRNKAQLLVLLTLLSVLFSQTSAWPLYRAPSALRLGDRIPFEGANEPDQVSLKEDIDMLQ

NALAENDTPYYDVSRNARHADGVFTSDFSKLLGQLSAKKYLESLMGKRVSSNISEDPVPVKR

HSDAVFTDNYTRLRKQMAVKKYLNSILNGKRSSEGESPDFPEELEK

Residues 125-152 constitute the active form:
HSDAVFTDNYTRLRKQMAVKKYLNSILN

VPAC₁ Interacting residues are likely (numbered from 1 using the active sequence):
H1, V5, F6, R14, K15, K21, Y22, L23, N24, and I26

VPAC₂ Interacting residues are likely (numbered from 1 using the active sequence):
H1, V5, T11, R14, K15, K21, Y22, L23, I26 and N28

2: VIP vasoactive intestinal peptide isoform 2 preprotein
>gi|37588853|ref|NP_919416.1|VIP peptides isoform 2 preproprotein {Homo sapiens}
(SEQ ID NO: 432)
MDTRNKAQLLVLLTLLSVLFSQTSAWPLYRAPSALRLGDRIPFEGANEPDQVSLKEDIDMLQ

NALAENDTPYYDVSRNARHADGVFTSDFSKLLGQLSAKKYLESLMGKRVSNISEDPVPVKR

HSDAVFTDNYTRLRKQMAVKKYLNSILNGKRSSEGESPDFPEELEK

Residues 124-151 constitute the active form:
HSDAVFTDNYTRLRKQMAVKKYLNSILN

VPAC₁ Interacting residues are likely (numbered from 1 using the active sequence):
H1, V5, F6, R14, K15, K21, Y22, L23, N24, and I26

VPAC₂ Interacting residues are likely (numbered from 1 using the active sequence):
H1, V5, T11, R14, K15, K21, Y22, L23, I26 and N28

3. VIP Synthetic sequence 1
(SEQ ID NO: 433)
HSDAVFTDNYTRLRKQVAAKKYLQSIKNKRY (Bay55-9837)

4. VIP Synthetic sequence 2
(SEQ ID NO: 434)
HADAVFTAAYARLRKQMAAKKALAAIAA (10Ala)

5. VIP Synthetic sequence 3
(SEQ ID NO: 435)
HSDAVFTDNYARLRKQMAVKKALNSILA (3Ala)

6. VIP Synthetic sequence 1
(SEQ ID NO: 436)
YFDAIFTNSYRKVLGQLSARKLLQDIMSR AcYF-GRF1-29

7. VIP Synthetic sequence 2
(SEQ ID NO: 437)
FTDNYTRLRKQMAVKKYLNSILN VIP 6-28

8. VIP Synthetic sequence 3
(SEQ ID NO: 438)
HSDAVFTDNYTRLRKQLAVKKYLNSILN (F-6 = p-Cl-dF)

9. VIP Synthetic sequence
(SEQ ID NO: 439)
Ac-HSDAVFTDNYTRLRKQVAAKKYLQSIKNKRY

10. VIP Synthetic sequence
(SEQ ID NO: 440)
HTDAVFTDNYTRLRKQVAAKKYLQSIKNKRY

11. VIP Synthetic sequence
(SEQ ID NO: 441)
HSEAVFTDNYTRLRKQVAAKKYLQSIKNKRY

-continued

12. VIP Synthetic sequence (SEQ ID NO: 442)
HSDAVFTDQYTRLRKQVAAKKYLQSIKQKRY

13. VIP Synthetic sequence (SEQ ID NO: 443)
HTEAVFTDNYTRLRKQVAAKKYLQSIKNKRY

14. VIP Synthetic sequence (SEQ ID NO: 444)
HTEAVFTDQYTRLRKQVAAKKYLQSIKQKRY 15. VIP Synthetic sequence (SEQ ID NO: 445)
Ac-HTDAVFTDQYTRLRKQVAAKKYLQSIKQKRY 16. VIP Synthetic sequence (SEQ ID NO: 446)
HSDAVFTDNYTRLRKQVAAKKYLQSIKNKRYC

17. VIP Synthetic sequence (SEQ ID NO: 447)
HSDAVFTDNYTRLRKQVAAKKYLQSIKNKRYC-PEG22kD

18. VIP Synthetic sequence (SEQ ID NO: 448)
HSDAVFTDNYTRLRKQVAAKKYLQSIKNKRYC-PEG43kD

19. VIP Synthetic sequence (SEQ ID NO: 449)
HSDAVFTDNYTRLRKQVAAKKYLQSIKNKRYSWC

20. VIP Synthetic sequence (SEQ ID NO: 450)
HSDAVFTDNYTRLRKQVAAKKYLQSIKNKRYSWC-PEG22kD

21. VIP Synthetic sequence (SEQ ID NO: 451)
HSDAVFTDNYTRLRKQVAAKKYLQSIKNKRYSWC-PEG43kD

22. VIP Synthetic sequence (SEQ ID NO: 452)
HSDAVFTDQYTRLRKQVAAKKYLQSIKQKRYC

23. VIP Synthetic sequence (SEQ ID NO: 453)
HSDAVFTDQYTRLRKQVAAKKYLQSIKQKRYC-PEG22kD

24. VIP Synthetic sequence (SEQ ID NO: 454)
HSDAVFTDQYTRLRKQVAAKKYLQSIKQKRYC-PEG43kD

25. VIP Synthetic sequence (SEQ ID NO: 455)
Ac-HSDAVFTENYTKLRKQN$_{le}$AAKK*YLND*LKKGGT(Ro25-1553)

26. VIP Synthetic sequence (SEQ ID NO: 456)
Ac-HSDAVFTENY$_{M}$TKLRKQN$_{le}$AAKK*YLND*LKK (Ro 25-1392)

27. VIP Synthetic sequence (SEQ ID NO: 457)
HSDAVFTDNYTRLRRQLAVRRYLNSILNGRR (LK312532)

28. VIP Synthetic sequence (SEQ ID NO: 458)
Ac-H$_{d}$FDAVFTNSYRKVLKRLSARKLLQDIL (PG 97-269)

29. VIP Synthetic sequence (SEQ ID NO: 459)
HSDAVFTNSYRKVLKRLSARKLLQDIL(k15r16l27VIP GFR)

30. VIP Synthetic sequence (SEQ ID NO: 460)
H$_{d}$ADAIFTA$_{ib}$AYRKVLAALA$_{ib}$ARKALAAAG$_{ab}$(GFR-6)

31. VIP Synthetic sequence (SEQ ID NO: 461)
HSDGLFTSEYSKMRGRAQVQKFIQNLM (R16-chicken)

-continued

32. VIP Synthetic sequence

HSDAVFTDYYTRLRKQMD$_{ip}$VKKYLNSILN (y9Dip18-VIP)

(SEQ ID NO: 462)

33. VIP Synthetic sequence

FTDYYTRLRKQMD$_{ip}$VKKYLNSILN (y9Dip18-VIP)

(SEQ ID NO: 463)

34. VIP Synthetic sequence

HSDAVFTDNYTK$_{m}$LRKQMAVKKYLNSIKKGGT (SEQ ID NO: 464)

35. VIP Synthetic sequence

Ac-HSDAVFTNSYRKVLKRLSARKLLQDIL (PG 97-268)

(SEQ ID NO: 465)

36. VIP Synthetic sequence

Ac-HDAI$_{d}$RTNSYRKVLKRLSAKKYLQDIN$_{leD}$R$_{h}$R (JV-1-53?)

(SEQ ID NO: 466)

37. VIP Synthetic sequence

Ac-H$_{d}$FDAIF$_{4cl}$TNRYRKVLA$_{bu}$QLSARKLLQDIN$_{leD}$R$_{h}$R (JV-1-51)

(SEQ ID NO: 467)

38. VIP synthetic sequence

HSDAVFTDQYTRLRKQLAAKKYLQSLKKKRY (RBAYL)

(SEQ ID NO: 468)

39. VIP synthetic sequence

HSDAVFTDNYTRLRKQVAAKKYLQSLKNKRY (rBAY)

(SEQ ID NO: 469)

40. VIP synthetic sequence

Hexanoyl-HSDAVFTDNYTRLRKQMAVKKYLNSILN (c6VIP)

(SEQ ID NO: 470)

41. VIP synthetic sequence

Hexanoyl-HSDAVFTDNYTRLRKQMAAKKYLNSIKK (c6a19k27k28-VIP)

(SEQ ID NO: 471)

HSDAVFTEQY(OMe)TRAibRAibQLAAAibOrnY(OMe)LQSIK AibOrn (SEQ ID NO: 472)

HSDAVFTEK(CO(CH$_2$)$_2$SH)Y(OMe)TOrnLRAibQVAAAibOrn YLQSIOrnOrn (SEQ ID NO: 473)

HSDAVFTEQY(OMe)TOrnLRAibQVAAAibOrnYLQSIOrnK(W) Orn (SEQ ID NO: 474)

HSDAVFTEQY(OMe)TOrnLRAibQVAAAibK(CO(CH$_2$)$_2$SH)YLQ SIOrnOrn (SEQ ID NO: 475)

HSDAVFTEQY(OMe)TOrnLRAibQVAAK CO(CH$_2$)$_2$SH)OrnYLQ SIOrnOrn (SEQ ID NO: 476)

HSDAVFTEQY(OMe)TOrnLRAibQVCAAibOrnYLQSIOrnOrn (SEQ ID NO: 477)

HSDAVFTEQY(OMe)TOrnLRCQVAAAibOrnYLQSIOrnOrn (SEQ ID NO: 478)

HSDAVFTEQY(OMe)TOrnLRAibQLAAAibOrnYLQSIOrnOrn (SEQ ID NO: 479)

HSDAVFTEQY(OMe)TOrnLRAibQVAAAibOrnYAibQSIOrnOrn (SEQ ID NO: 480)

HSDAVFTEQY(OMe)TOrnLRAibQVAAAibOrnYLQAibIOrnOrn (SEQ ID NO: 481)

HSDAVFTEQY(OMe)TOrnLRAibQVAAbuAibOrnYLQAibIOrnOrn (SEQ ID NO: 482)

HSDAVFTEQY(OMe)TOrnLRAibQLAAAibOrnYLQAibIOrnOrn (SEQ ID NO: 483)

HSDAVFTEQY(OMe)TOrnLRAibQLAAAibOrnYAibQAibIOrnOrn (SEQ ID NO: 484)

-continued

HSDAVFTEQY(OMe)TOrnLRAibQLAAbuAibOrnYAibQSIOrnOrn  (SEQ ID NO: 485)

HSDAVFTEQY(OMe)TOrnLRAibQLAAbuAibOrnYLQSIOrnOrn  (SEQ ID NO: 486)

HSDAVFTEQY(OMe)TOrnLRAibQLAAbuAibOrnYAibQAibIOrn Orn  (SEQ ID NO: 487)

HSDAVFTEQY(OMe)TOrnLRAibQLAAAibOrnYAibQSIOrnOrn  (SEQ ID NO: 488)

HSDAVFTEQY(OMe)TOrnLRK(W)QVAAAibOrnYLQSIOrnOrn  (SEQ ID NO: 489)

HSDAVFTEQY(OMe)TOrnLRAibQVAAAibOrnYLK(W)SIOrnOrn  (SEQ ID NO: 490)

HSDAVFTEQY(OMe)TOrnLRAibQK(W)AAAibOrnYLQSIOrnOrn  (SEQ ID NO: 491)

HSDAVFTEQY(OMe)TOrnLRK CO(CH$_2$)$_2$SH)QVAAibOrnYLQ SIOrnOrn  (SEQ ID NO: 492)

HSDAVFTEQY(OMe)TOrnLRAibQVAAAibK(W)YLQSIOrnOrn  (SEQ ID NO: 493)

HSDAVFTEQY(OMe)TOrnLRAibQVAAAibCYLQSIOrnOrn  (SEQ ID NO: 494)

HSDAVFTEQY(OMe)TOrnLRAibQLAAbuAibOrnYLQAibIOrnOrn  (SEQ ID NO: 495)

HSDAVFTEQY(OMe)TOrnLRAibQVAAAibOrnYLQSK(W)OrnOrn  (SEQ ID NO: 496)

HSDAVFTEQY(OMe)TOrnLRAibQLAAbuAibOrnYLQAibIOrnC Orn  (SEQ ID NO: 497)

HSDAVFTEQY(OMe)TOrnLRAibQLAAbuAibOrnYLQAibCOrn Orn  (SEQ ID NO: 498)

HSDAVFTEQY(OMe)TOrnLRAibQCAAbuAibOrnYLQAibIOrnOrn  (SEQ ID NO: 499)

HSDAVFTEQY(OMe)TOrnLRCQLAAbuAibOrnYLQAibIOrnOrn  (SEQ ID NO: 500)

HSDAVFTEQY(OMe)TOrnLRAibQVK CO(CH$_2$)$_2$SH)AAibOrn YLQSIOrnOrn  (SEQ ID NO: 501)

HSDAVFTEQY(OMe)TOrnLRAibQLAAbuAibOrnYLQSIOrnCOrn  (SEQ ID NO: 502)

HSDAVFTEQY(OMe)TOrnLRAibQLAAbuAibOrnYLQSCOrnOrn  (SEQ ID NO: 503)

HSDAVFTEQY(OMe)TOrnLRAibQLAAbuAibOrnYLQAibIOrn K CO(CH$_2$)$_2$SH)Orn  (SEQ ID NO: 504)

HSDAVFTEQY(OMe)TOrnLRAibQLAAbuAibOrnYLQSIOrn K CO(CH$_2$)$_2$SH)Orn  (SEQ ID NO: 505)

HSDAVFTEQY(OMe)TOrnLRK(W)QLAAbuAibOrnYLQAibIOrn Orn  (SEQ ID NO: 506)

HSDAVFTEQY(OMe)TOrnLRAibQLAAAibOrnYLQSIOrnOrnC  (SEQ ID NO: 507)

HSDAVFTEQY(OMe)TOrnLRAibQVAAAibOrnYLQSIOrnOrnC  (SEQ ID NO: 508)

HSDAVFTEQY(OMe)TOrnLRAibQLAAbuAibOrnYLQSIOrnOrnC  (SEQ ID NO: 509)

HSDAVFTEQY(OMe)TOrnLRAibQLAAbuAibOrnY(OMe)LQAibI OrnOrn  (SEQ ID NO: 510)

HSDAVFTEQY(OMe)TOrnLRAibQLAAbuAibOrnY(OMe)LQAibI OrnCOrn  (SEQ ID NO: 511)

-continued (SEQ ID NO: 512)
HSDAVFTEQY(OMe)TOrnLRAibQCAAbuAibOrnY(OMe)LQAibI OrnOrn (SEQ ID NO: 513)
HSDAVFTEQY(OMe)TOrnLRAibQLAAbuAibOrnYLQAibIOrn OrnC (SEQ ID NO: 514)
HSDAVFTEQY(OMe)TOrnLRAibQLAAbuAibOrnY(OMe)LQSI OrnOrn (SEQ ID NO: 515)
HSDAVFTEQY(OMe)TOrnLRAibQCAAbuAibOrnY(OMe)LQSI OrnOrn (SEQ ID NO: 516)
HSDAVFTEQY(OMe)TOrnLRAibQLAAbuAibOrnY(OMe)LQSI OrnCOrn (SEQ ID NO: 517)
HSDAVFTEQY(OMe)TOrnLRAibQLAbuAAibOrnYLQSIOrnOrn (SEQ ID NO: 518)
HSDAVFTEQY(OMe)TOrnLRAibQK CO(CH$_2$)$_2$SH)AAbu AibOrnYLQAibIOrnOrn (SEQ ID NO: 519)
HSDAVFTEQY(OMe)TOrnLRAibQK(W)AAbuAibOrnYLQ AibIOrnOrn 3. pituitary adenylate cyclase-activating polypeptide precursor {Homo sapiens}
>gi|153266792|ref|NP_001093203.1|pituitary adenylate cyclase-activating
polypeptide precursor {Homo sapiens}

(SEQ ID NO: 520)
MTMCSGARLALLVYGIIMHSSVYSSPAAAGLRFPGIRPEEEAYGEDGNPLPDFDGSEPPGAGS

PASAPRAAAAWYRPAGRRDVAHGILNEAYRKVLDQLSAGKHLQSLVARGVGGSLGGGAGD

DAEPLSKRHSDGIFTDSYSRYRKQMAVKKYLAAVLGKRYKQRVKNKGRRIAYL

Residues 132-158 constitute the active form PACAP-27:
HSDGIFTDSYSRYRKQMAVKKYLAAVL
Residues 132-158 constitute the active form PACAP-38:
HSDGIFTDSYSRYRKQMAVKKYLAAVLGKRYKQRVKNK
4. pituitary adenylate cyclase-activating polypeptide precursor {Homo sapiens}
>gi|153266795|ref|NP_001108.2|pituitary adenylate cyclase-activating
polypeptide precursor {Homo sapiens}

(SEQ ID NO: 521)
MTMCSGARLALLVYGIIMHSSVYSSPAAAGLRFPGIRPEEEAYGEDGNPLPDFDGSEPPGAGS

PASAPRAAAAWYRPAGRRDVAHGILNEAYRKVLDQLSAGKHLQSLVARGVGGSLGGGAGD

DAEPLSKRHSDGIFTDSYSRYRKQMAVKKYLAAVLGKRYKQRVKNKGRRIAYL

Residues 132-158 constitute the active form PACAP-27:
HSDGIFTDSYSRYRKQMAVKKYLAAVL
Residues 132-158 constitute the active form PACAP-38:
HSDGIFTDSYSRYRKQMAVKKYLAAVLGKRYKQRVKNK
39. PACAP-Antagonist (SEQ ID NO: 522)
FTDSYSRYRKQMAVKKYLAAVLGKRYKQRVKNK 40. Maxadilan peptide
>US6462016_1 Sequence 1 from Patent U.S. Pat. No. 6,462,016 inClaims gi: 27279414

(SEQ ID NO: 523)
CDATCQFRKAIDDCQKQAHHSNVLQTSVQTTATFTSMDTSQLPGNSVFKECMKQKKKEFKA

40. Maxadilan peptide 2

(SEQ ID NO: 524)
CDATCQFRKAIDDCQKQAHHSNVLQTSVQTTATFTSMDTSQLPGNSVFKECMKQKKKEFSS

GK

40. M65 peptide (SEQ ID NO: 525)
CDATCQFRKAIDDCQKQAHHSNVLPGNSVFKECMKQKKKEFKA

40. M65 peptide v2.

(SEQ ID NO: 526)
CDATCQFRKAIDDCQKQAHHSNVLGNSVFKECMKQKKKEFKA

41. M65 peptide
>US6462016_10 Sequence 10 from Patent U.S. Pat. No. 6,462,016 inClaims gi: 27279423

(SEQ ID NO: 527)
GSCDATCQFRKAIDDCQKQAHHSNVPGNSVFKECMKQKKKEFKAGK

-continued

The contents of this Table 4 also include relate to analogs comprising any agonist listed in US2009-US Application Serial\10/586,124, filed on Jun. 24, 2008
5. glucagon preproprotein
gi|4503945|ref|NP_002045.1|glucagon preproprotein {Homo sapiens}

(SEQ ID NO: 528)

MKSIYFVAGLFVMLVQGSWQRSLQDTEEKSRSFSASQADPLSDPDQMNEDKRHSQGTFTSD

YSKYLDSRRAQDFVQWLMNTKRNRNNIAKRHDEFERHAEGTFTSDVSSYLEGQAAKEFIAW

LVKGRGRRDFPEEVAIVEELGRRHADGSFSDEMNTILDNLAARDFINWLIQTKITDRK

Residues 21-50 constitute an active form Glicentin-related polypeptide (GRPP):

(SEQ ID NO: 529)

RSLQDTEEKSRSFSASQADPLSDPDQMNED

Residues 53-81 constitute an active form Glucagon:

(SEQ ID NO: 530)

HSQGTFTSDYSKYLDSRRAQDFVQWLMNT

Residues 92-128 constitute the pro-form of GLP-1

(SEQ ID NO: 531)

HDEFERHAEGTFTSDVSSYLEGQAAKEFIAWLVKGRG
Residues 98-128 constitute an active form of GLP-1
HAEGTFTSDVSSYLEGQAAKEFIAWLVKGRG
Residues 98-125 constitute an active form of GLP-1
HAEGTFTSDVSSYLEGQAAKEFIAWLVK Residues 146-178 constitute an active form GLP-2:

(SEQ ID NO: 532)

HADGSFSDEMNTILDNLAARDFINWLIQTKITD

6. Apolipoprotein-mimetic peptide (D4F, DWFKAFYDKVAEKFKEAF) (SEQ ID NO: 533) and other family members:

(SEQ ID NO: 534)

3F-2 (Ac-DKWKAVYDKFAEAFKEFL-NH2)

(SEQ ID NO: 535)

3F14 (Ac-DWLKAFYDKVAEKFKEAF-NH2

The baseline sequence of 18A is DWLKAFYDKVAEKLKEAF.
Ac-18A-NH2
Ac-{F318A}NH2
Ac-{F1418A}NH2
Ac-{F3,1418A}NH2
Ac-{F11,14,1718A}NH2
Ac-{F10,11,14,1718A}NH2
Ac-{F3,10,11,14,1718A}NH2
4F = Ac-DWFKAFYDKVAEKFKEAF-NH2 (18 mer)
4F-KVEPLRA-4F (43 mer)
4F-P-4F (37 mer)
4F-A-4F (37 mer)
apoA-IMilano (R173C) and apoA-IParis (R151C)
apolipoprotein A-I {Homo sapiens
gi|4557321|ref|NP_000030.1|apolipoprotein A-I preproprotein {Homo sapiens}

(SEQ ID NO: 536)

MKAAVLTLAVLFLTGSQARHFWQQDEPPQSPWDRVKDLATVYVDVLKDSGRDYVSQFEGS

ALGKQLNLKLLDNWDSVTSTFSKLREQLGPVTQEFWDNLEKETEGLRQEMSKDLEEVKAKV

QPYLDDFQKKWQEEMELYRQKVEPLRAELQEGARQKLHELQEKLSPLGEEMRDRARAHVD

ALRTHLAPYSDELRQRLAARLEALKENGGARLAEYHAKATEHLSTLSEKAKPALEDLRQGL

LPVLESFKVSFLSALEEYTKKLNTQ

I. apolipoprotein E {Homo sapiens}
>gi|178853|gb|AAB59397.1|apolipoprotein E {Homo sapiens}

(SEQ ID NO: 537)

MKVLWAALLVTFLAGCQAKVEQAVETEPEPELRQQTEWQSGQRWELALGRFWDYLRWVQ

TLSEQVQEELLSSQVTQELRALMDETMKELKAYKSELEEQLTPVAEETRARLSKELQAAQAR

LGADMEDVRGRLVQYRGEVQAMLGQSTEELRVRLASHLRKLRKRLLRDADDLQKRLAVY

QAGAREGAERGLSAIRERLGPLVEQGRVRAATVGSLAGQPLQERAQAWGERLRARMEEMG

SRTRDRLDEVKEQVAEVRAKLEEQAQQIRLQAEAFQARLKSWFEPLVEDMQRQWAGLVEK

VQAAVGTSAAPVPSDNH

-continued

```
II.  Ac-L V GRQLEEFL-NH
III. Ac-LLEQLNEQFNWVSRLANLTQGE-NH2
     Ac--PSGVTEVVVKLFDS-NH.sub.2
IV.  Ac-Q QTHMLDVMQD-NH.sub.2.
V.   Apolipoprotein C-I {Homo sapiens}
     >gi|32822890|gb|AAH55093.1|Apolipoprotein C-I {Homo sapiens}
                                                                          (SEQ ID NO: 538)
MRLFLSLPVLVVVLSIVLEGPAPAQGTPDVSSALDKLKEFGNTLEDKARELISRIKQSELSAK

MREWFSETFQKVKEKLKIDS

VI.  apolipoprotein J {Homo sapiens}
     >gi|27373753|gb|AAN87347.1|apolipoprotein J {Homo sapiens}
                                                                          (SEQ ID NO: 539)
CSTNNPSQAKLRRELDESLQVAERLTRKYNELLKSYQWKMLNTSSLLEQLNEQFNWVSRLA

NLTQGEDQYYLRVTT apoJ peptide 336--D-J336 = Ac-LLEQLNEQFNWVSRLANTQGE-NH2
ANP
>gi|23510319|ref|NP_006163.1|atrial natriuretic factor preproprotein {Homo sapiens}
                                                                          (SEQ ID NO: 540)
MSSFSTTTVSFLLLLAFQLLGQTRANPMYNAVSNADLMDFKNLLDHLEEKMPLEDEVVPPQ

VLSEPNEEAGAALSPLPEVPPWTGEVSPAQRDGGALGRGPWDSSDRSALLKSKLRALLTAPR

SLRRSSCFGGRMDRIGAQSGLGCNSFRY

Active form:
                                                                          (SEQ ID NO: 541)
RSLRRSSCFGGRMDRIGAQSGLGC Active form:
                                                                          (SEQ ID NO: 542)
RSLRRSSCFGGRMDRIGAQSGLGCNSFRY Active form:
                                                                          (SEQ ID NO: 543)
SLRRSSCFGGRMDRIGAQSGLGCNSFRY cardiodilatin
>gi|23510319: 26-92 atrial natriuretic factor preproprotein {Homo sapiens}
                                                                          (SEQ ID NO: 544)
NPMYNAVSNADLMDFKNLLDHLEEKMPLEDEVVPPQVLSEPNEEAGAALSPLPEVPPWTGE

VSPAQR

BNP
natriuretic peptides B preproprotein {Homo sapiens}
>gi|4505433|ref|NP_002512.1|natriuretic peptides B preproprotein {Homo sapiens}
                                                                          (SEQ ID NO: 545)
MDPQTAPSRALLLLLFLHLAFLGGRSHPLGSPGSASDLETSGLQEQRNHLQGKLSELQVEQTS

LEPLQESPRPTGVWKSREVATEGIRGHRKMVLYTLRAPRSPKMVQGSGCFGRKMDRISSSSG

LGCKVLRRH

Active form:
                                                                          (SEQ ID NO: 546)
SPKMVQGSGCFGRKMDRISSSSGLGCKVLRRH CNP
natriuretic peptide precursor C precursor {Homo sapiens}
>gi|13249346|ref|NP_077720.1|natriuretic peptide precursor C precursor {Homo sapiens}
                                                                          (SEQ ID NO: 547)
MHLSQLLACALLLTLLSLRPSEAKPGAPPKVPRTPPAEELAEPQAAGGGQKKGDKAPGGGG

ANLKGDRSRLLRDLRVDTKSRAAWARLLQEHPNARKYKGANKKGLSKGCFGLKLDRIGSM

SGLGC

Active form:
                                                                          (SEQ ID NO: 548)
GLSKGCFGLKLDRIGSMSGLGC urodilatin
>gi|226320|prf||1506430A urodilatin
                                                                          (SEQ ID NO: 549)
TAPRSLRRSSCFGGRMDRIGAQSGLGCNSFRY
```

-continued

Urodilatin

RPATSLRRSSCFGGRMDRIGAQSGLGCNSFRY (SEQ ID NO: 550)

neuropeptide Y preproprotein {Homo sapiens}
>gi|4505449|ref|NP_000896.1|neuropeptide Y preproprotein {Homo sapiens}

MLGNKRLGLSGLTLALSLLVCLGALAEAYPSKPDNPGEDAPAEDMARYYSALRHYINLITRQ (SEQ ID NO: 551)

RYGKRSSP (SEQ ID NO: 552)

ETLISDLLMRESTENVPRTRLEDPAMW (SEQ ID NO: 553)

Active form:
>gi|4505449: 29-64 neuropeptide Y preproprotein {Homo sapiens}

YPSKPDNPGEDAPAEDMARYYSALRHYINLITRQRY (SEQ ID NO: 554)

PYY
peptide YY precursor {Homo sapiens}
>gi|71361686|ref|NP_004151.2|Human peptide YY precursor

MVFVRRPWPALTTVLLALLVCLGALVDAYPIKPEAPREDASPEELNRYYASLRHYLNLVTRQ (SEQ ID NO: 555)

RYGKRDGP (SEQ ID NO: 556)

DTLLSKTFFPDGEDRPVRSRSEGPDLW (SEQ ID NO: 557)

Active form:
IKPEAPREDASPEELNRYYASLRHYLNLVTRQRY (SEQ ID NO: 558)

Active form:
IKPEAPGEDASPEELNRYYASLRHYLNLVTRQRY (SEQ ID NO: 559)

Active form:
YPIKPEAPREDASPEELNRYYASLRHYLNLVTRQRY (SEQ ID NO: 560)

Active form:
YPIKPEAPGEDASPEELNRYYASLRHYLNLVTRQRY (SEQ ID NO: 561)

adrenomedullin {Homo sapiens}
Active form:
YRQSMNNFQGLRSFGCRFGTCTVQKLAHQIYQFTDKDKDNVAPRSKISPQGY (SEQ ID NO: 562)

Pro-Adrenomedullin (N-20):
ARLDVAAEFRKKWNKWALSR (SEQ ID NO: 563)

PrePro-Adrenomedullin:
ELRMSSSYPTGLADVKAGPAQTLIRPQDMKGASRSPEDSSPDAARIRV (SEQ ID NO: 564)

Ghrelin analog sequences
{Ala1, D-Trp2,4, Leu6}-Ghrelin Receptor Agonist
AwFwLL (SEQ ID NO: 565)

{D-Trp1,3, Leu5}-Ghrelin Core-Ligand
wFwLL (SEQ ID NO: 566)

{Des-octanoyl}-Ghrelin, human
GSSFLSPEHQRVQQRKESKKPPAKLQPR (SEQ ID NO: 567)

Biotin-GS-S(n-octanoyl)-FLSPEHQRVQQRKESKKPPAKLQPR (SEQ ID NO: 568)

FAM-GS-S(n-octanoyl)-FLSPEHQRVQQRKESKKPPAKLQPR

TAMRA-GS-S(n-octanoyl)-FLSPEHQRVQQRKESKKPPAKLQPR

```
human Obestatin analog sequences
                                                                   (SEQ ID NO: 569)
FNAPFDVGIKLSGVQYQQHSQAL-NH2

PTH analog sequences
Parathyroid Hormone (1-34), human
                                                                   (SEQ ID NO: 570)
SVSEIQLMHNLGKHLNSMERVEWLRKKLQDVHNF Parathyroid Hormone (1-34), human biotinylated
                                                                   (SEQ ID NO: 571)
Biotin-SVSEIQLMHNLGKHLNSMERVEWLRKKLQDVHNF Parathyroid Hormone (1-34), human C-Terminal FAM-labeled

SVSEIQLMHNLGKHLNSMERVEWLRKKLQDVHNFK(FAM)

Parathyroid Hormone (1-34)-Lys(Biotin), human

SVSEIQLMHNLGKHLNSMERVEWLRKKLQDVHNFK(Biotin)

Parathyroid Hormone (1-34)-Lys(Biotin), human, FAM-labeled

FAM-SVSEIQLMHNLGKHLNSMERVEWLRKKLQDVHNFK(Biotin)

Parathyroid Hormone-Related Protein, PTHrP (107-111)
                                                                   (SEQ ID NO: 572)
TRSAW TIP 39, Tuberoinfundibular Neuropeptide
                                                                   (SEQ ID NO: 573)
SLALADDAAFRERARLLAALERRHWLNSYMHKLLVLDAP Hypercalcemia Malignancy Factor (1-40)
                                                                   (SEQ ID NO: 574)
AVSEHQLLHDKGKSIQDLRRRFFLHHLIAEIHTAEIRATS Acetalin analog sequences
Acetalin 1, Opioid Receptor Antagonist 1
                                                                   (SEQ ID NO: 575)
Ac-RFMWMR-NH2

Acetalin 2, Opioid Receptor Antagonist 2
                                                                   (SEQ ID NO: 576)
Ac-RFMWMK-NH2

Acetalin 3, Opioid Receptor Antagonist 3
                                                                   (SEQ ID NO: 577)
Ac-RFMWMT-NH2

ACTH analog sequences
{Glu10}-ACTH (1-17)
                                                                   (SEQ ID NO: 578)
SYSMEHFRWEKPVGKKR {Phe2, Nle4}-ACTH (1-24)
                                                                   (SEQ ID NO: 579)
SFS-Nle-EHFRWGKPVGKKRRPVKVYP ACTH (1-10)
                                                                   (SEQ ID NO: 580)
SYSMEHFRWG ACTH (1-13), human
                                                                   (SEQ ID NO: 581)
SYSMEHFRWGKPV ACTH (1-24), human
                                                                   (SEQ ID NO: 582)
SYSMEHFRWGKPVGKKRRPVKVYP ACTH (1-39), human
                                                                   (SEQ ID NO: 583)
SYSMEHFRWGKPVGKKRRPVKVYPNGAEDESAEAFPLEF ACTH (18-39), human (CLIP)
                                                                   (SEQ ID NO: 584)
RPVKVYPNGAEDESAEAFPLEF
```

ACTH (22-39)

(SEQ ID NO: 585)

VYPNGAEDESAEAFPLEF

ACTH (7-38), human (SEQ ID NO: 586)

FRWGKPVGKKRRPVKVYPNGAEDESAEAFPLE

Biotin-ACTH (1-39), human
Biotin-SYSMEHFRWGKPVGKKRRPVKVYPNGAEDESAEAFPLEF

Sauvagine (SEQ ID NO: 587)

Pyr-GPPISIDLSLELLRKMIEIEKQEKEKQQAANNRLLLDTI-NH2

AGRP (25-51)

(SEQ ID NO: 588)

LAPMEGIRRPDQALLPELPGLGLRAPL

AGRP (54-82)

(SEQ ID NO: 589)

TTAEQAEEDLLQEAQALAEVLDLQDREPR

AGRP (87-132), human (SEQ ID NO: 590)

Ac-CVRLHESCLGQQVPCCDPCATCYCRFFNAFCYCRKLGTAMNPCSRT

AGRP fragment (83-132), amide (SEQ ID NO: 591)

SSRRCVRLHESCLGQQVPCCDPCATCYCRFFNAFCYCRKLGTAMNPCSRT-NH2 (5 disulfide
bridges)

Allatostatin I (free acid)

(SEQ ID NO: 592)

APSGAQRLYGFGL

Allatostatin I, Dip-AST7, cockroach (SEQ ID NO: 593)

APSGAQRLYGFGL-NH2

Allatostatin II (SEQ ID NO: 594)

GDGRLYAFGL-NH2

Allatostatin III (SEQ ID NO: 595)

GGSLYSFGL-NH2

Allatostatin IV (SEQ ID NO: 596)

DRLYSFGL-NH2

Allatostatin VI (SEQ ID NO: 597)

YPQEHRFSFGL-NH2

Allatostatin VII (SEQ ID NO: 598)

DGRMYSFGL-NH2

Allatotropin, Mas-AT (SEQ ID NO: 599)

GFKNVEMMTARGF-NH2

{Ala16,17,20}-beta-Amyloid (1-28)

(SEQ ID NO: 600)

DAEFRHDSGYEVHHQAAVFAAEDVGSN

{Gln22}-beta-Amyloid (15-23)

(SEQ ID NO: 601)

QKLVFFAQD

{NMeG24, NMeI26} Human Islet Amyloid Polypeptide (IAPP) (22-27)

(SEQ ID NO: 602)

NF-(NMe-G)-A-(NMe-I)-L

Amylin (1-13), human (SEQ ID NO: 603)

KCNTATCATQRLA (Disulfide bridge: 2-7)

-continued

Amylin (1-37), human

KCNTATCATQRLANFLVHSSNNFGAILSSTNVGSNTY (Disulfide bridge: 2-7)    (SEQ ID NO: 604)

Amylin (20-29), human

SNNFGAILSS    (SEQ ID NO: 605)

Amylin (8-37), human

ATQRLANFLVHSSNNFGAILSSTNVGSNTY-NH2    (SEQ ID NO: 606)

Beta-Amyloid (12-24)

VHHQKLVFFAEDV    (SEQ ID NO: 607)

Beta-Amyloid (13-23)

HHQKLVFFAED    (SEQ ID NO: 608)

Beta-Amyloid (7-29)

DSGYEVHHQKLVFFAEDVGSNKG    (SEQ ID NO: 609)

Angiotensin
{Des-Asp1}-Angiotensin I, human

RVYIHPFHL    (SEQ ID NO: 610)

{Sar1, Ala8}-Angiotensin II

Sar-RVYIHPA    (SEQ ID NO: 611)

{Sar1, Val5, Ala8}-Angiotensin II, Saralasin

Sar-RVYVHPA    (SEQ ID NO: 612)

Angiotensin Converting Enzyme Inhibitor, BPP 9a
Pyr-WPRPQIPP
Angiotensin I Converting Enzyme 2, ACE-2/Caspase-1 Substrate    (SEQ ID NO: 613)

Mca-YVADAPK(Dnp)

Angiotensin I, human    (SEQ ID NO: 614)

DRVYIHPFHL

Angiotensin II Antipeptide    (SEQ ID NO: 615)

EGVYVHPV

Angiotensin I/II (3-8)    (SEQ ID NO: 616)

VYIHPF

Angiotensin I/II (4-8)    (SEQ ID NO: 617)

YIHPF

Angiotensin I/II (5-8)    (SEQ ID NO: 618)

IHPF

Angiotensin II Substrate    (SEQ ID NO: 619)

DRV-pY-IHPF

Angiotensin II, human    (SEQ ID NO: 620)

DRVYIHPF

Angiotensin III    (SEQ ID NO: 621)

RVYIHPF

Prorenin Peptide (33-42)    (SEQ ID NO: 622)

RIFLKRMPSI

Renin Substrate, human
(SEQ ID NO: 623)
DRVYIHPFHLVIHIN

Renin Inhibitor III
(SEQ ID NO: 624)
RRPFH-Sta-IHK-NH2

Annexin 1 (ANXA-1, Ac 2-12)
(SEQ ID NO: 625)
Ac-AMVSEFLKQAW

Anti-Inflammatory Peptide 1
(SEQ ID NO: 626)
MQMKKVLDS

Anti-Inflammatory Peptide 2
(SEQ ID NO: 627)
HDMNKVLDL

Anti-Inflammatory Peptide 3
(SEQ ID NO: 628)
MQMNKVLDS

Interleukin-6 Receptor Peptide
(SEQ ID NO: 629)
TSLPVQDSSSVP

WP9QY, TNF-alpha Antagonist
YCWSQYLCY (Disulfide bridge: between amino acid numbesr between 2 8)
{Ala13}-Apelin-13
(SEQ ID NO: 630)
QRPRLSHKGPMPA {Phe17}-Apelin 17
(SEQ ID NO: 631)
KFRRQRPRLSHKGPMPF {Pyr1}-Apelin-13
(SEQ ID NO: 632)
Pyr-RPRLSHKGPMPF-OH Apelin 12
(SEQ ID NO: 633)
RPRLSHKGPMPF Apelin-15 (63-75)
(SEQ ID NO: 634)
RRQRPRLSHKGPM Apelin-16, human, bovine
(SEQ ID NO: 635)
FRRQRPRLSHKGPMPF Apelin-36, human
(SEQ ID NO: 636)
LVQPRGSRNGPGPWQGGRRKFRRQRPRLSHKGPMPF Bak BH3, Bcl2 (72-87)
(SEQ ID NO: 637)
KGGGQVGRQLAIIGDDINR Bcl 9-2
GSEGLSKEQLEHRERSLQTLRDIERLLLRSGETEPFLKGPPGGAG-NH2

PR39, Anti-Apoptotic Factor
(SEQ ID NO: 638)
RRRPRPPYLPRPRPPPFFPPRLPPRIPPGFPPRFPPRFP Proapoptotic Peptide, (klaklak)2
(SEQ ID NO: 639)
klaklakklaklak-NH2, wherein all amino acid residues are D-amino acid residues

PUMA BH3
(SEQ ID NO: 640)
EEQWAREIGAQLRRMADDLNAQYER

-continued

RGD-targeted Proapoptotic Peptide
(SEQ ID NO: 641)
ACDCRGDCFC-GG-klaklakklaklak-NH2 (S—S bonded C1-C4 & C2-C3)

26Rfa, Hypothalamic Peptide, human
(SEQ ID NO: 642)
TSGPLGNLAEELNGYSRKKGGFSFRF-NH2

Catch-Relaxing Peptide (CARP)
(SEQ ID NO: 643)
AMPMLRL-NH2

Neuropeptide AF (hNPAF), Human
(SEQ ID NO: 644)
AGEGLNSQFWSLAAPQRF-NH2

NPSF (1-37), Neuropeptide SF (1-37)
(SEQ ID NO: 645)
SLNFEELKDWGPKNVIKMSTPAVNKMPHSFANLPLRF-NH2

AKH/RPCH family of arthropod neuropeptides
LOCUST (AKH-I):
(SEQ ID NO: 646)
pELNFTPNWGT CARAUSIUS (HTF-II):
(SEQ ID NO: 647)
pELTFTPNWGT

SYNTHETIC:
(SEQ ID NO: 648)
LTFTPNWGT

SYNTHETIC:
(SEQ ID NO: 649)
pELTFTPNWG

Mandauca/Heliothis (AKH)
pELTFTSSWG

CRUSTACEAN (RPCH)
(SEQ ID NO: 650)
pELNFSPGW

LOCUSTA (AKH-II)
(SEQ ID NO: 651)
pELNFSAGW

SCHISTOCERCA
(SEQ ID NO: 652)
pELNFSTGW

PERIPLANETA M-I
(SEQ ID NO: 653)
pEVNFSPNW

PERIPLANETA M-II
(SEQ ID NO: 654)
pELTFTPNW

NEUPHOETA/BLABERUS HTH
(SEQ ID NO: 655)
pEVNFSPGWT

ROMALEA-I
(SEQ ID NO: 656)
pEVNFTPNWGT

ROMALEA-II/Gryllus
(SEQ ID NO: 657)
pEVNFSAGW insulin receptor substrate 1 {Homo sapiens}
>gi|5031805|ref|NP_005535.1|insulin receptor substrate 1 {Homo sapiens}
(SEQ ID NO: 658)
MASPPESDGFSDVRKVGYLRKPKSMHKRFFVLRAASEAGGPARLEYYENEKKWRHKSSAPK

RSIPLESCFNINKRADSKNKHLVALYTRDEHFAIAADSEAEQDSWYQALLQLHNRAKGHHD

GAAALGAGGGGGSCSGSSGLGEAGEDLSYGDVPPGPAFKEVWQVILKPKGLGQTKNLIGIYR

-continued

```
LCLTSKTISFVKLNSEAAAVVLQLMNIRRCGHSENFFFIEVGRSAVTGPGEFWMQVDDSVVA

QNMHETILEAMRAMSDEFRPRSKSQSSSNCSNPISVPLRRHHLNNPPPSQVGLTRRSRTESITA

TSPASMVGGKPGSFRVRASSDGEGTMSRPASVDGSPVSPSTNRTHAHRHRGSARLHPPLNHS

RSIPMPASRCSPSATSPVSLSSSSTSGHGSTSDCLFPRRSSASVSGSPSDGGFISSDEYGSSPCDF

RSSFRSVTPDSLGHTPPARGEEELSNYICMGGKGPSTLTAPNGHYILSRGGNGHRCTPGTGLG

TSPALAGDEAASAADLDNRFRKRTHSAGTSPTITHQKTPSQSSVASIEEYTEMMPAYPPGGGS

GGRLPGHRHSAFVPTRSYPEEGLEMHPLERRGGHHRPDSSTLHTDDGYMPMSPGVAPVPSG

RKGSGDYMPMSPKSVSAPQQIINPIRRHPQRVDPNGYMMMSPSGGCSPDIGGGPSSSSSSSNA

VPSGTSYGKLWTNGVGGHHSHVLPHPKPPVESSGGKLLPCTGDYMNMSPVGDSNTSSPSDC

YYGPEDPQHKPVLSYYSLPRSFKHTQRPGEPEEGARHQHLRLSTSSGRLLYAATADDSSSSTS

SDSLGGGYCGARLEPSLPHPHHQVLQPHLPRKVDTAAQTNSRLARPTRLSLGDPKASTLPRA

REQQQQQQPLLHPPEPKSPGEYVNIEFGSDQSGYLSGPVAFHSSPSVRCPSQLQPAPREEETGT

EEYMKMDLGPGRRAAWQESTGVEMGRLGPAPPGAASICRPTRAVPSSRGDYMTMQMSCPR

QSYVDTSPAAPVSYADMRTGIAAEEVSLPRATMAAASSSSAASASPTGPQGAAELAAHSSLL

GGPQGPGGMSAFTRVNLSPNRNQSAKVIRADPQGCRRRHSSETFSSTPSATRVGNTVPFGAG

AAVGGGGGSSSSSEDVKRHSSASFENVWLRPGELGGAPKEPAKLCGAAGGLENGLNYIDLD

LVKDFKQCPQECTPEPQPPPPPPPHQPLGSGESSSTRRSSEDLSAYASISFQKQPEDRQ insulin {Homo sapiens}
>gi|386828|gb|AAA59172.1|insulin {Homo sapiens}
                                                                    (SEQ ID NO: 659)
MALWMRLLPLLALLALWGPDPAAAFVNQHLCGSHLVEALYLVCGERGFFYTPKTRREAED

LQVGQVELGGGPGAGSLQPLALEGSLQKRGIVEQCCTSICSLYQLENYCN

ACTIVE (human) INSULIN fragment:
Chain A:
                                                                    (SEQ ID NO: 660)
GIVEQCCTSICSLYQLENYCN Chain B:
                                                                    (SEQ ID NO: 661)
FVNQHLCGSHLVEALYLVCGERGFFYTPKT
(Modifications: Disulfide bridge between amino acid numbers 6-11, 7-7*, 20-19*)

Insulin Glargine
>A chain
                                                                    (SEQ ID NO: 662)
GIVEQCCTSICSLYQLENYCG >B chain
                                                                    (SEQ ID NO: 666)
FVNQHLCGSHLVEALYLVCGERGFFYTPKTRR,
In some embodiments the C-terminus is amidated. In some embodiments
the N terminus is acylated.

Insulin Lispro
>A chain
                                                                    (SEQ ID NO: 670)
GIVEQCCTSICSLYQLENYCN >B chain
                                                                    (SEQ ID NO: 673)
FVNQHLCGSHLVEALYLVCGERGFFYTKPT
In some embodiments the C-terminus is amidated. In some embodiments
the N terminus is acylated.
```

```
Insulin Aspart
>A chain
GIVEQCCTSICSLYQLENYCN
>B chain
                                                            (SEQ ID NO: 677)
FVNQHLCGSHLVEALYLVCGERGFFYTDKT
In some embodiments the C-terminus is amidated. In some embodiments
the N terminus is acylated.

Oxyntomodulin
>gi|125987831|sp|P01275.3|
MKSIYFVAGLFVMLVQGSWQRSLQDTEEKSRSFSASQADPLSDPDQMNEDKRHSQGTFTSD

YSKYLDSRRAQDFVQWLMNTKRNRNNIAKRHDEFERHAEGTFTSDVSSYLEGQAAKEFIAW

LVKGRGRRDFPEEVAIVEELGRRHADGSFSDEMNTILDNLAARDFINWLIQTKITDRK

Oxm
                                                            (SEQ ID NO: 681)
HisSerGlnGlyThrPheThrSerAspTyrSerLysTyrLeuAspSerArgArgAlaGlnAspPheValGln

TrpLeuMetAsnThrLysArgAsnArgAsnAsnIleAla

DHis1-Oxm
                                                            (SEQ ID NO: 682)
dHisSerGlnGlyThrPheThrSerAspTyrSerLysTyrLeuAspSerArgArgAlaGlnAspPheValGlnTrp

LeuMetAsnThrLysArgAsnArgAsnAsnIleAla

Ala2-
                                                            (SEQ ID NO: 683)
Oxm HisAlaGlnGlyThrPheThrSerAspTyrSerLysTyrLeuAspSerArgArgAlaGlnAspPheValGlnTrp

LeuMetAsnThrLysArgAsnArgAsnAsnIleAla

DHis1-Ala2-
                                                            (SEQ ID NO: 684)
Oxm dHisAlaGlnGlyThrPheThrSerAspTyrSerLysTyrLeuAspSerArgArgAlaGlnAspPheValGlnTrpLeu

MetAsnThrLysArgAsnArgAsnAsnIleAla

Oxm(ex15-18)
                                                            (SEQ ID NO: 686)
HisSerGlnGlyThrPheThrSerAspTyrSerLysTyrLeuGluGluGluAlaAlaGlnAspPheValGlnTrp

LeuMetAsnThrLysArgAsnArgAsnAsnIleAla

Oxm(ex15-21)
                                                            (SEQ ID NO: 687)
HisSerGlnGlyThrPheThrSerAspTyrSerLysTyrLeuGluGluGluAlaValArgLeuPheValGlnTrp

LeuMetAsnThrLysArgAsnArgAsnAsnIleAla

Oxm(ex15-23)
                                                            (SEQ ID NO: 688)
HisSerGlnGlyThrPheThrSerAspTyrSerLysTyrLeuGluGluGluAlaValArgLeuPheIleGlnTrp

LeuMetAsnThrLysArgAsnArgAsnAsnIleAla

Oxm(ex15-24)
                                                            (SEQ ID NO: 689)
HisSerGlnGlyThrPheThrSerAspTyrSerLysTyrLeuGluGluGluAlaValArgLeuPheIleGluTrp

LeuMetAsnThrLysArgAsnArgAsnAsnIleAla

Oxm(ex27-33)
                                                            (SEQ ID NO: 690)
HisSerGlnGlyThrPheThrSerAspTyrSerLysTyrLeuAspSerArgArgAlaGlnAspPheValGlnTrp

LeuLysAsnGlyGlyProSerSerAsnAsnIleAla

Oxm(ex29-33)
                                                            (SEQ ID NO: 691)
HisSerGlnGlyThrPheThrSerAspTyrSerLysTyrLeuAspSerArgArgAlaGlnAspPheValGlnTrp

LeuMetAsnGlyGlyProSerSerAsnAsnIleAla
```

Oxm(ex30-33)
(SEQ ID NO: 692)
HisSerGlnGlyThrPheThrSerAspTyrSerLysTyrLeuAspSerArgArgAlaGlnAspPheValGlnTrp

LeuMetAsnThrGlyProSerSerAsnAsnIleAla

Oxm(ex27-30)
(SEQ ID NO: 693)
His Ser Gln Gly Thr Phe Thr Ser Asp Tyr Ser Lys Tyr Leu Asp Ser Arg Arg Ala

Gln Asp Phe Val Gln Trp Leu Lys Asn Gly Gly Arg Asn Arg Asn Asn Ile Ala

Oxm19-37
(SEQ ID NO: 694)
AlaGlnAspPheValGlnTrpLeuMetAsnThrLysArgAsnArgAsnAsnIleAla

Oxm30-37
(SEQ ID NO: 695)
LysArgAsnArgAsnAsnIleAla

Oxm-Ala38
(SEQ ID NO: 698)
HisSerGlnGlyThrPheThrSerAspTyrSerLysTyrLeuAspSerArgArgAlaGlnAspPheValGlnTrp
LeuMet
AsnThrLysArgAsnArgAsnAsnIleAlaAla

Oxm-Ala38,39
(SEQ ID NO: 699)
HisSerGlnGlyThrPheThrSerAspTyrSerLysTyrLeuAspSerArgArgAlaGlnAspPheValGlnTrp

LeuMetAsnThrLysArgAsnArgAsnAsnIleAlaAlaAla

Oxm-Ala38-42
(SEQ ID NO: 700)
HisSerGlnGlyThrPheThrSerAspTyrSerLysTyrLeuAspSerArgArgAlaGlnAspPheValGlnTrp

LeuMetAsnThrLysArgAsnArgAsnAsnIleAlaAlaAlaAlaAlaAla

Oxm-Lys38-
(SEQ ID NO: 701)
Laur HisSerGlnGlyThrPheThrSerAspTyrSerLysTyrLeuAspSerArgArgAlaGlnAspPheValGlnTrp LeuMetAsnThrLysArgAsnArgAsnAsnIleAla(LysLAUROYL)

Oxm-Lys38-
(SEQ ID NO: 702)
Palm HisSerGlnGlyThrPheThrSerAspTyrSerLysTyrLeuAspSerArgArgAlaGlnAspPheValGlnTrp LeuMetAsnThrLysArgAsnArgAsnAsnIleAla(LysPALMITOYL)

Oxm-Ala38,39-
(SEQ ID NO: 703)
Lys40Laur HisSerGlnGlyThrPheThrSerAspTyrSerLysTyrLeuAspSerArgArgAlaGlnAspPheValGlnTrp LeuMet AsnThrLysArgAsnArgAsnAsnIleAlaAlaAla(LysLAUROYL)

Oxm-Ala38,39-
(SEQ ID NO: 704)
Lys40Palm HisSerGlnGlyThrPheThrSerAspTyrSerLysTyrLeuAspSerArgArgAlaGlnAspPheValGln TrpLeuMet AsnThrLysArgAsnArgAsnAsnIleAlaAlaAla(LysPALMITOYL)-(D-His1)-Ala2-

Oxm(ex15-23)
(SEQ ID NO: 705)
dHisAlaGlnGlyThrPheThrSerAspTyrSerLysTyrLeuGluGluGluAlaValArgLeuPheIleGlnTrp

LysAsnGlyGlyProSerSerArgAsnAsnIleAlaAlaAla(LysLAUROYL)(ex27-33)-Ala38,39-Lys40-

LAUROYL

-continued

MC-4R Agonist (Cyclo (β-Ala-His-D-Phe-Arg-Trp-Glu)-NH₂)
(SEQ ID NO: 706)
Ac-Nle-Asp-His-D-Tyr-Arg-Trp-Lys-NH₂

(SEQ ID NO: 707)
Ac-Lys-Tyr-Val-Nle-Gly-His-Phe-Arg-Trp-Asp-Arg-Phe-Gly-NH₂

(SEQ ID NO: 709)
Ac-Ser Tyr Ser Met Glu His Phe Arg Trp Gly Lys Pro Val NH₂

Biotin-β-Endomorphin, human
(SEQ ID NO: 710)
Biotin-YGGFMTSEKSQTPLVTLFKNAIIKNAYKKGE {Ala1,3,11,16}-Endothelin 1, human
(SEQ ID NO: 712)
ASASSLMDKEAVYFAHLDIIW Big Endothelin-1 (1-38), human
CSCSSLMDKECVYFCHLDIIWVNTPEHVVPYGLGSPRS (Disulfide bridge: 1-15 and 3-11)
Endothelin 1, human, porcine
(SEQ ID NO: 713)
CSCSSLMDKECVYFCHLDIIW (Disulfide bridge: 1-15 and 3-11)

Endothelin 2, human
(SEQ ID NO: 714)
CSCSSWLDKECVYFCHLDIIW (Disulfide bridge: 1-15 and 3-11)

Orphanin FQ2, (OFQ2, NOCII)
(SEQ ID NO: 715)
FSEFMRQYLVLSMQSSQ

{Des-His1, Glu8}-Exendin-4
(SEQ ID NO: 716)
GEGTPTSELSKQMEEEAVRLPIEWLKNGGPSSGAPPPS-NH2

Biotin-Exendin 4
(SEQ ID NO: 717)
Biotin-HGEGTFTSDLSKQMEEEAVRLFIEWLKNGGPSSGAPPPS-NH2

Exendin (10-39)
(SEQ ID NO: 718)
LSKQMEEEAVRLFIEWLKNGGPSSGAPPPS-NH2

Exendin (4-39)
(SEQ ID NO: 719)
GTFTSDLSKQMEEEAVRLFIEWLKNGGPSSGAPPPS-NH2

Exendin (5-39)
(SEQ ID NO: 720)
TFTSDLSKQMEEEAVRLFIEWLKNGGPSSGAPPPS-NH2

Exendin (7-39)
(SEQ ID NO: 721)
TSDLSKQMEEEAVRLFIEWLKNGGPSSGAPPPS-NH2

Exendin (9-39)
(SEQ ID NO: 722)
DLSKQMEEEAVRLFIEWLKNGGPSSGAPPPS-NH2

Exendin (9-39)
(SEQ ID NO: 723)
DLSKQMEEEAVRLFIEWLKNGGPSSGAPPPS-NH2

Exendin 3
(SEQ ID NO: 724)
HSDGTFTSDLSKQMEEEAVRLFIEWLKNGGPSSGAPPPS-NH2

Glicentin-Related Peptide (21-50), human
(SEQ ID NO: 725)
RSLQDTEEKSRSFSASQADPLSDPDQMNED-NH2

α1(I) Collagen (614-639), Type I Collagen α1(I) C-Telopeptide, human
(SEQ ID NO: 726)
SAGFDFSFLPQPPQEKAHDGGRYYRA FDC-SP (30-85), human
(SEQ ID NO: 727)
SISDSDELASGFFVFPYPYPFRPLPPIPFPRFPWFRRNFPIPIPESAPTTPLPSEK -continued FDC-SP (61-85), human  
(SEQ ID NO: 728)  
FPWFRRNFPIPIPESAPTTPLPSEK Fibrinopeptide A, human  
(SEQ ID NO: 729)  
ADSGEGDFLAEGGGVR Fibrinopeptide B, human  
(SEQ ID NO: 730)  
Pyr-GVNDNEEGFFSAR Gamma-Fibrinogen (377-395)  
(SEQ ID NO: 731)  
YSMKETTMKIIPFNRLSIG {Glu1}-Fibrinopeptide B Glufib  
(SEQ ID NO: 732)  
EGVNDNEEGFFSAR

EAK16-II  
(SEQ ID NO: 733)  
AEAEAKAKAEAEAKAK-NH2

Elastin-Like Octapeptide  
(SEQ ID NO: 734)  
GVGVPGVGVPGVGVPGVG

Fibrinogen β-Chain (24-42)  
(SEQ ID NO: 735)  
EEAPSLRPAPPPISGGGYR

Fibrinogen γ-Chain (117-133)  
(SEQ ID NO: 736)  
NNQKIVNLKEKVAQLEA

Fibrinogen γ-Chain (397-411)  
(SEQ ID NO: 737)  
GQQHHLGGAKQAGDV

Fibrinogen Binding Inhibitor Peptide  
(SEQ ID NO: 738)  
HHLGGAKQAGDV

Fibrinogen-Binding Peptide  
(SEQ ID NO: 739)  
EHIPA

{Ala6, D-Trp8}-Galanin (1-15)-ol  
(SEQ ID NO: 740)  
GWTLNAAwYLLGPHA-ol

{D-Trp6, 8, 9}-Galanin (1-15)-ol  
(SEQ ID NO: 741)  
GWTLNwAwwLLGPHA-ol

Biotin-Galanin, human  
(SEQ ID NO: 742)  
Biotin-GWTLNSAGYLLGPHAVGNHRSFSDKNGLTS Biotin-Galanin, human  
Biotin-GWTLNSAGYLLGPHAVGNHRSFSDKNGLTS  
Galanin (1-13)-Bradykinin (2-9), amide, M35  
(SEQ ID NO: 743)  
GWTLNSAGYLLGPPPGFSPFR-NH2

Galanin (1-13)-Neuropeptide Y (25-36), amide, M32  
(SEQ ID NO: 744)  
GWTLNSAGYLLGPRHYINLITRQRY-NH2

Galanin (1-13)-Pro-Pro-(Ala-Leu)2-Ala, amide  
(SEQ ID NO: 745)  
GWTLNSAGYLLGPPPALALA-NH2

Galanin (1-13)-Spantide I, C7  
(SEQ ID NO: 746)  
GWTLNSAGYLLGPrPKPQQwFwLL-NH2

Galanin (1-13)-Spantide I, C8
GWTLNSAGYLLGPrPKPQQwFwLL-NH2 (SEQ ID NO: 747)

Galanin (1-13)-Substance P (5-11), amide, Galantide
GWTLNSAGYLLGPQQFFGLM-NH2 (SEQ ID NO: 748)

Galanin (1-13)/Galanin Like Peptide (GALP) (9-21), common
GWTLNSAGYLLGP (SEQ ID NO: 749)

Galanin Message Associated Peptide, GMAP (1-41), amide
ELEPEDEARPGGFDRLQSEDKAIRTIMEFLAFLHLKEAGAL-NH2 (SEQ ID NO: 750)

Galanin Message Associated Peptide, GMAP (16-41), amide
LQSEDKAIRTIMEFLAFLHLKEAGAL-NH2 (SEQ ID NO: 751)

Galanin Message Associated Peptide, GMAP (25-41), amide
TIMEFLAFLHLKEAGAL-NH2 (SEQ ID NO: 752)

Galanin Message Associated Peptide, GMAP (44-59), amide
LPGLPSAASSEDAGQS-NH2 (SEQ ID NO: 753)

Galanin, human
GWTLNSAGYLLGPHAVGNHRSFSDKNGLTS
Galanin-Lys(Biotin), human
GWTLNSAGYLLGPHAVGNHRSFSDKNGLTSK(Biotin) (SEQ ID NO: 754)

Galanin-Lys(Biotin), human, FAM-labeled
FAM-GWTLNSAGYLLGPHAVGNHRSFSDKNGLTSK(Biotin)
Leptin (57-74)
VTGLDFIPGLHPILTLSK (SEQ ID NO: 755)

GIP (1-42), human
YAEGTFISDYSIAMDKIHQQDFVNWLLAQKGKKNDWKHNITQ
GIP (3-42), human
EGTFISDYSIAMDKIHQQDFVNWLLAQKGKKNDWKHNITQ (SEQ ID NO: 756)

(Leu15)-Gastrin-1, human
Pyr-GPWLEEEEEAYGWLDF-NH2 (SEQ ID NO: 757)

Big Gastrin-1, human
Pyr-LGPQGPPHLVADPSKKQGPWLEEEEEAYGWMDF-NH2 (SEQ ID NO: 758)

Biotin-Gastrin (1-17)
Biotin-EGPWLEEEEAYGWMDF-NH2 (SEQ ID NO: 759)

Biotin-Gastrin (1-17), phosphorylated
Biotin-EGPWLEEEEA-pY-GWMDF-NH2 (SEQ ID NO: 760)

Biotin-Gastrin Releasing Peptide, human
Biotin-VPLPAGGGTVLTKMYPRGNHWAVGHLM-NH2 (SEQ ID NO: 761)

Gastrin derived peptide
GPWLEEEEEAYGWMDFK-NH2 (SEQ ID NO: 762)

Gastrin Releasing Peptide (14-27), porcine and human
MYPRGNHWAVGHLM-NH2 (SEQ ID NO: 763)

Gastrin Releasing Peptide (20-27), porcine and human, acetylated
Ac-HWAVGHLM-NH2 (SEQ ID NO: 764)

-continued

Gastrin Releasing Peptide, human

VPLPAGGGTVLTKMYPRGNHWAVGHLM-NH2 (SEQ ID NO: 765)

Gastrin Releasing Peptide-Lys(Biotin), human
VPLPAGGGTVLTKMYPRGNHWAVGHLMK(Biotin)
Gastrin-1, human Pyr-GPWLEEEEEAYGWMDF-NH2 (SEQ ID NO: 766)

Gastrin-Releasing Peptide (1-17)

VPLPAGGGTVLTKMYPR (SEQ ID NO: 767)

GRP10, Gastrin-releasing Peptide 10/Neuromedin C, amidated

GNHWAVGHLM-NH2 (SEQ ID NO: 768)

{Des-His1, Glu9}-Glucagon (1-29), amide

SQGTFTSEYSKYLDSRRAQDFVQWLMNT-NH2 (SEQ ID NO: 769)

Glucagon-like Peptide-2, GLP-2 (146-178), human
HADGSFSDEMNTILDNLAARDFINWLIQTKITD
Peptide Histidine Isoleucinamide (PHI), Porcine (1-27)

HADGVFTSDFSRLLGQLSAKKYLESLI-NH2 (SEQ ID NO: 770)

Glucagon-Like Peptide 1, GLP-1(7-17)-Cys

HAEGTFTSDVSC (SEQ ID NO: 771)

{GalNAc-Ser}-Erythropoietin (Epo) (117-131)

EAISPPDAA-*S-AAPLR (*S = GalNAc-Ser) (SEQ ID NO: 772)

EGFR-1148, EGFR (1140-1152)

QISLDNPDYQQDF (SEQ ID NO: 773)

Growth Hormone Releasing Factor, GRF (1-29), amide, human

YADAIFTNSYRKVLGQLSARKLLQDIMSR-NH2 (SEQ ID NO: 774)

Growth Hormone Releasing Factor, GRF (1-40), amide, human

YADAIFTNSYRKVLGQLSARKLLQDIMSRQQGESNQERGA-NH2 (SEQ ID NO: 775)

Growth Hormone Releasing Factor, GRF (1-44), amide, human

YADAIFTNSYRKVLGQLSARKLLQDIMSRQQGESNQERGARARL-NH2 (SEQ ID NO: 776)

{D-Ala2}-Growth Hormone Releasing Factor, GRF (1-29), amide, human

YaDAIFTNSYRKVLGQLSARKLLQDIMSR-NH2 (SEQ ID NO: 777)

PEP1--inhibits membrane association of NS5A, hence impairing HCV replication

SGSWLRDVWDWICTVLTDFKTWLQSKLDYKD-NH2 (SEQ ID NO: 778)

Pep 4A

GSVVIVGRIILSGR-NH2 (SEQ ID NO: 779)

Pep 4AK

KKKGSVVIVGRIILSGR-NH2 (SEQ ID NO: 780)

HMGA N-Terminal Fragment

GAGQPSTSAQGQ (SEQ ID NO: 781)

AKT/PKB/Rac-Protein Kinase Substrate {ARKRERTYSFGHHA}, Biotinylated

Biotin-ARKRERTYSFGHHA (SEQ ID NO: 782)

5-TMR-ARKRERTYSFGHHA Competitively inhibits histone H2B phosphorylation
(Ki = 12 μM) by AKT

5-TMR-ARKRERTYSFGHHA (SEQ ID NO: 783)

-continued

T20  
Ac-YTSLIHSLIEESQNQQEKNEQELLELDKWASLWNWF-NH2 (SEQ ID NO: 784)

T22 ({Tyr5, 12, Lys7}-polyphemusin II)  
RRWCYRKCYKGYCYRKCR (SEQ ID NO: 785)

Skeletal Dihydropyridine Receptor (671-690)  
TSAQKAKAEERKRRKMSRGL (SEQ ID NO: 786)

Luteinizing Hormone-Releasing Hormone (LH-RH), human,  
Pyr-HWSYGLRPG-NH2 (SEQ ID NO: 787)

β-MSH, human  
AEKKDEGPYRMEHFRWGSPPKD (SEQ ID NO: 788)

γ-2-MSH (41-58)  
YVMGHFRWDRFG (SEQ ID NO: 789)

{D-Phe7}-ACTH, α-MSH (1-13), amide  
SYSMEHfRWGKPV-NH2 (SEQ ID NO: 790)

{Nle4, D-Phe7}-α-MSH, amide  
Ac-SYS-Nle-EHfRWGKPV-NH2 (SEQ ID NO: 791)

Melanin Concentrating Hormone, human, mouse, rat  
DFDMLRCMLGRVYRPCWQV (Disulfide bridge: 7-16) (SEQ ID NO: 792)

VA-ß-MSH, Lipotropin-γ, Proopiomelanocortin-derived  
VAAEKKDEGPYRMEHFRWGSPPKD (SEQ ID NO: 793)

Apolipoprotein B-100 (3136-3155), human  
KTTKQSFDLSVKAQYKKNKH (SEQ ID NO: 794)

alpha-9 Gliadin Peptide  
QVLQQSTYQLLQELCCQHLW (SEQ ID NO: 795)

MOG (8-21)  
PGYPIRALVGDEAE (SEQ ID NO: 796)

MOG (97-108)  
TCFFRDHSYQEE (SEQ ID NO: 797)

MOG (14-39), human  
ALVGDEVELPCRISPGKNATGMELGW (SEQ ID NO: 798)

MOG (50-74), human  
LYRNGKDQDGDAPEYRGRTELLKD (SEQ ID NO: 799)

MOG (27-50), human  
SPGKNATGMELGWYRPPFSRVVHL (SEQ ID NO: 800)

MOG (76-100), human  
IGEGKVTLRIRNVRFSDEGGFTCFF (SEQ ID NO: 801)

MOG (89-113), human  
RFSDEGGFTCFFRDHSYQEEAAMEL (SEQ ID NO: 802)

MOG (35-51)  
MEVGWYRSPFSRVVHLY (SEQ ID NO: 803)

MOG (35-52)

MEVGWYRSPFSRVVHLYR (SEQ ID NO: 804)

MOG (35-53)

MEVGWYRSPFSRVVHLYRN (SEQ ID NO: 805)

MOG (35-55), human

MEVGWYRPPFSRVVHLYRNGK (SEQ ID NO: 806)

MOG (101-120), human, mouse

RDHSYQEEAAMELKVEDPFY (SEQ ID NO: 807)

{Ala4}-MBP (1-11)

Ac-ASQARPSQRHG (SEQ ID NO: 808)

{Tyr4}-MBP (1-11)

Ac-ASQYRPSQRHG (SEQ ID NO: 809)

MBP (1-17)

ASQKRPSQRSKYLATAS (SEQ ID NO: 810)

MBP (1-20), Myelin Basic Protein (1-20)

ASQKRPSQRSKYLATASTMD (SEQ ID NO: 811)

MBP (111-129)

LSRFSWGAEGQRPGFGYGG (SEQ ID NO: 812)

MBP (131-155)

ASDYKSAHKGLKGVDAQGTLSKIFK (SEQ ID NO: 813)

Vasonatrin Peptide (1-27)

GLSKGCFGLKLDRIGSMSGLGCNSFRY (Disulfide bridge: 6-22)) (SEQ ID NO: 814)

{Ala5, ß-Ala8}-Neurokinin A (4-10)

DAFV-(ß-A)-LM-NH2 (SEQ ID NO: 815)

{D-Pro2, D-Trp6, 8, Nle10}-Neurokinin B

DpHDFwVwL-Nle-NH2 (SEQ ID NO: 816)

{Lys5, NMeLeu9, NIe10}-Neurokinin A (4-10)

DKFVG-(NMeL)-Nle-NH2 (SEQ ID NO: 817)

Neurokinin A, Substance K, Neuromedin L, NKA

HKTDSFVGLM-NH2 (SEQ ID NO: 818)

Neuromedin (B-30)

LSWDLPEPRSRAGKIRVHPRGNLWATGHFM-NH2 (SEQ ID NO: 819)

{Ser2}-Neuromedin C

GSHWAVGHLM-NH2 (SEQ ID NO: 820)

ß-Neuroprotectin (D-Ala1)

aDLIAYL-NH2 (SEQ ID NO: 821)

{Ala16, 17, 20}-beta-Amyloid (1-28)

DAEFRHDSGYEVHHQAAVFAAEDVGSNK (SEQ ID NO: 822)

26Rfa, Hypothalamic Peptide, human

TSGPLGNLAEELNGYSRKKGGFSFRF-NH2

Brain Neuropeptide I (SEQ ID NO: 823)

AGEGLSSPFWSLAAPQRF-NH2

Erythropoietin, Human (hEPO) Fragment (SEQ ID NO: 824)

MEVGQQAVEVWQGLALLSEAVLR

Neuropeptide NPW-23 (Human) (SEQ ID NO: 825)

WYKHVASPRYHTVGRAAGLLMGL

VGF Protein Precursor (491-507) (SEQ ID NO: 826)

PPEPVPPPRAAPAPTHV

{Gln4}-Neurotensin (SEQ ID NO: 827)

Pyr-LYQNKPRRPYIL

{D-Tyr11}-Neurotensin (SEQ ID NO: 828)

Pyr-LYENKPRRPyIL

{D-Trp11}-Neurotensin (SEQ ID NO: 829)

Pyr-LYENKPRRPwIL

{D-Phe11}-Neurotensin (SEQ ID NO: 830)

Pyr-LYENKPRRPHL

Neurotensin (SEQ ID NO: 831)

Pyr-LYENKPRRPYIL

Neuropeptide F (SEQ ID NO: 832)

PDKDFIVNPSDLVLDNKAALRDYLRQINEYFAIIGRPRF-NH2

PTD-p50 (NLS) Inhibitory Peptide (SEQ ID NO: 833)

DRQIKIWFQNRRMKWKKVQRKRQKLMP

PTD-p65-P1 Peptide (SEQ ID NO: 834)

DRQIKIWFQNRRMKWKKQLRRPSDRELSE

PTD-p65-P6 (Ser529/536) Inhibitory Peptide (SEQ ID NO: 835)

DRQIKIWFQNRRMKWKKNGLLSGDEDFSS

PTD-TRAF6 Inhibitory Peptide (SEQ ID NO: 836)

DRQIKIFQNRRMKWKKRKIPTEDEY

RNase S Complex Peptide (SEQ ID NO: 837)

Ac-KETAAAKFERQHMDSSTSA-NH2

IKKγ NEMO Binding Domain (NBD) Inhibitory Peptide (SEQ ID NO: 838)

DRQIKIWFQNRRMKWKKTALDWSWLQTE

{Trp5}-Oryzatensin (5-9), rice (SEQ ID NO: 839)

WPLPR

LVV-Hemorphin-6, Leu-Valorphin-Arg (SEQ ID NO: 840)

LVVYPWTQR

LVV-Hemorphin-7 (SEQ ID NO: 841)

LVVYPWTQRF

-continued

Nociceptin (1-11), (Orphanin FQ, or OFQ/N) (1-11)  
FGGFTGARKSA  
(SEQ ID NO: 842)

Nociceptin (1-13), amide  
FGGFTGARKSARK  
(SEQ ID NO: 843)

Nociceptin (1-7), (Orphanin FQ, or OFQ/N) (1-7)  
FGGFTGA  
(SEQ ID NO: 844)

Prepronociceptin (169-176), human  
TLHQNGNV  
(SEQ ID NO: 845)

Serorphin, BSA (399-404)  
YGFQNA  
(SEQ ID NO: 846)

Valorphin  
VVYPWTQ  
(SEQ ID NO: 847)

Orexin A, bovine, human, mouse, rat  
Pyr-PLPDCCRQKTCSCRLYELLHGAGNHAAGILTL-NH2 (Disulfide bridge: 6-12 and 7-14)  
(SEQ ID NO: 848)

Orexin B, human  
RSGPPGLQGRLQRLLQASGNHAAGILTM-NH2  
(SEQ ID NO: 849)

{Gla17, 21, 24}-Osteocalcin (1-49)  
YLYQWLGAPVPYPDPL-Gla-PRR-Gla-VC-Gla-LNPDCDELDHIGFQEAYRRFYGPV  
(Gla = γ-Carboxyglutamic Acid; Disulfide bridge: 23-29)  
(SEQ ID NO: 851)

Osteocalcin (37-49), human  
GFQEAYRRFYGPV  
(SEQ ID NO: 852)

Osteocalcin (7-19), human  
GAPVPYPDPLEPR  
(SEQ ID NO: 853)

Lys-OVA (257-264), KSIINFEKL  
KSIINFEKL  
(SEQ ID NO: 854)

{Arg8}-Vasopressin (AVP)  
CYFQNCPRG-NH2 (Disulfide bridge: 1-6)  
(SEQ ID NO: 855)

{Deamino-Cys1, D-Arg8}-Vasopressin, free acid)  
3-Mercaptopropionyl-YFQNCPrG (Disulfide bridge: 1-6  
(SEQ ID NO: 856)

Oxytocin  
CYIQNCPLG-NH2 (Disulfide bridge: 1-6)  
(SEQ ID NO: 857)

Serum Albumin (102-226)  
ADDKETCFAEEGKKLVAASQAALGL  
(SEQ ID NO: 858)

Apolipoprotein J (215-222)  
RPHFFFPK  
(SEQ ID NO: 859)

Apolipoprotein L (306-316)  
VNEPSILEMSR  
(SEQ ID NO: 860)

Catestatin, human  
SSMKLSFRARAYGFRGPGPL  
(SEQ ID NO: 861)

Pancreastatin (37-52), Human  
EEEEEMAVVPQGLFRG-NH2  
(SEQ ID NO: 862)

-continued

Pancreatic Polypeptide (30-53), human  
(SEQ ID NO: 863)  
APLEPVYPGDNATPEQMAQYAADL {Tyr0}-Hypercalcemia Malignancy Factor (1-40)  
(SEQ ID NO: 864)  
YAVSEHQLLHDKGKSIQDLRRRFFLHHLIAEIHTAEIRATS Hypercalcemia Malignancy Factor (1-34), (PLP) amide, human  
(SEQ ID NO: 865)  
AVSEHQLLHDKGKSIQDLRRRFFLHHLIAEIHTA-NH2

TIP 39, Tuberoinfundibular Neuropeptide  
(SEQ ID NO: 866)  
SLALADDAAFRERARLLAALERRHWLNSYMHKLLVLDAP PACAP-Related Peptide (PRP), human  
(SEQ ID NO: 867)  
DVAHGILNEAYRKVLDQLSAGKHLQSLVA Prolactin Releasing Peptide (1-31), human  
(SEQ ID NO: 868)  
SRTHRHSMEIRTPDINPAWYASRGIRPVGRF-NH2

Prolactin Releasing Peptide (12-31), human  
(SEQ ID NO: 869)  
TPDINPAWYASRGIRPVGRF-NH2

Calpain Inhibitor Peptide, B27-WT  
(SEQ ID NO: 870)  
DPMSSTYIEELGKREVTIPPKYRELLA 105Y, α1-antitrypsin (359-374)  
SIPPEVKFNKPFVYLI  
Acetyl-Calpastatin (184-210), CS peptide, human  
(SEQ ID NO: 871)  
Ac-DPMSSTYIEELGKREVTIPPKYRELLA-NH2

{Ala144}-PLP (139-151) A144-PLP(139-151)  
(SEQ ID NO: 872)  
HSLGKALGHPDKF

PLP (190-209)  
(SEQ ID NO: 873)  
SKTSASIGSLCADARMYGVL

PLP (48-70)  
(SEQ ID NO: 874)  
TYFSKNYQDYEYLINIHAFQYV

Acetyl-Tetradecapeptide Renin Substrate, Acetyl-Angiotensinogen (1-14), human  
(SEQ ID NO: 875)  
Ac-DRVYIHPFHLVIHN TP508, Thrombin-derived Peptide  
(SEQ ID NO: 876)  
AGYKPDEGKRGDACEGDSGGPFV Salusin-alpha  
(SEQ ID NO: 877)  
SGALPPAPAAPRPALRAQRAGPAGPGAK-NH2

Salusin-beta  
(SEQ ID NO: 878)  
AIFIFIRWLLKLGHHGRAPP

Prosaptide 769P (D-Ala2)  
(SEQ ID NO: 879)  
CaFLVKEVTKLIDNNKTEKEIL

Prosaptide TX14(A) (D-Ala2)  
(SEQ ID NO: 880)  
TaLIDNNATEEILY

Prosaptide, wild type  
(SEQ ID NO: 881)  
TKLIDNNKTEKEIL

Saposin C12
(SEQ ID NO: 882)
LIDNNKTEKEIL

Saposin C18
(SEQ ID NO: 883)
VKEVTKLIDNNKTEKEIL

Saposin C22
(SEQ ID NO: 884)
CEFLVKEVTKLIDNNKTEKEIL

Secretin, human
(SEQ ID NO: 885)
HSDGTFTSELSRLREGARLQRLLQGLV-NH2

CC Chemokine Receptor 3 Fragment I, amide
(SEQ ID NO: 886)
MTTSLDTVETFGTTSYYDDVGLLCEKADTR-NH2

CC Chemokine Receptor 3 Fragment II
(SEQ ID NO: 887)
MTTSLDTVETFGTTSYYDDVGLLC

DAP10 Signaling Fragment
(SEQ ID NO: 888)
PAQEDGKVYINMPGRG

Erythropoietin-Mimetic Peptide 17 (EMP17)
(SEQ ID NO: 889)
TYSCHFGPLTWVCKPQGG

Hsp Heat shock protein (3-13)
(SEQ ID NO: 890)
KTIAYDEEARR iNOS (507-531), human
(SEQ ID NO: 891)
RPKRREIPLKVLVKAVLFACMLMRK Notch 1 (1735-1752)
(SEQ ID NO: 892)
VLLFFVGCGVLLSRKRRR SmMLCKp, Smooth-Muscle Myosin Light-Chain Kinase (796-815), Calmodulin Binding
(SEQ ID NO: 893)
ARRKWQKTGHAVRAIGRLSS Tau-Protein (1-16)
(SEQ ID NO: 894)
MAEPRQEFEVMEDHAG Tau-Protein (323-335)
(SEQ ID NO: 895)
GSLGNIHHKPGGG Caveolin-1 Scaffolding Domain (82-101)
(SEQ ID NO: 896)
DGIWKASFTTFTVTKYWFYR Caveolin-3 (Cav-3), (55-74)
(SEQ ID NO: 897)
DGVWRVSYTTFTVSKYWCYR {Gly35, Asp37}-beta-Amyloid (1-42)
(SEQ ID NO: 898)
DAEFRHDSGYEVHHQKLVFFAEDVGSNKGAIIGLGVDGVVIA {Cys7}-beta-Amyloid (1-40)
(SEQ ID NO: 899)
DAEFRHCSGYEVHHQKLVFFAEDVGSNKGAIIGLMVGGVV beta-Amyloid (1-40)
(SEQ ID NO: 900)
DAEFRHDSGYEVHHQKLVFFAEDVGSNKGAIIGLMVGGVV {Cys3,6, Tyr8, Pro9}-Substance P
(SEQ ID NO: 901)
RPCPQCFYPLM-NH2 (Disulfide bridge: 3-6)

-continued

{4-Chloro-Phe}7,8-Substance P
(SEQ ID NO: 902)
RPKPQQ-F(4-Cl-F)-GLM-NH2

{Cys3,6, Tyr8, Pro10}-Substance P
(SEQ ID NO: 903)
RPCPQCFYGPM-NH2 (Disulfide bridge: 3-6)

Ranakinin
(SEQ ID NO: 904)
KPNPERFYGLM-NH2

Scyliorhinin I, Scy I, Shark Substance P Related Peptide
(SEQ ID NO: 905)
AKFDKFYGLM Substance P
(SEQ ID NO: 906)
RPKPQQFFGLM-NH2

SFLLRNPNDKYEPF, human Thrombin Receptor 42-55
(SEQ ID NO: 907)
SFLLRNPNDKYEPF

Tumor Necrosis Factor Receptor, TNFR (159-178) Analog
(SEQ ID NO: 908)
QEKQNTVATAHGFFLRENEG

CDIP2
(SEQ ID NO: 909)
KISLQRLKSYVITTSRCPQ

Pro-TNF-α (71-82), human
(SEQ ID NO: 910)
SPLAQAVRSSSR

TNF-α (10-36), human
(SEQ ID NO: 911)
DKPVAHVVANPQAEGQLQWLNRRANAL

TNF-α (31-45), human
(SEQ ID NO: 912)
RRANALLANGVELRD

Brevinin-2Eg
(SEQ ID NO: 913)
GIMDTLKNLAKTAGKGALQSLLNHASCKLSGQC (Disulfide bridge 27-33)

Brevinin-2Eh
(SEQ ID NO: 914)
GIMDTLKNLAKTAGKGALQSLLNHASCKLSKQC (Disulfide bridge 27-33)

Caloxin 1b1
(SEQ ID NO: 915)
TAWSEVLHLLSRGGG

Caloxin 2A1
(SEQ ID NO: 916)
VSNSNWPSFPSSGGG

Caloxin 3A1
(SEQ ID NO: 917)
WSSTSSVSAPLEFGGGGSAK

Delta-Toxin (1-26), *Staphylococcus aureus*
(SEQ ID NO: 918)
MAQDIISTIGDLVKWIIDTVNKFTKK Delta-Toxin (5-20), *Staphylococcus aureus*
(SEQ ID NO: 919)
IISTIGDLVKWIIDTV Sarafotoxin 6c
(SEQ ID NO: 920)
CTCNDMTDEECLNFCHQDVIW (Disulfide bridge: 1-15 and 3-11)

Vesicle-Associated Membrane Protein, VAMP (60-94)
(SEQ ID NO: 921)
LSELDDRADALQAGASQFETSAAKLKRKYWWKNLK -continued Vesicle-Associated Membrane Protein, VAMP (77-94)
(SEQ ID NO: 922)
SQFETSAAKLKRKYWWKNLK Helodermin
(SEQ ID NO: 923)
HSDAIFTQQYSKLLAKLALQKYLASILGSRTSPPP highly selective $CRF_2$ receptor antagonist K41498
(SEQ ID NO: 924)
dFHLLRKNleIEIEKQEKEKQQAANNRLLLDTI-NH2

Corticotropin-releasing factor receptor antagonist
(SEQ ID NO: 925)
DLTFHLLREMLEMAKAEQEAEQAALNRLLLEEA-NH2

Astressin CAS No: {170809-51-5}
Potent corticotropin-releasing factor (CRF) receptor antagonist ($K_i$ values are
2, 1.5 and 1 nM at $CRF_1$, $CRF_2\alpha$ and $CRF_2\beta$). Reduces ACTH
secretion, blocks delayed gastric emptying and is neuroprotective in vivo.
(SEQ ID NO: 926)
dFHLLREVLENleARAEQLAQE*AHKg*NRKLNleEII-NH2 E*-Kg* are cyclized. The cyclic structure has been fixed by amide bond between gamma-COOH group of glutamic acid and alpha-NH2 group of glycine coupled to the epsilon-NH2 group of lysine.

Stressin I
Potent and selective corticotropin releasing factor receptor-1 ($CRF_1$) agonist
($K_i$ values are 1.5 and 224 nM for $CRF_1$ and $CRF_2$ receptors
respectively). Increases ACTH levels and increases faecal pellet output in vivo
following i.p. administration.
(SEQ ID NO: 927)
Ac-PPISLDLTFHLLREVLENleARAEQLAQQE*HSK*AKLNleEII-NH2 E*-K* are cyclized. The cyclic structure has been fixed by amide bond between gamma-COOH group of glutamic acid and epsilon-NH2 group of lysine.

Human urocortin III-like sequences
(SEQ ID NO: 928)
MLMPVHFLLLLLLLLGGPRTGLPHKFYKAKPIFSCLNTALSEAEKGQWEDASLLSKR

SFHYLRSRDASSGEEEEGKEKKTFPISGARGGAGGTRYRYVSQAQPRGKPRQDTAKS

PHRTKFTLSLDVPTNIMNLLFNIAKAKNLRAQAAANAHLMAQIGRKK

Active Form: 120-137 urocortin III {Homo sapiens}
FTLSLDVPTNIMNLLFNI
(SEQ ID NO: 929)
FTLSLDVPTNIMNLLFNIAKAKNLRAQAAANAHLMAQI Human urocortin-2
(SEQ ID NO: 930)
IVLSLDVPIGLLQILLEQARARAAREQATTNARILARV Human Growth Hormone Releasing Factor (GHRF), GRF
YADAIFTNSYRKVLGQLSARKLLQDIMSR-NH2
JI-22 {Dat1, Orn12,21, Abu15, Nle27, Agm29} GHRF-(1-29)
JI-34 {Dat1, Orn12,21, Abu15, Nle27, Asp28, Agm29} GHRF-(1-29)
JI-36 {Dat1, Thr8, Orn12,21, Abu15, Nle27, Asp28, Agm29} GHRF-(1-29)
JI-38 {Dat1, Gln8, Orn12,21, Abu15, Nle27, Asp28, Agm29} GHRF-(1-29)
Dat = desaminotyrosine
Agm = agmatine
α-CGRP (human)
ACDTATCVTHRLAGLLSRSGGVVKNNFVPTNVGSKAF-NH2
Optional Disulfide bridge between C2 and C7
CGRP (rat)
SCNTATCVTHRLAGLLSRSGGVVKDNFVPTNVGSEAF-NH2
(SEQ ID NO: 931)
Optional Disulfide bridge between C2 and C7

PTHrP (Human) 1-37
(SEQ ID NO: 932)
AVSEHQLLHDKGKSIQDLRRFFLHHLIAEIHTAEIR

PTH (human) 1-34
(SEQ ID NO: 933)
SVSEIQLMHNLGKHLNSMERVEWLRKKLQDVHN

-continued

TIP 39, Tuberoinfundibular Neuropeptide (human)

(SEQ ID NO: 934)

SLALADDAAFRERARLLAALERRHWLNSYMHKLLVLDAP

TIP 39, Tuberoinfundibular Neuropeptide (mouse)
SLALADDAAFRERARLLAALERRRWLDSYMQKLLLLDAP
PTH2 Agonists
{His5}-PTH 1-34 (human)
{Ile5}-PTHrP 1-36
{Ile5, Trp23}-PTHrP 1-36 (human)
{Ile5, Trp23}-PTHrP 2-36 (human)
{Ile5, Trp23}-PTHrP 3-36 (human)
{Ile5, Trp23}-PTHrP 4-36 (human)
{Ile5, Trp23}-PTHrP 5-36 (human)
{Ile5, Trp23, Tyr36}-PTHrP 1-36-NH2 (human)
{Phe23}-PTH 1-34 (human)
PTH 1-34 (human)
PTH 1-34 (rat)
PTHrP 1-34
PTHrP 1-36 (human)
{125I} {Nle8,21, Tyr34}-PTH 1-34-NH2 (rat)
TIP39 (human/bovine)
TIP39 (mouse)
{Trp23}-PTHrP 1-36 (human)
{Trp23, Tyr36}-PTHrP 1-36-NH2 (human)
PTH2 Antagonists
{D-Trp12}-PTH 7-34 (bovine
{D-Trp12, Tyr34}-PTH 7-34 (bovine)
{Ile5, Trp23}-PTHrP 5-36
PTHrP 1-21/PTH 22-34
PTHrP 7-34
TIP39 7-39 (human/bovine)
TIP39 7-39 (mouse)
AF 12198
(Potent and selective antagonist for the human type I interleukin-1 (IL-1) receptor)

(SEQ ID NO: 935)

Ac-FEWTPGWYQXYALPL-NH2 X = 2-Carboxyazetidine human epidermal growth factor
>gi|46242544|gb|AAS83395.1|epidermal growth factor {Homo sapiens}

(SEQ ID NO: 936)

NSDSECPLSHDGYCLHDGVCMYIEALDKYACNCVVGYIGERCQYRDLKWWELR

{cPP1-7, NPY19-23, Ala31, Aib32, Gln34}-hPancreatic Polypeptide (SEQ ID NO: 937)

GPSQPTYPGDNATPEQMARYYSALRRYINMAXRQRY-NH2 X = Aib

Xenin 8. C-Terminal fragment of xenin, a neurotensin-like peptide; modulates
pancreatic insulin and glucagon secretion/effects.

(SEQ ID NO: 938)

HPKRPWIL

>gi|29725609|ref|NP_005219.2|epidermal growth factor receptor
isoform a precursor {Homo sapiens}

(SEQ ID NO: 939)

MRPSGTAGAALLALLAALCPASRALEEKKVCQGTSNKLTQLGTFEDHFLSLQRMFNNCEVV

LGNLEITYVQRNYDLSFLKTIQEVAGYVLIALNTVERIPLENLQIIRGNMYYENSYALAVLSN

YDANKTGLKELPMRNLQEILHGAVRFSNNPALCNVESIQWRDIVSSDFLSNMSMDFQNHLGS

CQKCDPSCPNGSCWGAGEENCQKLTKIICAQQCSGRCRGKSPSDCCHNQCAAGCTGPRESD

CLVCRKFRDEATCKDTCPPLMLYNPTTYQMDVNPEGKYSFGATCVKKCPRNYVVTDHGSC

VRACGADSYEMEEDGVRKCKKCEGPCRKVCNGIGIGEFKDSLSINATNIKHFKNCTSISGDLH

ILPVAFRGDSFTHTPPLDPQELDILKTVKEITGFLLIQAWPENRTDLHAFENLEIIRGRTKQHGQ

FSLAVVSLNITSLGLRSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFVENSECIQCHPEC

LPQAMNITCTGRGPDNCIQCAHYIDGPHCVKTCPAGVMGENNTLVWKYADAGHVCHLCHP

NCTYGCTGPGLEGCPTNGPKIPSIATGMVGALLLLLVVALGIGLFMRRRHIVRKRTLRRLLQE

RELVEPLTPSGEAPNQALLRILKETEFKKIKVLGSGAFGTVYKGLWIPEGEKVKIPVAIKELRE

ATSPKANKEILDEAYVMASVDNPHVCRLLGICLTSTVQLITQLMPFGCLLDYVREHKDNIGS

-continued

QYLLNWCVQIAKGMNYLEDRRLVHRDLAARNVLVKTPQHVKITDFGLAKLLGAEEKEYHA

EGGKVPIKWMALESILHRIYTHQSDVWSYGVTVWELMTFGSKPYDGIPASEISSILEKGERLP

QPPICTIDVYMIMVKCWMIDADSRPKFRELIIEFSKMARDPQRYLVIQGDERMHLPSPTDSNF

YRALMDEEDMDDVVDADEYLIPQQGFFSSPSTSRTPLLSSLSATSNNSTVACIDRNGLQSCPI

KEDSFLQRYSSDPTGALTEDSIDDTFLPVPEYINQSVPKRPAGSVQNPVYHNQPLNPAPSRDP

HYQDPHSTAVGNPEYLNTVQPTCVNSTFDSPAHWAQKGSHQISLDNPDYQQDFFPKEAKPN

GIFKGSTAENAEYLRVAPQSSEFIGA

>gi|41327736|ref|NP_958441.1|epidermal growth factor receptor isoform d precursor {Homo sapiens}

(SEQ ID NO: 940)

MRPSGTAGAALLALLAALCPASRALEEKKVCQGTSNKLTQLGTFEDHFLSLQRMFNNCEVV

LGNLEITYVQRNYDLSFLKTIQEVAGYVLIALNTVERIPLENLQIIRGNMYYENSYALAVLSN

YDANKTGLKELPMRNLQEILHGAVRFSNNPALCNVESIQWRDIVSSDFLSNMSMDFQNHLGS

CQKCDPSCPNGSCWGAGEENCQKLTKIICAQQCSGRCRGKSPSDCCHNQCAAGCTGPRESD

CLVCRKFRDEATCKDTCPPLMLYNPTTYQMDVNPEGKYSFGATCVKKCPRNYVVTDHGSC

VRACGADSYEMEEDGVRKCKKCEGPCRKVCNGIGIGEFKDSLSINATNIKHFKNCTSISGDLH

ILPVAFRGDSFTHTPPLDPQELDILKTVKEITGFLLIQAWPENRTDLHAFENLEIIRGRTKQHGQ

FSLAVVSLNITSLGLRSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFVENSECIQCHPEC

LPQAMNITCTGRGPDNCIQCAHYIDGPHCVKTCPAGVMGENNTLVWKYADAGHVCHLCHP

NCTYGPGNESLKAMLFCLFKLSSCNQSNDGSVSHQSGSPAAQESCLGWIPSLLPSEFQLGWG

GCSHLHAWPSASVIITASSCH

>gi|41327732|ref|NP_958439.1|epidermal growth factor receptor isoform b precursor {Homo sapiens}

(SEQ ID NO: 941)

MRPSGTAGAALLALLAALCPASRALEEKKVCQGTSNKLTQLGTFEDHFLSLQRMFNNCEVV

LGNLEITYVQRNYDLSFLKTIQEVAGYVLIALNTVERIPLENLQIIRGNMYYENSYALAVLSN

YDANKTGLKELPMRNLQEILHGAVRFSNNPALCNVESIQWRDIVSSDFLSNMSMDFQNHLGS

CQKCDPSCPNGSCWGAGEENCQKLTKIICAQQCSGRCRGKSPSDCCHNQCAAGCTGPRESD

CLVCRKFRDEATCKDTCPPLMLYNPTTYQMDVNPEGKYSFGATCVKKCPRNYVVTDHGSC

VRACGADSYEMEEDGVRKCKKCEGPCRKVCNGIGIGEFKDSLSINATNIKHFKNCTSISGDLH

ILPVAFRGDSFTHTPPLDPQELDILKTVKEITGFLLIQAWPENRTDLHAFENLEIIRGRTKQHGQ

FSLAVVSLNITSLGLRSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFVENSECIQCHPEC

LPQAMNITCTGRGPDNCIQCAHYIDGPHCVKTCPAGVMGENNTLVWKYADAGHVCHLCHP

NCTYGS

>gi|41327734|ref|NP_958440.1|epidermal growth factor receptor isoform c precursor {Homo sapiens}

(SEQ ID NO: 942)

MRPSGTAGAALLALLAALCPASRALEEKKVCQGTSNKLTQLGTFEDHFLSLQRMFNNCEVV

LGNLEITYVQRNYDLSFLKTIQEVAGYVLIALNTVERIPLENLQIIRGNMYYENSYALAVLSN

YDANKTGLKELPMRNLQEILHGAVRFSNNPALCNVESIQWRDIVSSDFLSNMSMDFQNHLGS

CQKCDPSCPNGSCWGAGEENCQKLTKIICAQQCSGRCRGKSPSDCCHNQCAAGCTGPRESD

CLVCRKFRDEATCKDTCPPLMLYNPTTYQMDVNPEGKYSFGATCVKKCPRNYVVTDHGSC

VRACGADSYEMEEDGVRKCKKCEGPCRKVCNGIGIGEFKDSLSINATNIKHFKNCTSISGDLH

ILPVAFRGDSFTHTPPLDPQELDILKTVKEITGLS

-continued

PHM 27 (human) Endogenous peptide product of human prepro-VIP and analog of porcine
PHI-27; potent agonist for the human calcitonin receptor (EC50 = 11 nM)

(SEQ ID NO: 943)

HADGVFTSDFSKLLGQLSAKKYLESLM-NH2

Calcitoninreceptor-stimulating peptide-1
(Endogenous central calcitonin (CT) receptor agonist that stimulates cAMP formation at
a potency 350-fold greater than CT (ED50 values are 0.2 and 71 nM respectively).
Displays no activity at calcitonin-gene related peptide (CGRP) and adrenomedullin
receptors. Inhibits formation of multinuclear osteoclasts with similar efficacy to CT
in vitro. Suppresses food intake and increases body temperature in free-feeding rats,
and significantly decreases plasma calcium levels in vivo.)

(SEQ ID NO: 944)

SCNTATCMTHRLVGLLSRSGSMVRSNLLPTKMGFKVFG-NH2

AC 187
(Orally active, potent amylin receptor antagonist (IC50 = 0.48 nM) that displays
38-fold and 400-fold selectivity over calcitonin and CGRP receptors respectively.
Blocks amyloid β-induced neurotoxicity by attenuating the activation of initiator
and effector caspases in vitro. Increases glucagon secretion, accelerates gastric
emptying, alters plasma glucose levels and increases food intake in vivo.)

(SEQ ID NO: 945)

Ac-VLGKLSQQLHKLQTYPRTNTGSNTY-NH2

VIP (guinea pig)
(Neuropeptide with many biological actions; plays a role in neurotransmission, smooth
muscle relaxation and has trophic and mitogenic actions.)

(SEQ ID NO: 946)

HSDALFTDTYTRLRKQMAMKKYLNSVLN-NH2

{Ala2,8,9,11,19,22,24,25,27,28}-VIP
(Highly selective agonist for the VPAC1 receptor (IC50 values are ~ 11.5-13.2
and >30000 nM for VPAC1 and VPAC2 receptors respectively)))

(SEQ ID NO: 947)

HADAVFTAAYARLRKQMAAKKALAAIAA-NH2

{Ac-Tyr1, D-Phe2}GRF 1-29, amide (human)
(VIP antagonist; inhibits {125I}iodo-VIP binding and selectively inhibits VIP-
and GRF-induced effects on adenylyl cyclase.)

(SEQ ID NO: 948)

Ac-YdFDAIFTNSYRKVLGQLSARKLLQDIMSR-NH2

VIP (6-28) (human, rat, porcine, bovine) (VIP antagonist.)

(SEQ ID NO: 949)

FTDNYTRLRKQMAVKKYLNSILN-NH2

{D-p-Cl-Phe6,Leu17}-VIP
(Selective vasoactive intestinal peptide (VIP) antagonist (IC50 = 125.8 nM).
Displays no activity on glucagon, secretin or GRF receptors.)

(SEQ ID NO: 950)

HSDAVFTDNYTRLRKQLAVKKYLNSILN-NH2  Phe-6 = p-Cl-D-Phe

Neurotensin (SEQ ID NO: 951)

XLYENKPRRPYIL  X = Pyroglutamic acid (Pyr) (pGlu)

N-stearyl-{Nle17}neurotensin(6-11)/VIP(7-28)
neurotensin(6-11)/PACAP (6-38)
human pancreatic polypeptide (SEQ ID NO: 952)

APLEPVYPGDNATPEQMAQYAADLRRYINMLTRPRY

Kinetensin (human) (Endogenous neurotensin-like peptide, originally isolated from
pepsin-treated human plasma. Induces histamine release from rat peritoneal mast
cells in vitro (ED50 ~ 10 mM).)

(SEQ ID NO: 953)

IARRHPYFL

JMV 449
(Potent, metabolically stable neurotensin receptor agonist peptide (IC50 = 0.15 nM
for inhibition of {125I}-NT binding to neonatal mouse brain; EC50 = 1.9 nM
for contraction of guinea pig ileum). Produces long-lasting hypothermic,
neuroprotective and analgesic effects in mice following central administration in
vivo.)

(SEQ ID NO: 954)

KKPYIL (Note: Lys-1-Lys-2 peptide bond replace with Psi(CH2—NH))

Neuromedin N (rat, mouse, porcine, canine)
(Endogenous neurotensin-like neuropeptide, originally isolated from porcine spinal
cord. Binds to neurotensin receptors (IC50 = 16.7 nM for inhibition of -continued {Trp11}-NT binding to rat brain receptors). Regulates guinea pig intestinal
smooth muscle contraction and produces hypotension in rats. Also induces hypothermia
following central administration in rats in vivo.)

(SEQ ID NO: 955)
KIPYIL des-His1-{Glu9}-Glucagon (1-29) amide
(Glucagon receptor antagonist (pA2 = 7.2 for inhibition of glucagon-induced
adenylyl cyclase activation in rat liver membranes); displays no agonist activity.
Enhances glucose-stimulated pancreatic insulin release in vitro. In vivo, blocks
added glucagon-induced hyperglycemia in normal rabbits without affecting
glycogenolysis. Also blocks endogenous glucagon-induced hyperglycemia in streptozocin
diabetic rats.)

(SEQ ID NO: 956)
SQGTFTSEYSKYLDSRRAQDFVQWLMNT-NH2

Antisauvagine-30
(Potent, selective and competitive corticotropin-releasing factor CRF2 receptor
antagonist (Kd values are 1.4 and 153.6 nM for binding to mouse CRF2β and
rat CRF1 receptors respectively). Inhibits sauvagine-stimulated cAMP accumulation
in HEK-mCRF2β cells (pA2 = 8.49). Prevents stress-enhanced fear
conditioning and MEK 1/2-dependent activation of ERK1/2 in mice in vivo.)

(SEQ ID NO: 957)
dFHLLRKMIEIEKQEKEKQQAANNRLLLDTI-NH2

>gi|76781480|ref|NP_001020537.2|vascular endothelial growth
factor A isoform a {Homo sapiens}

(SEQ ID NO: 958)
MTDRQTDTAPSPSYHLLPGRRRTVDAAASRGQGPEPAPGGGVEGVGARGVALKLFVQLLGC

SRFGGAVVRAGEAEPSGAARSASSGREEPQPEEGEEEEKEEERGPQWRLGARKPGSWTGEA

AVCADSAPAARAPQALARASGRGGRVARRGAEESGPPHSPSRRGSASRAGPGRASETMNFL

LSWVHWSLALLLYLHHAKWSQAAPMAEGGGQNHHEVVKFMDVYQRSYCHPIETLVDIFQE

YPDEIEYIFKPSCVPLMRCGGCCNDEGLECVPTEESNITMQIMRIKPHQGQHIGEMSFLQHNK

CECRPKKDRARQEKKSVRGKGKGQKRKRKKSRYKSWSVYVGARCCLMPWSLPGPHPCGPC

SERRKHLFVQDPQTCKCSCKNTDSRCKARQLELNERTCRCDKPRR

>gi|76781481|ref|NP_003367.4|vascular endothelial growth factor
A isoform b {Homo sapiens}

(SEQ ID NO: 959)
MTDRQTDTAPSPSYHLLPGRRRTVDAAASRGQGPEPAPGGGVEGVGARGVALKLFVQLLGC

SRFGGAVVRAGEAEPSGAARSASSGREEPQPEEGEEEEKEEERGPQWRLGARKPGSWTGEA

AVCADSAPAARAPQALARASGRGGRVARRGAEESGPPHSPSRRGSASRAGPGRASETMNFL

LSWVHWSLALLLYLHHAKWSQAAPMAEGGGQNHHEVVKFMDVYQRSYCHPIETLVDIFQE

YPDEIEYIFKPSCVPLMRCGGCCNDEGLECVPTEESNITMQIMRIKPHQGQHIGEMSFLQHNK

CECRPKKDRARQEKKSVRGKGKGQKRKRKKSRYKSWSVPCGPCSERRKHLFVQDPQTCKC

SCKNTDSRCKARQLELNERTCRCDKPRR gi|76781482|ref|NP_001020538.2|vascular endothelial growth factor
A isoform c {Homo sapiens}

(SEQ ID NO: 960)
MTDRQTDTAPSPSYHLLPGRRRTVDAAASRGQGPEPAPGGGVEGVGARGVALKLFVQLLGC

SRFGGAVVRAGEAEPSGAARSASSGREEPQPEEGEEEEKEEERGPQWRLGARKPGSWTGEA

AVCADSAPAARAPQALARASGRGGRVARRGAEESGPPHSPSRRGSASRAGPGRASETMNFL

LSWVHWSLALLLYLHHAKWSQAAPMAEGGGQNHHEVVKFMDVYQRSYCHPIETLVDIFQE

YPDEIEYIFKPSCVPLMRCGGCCNDEGLECVPTEESNITMQIMRIKPHQGQHIGEMSFLQHNK

CECRPKKDRARQEKKSVRGKGKGQKRKRKKSRPCGPCSERRKHLFVQDPQTCKCSCKNTDS

RCKARQLELNERTCRCDKPRR

>gi|76781483|ref|NP_001020539.2|vascular endothelial growth
factor A isoform d {Homo sapiens}
MTDRQTDTAPSPSYHLLPGRRRTVDAAASRGQGPEPAPGGGVEGVGARGVALKLFVQLLGC

SRFGGAVVRAGEAEPSGAARSASSGREEPQPEEGEEEEKEEERGPQWRLGARKPGSWTGEA

```
AVCADSAPAARAPQALARASGRGGRVARRGAEESGPPHSPSRRGSASRAGPGRASETMNFL

LSWVHWSLALLLYLHHAKWSQAAPMAEGGGQNHHEVVKFMDVYQRSYCHPIETLVDIFQE

YPDEIEYIFKPSCVPLMRCGGCCNDEGLECVPTEESNITMQIMRIKPHQGQHIGEMSFLQHNK

CECRPKKDRARQENPCGPCSERRKHLFVQDPQTCKCSCKNTDSRCKARQLELNERTCRCDK

PRR
```

>gi|76781487|ref|NP_001028928.1|vascular endothelial growth factor A isoform g {Homo sapiens}

(SEQ ID NO: 961)

```
MTDRQTDTAPSPSYHLLPGRRRTVDAAASRGQGPEPAPGGGVEGVGARGVALKLFVQLLGC

SRFGGAVVRAGEAEPSGAARSASSGREEPQPEEGEEEEKEEERGPQWRLGARKPGSWTGEA

AVCADSAPAARAPQALARASGRGGRVARRGAEESGPPHSPSRRGSASRAGPGRASETMNFL

LSWVHWSLALLLYLHHAKWSQAAPMAEGGGQNHHEVVKFMDVYQRSYCHPIETLVDIFQE

YPDEIEYIFKPSCVPLMRCGGCCNDEGLECVPTEESNITMQIMRIKPHQGQHIGEMSFLQHNK

CECRPKKDRARQENPCGPCSERRKHLFVQDPQTCKCSCKNTDSRCKARQLELNERTCRSLTR

KD
```

>gi|76781484|ref|NP_001020540.2|vascular endothelial growth factor A isoform e {Homo sapiens}

(SEQ ID NO: 962)

```
MTDRQTDTAPSPSYHLLPGRRRTVDAAASRGQGPEPAPGGGVEGVGARGVALKLFVQLLGC

SRFGGAVVRAGEAEPSGAARSASSGREEPQPEEGEEEEKEEERGPQWRLGARKPGSWTGEA

AVCADSAPAARAPQALARASGRGGRVARRGAEESGPPHSPSRRGSASRAGPGRASETMNFL

LSWVHWSLALLLYLHHAKWSQAAPMAEGGGQNHHEVVKFMDVYQRSYCHPIETLVDIFQE

YPDEIEYIFKPSCVPLMRCGGCCNDEGLECVPTEESNITMQIMRIKPHQGQHIGEMSFLQHNK

CECRPKKDRARQENPCGPCSERRKHLFVQDPQTCKCSCKNTDSRCKM
```

>gi|76781485|ref|NP_001020541.2|vascular endothelial growth factor A isoform f {Homo sapiens}

(SEQ ID NO: 963)

```
MTDRQTDTAPSPSYHLLPGRRRTVDAAASRGQGPEPAPGGGVEGVGARGVALKLFVQLLGC

SRFGGAVVRAGEAEPSGAARSASSGREEPQPEEGEEEEKEEERGPQWRLGARKPGSWTGEA

AVCADSAPAARAPQALARASGRGGRVARRGAEESGPPHSPSRRGSASRAGPGRASETMNFL

LSWVHWSLALLLYLHHAKWSQAAPMAEGGGQNHHEVVKFMDVYQRSYCHPIETLVDIFQE

YPDEIEYIFKPSCVPLMRCGGCCNDEGLECVPTEESNITMQIMRIKPHQGQHIGEMSFLQHNK

CECRPKKDRARQEKCDKPRR
```

>gi|4507887|ref|NP_003368.1|vascular endothelial growth factor B precursor {Homo sapiens}

(SEQ ID NO: 964)

```
MSPLLRRLLLAALLQLAPAQAPVSQPDAPGHQRKVVSWIDVYTRATCQPREVVVPLTVELM

GTVAKQLVPSCVTVQRCGGCCPDDGLECVPTGQHQVRMQILMIRYPSSQLGEMSLEEHSQC

ECRPKKKDSAVKPDRAATPHHRPQPRSVPGWDSAPGAPSPADITHPTPAPGPSAHAAPSTTSA

LTPGPAAAAADAAASSVAKGGA
```

>gi|4885653|ref|NP_005420.1|vascular endothelial growth factor C preproprotein {Homo sapiens}

(SEQ ID NO: 965)

```
MHLLGFFSVACSLLAAALLPGPREAPAAAAAFESGLDLSDAEPDAGEATAYASKDLEEQLRS

VSSVDELMTVLYPEYWKMYKCQLRKGGWQHNREQANLNSRTEETIKFAAAHYNTEILKSID

NEWRKTQCMPREVCIDVGKEFGVATNTFFKPPCVSVYRCGGCCNSEGLQCMNTSTSYLSKT

LFEITVPLSQGPKPVTISFANHTSCRCMSKLDVYRQVHSIIRRSLPATLPQCQAANKTCPTNYM

WNNHICRCLAQEDFMFSSDAGDDSTDGFHDICGPNKELDEETCQCVCRAGLRPASCGPHKEL
```

-continued

DRNSCQCVCKNKLFPSQCGANREFDENTCQCVCKRTCPRNQPLNPGKCACECTESPQKCLL

KGKKFHHQTCSCYRRPCTNRQKACEPGFSYSEEVCRCVPSYWKRPQMS

A-71623
(Potent CCK1 agonist (IC50 = 3.7 nM) with 1200-fold selectivity over the CCK2
receptor. Suppresses food intake following central or peripheral administration.)
(SEQ ID NO: 966)
XWKDF-NH2 Trp-1 = Boc-Trp, Lys-3 = Lys(Tac), Phe-5 = N-methyl-Phe Enterostatin
(N' terminal peptide fragment of procolipase that binds to the β-subunit of
F1-ATPase. Activates the ERK and cAMP signaling pathways, and downregulates expression
of Kruppel-like factor 4 (KLF4) and agouti-related peptide (AgRP) in vitro. Inhibits
insulin secretion from pancreatic β-cells by downregulating expression of dynamin2
and altering protein trafficking. Reduces dietary fat intake via activation of CCK1,
induces satiety, enhances memory-consolidation and exhibits hypocholesterolemic
activity in vivo. Orally active.))
(SEQ ID NO: 967)
APGPR Ac2-12
(Annexin/lipocortin 1-mimetic peptide; inhibits leukocyte extravasation. Reduces
neutrophil adhesion and emigration, and promotes detachment of neutrophils from
activated mesenteric endothelium in mice in vivo.)
Ac-AMVSEFLKQAW Ac2-26
(Annexin/lipocortin 1-mimetic peptide; inhibits leukocyte extravasation. Reduces
neutrophil adhesion and emigration, and promotes detachment of neutrophils from
activated mesenteric endothelium in mice in vivo. Anti-inflammatory.)
(SEQ ID NO: 968)
Ac-AMVSEFLKQAWFIENEEQEYVQTVK Peptide F9
(Peptide derived from the heparin-binding domain in the B1 chain of laminin. Binds to
heparin, promotes cell adhesion, and inhibits the migration towards, and adhesion of
metastatic fibrosarcoma cells to laminin.)
(SEQ ID NO: 969)
RYVVLPRPVCFEKGMNYTVR R18
(Antagonist of 14.3.3 proteins (KD ≈80 nM). Competitively inhibits 14.3.3-ligand
interactions without requiring phosphorylation. Blocks the ability of 14.3.3 to bind
to target proteins such as Raf-1, Bad, ASK1 and exoenzyme S. Induces apoptosis.)
(SEQ ID NO: 970)
PHCVPRDLSWLDLEANMCLP Thymosin β4
(Naturally occuring, potent regulator of actin polymerization present in human
platelets at a concentration of 200-500 µM. Sequesters G-actin monomers in a 1:1
ratio (Kd = 0.7-1.0 µM) and allows rapid filament polymerization in the
presence of profilin. Implicated in wound healing, induction of MMPs, chemotaxis,
angiogenesis, inflammatory processes and tumor progression.)
(SEQ ID NO: 971)
Ac-SDKPDMAEIEKFDKSKLKKTETQEKNPLPSKETIEQEKQAGES Anti-GluR4 blocking peptide
(Synthetic peptide ({K}-HTGTAIRQSSGLAVIASDLP) corresponding to the C-terminal
amino acids 883-902 of rat precursor GluR4 (Accession No. P19493) with a lysine
added at the N-terminus of the peptide. Immunogen used for anti-GluR4)
(SEQ ID NO: 972)
KHTGTAIRQSSGLAVIASDLP Anti-phospho-GluR1 (Ser831) phosphorylated blocking peptide
(Synthetic peptide (LIPQQ(pS)INEAI{K}) corresponding to amino acids 826-836 of
rat mature GluR1 (Accession No. P19490), with a phosphorylated serine at position
831, and a lysine added to the C-terminus for conjugation. Immunogen used for anti-
phospho-GluR1 (Ser831))
(SEQ ID NO: 973)
LIPQQSINEAI Ser-6 = phosphorylated Ser

PHV (1-42)
(SEQ ID NO: 974)
HADGVFTSDFSKLLGQLSAKKYLESLMGKRVSSNISEDPVPV

PRP
(SEQ ID NO: 975)
DVAHGILNQAYRKVLDQLSAGKHLQSLVA

-continued

PHM
HADGVFTSDFSKLLGQLSAKKYLESLM

>gi|4501947|ref|NP_000665.1|adenosine receptor A1
{Homo sapiens}
(SEQ ID NO: 976)

MPPSISAFQAAYIGIEVLIALVSVPGNVLVIWAVKVNQALRDATFCFIVSLAVADVAVGALVI

PLAILINIGPQTYFHTCLMVACPVLILTQSSILALLAIAVDRYLRVKIPLRYKMVVTPRRAAVAI

AGCWILSFVVGLTPMFGWNNLSAVERAWAANGSMGEPVIKCEFEKVISMEYMVYFNFFVW

VLPPLLLMVLIYLEVFYLIRKQLNKKVSASSGDPQKYYGKELKIAKSLALILFLFALSWLPLHI

LNCITLFCPSCHKPSILTYIAIFLTHGNSAMNPIVYAFRIQKFRVTFLKIWNDHFRCQPAPPIDED

LPEERPDD

>gi|4501951|ref|NP_000667.1|adenosine receptor A2b
{Homo sapiens}
(SEQ ID NO: 977)

MLLETQDALYVALELVIAALSVAGNVLVCAAVGTANTLQTPTNYFLVSLAAADVAVGLFAI

PFAITISLGFCTDFYGCLFLACFVLVLTQSSIFSLLAVAVDRYLAICVPLRYKSLVTGTRARGVI

AVLWVLAFGIGLTPFLGWNSKDSATNNCTEPWDGTTNESCCLVKCLFENVVPMSYMVYFNF

FGCVLPPLLIMLVIYIKIFLVACRQLQRTELMDHSRTTLQREIHAAKSLAMIVGIFALCWLPVH

AVNCVTLFQPAQGKNKPKWAMNMAILLSHANSVVNPIVYAYRNRDFRYTFHKIISRYLLCQ

ADVKSGNGQAGVQPALGVGL

>gi|4501953|ref|NP_000668.1|adenosine receptor A3 isoform 2
{Homo sapiens}
(SEQ ID NO: 978)

MPNNSTALSLANVTYITMEIFIGLCAIVGNVLVICVVKLNPSLQTTTFYFIVSLALADIAVGVL

VMPLAIVVSLGITIHFYSCLFMTCLLLIFTHASIMSLLAIAVDRYLRVKLTVRYKRVTTHRRIW

LALGLCWLVSFLVGLTPMFGWNMKLTSEYHRNVTFLSCQFVSVMRMDYMVYFSFLTWIFIP

LVVMCAIYLDIFYIIRNKLSLNLSNSKETGAFYGREFKTAKSLFLVLFLFALSWLPLSIINCIIYF

NGEVPQLVLYMGILLSHANSMMNPIVYAYKIKKFKETYLLILKACVVCHPSDSLDTSIEKNSE

>gi|4501957|ref|NP_000669.1|alpha-1D adrenergic receptor
{Homo sapiens}
(SEQ ID NO: 979)

MTFRDLLSVSFEGPRPDSSAGGSSAGGGGSAGGAAPSEGPAVGGVPGGAGGGGGVVGAGS

GEDNRSSAGEPGSAGAGGDVNGTAAVGGLVVSAQGVGVGVFLAAFILMAVAGNLLVILSV

ACNRHLQTVTNYFIVNLAVADLLLSATVLPFSATMEVLGFWAFGRAFCDVWAAVDVLCCT

ASILSLCTISVDRYVGVRHSLKYPAIMTERKAAAILALLWVVALVVSGPLLGWKEPVPPDE

RFCGITEEAGYAVFSSVCSFYLPMAVIVVMYCRVYVVARSTTRSLEAGVKRERGKASEVVLR

IHCRGAATGADGAHGMRSAKGHTFRSSLSVRLLKFSREKKAAKTLAIVVGVFVLCWFPFFFV

LPLGSLFPQLKPSEGVFKVIFWLGYFNSCVNPLIYPCSSREFKRAFLRLLRCQCRRRRRRRPLW

RVYGHHWRASTSGLRQDCAPSSGDAPPGAPLALTALPDPDPEPPGTPEMQAPVASRRKPPSA

FREWRLLGPFRRPTTQLRAKVSSLSHKIRAGGAQRAEAACAQRSEVEAVSLGVPHEVAEGAT

CQAYELADYSNLRETDI

>gi|4501959|ref|NP_000670.1|alpha-1B adrenergic receptor
{Homo sapiens}
(SEQ ID NO: 980)

MNPDLDTGHNTSAPAHWGELKNANFTGPNQTSSNSTLPQLDITRAISVGLVLGAFILFAIVGN

ILVILSVACNRHLRTPTNYFIVNLAMADLLLSFTVLPFSAALEVLGYWVLGRIFCDIWAAVDV

LCCTASILSLCAISIDRYIGVRYSLQYPTLVTRRKAILALLSVWVLSTVISIGPLLGWKEPAPND

DKECGVTEEPFYALFSSLGSFYIPLAVILVMYCRVYIVAKRTTKNLEAGVMKEMSNSKELTL

RIHSKNFHEDTLSSTKAKGHNPRSSIAVKLFKFSREKKAAKTLGIVVGMFILCWLPFFIALPLG

-continued

SLFSTLKPPDAVFKVVFWLGYFNSCLNPIIYPCSSKEFKRAFVRILGCQCRGRGRRRRRRRRL

GGCAYTYRPWTRGGSLERSQSRKDSLDDSGSCLSGSQRTLPSASPSPGYLGRGAPPPVELCAF

PEWKAPGALLSLPAPEPPGRRGRHDSGPLFTFKLLTEPESPGTDGGASNGGCEAAADVANGQ

PGFKSNMPLAPGQF

>gi|4501969|ref|NP_000015.1|adrenergic, beta-2-, receptor, surface {Homo sapiens}

(SEQ ID NO: 981)

MGQPGNGSAFLLAPNRSHAPDHDVTQQRDEVWVVGMGIVMSLIVLAIVFGNVLVITAIAKFE

RLQTVTNYFITSLACADLVMGLAVVPFGAAHILMKMWTFGNFWCEFWTSIDVLCVTASIETL

CVIAVDRYFAITSPFKYQSLLTKNKARVIILMVWIVSGLTSFLPIQMHWYRATHQEAINCYAN

ETCCDFFTNQAYAIASSIVSFYVPLVIMVFVYSRVFQEAKRQLQKIDKSEGRFHVQNLSQVEQ

DGRTGHGLRRSSKFCLKEHKALKTLGIIMGTFTLCWLPFFIVNIVHVIQDNLIRKEVYILLNWI

GYVNSGFNPLIYCRSPDFRIAFQELLCLRRSSLKAYGNGYSSNGNTGEQSGYHVEQEKENKLL

CEDLPGTEDFVGHQGTVPSDNIDSQGRNCSTNDSLL

>gi|4501997|ref|NP_000676.1|type-1 angiotensin II receptor {Homo sapiens}

(SEQ ID NO: 982)

MILNSSTEDGIKRIQDDCPKAGRHNYIFVMIPTLYSIIFVVGIFGNSLVVIVIYFYMKLKTVASV

FLLNLALADLCFLLTLPLWAVYTAMEYRWPFGNYLCKIASASVSFNLYASVFLLTCLSIDRYL

AIVHPMKSRLRRTMLVAKVTCIIIWLLAGLASLPAIIHRNVFFIENTNITVCAFHYESQNSTLPI

GLGLTKNILGFLFPFLIILTSYTLIWKALKKAYEIQKNKPRNDDIFKIIMAIVLFFFFSWIPHQIFT

FLDVLIQLGIIRDCRIADIVDTAMPITICIAYFNNCLNPLFYGFLGKKFKRYFLQLLKYIPPKAKS

HSNLSTKMSTLSYRPSDNVSSSTKKPAPCFEVE

>gi|4502331|ref|NP_000697.1|vasopressin V1a receptor {Homo sapiens}

(SEQ ID NO: 983)

MRLSAGPDAGPSGNSSPWWPLATGAGNTSREAEALGEGNGPPRDVRNEELAKLEIAVLAVT

FAVAVLGNSSVLLALHRTPRKTSRMHLFIRHLSLADLAVAFFQVLPQMCWDITYRFRGPDWL

CRVVKHLQVFGMFASAYMLVVMTADRYIAVCHPLKTLQQPARRSRLMIAAAWVLSFVLST

PQYFVFSMIEVNNVTKARDCWATFIQPWGSRAYVTWMTGGIFVAPVVILGTCYGFICYNIWC

NVRGKTASRQSKGAEQAGVAFQKGFLLAPCVSSVKSISRAKIRTVKMTFVIVTAYIVCWAPF

FIIQMWSVWDPMSVWTESENPTITITALLGSLNSCCNPWIYMFFSGHLLQDCVQSFPCCQNM

KEKFNKEDTDSMSRRQTFYSNNRSPTNSTGMWKDSPKSSKSIKFIPVST

>gi|4502333|ref|NP_000698.1|vasopressin V1b receptor {Homo sapiens}

(SEQ ID NO: 984)

MDSGPLWDANPTPRGTLSAPNATTPWLGRDEELAKVEIGVLATVLVLATGGNLAVLLTLGQ

LGRKRSRMHLFVLHLALTDLAVALFQVLPQLLWDITYRFQGPDLLCRAVKYLQVLSMFAST

YMLLAMTLDRYLAVCHPLRSLQQPGQSTYLLIAAPWLLAAIFSLPQVFIFSLREVIQGSGVLD

CWADFGFPWGPRAYLTWTTLAIFVLPVTMLTACYSLICHEICKNLKVKTQAWRVGGGWR

TWDRPSPSTLAATTRGLPSRVSSINTISRAKIRTVKMTFVIVLAYIACWAPFFSVQMWSVWDK

NAPDEDSTNVAFTISMLLGNLNSCCNPWIYMGFNSHLLPRPLRHLACCGGPQPRMRRRLSDG

SLSSRHTTLLTRSSCPATLSLSLSLTLSGRPRPEESPRDLELADGEGTAETIIF

>gi|4502359|ref|NP_001695.1|brain-specific angiogenesis inhibitor 3 precursor {Homo sapiens}

(SEQ ID NO: 985)

MKAVRNLLIYIFSTYLLVMFGFNAAQDFWCSTLVKGVIYGSYSVSEMFPKNFTNCTWTLENP

DPTKYSIYLKFSKKDLSCSNFSLLAYQFDHFSHEKIKDLLRKNHSIMQLCNSKNAFVFLQYDK

-continued

NFIQIRRVFPTNFPGLQKKGEEDQKSFFEFLVLNKVSPSQFGCHVLCTWLESCLKSENGRTESC

GIMYTKCTCPQHLGEWGIDDQSLILLNNVVLPLNEQTEGCLTQELQTTQVCNLTREAKRPPK

EEFGMMGDHTIKSQRPRSVHEKRVPQEQADAAKFMAQTGESGVEEWSQWSTCSVTCGQGS

QVRTRTCVSPYGTHCSGPLRESRVCNNTALCPVHGVWEEWSPWSLCSFTCGRGQRTRTRSC

TPPQYGGRPCEGPETHHKPCNIALCPVDGQWQEWSSWSQCSVTCSNGTQQRSRQCTAAAHG

GSECRGPWAESRECYNPECTANGQWNQWGHWSGCSKSCDGGWERRIRTCQGAVITGQQCE

GTGEEVRRCSEQRCPAPYEICPEDYLMSMVWKRTPAGDLAFNQCPLNATGTTSRRCSLSLHG

VAFWEQPSFARCISNEYRHLQHSIKEHLAKGQRMLAGDGMSQVTKTLLDLTQRKNFYAGDL

LMSVEILRNVTDTFKRASYIPASDGVQNFFQIVSNLLDEENKEKWEDAQQIYPGSIELMQVIE

DFIHIVGMGMMDFQNSYLMTGNVVASIQKLPAASVLTDINFPMKGRKGMVDWARNSEDRV

VIPKSIFTPVSSKELDESSVFVLGAVLYKNLDLILPTLRNYTVINSKIIVVTIRPEPKTTDSFLEIE

LAHLANGTLNPYCVLWDDSKTNESLGTWSTQGCKTVLTDASHTKCLCDRLSTFAILAQQPR

EIIMESSGTPSVTLIVGSGLSCLALITLAVVYAALWRYIRSERSIILINFCLSIISSNILILVGQTQT

HNKSICTTTTAFLHFFFLASFCWVLTEAWQSYMAVTGKIRTRLIRKRFLCLGWGLPALVVAT

SVGFTRTKGYGTDHYCWLSLEGGLLYAFVGPAAAVVLVNMVIGILVFNKLVSRDGILDKKL

KHRAGQMSEPHSGLTLKCAKCGVVSTTALSATTASNAMASLWSSCVVLPLLALTWMSAVL

AMTDKRSILFQILFAVFDSLQGFVIVMVHCILRREVQDAFRCRLRNCQDPINADSSSSFPNGH

AQIMTDFEKDVDIACRSVLHKDIGPCRAATITGTLSRISLNDDEEEKGTNPEGLSYSTLPGNVI

SKVIIQQPTGLHMPMSMNELSNPCLKKENSELRRTVYLCTDDNLRGADMDIVHPQERMMES

DYIVMPRSSVNNQPSMKEESKMNIGMETLPHERLLHYKVNPEFNMNPPVMDQFNMNLEQH

LAPQEHMQNLPFEPRTAVKNFMASELDDNAGLSRSETGSTISMSSLERRKSRYSDLDFEKVM

HTRKRHMELFQELNQKFQTLDRFRDIPNTSSMENPAPNKNPWDTFKNPSEYPHYTTINVLDT

EAKDALELRPAEWEKCLNLPLDVQEGDFQTEV

>gi|4502415|ref|NP_001707.1|Burkitt lymphoma receptor 1
isoform 1 {Homo sapiens}
(SEQ ID NO: 986)
MNYPLTLEMDLENLEDLFWELDRLDNYNDTSLVENHLCPATEGPLMASFKAVFVPVAYSLIF

LLGVIGNVLVLVILERHRQTRSSTETFLFHLAVADLLLVFILPFAVAEGSVGWVLGTFLCKTVI

ALHKVNFYCSSLLLACIAVDRYLAIVHAVHAYRHRRLLSIHITCGTIWLVGFLLALPEILFAKV

SQGHHNNSLPRCTFSQENQAETHAWFTSRFLYHVAGFLLPMLVMGWCYVGVVHRLRQAQR

RPQRQKAVRVAILVTSIFFLCWSPYHIVIFLDTLARLKAVDNTCKLNGSLPVAITMCEFLGLA

HCCLNPMLYTFAGVKFRSDLSRLLTKLGCTGPASLCQLFPSWRRSSLSESENATSLTTF

>gi|4502455|ref|NP_001718.1|bombesin receptor subtype-3
{Homo sapiens}
(SEQ ID NO: 987)
MAQRQPHSPNQTLISITNDTESSSSVVSNDNTNKGWSGDNSPGIEALCAIYITYAVIISVGILGN

AILIKVFFKTKSMQTVPNIFITSLAFGDLLLLLTCVPVDATHYLAEGWLFGRIGCKVLSFIRLTS

VGVSVFTLTILSADRYKAVVKPLERQPSNAILKTCVKAGCVWIVSMIFALPEAIFSNVYTFRD

PNKNMTFESCTSYPVSKKLLQEIHSLLCFLVFYIIPLSIISVYYSLIARTLYKSTLNIPTEEQSHAR

KQIESRKRIARTVLVLVALFALCWLPNHLLYLYHSFTSQTYVDPSAMHFIFTIFSRVLAFSNSC

VNPFALYWLSKSFQKHFKAQLFCCKAERPEPPVADTSLTTLAVMGTVPGTGSIQMSEISVTSF

TGCSVKQAEDRF

-continued

>gi|4502509|ref|NP_001727.1|C5a anaphylatoxin chemotactic
receptor {Homo sapiens}

(SEQ ID NO: 988)

MNSFNYTTPDYGHYDDKDTLDLNTPVDKTSNTLRVPDILALVIFAVVFLVGVLGNALVVWV

TAFEAKRTINAIWFLNLAVADFLSCLALPILFTSIVQHHHWPFGGAACSILPSLILLNMYASILL

LATISADRFLLVFKPIWCQNFRGAGLAWIACAVAWGLALLLTIPSFLYRVVREEYFPPKVLCG

VDYSHDKRRERAVAIVRLVLGFLWPLLTLTICYTFILLRTWSRRATRSTKTLKVVVAVVASFF

IFWLPYQVTGIMMSFLEPSSPTFLLLNKLDSLCVSFAYINCCINPIIYVVAGQGFQGRLRKSLPS

LLRNVLTEESVVRESKSFTRSTVDTMAQKTQAV

>gi|4502547|ref|NP_001733.1|calcitonin receptor isoform 2
precursor {Homo sapiens}

(SEQ ID NO: 989)

MRFTFTSRCLALFLLLNHPTPILPAFSNQTYPTIEPKPFLYVVGRKKMMDAQYKCYDRMQQL

PAYQGEGPYCNRTWDGWLCWDDTPAGVLSYQFCPDYFPDFDPSEKVTKYCDEKGVWFKHP

ENNRTWSNYTMCNAFTPEKLKNAYVLYYLAIVGHSLSIFTLVISLGIFVFFRSLGCQRVTLHK

NMFLTYILNSMIIIHLVEVVPNGELVRRDPVSCKILHFFHQYMMACNYFWMLCEGIYLHTLI

VVAVFTEKQRLRWYYLLGWGFPLVPTTIHAITRAVYFNDNCWLSVETHLLYIIHGPVMAAL

VVNFFFLLNIVRVLVTKMRETHEAESHMYLKAVKATMILVPLLGIQFVVFPWRPSNKMLGKI

YDYVMHSLIHFQGFFVATIYCFCNNEVQTTVKRQWAQFKIQWNQRWGRRPSNRSARAAAA

AAEAGDIPIYICHQELRNEPANNQGEESAEIIPLNIIEQESSA

>gi|4502607|ref|NP_000721.1|cholecystokinin receptor type A
{Homo sapiens}

(SEQ ID NO: 990)

MDVVDSLLVNGSNITPPCELGLENETLFCLDQPRPSKEWQPAVQILLYSLIFLLSVLGNTLVIT

VLIRNKRMRTVTNIFLLSLAVSDLMLCLFCMPFNLIPNLLKDFIFGSAVCKTTTYFMGTSVSVS

TFNLVAISLERYGAICKPLQSRVWQTKSHALKVIAATWCLSFTIMTPYPIYSNLVPFTKNNNQ

TANMCRFLLPNDVMQQSWHTFLLLILFLIPGIVMMVAYGLISLELYQGIKFEASQKKSAKERK

PSTTSSGKYEDSDGCYLQKTRPPRKLELRQLSTGSSSRANRIRSNSSAANLMAKKRVIRMLIVI

VVLFFLCWMPIFSANAWRAYDTASAERRLSGTPISFILLLSYTSSCVNPIIYCFMNKRFRLGFM

ATFPCCPNPGPPGARGEVGEEEEGGTTGASLSRFSYSHMSASVPPQ

>gi|4502631|ref|NP_001286.1|C-C chemokine receptor type 1
{Homo sapiens}

(SEQ ID NO: 991)

METPNTTEDYDTTTEFDYGDATPCQKVNERAFGAQLLPPLYSLVFVIGLVGNILVVLVQY

KRLKNMTSIYLLNLAISDLLFLFTLPFWIDYKLKDDWVFGDAMCKILSGFYYTGLYSEIFFIIL

LTIDRYLAIVHAVFALRARTVTFGVITSIIIWALAILASMPGLYFSKTQWEFTHHTCSLHFPHES

LREWKLFQALKLNLFGLVLPLLVMIICYTGIIKILLRRPNEKKSKAVRLIFVIMIIFFLFWTPYN

LTILISVFQDFLFTHECEQSRHLDLAVQVTEVIAYTHCCVNPVIYAFVGERFRKYLRQLFHRR

VAVHLVKWLPFLSVDRLERVSSTSPSTGEHELSAGF

>gi|4502637|ref|NP_001828.1|C-C chemokine receptor type 3
isoform 1 {Homo sapiens}

(SEQ ID NO: 992)

MTTSLDTVETFGTTSYYDDVGLLCEKADTRALMAQFVPPLYSLVFTVGLLGNVVVVMILIKY

RRLRIMTNIYLLNLAISDLLFLVTLPFWIHYVRGHNWVFGHGMCKLLSGFYHTGLYSEIFFIIL

LTIDRYLAIVHAVFALRARTVTFGVITSIVTWGLAVLAALPEFIFYETEELFEETLCSALYPEDT

VYSWRHFHTLRMTIFCLVLPLLVMAICYTGIIKTLLRCPSKKKYKAIRLIFVIMAVFFIFWTPY

NVAILLSSYQSILFGNDCERSKHLDLVMLVTEVIAYSHCCMNPVIYAFVGERFRKYLRHFFHR

HLLMHLGRYIPFLPSEKLERTSSVSPSTAEPELSIVF

```
>gi|4502639|ref|NP_000570.1|chemokine (C-C motif) receptor 5
{Homo sapiens}
                                                                (SEQ ID NO: 993)
MDYQVSSPIYDINYYTSEPCQKINVKQIAARLLPPLYSLVFIFGFVGNMLVLILINCKRLKSMT

DIYLLNLAISDLFFLLTVPFWAHYAAAQWDFGNTMCQLLTGLYFIGFFSGIFFIILLTIDRYLAV

VHAVFALKARTVTFGVVTSVITWVVAVFASLPGIIFTRSQKEGLHYTCSSHFPYSQYQFWKN

FQTLKIVILGLVLPLLVMVICYSGILKTLLRCRNEKKRHRAVRLIFTIMIVYFLFWAPYNIVLLL

NTFQEFFGLNNCSSSNRLDQAMQVTETLGMTHCCINPIIYAFVGEKFRNYLLVFFQKHIAKRF

CKCCSIFQQEAPERASSVYTRSTGEQEISVGL

>gi|4502641|ref|NP_001829.1|chemokine (C-C motif) receptor 7
precursor {Homo sapiens}
                                                                (SEQ ID NO: 994)
MDLGKPMKSVLVVALLVIFQVCLCQDEVTDDYIGDNTTVDYTLFESLCSKKDVRNFKAWFL

PIMYSIICFVGLLGNGLVVLTYIYFKRLKTMTDTYLLNLAVADILFLLTLPFWAYSAAKSWVF

GVHFCKLIFAIYKMSFFSGMLLLLCISIDRYVAIVQAVSAHRHRARVLLISKLSCVGIWILATV

LSIPELLYSDLQRSSSEQAMRCSLITEHVEAFITIQVAQMVIGFLVPLLAMSFCYLVIIRTLLQA

RNFERNKAIKVIIAVVVVFIVFQLPYNGVVLAQTVANFNITSSTCELSKQLNIAYDVTYSLACV

RCCVNPFLYAFIGVKFRNDLFKLFKDLGCLSQEQLRQWSSCRHIRRSSMSVEAETTTTFSP

>gi|4502817|ref|NP_000730.1|cholinergic receptor, muscarinic 2
{Homo sapiens}
                                                                (SEQ ID NO: 995)
MNNSTNSSNNSLALTSPYKTFEVVFIVLVAGSLSLVTIIGNILVMVSIKVNRHLQTVNNYFLFS

LACADLIIGVFSMNLYTLYTVIGYWPLGPVVCDLWLALDYVVSNASVMNLLIISFDRYFCVT

KPLTYPVKRTTKMAGMMIAAAWVLSFILWAPAILFWQFIVGVRTVEDGECYIQFFSNAAVTF

GTAIAAFYLPVIIMTVLYWHISRASKSRIKKDKKEPVANQDPVSPSLVQGRIVKPNNNNMPSS

DDGLEHNKIQNGKAPRDPVTENCVQGEEKESSNDSTSVSAVASNMRDDEITQDENTVSTSLG

HSKDENSKQTCIRIGTKTPKSDSCTPTNTTVEVVGSSGQNGDEKQNIVARKIVKMTKQPAKK

KPPPSREKKVTRTILAILLAFIITWAPYNVMVLINTFCAPCIPNTVWTIGYWLCYINSTINPACY

ALCNATFKKTFKHLLMCHYKNIGATR

>gi|4502819|ref|NP_000731.1|cholinergic receptor, muscarinic 3
{Homo sapiens}
                                                                (SEQ ID NO: 996)
MTLHNNSTTSPLFPNISSSWIHSPSDAGLPPGTVTHFGSYNVSRAAGNFSSPDGTTDDPLGGHT

VWQVVFIAFLTGILALVTIIGNILVIVSFKVNKQLKTVNNYFLLSLACADLIIGVISMNLFTTYII

MNRWALGNLACDLWLAIDYVASNASVMNLLVISFDRYFSITRPLTYRAKRTTKRAGVMIGL

AWVISFVLWAPAILFWQYFVGKRTVPPGECFIQFLSEPTITFGTAIAAFYMPVTIMTILYWRIY

KETEKRTKELAGLQASGTEAETENFVHPTGSSRSCSSYELQQQSMKRSNRRKYGRCHFWFTT

KSWKPSSEQMDQDHSSSDSWNNNDAAASLENSASSDEEDIGSETRAIYSIVLKLPGHSTILNS

TKLPSSDNLQVPEEELGMVDLERKADKLQAQKSVDDGGSFPKSFSKLPIQLESAVDTAKTSD

VNSSVGKSTATLPLSFKEATLAKRFALKTRSQITKRKRMSLVKEKKAAQTLSAILLAFIITWTP

YNIMVLVNTFCDSCIPKTFWNLGYWLCYINSTVNPVCYALCNKTFRTTFKMLLL

CQCDKKKRRKQQYQQRQSVIFHKRAPEQAL

>gi|4502929|ref|NP_001832.1|cannabinoid receptor 2
{Homo sapiens}
                                                                (SEQ ID NO: 997)
MEECWVTEIANGSKDGLDSNPMKDYMILSGPQKTAVAVLCTLLGLLSALENVAVLYLILSSH

QLRRKPSYLFIGSLAGADFLASVVFACSFVNFHVFHGVDSKAVFLLKIGSVTMTFTASVGSLL

LTAIDRYLCLRYPPSYKALLTRGRALVTLGIMWVLSALVSYLPLMGWTCCPRPCSELFPLIPN
```

-continued

DYLLSWLLFIAFLFSGIIYTYGHVLWKAHQHVASLSGHQDRQVPGMARMRLDVRLAKTLGL

VLAVLLICWFPVLALMAHSLATTLSDQVKKAFAFCSMLCLINSMVNPVIYALRSGEIRSSAHH

CLAHWKKCVRGLGSEAKEEAPRSSVTETEADGKITPWPDSRDLDLSDC

>gi|4503171|ref|NP_001328.1|CX3C chemokine receptor 1
isoform b {Homo sapiens}
(SEQ ID NO: 998)

MDQFPESVTENFEYDDLAEACYIGDIVVFGTVFLSIFYSVIFAIGLVGNLLVVFALTNSKKPKS

VTDIYLLNLALSDLLFVATLPFWTHYLINEKGLHNAMCKFTTAFFFIGFFGSIFFITVISIDRYL

AIVLAANSMNNRTVQHGVTISLGVWAAAILVAAPQFMFTKQKENECLGDYPEVLQEIWPVL

RNVETNFLGFLLPLLIMSYCYFRIIQTLFSCKNHKKAKAIKLILLVVIVFFLFWTPYNVMIFLET

LKLYDFFPSCDMRKDLRLALSVTETVAFSHCCLNPLIYAFAGEKFRRYLYHLYGKCLAVLCG

RSVHVDFSSSESQRSRHGSVLSSNFTYHTSDGDALLLL

>gi|4503175|ref|NP_003458.1|chemokine (C—X—C motif) receptor 4
isoform b {Homo sapiens}
(SEQ ID NO: 999)

MEGISIYTSDNYTEEMGSGDYDSMKEPCFREENANFNKIFLPTIYSIIFLTGIVGNGLVILVMG

YQKKLRSMTDKYRLHLSVADLLFVITLPFWAVDAVANWYFGNFLCKAVHVIYTVNLYSSVL

ILAFISLDRYLAIVHATNSQRPRKLLAEKVVYVGVWIPALLLTIPDFIFANVSEADDRYICDRF

YPNDLWVVVFQFQHIMVGLILPGIVILSCYCIIISKLSHSKGHQKRKALKTTVILILAFFACWLP

YYIGISIDSFILLEIIKQGCEFENTVHKWISITEALAFFHCCLNPILYAFLGAKFKTSAQHALTSV

SRGSSLKILSKGKRGGHSSVSTESESSSFHSS

>gi|4503383|ref|NP_000785.1|d (1A) dopamine receptor
{Homo sapiens}
(SEQ ID NO: 1000)

MRTLNTSAMDGTGLVVERDFSVRILTACFLSLLILSTLLGNTLVCAAVIRFRHLRSKVTNFFVI

SLAVSDLLVAVLVMPWKAVAEIAGFWPFGSFCNIWVAFDIMCSTASILNLCVISVDRYWAISS

PFRYERKMTPKAAFILISVAWTLSVLISFIPVQLSWHKAKPTSPSDGNATSLAETIDNCDSSLSR

TYAISSSVISFYIPVAIMIVTYTRIYRIAQKQIRRIAALERAAVHAKNCQTTTGNGKPVECSQPE

SSFKMSFKRETKVLKTLSVIMGVFVCCWLPFFILNCILPFCGSGETQPFCIDSNTFDVFVWFGW

ANSSLNPIIYAFNADFRKAFSTLLGCYRLCPATNNAIETVSINNNGAAMFSSHHEPRGSISKEC

NLVYLIPHAVGSSEDLKKEEAAGIARPLEKLSPALSVILDYDTDVSLEKIQPITQNGQHPT

>gi|4503385|ref|NP_000786.1|d(2) dopamine receptor isoform
long {Homo sapiens}
(SEQ ID NO: 1001)

MDPLNLSWYDDDLERQNWSRPFNGSDGKADRPHYNYYATLLTLLIAVIVFGNVLVCMAVS

REKALQTTTNYLIVSLAVADLLVATLVMPWVVYLEVVGEWKFSRIHCDIFVTLDVMMCTAS

ILNLCAISIDRYTAVAMPMLYNTRYSSKRRVTVMISIVWVLSFTISCPLLFGLNNADQNECIIA

NPAFVVYSSIVSFYVPFIVTLLVYIKIYIVLRRRRKRVNTKRSSRAFRAHLRAPLKGNCTHPED

MKLCTVIMKSNGSFPVNRRRVEAARRAQELEMEMLSSTSPPERTRYSPIPPSHHQLTLPDPSH

HGLHSTPDSPAKPEKNGHAKDHPKIAKIFEIQTMPNGKTRTSLKTMSRRKLSQQKEKKATQM

LAIVLGVFIICWLPFFITHILNIHCDCNIPPVLYSAFTWLGYVNSAVNPIIYTTFNIEFRKAFLKIL

HC

>gi|4503391|ref|NP_000789.1|d(1B) dopamine receptor
{Homo sapiens}
(SEQ ID NO: 1002)

MLPPGSNGTAYPGQFALYQQLAQGNAVGGSAGAPPLGPSQVVTACLLTLLIIWTLLGNVLVC

AAIVRSRHLRANMTNVFIVSLAVSDLFVALLVMPWKAVAEVAGYWPFGAFCDVWVAFDIM

CSTASILNLCVISVDRYWAISRPFRYKRKMTQRMALVMVGLAWTLSILISFIPVQLNWHRDQ

AASWGGLDLPNNLANWTPWEEDFWEPDVNAENCDSSLNRTYAISSSLISFYIPVAIMIVTYTR

IYRIAQVQIRRISSLERAAEHAQSCRSSAACAPDTSLRASIKKETKVLKTLSVIMGVFVCCWLP

FFILNCMVPFCSGHPEGPPAGFPCVSETTFDVFVWFGWANSSLNPVIYAFNADFQKVFAQLLG

CSHFCSRTPVETVNISNELISYNQDIVFHKEIAAAYIHMMPNAVTPGNREVDNDEEEGPFDRM

FQIYQTSPDGDPVAESVWELDCEGEISLDKITPFTPNGFH

>gi|4503459|ref|NP_003766.1|sphingosine-1-phosphate receptor 4 precursor {Homo sapiens} (SEQ ID NO: 1003)

MNATGTPVAPESCQQLAAGGHSRLIVLHYNHSGRLAGRGGPEDGGLGALRGLSVAASCLVV

LENLLVLAAITSHMRSRRWVYYCLVNITLSDLLTGAAYLANVLLSGARTFRLAPAQWFLREG

LLFTALAASTFSLLFTAGERFATMVRPVAESGATKTSRVYGFIGLCWLLAALLGMLPLLGWN

CLCAFDRCSSLLPLYSKRYILFCLVIFAGVLATIMGLYGAIFRLVQASGQKAPRPAARRKARR

LLKTVLMILLAFLVCWGPLFGLLLADVFGSNLWAQEYLRGMDWILALAVLNSAVNPIIYSFR

SREVCRAVLSFLCCGCLRLGMRGPGDCLARAVEAHSGASTTDSSLRPRDSFRGSRSLSFRMR

EPLSSISSVRSI

>gi|4503465|ref|NP_001948.1|endothelin-1 receptor isoform a precursor {Homo sapiens} (SEQ ID NO: 1004)

METLCLRASFWLALVGCVISDNPERYSTNLSNHVDDFTTFRGTELSFLVTTHQPTNLVLPSNG

SMHNYCPQQTKITSAFKYINTVISCTIFIVGMVGNATLLRIIYQNKCMRNGPNALIASLALGDL

IYVVIDLPINVFKLLAGRWPFDHNDFGVFLCKLFPFLQKSSVGITVLNLCALSVDRYRAVASW

SRVQGIGIPLVTAIEIVSIWILSFILAIPEAIGFVMVPFEYRGEQHKTCMLNATSKFMEFYQDVK

DWWLFGFYFCMPLVCTAIFYTLMTCEMLNRRNGSLRIALSEHLKQRREVAKTVFCLVVIFAL

CWFPLHLSRILKKTVYNEMDKNRCELLSFLLLMDYIGINLATMNSCINPIALYFVSKKFKNCF

QSCLCCCCYQSKSLMTSVPMNGTSIQWKNHDQNNHNTDRSSHKDSMN

>gi|4503779|ref|NP_002020.1|fMet-Leu-Phe receptor {Homo sapiens} (SEQ ID NO: 1005)

METNSSLPTNISGGTPAVSAGYLFLDIITYLVFAVTFVLGVLGNGLVIWVAGFRMTHTVTTIS

YLNLAVADFCFTSTLPFFMVRKAMGGHWPFGWFLCKFVFTIVDINLFGSVFLIALIALDRCVC

VLHPVWTQNHRTVSLAKKVIIGPWVMALLLTLPVIIRVTTVPGKTGTVACTFNFSPWTNDPK

ERINVAVAMLTVRGIIRFIIGFSAPMSIVAVSYGLIATKIHKQGLIKSSRPLRVLSFVAAAFFLC

WSPYQVVALIATVRIRELLQGMYKEIGIAVDVTSALAFFNSCLNPMLYVFMGQDFRERLIHA

LPASLERALTEDSTQTSDTATNSTLPSAEVELQAK

>gi|4503781|ref|NP_001453.1|N-formyl peptide receptor 2 {Homo sapiens} (SEQ ID NO: 1006)

METNFSTPLNEYEEVSYESAGYTVLRILPLVVLGVTFVLGVLGNGLVIWVAGFRMTRTVTTI

CYLNLALADFSFTATLPFLIVSMAMGEKWPFGWFLCKLIHIVVDINLFGSVPLIGFIALDRCIC

VLHPVWAQNHRTVSLAMKVIVGPWILALVLTLPVFLFLTTVTIPNGDTYCTFNFASWGGTPE

ERLKVAITMLTARGIIRFVIGFSLPMSIVAICYGLIAAKIHKKGMIKSSRPLRVLTAVVASFFIC

WFPFQLVALLGTVWLKEMLFYGKYKIIDILVNPTSSLAFFNSCLNPMLYVFVGQDFRERLIHS

LPTSLERALSEDSAPTNDTAANSASPPAETELQAM

>gi|4503905|ref|NP_003848.1|galanin receptor type 2 {Homo sapiens} (SEQ ID NO: 1007)

MNVSGCPGAGNASQAGGGGGWHPEAVIVPLLFALIFLVGTVGNTLVLAVLLRGGQAVSTTN

LFILNLGVADLCFILCCVPFQATIYTLDGWVFGSLLCKAVHFLIFLTMHASSFTLAAVSLDRYL

AIRYPLHSRELRTPRNALAAIGLIWGLSLLFSGPYLSYYRQSQLANLTVCHPAWSAPRRRAM

DICTFVFSYLLPVLVLGLTYARTLRYLWRAVDPVAAGSGARRAKRKVTRMILIVAALFCLCW

MPHHALILCVWFGQFPLTRATYALRILSHLVSYANSCVNPIVYALVSKHFRKGFRTICAGLLG

RAPGRASGRVCAAARGTHSGSVLERESSDLLHMSEAAGALRPCPGASQPCILEPCPGPSWQG

PKAGDSILTVDVA

>gi|4503907|ref|NP_003605.1|galanin receptor type 3
{Homo sapiens}
(SEQ ID NO: 1008)

MADAQNISLDSPGSVGAVAVPVVFALIFLLGTVGNGLVLAVLLQPGPSAWQEPGSTTDLFIL

NLAVADLCFILCCVPFQATIYTLDAWLFGALVCKAVHLLIYLTMYASSFTLAAVSVDRYLAV

RHPLRSRALRTPRNARAAVGLVWLLAALFSAPYLSYYGTVRYGALELCVPAWEDARRRAL

DVATFAAGYLLPVAVVSLAYGRTLRFLWAAVGPAGAAAAEARRRATGRAGRAMLAVAAL

YALCWGPHHALILCFWYGRFAFSPATYACRLASHCLAYANSCLNPLVYALASRHFRARFRR

LWPCGRRRRHRARRALRRVRPASSGPPGCPGDARPSGRLLAGGGQGPEPREGPVHGGEAAR

GPE

>gi|4503947|ref|NP_000151.1|glucagon receptor precursor
{Homo sapiens}
(SEQ ID NO: 1009)

MPPCQPQRPLLLLLLLLACQPQVPSAQVMDFLFEKWKLYGDQCHHNLSLLPPPTELVCNRTF

DKYSCWPDTPANTTANISCPWYLPWHHKVQHRFVFKRCGPDGQWVRGPRGQPWRDASQC

QMDGEEIEVQKEVAKMYSSFQVMYTVGYSLSLGALLLALAILGGLSKLHCTRNAIHANLFAS

FVLKASSVLVIDGLLRTRYSQKIGDDLSVSTWLSDGAVAGCRVAAVFMQYGIVANYCWLLV

EGLYLHNLLGLATLPERSFFSLYLGIGWGAPMLFVVPWAVVKCLFENVQCWTSNDNMGFW

WILRFPVFLAILINFFIFVRIVQLLVAKLRARQMHHTDYKFRLAKSTLTLIPLLGVHEVVFAFV

TDEHAQGTLRSAKLFFDLFLSSFQGLLVAVLYCFLNKEVQSELRRRWHRWRLGKVLWEERN

TSNHRASSSPGHGPPSKELQFGRGGGSQDSSAETPLAGGLPRLAESPF

>gi|4503999|ref|NP_000155.1|gastric inhibitory polypeptide
receptor precursor {Homo sapiens}
(SEQ ID NO: 1010)

MTTSPILQLLLRLSLCGLLLQRAETGSKGQTAGELYQRWERYRRECQETLAAAEPPSGLACN

GSFDMYVCWDYAAPNATARASCPWYLPWHHHVAAGFVLRQCGSDGQWGLWRDHTQCEN

PEKNEAFLDQRLILERLQVMYTVGYSLSLATLLLALLILSLFRRLHCTRNYIHINLFTSFMLRA

AAILSRDRLLPRPGPYLGDQALALWNQALAACRTAQIVTQYCVGANYTWLLVEGVYLHSLL

VLVGGSEEGHFRYYLLLGWGAPALFVIPWVIVRYLYENTQCWERNEVKAIWWIIRTPILMTI

LINFLIFIRILGILLSKLRTRQMRCRDYRLRLARSTLTLVPLLGVHEVVFAPVTEEQARGALRF

AKLGFEIFLSSFQGFLVSVLYCFINKEVQSEIRRGWHHCRLRRSLGEEQRQLPERAFRALPSGS

GPGEVPTSRGLSSGTLPGPGNEASRELESYC

>gi|4504059|ref|NP_000397.1|gonadotropin-releasing hormone
receptor isoform 1 {Homo sapiens}
(SEQ ID NO: 1011)

MANSASPEQNQNHCSAINNSIPLMQGNLPTLTLSGKIRVTVTFFLFLLSATFNASFLLKLQKW

TQKKEKGKKLSRMKLLLKHLTLANLLETLIVMPLDGMWNITVQWYAGELLCKVLSYLKLFS

MYAPAFMMVVISLDRSLAITRPLALKSNSKVGQSMVGLAWILSSVFAGPQLYIFRMIHLADSS

GQTKVFSQCVTHCSFSQWWHQAFYNFFTFSCLFIIPLFIMLICNAKIIFTLTRVLHQDPHELQL

NQSKNNIPRARLKTLKMTVAFATSFTVCWTPYYVLGIWYWFDPEMLNRLSDPVNHFFFLFAF

LNPCFDPLIYGYFSL

-continued

>gi|4504091|ref|NP_001496.1|G-protein coupled estrogen
receptor 1 {Homo sapiens}
(SEQ ID NO: 1012)

MDVTSQARGVGLEMYPGTAQPAAPNTTSPELNLSHPLLGTALANGTGELSEHQQYVIGLFLS

CLYTIFLFPIGFVGNILILVVNISFREKMTIPDLYFINLAVADLILVADSLIEVFNLHERYYDIAV

LCTFMSLFLQVNMYSSVFFLTWMSFDRYIALARAMRCSLFRTKHHARLSCGLIWMASVSAT

LVPFTAVHLQHTDEACFCFADVREVQWLEVTLGFIVPFAIIGLCYSLIVRVLVRAHRHRGLRP

RRQKALRMILAVVLVFFVCWLPENVFISVHLLQRTQPGAAPCKQSFRHAHPLTGHIVNLAAF

SNSCLNPLIYSFLGETFRDKLRLYIEQKTNLPALNRFCHAALKAVIPDSTEQSDVRFSSAV

>gi|4504093|ref|NP_001497.1|G protein-coupled receptor 32
{Homo sapiens}
(SEQ ID NO: 1013)

MNGVSEGTRGCSDRQPGVLTRDRSCSRKMNSSGCLSEEVGSLRPLTVVILSASIVVGVLGNG

LVLWMTVFRMARTVSTVCFFHLALADFMLSLSLPIAMYYIVSRQWLLGEWACKLYITFVFLS

YFASNCLLVFISVDRCISVLYPVWALNHRTVQRASWLAFGVWLLAAALCSAHLKFRTTRKW

NGCTHCYLAFNSDNETAQIWIEGVVEGHIIGTIGHFLLGFLGPLAIIGTCAHLIRAKLLREGWV

HANRPKRLLLVLVSAFFIFWSPFNVVLLVHLWRRVMLKEIYHPRMLLILQASFALGCVNSSL

NPFLYVFVGRDFQEKFFQSLTSALARAFGEEEFLSSCPRGNAPRE

>gi|4504095|ref|NP_001498.1|motilin receptor
{Homo sapiens}
(SEQ ID NO: 1014)

MGSPWNGSDGPEGAREPPWPALPPCDERRCSPFPLGALVPVTAVCLCLFVVGVSGNVVTVM

LIGRYRDMRTTTNLYLGSMAVSDLLILLGLPFDLYRLWRSRPWVFGPLLCRLSLYVGEGCTY

ATLLHMTALSVERYLAICRPLRARVLVTRRRVRALIAVLWAVALLSAGPFLFLVGVEQDPGI

SVVPGLNGTARIASSPLASSPPLWLSRAPPPSPPSGPETAEAAALFSRECRPSPAQLGALRVML

WVTTAYFFLPFLCLSILYGLIGRELWSSRRPLRGPAASGRERGHRQTVRVLLVVVLAFIICWL

PFHVGRIIYINTEDSRMMYFSQYFNIVALQLFYLSASINPILYNLISKKYRAAAFKLLLARKSRP

RGFHRSRDTAGEVAGDTGGDTVGYTETSANVKTMG

>gi|4504097|ref|NP_001499.1|G-protein coupled receptor 39
{Homo sapiens}
(SEQ ID NO: 1015)

MASPSLPGSDCSQIIDHSHVPEFEVATWIKITLILVYLIIFVMGLLGNSATIRVTQVLQKKGYLQ

KEVTDHMVSLACSDILVFLIGMPMEFYSIIWNPLTTSSYTLSCKLHTFLFEACSYATLLHVLTL

SFERYIAICHPFRYKAVSGPCQVKLLIGFVWVTSALVALPLLFAMGTEYPLVNVPSHRGLTCN

RSSTRHHEQPETSNMSICTNLSSRWTVFQSSIFGAFVVYLVVLLSVAFMCWNMMQVLMKSQ

KGSLAGGTRPPQLRKSESEESRTARRQTIIFLRLIVVTLAVCWMPNQIRRIMAAAKPKHDWTR

SYFRAYMILLPFSETFFYLSSVINPLLYTVSSQQFRRVFVQVLCCRLSLQHANHEKRLRVHAH

STTDSARFVQRPLLFASRRQSSARRTEKIFLSTFQSEAEPQSKSQSLSLESLEPNSGAKPANSAA

ENGFQEHEV

>gi|4504099|ref|NP_001495.1|C—X—C chemokine receptor type 3
isoform A {Homo sapiens}
(SEQ ID NO: 1016)

MVLEVSDHQVLNDAEVAALLENFSSSYDYGENESDSCCTSPPCPQDFSLNFDRAFLPALYSLL

FLLGLLGNGAVAAVLLSRRTALSSTDTFLLHLAVADTLLVLTLPLWAVDAAVQWVFGSGLC

KVAGALFNINFYAGALLLACISFDRYLNIVHATQLYRRGPPARVTLTCLAVWGLCLLFALPD

FIFLSAHHDERLNATHCQYNFPQVGRTALRVLQLVAGFLLPLLVMAYCYAHILAVLLVSRGQ

RRLRAMRLVVVVVVAFALCWTPYHLVVLVDILMDLGALARNCGRESRVDVAKSVTSGLGY

MHCCLNPLLYAFVGVKFRERMWMLLLRLGCPNQRGLQRQPSSSRRDSSWSETSEASYSGL

```
>gi|4504141|ref|NP_000832.1|metabotropic glutamate receptor 4
precursor {Homo sapiens}
                                                                        (SEQ ID NO: 1017)
MPGKRGLGWWWARLPLCLLLSLYGPWMPSSLGKPKGHPHMNSIRIDGDITLGGLFPVHGRG

SEGKPCGELKKEKGIHRLEAMLFALDRINNDPDLLPNITLGARILDTCSRDTHALEQSLTFVQ

ALIEKDGTEVRCGSGGPPIITKPERVVGVIGASGSSVSIMVANILRLFKIPQISYASTAPDLSDNS

RYDFFSRVVPSDTYQAQAMVDIVRALKWNYVSTVASEGSYGESGVEAFIQKSREDGGVCIA

QSVKIPREPKAGEFDKIIRRLLETSNARAVIIFANEDDIRRVLEAARRANQTGHFFWMGSDSW

GSKIAPVLHLEEVAEGAVTILPKRMSVRGFDRYFSSRTLDNNRRNIWFAEFWEDNFHCKLSR

HALKKGSHVKKCTNRERIGQDSAYEQEGKVQFVIDAVYAMGHALHAMHRDLCPGRVGLCP

RMDPVDGTQLLKYIRNVNFSGIAGNPVTFNENGDAPGRYDIYQYQLRNDSAEYKVIGSWTD

HLHLRIERMHWPGSGQQLPRSICSLPCQPGERKKTVKGMPCCWHCEPCTGYQYQVDRYTCK

TCPYDMRPTENRTGCRPIPIIKLEWGSPWAVLPLFLAVVGIAATLFVVITFVRYNDTPIVKASG

RELSYVLLAGIFLCYATTFLMIAEPDLGTCSLRRIFLGLGMSISYAALLTKTNRIYRIFEQGKRS

VSAPRFISPASQLAITFSLISLQLLGICVWFVVDPSHSVVDFQDQRTLDPRFARGVLKCDISDLS

LICLLGYSMLLMVTCTVYAIKTRGVPETFNEAKPIGFTMYTTCIVWLAFIPIFFGTSQSADKLY

IQTTTLTVSVSLSASVSLGMLYMPKVYIILFHPEQNVPKRKRSLKAVVTAATMSNKFTQKGN

FRPNGEAKSELCENLEAPALATKQTYVTYTNHAI

>gi|4504143|ref|NP_000833.1|metabotropic glutamate receptor 5
isoform b precursor {Homo sapiens}
                                                                        (SEQ ID NO: 1018)
MVLLLILSVLLLKEDVRGSAQSSERRVVAHMPGDIIIGALFSVHHQPTVDKVHERKCGAVRE

QYGIQRVEAMLHTLERINSDPTLLPNITLGCEIRDSCWHSAVALEQSIEFIRDSLISSEEEGLV

RCVDGSSSSFRSKKPIVGVIGPGSSSVAIQVQNLLQLFNIPQIAYSATSMDLSDKTLFKYFMRV

VPSDAQQARAMVDIVKRYNWTYVSAVHTEGNYGESGMEAFKDMSAKEGICIAHSYKIYSN

AGEQSFDKLLKKLTSHLPKARVVACFCEGMTVRGLLMAMRRLGLAGEFLLLGSDGWADRY

DVTDGYQREAVGGITIKLQSPDVKWFDDYYLKLRPETNHRNPWFQEFWQHRFQCRLEGFPQ

ENSKYNKTCNSSLTLKTHHVQDSKMGFVINAIYSMAYGLHNMQMSLCPGYAGLCDAMKPI

DGRKLLESLMKTNFTGVSGDTILFDENGDSPGRYEIMNFKEMGKDYFDYINVGSWDNGELK

MDDDEVWSKKSNIIRSVCSEPCEKGQIKVIRKGEVSCCWTCTPCKENEYVFDEYTCKACQLG

SWPTDDLTGCDLIPVQYLRWGDPEPIAAVFACLGLLATLFVTVVFIIYRDTPVVKSSSRELC

YIILAGICLGYLCTFCLIAKPKQIYCYLQRIGIGLSPAMSYSALVTKTNRIARILAGSKKKICTK

KPRFMSACAQLVIAFILICIQLGIIVALFIMEPPDIMHDYPSIREVYLICNTTNLGVVTPLGYNGL

LILSCTFYAFKTRNVPANFNEAKYIAFTMYTTCIIWLAFVPIYFGSNYKIITMCFSVSLSATVAL

GCMFVPKVYIILAKPERNVRSAFTTSTVVRMHVGDGKSSAASRSSSLVNLWKRRGSSGETL

SSNGKSVTWAQNEKSSRGQHLWQRLSIHINKKENPNQTAVIKPFPKSTESRGLGAGAGAGGS

AGGVGATGGAGCAGAGPGGPESPDAGPKALYDVAEAEEHFPAPARPRSPSPISTLSHRAGSA

SRTDDDVPSLHSEPVARSSSSQGSLMEQISSVVTRFTANISELNSMMLSTAAPSPGVGAPLCSS

YLIPKEIQLPTTMTTFAEIQPLPAIEVTGGAQPAAGAQAAGDAARESPAAGPEAAAAKPDLEE

LVALTPPSPFRDSVDSGSTTPNSPVSESALCIPSSPKYDTLIIRDYTQSSSSL

>gi|4504147|ref|NP_000835.1|metabotropic glutamate receptor 7
isoform a precursor{Homo sapiens}
                                                                        (SEQ ID NO: 1019)
MVQLRKLLRVLTLMKFPCCVLEVLLCALAAAARGQEMYAPHSIRIEGDVTLGGLFPVHAKG

PSGVPCGDIKRENGIHRLEAMLYALDQINSDPNLLPNVTLGARILDTCSRDTYALEQSLTFVQ
```

-continued

ALIQKDTSDVRCTNGEPPVFVKPEKVVGVIGASGSSVSIMVANILRLFQIPQISYASTAPELSD

DRRYDFFSRVVPPDSFQAQAMVDIVKALGWNYVSTLASEGSYGEKGVESFTQISKEAGGLCI

AQSVRIPQERKDRTIDFDRIIKQLLDTPNSRAVVIFANDEDIKQILAAAKRADQVGHFLWVGS

DSWGSKINPLHQHEDIAEGAITIQPKRATVEGFDAYFTSRTLENNRRNVWFAEYWEENFNCK

LTISGSKKEDTDRKCTGQERIGKDSNYEQEGKVQFVIDAVYAMAHALHHMNKDLCADYRG

VCPEMEQAGGKKLLKYIRNVNFNGSAGTPVMFNKNGDAPGRYDIFQYQTTNTSNPGYRLIG

QWTDELQLNIEDMQWGKGVREIPASVCTLPCKPGQRKKTQKGTPCCWTCEPCDGYQYFD

EMTCQHCPYDQRPNENRTGCQDIPIIKLEWHSPWAVIPVFLAMLGIIATIFVMATFIRYNDTPI

VRASGRELSYVLLTGIFLCYIITFLMIAKPDVAVCSFRRVFLGLGMCISYAALLTKTNRIYRIFE

QGKKSVTAPRLISPTSQLAITSSLISVQLLGVFIWFGVDPPNIIIDYDEHKTMNPEQARGVLKCD

ITDLQIICSLGYSILLMVTCTVYAIKTRGVPENFNEAKPIGFTMYTTCIVWLAFIPIFFGTAQSAE

KLYIQTTTLTISMNLSASVALGMLYMPKVYIIIFHPELNVQKRKRSFKAVVTAATMSSRLSHK

PSDRPNGEAKTELCENVDPNSPAAKKKYVSYNNLVI

>gi|4504379|ref|NP_003658.1|leucine-rich repeat-containing
G protein-coupled receptor 5 precursor {Homo sapiens}
(SEQ ID NO: 1020)

MDTSRLGVLLSLPVLLQLATGGSSPRSGVLLRGCPTHCHCEPDGRMLLRVDCSDLGLSELPS

NLSVFTSYLDLSMNNISQLLPNPLPSLRFLEELRLAGNALTYIPKGAFTGLYSLKVLMLQNNQ

LRHVPTEALQNLRSLQSLRLDANHISYVPPSCFSGLHSLRHLWLDDNALTEIPVQAFRSLSAL

QAMTLALNKIHHIPDYAFGNLSSLVVLHLHNNRIHSLGKKCFDGLHSLETLDLNYNNLDEFP

TAIRTLSNLKELGFHSNNIRSIPEKAFVGNPSLITIHFYDNPIQFVGRSAFQHLPELRTLTLNGAS

QITEFPDLTGTANLESLTLTGAQISSLPQTVCNQLPNLQVLDLSYNLLEDLPSFSVCQKLQKID

LRHNEIYEIKVDTFQQLLSLRSLNLAWNKIAIIHPNAFSTLPSLIKLDLSSNLLSSFPITGLHGLT

HLKLTGNHALQSLISSENFPELKVIEMPYAYQCCAFGVCENAYKISNQWNKGDNSSMDDLH

KKDAGMFQAQDERDLEDFLLDFEEDLKALHSVQCSPSPGPFKPCEHLLDGWLIRIGVWTIAV

LALTCNALVTSTVFRSPLYISPIKLLIGVIAAVNMLTGVSSAVLAGVDAFTFGSFARHGAWWE

NGVGCHVIGFLSIFASESSVFLLTLAALERGFSVKYSAKFETKAPFSSLKVIILLCALLALTMA

AVPLLGGSKYGASPLCLPLPFGEPSTMGYMVALILLNSLCFLMMTIAYTKLYCNLDKGDLEN

IWDCSMVKHIALLLFTNCILNCPVAFLSFSSLINLTFISPEVIKFILLVVVPLPACLNPLLYILFNP

HFKEDLVSLRKQTYVWTRSKHPSLMSINSDDVEKQSCDSTQALVTFTSSSITYDLPPSSVPSPA

YPVTESCHLSSVAFVPCL

>gi|4504491|ref|NP_000852.1|histamine H1 receptor
{Homo sapiens}
(SEQ ID NO: 1021)

MSLPNSSCLLEDKMCEGNKTTMASPQLMPLVVVLSTICLVTVGLNLLVLYAVRSERKLHTV

GNLYIVSLSVADLIVGAVVMPMNILYLLMSKWSLGRPLCLFWLSMDYVASTASIFSVFILCID

RYRSVQQPLRYLKYRTKTRASATILGAWFLSFLWVIPILGWNHFMQQTSVRREDKCETDFYD

VTWFKVMTAIINFYLPTLLMLWFYAKIYKAVRQHCQHRELINRSLPSFSEIKLRPENPKGDAK

KPGKESPWEVLKRKPKDAGGGSVLKSPSQTPKEMKSPVVFSQEDDREVDKLYCFPLDIVHM

QAAAEGSSRDYVAVNRSHGQLKTDEQGLNTHGASEISEDQMLGDSQSFSRTDSDTTTETAPG

KGKLRSGSNTGLDYIKFTWKRLRSHSRQYVSGLHMNRERKAAKQLGFIMAAFILCWIPYFIFF

MVIAFCKNCCNEHLHMFTIWLGYINSTLNPLIYPLCNENFKKTFKRILHIRS

-continued

>gi|4504533|ref|NP_000854.1|5-hydroxytryptamine receptor 1B
{Homo sapiens}

(SEQ ID NO: 1022)

MEEPGAQCAPPPPAGSETWVPQANLSSAPSQNCSAKDYIYQDSISLPWKVLLVMLLALITLAT

TLSNAFVIATVYRTRKLHTPANYLIASLAVTDLLVSILVMPISTMYTVTGRWTLGQVVCDFW

LSSDITCCTASILHLCVIALDRYWAITDAVEYSAKRTPKRAAVMIALVWVFSISISLPPFFWRQ

AKAEEEVSECVVNTDHILYTVYSTVGAFYFPTLLLIALYGRIYVEARSRILKQTPNRTGKRLT

RAQLITDSPGSTSSVTSINSRVPDVPSESGSPVYVNQVKVRVSDALLEKKKLMAARERKATKT

LGIILGAFIVCWLPFFIISLVMPICKDACWFHLAIFDFFTWLGYLNSLINPIIYTMSNEDFKQAFH

KLIRFKCTS

>gi|4504535|ref|NP_000855.1|5-hydroxytryptamine receptor 1D
{Homo sapiens}

(SEQ ID NO: 1023)

MSPLNQSAEGLPQEASNRSLNATETSEAWDPRTLQALKISLAVVLSVITLATVLSNAFVLTTIL

LTRKLHTPANYLIGSLATTDLLVSILVMPISIAYTITHTWNFGQILCDIWLSSDITCCTASILHLC

VIALDRYWAITDALEYSKRRTAGHAATMIAIVWAISICISIPPLFWRQAKAQEEMSDCLVNTS

QISYTIYSTCGAFYIPSVLLIILYGRIYRAARNRILNPPSLYGKRFTTAHLITGSAGSSLCSLNSSL

HEGHSHSAGSPLFFNHVKIKLADSALERKRISAARERKATKILGIILGAFIICWLPFFVVSLVLPI

CRDSCWIHPALFDFFTWLGYLNSLINPIIYTVFNEEFRQAFQKIVPFRKAS

>gi|4504537|ref|NP_000856.1|5-hydroxytryptamine receptor 1E
{Homo sapiens}

(SEQ ID NO: 1024)

MNITNCTTEASMAIRPKTITEKMLICMTLVVITTLTTLLNLAVIMAIGTTKKLHQPANYLICSL

AVTDLLVAVLVMPLSIIYIVMDRWKLGYFLCEVWLSVDMTCCTCSILHLCVIALDRYWAITN

AIEYARKRTAKRAALMILTVWTISIFISMPPLFWRSHRRLSPPPSQCTIQHDHVIYTIYSTLGAF

YIPLTLILILYYRIYHAAKSLYQKRGSSRHLSNRSTDSQNSFASCKLTQTFCVSDFSTSDPTTEF

EKFHASIRIPPFDNDLDHPGERQQISSTRERKAARILGLILGAFILSWLPFFIKELIVGLSIYTVSS

EVADFLTWLGYVNSLINPLLYTSFNEDFKLAFKKLIRCREHT

>gi|4504541|ref|NP_000859.1|5-hydroxytryptamine receptor 2C
{Homo sapiens}

(SEQ ID NO: 1025)

MVNLRNAVHSFLVHLIGLLVWQCDISVSPVAAIVTDIFNTSDGGRFKFPDGVQNWPALSIVIII

IMTIGGNILVIMAVSMEKKLHNATNYFLMSLAIADMLVGLLVMPLSLLAILYDYVWPLPRYL

CPVWISLDVLFSTASIMHLCAISLDRYVAIRNPIEHSRFNSRTKAIMKIAIVWAISIGVSVPIPVI

GLRDEEKVFVNNTTCVLNDPNFVLIGSFVAFFIPLTIMVITYCLTIYVLRRQALMLLHGHTEEP

PGLSLDFLKCCKRNTAEEENSANPNQDQNARRRKKKERRPRGTMQAINNERKASKVLGIVFF

VFLIMWCPFFITNILSVLCEKSCNQKLMEKLLNVFVWIGYVCSGINPLVYTLFNKIYRRAFSN

YLRCNYKVEKKPPVRQIPRVAATALSGRELNVNIYRHTNEPVIEKASDNEPGIEMQVENLELP

VNPSSVVSERISSV

>gi|4504545|ref|NP_000862.1|5-hydroxytryptamine receptor 6
{Homo sapiens}

(SEQ ID NO: 1026)

MVPEPGPTANSTPAWGAGPPSAPGGSGWVAAALCVVIALTAAANSLLIALICTQPALRNTSN

FFLVSLFTSDLMVGLVVMPPAMLNALYGRWVLARGLCLLWTAFDVMCCSASILNLCLISLD

RYLLILSPLRYKLRMTPLRALALVLGAWSLAALASFLPLLLGWHELGHARPPVPGQCRLLAS

LPFVLVASGLTFFLPSGAICFTYCRILLAARKQAVQVASLTTGMASQASETLQVPRTPRPGVE

SADSRRLATKHSRKALKASLTLGILLGMFFVTWLPFFVANIVQAVCDCISPGLFDVLTWLGY

-continued

CNSTMNPIIYPLFMRDFKRALGRFLPCPRCPRERQASLASPSLRTSHSGPRPGLSLQQVLPLPLP

PDSDSDSDAGSGGSSGLRLTAQLLLPGEATQDPPLPTRAAAAVNFFNIDPAEPELRPHPLGIPTN

>gi|4504547|ref|NP_000863.1|5-hydroxytryptamine receptor 7
isoform a {Homo sapiens}
(SEQ ID NO: 1027)

MMDVNSSGRPDLYGHLRSFLLPEVGRGLPDLSPDGGADPVAGSWAPHLLSEVTASPAPTWD

APPDNASGCGEQINYGRVEKVVIGSILTLITLLTIAGNCLVVISVCFVKKLRQPSNYLIVSLALA

DLSVAVAVMPFVSVTDLIGGKWIFGHFFCNVFIAMDVMCCTASIMTLCVISIDRYLGITRPLT

YPVRQNGKCMAKMILSVWLLSASITLPPLFGWAQNVNDDKVCLISQDFGYTIYSTAVAFYIP

MSVMLFMYYQIYKAARKSAAKHKFPGFPRVEPDSVIALNGIVKLQKEVEECANLSRLLKHER

KNISIFKREQKAATTLGIIVGAFTVCWLPFFLLSTARPFICGTSCSCIPLWVERTFLWLGYANSL

INPFIYAFFNRDLRTTYRSLLQCQYRNINRKLSAAGMHEALKLAERPERPEFVLQNADYCRK

KGHDS

>gi|4504681|ref|NP_000625.1|C-X-C chemokine receptor type 1
{Homo sapiens}
(SEQ ID NO: 1028)

MSNITDPQMWDFDDLNFTGMPPADEDYSPCMLETETLNKYVVIIAYALVFLLSLLGNSLVML

VILYSRVGRSVTDVYLLNLALADLLFALTLPIWAASKVNGWIFGTFLCKVVSLLKEVNFYSGI

LLLACISVDRYLAIVHATRTLTQKRHLVKFVCLGCWGLSMNLSLPFFLFRQAYHPNNSSPVC

YEVLGNDTAKWRMVLRILPHTFGFIVPLFVMLFCYGFTLRTLFKAHMGQKHRAMRVIFAVV

LIFLLCWLPYNLVLLADTLMRTQVIQESCERRNNIGRALDATEILGFLHSCLNPIIYAFIGQNFR

HGFLKILAMHGLVSKEFLARHRVTSYTSSSVNVSSNL

>gi|4504683|ref|NP_001548.1|C-X-C chemokine receptor type 2
{Homo sapiens}
(SEQ ID NO: 1029)

MEDFNMESDSFEDFWKGEDLSNYSYSSTLPPFLLDAAPCEPESLEINKYFVVIIYALVFLLSLL

GNSLVMLVILYSRVGRSVTDVYLLNLALADLLFALTLPIWAASKVNGWIFGTFLCKVVSLLK

EVNFYSGILLLACISVDRYLAIVHATRTLTQKRYLVKFICLSIWGLSLLLALPVLLFRRTVYSS

NVSPACYEDMGNNTANWRMLLRILPQSFGFIVPLLIMLFCYGFTLRTLFKAHMGQKHRAMR

VIFAVVLIFLLCWLPYNLVLLADTLMRTQVIQETCERRNHIDRALDATEILGILHSCLNPLIYA

FIGQKFRHGLLKILAIHGLISKDSLPKDSRPSFVGSSSGHTSTTL

>gi|4505127|ref|NP_000520.1|adrenocorticotropic hormone receptor
{Homo sapiens}
(SEQ ID NO: 1030)

MKHIINSYENINNTARNNSDCPRVVLPEEIFFTISIVGVLENLIVLLAVFKNKNLQAPMYFFICS

LAISDMLGSLYKILENILIILRNMGYLKPRGSFETTADDIIDSLFVLSLLGSIFSLSVIAADRYITIF

HALRYHSIVTMRRTVVVLTVIWTFCTGTGITMVIFSHHVPTVITFTSLFPLMLVFILCLYVHMF

LLARSHTRKISTLPRANMKGAITLTILLGVFIFCWAPFVLHVLLMTFCPSNPYCACYMSLFQV

NGMLIMCNAVIDPFIYAFRSPELRDAFKKMIFCSRYW

>gi|4505445|ref|NP_000900.1|neuropeptide Y receptor type 1
{Homo sapiens}
(SEQ ID NO: 1031)

MNSTLFSQVENHSVHSNFSEKNAQLLAFENDDCHLPLAMIFTLALAYGAVIILGVSGNLALIII

ILKQKEMRNVTNILIVNLSFSDLLVAIMCLPFTFVYTLMDHWVFGEAMCKLNPFVQCVSITVS

IFSLVLIAVERHQLIINPRGWRPNNRHAYVGIAVIWVLAVASSLPFLIYQVMTDEPFQNVTLD

AYKDKYVCFDQFPSDSHRLSYTTLLLVLQYFGPLCFIFICYFKIYIRLKRRNNMMDKMRDNK

-continued

```
YRSSETKRINIMLLSIVVAFAVCWLPLTIFNTVFDWNHQIIATCNHNLLFLLCHLTAMISTCVN

PIFYGFLNKNFQRDLQFFFNFCDFRSRDDDYETIAMSTMHTDVSKTSLKQASPVAFKKINNND

DNEKI
```

>gi|4505447|ref|NP_000901.1|neuropeptide Y receptor Y2
{Homo sapiens}

(SEQ ID NO: 1032)

```
MGPIGAEADENQTVEEMKVEQYGPQTTPRGELVPDPEPELIDSTKLIEVQVVLILAYCSIILLG

VIGNSLVIHVVIKFKSMRTVTNFFIANLAVADLLVNTLCLPFTLTYTLMGEWKMGPVLCHLV

PYAQGLAVQVSTITLTVIALDRHRCIVYHLESKISKRISFLIIGLAWGISALLASPLAIFREYSLIE

IIPDFEIVACTEKWPGEEKSIYGTVYSLSSLLILYVLPLGIISFSYTRIWSKLKNHVSPGAANDH

YHQRRQKTTKMLVCVVVVFAVSWLPLHAFQLAVDIDSQVLDLKEYKLIFTVFHIIAMCSTFA

NPLLYGWMNSNYRKAFLSAFRCEQRLDAIHSEVSVTFKAKKNLEVRKNSGPNDSFTEATNV
```

>gi|4505513|ref|NP_000904.1|opiate receptor -like 1
{Homo sapiens}

(SEQ ID NO: 1033)

```
MEPLFPAPFWEVIYGSHLQGNLSLLSPNHSLLPPHLLLNASHGAFLPLGLKVTIVGLYLAVCV

GGLLGNCLVMYVILRHTKMKTATNIYIFNLALADTLVLLTLPFQGTDILLGFWPFGNALCKT

VIAIDYYNMFTSTFTLTAMSVDRYVAICHPIRALDVRTSSKAQAVNVAIWALASVVGVPVAI

MGSAQVEDEEIECLVEIPTPQDYWGPVFAICIFLFSFIVPVLVISVCYSLMIRRLRGVRLLSGSR

EKDRNLRRITRLVLVVVAVFVGCWTPVQVFVLAQGLGVQPSSETAVAILRFCTALGYVNSCL

NPILYAFLDENFKACFRKFCCASALRRDVQVSDRVRSIAKDVALACKTSETVPRPA
```

>gi|4505557|ref|NP_002554.1|P2Y purinoceptor 1
{Homo sapiens}

(SEQ ID NO: 1034)

```
MTEVLWPAVPNGTDAAFLAGPGSSWGNSTVASTAAVSSSFKCALTKTGFQFYYLPAVYILVF

IIGFLGNSVAIWMFVFHMKPWSGISVYMFNLALADFLYVLTLPALIFYYFNKTDWIFGDAMC

KLQRFIFHVNLYGSILFLTCISAHRYSGVVYPLKSLGRLKKKNAICISVLVWLIVVVAISPILFY

SGTGVRKNKTITCYDTTSDEYLRSYFIYSMCTTVAMFCVPLVLILGCYGLIVRALIYKDLDNS

PLRRKSIYLVIIVLTVFAVSYIPFHVMKTMNLRARLDFQTPAMCAFNDRVYATYQVTRGLAS

LNSCVDPILYFLAGDTFRRRLSRATRKASRRSEANLQSKSEDMTLNILPEFKQNGDTSL
```

>gi|4505561|ref|NP_002556.1|pyrimidinergic receptor P2Y4
{Homo sapiens}

(SEQ ID NO: 1035)

```
MASTESSLLRSLGLSPGPGSSEVELDCWFDEDFKFILLPVSYAVVFVLGLGLNAPTLWLFIFRL

RPWDATATYMFHLALSDTLYVLSLPTLIYYYAAHNHWPFGTEICKFVRLFYWNLYCSVLFL

TCISVHRYLGICHPLRALRWGRPRLAGLLCLAVWLVVAGCLVPNLFFVTTSNKGTTVLCHDT

TRPEEFDHYVHFSSAVMGLLFGVPCLVTLVCYGLMARRLYQPLPGSAQSSSRLRSLRTIAVV

LTVFAVCFVPFHITRTIYYLARLLEADCRVLNIVNVVYKVTRPLASANSCLDPVLYLLTGDKY

RRQLRQLCGGGKPQPRTAASSLALVSLPEDSSCRWAATPQDSSCSTPRADRL
```

>gi|4506241|ref|NP_000943.1|platelet-activating factor receptor
{Homo sapiens}

(SEQ ID NO: 1036)

```
MEPHDSSHMDSEFRYTLFPIVYSIIFVLGVIANGYVLWVFARLYPCKKFNEIKIFMVNLTMAD

MLFLITLPLWIVYYQNQGNWILPKFLCNVAGCLFFINTYCSVAFLGVITYNRFQAVTRPIKTA

QANTRKRGISLSLVIWVAIVGAASYFLILDSTNTVPDSAGSGNVTRCFEHYEKGSVPVLIIHIFI

VFSFFLVFLIILFCNLVIIRTLLMQPVQQQRNAEVKRRALWMVCTVLAVFIICFVPHHVVQLP

WTLAELGFQDSKFHQAINDAHQVTLCLLSTNCVLDPVIYCFLTKKFRKHLTEKFYSMRSSRK

CSRATTDTVTEVVVPFNQIPGNSLKN
```

```
>gi|4506259|ref|NP_000949.1|prostaglandin E2 receptor EP4
subtype {Homo sapiens}
                                                                (SEQ ID NO: 1037)
MSTPGVNSSASLSPDRLNSPVTIPAVMFIFGVVGNLVAIVVLCKSRKEQKETTFYTLVCGLAV

TDLLGTLLVSPVTIATYMKGQWPGGQPLCEYSTFILLFFSLSGLSIICAMSVERYLAINHAYFY

SHYVDKRLAGLTLFAVYASNVLFCALPNMGLGSSRLQYPDTWCFIDWTTNVTAHAAYSYM

YAGFSSFLILATVLCNVLVCGALLRMHRQFMRRTSLGTEQHHAAAAASVASRGHPAASPAL

PRLSDFRRRRSFRRIAGAEIQMVILLIATSLVVLICSIPLVVRVFVNQLYQPSLEREVSKNPDLQ

AIRIASVNPILDPWIYILLRKTVLSKAIEKIKCLFCRIGGSRRERSGQHCSDSQRTSSAMSGHSR

SFISRELKEISSTSQTLLPDLSLPDLSENGLGGRNLLPGVPGMGLAQEDTTSLRTLRISETSDSS

QGQDSESVLLVDEAGGSGRAGPAPKGSSLQVTFPSETLNLSEKCI

>gi|4506261|ref|NP_000950.1|prostaglandin F2-alpha receptor
isoform a precursor {Homo sapiens}
                                                                (SEQ ID NO: 1038)
MSMNNSKQLVSPAAALLSNTTCQTENRLSVFFSVIFMTVGILSNSLAIAILMKAYQRFRQKSK

ASFLLLASGLVITDFFGHLINGAIAVFVYASDKEWIRFDQSNVLCSIFGICMVFSGLCPLLLGSV

MAIERCIGVTKPIFHSTKITSKHVKMMLSGVCLFAVFIALLPILGHRDYKIQASRTWCFYNTED

IKDWEDRFYLLLFSFLGLLALGVSLLCNAITGITLLRVKFKSQQHRQGRSHHLEMVIQLLAIM

CVSCICWSPFLVTMANIGINGNHSLETCETTLFALRMATWNQILDPWVYILLRKAVLKNLYK

LASQCCGVHVISLHIWELSSIKNSLKVAAISESPVAEKSAST

>gi|4506263|ref|NP_000951.1|prostaglandin I2 (prostacyclin)
receptor (IP) {Homo sapiens}
                                                                (SEQ ID NO: 1039)
MADSCRNLTYVRGSVGPATSTLMFVAGVVGNGLALGILSARRPARPSAFAVLVTGLAATDL

LGTSFLSPAVFVAYARNSSLLGLARGGPALCDAFAFAMTFFGLASMLILFAMAVERCLALSH

PYLYAQLDGPRCARLALPAIYAFCVLFCALPLLGLGQHQQYCPGSWCFLRMRWAQPGGAAF

SLAYAGLVALLVAAIFLCNGSVTLSLCRMYRQQKRHQGSLGPRPRTGEDEVDHLILLALMTV

VMAVCSLPLTIRCFTQAVAPDSSSEMGDLLAFRFYAFNPILDPWVFILFRKAVFQRLKLWVCC

LCLGPAHGDSQTPLSQLASGRRDPRAPSAPVGKEGSCVPLSAWGEGQVEPLPPTQQSSGSAV

GTSSKAEASVACSLC

>gi|4506271|ref|NP_000307.1|parathyroid hormone receptor 1
precursor {Homo sapiens}
                                                                (SEQ ID NO: 1040)
MGTARIAPGLALLLCCPVLSSAYALVDADDVMTKEEQIFLLHRAQAQCEKRLKEVLQRPASI

MESDKGWTSASTSGKPRKDKASGKLYPESEEDKEAPTGSRYRGRPCLPEWDHILCWPLGAP

GEVVAVPCPDYIYDFNHKGHAYRRCDRNGSWELVPGHNRTWANYSECVKFLTNETREREV

FDRLGMIYTVGYSVSLASLTVAVLILAYFRRLHCTRNYIHMHLFLSFMLRAVSIFVKDAVLYS

GTLWQVQMHYEMLFNSFQGFFVAIIYCFCNGEVQAEIKKSWSRWTLALDFKRKARSGSSSY

SYGPMVSHTSVTNVGPRVGLGLPLSPRLLPTATTNGHPQLPGHAKPGTPALETLETTPPAMA

APKDDGFLNGSCSGLDEEASGPERPPALLQEEWETVM

>gi|4506403|ref|NP_003970.1|retinoic acid-induced protein 3 {Homo sapiens}
                                                                (SEQ ID NO: 1041)
MATTVPDGCRNGLKSKYYRLCDKAEAWGIVLETVATAGVVTSVAFMLTLPILVCKVQDSNR

RKMLPTQFLFLLGVLGIFGLTFAFIIGLDGSTGPTRFFLFGILFSICFSCLLAHAVSLTKLVRGRK

PLSLLVILGLAVGFSLVQDVIAIEYIVLTMNRTNVNVFSELSAPRRNEDFVLLLTYVLFLMALT

FLMSSFTFCGSFTGWKRHGAHIYLTMLLSIAIWVAWITLLMLPDFDRRWDDTILSSALAANG
```

```
WVFLLAYVSPEFWLLTKQRNPMDYPVEDAFCKPQLVKKSYGVENRAYSQEEITQGFEETGD

TLYAPYSTHFQLQNQPPQKEFSIPRAHAWPSPYKDYEVKKEGS
```

>gi|4507343|ref|NP_001049.1|substance-P receptor isoform long {Homo sapiens}
(SEQ ID NO: 1042)

```
MDNVLPVDSDLSPNISTNTSEPNQFVQPAWQIVLWAAAYTVIVVTSVVGNVVVMWIILAHK

RMRTVTNYFLVNLAFAEASMAAFNTVVNFTYAVHNEWYYGLFYCKFHNFFPIAAVFASIYS

MTAVAFDRYMAIIHPLQPRLSATATKVVICVIWVLALLLAFPQGYYSTTETMPSRVVCMIEW

PEHPNKIYEKVYHICVTVLIYFLPLLVIGYAYTVVGITLWASEIPGDSSDRYHEQVSAKRKVV

KMMIVVVCTFAICWLPFHIFFLLPYINPDLYLKKFIQQVYLAIMWLAMSSTMYNPIIYCCLND

RFRLGFKHAFRCCPFISAGDYEGLEMKSTRYLQTQGSVYKVSRLETTISTVVGAHEEEPEDGP

KATPSSLDLTSNCSSRSDSKTMTESFSFSSNVLS
```

>gi|4507381|ref|NP_001051.1|thromboxane A2 receptor isoform alpha {Homo sapiens}
(SEQ ID NO: 1043)

```
MWPNGSSLGPCFRPTNITLEERRLIASPWFAASFCVVGLASNLLALSVLAGARQGGSHTRSSF

LTFLCGLVLTDFLGLLVTGTIVVSQHAALFEWHAVDPGCRLCRFMGVVMIFFGLSPLLLGAA

MASERYLGITRPFSRPAVASQRRAWATVGLVWAAALALGLLPLLGVGRYTVQYPGSWCFLT

LGAESGDVAFGLLFSMLGGLSVGLSFLLNTVSVATLCHVYHGQEAAQQRPRDSEVEMMAQL

LGIMVVASVCWLPLLVFIAQTVLRNPPAMSPAGQLSRTTEKELLIYLRVATWNQILDPWVYIL

FRRAVLRRLQPRLSTRPRSLSLQPQLTQRSGLQ
```

>gi|4507681|ref|NP_003292.1|thyrotropin-releasing hormone receptor {Homo sapiens}
(SEQ ID NO: 1044)

```
MENETVSELNQTQLQPRAVVALEYQVVTILLVLIICGLGIVGNIMVVLVVMRTKHMRTPTNC

YLVSLAVADLMVLVAAGLPNITDSIYGSWVYGYVGCLCITYLQYLGINASSCSITAFTIERYIA

ICHPIKAQFLCTFSRAKKIIIFVWAFTSLYCMLWFFLLDLNISTYKDAIVISCGYKISRNYYSPIY

LMDFGVFYVVPMILATVLYGFIARILFLNPIPSDPKENSKTWKNDSTHQNTNLNVNTSNRCFN

STVSSRKQVTKMLAVVVILFALLWMPYRTLVVVNSFLSSPFQENWFLLFCRICIYLNSAINPVI

YNLMSQKFRAAFRKLCNCKQKPTEKPANYSVALNYSVIKESDHFSTELDDITVTDTYLSATK

VSFDDTCLASEVSFSQS
```

>gi|4557265|ref|NP_000675.1|beta-1 adrenergic receptor {Homo sapiens}
(SEQ ID NO: 1045)

```
MGAGVLVLGASEPGNLSSAAPLPDGAATAARLLVPASPPASLLPPASESPEPLSQQWTAGMG

LLMALIVLLIVAGNVLVIVAIAKTPRLQTLTNLFIMSLASADLVMGLLVVPFGATIVVWGRW

EYGSFFCELWTSVDVLCVTASIETLCVIALDRYLAITSPFRYQSLLTRARARGLVCTVWAISAL

VSFLPILMHWWRAESDEARRCYNDPKCCDFVTNRAYAIASSVVSFYVPLCIMAFVYLRVFRE

AQKQVKKIDSCERRFLGGPARPPSPSPSPVPAPAPPPGPPRPAAAAATAPLANGRAGKRRPSR

LVALREQKALKTLGIIMGVFTLCWLPFFLANVVKAFHRELVPDRLFVFFNWLGYANSAFNPII

YCRSPDFRKAFQGLLCCARRAARRRHATHGDRPRASGCLARPGPPPSPGAASDDDDDDVVG

ATPPARLLEPWAGCNGGAAADSDSSLDEPCRPGFASESKV
```

>gi|4557267|ref|NP_000016.1|adrenergic, beta-3-, receptor {Homo sapiens}
(SEQ ID NO: 1046)

```
MAPWPHENSSLAPWPDLPTLAPNTANTSGLPGVPWEAALAGALLALAVLATVGGNLLVIVA

IAWTPRLQTMTNVFVTSLAAADLVMGLLVVPPAATLALTGHWPLGATGCELWTSVDVLCV

TASIETLCALAVDRYLAVTNPLRYGALVTKRCARTAVVLVWVVSAAVSFAPIMSQWWRVG

ADAEAQRCHSNPRCCAFASNMPYVLLSSSVSFYLPLLVMLFVYARVFVVATRQLRLLRGEL

GRFPPEESPPAPSRSLAPAPVGTCAPPEGVPACGRRPARLLPLREHRALCTLGLIMGTFTLCWL
```

```
PFFLANVLRALGGPSLVPGPAFLALNWLGYANSAFNPLIYCRSPDFRSAFRRLLCRCGRRLPP

EPCAAARPALFPSGVPAARSSPAQPRLCQRLDGASWGVS
```

>gi|4557345|ref|NP_000045.1|vasopressin V2 receptor isoform 1 {Homo sapiens}
(SEQ ID NO: 1047)

```
MLMASTTSAVPGHPSLPSLPSNSSQERPLDTRDPLLARAELALLSIVFVAVALSNGLVAALA

RRGRRGHWAPIHVFIGHLCLADLAVALFQVLPQLAWKATDRFRGPDALCRAVKYLQMVGM

YASSYMILAMTLDRHRAICRPMLAYRHGSGAHWNRPVLVAWAFSLLLSLPQLFIFAQRNVE

GGSGVTDCWACFAEPWGRRTYVTWIALMVFVAPTLGIAACQVLIFREIHASLVPGPSERPGG

RRRGRRTGSPGEGAHVSAAVAKTVRMTLVIVVVYVLCWAPFFLVQLWAAWDPEAPLEGAP

FVLLMLLASLNSCTNPWIYASFSSSVSSELRSLLCCARGRTPPSLGPQDESCTTASSSLAKDTSS
```

>gi|4557359|ref|NP_000614.1|B2 bradykinin receptor {Homo sapiens}
(SEQ ID NO: 1048)

```
MFSPWKISMFLSVREDSVPTTASFSADMLNVTLQGPTLNGTFAQSKCPQVEWLGWLNTIQPP

FLWVLFVLATLENIFVLSVFCLHKSSCTVAEIYLGNLAAADLILACGLPFWAITISNNFDWLFG

ETLCRVVNAIISMNLYSSICFLMLVSIDRYLALVKTMSMGRMRGVRWAKLYSLVIWGCTLLL

SSPMLVFRTMKEYSDEGHNVTACVISYPSLIWEVFTNMLLNVVGFLLPLSVITFCTMQIMQVL

RNNEMQKFKEIQTERRATVLVLVVLLLFIICWLPFQISTFLDTLHRLGILSSCQDERIIDVITQIA

SFMAYSNSCLNPLVYVIVGKRFRKKSWEVYQGVCQKGGCRSEPIQMENSMGTLRTSISVERQ

IHKLQDWAGSRQ
```

>gi|4557547|ref|NP_000106.1|endothelin B receptor isoform 1 precursor {Homo sapiens}
(SEQ ID NO: 1049)

```
MQPPPSLCGRALVALVLACGLSRIWGEERGFPPDRATPLLQTAEIMTPPTKTLWPKGSNASLA

RSLAPAEVPKGDRTAGSPPRTISPPPCQGPIEIKETFKYINTVVSCLVFVLGIIGNSTLLRIIYKN

KCMRNGPNILIASLALGDLLHIVIDIPINVYKLLAEDWPFGAEMCKLVPFIQKASVGITVLSLC

ALSIDRYRAVASWSRIKGIGVPKWTAVEIVLIWVVSVVLAVPEAIGFDIITMDYKGSYLRICLL

HPVQKTAFMQFYKTAKDWWLFSFYFCLPLAITAFFYTLMTCEMLRKKSGMQIALNDHLKQR

REVAKTVFCLVLVFALCWLPLHLSRILKLTLYNQNDPNRCELLSFLLVLDYIGINMASLNSCI

NPIALYLVSKRFKNCFKSCLCCWCQSFEEKQSLEEKQSCLKFKANDHGYDNFRSSNKYSSS
```

>gi|4557857|ref|NP_001040.1|somatostatin receptor type 1 {Homo sapiens}
(SEQ ID NO: 1050)

```
MFPNGTASSPSSSPSPSPGSCGEGGGSRGPGAGAADGMEEPGRNASQNGTLSEGQGSAILISFI

YSVVCLVGLCGNSMVIYVILRYAKMKTATNIYILNLAIADELLMLSVPFLVTSTLLRHWPFGA

LLCRLVLSVDAVNMFTSIYCLTVLSVDRYVAVVHPIKAARYRRPTVAKVVNLGVWVLSLLV

ILPIVVFSRTAANSDGTVACNMLMPEPAQRWLVGFVLYTFLMGFLLPVGAICLCYVLIIAKM

RMVALKAGWQQRKRSERKITLMVMMVVMVFVICWMPFYVVQLVNVFAEQDDATVSQLSV

ILGYANSCANPILYGFLSDNFKRSFQRILCLSWMDNAAEEPVDYYATALKSRAYSVEDFQPE

NLESGGVFRNGTCTSRITTL
```

>gi|4557859|ref|NP_001041.1|somatostatin receptor type 2 {Homo sapiens}
(SEQ ID NO: 1051)

```
MDMADEPLNGSHTWLSIPFDLNGSVVSTNTSNQTEPYYDLTSNAVLTFIYFVVCIIGLCGNTL

VIYVILRYAKMKTITNIYILNLAIADELFMLGLPFLAMQVALVHWPFGKAICRVVMTVDGINQ

FTSIFCLTVMSIDRYLAVVHPIKSAKWRRPRTAKMITMAVWGVSLLVILPIMIYAGLRSNQW

GRSSCTINWPGESGAWYTGFIIYTFILGFLVPLTIICLCYLFIIIKVKSSGIRVGSSKRKKSEKKVT

RMVSIVVAVFIFCWLPFYIFNVSSVSMAISPTPALKGMFDFVVVLTYANSCANPILYAFLSDNF

KKSFQNVLCLVKVSGTDDGERSDSKQDKSRLNETTETQRTLLNGDLQTSI
```

```
>gi|4557861|ref|NP_001042.1|somatostatin receptor type 3 {Homo sapiens}
                                                                        (SEQ ID NO: 1052)
MDMLHPSSVSTTSEPENASSAWPPDATLGNVSAGPSPAGLAVSGVLIPLVYLVVCVVGLLGN

SLVIYVVLRHTASPSVTNVYILNLALADELFMLGLPFLAAQNALSYWPFGSLMCRLVMAVD

GINQFTSIFCLTVMSVDRYLAVVHPTRSARWRTAPVARTVSAAVWVASAVVVLPVVVFSGV

PRGMSTCHMQWPEPAAAWRAGFIIYTAALGFFGPLLVICLCYLLIVVKVRSAGRRVWAPSCQ

RRRRSERRVTRMVVAVVALFVLCWMPFYVLNIVNVVCPLPEEPAFFGLYFLVVALPYANSC

ANPILYGFLSYRFKQGFRRVLLRPSRRVRSQEPTVGPPEKTEEEDEEEEDGEESREGGKGKEM

NGRVSQITQPGTSGQERPPSRVASKEQQLLPQEASTGEKSSTMRISYL

>gi|4557865|ref|NP_001044.1|somatostatin receptor type 5 {Homo sapiens}
                                                                        (SEQ ID NO: 1053)
MEPLFPASTPSWNASSPGAASGGGDNRTLVGPAPSAGARAVLVPVLYLLVCAAGLGGNTLVI

YVVLRFAKMKTVTNIYILNLAVADVLYMLGLPFLATQNAASFWPFGPVLCRLVMTLDGVNQ

FTSVFCLTVMSVDRYLAVVHPLSSARWRRPRVAKLASAAAWVLSLCMSLPLLVFADVQEGG

TCNASWPEPVGLWGAVFIIYTAVLGFFAPLLVICLCYLLIVVKVRAAGVRVGCVRRRSERKV

TRMVLVVVLVFAGCWLPFFTVNIVNLAVALPQEPASAGLYFFVVILSYANSCANPVLYGFLS

DNFRQSFQKVLCLRKGSGAKDADATEPRPDRIRQQQEATPPAHRAAANGLMQTSKL

>gi|4757888|ref|NP_004045.1|C3a anaphylatoxin chemotactic receptor {Homo sapiens}
                                                                        (SEQ ID NO: 1054)
MASFSAETNSTDLLSQPWNEPPVILSMVILSLTFLLGLPGNGLVLWVAGLKMQRTVNTIWFL

HLTLADLLCCLSLPFSLAHLALQGQWPYGRFLCKLIPSIIVLNMFASVFLLTAISLDRCLVVFK

PIWCQNHRNVGMACSICGCIWVVAFVMCIPVFVYREIFTTDNHNRCGYKFGLSSSLDYPDFY

GDPLENRSLENIVQPPGEMNDRLDPSSFQTNDHPWTVPTVFQPQTFQRPSADSLPRGSARLTS

QNLYSNVFKPADVVSPKIPSGFPIEDHETSPLDNSDAFLSTHLKLFPSASSNSFYESELPQGFQD

YYNLGQFTDDDQVPTPLVAITITRLVVGFLLPSVIMIACYSFIVFRMQRGRFAKSQSKTFRVA

VVVVAVFLVCWTPYHIFGVLSLLTDPETPLGKTLMSWDHVCIALASANSCFNPFLYALLGKD

FRKKARQSIQGILEAAFSEELTRSTHCPSNNVISERNSTTV

>gi|4758014|ref|NP_004063.1|chemokine receptor -like 1 isoform b {Homo sapiens}
                                                                        (SEQ ID NO: 1055)
MEDEDYNTSISYGDEYPDYLDSIVVLEDLSPLEARVTRIFLVVVYSIVCFLGILGNGLVIIIATF

KMKKTVNMVWFLNLAVADFLFNVFLPIHITYAAMDYHWVFGTAMCKISNFLLIHNMFTSVF

LLTIISSDRCISVLLPVWSQNHRSVRLAYMACMVIWVLAFFLSSPSLVFRDTANLHGKISCFNN

FSLSTPGSSSWPTHSQMDPVGYSRHMVVTVTRFLCGFLVPVLIITACYLTIVCKLQRNRLAKT

KKPFKIIVTIIITFFLCWCPYHTLNLLELHHTAMPGSVFSLGLPLATALAIANSCMNPILYVFMG

QDFKKFKVALFSRLVNALSEDTGHSSYPSHRSFTKMSSMNERTSMNERETGML

>gi|4758326|ref|NP_004092.1|proteinase-activated receptor 3 precursor {Homo sapiens}
                                                                        (SEQ ID NO: 1056)
MKALIFAAAGLLLLLPTFCQSGMENDTNNLAKPTLPIKTFRGAPPNSFEEFPFSALEGWTGATI

TVKIKCPEESASHLHVKNATMGYLTSSLSTKLIPAIYLLVFVVGVPANAVTWMLFFRTRSIC

TTVFYTNLAIADFLFCVTLPFKIAYHLNGNNWVFGEVLCRATTVIFYGNMYCSILLLACISINR

YLAIVHPFTYRGLPKHTYALVTCGLVWATVFLYMLPFFILKQEYYLVQPDITTCHDVHNTCE

SSSPFQLYYFISLAFFGFLIPFVLIIYCYAAIIRTLNAYDHRWLWYVKASLLILVIFTICFAPSNIIL

IIHHANYYYNNTDGLYFIYLIALCLGSLNSCLDPFLYFLMSKTRNHSTAYLTK
```

```
>gi|4758438|ref|NP_004237.1|glucagon-like peptide 2 receptor precursor {Homo sapiens}
                                                                  (SEQ ID NO: 1057)
MKLGSSRAGPGRGSAGLLPGVHELPMGIPAPWGTSPLSFHRKCSLWAPGRPFLTLVLLVSIKQ

VTGSLLEETTRKWAQYKQACLRDLLKEPSGIFCNGTFDQYVCWPHSSPGNVSVPCPSYLPW

WSEESSGRAYRHCLAQGTWQTIENATDIWQDDSECSENHSFKQNVDRYALLSTLQLMYTVG

YSFSLISLFLALTLLLFLRKLHCTRNYIHMNLFASFILRTLAVLVKDVVFYNSYSKRPDNENG

WMSYLSEMSTSCRSVQVLLHYFVGANYLWLLVEGLYLHTLLEPTVLPERRLWPRYLLLGW

AFPVLFVVPWGFARAHLENTGCWTTNGNKKIWWIIRGPMMLCVTVNFFIFLKILKLLISKLK

AHQMCFRDYKYRLAKSTLVLIPLLGVHEILFSFITDDQVEGFAKLIRLFIQLTLSSFHGFLVAL

QYGFANGEVKAELRKYWVRFLLARHSGCRACVLGKDFRFLGKCPKKLSEGDGAEKLRKLQ

PSLNSGRLLHLAMRGLGELGAQPQQDHARWPRGSSLSECSEGDVTMANTMEEILEESEI

>gi|4758474|ref|NP_004239.1|prolactin-releasing peptide receptor {Homo sapiens}
                                                                  (SEQ ID NO: 1058)
MASSTTRGPRVSDLFSGLPPAVTTPANQSAEASAGNGSVAGADAPAVTPFQSLQLVHQLKGL

IVLLYSVVVVVGLVGNCLLVLVIARVRRLHNVTNFLIGNLALSDVLMCTACVPLTLAYAFEP

RGWVFGGGLCHLVFFLQPVTVYVSVFTLTTIAVDRYVVLVHPLRRRISLRLSAYAVLAIWAL

SAVLALPAAVHTYHVELKPHDVRLCEEFWGSQERQRQLYAWGLLLVTYLLPLLVILLSYVR

VSVKLRNRVVPGCVTQSQADWDRARRRRTFCLLVVVVVVFAVCWLPLHVFNLLRDLDPHA

IDPYAFGLVQLLCHWLAMSSACYNPFIYAWLHDSFREELRKLLVAWPRKIAPHGQNMTVSV

VI

>gi|4758864|ref|NP_004145.1|pyrimidinergic receptor P2Y6 {Homo sapiens}
                                                                  (SEQ ID NO: 1059)
MEWDNGTGQALGLPPTTCVYRENFKQLLLPPVYSAVLAAGLPLNICVITQICTSRRALTRTA

VYTLNLALADLLYACSLPLLIYNYAQGDHWPFGDFACRLVRFLFYANLHGSILFLTCISFQRY

LGICHPLAPWHKRGGRRAAWLVCVAVWLAVTTQCLPTAIFAATGIQRNRTVCYDLSPPALA

THYMPYGMALTVIGFLLPFAALLACYCLLACRLCRQDGPAEPVAQERRGKAARMAVVVAA

AFAISFLPFHITKTAYLAVRSTPGVPCTVLEAFAAAYKGTRPFASANSVLDPILFYFTQKKFRR

RPHELLQKLTAKWQRQGR

>gi|4826706|ref|NP_004942.1|G-protein coupled receptor 183 {Homo sapiens}
                                                                  (SEQ ID NO: 1060)
MDIQMANNFTPPSATPQGNDCDLYAHHSTARIVMPLHYSLVFIIGLVGNLLALVVIVQNRKKI

NSTTLYSTNLVISDILFTTALPTRIAYYAMGFDWRIGDALCRITALVFYINTYAGVNFMTCLSI

DRFIAVVHPLRYNKIKRIEHAKGVCIFVWILVFAQTLPLLINPMSKQEAERITCMEYPNFEETK

SLPWILLGACFIGYVLPLIIILICYSQICCKLFRTAKQNPLTEKSGVNKKALNTIILIIVVFVLCFT

PYHVAIIQHMIKKLRFSNFLECSQRHSFQISLHFTVCLMNFNCCMDPFIYFFACKGYKRKVMR

MLKRQVSVSISSAVKSAPEENSREMTETQMMIHSKSSNGK

>gi|4826954|ref|NP_005039.1|parathyroid hormone 2 receptor precursor {Homo sapiens}
                                                                  (SEQ ID NO: 1061)
MAGLGASLHVWGWLMLGSCLLARAQLDSDGTITIEEQIVLVLKAKVQCELNITAQLQEGEG

NCFPEWDGLICWPRGTVGKISAVPCPPYIYDFNHKGVAFRHCNPNGTWDFMHSLNKTWANY

SDCLRFLQPDISIGKQEFFERLYVMYTVGYSISFGSLAVAILIIGYFRRLHCTRNYIHMHLFVSF

MLRATSIFVKDRVVHAHIGVKELESLIMQDDPQNSIEATSVDKSQYIGCKIAVVMFIYFLATN

YYWILVEGLYLHNLIFVAFFSDTKYLWGFILIGWGFPAAFVAAWAVARATLADARCWELSA

GDIKWIYQAPILAAIGLNFILFLNTVRVLATKIWETNAVGHDTRKQYRLAKSTLVLVLVFGV

HYIVFVCLPHSFTGLGWEIRMHCELFFNSFQGFFVSIIYCYCNGEVQAEVKKMWSRWNLSVD
```

-continued

WKRTPPCGSRRCGSVLTTVTHSTSSQSQVAASTRMVLISGKAAKIASRQPDSHITLPGYVWSN

SEQDCLPHSFHEETKEDSGRQGDDILMEKPSRPMESNPDTEGCQGETEDVL

>gi|4885057|ref|NP_005152.1|apelin receptor {Homo sapiens}
(SEQ ID NO: 1062)

MEEGGDFDNYYGADNQSECEYTDWKSSGALIPAIYMLVFLLGTTGNGLVLWTVFRSSREKR

RSADIFIASLAVADLTFVVTLPLWATYTYRDYDWPFGTFFCKLSSYLIFVNMYASVFCLTGLS

FDRYLAIVRPVANARLRLRVSGAVATAVLWVLAALLAMPVMVLRTTGDLENTTKVQCYMD

YSMVATVSSEWAWEVGLGVSSTTVGFVVPFTIMLTCYFFIAQTIAGHFRKERIEGLRKRRRLL

SIIVVLVVTFALCWMPYHLVKTLYMLGSLLHWPCDFDLFLMNIFPYCTCISYVNSCLNPFLYA

FFDPRFRQACTSMLCCGQSRCAGTSHSSSGEKSASYSSGHSQGPGPNMGKGGEQMHEKSIPY

SQETLVVD

>gi|4885121|ref|NP_005192.1|C-C chemokine receptor type 8 {Homo sapiens}
(SEQ ID NO: 1063)

MDYTLDLSVTTVTDYYYPDIFSSPCDAELIQTNGKLLLAVFYCLLFVFSLLGNSLVILVLVVC

KKLRSITDVYLLNLALSDLLFVFSFPFQTYYLLDQWVFGTVMCKVVSGFYYIGFYSSMFFITL

MSVDRYLAVVHAVYALKVRTIRMGTTLCLAVWLTAIMATIPLLVFYQVASEDGVLQCYSFY

NQQTLKWKIFTNFKMNILGLLIPFTIFMFCYIKILHQLKRCQNHNKTKAIRLVLIVVIASLLFW

VPFNVVLFLTSLHSMHILDGCSISQQLTYATHVTEIISFTHCCVNPVIYAFVGEKFKKHLSEIFQ

KSCSQIFNYLGRQMPRESCEKSSSCQQHSSRSSSVDYIL

>gi|4885295|ref|NP_005279.1|G-protein coupled receptor 12 {Homo sapiens}
(SEQ ID NO: 1064)

MNEDLKVNLSGLPRDYLDAAAAENISAAVSSRVPAVEPEPELVVNPWDIVLCTSGTLISCEN

AIVVLIIFHNPSLRAPMFLLIGSLALADLLAGIGLITNFVFAYLLQSEATKLVTIGLIVASFSASV

CSLLAITVDRYLSLYYALTYHSERTVTFTYVMLVMLWGTSICLGLLPVMGWNCLRDESTCS

VVRPLTKNNAAILSVSFLFMFALMLQLYIQICKIVMRHAHQIALQHHFLATSHYVTTRKGVST

LAIILGTFAACWMPFTLYSLIADYTYPSIYTYATLLPATYNSIINPVIYAFRNQEIQKALCLICCG

CIPSSLAQRARSPSDV

>gi|4885299|ref|NP_005281.1|G protein-coupled receptor 15 {Homo sapiens}
(SEQ ID NO: 1065)

MDPEETSVYLDYYYATSPNSDIRETHSHVPYTSVFLPVFYTAVFLTGVLGNLVLMGALHFKP

GSRRLIDIFIINLAASDFIFLVTLPLWVDKEASLGLWRTGSFLCKGSSYMISVNMHCSVLLLTC

MSVDRYLAIVWPVVSRKFRRTDCAYVVCASIWFISCLLGLPTLLSRELTLIDDKPYCAEKKAT

PIKLIWSLVALIFTFFVPLLSIVTCYCCIARKLCAHYQQSGKHNKKLKKSIKIIFIVVAAFLVSW

LPFNTFKFLAIVSGLRQEHYLPSAILQLGMEVSGPLAFANSCVNPFIYYIFDSYIRRAIVHCLCP

CLKNYDFGSSTETSDSHLTKALSTFIHAEDFARRRKRSVSL

>gi|4885301|ref|NP_005282.1|uracil nucleotide/cysteinyl leukotriene receptor isoform a {Homo sapiens}
(SEQ ID NO: 1066)

MSKRSWWAGSRKPPREMLKLSGSDSSQSMNGLEVAPPGLITNFSLATAEQCGQETPLENMLF

ASFYLLDFILALVGNTLALWLFIRDHKSGTPANVFLMHLAVADLSCVLVLPTRLVYHFSGNH

WPFGEIACRLTGFLFYLNMYASIYFLTCISADRFLAIVHPVKSLKLRRPLYAHLACAFLWVVV

AVAMAPLLVSPQTVQTNHTVVCLQLYREKASHHALVSLAVAFTFPFITTVTCYLLIIRSLRQG

LRVEKRLKTKAVRMIAIVLAIFLVCFVPYHVNRSVYVLHYRSHGASCATQRILALANRITSCL

TSLNGALDPIMYFFVAEKFRHALCNLLCGKRLKGPPPSFEGKTNESSLSAKSEL

```
>gi|4885307|ref|NP_005285.1|G protein-coupled receptor 21 {Homo sapiens}
                                                                            (SEQ ID NO: 1067)
MNSTLDGNQSSHPFCLLAFGYLETVNFCLLEVLIIVFLTVLIISGNIIVIFVFHCAPLLNHHTTSY

FIQTMAYADLFVGVSCVVPSLSLLHHPLPVEESLTCQIFGFVVSVLKSVSMASLACISIDRYIAI

TKPLTYNTLVTPWRLRLCIFLIWLYSTLVFLPSFFHWGKPGYHGDVFQWCAESWHTDSYFTL

FIVMMLYAPAALIVCFTYFNIFRICQQHTKDISERQARFSSQSGETGEVQACPDKRYAMVLFRI

TSVFYILWLPYIIYFLLESSTGHSNRFASFLTTWLAISNSFCNCVIYSLSNSVFQRGLKRLSGAM

CTSCASQTTANDPYTVRSKGPLNGCHI

>gi|4885311|ref|NP_005287.1|lysophosphatidic acid receptor 4 {Homo sapiens}
                                                                            (SEQ ID NO: 1068)
MGDRRFIDFQFQDSNSSLRPRLGNATANNTCIVDDSFKYNLNGAVYSVVFILGLITNSVSLFV

FCFRMKMRSETAIFITNLAVSDLLFVCTLPFKIFYNFNRHWPFGDTLCKISGTAFLTNIYGSML

FLTCISVDRFLAIVYPERSRTIRTRRNSAIVCAGVWILVLSGGISASLFSTTNVNNATTTCFEGF

SKRVWKTYLSKITIFIEVVGFIIPLILNVSCSSVVLRTLRKPATLSQIGTNKKKVLKMITVHMAV

FVVCFVPYNSVLFLYALVRSQAITNCFLERFAKIMYPITLCLATLNCCFDPFIYYFTLESFQKSF

YINAHIRMESLFKTETPLTTKPSLPAIQEEVSDQTTNNGGELMLESTF

>gi|4885319|ref|NP_005291.1|probable G-protein coupled receptor 34 {Homo sapiens}
                                                                            (SEQ ID NO: 1069)
MRSHTITMTTTSVSSWPYSSHRMRFITNHSDQPPQNFSATPNVTTCPMDEKLLSTVLTTSYSVI

FIVGLVGNIIALYVFLGIHRKRNSIQIYLLNVAIADLLLIFCLPFRIMYHINQNKWTLGVILCKV

VGTLFYMNMYISIILLGFISLDRYIKINRSIQQRKAITTKQSIYVCCIVWMLALGGFLTMIILTLK

KGGHNSTMCFHYRDKHNAKGEAIFNFILVVMFWLIFLLIILSYIKIGKNLLRISKRRSKFPNSG

KYATTARNSFIVLIIFTICFVPYHAFRFIYISSQLNVSSCYWKEIVHKTNEIMLVLSSFNSCLDPV

MYFLMSSNIRKIMCQLLFRRFQGEPSRSESTSEFKPGYSLHDTSVAVKIQSSSKST

>gi|4885323|ref|NP_005293.1|probable G-protein coupled receptor 37 precursor
{Homo sapiens}
                                                                            (SEQ ID NO: 1070)
MRAPGALLARMSRLLLLLLLKVSASSALGVAPASRNETCLGESCAPTVIQRRGRDAWGPGNS

ARDVLRARAPREEQGAAFLAGPSWDLPAAPGRDPAAGRGAEASAAGPPGPPTRPPGPWRW

KGARGQEPSETLGRGNPTALQLFLQISEEEEKGPRGAGISGRSQEQSVKTVPGASDLFYWPRR

AGKLQGSHHKPLSKTANGLAGHEGWTIALPGRALAQNGSLGEGIHEPGGPRRGNSTNRRVR

LKNPFYPLTQESYGAYAVMCLSVVIFGTGIIGNLAVMCIVCHNYYMRSISNSLLANLAFWDF

LIIFFCLPLVIFHELTKKWLLEDFSCKIVPYIEVASLGVTTFTLCALCIDRFRAATNVQMYYEMI

ENCSSTTAKLAVIWVGALLLALPEVVLRQLSKEDLGFSGRAPAERCIIKISPDLPDTIYVLALT

YDSARLWWYFGCYFCLPTLFTITCSLVTARKIRKAEKACTRGNKRQIQLESQMNCTVVALTI

LYGFCIIPENICNIVTAYMATGVSQQTMDLLNIISQFLLFFKSCVTPVLLFCLCKPFSRAFMECC

CCCCEECIQKSSTVTSDDNDNEYTTELELSPFSTIRREMSTFASVGTHC

>gi|4885325|ref|NP_005272.1|G protein-coupled receptor 3 {Homo sapiens}
                                                                            (SEQ ID NO: 1071)
MMWGAGSPLAWLSAGSGNVNVSSVGPAEGPTGPAAPLPSPKAWDVVLCISGTLVSCENALV

VAIIVGTPAFRAPMFLLVGSLAVADLLAGLGLVLHFAAVFCIGSAEMSLVLVGVLAMAFTASI

GSLLAITVDRYLSLYNALTYYSETTVTRTYVMLALVWGGALGLGLLPVLAWNCLDGLTTCG

VVYPLSKNHLVVLAIAFFMVFGIMLQLYAQICRIVCRHAQQIALQRHLLPASHYVATRKGIAT

LAVVLGAFAACWLPFTVYCLLGDAHSPPLYTYLTLLPATYNSMINPIIYAFRNQDVQKVLWA

VCCCCSSSKIPFRSRSPSDV
```

-continued

>gi|4885327|ref|NP_005294.1|free fatty acid receptor 1 {Homo sapiens}     (SEQ ID NO: 1072)

MDLPPQLSFGLYVAAFALGFPLNVLAIRGATAHARLRLTPSLVYALNLGCSDLLLTVSLPLKA

VEALASGAWPLPASLCPVFAVAHFFPLYAGGGFLAALSAGRYLGAAFPLGYQAFRRPCYSW

GVCAAIWALVLCHLGLVFGLEAPGGWLDHSNTSLGINTPVNGSPVCLEAWDPASAGPARFS

LSLLLFFLPLAITAFCYVGCLRALARSGLTHRRKLRAAWVAGGALLTLLLCVGPYNASNVAS

FLYPNLGGSWRKLGLITGAWSVVLNPLVTGYLGRGPGLKTVCAARTQGGKSQK

>gi|4885329|ref|NP_005295.1|free fatty acid receptor 3 {Homo sapiens}     (SEQ ID NO: 1073)

MDTGPDQSYFSGNHWFVFSVYLLTFLVGLPLNLLALVVFVGKLQRRPVAVDVLLLNLTASD

LLLLLFLPFRMVEAANGMHWPLPFILCPLSGFIFFTTIYLTALFLAAVSIERFLSVAHPLWYKT

RPRLGQAGLVSVACWLLASAHCSVVYVIEFSGDISHSQGTNGTCYLEFRKDQLAILLPVRLE

MAVVLFVVPLIITSYCYSRLVWILGRGGSHRRQRRVAGLLAATLLNFLVCFGPYNVSHVVGY

ICGESPAWRIYVTLLSTLNSCVDPFVYYFSSSGFQADFHELLRRLCGLWGQWQQESSMELKE

QKGGEEQRADRPAERKTSEHSQGCGTGGQVACAES

>gi|4885333|ref|NP_005297.1|free fatty acid receptor 2 {Homo sapiens}     (SEQ ID NO: 1074)

MLPDWKSSLILMAYIIIFLTGLPANLLALRAFVGRIRQPQPAPVHILLLSLTLADLLLLLLLPFKI

IEAASNFRWYLPKVVCALTSFGFYSSIYCSTWLLAGISIERYLGVAFPVQYKLSRRPLYGVIAA

LVAWVMSFGHCTIVIIVQYLNTTEQVRSGNEITCYENFTDNQLDVVLPVRLELCLVLFFIPMA

VTIFCYWRFVWIMLSQPLVGAQRRRRAVGLAVVTLLNFLVCFGPYNVSHLVGYHQRKSPW

WRSIAVVFSSLNASLDPLLFYFSSSVVRRAFGRGLQVLRNQGSSLLGRRGKDTAEGTNEDRG

VGQGEGMPSSDFTTE

>gi|4885335|ref|NP_005273.1|G-protein coupled receptor 4 {Homo sapiens}     (SEQ ID NO: 1075)

MGNHTWEGCHVDSRVDHLFPPSLYIFVIGVGLPTNCLALWAAYRQVQQRNELGVYLMNLSI

ADLLYICTLPLWVDYFLHHDNWIHGPGSCKLFGFIFYTNIYISIAFLCCISVDRYLAVAHPLRF

ARLRRVKTAVAVSSVVWATELGANSAPLFHDELFRDRYNHTFCFEKFPMEGWVAWMNLYR

VFVGFLFPWALMLLSYRGILRAVRGSVSTERQEKAKIKRLALSLIAIVLVCFAPYHVLLLSRS

AIYLGRPWDCGFEERVFSAYHSSLAFTSLNCVADPILYCLVNEGARSDVAKALHNLLRFLAS

DKPQEMANASLTLETPLTSKRNSTAKAMTGSWAATPPSQGDQVQLKMLPPAQ

>gi|4885339|ref|NP_005274.1|chemokine XC receptor 1 {Homo sapiens}     (SEQ ID NO: 1076)

MESSGNPESTTFFYYDLQSQPCENQAWVFATLATTVLYCLVFLLSLVGNSLVLWVLVKYESL

ESLTNIFILNLCLSDLVFACLLPVWISPYHWGWVLGDFLCKLLNMIFSISLYSSIFFLTIMTIHRY

LSVVSPLSTLRVPTLRCRVLVTMAVWVASILSSILDTIFHKVLSSGCDYSELTWYLTSVYQHN

LFFLLSLGIILFCYVEILRTLFRSRSKRRHRTVKLIFAIVVAYFLSWGPYNFTLFLQTLFRTQIIRS

CEAKQQLEYALLICRNLAFSHCCFNPVLYVFVGVKFRTHLKHVLRQFWFCRLQAPSPASIPHS

PGAFAYEGASFY

>gi|4885341|ref|NP_005275.1|G-protein coupled receptor 6 {Homo sapiens}     (SEQ ID NO: 1077)

MNASAASLNDSQVVVVAAEGAAAAATAAGGPDTGEWGPPAAAALGAGGGANGSLELSSQ

LSAGPPGLLLPAVNPWDVLLCVSGTVIAGENALVVALIASTPALRTPMFVLVGSLATADLLA

GCGLILHFVFQYLVPSETVSLLTVGFLVASFAASVSSLLAITVDRYLSLYNALTYYSRRTLLGV

HLLLAATWTVSLGLGLLPVLGWNCLAERAACSVVRPLARSHVALLSAAFFMVFGIMLHLYV

-continued

RICQVVWRHAHQIALQQHCLAPPHLAATRKGVGTLAVVLGTFGASWLPFAIYCVVGSHEDP

AVYTYATLLPATYNSMINPIIYAFRNQEIQRALWLLLCGCFQSKVPFRSRSPSEV

>gi|4885361|ref|NP_005305.1|gastrin-releasing peptide receptor {Homo sapiens}
(SEQ ID NO: 1078)

MALNDCFLLNLEVDHFMHCNISSHSADLPVNDDWSHPGILYVIPAVYGVIILIGLIGNITLIKIF

CTVKSMRNVPNLFISSLALGDLLLLITCAPVDASRYLADRWLFGRIGCKLIPFIQLTSVGVSVF

TLTALSADRYKAIVRPMDIQASHALMKICLKAAFIWIISMLLAIPEAVFSDLHPFHEESTNQTFI

SCAPYPHSNELHPKIHSMASFLVFYVIPLSIISVYYYFIAKNLIQSAYNLPVEGNIHVKKQIESR

KRLAKTVLVFVGLFAFCWLPNHVIYLRSYHYSEVDTSMLHFVTSICARLLAFTNSCVNPFA

LYLLSKSFRKQFNTQLLCCQPGLIIRSHSTGRSTTCMTSLKSTNPSVATFSLINGNICHERYV

>gi|5031621|ref|NP_005786.1|calcitonin gene-related peptide type 1 receptor precursor{Homo sapiens}
(SEQ ID NO: 1079)

MEKKCTLYFLVLLPFFMILVTAELEESPEDSIQLGVTRNKIMTAQYECYQKIMQDPIQQAEGV

YCNRTWDGWLCWNDVAAGTESMQLCPDYFQDFDPSEKVTKICDQDGNWFRHPASNRTWT

NYTQCNVNTHEKVKTALNLFYLTIIGHGLSIASLLISLGIFFYFKSLSCQRITLHKNLFFSFVCN

SVVTIIHLTAVANNQALVATNPVSCKVSQFIHLYLMGCNYFWMLCEGIYLHTLIVVAVFAEK

QHLMWYYFLGWGFPLIPACIHAIARSLYYNDNCWISSDTHLLYIIHGPICAALLVNLFFLLNIV

RVLITKLKVTHQAESNLYMKAVRATLILVPLLGIEFVLIPWRPEGKIAEEVYDYIMHILMHFQ

GLLVSTIFCFFNGEVQAILRRNWNQYKIQFGNSFSNSEALRSASYTVSTISDGPGYSHDCPSEH

LNGKSIHDIENVLLKPENLYN

>gi|5031627|ref|NP_005499.1|C-C chemokine receptor type 4 {Homo sapiens}
(SEQ ID NO: 1080)

MNPTDIADTTLDESIYSNYYLYESIPKPCTKEGIKAFGELFLPPLYSLVFVFGLLGNSVVVLVL

FKYKRLRSMTDVYLLNLAISDLLFVFSLPFWGYYAADQWVFGLGLCKMISWMYLVGFYSGI

FFVMLMSIDRYLAIVHAVFSLRARTLTYGVITSLATWSVAVFASLPGFLFSTCYTERNHTYCK

TKYSLNSTTWKVLSSLEINILGLVIPLGIMLFCYSMIIRTLQHCKNEKKNKAVKMIFAVVVLFL

GFWTPYNIVLFLETLVELEVLQDCTFERYLDYAIQATETLAFVHCCLNPIIYFFLGEKFRKYIL

QLFKTCRGLFVLCQYCGLLQIYSADTPSSSYTQSTMDHDLHDAL

>gi|5174535|ref|NP_005904.1|melanocortin 5 receptor {Homo sapiens}
(SEQ ID NO: 1081)

MNSSFHLHFLDLNLNATEGNLSGPNVKNKSSPCEDMGIAVEVFLTLGVISLLENILVIGAIVKN

KNLHSPMYFFVCSLAVADMLVSMSSAWETITIYLLNNKHLVIADAFVRHIDNVFDSMICISVV

ASMCSLLAIAVDRYVTIFYALRYHHIMTARRSGAIIAGIWAFCTGCGIVFILYSESTYVILCLIS

MFFAMLFLLVSLYIHMFLLARTHVKRIAALPGASSARQRTSMQGAVTVTMLLGVFTVCWAP

FFLHLTLMLSCPQNLYCSRFMSHFNMYLILIMCNSVMDPLIYAFRSQEMRKTFKEIICCRGFRI

ACSFPRRD

>gi|5174593|ref|NP_005949.1|melatonin receptor 1A {Homo sapiens}
(SEQ ID NO: 1082)

MQGNGSALPNASQPVLRGDGARPSWLASALACVLIFTIVVDILGNLLVILSVYRNKKLRNAG

NIFVVSLAVADLVVAIYPYPLVLMSIFNNGWNLGYLHCQVSGFLMGLSVIGSIFNITGIAINRY

CYICHSLKYDKLYSSKNSLCYVLLIWLLTAAVLPNLRAGTLQYDPRIYSCTFAQSVSSAYTI

AVVVFHFLVPMIIVIFCYLRIWILVLQVRQRVKPDRKPKLKPQDFRNFVTMFVVFVLFAICWA

PLNFIGLAVASDPASMVPRIPEWLFVASYYMAYFNSCLNAIIYGLLNQNFRKEYRRIIVSLCTA

RVFFVDSSNDVADRVKWKPSPLMTNNNVVKVDSV

>gi|5174595|ref|NP_005950.1|melatonin receptor 1B {Homo sapiens}
(SEQ ID NO: 1083)

MSENGSFANCCEAGGWAVRPGWSGAGSARPSRTPRPPWVAPALSAVLIVTTAVDVVGNLL

VILSVLRNRKLRNAGNLFLVSLALADLVVAFYPYPLILVAIFYDGWALGEEHCKASAFVMGL

SVIGSVFNITAIAINRYCYICHSMAYHRIYRRWHTPLHICLIWLLTVVALLPNFFVGSLEYDPRI

YSCTFIQTASTQYTAAVVVIHFLLPIAVVSFCYLRIWVLVLQARRKAKPESRLCLKPSDLRSFL

TMFVVFVIFAICWAPLNCIGLAVAINPQEMAPQIPEGLFVTSYLLAYFNSCLNAIVYGLLNQNF

RREYKRILLALWNPRHCIQDASKGSHAEGLQSPAPPIIGVQHQADAL

>gi|5453666|ref|NP_006134.1|probable G-protein coupled receptor 19 {Homo sapiens}
(SEQ ID NO: 1084)

MVFAHRMDNSKPHLIIPTLLVPLQNRSCTETATPLPSQYLMELSEEHSWMSNQTDLHYVLKP

GEVATASIFFGILWLFSIFGNSLVCLVIHRSRRTQSTTNYFVVSMACADLLISVASTPFVLLQFT

TGRWTLGSATCKVVRYFQYLTPGVQIYVLLSICIDRFYTIVYPLSFKVSREKAKKMIAASWIF

DAGFVTPVLFFYGSNWDSHCNYFLPSSWEGTAYTVIHFLVGFVIPSVLIILFYQKVIKYIWRIG

TDGRTVRRTMNIVPRTKVKTIKMFLILNLLFLLSWLPFHVAQLWHPHEQDYKKSSLVFTAIT

WISFSSSASKPTLYSIYNANFRRGMKETFCMSSMKCYRSNAYTITTSSRMAKKNYVGISEIPS

MAKTITKDSIYDSFDREAKEKKLAWPINSNPPNTFV

>gi|5453796|ref|NP_006165.1|neuropeptide Y receptor Y5 {Homo sapiens}
(SEQ ID NO: 1085)

MDLELDEYYNKTLATENNTAATRNSDFPVWDDYKSSVDDLQYFLIGLYTFVSLLGFMGNLL

ILMALMKKRNQKTTVNFLIGNLAFSDILVVLFCSPFTLTSVLLDQWMFGKVMCHIMPFLQCV

SVLVSTLILISIAIVRYHMIKHPISNNLTANHGYFLIATVWTLGFAICSPLPVFHSLVELQETFGS

ALLSSRYLCVESWPSDSYRIAFTISLLLVQYILPLVCLTVSHTSVCRSISCGLSNKENRLEENEM

INLTLHPSKKSGPQVKLSGSHKWSYSFIKKHRRRYSKKTACVLPAPERPSQENHSRILPENFGS

VRSQLSSSSKFIPGVPTCFEIKPEENSDVHELRVKRSVTRIKKRSRSVFYRLTILILVFAVSWMP

LHLFHVVTDFNDNLISNRHFKLVYCICHLLGMMSCCLNPILYGFLNNGIKADLVSLIHCLHM

>gi|5729798|ref|NP_006630.1|cysteinyl leukotriene receptor 1 {Homo sapiens}
(SEQ ID NO: 1086)

MDETGNLTVSSATCHDTIDDFRNQVYSTLYSMISVVGFFGNGFVLYVLIKTYHKKSAFQVYM

INLAVADLLCVCTLPLRVVYYVHKGIWLFGDFLCRLSTYALYVNLYCSIFFMTAMSFFRCIAI

VFPVQNINLVTQKKARFVCVGIWIFVILTSSPFLMAKPQKDEKNNTKCFEPPQDNQTKNHVL

VLHYVSLFVGFIIPFVIIIVCYTMIILTLLKKSMKKNLSSHKKAIGMIMVVTAAFLVSFMPYHIQ

RTIHLHFLHNETKPCDSVLRMQKSVVITLSLAASNCCFDPLLYFFSGGNFRKRLSTFRKHSLSS

VTYVPRKKASLPEKGEEICKV

>gi|5730106|ref|NP_006555.1|C-X-C chemokine receptor type 6 {Homo sapiens}
(SEQ ID NO: 1087)

MAEHDYHEDYGFSSFNDSSQEEHQDFLQFSKVFLPCMYLVVFVCGLVGNSLVLVISIFYHKL

QSLTDVFLVNLPLADLVFVCTLPFWAYAGIHEWVFGQVMCKSLLGIYTINFYTSMLILTCITV

DRFIVVVKATKAYNQQAKRMTWGKVTSLLIWVISLLVSLPQIIYGNVFNLDKLICGYHDEAIS

TVVLATQMTLGFFLPLLTMIVCYSVIIKTLLHAGGFQKHRSLKIIFLVMAVFLLTQMPFNLMK

FIRSTHWEYYAMTSFHYTIMVTEAIAYLRACLNPVLYAFVSLKFRKNFWKLVKDIGCLPYLG

VSHQWKSSEDNSKTFSASHNVEATSMFQL

>gi|5803025|ref|NP_006785.1|probable G-protein coupled receptor 75 {Homo sapiens}
(SEQ ID NO: 1088)

MNSTGHLQDAPNATSLHVPHSQEGNSTSLQEGLQDLIHTATLVTCTFLLAVIFCLGSYGNFIV

FLSFFDPAFRKFRTNFDFMILNLSFCDLFICGVTAPMFTFVLFFSSASSIPDAFCFTFHLTSSGFII

-continued

```
MSLKTVAVIALHRLRMVLGKQPNRTASFPCTVLLTLLLWATSFTLATLATLKTSKSHLCLPM

SSLIAGKGKAILSLYVVDFTFCVAVVSVSYIMIAQTLRKNAQVRKCPPVITVDASRPQPFMGV

PVQGGGDPIQCAMPALYRNQNYNKLQHVQTRGYTKSPNQLVTPAASRLQLVSAINLSTAKD

SKAVVTCVIIVLSVLVCCLPLGISLVQVVLSSNGSFILYQFELFGFTLIFFKSGLNPFIYSRNSAG

LRRKVLWCLQYIGLGFFCCKQKTRLRAMGKGNLEVNRNKSSHHETNSAYMLSPKPQKKFV

DQACGPSHSKESMVSPKISAGHQHCGQSSSTPINTRIEPYYSIYNSSPSQEESSPCNLQPVNSFG

FANSYIAMHYHTTNDLVQEYDSTSAKQIPVPSV
```

>gi|5921992|ref|NP_000666.2|adenosine receptor A2a {Homo sapiens}     (SEQ ID NO: 1089)

```
MPIMGSSVYITVELAIAVLAILGNVLVCWAVWLNSNLQNVTNYFVVSLAAADIAVGVLAIPF

AITISTGFCAACHGCLFIACFVLVLTQSSIFSLLAIAIDRYIAIRIPLRYNGLVTGTRAKGIIAICW

VLSFAIGLTPMLGWNNCGQPKEGKNHSQGCGEGQVACLFEDVVPMNYMVYFNFFACVLVP

LLLMLGVYLRIFLAARRQLKQMESQPLPGERARSTLQKEVHAAKSLAIIVGLFALCWLPLHII

NCFTFFCPDCSHAPLWLMYLAIVLSHTNSVVNPFIYAYRIREFRQTFRKIIRSHVLRQQEPFKA

AGTSARVLAAHGSDGEQVSLRLNGHPPGVWANGSAPHPERRPNGYALGLVSGGSAQESQG

NTGLPDVELLSHELKGVCPEPPGLDDPLAQDGAGVS
```

>gi|6005705|ref|NP_009195.1|G-protein coupled receptor 182 {Homo sapiens}     (SEQ ID NO: 1090)

```
MSVKPSWGPGPSEGVTAVPTSDLGEIHNWTELLDLFNHTLSECHVELSQSTKRVVLFALYLA

MFVVGLVENLLVICVNWRGSGRAGLMNLYILNMAIADLGIVLSLPVWMLEVTLDYTWLWG

SFSCRFTHYFYFVNMYSSIFFLVCLSVDRYVTLTSASPSWQRYQHRVRRAMCAGIWVLSAIIP

LPEVVHIQLVEGPEPMCLFMAPFETYSTWALAVALSTTILGFLLPFPLITVFNVLTACRLRQPG

QPKSRRHCLLLCAYVAVFVMCWLPYHVTLLLLTLHGTHISLHCHLVHLLYFFYDVIDCFSML

HCVINPILYNFLSPHFRGRLLNAVVHYLPKDQTKAGTCASSSSCSTQHSIIITKGDSQPAAAAP

HPEPSLSFQAHHLLPNTSPISPTQPLTPS
```

>gi|6323236|ref|NP_013308.1|Hrd3p {Saccharomyces cerevisiae}     (SEQ ID NO: 1091)

```
MITLLLYLCVICNAIVLIRADSIADPWPEARHLLNTIAKSRDPMKEAAMEPNADEFVGFYVPM

DYSPRNEEKNYQSIWQNEITDSQRHIYELLVQSSEQFNNSEATYTLSQIHLWSQYNFPHNMTL

AHKYLEKFNDLTHFTNHSAIFDLAVMYATGGCASGNDQTVIPQDSAKALLYYQRAAQLGNL

KAKQVLAYKYYSGFNVPRNFHKSLVLYRDIAEQLRKSYSRDEWDIVFPYWESYNVRISDFES

GLLGKGLNSVPSSTVRKRTTRPDIGSPFIAQVNGVQMTLQIEPMGRFAFNGNDGNINGDEDD

EDASERRIIRIYYAALNDYKGTYSQSRNCERAKNLLELTYKEFQPHVDNLDPLQVFYYVRCL

QLLGHMYFTGEGSSKPNIHMAEEILTTSLEISRRAQGPIGRACIDLGLINQYITNNISQAISYYM

KAMKTQANNGIVEFQLSKLATSFPEEKIGDPFNLMETAYLNGFIPAIYEFAVMIESGMNSKSS

VENTAYLFKTFVDKNEAIMAPKLRTAFAALINDRSEVALWAYSQLAEQGYETAQVSAAYLM

YQLPYEFEDPPRTTDQRKTLAISYYTRAFKQGNIDAGVVAGDIYFQMQNYSKAMALYQGAA

LKYSIQAIWNLGYMHEHGLGVNRDFHLAKRYYDQVSEHDHRFYLASKLSVLKLHLKSWLT

WITREKVNYWKPSSPLNPNEDTQHSKTSWYKQLTKILQRMRHKEDSDKAAEDSHKHRTVV

QNGANHRGDDQEEASEILGFQMEDLVTMGCILGIFLLSILMSTLAARRGWNVRFNGAQLNA

NGNRQQEQQQQQAQGPPGWDFNVQIFAI
```

>gi|6912348|ref|NP_036284.1|lysophosphatidic acid receptor 3 {Homo sapiens}
(SEQ ID NO: 1092)

MNECHYDKHMDFFYNRSNTDTVDDWTGTKLVIVLCVGTFFCLFIFFSNSLVIAAVIKNRKFH

FPFYYLLANLAAADFFAGIAYVFLMFNTGPVSKTLTVNRWFLRQGLLDSSLTASLTNLLVIAV

ERHMSIMRMRVHSNLTKKRVTLLILLVWAIAIFMGAVPTLGWNCLCNISACSSLAPIYSRSYL

VFWTVSNLMAFLIMVVVYLRIYVYVKRKTNVLSPHTSGSISRRRTPMKLMKTVMTVLGAFV

VCWTPGLVVLLLDGLNCRQCGVQHVKRWFLLLALLNSVVNPIIYSYKDEDMYGTMKKMIC

CFSQENPERRPSRIPSTVLSRSDTGSQYIEDSISQGAVCNKSTS

>gi|6912464|ref|NP_036434.1|latrophilin-2 precursor {Homo sapiens}
(SEQ ID NO: 1093)

MVSSGCRMRSLWFIIVISFLPNTEGFSRAALPFGLVRRELSCEGYSIDLRCPGSDVIMIESANYG

RTDDKICDADPFQMENTDCYLPDAFKIMTQRCNNRTQCIVVTGSDVFPDPCPGTYKYLEVQY

ECVPYIFVCPGTLKAIVDSPCIYEAEQKAGAWCKDPLQAADKIYFMPWTPYRTDTLIEYASLE

DFQNSRQTTTYKLPNRVDGTGFVVYDGAVFFNKERTRNIVKFDLRTRIKSGEAIINYANYHD

TSPYRWGGKTDIDLAVDENGLWVIYATEQNNGMIVISQLNPYTLRFEATWETVYDKRAASN

AFMICGVLYVVRSVYQDNESETGKNSIDYIYNTRLNRGEYVDVPFPNQYQYIAAVDYNPRD

NQLYVWNNNFILRYSLEFGPPDPAQVPTTAVTITSSAELFKTIISTTSTTSQKGPMSTTVAGSQ

EGSKGTKPPPAVSTTKIPPITNIFPLPERFCEALDSKGIKWPQTQRGMMVERPCPKGTRGTASY

LCMISTGTWNPKGPDLSNCTSHWVNQLAQKIRSGENAASLANELAKHTKGPVFAGDVSSSV

RLMEQLVDILDAQLQELKPSEKDSAGRSYNKAIVDTVDNLLRPEALESWKHMNSSEQAHTA

TMLLDTLEEGAFVLADNLLEPTRVSMPTENIVLEVAVLSTEGQIQDFKFPLGIKGAGSSIQLSA

NTVKQNSRNGLAKLVFIIYRSLGQFLSTENATIKLGADFIGRNSTIAVNSHVISVSINKESSRVY

LTDPVLFTLPHIDPDNYFNANCSFWNYSERTMMGYWSTQGCKLVDTNKTRTTCACSHLTNF

AILMAHREIAYKDGVHELLLTVITWVGIVISLVCLAICIFTFCFFRGLQSDRNTIHKNLCINLFIA

EFIFLIGIDKTKYAIACPIFAGLLHFFFLAAFAWMCLEGVQLYLMLVEVFESEYSRKKYYYVA

GYLFPATVVGVSAAIDYKSYGTEKACWLHVDNYFIWSFIGPVTFIILLNIIFLVITLCKMVKHS

NTLKPDSSRLENIKSWVLGAFALLCLLGLTWSFGLLFINEETIVMAYLFTIFNAFQGVFIFIFHC

ALQKKVRKEYGKCFRHSYCCGGLPTESPHSSVKASTTRTSARYSSGTQSRIRRMWNDTVRK

QSESSFISGDINSTSTLNQGHSLNNARDTSAMDTLPLNGNFNNSYSLHKGDYNDSVQVVDCG

LSLNDTAFEKMIISELVHNNLRGSSKTHNLELTLPVKPVIGGSSSEDDAIVADASSLMHSDNPG

LELHHKELEAPLIPQRTHSLLYQPQKKVKSEGTDSYVSQLTAEAEDHLQSPNRDSLYTSMPNL

RDSPYPESSPDMEEDLSPSRRSENEDIYYKSMPNLGAGHQLQMCYQISRGNSDGYIIPINKEGC

IPEGDVREGQMQLVTSL

>gi|6912538|ref|NP_036476.1|neurotensin receptor type 2 {Homo sapiens}
(SEQ ID NO: 1094)

METSSPRPPRPSSNPGLSLDARLGVDTRLWAKVLFTALYALIWALGAAGNALSVHVVLKAR

AGRAGRLRHHVLSLALAGLLLLLVGVPVELYSFVWFHYPWVFGDLGCRGYYFVHELCAYA

TVLSVAGLSAERCLAVCQPLRARSLLTPRRTRWLVALSWAASLGLALPMAVIMGQKHELET

ADGEPEPASRVCTVLVSRTALQVFIQVNVLVSFVLPLALTAFLNGVTVSHLLALCSQVPSTST

PGSSTPSRLELLSEEGLLSFIVWKKTFIQGGQVSLRHKDVRRIRSLQRSVQVLRAIVVMYVIC

WLPYHARRLMYCYVPDDAWTDPLYNFYHYFYMVTNTLFYVSSAVTPLLYNAVSSSFRKLFL

EAVSSLCGEHHPMKRLPPKPQSPTLMDTASGFGDPPETRT

>gi|7019387|ref|NP_037477.1|probable G-protein coupled receptor 132 {Homo sapiens}
(SEQ ID NO: 1095)

MCPMLLKNGYNGNATPVTTTAPWASLGLSAKTCNNVSFEESRIVLVVVYSAVCTLGVPANC

LTAWLALLQVLQGNVLAVYLLCLALCELLYTGTLPLWVIYIRNQHRWTLGLLACKVTAYIFF

CNIYVSILFLCCISCDRFVAVVYALESRGRRRRRTAILISACIFILVGIVHYPVFQTEDKETCFD

MLQMDSRIAGYYYARFTVGFAIPLSIIAFTNHRIFRSIKQSMGLSAAQKAKVKHSAIAVVVIFL

VCFAPYHLVLLVKAAAFSYYRGDRNAMCGLEERLYTASVVFLCLSTVNGVADPIIYVLATD

HSRQEVSRIHKGWKEWSMKTDVTRLTHSRDTEELQSPVALADHYTFSRPVHPPGSPCPAKRL

IEESC

>gi|7108336|ref|NP_036257.1|cholinergic receptor, muscarinic 5 {Homo sapiens}
(SEQ ID NO: 1096)

MEGDSYHNATTVNGTPVNHQPLERHRLWEVITIAAVTAVVSLITIVGNVLVMISFKVNSQLK

TVNNYYLLSLACADLIIGIFSMNLYTTYILMGRWALGSLACDLWLALDYVASNASVMNLLVI

SFDRYFSITRPLTYRAKRTPKRAGIMIGLAWLISFILWAPAILCWQYLVGKRTVPLDECQIQFL

SEPTITFGTAIAAFYIPVSVMTILYCRIYRETEKRTKDLADLQGSDSVTKAEKRKPAHRALFRS

CLRCPRPTLAQRERNQASWSSSRRSTSTTGKPSQATGPSANWAKAEQLTTCSSYPSSEDEDKP

ATDPVLQVVYKSQGKESPGEEFSAEETEETFVKAETEKSDYDTPNYLLSPAAAHRPKSQKCV

AYKFRLVVKADGNQETNNGCHKVKIMPCPFPVAKEPSTKGLNPNPSHQMTKRKRVVLVKE

RKAAQTLSAILLAFIITWTPYNIMVLVSTFCDKCVPVTLWHLGYWLCYVNSTVNPICYALCN

RTFRKTFKMLLLCRWKKKKVEEKLYWQGNSKLP

>gi|7305013|ref|NP_004711.2|lysophosphatidic acid receptor 2 {Homo sapiens}
(SEQ ID NO: 1097)

MVIMGQCYYNETIGFFYNNSGKELSSHWRPKDVVVVALGLTVSVLVLLTNLLVIAAIASNRR

FHQPIYYLLGNLAAADLFAGVAYLFLMFHTGPRTARLSLEGWFLRQGLLDTSLTASVATLLA

IAVERHRSVMAVQLHSRLPRGRVVMLIVGVWVAALGLGLLPAHSWHCLCALDRCSRMAPL

LSRSYLAVWALSSLLVFLLMVAVYTRIFFYVRRRVQRMAEHVSCHPRYRETTLSLVKTVVIIL

GAFVVCWTPGQVVLLLDGLGCESCNVLAVEKYFLLLAEANSLVNAAVYSCRDAEMRRTFR

RLLCCACLRQSTRESVHYTSSAQGGASTRIMLPENGHPLMDSTL

>gi|7657136|ref|NP_055188.1|probable G-protein coupled receptor 160 {Homo sapiens}
(SEQ ID NO: 1098)

MTALSSENCSFQYQLRQTNQPLDVNYLLFLIILGKILLNILTLGMRRKNTCQNFMEYFCISLAF

VDLLLLVNISIILYFRDFVLLSIRFTKYHICLFTQIISFTYGFLHYPVFLTACIDYCLNFSKTTKLS

FKCQKLFYFFTVILIWISVLAYVLGDPAIYQSLKAQNAYSRHCPFYVSIQSYWLSFFMVMILFV

AFITCWEEVTTLVQAIRITSYMNETILYFPFSSHSSYTVRSKKIFLSKLIVCFLSTWLPFVLLQVI

IVLLKVQIPAYIEMNIPWLYFVNSFLIATVYWFNCHKLNLKDIGLPLDPFVNWKCCFIPLTIPN

LEQIEKPISIMIC

>gi|7669548|ref|NP_001050.1|tachykinin receptor 3 {Homo sapiens}
(SEQ ID NO: 1099)

MATLPAAETWIDGGGGVGADAVNLTASLAAGAATGAVETGWLQLLDQAGNLSSSPSALGL

PVASPAPSQPWANLTNQFVQPSWRIALWSLAYGVVVAVLGNLIVIWIILAHKRMRTVTN

YFLVNLAFSDASMAAFNTLVNFIYALHSEWYFGANYCRFQNFFPITAVFASIYSMTAIAVDRY

MAIIDPLKPRLSATATKIVIGSIWILAFLLAFPQCLYSKTKVMPGRTLCFVQWPEGPKQHFTYH

IIVIILVYCFPLLIMGITYTIVGITLWGGEIPGDTCDKYHEQLKAKRKVVKMMIIVVMTFAICW

LPYHIYFILTAIYQQLNRWKYIQQVYLASFWLAMSSTMYNPIIYCCLNKRFRAGFKRAFRWC

```
PFIKVSSYDELELKTTRFHPNRQSSMYTVTRMESMTVVFDPNDADTTRSSRKKRATPRDPSFN

GCSRRNSKSASATSSFISSPYTSVDEYS
```

>gi|7706103|ref|NP_057652.1|relaxin/insulin-like family peptide receptor 3
{Homo sapiens}

(SEQ ID NO: 1100)

```
MQMADAATIATMNKAAGGDKLAELFSLVPDLLEAANTSGNASLQLPDLWWELGLELPDGA

PPGHPPGSGGAESADTEARVRILISVVYWVVCALGLAGNLLVLYLMKSMQGWRKSSINLFV

TNLALTDFQFVLTLPFWAVENALDFKWPFGKAMCKIVSMVTSMNMYASVFFLTAMSVTRY

HSVASALKSHRTRGHGRGDCCGRSLGDSCCFSAKALCVWIWALAALASLPSAIFSTTVKVM

GEELCLVRFPDKLLGRDRQFWLGLYHSQKVLLGFVLPLGIIILCYLLLVRFIADRRAAGTKGG

AAVAGGRPTGASARRLSKVTKSVTIVVLSFFLCWLPNQALTTWSILIKFNAVPFSQEYFLCQV

YAFPVSVCLAHSNSCLNPVLYCLVRREFRKALKSLLWRIASPSITSMRPFTATTKPEHEDQGL

QAPAPPHAAAEPDLLYYPPGVVVYSGGRYDLLPSSSAY
```

>gi|7706451|ref|NP_057319.1|G-protein coupled receptor family C group 5 member B
precursor {Homo sapiens}

(SEQ ID NO: 1101)

```
MFVASERKMRAHQVLTFLLLFVITSVASENASTSRGCGLDLLPQYVSLCDLDAIWGIVVEAV

AGAGALITLLLMLILLVRLPFIKEKEKKSPVGLHFLFLLGTLGLFGLTFAFIIQEDETICSVRRFL

WGVLFALCFSCLLSQAWRVRRLVRHGTGPAGWQLVGLALCLMLVQVIIAVEWLVLTVLRD

TRPACAYEPMDFVMALIYDMVLLVVTLGLALFTLCGKFKRWKLNGAFLLITAFLSVLIWVA

WMTMYLFGNVKLQQGDAWNDPTLAITLAASGWVFVIFHAIPEIHCTLLPALQENTPNYFDTS

QPRMRETAFEEDVQLPRAYMENKAFSMDEHNAALRTAGFPNGSLGKRPSGSLGKRPSAPFR

SNVYQPTEMAVVLNGGTIPTAPPSHTGRHLW
```

>gi|8923705|ref|NP_061124.1|G-protein coupled receptor family C group 5 member D
{Homo sapiens}

(SEQ ID NO: 1102)

```
MYKDCIESTGDYFLLCDAEGPWGIILESLAILGIVVTILLLLAFLFLMRKIQDCSQWNVLPTQL

LFLLSVLGLFGLAFAFIIELNQQTAPVRYFLFGVLFALCFSCLLAHASNLVKLVRGCVSFSWTT

ILCIAIGCSLLQIIIATEYVTLIMTRGMMFVNMTPCQLNVDFVVLLVYVLFLMALTFFVSKATF

CGPCENWKQHGRLIFITVLFSIIIWVVWISMLLRGNPQFQRQPQWDDPVVCIALVTNAWVFLL

LYIVPELCILYRSCRQECPLQGNACPVTAYQHSFQVENQELSRARDSDGAEEDVALTSYGTPI

QPQTVDPTQECFIPQAKLSPQQDAGGV
```

>gi|8923873|ref|NP_060955.1|G protein-coupled receptor 77 {Homo sapiens}

(SEQ ID NO: 1103)

```
MGNDSVSYEYGDYSDLSDRPVDCLDGACLAIDPLRVAPLPLYAAIFLVGVPGNAMVAWVA

GKVARRRVGATWLLHLAVADLLCCLSLPILAVPIARGGHWPYGAVGCRALPSIILLTMYASV

LLLAALSADLCFLALGPAWWSTVQRACGVQVACGAAWTLALLLTVPSAIYRRLHQEHFPAR

LQCVVDYGGSSSTENAVTAIRFLFGFLGPLVAVASCHSALLCWAARRCRPLGTAIVVGFFVC

WAPYHLLGLVLTVAAPNSALLARALRAEPLIVGLALAHSCLNPMLFLYFGRAQLRRSLPAAC

HWALRESQGQDESVDSKKSTSHDLVSEMEV
```

>gi|9506745|ref|NP_061822.1|urotensin 2 receptor {Homo sapiens}

(SEQ ID NO: 1104)

```
MALTPESPSSFPGLAATGSSVPEPPGGPNATLNSSWASPTEPSSLEDLVATGTIGTLLSAMGVV

GVVGNAYTLVVTCRSLRAVASMYVYVVNLALADLLYLLSIPFIVATYVTKEWHFGDVGCRV

LFGLDFLTMHASIFTLTVMSSERYAAVLRPLDTVQRPKGYRKLLALGTWLLALLLTPVMLA

MRLVRRGPKSLCLPAWGPRAHRAYLTLLFATSIAGPGLLIGLLYARLARAYRRSQRASFKRA

RRPGARALRLVLGIVLLFWACFLPFWLWQLLAQYHQAPLAPRTARIVNYLTTCLTYGNSCA
```

-continued

NPFLYTLLTRNYRDHLRGRVRGPGSGGGRGPVPSLQPRARFQRCSGRSLSSCSPQPTDSLVLA

PAAPARPAPEGPRAPA

>gi|9506747|ref|NP_061844.1|G protein-coupled receptor 27 {Homo sapiens}
(SEQ ID NO: 1105)

MANASEPGGSGGGEAAALGLKLATLSLLLCVSLAGNVLFALLIVRERSLHRAPYYLLLDLCL

ADGLRALACLPAVMLAARRAAAAAGAPPGALGCKLLAFLAALFCFHAAFLLLGVGVTRYL

AIAHHRFYAERLAGWPCAAMLVCAAWALALAAAFPPVLDGGGDDEDAPCALEQRPDGAPG

ALGFLLLLAVVVGATHLVYLRLLFFIHDRRKMRPARLVPAVSHDWTFHGPGATGQAAANW

TAGFGRGPTPPALVGIRPAGPGRGARRLLVLEEFKTEKRLCKMFYAVTLLFLLLWGPYVVAS

YLRVLVRPGAVPQAYLTASVWLTFAQAGINPVVCFLFNRELRDCFRAQFPCCQSPRTTQATH

PCDLKGIGL

>gi|9507143|ref|NP_061842.1|probable G-protein coupled receptor 173 {Homo sapiens}
(SEQ ID NO: 1106)

MANTTGEPEEVSGALSPPSASAYVKLVLLGLIMCVSLAGNAILSLLVLKERALHKAPYYFLL

DLCLADGIRSAVCFPFVLASVRHGSSWTFSALSCKIVAFMAVLFCFHAAFMLFCISVTRYMAI

AHHRFYAKRMTLWTCAAVICMAWTLSVAMAFPPVFDVGTYKFIREEDQCIFEHRYFKANDT

LGFMLMLAVLMAATHAVYGKLLLFEYRHRKMKPVQMVPAISQNWTFHGPGATGQAAAN

WIAGFGRGPMPPTLLGIRQNGHAASRRLLGMDEVKGEKQLGRMFYAITLLFLLLWSPYIVAC

YWRVFVKACAVPHRYLATAVWMSFAQAAVNPIVCFLLNKDLKKCLRTHAPCWGTGGAPA

PREPYCVM

>gi|9627743|ref|NP_054030.1|protein tyrosine phosphatase {Autographa californica nucleopolyhedrovirus}
(SEQ ID NO: 1107)

MFPARWHNYLQCGQVIKDSNLICFKTPLRPELFAYVTSEEDVWTAEQIVKQNPSIGAIIDLTN

TSKYYDGVHFLRAGLLYKKIQVPGQTLPPESIVQEFIDTVKEFTEKCPGMLVGVHCTHGINRT

GYMVCRYLMHTLGIAPQEAIDRFEKARGHKIERQNYVQDLLI

>gi|9951913|ref|NP_062832.1|probable G-protein coupled receptor 162 isoform 2 {Homo sapiens}
(SEQ ID NO: 1108)

MARGGAGAEEASLRSNALSWLACGLLALLANAWIILSISAKQQKHKPLELLLCFLAGTHILM

AAVPLTTFAVVQLRRQASSDYDWNESICKVFVSTYYTLALATCFTVASLSYHRMWMVRWP

VNYRLSNAKKQALHAVMGIWMVSFILSTLPSIGWHNNGERYYARGCQFIVSKIGLGFGVCFS

LLLLGGIVMGLVCVAITFYQTLWARPRRARQARRVGGGGGTKAGGPGALGTRPAFEVPAIV

VEDARGKRRSSLDGSESAKTSLQVTNLVSAIVFLYDSLTGVPILVVSFFSLKSDSAPPWMVLA

VLWCSMAQTLLLPSFIWSCERYRADVRTVWEQCVAIMSEEDGDDDGGCDDYAEGRVCKVR

FDANGATGPGSRDPAQVKLLPGRHMLFPPLERVHYLQVPLSRRLSHDETNIFSTPREPGSFLH

KWSSSDDIRVLPAQSRALGGPPEYLGQRHRLEDEEDEEEAEGGGLASLRQFLESGVLGSGGG

PPRGPGFFREEITTFIDETPLPSPTASPGHSPRRPRPLGLSPRRLSLGSPESRAVGLPLGLSAGRR

CSLTGGEESARAWGGSWGPGNPIFPQLTL

>gi|9966839|ref|NP_065103.1|G protein-coupled receptor 84 {Homo sapiens}
(SEQ ID NO: 1109)

MWNSSDANFSCYHESVLGYRYVAVSWGVVVAVTGTVGNVLTLLALAIQPKLRTRFNLLIAN

LTLADLLYCTLLQPFSVDTYLHLHWRTGATFCRVFGLLLFASNSVSILTLCLIALGRYLLIAHP

KLFPQVFSAKGIVLALVSTWVVGVASFAPLWPIYILVPVVCTCSFDRIRGRPYTTILMGIYFVL

GLSSVGIFYCLIHRQVKRAAQALDQYKLRQASIHSNHVARTDEAMPGRFQELDSRLASGGPS

EGISSEPVSAATTQTLEGDSSEVGDQINSKRAKQMAEKSPPEASAKAQPIKGARRAPDSSSEF

-continued

GKVTRMCFAVFLCFALSYIPFLLLNILDARVQAPRVVHMLAANLTWLNGCINPVLYAAMNR

QFRQAYGSILKRGPRSFHRLH

>gi|9966851|ref|NP_065110.1|cysteinyl leukotriene receptor 2 {Homo sapiens}
(SEQ ID NO: 1110)

MERKFMSLQPSISVSEMEPNGTFSNNNSRNCTIENFKREFFPIVYLIIFFWGVLGNGLSIYVFLQ

PYKKSTSVNVFMLNLAISDLLFISTLPFRADYYLRGSNWIFGDLACRIMSYSLYVNMYSSIYFL

TVLSVVRFLAMVHPFRLLHVTSIRSAWILCGIIWILIMASSIMLLDSGSEQNGSVTSCLELNLY

KIAKLQTMNYIALVVGCLLPFFTLSICYLLIIRVLLKVEVPESGLRVSHRKALTTIIITLIIFFLCF

LPYHTLRTVHLTTWKVGLCKDRLHKALVITLALAAANACFNPLLYYFAGENFKDRLKSALR

KGHPQKAKTKCVFPVSVWLRKETRV

>gi|9966879|ref|NP_065133.1|lysophosphatidic acid receptor 5 {Homo sapiens}
(SEQ ID NO: 1111)

MLANSSSTNSSVLPCPDYRPTHRLHLVVYSLVLAAGLPLNALALWVFLRALRVHSVVSVYM

CNLAASDLLFTLSLPVRLSYYALHHWPFPDLLCQTTGAIFQMNMYGSCIFLMLINVDRYAAI

VHPLRLRHLRRPRVARLLCLGVWALILVFAVPAARVHRPSRCRYRDLEVRLCFESFSDELWK

GRLLPLVLLAEALGFLLPLAAVVYSSGRVFWTLARPDATQSQRRRKTVRLLLANLVIFLLCF

VPYNSTLAVYGLLRSKLVAASVPARDRVRGVLMVMVLLAGANCVLDPLVYYFSAEGFRNT

LRGLGTPHRARTSATNGTRAALAQSERSAVTTDATRPDAASQGLLRPSDSHSLSSFTQCPQDS

AL

>gi|10092633|ref|NP_055314.1|putative P2Y purinoceptor 10 {Homo sapiens}
(SEQ ID NO: 1112)

MANLDKYTETFKMGSNSTSTAEIYCNVTNVKFQYSLYATTYILIFIPGLLANSAALWVLCRFI

SKKNKAIIFMINLSVADLAHVLSLPLRIYYYISHHWPFQRALCLLCFYLKYLNMYASICFLTCI

SLQRCFFLLKPFRARDWKRRYDVGISAAIWIVVGTACLPFPILRSTDLNNNKSCFADLGYKQ

MNAVALVGMITVAELAGFVIPVIIAWCTWKTTISLRQPPMAFQGISERQKALRMVFMCAAV

FFICFTPYHINFIFYTMVKETIISSCPVVRIALYFHPFCLCLASLCCLLDPILYYFMASEFRDQLS

RHGSSVTRSRLMSKESGSSMIG

>gi|10835015|ref|NP_001461.1|gamma-aminobutyric acid(GABA) B receptor 1 isoform
a precursor {Homo sapiens}
(SEQ ID NO: 1113)

MLLLLLLAPLFLRPPGAGGAQTPNATSEGCQIIHPPWEGGIRYRGLTRDQVKAINFLPVDYEIE

YVCRGEREVVGPKVRKCLANGSWTDMDTPSRCVRICSKSYLTLENGKVFLTGGDLPALDGA

RVDFRCDPDFHLVGSSRSICSQGQWSTPKPHCQVNRTPHSERRAVYIGALFPMSGGWPGGQA

CQPAVEMALEDVNSRRDILPDYELKLIHHDSKCDPGQATKYLYELLYNDPIKIILMPGCSSVS

TLVAEAARMWNLIVLSYGSSSPALSNRQRFPTFFRTHPSATLHNPTRVKLFEKWGWKKIATI

QQTTEVFTSTLDDLEERVKEAGIEITFRQSFFSDPAVPVKNLKRQDARIIVGLFYETEARKVFC

EVYKERLFGKKYVWFLIGWYADNWFKIYDPSINCTVDEMTEAVEGHITTEIVMLNPANTRSI

SNMTSQEFVEKLTKRLKRHPEETGGFQEAPLAYDAIWALALALNKTSGGGRSGVRLEDFN

YNNQTITDQIYRAMNSSSFEGVSGHVVFDASGSRMAWTLIEQLQGGSYKKIGYYDSTKDDLS

WSKTDKWIGGSPPADQTLVIKTFRFLSQKLFISVSVLSSLGIVLAVVCLSFNIYNSHVRYIQNS

QPNLNNLTAVGCSLALAAVFPLGLDGYHIGRNQFPFVCQARLWLLGLGFSLGYGSMFTKIW

WVHTVFTKKEEKKEWRKTLEPWKLYATVGLLVGMDVLTLAIWQIVDPLHRTIETFAKEEPK

EDIDVSILPQLEHCSSRKMNTWLGIFYGYKGLLLLLGIFLAYETKSVSTEKINDHRAVGMAIY

NVAVLCLITAPVTMILSSQQDAAFAFASLAIVFSSYITLVVLFVPKMRRLITRGEWQSEAQDT

-continued

MKTGSSTNNNEEEKSRLLEKENRELEKIIAEKEERVSELRHQLQSRQQLRSRRHPPTPPEPSGG

LPRGPPEPPDRLSCDGSRVHLLYK

>gi|10835175|ref|NP_000612.1|5-hydroxytryptamine receptor 2A isoform 1 {Homo sapiens}
(SEQ ID NO: 1114)

MDILCEENTSLSSTTNSLMQLNDDTRLYSNDFNSGEANTSDAFNWTVDSENRTNLSCEGCLS

PSCLSLLHLQEKNWSALLTAVVIILTIAGNILVIMAVSLEKKLQNATNYFLMSLAIADMLLGF

LVMPVSMLTILYGYRWPLPSKLCAVWIYLDVLFSTASIMHLCAISLDRYVAIQNPIHHSRFNS

RTKAFLKIIAVWTISVGISMPIPVFGLQDDSKVFKEGSCLLADDNFVLIGSFVSFFIPLTIMVITY

FLTIKSLQKEATLCVSDLGTRAKLASFSFLPQSSLSSEKLFQRSIHREPGSYTGRRTMQSISNEQ

KACKVLGIVFFLFVVMWCPFFITNIMAVICKESCNEDVIGALLNVFVWIGYLSSAVNPLVYTL

FNKTYRSAFSRYIQCQYKENKKPLQLILVNTIPALAYKSSQLQMGQKKNSKQDAKTTDNDCS

MVALGKQHSEEASKDNSDGVNEKVSCV

>gi|10835197|ref|NP_000857.1|5-hydroxytryptamine receptor 1F {Homo sapiens}
(SEQ ID NO: 1115)

MDFLNSSDQNLTSEELLNRMPSKILVSLTLSGLALMTTTINSLVIAAIIVTRKLHHPANYLICSL

AVTDFLVAVLVMPFSIVYIVRESWIMGQVVCDIWLSVDITCCTCSILHLSAIALDRYRAITDAV

EYARKRTPKHAGIMITIVWIISVFISMPPLFWRHQGTSRDDECIIKHDHIVSTIYSTFGAFYIPLA

LILILYYKIYRAAKTLYHKRQASRIAKEEVNGQVLLESGEKSTKSVSTSYVLEKSLSDPSTDFD

KIHSTVRSLRSEFKHEKSWRRQKISGTRERKAATTLGLILGAFVICWLPFFVKELVVNVCDKC

KISEEMSNFLAWLGYLNSLINALIYTIFNEDFKKAFQKLVRCRC

>gi|11321563|ref|NP_000861.1|5-hydroxytryptamine receptor 4 isoform b {Homo sapiens}
(SEQ ID NO: 1116)

MDKLDANVSSEEGFGSVEKVVLLTFLSTVILMAILGNLLVMVAVCWDRQLRKIKTNYFIVSL

AFADLLVSVLVMPFGAIELVQDIWIYGEVFCLVRTSLDVLLTTASIFHLCCISLDRYYAICCQP

LVYRNKMTPLRIALMLGGCWVIPTFISFLPIMQGWNNIGIIDLIEKRKFNQNSNSTYCVFMVN

KPYAITCSVVAFYIPFLLMVLAYYRIYVTAKEHAHQIQMLQRAGASSESRPQSADQHSTHRM

RTETKAAKTLCIIMGCFCLCWAPFFVTNIVDPFIDYTVPGQVWTAFLWLGYINSGLNPFLYAF

LNKSFRRAFLIILCCDDERYRRPSILGQTVPCSTTTINGSTHVLRDAVECGGQWESQCHPPATS

PLVAAQPSDT

>gi|11545887|ref|NP_071429.1|neuropeptide FF receptor 1 {Homo sapiens}
(SEQ ID NO: 1117)

MEGEPSQPPNSSWPLSQNGTNTEATPATNLTFSSYYQHTSPVAAMFIVAYALIFLLCMVGNTL

VCFIVLKNRHMHTVTNMFILNLAVSDLLVGIFCMPTTLVDNLITGWPFDNATCKMSGLVQG

MSVSASVFTLVAIAVERFRCIVHPFREKLTLRKALVTIAVIWALALLIMCPSAVTLTVTREEHH

FMVDARNRSYPLYSCWEAWPEKGMRRVYTTVLFSHIYLAPLALIVVMYARIARKLCQAPGP

APGGEEAADPRASRRRARVVHMLVMVALFFTLSWLPLWALLLLIDYGQLSAPQLHLVTVYA

FPPFAHWLAFFNSSANPIIYGYFNENFRRGFQAAFRARLCPRPSGSHKEAYSERPGGLLHRRVF

VVVRPSDSGLPSESGPSSGAPRPGRLPLRNGRVAHHGLPREGPGCSHLPLTIPAWDI

>gi|12232483|ref|NP_073625.1|P2Y purinoceptor 12 {Homo sapiens}
(SEQ ID NO: 1118)

MQAVDNLTSAPGNTSLCTRDYKITQVLFPLLYTVLFFVGLITNGLAMRIFFQIRSKSNFIIFLKN

TVISDLLMILTFPFKILSDAKLGTGPLRTFVCQVTSVIFYFTMYISISFLGLITIDRYQKTTRPFKT

SNPKNLLGAKILSVVIWAFMFLLSLPNMILTNRQPRDKNVKKCSFLKSEFGLVWHEIVNYICQ

VIFWINFLIVIVCYTLITKELYRSYVRTRGVGKVPRKKVNVKVFIIIAVFFICFVPFHFARIPYTL

```
SQTRDVFDCTAENTLFYVKESTLWLTSLNACLDPFIYFFLCKSFRNSLISMLKCPNSATSLSQD

NRKKEQDGGDPNEETPM

>gi|13027636|ref|NP_001391.2|sphingosine 1-phosphate receptor 1 {Homo sapiens}
                                                                             (SEQ ID NO: 1119)
MGPTSVPLVKAHRSSVSDYVNYDIIVRHYNYTGKLNISADKENSIKLTSVVFILICCFIILENIF

VLLTIWKTKKFHRPMYYFIGNLALSDLLAGVAYTANLLLSGATTYKLTPAQWFLREGSMFV

ALSASVFSLLAIAIERYITMLKMKLHNGSNNFRLFLLISACWVISLILGGLPIMGWNCISALSSC

STVLPLYHKHYILFCTTVFTLLLLSIVILYCRIYSLVRTRSRRLTFRKNISKASRSSEKSLALLKT

VIIVLSVFIACWAPLFILLLLDVGCKVKTCDILFRAEYFLVLAVLNSGTNPIIYTLTNKEMRRAF

IRIMSCCKCPSGDSAGKFKRPIIAGMEFSRSKSDNSSHPQKDEGDNPETIMSSGNVNSSS

>gi|13236497|ref|NP_076917.1|5-hydroxytryptamine receptor 5A {Homo sapiens}
                                                                             (SEQ ID NO: 1120)
MDLPVNLTSFSLSTPSPLETNHSLGKDDLRPSSPLLSVFGVLILTLLGFLVAATFAWNLLVLAT

ILRVRTFHRVPHNLVASMAVSDVLVAALVMPLSLVHELSGRRWQLGRRLCQLWIACDVLCC

TASIWNVTAIALDRYWSITRHMEYTLRTRKCVSNVMIALTWALSAVISLAPLLFGWGETYSE

GSEECQVSREPSYAVFSTVGAFYLPLCVVLFVYWKIYKAAKFRVGSRKTNSVSPISEAVEVK

DSAKQPQMVFTVRHATVTFQPEGDTWREQKEQRAALMVGILIGVFVLCWIPFFLTELISPLCS

CDIPAIWKSIFLWLGYSNSFFNPLIYTAFNKNYNSAFKNFFSRQH

>gi|13325064|ref|NP_001399.1|cadherin EGF LAG seven-pass G-type receptor 2
precursor {Homo sapiens}
                                                                             (SEQ ID NO: 1121)
MRSPATGVPLPTPPPPLLLLLLLLPPPLLGDQVGPCRSLGSRGRGSSGACAPMGWLCPSSAS

NLWLYTSRCRDAGTELTGHLVPHHDGLRVWCPESEAHIPLPPAPEGCPWSCRLLGIGGHLSP

QGKLTLPEEHPCLKAPRLRCQSCKLAQAPGLRAGERSPEESLGGRRKRNVNTAPQFQPPSYQ

ATVPENQPAGTPVASLRAIDPDEGEAGRLEYTMDALFDSRSNQFFSLDPVTGAVTTAEELDR

ETKSTHVFRVTAQDHGMPRRSALATLTILVTDTNDHDPVFEQQEYKESLRENLEVGYEVLTV

RATDGDAPPNANILYRLLEGSGGSPSEVFEIDPRSGVIRTRGPVDREEVESYQLTVEASDQGR

DPGPRSTTAAVFLSVEDDNDNAPQFSEKRYVVQVREDVTPGAPVLRVTASDRDKGSNAVVH

YSIMSGNARGQFYLDAQTGALDVVSPLDYETTKEYTLRVRAQDGGRPPLSNVSGLVTVQVL

DINDNAPIFVSTPFQATVLESVPLGYLVLHVQAIDADAGDNARLEYRLAGVGHDFPFTINNGT

GWISVAAELDREEVDFYSFGVEARDHGTPALTASASVSVTVLDVNDNNPTFTQPEYTVRLNE

DAAVGTSVVTVSAVDRDAHSVITYQITSGNTRNRFSITSQSGGGLVSLALPLDYKLERQYVL

AVTASDGTRQDTAQIVVNVTDANTHRPVFQSSHYTVNVNEDRPAGTTVVLISATDEDTGEN

ARITYFMEDSIPQFRIDADTGAVTTQAELDYEDQVSYTLAITARDNGIPQKSDTTYLEILVNDV

NDNAPQFLRDSYQGSVYEDVPPFTSVLQISATDRDSGLNGRVFYTFQGGDDGDGDFIVESTS

GIVRTLRRLDRENVAQYVLRAYAVDKGMPPARTPMEVTVTVLDVNDNPPVFEQDEFDVFVE

ENSPIGLAVARVTATDPDEGTNAQIMYQIVEGNIPEVFQLDIFSGELTALVDLDYEDRPEYVL

VIQATSAPLVSRATVHVRLLDRNDNPPVLGNFEILFNNYVTNRSSSFPGGAIGRVPAHDPDISD

SLTYSFERGNELSLVLLNASTGELKLSRALDNNRPLEAIMSVLVSDGVHSVTAQCALRVTIIT

DEMLTHSITLRLEDMSPERFLSPLLGLFIQAVAATLATPPDHVVVFNVQRDTDAPGGHILNVS

LSVGQPPGPGGGPPFLPSEDLQERLYLNRSLLTAISAQRVLPFDDNICLREPCENYMRCVSVLR

FDSSAPFIASSSVLFRPIHPVGGLRCRCPPGFTGDYCETEVDLCYSRPCGPHGRCRSREGGYTC

LCRDGYTGEHCEVSARSGRCTPGVCKNGGTCVNLLVGGFKCDCPSGDFEKPYCQVTTRSFP

AHSFITFRGLRQRFHFTLALSFATKERDGLLLYNGRFNEKHDFVALEVIQEQVQLTFSAGEST
```

-continued

```
TTVSPFVPGGVSDGQWHTVQLKYYNKPLLGQTGLPQGPSEQKVAVVTVDGCDTGVALRFG

SVLGNYSCAAQGTQGGSKKSLDLTGPLLLGGVPDLPESFPVRMRQFVGCMRNLQVDSRHID

MADFIANNGTVPGCPAKKNVCDSNTCHNGGTCVNQWDAFSCECPLGFGGKSCAQEMANPQ

HFLGSSLVAWHGLSLPISQPWYLSLMFRTRQADGVLLQAITRGRSTITLQLREGHVMLSVEG

TGLQASSLRLEPGRANDGDWHHAQLALGASGGPGHAILSFDYGQQRAEGNLGPRLHGLHLS

NITVGGIPGPAGGVARGFRGCLQGVRVSDTPEGVNSLDPSHGESINVEQGCSLPDPCDSNPCP

ANSYCSNDWDSYSCSCDPGYYGDNCTNVCDLNPCEHQSVCTRKPSAPHGYTCECPPNYLGP

YCETRIDQPCPRGWWGHPTCGPCNCDVSKGFDPDCNKTSGECHCKENHYRPPGSPTCLLCD

CYPTGSLSRVCDPEDGQCPCKPGVIGRQCDRCDNPFAEVTTNGCEVNYDSCPRAIEAGIWWP

RTRFGLPAAAPCPKGSFGTAVRHCDEHRGWLPPNLFNCTSITFSELKGFAERLQRNESGLDSG

RSQQLALLLRNATQHTAGYFGSDVKVAYQLATRLLAHESTQRGFGLSATQDVHFTENLLRV

GSALLDTANKRHWELIQQTEGGTAWLLQHYEAYASALAQNMRHTYLSPFTIVTPNIVISVVR

LDKGNFAGAKLPRYEALRGEQPPDLETTVILPESVFRETPPVVRPAGPGEAQEPEELARRQRR

HPELSQGEAVASVIIYRTLAGLLPHNYDPDKRSLRVPKRPIINTPVVSISVHDDEELLPRALDK

PVTVQFRLLETEERTKPICVFWNHSILVSGTGGWSARGCEVVFRNESHVSCQCNHMTSFAVL

MDVSRRENGEILPLKTLTYVALGVTLAALLLTFFFLTLLRILRSNQHGIRRNLTAALGLAQLV

FLLGINQADLPFACTVIAILLHFLYLCTFSWALLEALHLYRALTEVRDVNTGPMRFYYMLGW

GVPAFITGLAVGLDPEGYGNPDFCWLSIYDTLIWSFAGPVAFAVSMSVFLYILAARASCAAQ

RQGFEKKGPVSGLQPSFAVLLLLSATWLLALLSVNSDTLLFHYLFATCNCIQGPFIFLSYVVLS

KEVRKALKLACSRKPSPDPALTTKSTLTSSYNCPSPYADGRLYQPYGDSAGSLHSTSRSGKSQ

PSYIPFLLREESALNPGQGPPGLGDPGSLFLEGQDQQHDPDTDSDSDLSLEDDQSGSYASTHSS

DSEEEEEEEEEEAAFPGEQGWDSLLGPGAERLPLHSTPKDGGPGPGKAPWPGDFGTTAKESS

GNGAPEERLRENGDALSREGSLGPLPGSSAQPHKGILKKKCLPTISEKSSLLRLPLEQCTGSSR

GSSASEGSRGGPPPRPPPRQSLQEQLNGVMPIAMSIKAGTVDEDSSGSEFLFFNFLH
```

>gi|13435405|ref|NP_071640.1|histamine H2 receptor isoform 2 {Homo sapiens}
(SEQ ID NO: 1122)

```
MAPNGTASSFCLDSTACKITITVVLAVLILITVAGNVVVCLAVGLNRRLRNLTNCFIVSLAITD

LLLGLLVLPFSAIYQLSCKWSFGKVFCNIYTSLDVMLCTASILNLFMISLDRYCAVMDPLRYP

VLVTPVRVAISLVLIWVISITLSFLSIHLGWNSRNETSKGNHTTSKCKVQVNEVYGLVDGLVT

FYLPLLIMCITYYRIFKVARDQAKRINHISSWKAATIREHKATVTLAAVMGAFIICWFPYFTAF

VYRGLRGDDAINEVLEAIVLWLGYANSALNPILYAALNRDFRTGYQQLFCCRLANRNSHKTS

LRSNASQLSRTQSREPRQQEEKPLKLQVWSGTEVTAPQGATDR
```

>gi|13540517|ref|NP_110387.1|endothelial differentiation, sphingolipid G-protein-coupled receptor, 8 {Homo sapiens}
(SEQ ID NO: 1123)

```
MESGLLRPAPVSEVIVLHYNYTGKLRGARYQPGAGLRADAVVCLAVCAFIVLENLAVLLVL

GRHPRFHAPMFLLLGSLTLSDLLAGAAYAANILLSGPLTLKLSPALWFAREGGVFVALTASV

LSLLAIALERSLTMARRGPAPVSSRGRTLAMAAAAWGVSLLLGLLPALGWNCLGRLDACST

VLPLYAKAYVLFCVLAFVGILAAICALYARIYCQVRANARRLPARPGTAGTTSTRARRKPRS

LALLRTLSVVLLAFVACWGPLFLLLLLDVACPARTCPVLLQADPFLGLAMANSLLNPIIYTLT

NRDLRHALLRLVCCGRHSCGRDPSGSQQSASAAEASGGLRRCLPPGLDGSFSGSERSSPQRD

GLDTSGSTGSPGAPTAARTLVSEPAAD
```

-continued

>gi|13540557|ref|NP_110411.1|probable G-protein coupled receptor 63 {Homo sapiens}
(SEQ ID NO: 1124)
MVFSAVLTAFHTGTSNTTFVVYENTYMNITLPPPFQHPDLSPLLRYSFETMAPTGLSSLTVNS

TAVPTTPAAFKSLNLPLQITLSAIMIFILFVSFLGNLVVCLMVYQKAAMRSAINILLASLAFAD

MLLAVLNMPFALVTILTTRWIFGKFFCRVSAMFFWLFVIEGVAILLIISIDRFLIIVQRQDKLNP

YRAKVLIAVSWATSFCVAFPLAVGNPDLQIPSRAPQCVFGYTTNPGYQAYVILISLISFFIPFLV

ILYSFMGILNTLRHNALRIHSYPEGICLSQASKLGLMSLQRPFQMSIDMGFKTRAFTTILILFAV

FIVCWAPFTTYSLVATFSKHFYYQHNFFEISTWLLWLCYLKSALNPLIYYWRIKKFHDACLD

MMPKSFKFLPQLPGHTKRRIRPSAVYVCGEHRTVV

>gi|13929467|ref|NP_001287.2|chemokine-binding protein 2 {Homo sapiens}
(SEQ ID NO: 1125)
MAATASPQPLATEDADSENSSFYYYDYLDEVAFMLCRKDAVVSFGKVFLPVFYSLIFVLGLS

GNLLLLMVLLRYVPRRRMVEIYLLNLAISNLLFLVTLPFWGISVAWHWVFGSFLCKMVSTLY

TINFYSGIFFISCMSLDKYLEIVHAQPYHRLRTRAKSLLLATIVWAVSLAVSIPDMVFVQTHEN

PKGVWNCHADFGGHGTIWKLFLRFQQNLLGFLLPLLAMIFFYSRIGCVLVRLRPAGQGRALK

IAAALVVAFFVLWFPYNLTLFLHTLLDLQVFGNCEVSQHLDYALQVTESIAFLHCCFSPILYA

FSSHRFRQYLKAFLAAVLGWHLAPGTAQASLSSCSESSILTAQEEMTGMNDLGERQSENYPN

KEDVGNKSA

>gi|14043044|ref|NP_006632.2|C-C chemokine receptor type 9 isoform B {Homo sapiens}
(SEQ ID NO: 1126)
MADDYGSESTSSMEDYVNFNFTDFYCEKNNVRQFASHFLPPLYWLVFIVGALGNSLVILVY

WYCTRVKTMTDMFLLNLAIADLLFLVTLPFWAIAAADQWKFQTFMCKVVNSMYKMNFYS

CVLLIMCISVDRYIAIAQAMRAHTWREKRLLYSKMVCFTIWVLAAALCIPEILYSQIKEESGIA

ICTMVYPSDESTKLKSAVLTLKVILGFFLPFVVMACCYTIIIHTLIQAKKSSKHKALKVTITVLT

VFVLSQFPYNCILLVQTIDAYAMFISNCAVSTNIDICFQVTQTIAFFHSCLNPVLYVFVGERFRR

DLVKTLKNLGCISQAQWVSFTRREGSLKLSSMLLETTSGALSL

>gi|14211849|ref|NP_115942.1|probable G-protein coupled receptor 174 {Homo sapiens}
(SEQ ID NO: 1127)
MPANYTCTRPDGDNTDFRYFIYAVTYTVILVPGLIGNILALWVFYGYMKETKRAVIFMINLAI

ADLLQVLSLPLRIFYYLNHDWPFGPGLCMFCFYLKYVNMYASIYFLVCISVRRFWFLMYPFR

FHDCKQKYDLYISIAGWLIICLACVLFPLLRTSDDTSGNRTKCFVDLPTRNVNLAQSVVMMTI

GELIGFVTPLLIVLYCTWKTVLSLQDKYPMAQDLGEKQKALKMILTCAGVFLICFAPYHFSFP

LDFLVKSNEIKSCLARRVILIFHSVALCLASLNSCLDPVIYYFSTNEFRRRLSRQDLHDSIQLHA

KSFVSNHTASTMTPELC

>gi|14211851|ref|NP_115943.1|G-protein coupled receptor 81 {Homo sapiens}
(SEQ ID NO: 1128)
MYNGSCCRIEGDTISQVMPPLLIVAFVLGALGNGVALCGFCFHMKTWKPSTVYLFNLAVAD

FLLMICLPFRTDYYLRRRHWAFGDIPCRVGLFTLAMNRAGSIVFLTVVAADRYFKVVHPHHA

VNTISTRVAAGIVCTLWALVILGTVYLLLENHLCVQETAVSCESFIMESANGWHDIMFQLEFF

MPLGIILFCSFKIVWSLRRRQQLARQARMKKATRFIMVVAIVFITCYLPSVSARLYFLWTVPSS

ACDPSVHGALHITLSFTYMNSMLDPLVYYFSSPSFPKFYNKLKICSLKPKQPGHSKTQRPEEM

PISNLGRRSCISVANSFQSQSDGQWDPHIVEWH

>gi|14251205|ref|NP_067637.2|histamine H4 receptor isoform 1 {Homo sapiens}
(SEQ ID NO: 1129)
MPDTNSTINLSLSTRVTLAFFMSLVAFAIMLGNALVILAFVVDKNLRHRSSYFFLNLAISDFFV

GVISIPLYIPHTLFEWDFGKEICVFWLTTDYLLCTASVYNIVLISYDRYLSVSNAVSYRTQHTG

-continued

```
VLKIVTLMVAVWVLAFLVNGPMILVSESWKDEGSECEPGFFSEWYILAITSFLEFVIPVILVAY

FNMNIYWSLWKRDHLSRCQSHPGLTAVSSNICGHSFRGRLSSRRSLSASTEVPASFHSERQRR

KSSLMFSSRTKMNSNTIASKMGSFSQSDSVALHQREHVELLRARRLAKSLAILLGVFAVCWA

PYSLFTIVLSFYSSATGPKSVWYRIAFWLQWFNSFVNPLLYPLCHKRFQKAFLKIFCIKKQPLP

SQHSRSVSS
```

>gi|14589869|ref|NP_116743.1|Burkitt lymphoma receptor 1 isoform 2 {Homo sapiens}
(SEQ ID NO: 1130)

```
MASFKAVFVPVAYSLIFLLGVIGNVLVLVILERHRQTRSSTETFLFHLAVADLLLVFILPFAVA

EGSVGWVLGTFLCKTVIALHKVNFYCSSLLLACIAVDRYLAIVHAVHAYRHRRLLSIHITCGT

IWLVGFLLALPEILFAKVSQGHHNNSLPRCTFSQENQAETHAWFTSRFLYHVAGFLLPMLVM

GWCYVGVVHRLRQAQRRPQRQKAVRVAILVTSIFFLCWSPYHIVIFLDTLARLKAVDNTCKL

NGSLPVAITMCEFLGLAHCCLNPMLYTFAGVKFRSDLSRLLTKLGCTGPASLCQLFPSWRRSS

LSESENATSLTTF
```

>gi|15029528|ref|NP_005283.1|N-arachidonyl glycine receptor {Homo sapiens}
(SEQ ID NO: 1131)

```
MITLNNQDQPVPFNSSHPDEYKIAALVFYSCIFIIGLFVNITALWVFSCTTKKRTTVTIYMMNV

ALVDLIFIMTLPFRMFYYAKDEWPFGEYFCQILGALTVFYPSIALWLLAFISADRYMAIVQPK

YAKELKNTCKAVLACVGVWIMTLTTTTPLLLLYKDPDKDSTPATCLKISDIIYLKAVNVLNL

TRLTFFFLIPLFIMIGCYLVIIHNLLHGRTSKLKPKVKEKSIRIIITLLVQVLVCFMPFHICFAFLM

LGTGENSYNPWGAFTTFLMNLSTCLDVILYYIVSKQFQARVISVMLYRNYLRSMRRKSFRSG

SLRSLSNINSEML
```

>gi|15619006|ref|NP_004615.2|vasoactive intestinal polypeptide receptor 1 precursor {Homo sapiens}
(SEQ ID NO: 1132)

```
MRPPSPLPARWLCVLAGALAWALGPAGGQAARLQEECDYVQMIEVQHKQCLEEAQLENETI

GCSKMWDNLTCWPATPRGQVVVLACPLIFKLFSSIQGRNVSRSCTDEGWTHLEPGPYPIACG

LDDKAASLDEQQTMFYGSVKTGYTIGYGLSLATLLVATAILSLFRKLHCTRNYIHMHLFISFIL

RAAAVFIKDLALFDSGESDQCSEGSVGCKAAMVFFQYCVMANFFWLLVEGLYLYTLLAVSF

FSERKYFWGYILIGWGVPSTFTMVWTIARIHFEDYGCWDTINSSLWWIIKGPILTSILVNFILFI

CIIRILLQKLRPPDIRKSDSSPYSRLARSTLLLIPLFGVHYIMFAFFPDNFKPEVKMVFELVVGSF

QGFVVAILYCFLNGEVQAELRRKWRRWHLQGVLGWNPKYRHPSGGSNGATCSTQVSMLTR

VSPGARRSSSFQAEVSLV
```

>gi|16418463|ref|NP_443199.1|MAS1 oncogene-like {Homo sapiens}
(SEQ ID NO: 1133)

```
MVWGKICWFSQRAGWTVFAESQISLSCSLCLHSGDQEAQNPNLVSQLCGVFLQNETNETIH

MQMSMAVGQQALPLNIIAPKAVLVSLCGVLLNGTVFWLLCCGATNPYMVYILHLVAADVIY

LCCSAVGFLQVTLLTYHGVVFFIPDFLAILSPFSFEVCLCLLVAISTERCVCVLFPIWYRCHRPK

YTSNVVCTLIWGLPFCINIVKSLFLTYWKHVKACVIFLKLSGLFHAILSLVMCVSSLTLLIRFL

CCSQQQKATRVYAVVQISAPMFLLWALPLSVAPLITDFKMFVTTSYLISLFLIINSSANPIIYFF

VGSLRKKRLKESLRVILQRALADKPEVGRNKKAAGIDPMEQPHSTQHVENLLPREHRVDVET
```

>gi|16751917|ref|NP_444508.1|trace amine associated receptor 8 {Homo sapiens}
(SEQ ID NO: 1134)

```
MTSNFSQPVVQLCYEDVNGSCIETPYSPGSRVILYTAFSFGSLLAVFGNLLVMTSVLHFKQLH

SPTNFLIASLACADFLVGVTVMLFSMVRTVESCWYFGAKFCTLHSCCDVAFCYSSVLHLCFIC

IDRYIVVTDPLVYATKFTVSVSGICISVSWILPLTYSGAVFYTGVNDDGLEELVSALNCVGGC

QIIVSQGWVLIDFLLFFIPTLVMIILYSKIFLIAKQQAIKIETTSSKVESSSESYKIRVAKRERKAA
```

-continued

KTLGVTVLAFVISWLPYTVDILIDAFMGFLTPAYIYEICCWSAYYNSAMNPLIYALFYPWFRK

AIKLILSGDVLKASSSTISLFLE

>gi|16876435|ref|NP_473362.1|probable G-protein coupled receptor 101 {Homo sapiens}
(SEQ ID NO: 1135)

MTSTCTNSTRESNSSHTCMPLSKMPISLAHGIIRSTVLVIFLAASFVGNIVLALVLQRKPQLLQ

VTNRFIFNLLVTDLLQISLVAPWVVATSVPLFWPLNSHFCTALVSLTHLFAFASVNTIVVVSV

DRYLSIIHPLSYPSKMTQRRGYLLLYGTWIVAILQSTPPLYGWGQAAFDERNALCSMIWGASP

SYTILSVVSFIVIPLIVMIACYSVVFCAARRQHALLYNVKRHSLEVRVKDCVENEDEEGAEKK

EEFQDESEFRRQHEGEVKAKEGRMEAKDGSLKAKEGSTGTSESSVEARGSEEVRESSTVASD

GSMEGKEGSTKVEENSMKADKGRTEVNQCSIDLGEDDMEFGEDDINFSEDDVEAVNIPESLP

PSRRNSNSNPPLPRCYQCKAAKVIFIIIFSYVLSLGPYCFLAVLAVWVDVETQVPQWVITIIIWL

FFLQCCIHPYVYGYMHKTIKKEIQDMLKKFFCKEKPPKEDSHPDLPGTEGGTEGKIVPSYDSA

TFP

>gi|16950636|ref|NP_001392.2|lysophosphatidic acid receptor 1 {Homo sapiens}
(SEQ ID NO: 1136)

MAAISTSIPVISQPQFTAMNEPQCFYNESIAFFYNRSGKHLATEWNTVSKLVMGLGITVCIFIM

LANLLVMVAIYVNRRFHFPIYYLMANLAAADFFAGLAYFYLMFNTGPNTRRLTVSTWLLRQ

GLIDTSLTASVANLLAIAIERHITVFRMQLHTRMSNRRVVVVIVVIWTMAIVMGAIPSVGWNC

ICDIENCSNMAPLYSDSYLVFWAIFNLVTFVVMVVLYAHIFGYVRQRTMRMSRHSSGPRRNR

DTMMSLLKTVVIVLGAFIICWTPGLVLLLLDVCCPQCDVLAYEKFFLLLAEFNSAMNPIIYSY

RDKEMSATFRQILCCQRSENPTGPTEGSDRSASSLNHTILAGVHSNDHSVV

>gi|17978491|ref|NP_510966.1|CD97 antigen isoform 1 precursor {Homo sapiens}
(SEQ ID NO: 1137)

MGGRVFLAFCVWLTLPGAETQDSRGCARWCPQNSSCVNATACRCNPGFSSFSEIITTPTETCD

DINECATPSKVSCGKFSDCWNTEGSYDCVCSPGYEPVSGAKTFKNESENTCQDVDECQQNPR

LCKSYGTCVNTLGSYTCQCLPGFKFIPEDPKVCTDVNECTSGQNPCHSSTHCLNNVGSYQCR

CRPGWQPIPGSPNGPNNTVCEDVDECSSGQHQCDSSTVCFNTVGSYSCRCRPGWKPRHGIPN

NQKDTVCEDMTFSTWTPPPGVHSQTLSRFFDKVQDLGRDSKTSSAEVTIQNVIKLVDELMEA

PGDVEALAPPVRHLIATQLLSNLEDIMRILAKSLPKGPFTYISPSNTELTLMIQERGDKNVTMG

QSSARMKLNWAVAAGAEDPGPAVAGILSIQNMTTLLANASLNLHSKKQAELEEIYESSIRGV

QLRRLSAVNSIFLSHNNTKELNSPILFAFSHLESSDGEAGRDPPAKDVMPGPRQELLCAFWKS

DSDRGGHWATEGCQVLGSKNGSTTCQCSHLSSFAILMAHYDVEDWKLTLITRVGLALSLFC

LLLCILTFLLVRPIQGSRTTIHLHLCICLFVGSTIFLAGIENEGGQVGLRCRLVAGLLHYCFLAA

FCWMSLEGLELYFLVVRVFQGQGLSTRWLCLIGYGVPLLIVGVSAAIYSKGYGRPRYCWLDF

EQGFLWSFLGPVTFIILCNAVIFVTTVWKLTQKFSEINPDMKKLKKARALTITAIAQLFLLGCT

WVFGLFIFDDRSLVLTYVFTILNCLQGAFLYLLHCLLNKKVREEYRKWACLVAGGSKYSEFT

STTSGTGHNQTRALRASESGI

>gi|18201870|ref|NP_543007.1|probable G-protein coupled receptor 82 {Homo sapiens}
(SEQ ID NO: 1138)

MNNNTTCIQPSMISSMALPIIYILLCIVGVFGNTLSQWIFLTKIGKKTSTHIYLSHLVTANLLVC

SAMPFMSIYFLKGFQWEYQSAQCRVVNFLGTLSMHASMFVSLLILSWIAISRYATLMQKDSS

QETTSCYEKIFYGHLLKKFRQPNFARKLCIYIWGVVLGIIIPVTVYYSVIEATEGEESLCYNRQ

MELGAMISQIAGLIGTTFIGFSFLVVLTSYYSFVSHLRKIRTCTSIMEKDLTYSSVKRHLLVIQIL

LIVCFLPYSIFKPIFYVLHQRDNCQQLNYLIETKNILTCLASARSSTDPIIFLLLDKTFKKTLYNL

FTKSNSAHMQSYG

-continued

>gi|18677729|ref|NP_570718.1|relaxin receptor 2 isoform 1 {Homo sapiens}
(SEQ ID NO: 1139)

MIVFLVFKHLFSLRLITMFFLLHFIVLINVKDFALTQGSMITPSCQKGYFPCGNLTKCLPRAFH

CDGKDDCGNGADEENCGDTSGWATIFGTVHGNANSVALTQECFLKQYPQCCDCKETELEC

VNGDLKSVPMISNNVTLLSLKKNKIHSLPDKVFIKYTKLKKIFLQHNCIRHISRKAFFGLCNLQ

ILYLNHNCITTLRPGIFKDLHQLTWLILDDNPITRISQRLFTGLNSLFFLSMVNNYLEALPKQM

CAQMPQLNWVDLEGNRIKYLTNSTFLSCDSLTVLFLPRNQIGFVPEKTFSSLKNLGELDLSSN

TITELSPHLFKDLKLLQKLNLSSNPLMYLHKNQFESLKQLQSLDLERIEIPNINTRMFQPMKNL

SHIYFKNFRYCSYAPHVRICMPLTDGISSFEDLLANNILRIFVWVIAFITCFGNLFVIGMRSFIKA

ENTTHAMSIKILCCADCLMGVYLFFVGIFDIKYRGQYQKYALLWMESVQCRLMGFLAMLST

EVSVLLLTYLTLEKFLVIVFPFSNIRPGKRQTSVILICIWMAGFLIAVIPFWNKDYFGNFYGKN

GVCFPLYYDQTEDIGSKGYSLGIFLGVNLLAFLIIVFSYITMFCSIQKTALQTTEVRNCFGREV

AVANRFFFIVFSDAICWIPVFVVKILSLFRVEIPDTMTSWIVIFFLPVNSALNPILYTLTTNFFKD

KLKQLLHKHQRKSIFKIKKKSLSTSIVWIEDSSSLKLGVLNKITLGDSIMKPVS

>gi|19923245|ref|NP_004373.2|corticotropin-releasing factor receptor 1 isoform 2
{Homo sapiens}
(SEQ ID NO: 1140)

MGGHPQLRLVKALLLLGLNPVSASLQDQHCESLSLASNISGLQCNASVDLIGTCWPRSPAGQ

LVVRPCPAFFYGVRYNTTNNGYRECLANGSWAARVNYSECQEILNEEKKSKVHYHVAVIIN

YLGHCISLVALLVAFVLFLRLRSIRCLRNIIHWNLISAFILRNATWFVVQLTMSPEVHQSNVG

WCRLVTAAYNYFHVTNFFWMFGEGCYLHTAIVLTYSTDRLRKWMFICIGWGVPFPIIVAWAI

GKLYYDNEKCWFGKRPGVYTDYIYQGPMILVLLINFIFLFNIVRILMTKLRASTTSETIQYRKA

VKATLVLLPLLGITYMLFFVNPGEDEVSRVVFIYFNSFLESFQGFFVSVFYCFLNSEVRSAIRK

RWHRWQDKHSIRARVARAMSIPTSPTRVSFHSIKQSTAV

>gi|19923975|ref|NP_612454.1|G protein-coupled receptor 146 {Homo sapiens}
(SEQ ID NO: 1141)

MWSCSWFNGTGLVEELPACQDLQLGLSLLSLLGLVVGVPVGLCYNALLVLANLHSKASMT

MPDVYFVNMAVAGLVLSALAPVHLLGPPSSRWALWSVGGEVHVALQIPFNVSSLVAMYST

ALLSLDHYIERALPRTYMASVYNTRHVCGFVWGGALLTSFSSLLFYICSHVSTRALECAKMQ

NAEAADATLVFIGYVVPALATLYALVLLSRVRREDTPLDRDTGRLEPSAHRLLVATVCTQFG

LWTPHYLILLGHTVIISRGKPVDAHYLGLLHFVKDFSKLLAFSSSFVTPLLYRYMNQSFPSKL

QRLMKKLPCGDRHCSPDHMGVQQVLA

>gi|20373179|ref|NP_620414.1|G protein-coupled receptor 73 {Homo sapiens}
(SEQ ID NO: 1142)

METTMGFMDDNATNTSTSFLSVLNPHGAHATSFPFNFSYSDYDMPLDEDEDVTNSRTFFAA

KIVIGMALVGIMLVCGIGNFIFIAALVRYKKLRNLTNLLIANLAISDFLVAIVCCPFEMDYYVV

RQLSWEHGHVLCTSVNYLRTVSLYVSTNALLAIAIDRYLAIVHPLRPRMKCQTATGLIALVW

TVSILIAIPSAYFTTETVLVIVKSQEKIFCGQIWPVDQQLYYKSYFLFIFGIEFVGPVVTMTLCY

ARISRELWFKAVPGFQTEQIRKRLRCRRKTVLVLMCILTAYVLCWAPFYGFTIVRDFFPTVFV

KEKHYLTAFYIVECIAMSNSMINTLCFVTVKNDTVKYFKKIMLLHWKASYNGGKSSADLDL

KTIGMPATEEVDCIRLK

>gi|20544172|ref|NP_000701.2|B1 bradykinin receptor {Homo sapiens}
(SEQ ID NO: 1143)

MASSWPPLELQSSNQSQLFPQNATACDNAPEAWDLLHRVLPTFIISICFFGLLGNLFVLLVFLL

PRRQLNVAEIYLANLAASDLVFVLGLPFWAENIWNQFNWPFGALLCRVINGVIKANLFISIFL

VVAISQDRYRVLVHPMASRRQQRRRQARVTCVLIWVVGGLLSIPTFLLRSIQAVPDLNITACI

-continued

LLLPHEAWHFARIVELNILGFLLPLAAIVFFNYHILASLRTREEVSRTRCGGRKDSKTTALILTL

VVAFLVCWAPYHFFAFLEFLFQVQAVRGCFWEDFIDLGLQLANFFAFTNSSLNPVIYVFVGR

LFRTKVWELYKQCTPKSLAPISSSHRKEIFQLFWRN

>gi|21264324|ref|NP_612200.1|trace amine associated receptor 1 {Homo sapiens}
(SEQ ID NO: 1144)

MMPFCHNIINISCVKNNWSNDVRASLYSLMVLIILTTLVGNLIVIVSISHFKQLHTPTNWLIHS

MATVDFLLGCLVMPYSMVRSAEHCWYFGEVFCKIHTSTDIMLSSASIFHLSFISIDRYYAVCD

PLRYKAKMNILVICVMIFISWSVPAVFAFGMIFLELNFKGAEEIYYKHVHCRGGCSVFFSKISG

VLTFMTSFYIPGSIMLCVYYRIYLIAKEQARLISDANQKLQIGLEMKNGISQSKERKAVKTLGI

VMGVFLICWCPFFICTVMDPFLHYIIPPTLNDVLIWFGYLNSTFNPMVYAFFYPWFRKALKM

MLFGKIFQKDSSRCKLFLELSS

>gi|21361557|ref|NP_003373.2|vasoactive intestinal polypeptide receptor 2 {Homo sapiens}
(SEQ ID NO: 1145)

MRTLLPPALLTCWLLAPVNSIHPECRFHLEIQEEETKCAELLRSQTEKHKACSGVWDNITCW

RPANVGETVTVPCPKVFSNFYSKAGNISKNCTSDGWSETFPDFVDACGYSDPEDESKITFYIL

VKAIYTLGYSVSLMSLATGSIILCLFRKLHCTRNYIHLNLFLSFILRAISVLVKDDVLYSSSGTL

HCPDQPSSWVGCKLSLVFLQYCIMANFFWLLVEGLYLHTLLVAMLPPRRCFLAYLLIGWGLP

TVCIGAWTAARLYLEDTGCWDTNDHSVPWWVIRIPILISIIVNFVLFISIIRILLQKLTSPDVGG

NDQSQYKRLAKSTLLLIPLFGVHYMVFAVFPISISSKYQILFELCLGSFQGLVVAVLYCFLNSE

VQCELKRKWRSRCPTPSASRDYRVCGSSFSRNGSEGALQFHRGSRAQSFLQTETSVI

>gi|21426829|ref|NP_658986.1|prokineticin receptor 2 {Homo sapiens}
(SEQ ID NO: 1146)

MAAQNGNTSFTPNFNPPQDHASSLSFNFSYGDYDLPMDEDEDMTKTRTFFAAKIVIGIALAGI

MLVCGIGNFVFIAALTRYKKLRNLTNLLIANLAISDFLVAIICCPFEMDYYVVRQLSWEHGHV

LCASVNYLRTVSLYVSTNALLAIAIDRYLAIVHPLKPRMNYQTASFLIALVWMVSILIAIPSAY

FATETVLFIVKSQEKIFCGQIWPVDQQLYYKSYFLFIFGVEFVGPVVTMTLCYARISRELWFK

AVPGFQTEQIRKRLRCRRKTVLVLMCILTAYVLCWAPFYGFTIVRDFFPTVFVKEKHYLTAF

YVVECIAMSNSMINTVCFVTVKNNTMKYFKKMMLLHWRPSQRGSKSSADLDLRTNGVPTT

EEVDCIRLK

>gi|22507376|ref|NP_683765.1|oxoeicosanoid receptor 1 {Homo sapiens}
(SEQ ID NO: 1147)

MLCHRGGQLIVPIIPLCPEHSCRGRRLQNLLSGPWPKQPMELHNLSSPSPSLSSSVLPPSFSPSP

SSAPSAFTTVGGSSGGPCHPTSSSLVSAFLAPILALEFVLGLVGNSLALFIFCIHTRPWTSNTVF

LVSLVAADFLLISNLPLRVDYYLLHETWRFGAAACKVNLFMLSTNRTASVVFLTAIALNRYL

KVVQPHHVLSRASVGAAARVAGGLWVGILLLNGHLLLSTFSGPSCLSYRVGTKPSASLRWH

QALYLLEFFLPLALILFAIVSIGLTIRNRGLGGQAGPQRAMRVLAMVVAVYTICFLPSIIFGMA

SMVAFWLSACRSLDLCTQLFHGSLAFTYLNSVLDPVLYCFSSPNFLHQSRALLGLTRGRQGP

VSDESSYQPSRQWRYREASRKAEAIGKLKVQGEVSLEKEGSSQG

>gi|23238240|ref|NP_000677.2|type-2 angiotensin II receptor {Homo sapiens}
(SEQ ID NO: 1148)

MKGNSTLATTSKNITSGLHFGLVNISGNNESTLNCSQKPSDKHLDAIPILYYIIFVIGFLVNIVV

VTLFCCQKGPKKVSSIYIFNLAVADLLLLATLPLWATYYSRYDWLFGPVMCKVFGSFLTLN

MFASIFFITCMSVDRYQSVIYPFLSQRRNPWQASYIVPLVWCMACLSSLPTFYFRDVRTIEYLG

VNACIMAFPPEKYAQWSAGIALMKNILGFIIPLIFIATCYFGIRKHLLKTNSYGKNRITRDQVL

KMAAAVVLAFIICWLPFHVLTFLDALAWMGVINSCEVIAVIDLALPFAILLGFTNSCVNPFLY

CFVGNRFQQKLRSVFRVPITWLQGKRESMSCRKSSSLREMETFVS

>gi|23397681|ref|NP_038475.2|EGF-like module-containing mucin-like hormone receptor-like 2 isoform a {Homo sapiens}

(SEQ ID NO: 1149)

MGGRVFLVFLAFCVWLTLPGAETQDSRGCARWCPQDSSCVNATACRCNPGFSSFSEIITTPM

ETCDDINECATLSKVSCGKFSDCWNTEGSYDCVCSPGYEPVSGAKTFKNESENTCQDVDECQ

QNPRLCKSYGTCVNTLGSYTCQCLPGFKLKPEDPKLCTDVNECTSGQNPCHSSTHCLNNVGS

YQCRCRPGWQPIPGSPNGPNNTVCEDVDECSSGQHQCDSSTVCFNTVGSYSCRCRPGWKPR

HGIPNNQKDTVCEDMTFSTWTPPPGVHSQTLSRFFDKVQDLGRDYKPGLANNTIQSILQALD

ELLEAPGDLETLPRLQQHCVASHLLDGLEDVLRGLSKNLSNGLLNFSYPAGTELSLEVQKQV

DRSVTLRQNQAVMQLDWNQAQKSGDPGPSVVGLVSIPGMGKLLAEAPLVLEPEKQMLLHE

THQGLLQDGSPILLSDVISAFLSNNDTQNLSSPVTFTFSHRSVIPRQKVLCVFWEHGQNGCGH

WATTGCSTIGTRDTSTICRCTHLSSFAVLMAHYDVQEEDPVLTVITYMGLSVSLLCLLLAALT

FLLCKAIQNTSTSLHLQLSLCLFLAHLLFLVAIDQTGHKVLCSIIAGTLHYLYLATLTWMLLEA

LYLFLTARNLTVVNYSSINRFMKKLMFPVGYGVPAVTVAISAASRPHLYGTPSRCWLQPEKG

FIWGFLGPVCAIFSVNLVLFLVTLWILKNRLSSLNSEVSTLRNTRMLAFKATAQLFILGCTWC

LGILQVGPAARVMAYLFTIINSLQGVFIFLVYCLLSQQVREQYGKWSKGIRKLKTESEMHTLS

SSAKADTSKPSTVN

>gi|23463303|ref|NP_002557.2|purinergic receptor P2Y11 {Homo sapiens}

(SEQ ID NO: 1150)

MAANVSGAKSCPANFLAAADDKLSGFQGDFLWPILVVEFLVAVASNGLALYRFSIRKQRPW

HPAVVFSVQLAVSDLLCALTLPPLAAYLYPPKHWRYGEAACRLERFLFTCNLLGSVIFITCISL

NRYLGIVHPFFARSHLRPKHAWAVSAAGWVLAALLAMPTLSFSHLKRPQQGAGNCSVARPE

ACIKCLGTADHGLAAYRAYSLVLAGLGCGLPLLLTLAAYGALGRAVLRSPGMTVAEKLRVA

ALVASGVALYASSYVPYHIMRVLNVDARRRWSTRCPSFADIAQATAALELGPYVGYQVMR

GLMPLAFCVHPLLYMAAVPSLGCCCRHCPGYRDSWNPEDAKSTGQALPLNATAAPKPSEPQ

SRELSQ

>gi|23592220|ref|NP_703143.1|G-protein coupled receptor 26 {Homo sapiens}

(SEQ ID NO: 1151)

MNSWDAGLAGLLVGTMGVSLLSNALVLLCLLHSADIRRQAPALFTLNLTCGNLLCTVVNMP

LTLAGVVAQRQPAGDRLCRLAAFLDTFLAANSMLSMAALSIDRWVAVVFPLSYRAKMRLR

DAALMVAYTWLHALTFPAAALALSWLGFHQLYASCTLCSRRPDERLRFAVFTGAFHALSFL

LSFVVLCCTYLKVLKVARFHCKRIDVITMQTLVLLVDLHPSVRERCLEEQKRRRQRATKKIST

FIGTFLVCFAPYVITRLVELFSTVPIGSHWGVLSKCLAYSKAASDPFVYSLLRHQYRKSCKEIL

NRLLHRRSIHSSGLTGDSHSQNILPVSE

>gi|24475871|ref|NP_722579.1|G protein-coupled receptor 114 precursor {Homo sapiens}

(SEQ ID NO: 1152)

MDHCGALFLCLCLLTLQNATTETWEELLSYMENMQVSRGRSSVFSSRQLHQLEQMLLNTSF

PGYNLTLQTPTIQSLAFKLSCDFSGLSLTSATLKRVPQAGGQHARGQHAMQFPAELTRDACK

TRPRELRLICIYFSNTHFFKDENNSSLLNNYVLGAQLSHGHVNNLRDPVNISFWHNQSLEGYT

LTCVFWKEGARKQPWGGWSPEGCRTEQPSHSQVLCRCNHLTYFAVLMQLSPALVPAELLAP

LTYISLVGCSISIVASLITVLLHFHFRKQSDSLTRIHMNLHASVLLLNIAFLLSPAFAMSPVPGS

ACTALAAALHYALLSCLTWMAIEGFNLYLLLGRVYNIYIRRYVFKLGVLGWGAPALLVLLS

LSVKSSVYGPCTIPVFDSWENGTGFQNMSICWVRSPVVHSVLVMGYGGLTSLFNLVVLAWA

LWTLRRLRERADAPSVRACHDTVTVLGLTVLLGTTWALAFFSFGVFLLPQLFLFTILNSLYGF

FLFLWFCSQRCRSEAEAKAQIEAFSSSQTTQ

>gi|24476016|ref|NP_722561.1|G protein-coupled receptor 161 isoform 2 {Homo sapiens}
(SEQ ID NO: 1153)

MSLNSSLSCRKELSNLTEEEGGEGGVIITQFIAIIVITIFVCLGNLVIVVTLYKKSYLLTLSNKFV

FSLTLSNFLLSVLVLPFVVTSSIRREWIFGVVWCNFSALLYLLISSASMLTLGVIAIDRYYAVL

YPMVYPMKITGNRAVMALVYIWLHSLIGCLPPLFGWSSVEFDEFKWMCVAAWHREPGYTA

FWQIWCALFPFLVMLVCYGFIFRVARVKARKVHCGTVVIVEEDAQRTGRKNSSTSTSSSGSR

RNAFQGVVYSANQCKALITILVVLGAFMVTWGPYMVVIASEALWGKSSVSPSLETWATWLS

FASAVCHPLIYGLWNKTVRKELLGMCFGDRYYREPFVQRQRTSRLFSISNRITDLGLSPHLTA

LMAGGQPLGHSSSTGDTGFSCSQDSGTDMMLLEDYTSDDNPPSHCTCPPKRRSSVTFEDEVE

QIKEAAKNSILHVKAEVHKSLDSYAASLAKAIEAEAKINLFGEEALPGVLVTARTVPGGGFG

GRRGSRTLVSQRLQLQSIEEGDVLAAEQR

>gi|28173558|ref|NP_778237.1|trace amine-associated receptor 6 {Homo sapiens}
(SEQ ID NO: 1154)

MSSNSSLLVAVQLCYANVNGSCVKIPFSPGSRVILYIVFGFGAVLAVFGNLLVMISILHFKQLH

SPTNFLVASLACADFLVGVTVMPFSMVRTVESCWYFGRSFCTFHTCCDVAFCYSSLFHLCFIS

IDRYIAVTDPLVYPTKFTVSVSGICISVSWILPLMYSGAVFYTGVYDDGLEELSDALNCIGGCQ

TVVNQNWVLTDFLSFFIPTFIMIILYGNIFLVARRQAKKIENTGSKTESSSESYKARVARRERK

AAKTLGVTVVAFMISWLPYSIDSLIDAFMGFITPACIYEICCWCAYYNSAMNPLIYALFYPWF

RKAIKVIVTGQVLKNSSATMNLFSEHI

>gi|28466969|ref|NP_000944.1|prostaglandin D2 receptor {Homo sapiens}
(SEQ ID NO: 1155)

MKSPFYRCQNTTSVEKGNSAVMGGVLFSTGLLGNLLALGLLARSGLGWCSRRPLRPLPSVFY

MLVCGLTVTDLLGKCLLSPVVLAAYAQNRSLRVLAPALDNSLCQAFAFFMSFFGLSSTLQLL

AMALECWLSLGHPFFYRRHITLRLGALVAPVVSAFSLAFCALPFMGFGKFVQYCPGTWCFIQ

MVHEEGSLSVLGYSVLYSSLMALLVLATVLCNLGAMRNLYAMHRRLQRHPRSCTRDCAEP

RADGREASPQPLEELDHLLLLALMTVLFTMCSLPVIYRAYYGAFKDVKEKNRTSEEAEDLRA

LRFLSVISIVDPWIFIIFRSPVFRIFFHKIFIRPLRYRSRCSNSTNMESSL

>gi|28872720|ref|NP_002555.2|P2Y purinoceptor 2 {Homo sapiens}
(SEQ ID NO: 1156)

MAADLGPWNDTINGTWDGDELGYRCRFNEDFKYVLLPVSYGVVCVPGLCLNAVALYIFLC

RLKTWNASTTYMFHLAVSDALYAASLPLLVYYYARGDHWPFSTVLCKLVRFLFYTNLYCSI

LFLTCISVHRCLGVLRPLRSLRWGRARYARRVAGAVWVLVLACQAPVLYFVTTSARGGRVT

CHDTSAPELFSRFVAYSSVMLGLLFAVPFAVILVCYVLMARRLLKPAYGTSGGLPRAKRKSV

RTIAVVLAVFALCFLPFHVTRTLYYSFRSLDLSCHTLNAINMAYKVTRPLASANSCLDPVLYF

LAGQRLVRFARDAKPPTGPSPATPARRRLGLRRSDRTDMQRIEDVLGSSEDSRRTESTPAGSE

NTKDIRL

>gi|28875799|ref|NP_795344.1|gastrin/cholecystokinin type B receptor {Homo sapiens}
(SEQ ID NO: 1157)

MELLKLNRSVQGTGPGPGASLCRPGAPLLNSSSVGNLSCEPPRIRGAGTRELELAIRITLYAVI

FLMSVGGNMLIIVVLGLSRRLRTVTNAFLLSLAVSDLLLAVACMPFTLLPNLMGTFIFGTVIC

KAVSYLMGVSVSVSTLSLVAIALERYSAICRPLQARVWQTRSHAARVIVATWLLSGLLMVPY

PVYTVVQPVGPRVLQCVHRWPSARVRQTWSVLLLLLLFFIPGVVMAVAYGLISRELYLGLRF

DGDSDSDSQSRVRNQGGLPGAVHQNGRCRPETGAVGEDSDGCYVQLPRSRPALELTALTAP

```
GPGSGSRPTQAKLLAKKRVVRMLLVIVVLFFLCWLPVYSANTWRAFDGPGAHRALSGAPISF

IHLLSYASACVNPLVYCFMHRRFRQACLETCARCCPRPPRARPRALPDEDPPTPSIASLSRLSY

TTISTLGPG
```

>gi|29171311|ref|NP_808219.1|G-protein coupled receptor 109A {Homo sapiens}
(SEQ ID NO: 1158)

```
MNRHHLQDHFLEIDKKNCCVFRDDFIVKVLPPVLGLEFIFGLLGNGLALWIFCFHLKSWKSSR

IFLFNLAVADFLLIICLPFLMDNYVRRWDWKFGDIPCRLMLFMLAMNRQGSIIFLTVVAVDR

YFRVVHPHHALNKISNRTAAIISCLLWGITIGLTVHLLKKKMPIQNGGANLCSSFSICHTFQWH

EAMFLLEFFLPLGIILFCSARIIWSLRQRQMDRHAKIKRAITFIMVVAIVFVICFLPSVVVRIRIF

WLLHTSGTQNCEVYRSVDLAFFITLSFTYMNSMLDPVVYYFSSPSFPNFFSTLINRCLQRKMT

GEPDNNRSTSVELTGDPNKTRGAPEALMANSGEPWSPSYLGPTSP
```

>gi|29171759|ref|NP_001109.2|pituitary adenylate cyclase-activating polypeptide
type I receptor precursor {Homo sapiens}
(SEQ ID NO: 1159)

```
MAGVVHVSLAALLLLPMAPAMHSDCIFKKEQAMCLEKIQRANELMGFNDSSPGCPGMWDN

ITCWKPAHVGEMVLVSCPELFRIFNPDQVWETETIGESDFGDSNSLDLSDMGVVSRNCTEDG

WSEPFPHYFDACGFDEYESETGDQDYYYLSVKALYTVGYSTSLVTLTTAMVILCRFRKLHCT

RNFIHMNLFVSFMLRAISVFIKDWILYAEQDSNHCFISTVECKAVMVFFHYCVVSNYFWLFIE

GLYLFTLLVETFFPERRYFYWYTIIGWGTPTVCVTVWATLRLYFDDTGCWDMNDSTALWW

VIKGPVVGSIMVNFVLFIGIIVILVQKLQSPDMGGNESSIYLRLARSTLLLIPLFGIHYTVFAFSP

ENVSKRERLVFELGLGSFQGFVVAVLYCFLNGEVQAEIKRKWRSWKVNRYFAVDFKHRHPS

LASSGVNGGTQLSILSKSSSQIRMSGLPADNLAT
```

>gi|30023826|ref|NP_835230.1|P2Y purinoceptor 8 {Homo sapiens}
(SEQ ID NO: 1160)

```
MQVPNSTGPDNATLQMLRNPAIAVALPVVYSLVAAVSIPGNLFSLWVLCRRMGPRSPSVIFM

INLSVTDLMLASVLPFQIYYHCNRHHWVFGVLLCNVVTVAFYANMYSSILTMTCISVERFLG

VLYPLSSKRWRRRRYAVAACAGTWLLLLTALSPLARTDLTYPVHALGIITCFDVLKWTMLPS

VAMWAVFLFTIFILLFLIPFVITVACYTATILKLLRTEEAHGREQRRRAVGLAAVVLLAFVTCF

APNNFVLLAHIVSRLFYGKSYYHVYKLTLCLSCLNNCLDPFVYYFASREFQLRLREYLGCRR

VPRDTLDTRRESLFSARTTSVRSEAGAHPEGMEGATRPGLQRQESVF
```

>gi|30425400|ref|NP_848566.1|glucose-dependent insulinotropic receptor {Homo sapiens}
(SEQ ID NO: 1161)

```
MESSFSFGVILAVLASLIIATNTLVAVAVLLLIHKNDGVSLCFTLNLAVADTLIGVAISGLLTD

QLSSPSRPTQKTLCSLRMAFVTSSAAASVLTVMLITFDRYLAIKQPFRYLKIMSGFVAGACIA

GLWLVSYLIGFLPLGIPMFQQTAYKGQCSFFAVFHPHFVLTLSCVGFFPAMLLFVFFYCDMLK

IASMHSQQIRKMEHAGAMAGGYRSPRTPSDFKALRTVSVLIGSFALSWTPFLITGIVQVACQE

CHLYLVLERYLWLLGVGNSLLNPLIYAYWQKEVRLQLYHMALGVKKVLTSFLLFLSARNCG

PERPRESSCHIVTISSSEFDG
```

>gi|30581164|ref|NP_005277.2|neuropeptides B/W receptor type 2 {Homo sapiens}
(SEQ ID NO: 1162)

```
MQAAGHPEPLDSRGSFSLPTMGANVSQDNGTGHNATFSEPLPFLYVLLPAVYSGICAVGLTG

NTAVILVILRAPKMKTVTNVFILNLAVADGLFTLVLPVNIAEHLLQYWPFGELLCKLVLAVD

HYNIFSSIYFLAVMSVDRYLVVLATVRSRHMPWRTYRGAKVASLCVWLGVTVLVLPFFSFA

GVYSNELQVPSCGLSFPWPEQVWFKASRVYTLVLGFVLPVCTICVLYTDLLRRLAVRLRSG

AKALGKARRKVTVLVLVVVLAVCLLCWTPFHLASVVALTTDLPQTPLVISMSYVITSLSYANS

CLNPFLYAFLDDNFRKNFRSILRC
```

-continued

\>gi|30795217|ref|NP_848540.1|chemokine (C-C motif) receptor -like 1 {Homo sapiens}
(SEQ ID NO: 1163)

MALEQNQSTDYYYEENEMNGTYDYSQYELICIKEDVREFAKVFLPVFLTIVFVIGLAGNSMV

VAIYAYYKKQRTKTDVYILNLAVADLLLLFTLPFWAVNAVHGWVLGKIMCKITSALYTLNF

VSGMQFLACISIDRYVAVTKVPSQSGVGKPCWIICFCVWMAAILLSIPQLVFYTVNDNARCIPI

FPRYLGTSMKALIQMLEICIGFVVPFLIMGVCYFITARTLMKMPNIKISRPLKVLLTVVIVFIVT

QLPYNIVKFCRAIDIIYSLITSCNMSKRMDIAIQVTESIALFHSCLNPILYVFMGASFKNYVMKV

AKKYGSWRRQRQSVEEFPFDSEGPTEPTSTFSI

\>gi|31083315|ref|NP_009158.3|probable G-protein coupled receptor 45 {Homo sapiens}
(SEQ ID NO: 1164)

MACNSTSLEAYTYLLLNTSNASDSGSTQLPAPLRISLAIVMLLMTVVGFLGNTVVCIIVYQRP

AMRSAINLLLATLAFSDIMLSLCCMPFTAVTLITVRWHFGDHFCRLSATLYWFFVLEGVAILL

IISVDRFLIIVQRQDKLNPRRAKVIIAVSWVLSFCIAGPSLTGWTLVEVPARAPQCVLGYTELP

ADRAYVVTLVVAVFFAPFGVMLCAYMCILNTVRKNAVRVHNQSDSLDLRQLTRAGLRRLQ

RQQQVSVDLSFKTKAFTTILILFVGFSLCWLPHSVYSLLSVFSQRFYCGSSFYATSTCVLWLSY

LKSVFNPIVYCWRIKKFREACIELLPQTFQILPKVPERIRRRIQPSTVYVCNENQSAV

\>gi|31083344|ref|NP_064707.1|C-X-C chemokine receptor type 7 {Homo sapiens}
(SEQ ID NO: 1165)

MDLHLFDYSEPGNFSDISWPCNSSDCIVVDTVMCPNMPNKSVLLYTLSFIYIFIFVIGMIANSV

VVWVNIQAKTTGYDTHCYILNLAIADLWVVLTIPVWVVSLVQHNQWPMGELTCKVTHLIFS

INLFGSIFFLTCMSVDRYLSITYFTNTPSSRKKMVRRVVCILVWLLAFCVSLPDTYYLKTVTSA

SNNETYCRSFYPEHSIKEWLIGMELVSVVLGFAVPFSIIAVFYFLLARAISASSDQEKHSSRKIIF

SYVVVFLVCWLPYHVAVLLDIFSILHYIPFTCRLEHALFTALHVTQCLSLVHCCVNPVLYSFIN

RNYRYELMKAFIFKYSAKTGLTKLIDASRVSETEYSALEQSTK

\>gi|31657138|ref|NP_000136.2|follicle-stimulating hormone receptor isoform 1 precursor {Homo sapiens}
(SEQ ID NO: 1166)

MALLLVSLLAFLSLGSGCHHRICHCSNRVFLCQESKVTEIPSDLPRNAIELRFVLTKLRVIQKG

AFSGFGDLEKIEISQNDVLEVIEADVFSNLPKLHEIRIEKANNLLYINPEAFQNLPNLQYLLISN

TGIKHLPDVHKIHSLQKVLLDIQDNINIHTIERNSFVGLSFESVILWLNKNGIQEIHNCAFNGTQ

LDELNLSDNNNLEELPNDVFHGASGPVILDISRTRIHSLPSYGLENLKKLRARSTYNLKKLPTL

EKLVALMEASLTYPSHCCAFANWRRQISELHPICNKSILRQEVDYMTQARGQRSSLAEDNES

SYSRGFDMTYTEFDYDLCNEVVDVTCSPKPDAFNPCEDIMGYNILRVLIWFISILAITGNIIVLV

ILTTSQYKLTVPRFLMCNLAFADLCIGIYLLLIASVDIHTKSQYHNYAIDWQTGAGCDAAGFF

TVFASELSVYTLTAITLERWHTITHAMQLDCKVQLRHAASVMVMGWIFAFAAALFPIFGISSY

MKVSICLPMDIDSPLSQLYVMSLLVLNVLAFVVICGCYIHIYLTVRNPNIVSSSSDTRIAKRMA

MLIFTDFLCMAPISFFAISASLKVPLITVSKAKILLVLFHPINSCANPFLYAIFTKNFRRDFFILLS

KCGCYEMQAQIYRTETSSTVHNTHPRNGHCSSAPRVTSGSTYILVPLSHLAQN

\>gi|31881630|ref|NP_000947.2|prostaglandin E2 receptor EP2 subtype {Homo sapiens}
(SEQ ID NO: 1167)

MGNASNDSQSEDCETRQWLPPGESPAISSVMFSAGVLGNLIALALLARRWRGDVGCSAGRR

SSLSLFHVLVTELVFTDLLGTCLISPVVLASYARNQTLVALAPESRACTYFAFAMTFFSLATM

LMLFAMALERYLSIGHPYFYQRRVSRGGLAVLPVIYAVSLLFCSLPLLDYGQYVQYCPGTW

CFIRHGRTAYLQLYATLLLLLIVSVLACNFSVILNLIRMHRRSRRSRCGPSLGSGRGGPGARRR

GERVSMAEETDHLILLAIMTITFAVCSLPFTIFAYMNETSSRKEKWDLQALRFLSINSIIDPWVF

AILRPPVLRLMRSVLCCRISLRTQDATQTSCSTQSDASKQADL

-continued

>gi|31881792|ref|NP_858043.1|leukotriene B4 receptor 1 {Homo sapiens}
(SEQ ID NO: 1168)

MNTTSSAAPPSLGVEFISLLAIILLSVALAVGLPGNSFVVWSILKRMQKRSVTALMVLNLALA

DLAVLLTAPFFLHFLAQGTWSFGLAGCRLCHYVCGVSMYASVLLITAMSLDRSLAVARPFVS

QKLRTKAMARRVLAGIWVLSFLLATPVLAYRTVVPWKTNMSLCFPRYPSEGHRAFHLIFEA

VTGFLLPFLAVVASYSDIGRRLQARRFRRSRRTGRLVVLIILTFAAFWLPYHVVNLAEAGRAL

AGQAAGLGLVGKRLSLARNVLIALAFLSSSVNPVLYACAGGGLLRSAGVGFVAKLLEGTGS

EASSTRRGGSLGQTARSGPAALEPGPSESLTASSPLKLNELN

>gi|32261309|ref|NP_072093.2|probable G-protein coupled receptor 135 {Homo sapiens}
(SEQ ID NO: 1169)

MEEPQPPRPPASMALLGSQHSGAPSAAGPPGGTSSAATAAVLSFSTVATAALGNLSDASGGG

TAAAPGGGGLGGSGAAREAGAAVRRPLGPEAAPLLSHGAAVAAQALVLLLIFLLSSLGNCA

VMGVIVKHRQLRTVTNAFILSLSLSDLLTALLCLPAAFLDLFTPPGGSAPAAAAGPWRGFCA

ASRFFSSCFGIVSTLSVALISLDRYCAIVRPPREKIGRRRALQLLAGAWLTALGFSLPWELLGA

PRELAAAQSFHGCLYRTSPDPAQLGAAFSVGLVVACYLLPFLLMCFCHYHICKTVRLSDVRV

RPVNTYARVLRFFSEVRTATTVLIMIVFVICCWGPYCFLVLLAAARQAQTMQAPSLLSVVAV

WLTWANGAINPVIYAIRNPNISMLLGRNREEGYRTRNVDAFLPSQGPGLQARSRSRLRNRYA

NRLGACNRMSSSNPASGVAGDVAMWARKNPVVLFCREGPPEPVTAVTKQPKSEAGDTSL

>gi|32307152|ref|NP_000907.2|oxytocin receptor {Homo sapiens}
(SEQ ID NO: 1170)

MEGALAANWSAEAANASAAPPGAEGNRTAGPPRRNEALARVEVAVLCLILLLALSGNACVL

LALRTTRQKHSRLFFFMKHLSIADLVVAVFQVLPQLLWDITFRFYGPDLLCRLVKYLQVVGM

FASTYLLLLMSLDRCLAICQPLRSLRRRTDRLAVLATWLGCLVASAPQVHIFSLREVADGVF

DCWAVFIQPWGPKAYITWITLAVYIVPVIVLAACYGLISFKIWQNLRLKTAAAAAEAPEGA

AAGDGGRVALARVSSVKLISKAKIRTVKMTFIIVLAFIVCWTPFFFVQMWSVWDANAPKEAS

AFIIVMLLASLNSCCNPWIYMLFTGHLFHELVQRFLCCSASYLKGRRLGETSASKKSNSSSFV

LSHRSSSQRSCSQPSTA

>gi|32307159|ref|NP_001874.2|corticotropin-releasing factor receptor 2 precursor
{Homo sapiens}
(SEQ ID NO: 1171)

MDAALLHSLLEANCSLALAEELLLDGWGPPLDPEGPYSYCNTTLDQIGTCWPRSAAGALVE

RPCPEYFNGVKYNTTRNAYRECLENGTWASKINYSQCEPILDDKQRKYDLHYRIALVVNYL

GHCVSVAALVAAFLLFLALRSIRCLRNVIHWNLITTFILRNVMWFLLQLVDHEVHESNEVWC

RCITTIFNYFVVTNFFWMFVEGCYLHTAIVMTYSTERLRKCLFLFIGWCIPFPIIVAWAIGKLY

YENEQCWFGKEPGDLVDYIYQGPIILVLLINFVFLFNIVRILMTKLRASTTSETIQYRKAVKAT

LVLLPLLGITYMLFFVNPGEDDLSQIMFIYFNSFLQSFQGFFVSVFYCFFNGEVRSAVRKRWH

RWQDHHSLRVPMARAMSIPTSPTRISFHSIKQTAAV

>gi|32401433|ref|NP_861455.1|G protein-coupled receptor 142 {Homo sapiens}
(SEQ ID NO: 1172)

MSIMMLPMEQKIQWVPTSLQDITAVLGTEAYTEEDKSMVSHAQKSQHSCLSHSRWLRSPQV

TGGSWDLRIRPSKDSSSFRQAQCLRKDPGANNHLESQGVRGTAGDADRELRGPSEKATAGQ

PRVTLLPTPHVSGLSQEFESHWPEIAERSPCVAGVIPVIYYSVLLGLGLPVSLLTAVALARLAT

RTRRPSYYYLLALTASDIIIQVVIVFAGFLLQGAVLARQVPQAVVRTANILEFAANHASVWIAI

LLTVDRYTALCHPLHHRAASSPGRTRRAIAAVLSAALLTGIPFYWWLDMWRDTDSPRTLDE

VLKWAHCLTVYFIPCGVFLVTNSAIIHRLRRRGRSGLQPRVGKSTAILLGITTLFTLLWAPRVF

-continued

VMLYHMYVAPVHRDWRVHLALDVANMVAMLHTAANFGLYCFVSKTFRATVRQVIHDAY

LPCTLASQPEGMAAKPVMEPPGLPTGAEV

>gi|32401435|ref|NP_861456.1|G protein-coupled receptor 141 {Homo sapiens}
(SEQ ID NO: 1173)

MPGHNTSRNSSCDPIVTPHLISLYFIVLIGGLVGVISILFLLVKMNTRSVTTMAVINLVVVHSVF

LLTVPFRLTYLIKKTWMFGLPFCKFVSAMLHIHMYLTFLFYVVILVTRYLIFFKCKDKVEFYR

KLHAVAASAGMWTLVIVIVVPLVVSRYGIHEEYNEEHCFKFHKELAYTYVKIINYMIVIFVIA

VAVILLVFQVFIIMLMVQKLRHSLLSHQEFWAQLKNLFFIGVILVCFLPYQFFRIYYLNVVTHS

NACNSKVAFYNEIFLSVTAISCYDLLLFVFGGSHWFKQKIIGLWNCVLCR

>gi|32483397|ref|NP_000788.2|d(4)dopamine receptor {Homo sapiens}
(SEQ ID NO: 1174)

MGNRSTADADGLLAGRGPAAGASAGASAGLAGQGAAALVGGVLLIGAVLAGNSLVCVSVA

TERALQTPTNSFIVSLAAADLLLALLVLPLFVYSEVQGGAWLLSPRLCDALMAMDVMLCTA

SIFNLCAISVDRFVAVAVPLRYNRQGGSRRQLLLIGATWLLSAAVAAPVLCGLNDVRGRDPA

VCRLEDRDYVVYSSVCSFFLPCPLMLLLYWATFRGLQRWEVARRAKLHGRAPRRPSGPGPP

SPTPPAPRLPQDPCGPDCAPPAPGLPRGPCGPDCAPAAPSLPQDPCGPDCAPPAPGLPPDPCGS

NCAPPDAVRAAALPPQTPPQTRRRRRAKITGRERKAMRVLPVVVGAFLLCWTPFFVVHITQA

LCPACSVPPRLVSAVTWLGYVNSALNPVIYTVFNAEFRNVFRKALRACC

>gi|32490567|ref|NP_871001.1|relaxin-3 receptor 2 {Homo sapiens}
(SEQ ID NO: 1175)

MPTLNTSASPPTFFWANASGGSVLSADDAPMPVKFLALRLMVALAYGLVGAIGLLGNLAVL

WVLSNCARRAPGPPSDTFVFNLALADLGLALTLPFWAAESALDFHWPFGGALCKMVLTATV

LNVYASIFLITALSVARYWVVAMAAGPGTHLSLFWARIATLAVWAAAALVTVPTAVFGVEG

EVCGVRLCLLRFPSRYWLGAYQLQRVVLAFMVPLGVITTSYLLLLAFLQRRQRRQDSRVV

ARSVRILVASFFLCWFPNHVVTLWGVLVKFDLVPWNSTFYTIQTYVFPVTTCLAHSNSCLNP

VLYCLLRREPRQALAGTFRDLRLRLWPQGGGWVQQVALKQVGRRWVASNPRESRPSTLLT

NLDRGTPG

>gi|33598960|ref|NP_000673.2|alpha-2B adrenergic receptor {Homo sapiens}
(SEQ ID NO: 1176)

MDHQDPYSVQATAAIAAAITFLILFTIFGNALVILAVLTSRSLRAPQNLFLVSLAAADILVATLI

IPFSLANELLGYWYFRRTWCEVYLALDVLFCTSSIVHLCAISLDRYWAVSRALEYNSKRTPRR

IKCIILTVWLIAAVISLPPLIYKGDQGPQPRGRPQCKLNQEAWYILASSIGSFFAPCLIMILVYLR

IYLIAKRSNRRGPRAKGGPGQGESKQPRPDHGGALASAKLPALASVASAREVNGHSKSTGEK

EEGETPEDTGTRALPPSWAALPNSGQGQKEGVCGASPEDEAEEEEEEEEEEECEPQAVPVSP

ASACSPPLQQPQGSRVLATLRGQVLLGRGVGAIGGQWWRRRAQLTREKRFTFVLAVVIGVF

VLCWFPFFFSYSLGAICPKHCKVPHGLFQFFFWIGYCNSSLNPVIYTIFNQDFRRAFRRILCRP

WTQTAW

>gi|33695097|ref|NP_005292.2|G protein-coupled receptor 35 {Homo sapiens}
(SEQ ID NO: 1177)

MNGTYNTCGSSDLTWPPAIKLGFYAYLGVLLVLGLLLNSLALWVFCCRMQQWTETRIYMT

NLAVADLCLLCTLPFVLHSLRDTSDTPLCQLSQGIYLTNRYMSISLVTAIAVDRYVAVRHPLR

ARGLRSPRQAAAVCAVLWVLVIGSLVARWLLGIQEGGFCFRSTRHNFNSMAFPLLGFYLPLA

VVVFCSLKVVTALAQRPPTDVGQAEATRKAARMVWANLLVFVVCFLPLHVGLTVRLAVG

WNACALLETIRRALYITSKLSDANCCLDAICYYYMAKEFQEASALAVAPSAKAHKSQDSLCV

TLA

-continued

\>gi|33695104|ref|NP_003599.2|G protein-coupled receptor 65 {Homo sapiens}
(SEQ ID NO: 1178)

MNSTCIEEQHDLDHYLFPIVYIFVIIVSIPANIGSLCVSFLQAKKESELGIYLFSLSLSDLLYALT

LPLWIDYTWNKDNWTFSPALCKGSAFLMYMNFYSSTAFLTCIAVDRYLAVVYPLKFFFLRTR

RFALMVSLSIWILETIFNAVMLWEDETVVEYCDAEKSNFTLCYDKYPLEKWQINLNLFRTCT

GYAIPLVTILICNRKVYQAVRHNKATENKEKKRIIKLLVSITVTFVLCFTPFHVMLLIRCILEHA

VNFEDHSNSGKRTYTMYRITVALTSLNCVADPILYCFVTETGRYDMWNILKFCTGRCNTSQR

QRKRILSVSTKDTMELEVLE

\>gi|33695107|ref|NP_005674.2|G-protein coupled receptor 55 {Homo sapiens}
(SEQ ID NO: 1179)

MSQQNTSGDCLFDGVNELMKTLQFAVHIPTFVLGLLLNLLAIHGFSTFLKNRWPDYAATSIY

MINLAVFDLLLVLSLPFKMVLSQVQSPFPSLCTLVECLYFVSMYGSVFTICFISMDRFLAIRYP

LLVSHLRSPRKIFGICCTIWVLVWTGSIPIYSFHGKVEKYMCFHNMSDDTWSAKVFFPLEVFG

FLLPMGIMGFCCSRSIHILLGRRDHTQDWVQQKACIYSIAASLAVFVVSFLPVHLGFFLQFLV

RNSFIVECRAKQSISFFLQLSMCFSNVNCCLDVFCYYFVIKEFRMNIRAHRPSRVQLVLQDTTI

SRG

\>gi|33695113|ref|NP_005758.2|G-protein coupled purinergic receptor P2Y5 {Homo sapiens}
(SEQ ID NO: 1180)

MVSVNSSHCFYNDSFKYTLYGCMFSMVFVLGLISNCVAIYIFICVLKVRNETTTYMINLAMS

DLLFVFTLPFRIFYFTTRNWPFGDLLCKISVMLFYTNMYGSILFLTCISVDRFLAIVYPFKSKTL

RTKRNAKIVCTGVWLTVIGGSAPAVFVQSTHSQGNNASEACFENFPEATWKTYLSRIVIFIEIV

GFFIPLILNVTCSSMVLKTLTKPVTLSRSKINKTKVLKMIFVHLIIFCFCFVPYNINLILYSLVRT

QTFVNCSVVAAVRTMYPITLCIAVSNCCFDPIVYYFTSDTIQNSIKMKNWSVRRSDFRFSEVH

GAENFIQHNLQTLKSKIFDNESAA

\>gi|34577052|ref|NP_005233.3|proteinase-activated receptor 2 precursor {Homo sapiens}
(SEQ ID NO: 1181)

MRSPSAAWLLGAAILLAASLSCSGTIQGTNRSSKGRSLIGKVDGTSHVTGKGVTVETVFSVDE

FSASVLTGKLTTVFLPIVYTIVFVVGLPSNGMALWVFLFRTKKKHPAVIYMANLALADLLSVI

WFPLKIAYHIHGNNWIYGEALCNVLIGFFYGNMYCSILFMTCLSVQRYWVIVNPMGHSRKK

ANIAIGISLAIWLLILLVTIPLYVVKQTIFIPALNITTCHDVLPEQLLVGDMFNYFLSLAIGVFLF

PAFLTASAYVLMIRMLRSSAMDENSEKKRKRAIKLIVTVLAMYLICFTPSNLLLVVHYFLIKS

QGQSHVYALYIVALCLSTLNSCIDPFVYYFVSHDFRDHAKNALLCRSVRTVKQMQVSLTSKK

HSRKSSSYSSSSTTVKTSY

\>gi|36951012|ref|NP_005270.2|probable G-protein coupled receptor 1 {Homo sapiens}
(SEQ ID NO: 1182)

MEDLEETLFEEFENYSYDLDYYSLESDLEEKVQLGVVHWVSLVLYCLAFVLGIPGNAIVIWF

TGFKWKKTVTTLWFLNLAIADFIFLLFLPLYISYVAMNFHWPFGIWLCKANSFTAQLNMFAS

VFFLTVISLDHYIHLIHPVLSHRHRTLKNSLIVIIFIWLLASLIGGPALYFRDTVEFNNHTLCYNN

FQKHDPDLTLIRHHVLTWVKFIIGYLFPLLTMSICYLCLIFKVKKRSILISSRHFWTILVVVVAF

VVCWTPYHLFSIWELTIHHNSYSHHVMQAGIPLSTGLAFLNSCLNPILYVLISKKFQARFRSSV

AEILKYTLWEVSCSGTVSEQLRNSETKNLCLLETAQ

\>gi|36951034|ref|NP_543009.2|G-protein coupled receptor 78 {Homo sapiens}
(SEQ ID NO: 1183)

MGPGEALLAGLLVMVLAVALLSNALVLLCCAYSAELRTRASGVLLVNLSLGHLLLAALDMP

FTLLGVMRGRTPSAPGACQVIGFLDTFLASNAALSVAALSADQWLAVGFPLRYAGRLRPRY

AGLLLGCAWGQSLAFSGAALGCSWLGYSSAFASCSLRLPPEPERPRFAAFTATLHAVGFVLP

LAVLCLTSLQVHRVARRHCQRMDTVTMKALALLADLHPSVRQRCLIQQKRRRHRATRKIGI

-continued

AIATFLICFAPYVMTRLAELVPFVTVNAQWGILSKCLTYSKAVADPFTYSLLRRPFRQVLAG

MVHRLLKRTPRPASTHDSSLDVAGMVHQLLKRTPRPASTHNGSVDTENDSCLQQTH

>gi|37187860|ref|NP_004358.2|C-C chemokine receptor type 6 {Homo sapiens}
(SEQ ID NO: 1184)

MSGESMNFSDVFDSSEDYFVSVNTSYYSVDSEMLLCSLQEVRQFSRLFVPIAYSLICVFGLLG

NILVVITFAFYKKARSMTDVYLLNMAIADILFVLTLPFWAVSHATGAWVFSNATCKLLKGIY

AINFNCGMLLLTCISMDRYIAIVQATKSFRLRSRTLPRSKIICLVVWGLSVIISSSTFVFNQKYN

TQGSDVCEPKYQTVSEPIRWKLLMLGLELLFGFFIPLMFMIFCYTFIVKTLVQAQNSKRHKAI

RVIIAVVLVFLACQIPHNMVLLVTAANLGKMNRSCQSEKLIGYTKTVTEVLAFLHCCLNPVL

YAFIGQKFRNYFLKILKDLWCVRRKYKSSGFSCAGRYSENISRQTSETADNDNASSFTM

>gi|37577159|ref|NP_000379.2|calcium-sensing receptor precursor {Homo sapiens}
(SEQ ID NO: 1185)

MAFYSCCWVLLALTWHTSAYGPDQRAQKKGDIILGGLFPIHFGVAAKDQDLKSRPESVECIR

YNFRGFRWLQAMIFAIEEINSSPALLPNLTLGYRIFDTCNTVSKALEATLSFVAQNKIDSLNLD

EFCNCSEHIPSTIAVVGATGSGVSTAVANLLGLFYIPQVSYASSSRLLSNKNQFKSFLRTIPNDE

HQATAMADIIEYFRWNWVGTIAADDDYGRPGIEKFREEAEERDICIDFSELISQYSDEEEIQHV

VEVIQNSTAKVIVVFSSGPDLEPLIKEIVRRNITGKIWLASEAWASSSLIAMPQYFHVVGGTIGF

ALKAGQIPGFREFLKKVHPRKSVHNGFAKEFWEETFNCHLQEGAKGPLPVDTFLRGHEESGD

RFSNSSTAFRPLCTGDENISSVETPYIDYTHLRISYNVYLAVYSIAHALQDIYTCLPGRGLFTNG

SCADIKKVEAWQVLKHLRHLNFTNNMGEQVTFDECGDLVGNYSIINWHLSPEDGSIVFKEV

GYYNVYAKKGERLFINEEKILWSGFSREVPFSNCSRDCLAGTRKGIIEGEPTCCFECVECPDGE

YSDETDASACNKCPDDFWSNENHTSCIAKEIEFLSWTEPFGIALTLFAVLGIFLTAFVLGVFIK

FRNTPIVKATNRELSYLLLFSLLCCFSSSLFFIGEPQDWTCRLRQPAFGISFVLCISCILVKTNRV

LLVFEAKIPTSFHRKWWGLNLQFLLVFLCTFMQIVICVIWLYTAPPSSYRNQELEDEIIFITCHE

GSLMALGFLIGYTCLLAAICFFFAFKSRKLPENFNEAKFITFSMLIFFIVWISFIPAYASTYGKFV

SAVEVIAILAASFGLLACIFFNKIYIILFKPSRNTIEEVRCSTAAHAFKVAARATLRRSNVSRKR

SSSLGGSTGSTPSSSISSKSNSEDPFPQPERQKQQQPLALTQQEQQQQPLTLPQQQRSQQQPRC

KQKVIFGSGTVTFSLSFDEPQKNAMAHRNSTHQNSLEAQKSSDTLTRHQPLLPLQCGETDLD

LTVQETGLQGPVGGDQRPEVEDPEELSPALVVSSSQSFVISGGGSTVTENVVNS

>gi|37622910|ref|NP_000729.2|cholinergic receptor, muscarinic 1 {Homo sapiens}
(SEQ ID NO: 1186)

MNTSAPPAVSPNITVLAPGKGPWQVAFIGITTGLLSLATVTGNLLVLISFKVNTELKTVNNYF

LLSLACADLIIGTFSMNLYTTYLLMGHWALGTLACDLWLALDYVASNASVMNLLLISFDRYF

SVTRPLSYRAKRTPRRAALMIGLAWLVSFVLWAPAILFWQYLVGERTVLAGQCYIQFLSQPII

TFGTAMAAFYLPVTVMCTLYWRIYRETENRARELAALQGSETPGKGGGSSSSSERSQPGAEG

SPETPPGRCCRCCRAPRLLQAYSWKEEEEEDEGSMESLTSSEGEEPGSEVVIKMPMVDPEAQ

APTKQPPRSSPNTVKRPTKKGRDRAGKGQKPRGKEQLAKRKTFSLVKEKKAARTLSAILLAF

ILTWTPYNIMVLVSTFCKDCVPETLWELGYWLCYVNSTINPMCYALCNKAFRDTFRLLLLCR

WDKRRWRKIPKRPGSVHRTPSRQC

>gi|38194224|ref|NP_005289.2|G protein-coupled receptor 25 {Homo sapiens}
(SEQ ID NO: 1187)

MAPTEPWSPSPGSAPWDYSGLDGLEELELCPAGDLPYGYVYIPALYLAAFAVGLLGNAFVV

WLLAGRRGPRRLVDTFVLHLAAADLGFVLTLPLWAAAALGGRWPFGDGLCKLSSFALG

TRCAGALLLAGMSVDRYLAVVKLLEARPLRTPRCALASCCGVWAVALLAGLPSLVYRGLQP

-continued

LPGGQDSQCGEEPSHAFQGLSLLLLLLTFVLPLVVTLFCYCRISRRLRRPPHVGRARRNSLRIIF

AIESTFVGSWLPFSALRAVFHLARLGALPLPCPLLLALRWGLTIATCLAFVNSCANPLIYLLLD

RSFRARALDGACGRTGRLARRISSASSLSRDDSSVFRCRAQAANTASASW

>gi|38455410|ref|NP_940799.1|growth hormone secretagogue receptor type 1
isoform 1a {Homo sapiens}

(SEQ ID NO: 1188)

MWNATPSEEPGFNLTLADLDWDASPGNDSLGDELLQLFPAPLLAGVTATCVALFVVGIAGN

LLTMLVVSRFRELRTTTNLYLSSMAFSDLLIFLCMPLDLVRLWQYRPWNFGDLLCKLFQFVS

ESCTYATVLTITALSVERYFAICFPLRAKVVVTKGRVKLVIFVIWAVAFCSAGPIFVLVGVEHE

NGTDPWDTNECRPTEFAVRSGLLTVMVWVSSIFFFLPVFCLTVLYSLIGRKLWRRRRGDAVV

GASLRDQNHKQTVKMLAVVVFAFILCWLPFHVGRYLFSKSFEPGSLEIAQISQYCNLVSFVLF

YLSAAINPILYNIMSKKYRVAVFRLLGFEPFSQRKLSTLKDESSRAWTESSINT

>gi|38455413|ref|NP_002021.3|N-formyl peptide receptor 3 {Homo sapiens}

(SEQ ID NO: 1189)

METNFSIPLNETEEVLPEPAGHTVLWIFSLLVHGVTFVFGVLGNGLVIWVAGFRMTRTVNTIC

YLNLALADFSFSAILPFRMVSVAMREKWPFGSFLCKLVHVMIDINLFVSVYLITIIALDRCICV

LHPAWAQNHRTMSLAKRVMTGLWIFTIVLTLPNFIFWTTISTTNGDTYCIFNFAFWGDTAVE

RLNVFITMAKVFLILHFIIGFSVPMSIITVCYGIIAAKIHRNHMIKSSRPLRVFAAVVASFFICWF

PYELIGILMAVWLKEMLLNGKYKIILVLINPTSSLAFFNSCLNPILYVFMGRNFQERLIRSLPTS

LERALTEVPDSAQTSNTDTTSASPPEETELQAM

>gi|38505172|ref|NP_000948.2|prostaglandin E receptor 3, subtype EP3
isoform 1 {Homo sapiens}

(SEQ ID NO: 1190)

MKETRGYGGDAPFCTRLNHSYTGMWAPERSAEARGNLTRPPGSGEDCGSVSVAFPITMLLT

GFVGNALAMLLVSRSYRRRESKRKKSFLLCIGWLALTDLVGQLLTTPVVIVVYLSKQRWEHI

DPSGRLCTFFGLTMTVFGLSSLFIASAMAVERALAIRAPHWYASHMKTRATRAVLLGVWLA

VLAFALLPVLGVGQYTVQWPGTWCFISTGRGGNGTSSSHNWGNLFFASAFAFLGLLALTVTF

SCNLATIKALVSRCRAKATASQSSAQWGRITTETAIQLMGIMCVLSVCWSPLLIMMLKMIFN

QTSVEHCKTHTEKQKECNFFLIAVRLASLNQILDPWVYLLLRKILLRKFCQMRKRRLREQAP

LLPTSTVIDPSRFCAQPFRWFLDLSFPAMSSSHPQLPLTLASFKLLREPCSVQLS

>gi|38505194|ref|NP_000946.2|prostaglandin E2 receptor EP1 subtype {Homo sapiens}

(SEQ ID NO: 1191)

MSPCGPLNLSLAGEATTCAAPWVPNTSAVPPSGASPALPIFSMTLGAVSNLLALALLAQAAG

RLRRRRSAATFLLFVASLLATDLAGHVIPGALVLRLYTAGRAPAGGACHFLGGCMVFFGLCP

LLLGCGMAVERCVGVTRPLLHAARVSVARARLALAAVAAVALAVALLPLARVGRYELQYP

GTWCFIGLGPPGGWRQALLAGLFASLGLVALLAALVCNTLSGLALLRARWRRRSRPPPAS

GPDSRRRWGAHGPRSASASSASSIASASTFFGGSRSSGSARRARAHDVEMVGQLVGIMVVSC

ICWSPMLVLVALAVGGWSSTSLQRPLFLAVRLASWNQILDPWVYILLRQAVLRQLLRLLPPR

AGAKGGPAGLGLTPSAWEASSLRSSRHSGLSHF

>gi|38678524|ref|NP_859528.1|opsin 5 isoform 1 {Homo sapiens}

(SEQ ID NO: 1192)

MALNHTALPQDERLPHYLRDGDPFASKLSWEADLVAGFYLTIIGILSTFGNGYVLYMSSRRK

KKLRPAEIMTINLAVCDLGISVVGKPFTIISCFCHRWVFGWIGCRWYGWAGFFFGCGSLITMT

AVSLDRYLKICYLSYGVWLKRKHAYICLAAIWAYASFWTTMPLVGLGDYVPEPFGTSCTLD

WWLAQASVGGQVFILNILFFCLLLPTAVIVFSYVKIIAKVKSSSKEVAHFDSRIHSSHVLEMKL

TKVAMLICAGFLIAWIPYAVVSVWSAFGRPDSIPIQLSVVPTLLAKSAAMYNPIIYQVIDYKFA

CCQTGGLKATKKKSLEGFRLHTVTTVRKSSAVLEIHEEWE

-continued

>gi|38683844|ref|NP_057167.2|cannabinoid receptor 1 isoform a {Homo sapiens}
(SEQ ID NO: 1193)
MKSILDGLADTTFRTITTDLLYVGSNDIQYEDIKGDMASKLGYFPQKFPLTSFRGSPFQEKMT

AGDNPQLVPADQVNITEFYNKSLSSFKENEENIQCGENFMDIECFMVLNPSQQLAIAVLSLTL

GTFTVLENLLVLCVILHSRSLRCRPSYHFIGSLAVADLLGSVIFVYSFIDFHVFHRKDSRNVFLF

KLGGVTASFTASVGSLFLTAIDRYISIHRPLAYKRIVTRPKAVVAFCLMWTIAIVIAVLPLLGW

NCEKLQSVCSDIFPHIDETYLMFWIGVTSVLLLFIVYAYMYILWKAHSHAVRMIQRGTQKSIII

HTSEDGKVQVTRPDQARMDIRLAKTLVLILVVLIICWGPLLAIMVYDVFGKMNKLIKTVFAF

CSMLCLLNSTVNPIIYALRSKDLRHAFRSMFPSCEGTAQPLDNSMGDSDCLHKHANNAASVH

RAAESCIKSTVKIAKVTMSVSTDTSAEAL

>gi|38788193|ref|NP_005217.2|sphingosine-1-phosphate receptor 3 {Homo sapiens}
(SEQ ID NO: 1194)
MATALPPRLQPVRGNETLREHYQYVGKLAGRLKEASEGSTLTTVLFLVICSFIVLENLMVLIA

IWKNNKFHNRMYFFIGNLALCDLLAGIAYKVNILMSGKKTFSLSPTVWFLREGSMFVALGAS

TCSLLAIAIERHLTMIKMRPYDANKRHRVFLLIGMCWLIAFTLGALPILGWNCLHNLPDCSTIL

PLYSKKYIAFCISIFTAILVTIVILYARIYFLVKSSSRKVANHNNSERSMALLRTVVIVVSVFIAC

WSPLFILFLIDVACRVQACPILFKAQWFIVLAVLNSAMNPVIYTLASKEMRRAFFRLVCNCLV

RGRGARASPIQPALDPSRSKSSSSNNSSHSPKVKEDLPHTAPSSCIMDKNAALQNGIFCN

>gi|39725940|ref|NP_000903.2|kappa-type opioid receptor {Homo sapiens}
(SEQ ID NO: 1195)
MDSPIQIFRGEPGPTCAPSACLPPNSSAWFPGWAEPDSNGSAGSEDAQLEPAHISPAIPVIITAV

YSVVFVVGLVGNSLVMFVIIRYTKMKTATNIYIFNLALADALVTTTMPFQSTVYLMNSWPFG

DVLCKIVISIDYYNMFTSIFTLTMMSVDRYIAVCHPVKALDFRTPLKAKIINICIWLLSSSVGIS

AIVLGGTKVREDVDVIECSLQFPDDDYSWWDLFMKICVFIFAFVIPVLIIIVCYTLMILRLKSV

RLLSGSREKDRNLRRITRLVLVVVAVFVVCWTPIHIFILVEALGSTSHSTAALSSYYFCIALGY

TNSSLNPILYAFLDENFKRCFRDFCFPLKMRMERQSTSRVRNTVQDPAYLRDIDGMNKPV

>gi|40217829|ref|NP_003476.2|ovarian cancer G-protein coupled receptor 1 {Homo sapiens}
(SEQ ID NO: 1196)
MRSVAPSGPKMGNITADNSSMSCTIDHTIHQTLAPVVYVTVLVVGFPANCLSLYFGYLQIKA

RNELGVYLCNLTVADLFYICSLPFWLQYVLQHDNWSHGDLSCQVCGILLYENIYISVGFLCCI

SVDRYLAVAHPFRFHQFRTLKAAVGVSVVIWAKELLTSIYFLMHEEVIEDENQHRVCFEHYPI

QAWQRAINYYRFLVGFLFPICLLLASYQGILRAVRRSHGTQKSRKDQIQRLVLSTVVIFLACF

LPYHVLLLVRSVWEASCDFAKGVFNAYHFSLLLTSFNCVADPVLYCFVSETTHRDLARLRGA

CLAFLTCSRTGRAREAYPLGAPEASGKSGAQGEEPELLTKLHPAFQTPNSPGSGGFPTGRLA

>gi|40217833|ref|NP_061123.3|G-protein coupled receptor family C group 5 member
C isoform b {Homo sapiens}
(SEQ ID NO: 1197)
MGTQPEPGLGARMAIHKALVMCLGLPLFLFPGAWAQGHVPPGCSQGLNPLYYNLCDRSGA

WGIVLEAVAGAGIVTTFVLTIILVASLPFVQDTKKRSLLGTQVFFLLGTLGLFCLVFACVVKP

DFSTCASRRFLFGVLFAICFSCLAAHVFALNFLARKNHGPRGWVIFTVALLLTLVEVIINTEWL

IITLVRGSGEGGPQGNSSAGWAVASPCAIANMDFVMALIYVMLLLLGAFLGAWPALCGRYK

RWRKHGVFVLLTTATSVAIWVVWIVMYTYGNKQHNSPTWDDPTLAIALAANAWAFVLFYV

IPEVSQVTKSSPEQSYQGDMYPTRGVGYETILKEQKGQSMFVENKAFSMDEPVAAKRPVSPY

SGYNGQLLTSVYQPTEMALMHKVPSEGAYDIILPRATANSQVMGSANSTLRAEDMYSAQSH

QAATPPKDGKNSQVFRNPYVWD

-continued

>gi|40255245|ref|NP_005449.5|gamma-aminobutyric acid type B receptor subunit 2
precursor {Homo sapiens}
(SEQ ID NO: 1198)

MASPRSSGQPGPPPPPPPPPARLLLLLLLPLLLPLAPGAWGWARGAPRPPPSSPPLSIMGLMPL

TKEVAKGSIGRGVLPAVELAIEQIRNESLLRPYFLDLRLYDTECDNAKGLKAFYDAIKYGPNH

LMVFGGVCPSVTSIIAESLQGWNLVQLSFAATTPVLADKKKYPYFFRTVPSDNAVNPAILKLL

KHYQWKRVGTLTQDVQRFSEVRNDLTGVLYGEDIEISDTESFSNDPCTSVKKLKGNDVRIIL

GQFDQNMAAKVFCCAYEENMYGSKYQWIIPGWYEPSWWEQVHTEANSSRCLRKNLLAAM

EGYIGVDFEPLSSKQIKTISGKTPQQYEREYNNKRSGVGPSKFHGYAYDGIWVIAKTLQRAM

ETLHASSRHQRIQDFNYTDHTLGRIILNAMNETNFFGVTGQVVFRNGERMGTIKFTQFQDSRE

VKVGEYNAVADTLEIINDTIRFQGSEPPKDKTIILEQLRKISLPLYSILSALTILGMIMASAFLFF

NIKNRNQKLIKMSSPYMNNLIILGGMLSYASIFLFGLDGSFVSEKTFETLCTVRTWILTVGYTT

AFGAMFAKTWRVHAIFKNVKMKKKIIKDQKLLVIVGGMLLIDLCILICWQAVDPLRRTVEKY

SMEPDPAGRDISIRPLLEHCENTHMTIWLGIVYAYKGLLMLFGCFLAWETRNVSIPALNDSKY

IGMSVYNVGIMCIIGAAVSFLTRDQPNVQFCIVALVIIFCSTITLCLVFVPKLITLRTNPDAATQ

NRRFQFTQNQKKEDSKTSTSVTSVNQASTSRLEGLQSENHRLRMKITELDKDLEEVTMQLQD

TPEKTTYIKQNHYQELNDILNLGNFTESTDGGKAILKNHLDQNPQLQWNTTEPSRTCKDPIED

INSPEHIQRRLSLQLPILHHAYLPSIGGVDASCVSPCVSPTASPRHRHVPPSFRVMVSGL

>gi|40385873|ref|NP_954713.1|G protein-coupled receptor 150 {Homo sapiens}
(SEQ ID NO: 1199)

MEDLFSPSILPPAPNISVPILLGWGLNLTLGQGAPASGPPSRRVRLVFLGVILVVAVAGNTTVL

CRLCGGGGPWAGPKRRKMDFLLVQLALADLYACGGTALSQLAWELLGEPRAATGDLACRF

LQLLQASGRGASAHLVVLIALERRRAVRLPHGRPLPARALAALGWLLALLLALPPAFVVRGD

SPSPLPPPPPPTSLQPGAPPAARAWPGERRCHGIFAPLPRWHLQVYAFYEAVAGFVAPVTVLG

VACGHLLSVWWRHRPQAPAAAAPWSASPGRAPAPSALPRAKVQSLKMSLLLALLFVGCELP

YFAARLAAAWSSGPAGDWEGEGLSAALRVVAMANSALNPFVYLFFQAGDCRLRRQLRKRL

GSLCCAPQGGAEDEEGPRGHQALYRQRWPHPHYHHARREPLDEGGLRPPPPRPRPLPCSCES

AF

>gi|40807489|ref|NP_001965.3|EGF-like module-containing mucin-like hormone
receptor-like 1 precursor {Homo sapiens}
(SEQ ID NO: 1200)

MRGFNLLLFWGCCVMHSWEGHIRPTRKPNTKGNNCRDSTLCPAYATCTNTVDSYYCACKQ

GFLSSNGQNHFKDPGVRCKDIDECSQSPQPCGPNSSCKNLSGRYKCSCLDGFSSPTGNDWVP

GKPGNFSCTDINECLTSSVCPEHSDCVNSMGSYSCSCQVGFISRNSTCEDVDECADPRACPEH

ATCNNTVGNYSCFCNPGFESSSGHLSFQGLKASCEDIDECTEMCPINSTCTNTPGSYFCTCHP

GFAPSNGQLNFTDQGVECRDIDECRQDPSTCGPNSICTNALGSYSCGCIAGFHPNPEGSQKDG

NFSCQRVLFKCKEDVIPDNKQIQQCQEGTAVKPAYVSFCAQINNIFSVLDKVCENKTTVVSLK

NTTESFVPVLKQISTWTKFTKEETSSLATVFLESVESMTLASFWKPSANITPAVRTEYLDIESK

VINKECSEENVTLDLVAKGDKMKIGCSTIEESESTETTGVAFVSFVGMESVLNERFFKDHQAP

LTTSEIKLKMNSRVVGGIMTGEKKDGFSDPIIYTLENIQPKQKFERPICVSWSTDVKGGRWTS

FGCVILEASETYTICSCNQMANLAVIMASGELTMDFSLYIISHVGIIISLVCLVLAIATFLLCRSI

RNHNTYLHLHLCVCLLLAKTLFLAGIHKTDNKMGCAIIAGFLHYLFLACFFWMLVEAVILFL

MVRNLKVVNYFSSRNIKMLHICAFGYGLPMLVVVISASVQPQGYGMHNRCWLNTETGFIWS

-continued

```
FLGPVCTVIVINSLLLTWTLWILRQRLSSVNAEVSTLKDTRLLTFKAFAQLFILGCSWVLGIFQI

GPVAGVMAYLFTIINSLQGAFIFLIHCLLNGQVREEYKRWITGKTKPSSQSQTSRILLSSMPSA

SKTG
```

>gi|41281557|ref|NP_055736.2|latrophilin-1 isoform 2 precursor {Homo sapiens}
(SEQ ID NO: 1201)

```
MARLAAVLWNLCVTAVLVTSATQGLSRAGLPFGLMRRELACEGYPIELRCPGSDVIMVENA

NYGRTDDKICDADPFQMENVQCYLPDAFKIMSQRCNNRTQCVVVAGSDAFPDPCPGTYKYL

EVQYDCVPYIFVCPGTLQKVLEPTSTHESEHQSGAWCKDPLQAGDRIYVMPWIPYRTDTLTE

YASWEDYVAARHTTTYRLPNRVDGTGFVVYDGAVFYNKERTRNIVKYDLRTRIKSGETVIN

TANYHDTSPYRWGGKTDIDLAVDENGLWVIYATEGNNGRLVVSQLNPYTLRFEGTWETGY

DKRSASNAFMVCGVLYVLRSVYVDDDSEAAGNRVDYAFNTNANREEPVSLTFPNPYQFISS

VDYNPRDNQLYVWNNYFVVRYSLEFGPPDPSAGPATSPPLSTTTTARPTPLTSTASPAATTPL

RRAPLTTHPVGAINQLGPDLPPATAPVPSTRRPPAPNLHVSPELFCEPREVRRVQWPATQQGM

LVERPCPKGTRGIASFQCLPALGLWNPRGPDLSNCTSPWVNQVAQKIKSGENAANIASELAR

HTRGSIYAGDVSSSVKLMEQLLDILDAQLQALRPIERESAGKNYNKMHKRERTCKDYIKAVV

ETVDNLLRPEALESWKDMNATEQVHTATMLLDVLEEGAFLLADNVREPARFLAAKENVVL

EVTVLNTEGQVQELVFPQEEYPRKNSIQLSAKTIKQNSRNGVVKVVFILYNNLGLFLSTENAT

VKLAGEAGPGGPGGASLVVNSQVIAASINKESSRVFLMDPVIFTVAHLEDKNHFNANCSFWN

YSERSMLGYWSTQGCRLVESNKTHTTCACSHLTNFAVLMAHREIYQGRINELLLSVITWVGI

VISLVCLAICISTFCFLRGLQTDRNTIHKNLCINLFLAELLFLVGIDKTQYEIACPIFAGLLHYFF

LAAFSWLCLEGVHLYLLLVEVFESEYSRTKYYYLGGYCFPALVVGIAAAIDYRSYGTEKAC

WLRVDNYFIWSFIGPVSFVIVVNLVFLMVTLHKMIRSSSVLKPDSSRLDNIKSWALGAIALLF

LLGLTWAFGLLFINKESVVMAYLFTTFNAFQGVFIFVFHCALQKKVHKEYSKCLRHSYCCIRS

PPGGTHGSLKTSAMRSNTRYYTGTQSRIRRMWNDTVRKQTESSFMAGDINSTPTLNRGTMG

NHLLTNPVLQPRGGTSPYNTLIAESVGFNPSSPPVFNSPGSYREPKHPLGGREACGMDTLPLN

GNFNNSYSLRSGDFPPGDGGPEPPRGRNLADAAAFEKMIISELVHNNLRGSSSAAKGPPPPEP

PVPPVPGGGEEEAGGPGGADRAEIELLYKALEEPLLLPRAQSVLYQSDLDESESCTAEDGAT

SRPLSSPPGRDSLYASGANLRDSPSYPDSSPEGPSEALPPPPPAPPGPPEIYYTSRPPALVARNPL

QGYYQVRRPSHEGYLAAPGLEGPGPDGDGQMQLVTSL
```

>gi|41584200|ref|NP_005673.3|G-protein coupled receptor 56 isoform a precursor {Homo sapiens}
(SEQ ID NO: 1202)

```
MTPQSLLQTTLFLLSLLFLVQGAHGRGHREDFRFCSQRNQTHRSSLHYKPTPDLRISIENSEEA

LTVHAPFPAAHPASRSFPDPRGLYHFCLYWNRHAGRLHLLYGKRDFLLSDKASSLLCFQHQE

ESLAQGPPLLATSVTSWWSPQNISLPSAASFTFSFHSPPHTAAHNASVDMCELKRDLQLLSQF

LKHPQKASRRPSAAPASQQLQSLESKLTSVRFMGDMVSFEEDRINATVWKLQPTAGLQDLHI

HSRQEEEQSEIMEYSVLLPRTLFQRTKGRSGEAEKRLLLVDFSSQALFQDKNSSQVLGEKVLG

IVVQNTKVANLTEPVVLTFQHQLQPKNVTLQCVFWVEDPTLSSPGHWSSAGCETVRRETQTS

CFCNHLTYFAVLMVSSVEVDAVHKHYLSLLSYVGCVVSALACLVTIAAYLCSRVPLPCRRKP

RDYTIKVHMNLLLAVFLLDTSFLLSEPVALTGSEAGCRASAIFLHFSLLTCLSWMGLEGYNLY

RLVVEVFGTYVPGYLLKLSAMGWGFPIFLVTLVALVDVDNYGPIILAVHRTPEGVIYPSMCW

IRDSLVSYITNLGLFSLVFLFNMAMLATMVVQILRLRPHTQKWSHVLTLLGLSLVLGLPWALI

FFSFASGTFQLVVLYLFSIITSFQGFLIFIWYWSMRLQARGGPSPLKSNSDSARLPISSGSTSSSRI
```

>gi|42794265|ref|NP_944605.2|mas-related G-protein coupled receptor member D {Homo sapiens}
(SEQ ID NO: 1203)

MNQTLNSSGTVESALNYSRGSTVHTAYLVLSSLAMFTCLCGMAGNSMVIWLLGFRMHRNPF

CIYILNLAAADLLFLFSMASTLSLETQPLVNTTDKVHELMKRLMYFAYTVGLSLLTAISTQRC

LSVLFPIWFKCHRPRHLSAWVCGLLWTLCLLMNGLTSSFCSKFLKFNEDRCFRVDMVQAALI

MGVLTPVMTLSSLTLFVWVRRSSQQWRRQPTRLFVVVLASVLVFLICSLPLSIYWFVLYWLS

LPPEMQVLCFSLSRLSSSVSSSANPVIYFLVGSRRSHRLPTRSLGTVLQQALREEPELEGGETPT

VGTNEMGA

>gi|42822887|ref|NP_002027.2|Duffy blood group antigen isoform b {Homo sapiens}
(SEQ ID NO: 1204)

MGNCLHRAELSPSTENSSQLDFEDVWNSSYGVNDSFPDGDYGANLEAAAPCHSCNLLDDSA

LPFFILTSVLGILASSTVLFMLFRPLFRWQLCPGWPVLAQLAVGSALFSIVVPVLAPGLGSTRS

SALCSLGYCVWYGSAFAQALLLGCHASLGHRLGAGQVPGLTLGLTVGIWGVAALLTLPVTL

ASGASGGLCTLIYSTELKALQATHTVACLAIFVLLPLGLFGAKGLKKALGMGPGPWMNILW

AWFIFWWPHGVVLGLDFLVRSKLLLLSTCLAQQALDLLLNLAEALAILHCVATPLLLALFCH

QATRTLLPSLPLPEGWSSHLDTLGSKS

>gi|45433552|ref|NP_942122.2|probable G-protein coupled receptor 133 precursor {Homo sapiens}
(SEQ ID NO: 1205)

MEKLLRLCCWYSWLLLFYYNFQVRGVYSRSQDHPGFQVLASASHYWPLENVDGIHELQDT

TGDIVEGKVNKGIYLKEEKGVTLLYYGRYNSSCISKPEQCGPEGVTFSFFWKTQGEQSRPIPS

AYGGQVISNGFKVCSSGGRGSVELYTRDNSMTWEASFSPPGPYWTHVLFTWKSKEGLKVYV

NGTLSTSDPSGKVSRDYGESNVNLVIGSEQDQAKCYENGAFDEFIIWERALTPDEIAMYFTAA

IGKHALLSSTLPSLFMTSTASPVMPTDAYHPIITNLTEERKTFQSPGVILSYLQNVSLSLPSKSLS

EQTALNLTKTFLKAVGEILLLPGWIALSEDSAVVLSLIDTIDTVMGHVSSNLHGSTPQVTVEG

SSAMAEFSVAKILPKTVNSSHYRFPAHGQSFIQIPHEAFHRHAWSTVVGLLYHSMHYYLNNI

WPAHTKIAEAMHHQDCLLFATSHLISLEVSPPPTLSQNLSGSPLITVHLKHRLTRKQHSEATNS

SNRVFVYCAFLDFSSGEGVWSNHGCALTRGNLTYSVCRCTHLTNFAILMQVVPLELARGHQ

VALSSISYVGCSLSVLCLVATLVTFAVLSSVSTIRNQRYHIHANLSFAVLVAQVLLLISFRLEP

GTTPCQVMAVLLHYFFLSAFAWMLVEGLHLYSMVIKVFGSEDSKHRYYYGMGWGFPLLICI

ISLSFAMDSYGTSNNCWLSLASGAIWAFVAPALFVIVVNIGILIAVTRVISQISADNYKIHGDPS

AFKLTAKAVAVLLPILGTSWVFGVLAVNGCAVVFQYMFATLNSLQGLFIFLFHCLLNSEVRA

AFKHKTKVWSLTSSSARTSNAKPFHSDLMNGTRPGMASTKLSPWDKSSHSAHRVDLSAV

>gi|46243671|ref|NP_996880.1|G protein-coupled receptor 152 {Homo sapiens}
(SEQ ID NO: 1206)

MDTTMEADLGATGHRPRTELDDEDSYPQGGWDTVFLVALLLLGLPANGLMAWLAGSQAR

HGAGTRLALLLLSLALSDFLFLAAAAFQILEIRHGGHWPLGTAACRFYYFLWGVSYSSGLFLL

AALSLDRCLLALCPHWYPGHRPVRLPLWVCAGVWVLATLFSVPWLVFPEAAVWWYDLVIC

LDFWDSEELSLRMLEVLGGFLPFLLLLVCHVLTQATACRTCHRQQQPAACRGFARVARTILS

AYVVLRLPYQLAQLLYLAFLWDVYSGYLLWEALVYSDYLILLNSCLSPFLCLMASADLRTLL

RSVLSSFAAALCEERPGSFTPTEPQTQLDSEGPTLPEPMAEAQSQMDPVAQPQVNPTLQPRSD

PTAQPQLNPTAQPQSDPTAQPQLNLMAQPQSDSVAQPQADTNVQTPAPAASSVPSPCDEASP

TPSSHPTPGALEDPATPPASEGESPSSTPPEAAPGAGPT

\>gi|46358417|ref|NP_000831.2|metabotropic glutamate receptor 3 precursor {Homo sapiens}
(SEQ ID NO: 1207)

MKMLTRLQVLTLALFSKGFLLSLGDHNFLRREIKIEGDLVLGGLFPINEKGTGTEECGRINED

RGIQRLEAMLFAIDEINKDDYLLPGVKLGVHILDTCSRDTYALEQSLEFVRASLTKVDEAEY

MCPDGSYAIQENIPLLIAGVIGGSYSSVSIQVANLLRLFQIPQISYASTSAKLSDKSRYDYFART

VPPDFYQAKAMAEILRFFNWTYVSTVASEGDYGETGIEAFEQEARLRNICIATAEKVGRSNIR

KSYDSVIRELLQKPNARVVVLFMRSDDSRELIAAASRANASFTWVASDGWGAQESIIKGSEH

VAYGAITLELASQPVRQFDRYFQSLNPYNNHRNPWFRDFWEQKFQCSLQNKRNHRRVCDK

HLAIDSSNYEQESKIMFVVNAVYAMAHALHKMQRTLCPNTTKLCDAMKILDGKKLYKDYL

LKINFTAPFNPNKDADSIVKFDTFGDGMGRYNVFNFQNVGGKYSYLKVGHWAETLSLDVNS

IHWSRNSVPTSQCSDPCAPNEMKNMQPGDVCCWICIPCEPYEYLADEFTCMDCGSGQWPTA

DLTGCYDLPEDYIRWEDAWAIGPVTIACLGFMCTCMVVTFIKHNNTPLVKASGRELCYILL

FGVGLSYCMTFFFIAKPSPVICALRRLGLGSSFAICYSALLTKTNCIARIFDGVKNGAQRPKFIS

PSSQVFICLGLILVQIVMVSVWLILEAPGTRRYTLAEKRETVILKCNVKDSSMLISLTYDVILVI

LCTVYAFKTRKCPENFNEAKFIGFTMYTTCIIWLAFLPIFYVTSSDYRVQTTTMCISVSLSGFV

VLGCLFAPKVHIILFQPQKNVVTHRLHLNRFSVSGTGTTYSQSSASTYVPTVCNGREVLDSTT

SSL

\>gi|46395496|ref|NP_997055.1|neuropeptide S receptor isoform A {Homo sapiens}
(SEQ ID NO: 1208)

MPANFTEGSFDSSGTGQTLDSSPVACTETVTFTEVVEGKEWGSFYYSFKTEQLITLWVLFVFT

IVGNSVVLFSTWRRKKKSRMTFFVTQLAITDSFTGLVNILTDINWRFTGDFTAPDLVCRVVRY

LQVVLLYASTYVLVSLSIDRYHAIVYPMKFLQGEKQARVLIVIAWSLSFLFSIPTLIIFGKRTLS

NGEVQCWALWPDDSYWTPYMTIVAFLVYFIPLTIISIMYGIVIRTIWIKSKTYETVISNCSDGK

LCSSYNRGLISKAKIKAIKYSIIIILAFICCWSPYFLFDILDNFNLLPDTQERFYASVIIQNLPALN

SAINPLIYCVFSSSISFPCREQRSQDSRMTFRERTERHEMQILSKPEFI

\>gi|47271392|ref|NP_149039.2|succinate receptor 1 {Homo sapiens}
(SEQ ID NO: 1209)

MLGIMAWNATCKNWLAAEEAALEKYYLSIFYGIEFVVGVLGNTIVVYGYIFSLKNWNSSNIYL

FNLSVSDLAFLCTLPMLIRSYANGNWIYGDVLCISNRYVLHANLYTSILFLTFISIDRYLIIKYPF

REHLLQKKEFAILISLAIWVLVTLELLPILPLINPVITDNGTTCNDFASSGDPNYNLIYSMCLTL

LGFLIPLFVMCFFYYKIALFLKQRNRQVATALPLEKPLNLVIMAVVIFSVLFTPYHVMRNVRI

ASRLGSWKQYQCTQVVINSFYIVTRPLAFLNSVINPVFYFLLGDHFRDMLMNQLRHNFKSLT

SFSRWAHELLLSFREK

\>gi|50897278|ref|NP_001002911.1|probable G-protein coupled receptor 139 {Homo sapiens}
(SEQ ID NO: 1210)

MEHTHAHLAANSSLSWWSPGSACGLGFVPVVYYSLLLCLGLPANILTVIILSQLVARRQKSS

YNYLLALAAADILVLFFIVFVDFLLEDFILNMQMPQVPDKIIEVLEFSSIHTSIWITVPLTIDRYI

AVCHPLKYHTVSYPARTRKVIVSVYITCFLTSIPYYWWPNIWTEDYISTSVHHVLIWIHCFTV

YLVPCSIFFILNSIIVYKLRRKSNFRLRGYSTGKTTAILFTITSIFATLWAPRIIMILYHLYGAPIQ

NRWLVHIMSDIANMLALLNTAINFFLYCFISKRFRTMAAATLKAFFKCQKQPVQFYTNHNFSI

TSSPWISPANSHCIKMLVYQYDKNGKPIKVSP

\>gi|52426748|ref|NP_000732.2|cholinergic receptor, muscarinic 4 {Homo sapiens}
(SEQ ID NO: 1211)

MANFTPVNGSSGNQSVRLVTSSSHNRYETVEMVFIATVTGSLSLVTVVGNILVMLSIKVNRQ

LQTVNNYFLFSLACADLIIGAFSMNLYTVYIIKGYWPLGAVVCDLWLALDYVVSNASVMNL

```
LIISFDRYFCVTKPLTYPARRTTKMAGLMIAAAWVLSFVLWAPAILFWQFVVGKRTVPDNQC

FIQFLSNPAVTFGTAIAAFYLPVVIMTVLYIHISLASRSRVHKHRPEGPKEKKAKTLAFLKSPL

MKQSVKKPPPGEAAREELRNGKLEEAPPPALPPPPRPVADKDTSNESSSGSATQNTKERPATE

LSTTEATTPAMPAPPLQPRALNPASRWSKIQIVTKQTGNECVTAIEIVPATPAGMRPAANVAR

KFASIARNQVRKKRQMAARERKVTRTIFAILLAFILTWTPYNVMVLVNTFCQSCIPDTVWSIG

YWLCYVNSTINPACYALCNATFKKTFRHLLLCQYRNIGTAR
```

>gi|52426789|ref|NP_543008.3|2-oxoglutarate receptor 1 {Homo sapiens} (SEQ ID NO: 1212)

```
MNEPLDYLANASDFPDYAAAFGNCTDENIPLKMHYLPVIYGIIFLVGFPGNAVVISTYIFKMR

PWKSSTIIMLNLACTDLLYLTSLPFLIHYYASGENWIFGDFMCKFIRFSFHFNLYSSILFLTCFSI

FRYCVIIHPMSCFSIHKTRCAVVACAVVWIISLVAVIPMTFLITSTNRTNRSACLDLTSSDELNT

IKWYNLILTATTFCLPLVIVTLCYTTIIHTLTHGLQTDSCLKQKARRLTILLLLAFYVCFLPFHIL

RVIRIESRLLSISCSIENQIHEAYIVSRPLAALNTFGNLLLYVVVSDNFQQAVCSTVRCKVSGNL

EQAKKISYSNNP
```

>gi|53828924|ref|NP_005276.2|neuropeptides B/W receptor type 1 {Homo sapiens} (SEQ ID NO: 1213)

```
MDNASFSEPWPANASGPDPALSCSNASTLAPLPAPLAVAVPVVYAVICAVGLAGNSAVLYV

LLRAPRMKTVTNLFILNLAIADELFTLVLPINIADFLLRQWPFGELMCKLIVAIDQYNTFSSLY

FLTVMSADRYLVVLATAESRRVAGRTYSAARAVSLAVWGIVTLVVLPFAVFARLDDEQGRR

QCVLVFPQPEAFWWRASRLYTLVLGFAIPVSTICVLYTTLLCRLHAMRLDSHAKALERAKKR

VTFLVVAILAVCLLCWTPYHLSTVVALTTDLPQTPLVIAISYFITSLSYANSCLNPFLYAFLDA

SFRRNLRQLITCRAAA
```

>gi|55953085|ref|NP_859529.2|G-protein coupled receptor 120 {Homo sapiens} (SEQ ID NO: 1214)

```
MSPECARAAGDAPLRSLEQANRTRFPFFSDVKGDHRLVLAAVETTVLVLIFAVSLLGNVCAL

VLVARRRRGATACLVLNLFCADLLFISAIPLVLAVRWTEAWLLGPVACHLLFYVMTLSGSV

TILTLAAVSLERMVCIVHLQRGVRGPGRRARAVLLALIWGYSAVAALPLCVFFRVVPQRLPG

ADQEISICTLIWPTIPGEISWDVSFVTLNFLVPGLVIVISYSKILQTSEHLLDARAVVTHSEITKA

SRKRLTVSLAYSESHQIRVSQQDFRLFRTLFLLMVSFFIMWSPIIITILLILIQNFKQDLVIWPSLF

FWVVAFTFANSALNPILYNMTLCRNEWKKIFCCFWFPEKGAILTDTSVKRNDLSIISG
```

>gi|55956923|ref|NP_000515.2|5-hydroxytryptamine receptor 1A {Homo sapiens} (SEQ ID NO: 1215)

```
MDVLSPGQGNNTTSPPAPFETGGNTTGISDVTVSYQVITSLLLGTLIFCAVLGNACVVAAIAL

ERSLQNVANYLIGSLAVTDLMVSVLVLPMAALYQVLNKWTLGQVTCDLFIALDVLCCTSSIL

HLCAIALDRYWAITDPIDYVNKRTPRRAAALISLTWLIGFLISIPPMLGWRTPEDRSDPDACTIS

KDHGYTIYSTFGAFYIPLLLMLVLYGRIFRAARFRIRKTVKKVEKTGADTRHGASPAPQPKKS

VNGESGSRNWRLGVESKAGGALCANGAVRQGDDGAALEVIEVHRVGNSKEHLPLPSEAGPT

PCAPASFERKNERNAEAKRKMALARERKTVKTLGIIMGTFILCWLPFFIVALVLPFCESSCHM

PTLLGAIINWLGYSNSLLNPVIYAYFNKDFQNAFKKIIKCKFCRQ
```

>gi|57165355|ref|NP_001008701.1|latrophilin-1 isoform 1 precursor {Homo sapiens} (SEQ ID NO: 1216)

```
MARLAAVLWNLCVTAVLVTSATQGLSRAGLPFGLMRRELACEGYPIELRCPGSDVIMVENA

NYGRTDDKICDADPFQMENVQCYLPDAFKIMSQRCNNRTQCVVVAGSDAFPDPCPGTYKYL

EVQYDCVPYKVEQKVFVCPGTLQKVLEPTSTHESEHQSGAWCKDPLQAGDRIYVMPWIPYR

TDTLTEYASWEDYVAARHTTTYRLPNRVDGTGFVVYDGAVFYNKERTRNIVKYDLRTRIKS

GETVINTANYHDTSPYRWGGKTDIDLAVDENGLWVIYATEGNNGRLVVSQLNPYTLRFEGT
```

-continued

```
WETGYDKRSASNAFMVCGVLYVLRSVYVDDDSEAAGNRVDYAFNTNANREEPVSLTFPNP

YQFISSVDYNPRDNQLYVWNNYFVVRYSLEFGPPDPSAGPATSPPLSTTTTARPTPLTSTASPA

ATTPLRRAPLTTHPVGAINQLGPDLPPATAPVPSTRRPPAPNLHVSPELFCEPREVRRVQWPA

TQQGMLVERPCPKGTRGIASFQCLPALGLWNPRGPDLSNCTSPWVNQVAQKIKSGENAANIA

SELARHTRGSIYAGDVSSSVKLMEQLLDILDAQLQALRPIERESAGKNYNKMHKRERTCKDY

IKAVVETVDNLLRPEALESWKDMNATEQVHTATMLLDVLEEGAFLLADNVREPARFLAAKE

NVVLEVTVLNTEGQVQELVFPQEEYPRKNSIQLSAKTIKQNSRNGVVKVVFILYNNLGLFLST

ENATVKLAGEAGPGGPGGASLVVNSQVIAASINKESSRVFLMDPVIFTVAHLEDKNHFNANC

SFWNYSERSMLGYWSTQGCRLVESNKTHTTCACSHLTNFAVLMAHREIYQGRINELLLSVIT

WVGIVISLVCLAICISTFCFLRGLQTDRNTIHKNLCINLFLAELLFLVGIDKTQYEIACPIFAGLL

HYFFLAAFSWLCLEGVHLYLLLVEVFESEYSRTKYYYLGGYCFPALVVGIAAAIDYRSYGTE

KACWLRVDNYFIWSFIGPVSFVIVVNLVFLMVTLHKMIRSSSVLKPDSSRLDNIKSWALGAIA

LLFLLGLTWAFGLLFINKESVVMAYLFTTFNAFQGVFIFVPHCALQKKVHKEYSKCLRHSYC

CIRSPPGGTHGSLKTSAMRSNTRYYTGTQSRIRRMWNDTVRKQTESSFMAGDINSTPTLNRG

TMGNHLLTNPVLQPRGGTSPYNTLIAESVGFNPSSPPVFNSPGSYREPKHPLGGREACGMDTL

PLNGNFNNSYSLRSGDFPPGDGGPEPPRGRNLADAAAFEKMIISELVHNNLRGSSSAAKGPPP

PEPPVPPVPGGGEEEAGGPGGADRAEIELLYKALEEPLLLPRAQSVLYQSDLDESESCTAED

GATSRPLSSPPGRDSLYASGANLRDSPSYPDSSPEGPSEALPPPPPAPPGPPEIYYTSRPPALVA

RNPLQGYYQVRRPSHEGYLAAPGLEGPGPDGDGQMQLVTSL

>gi|57165371|ref|NP_114142.3|probable G-protein coupled receptor 61 {Homo sapiens}
                                                                  (SEQ ID NO: 1217)
MESSPIPQSSGNSSTLGRVPQTPGPSTASGVPEVGLRDVASESVALFFMLLLDLTAVAGNAAV

MAVIAKTPALRKFVFVPHLCLVDLLAALTLMPLAMLSSSALFDHALFGEVACRLYLFLSVCF

VSLAILSVSAINVERYYYVVHPMRYEVRMTLGLVASVLVGVWVKALAMASVPVLGRVSWE

EGAPSVPPGCSLQWSHSAYCQLFVVVFAVLYFLLPLLLILVVYCSMFRVARVAAMQHGPLPT

WMETPRQRSESLSSRSTMVTSSGAPQTTPHRTFGGGKAAVVLLAVGGQFLLCWLPYFSFHLY

VALSAQPISTGQVESVVTWIGYFCFTSNPFFYGCLNRQIRGELSKQFVCFFKPAPEEELRLPSR

EGSIEENFLQFLQGTGCPSESWVSRPLPSPKQEPPAVDFRIPGQIAEETSEFLEQQLTSDIIMSDS

YLRPAASPRLES

>gi|57977305|ref|NP_919227.2|G protein-coupled receptor 151 {Homo sapiens}
                                                            (SEQ ID NO: 1218)
MLAAAFADSNSSSMNVSFAHLHFAGGYLPSDSQDWRTIIPALLVAVCLVGFVGNLCVIGILL

HNAWKGKPSMIHSLILNLSLADLSLLLFSAPIRATAYSKSVWDLGWFVCKSSDWFIHTCMAA

KSLTIVVVAKVCFMYASDPAKQVSIHNYTIWSVLVAIWTVASLLPLPEWFFSTIRHHEGVEM

CLVDVPAVAEEFMSMFGKLYPLLAFGLPLFFASFYFWRAYDQCKKRGTKTQNLRNQIRSKQ

VTVMLLSIAIISALLWLPEWVAWLWVWHLKAAGPAPPQGFIALSQVLMFSISSANPLIFLVMS

EEFREGLKGVWKWMITKKPPTVSESQETPAGNSEGLPDKVPSPESPASIPEKEKPSSPSSGKGK

TEKAEIPILPDVEQFWHERDTVPSVQDNDPIPWEHEDQETGEGVK

>gi|58530851|ref|NP_000814.2|growth hormone-releasing hormone receptor isoform a
precursor
{Homo sapiens}
                                                            (SEQ ID NO: 1219)
MDRRMWGAHVFCVLSPLPTVLGHMHPECDFITQLREDESACLQAAEEMPNTTLGCPATWD

GLLCWPTAGSGEWVTLPCPDFFSHFSSESGAVKRDCTITGWSEPFPPYPVACPVPLELLAEEE
```

-continued

SYFSTVKIIYTVGHSISIVALFVAITILVALRRLHCPRNYVHTQLFTTFILKAGAVFLKDAALFH

SDDTDHCSFSTVLCKVSVAASHFATMTNFSWLLAEAVYLNCLLASTSPSSRRAFWWLVLAG

WGLPVLFTGTWVSCKLAFEDIACWDLDDTSPYWWIIKGPIVLSVGVNFGLFLNIIRILVRKLE

PAQGSLHTQSQYWRLSKSTLFLIPLFGIHYIIFNFLPDNAGLGIRLPLELGLGSFQGFIVAILYCF

LNQEVRTEISRKWHGHDPELLPAWRTRAKWTTPSRSAAKVLTSMC

>gi|59710093|ref|NP_722576.3|probable G-protein coupled receptor 112 {Homo sapiens}
(SEQ ID NO: 1220)

MKEHIIYQKLYGLILMSSFIFLSDTLSLKGKKLDFFGRGDTYVSLIDTIPELSRFTACIDLVFMD

DNSRYWMAFSYITNNALLGREDIDLGLAGDHQQLILYRLGKTFSIRHHLASFQWHTICLIWD

GVKGKLELFLNKERILEVTDQPHNLTPHGTLFLGHFLKNESSEVKSMMRSFPGSLYYFQLWD

HILENEEFMKCLDGNIVSWEEDVWLVNKIIPTVDRTLRCFVPENMTIQEKSTTVSQQIDMTTP

SQITGVKPQNTAHSSTLLSQSIPIFATDYTTISYSNTTSPPLETMTAQKILKTLVDETATFAVDV

LSTSSAISLPTQSISIDNTTNSMKKTKSPSSESTKTTKMVEAMATEIFQPPTPSNFLSTSRFTKNS

VVSTTSAIKSQSAVTKTTSLFSTIESTSMSTTPCLKQKSTNTGALPISTAGQEFIESTAAGTVPW

FTVEKTSPASTHVGTASSFPPEPVLISTAAPVDSVFPRNQTAFPLATTDMKIAFTVHSLTLPTRL

IETTPAPRTAETELTSTNFQDVSLPRVEDAMSTSMSKETSSKTFSFLTSFSFTGTESVQTVIDAE

ATRTALTPEITLASTVAETMLSSTITGRVYTQNTPTADGHLLTLMSTRSASTSKAPESGPTSTT

DEAAHLFSSNETIWTSRPDQALLASMNTTTILTFVPNENFTSAFHENTTYTEYLSATTNITPLK

ASPEGKGTTANDATTARYTTAVSKLTSPWFANFSIVSGTTSITNMPEFKLTTLLLKTIPMSTKP

ANELPLTPRETVVPSVDIISTLACIQPNFSTEESASETTQTEINGAIVFGGTTTPVPKSATTQRLN

ATVTRKEATSHYLMRKSTIAAVAEVSPFSTMLEVTDESAQRVTASVTVSSFPDIEKLSTPLDN

KTATTEVRESWLLTKLVKTTPRSSYNEMTEMFNFNHTYVAHWTSETSEGISAGSPTSGSTHIF

GEPLGASTTRISETSFSTTPTDRTATSLSDGILPPQPTAAHSSATPVPVTHMFSLPVNGSSVVAE

ETEVTMSEPSTLARAFSTSVLSDVSNLSSTTMTTALVPPLDQTASTTIVIVPTHGDLIRTTSEAT

VISVRKTSMAVPSLTETPFHSLRLSTPVTAKAETTLFSTSVDTVTPSTHTLVCSKPPPDNIPPAS

STHVISTTSTPEATQPISQVEETSTYALSFPYTFSGGGVVASLATGTTETSVVDETTPSHISANK

LTTSVNSHISSSATYRVHTPVSIQLVTSTSVLSSDKDQMTISLGKTPRTMEVTEMSPSKNSFISY

SRGTPSLEMTDTGFPETTKISSHQTHSPSEIPLGTPSDGNLASSPTSGSTQITPTLTSSNTVGVHI

PEMSTSLGKTALPSQALTITTFLCPEKESTSALPAYTPRTVEMIVNSTYVTHSVSYGQDTSFVD

TTTSSSTRISNPMDINTTFSHLHSLRTQPEVTSVASFISESTQTFPESLSLSTAGLYNDGFTVLSD

RITTAFSVPNVPTMLPRESSMATSTPIYQMSSLPVNVTAFTSKKVSDTPPIVITKSSKTMHPGC

LKSPCTATSGPMSEMSSIPVNNSAFTPATVSSDTSTRVGLFSTLLSSVTPRTTMTMQTSTLDVT

PVIYAGATSKNKMVSSAFTTEMIEAPSRITPTTFLSPTEPTLPFVKTVPTTIMAGIVTPFVGTTA

FSPLSSKSTGAISSIPKTTFSPFLSATQQSSQADEATTLGILSGITNRSLSTVNSGTGVALTDTYS

RITVPENMLSPTHADSLHTSFNIQVSPSLTSFKSASGPTKNVKTTTNCFSSNTRKMTSLLEKTS

LTNYATSLNTPVSYPPWTPSSATLPSLTSFVYSPHSTEAEISTPKTSPPPTSQMVEFPVLGTRMT

SSNTQPLLMTSWNIPTAEGSQFPISTTINVPTSNEMETETLHLVPGPLSTFTASQTGLVSKDVM

AMSSIPMSGILPNHGLSENPSLSTSLRAITSTLADVKHTFEKMTTSVTPGTTLPSILSGATSGSVI

SKSPILTWLLSSLPSGSPPATVSNAPHVMTSSTVEVSKSTFLTSDMISAHPFTNLTTLPSATMST

ILTRTIPTPTLGGITTGFPTSLPMSINVTDDIVYISTHPEASSRTTITANPRTVSHPSSFSRKTMSP

STTDHTLSVGAMPLPSSTITSSWNRIPTASSPSTLIIPKPTLDSLLNIMTTTSTVPGASFPLISTGV

TYPFTATVSSPISSFFETTWLDSTPSFLSTEASTSPTATKSTVSFYNVEMSFSVFVEEPRIPITSVI

```
NEFTENSLNSIFQNSEFSLATLETQIKSRDISEEEMVMDRAILEQREGQEMATISYVPYSCVCQ

VIIKASSSLASSELMRKIKSKIHGNFTHGNFTQDQLTLLVNCEHVAVKKLEPGNCKADETASK

YKGTYKWLLTNPTETAQTRCIKNEDGNATRFCSISINTGKSQWEKPKFKQCKLLQELPDKIV

DLANITISDENAEDVAEHILNLINESPALGKEETKIIVSKISDISQCDEISMNLTHVMLQIINVVL

EKQNNSASDLHEISNEILRIIERTGHKMEFSGQIANLTVAGLALAVLRGDHTFDGMAFSIHSYE

EGTDPEIFLGNVPVGGILASIYLPKSLTERIPLSNLQTILFNFFGQTSLFKTKNVTKALTTYVVS

ASISDDMFIQNLADPVVITLQHIGGNQNYGQVHCAFWDFENNNGLGGWNSSGCKVKETNVN

YTICQCDHLTHFGVLMDLSRSTVDSVNEQILALITYTGCGISSIFLGVAVVTYIAFHKLRKDYP

AKILINLCTALLMLNLVFLINSWLSSFQKVGVCITAAVALHYFLLVSFTWMGLEAVHMYLAL

VKVFNIYIPNYILKFCLVGWGIPAIMVAITVSVKKDLYGTLSPTTPFCWIKDDSIFYISVVAYFC

LIFLMNLSMFCTVLVQLNSVKSQIQKTRRKMILHDLKGTMSLTFLLGLTWGFAFFAWGPMR

NFFLYLFAIFNTLQGFFIFVFHCVMKESVREQWQIHLCCGWLRLDNSSDGSSRCQIKVGYKQE

GLKKIFEHKLLTPSLKSTATSSTFKSLGSAQGTPSEISFPNDDFDKDPYCSSP
```

>gi|59823631|ref|NP_660333.2|probable G-protein coupled receptor 125 precursor {Homo sapiens} (SEQ ID NO: 1221)

```
MEPPGRRRGRAQPPLLLPLSLLALLALLGGGGGGAAALPAGCKHDGRPRGAGRAAGAAE

GKVVCSSLELAQVLPPDTLPNRTVTLILSNNKISELKNGSFSGLSLLERLDLRNNLISSIDPGAF

WGLSSLKRLDLTNNRIGCLNADIFRGLTNLVRLNLSGNLFSSLSQGTFDYLASLRSLEFQTEY

LLCDCNILWMHRWVKEKNITVRDTRCVYPKSLQAQPVTGVKQELLTCDPPLELPSFYMTPSH

RQVVFEGDSLPFQCMASYIDQDMQVLWYQDGRIVETDESQGIFVEKNMIHNCSLIASALTISN

IQAGSTGNWGCHVQTKRGNNTRTVDIVVLESSAQYCPPERVVNNKGDFRWPRTLAGITAYL

QCTRNTHGSGIYPGNPQDERKAWRRCDRGGFWADDDYSRCQYANDVTRVLYMFNQMPLN

LTNAVATARQLLAYTVEAANFSDKMDVIFVAEMIEKFGRFTKEEKSKELGDVMVDIASNIML

ADERVLWLAQREAKACSRIVQCLQRIATYRLAGGAHVYSTYSPNIALEAYVIKSTGFTGMTC

TVFQKVAASDRTGLSDYGRRDPEGNLDKQLSFKCNVSNTFSSLALKNTIVEASIQLPPSLFSPK

QKRELRPTDDSLYKLQLIAFRNGKLFPATGNSTNLADDGKRRTVVTPVILTKIDGVNVDTHHI

PVNVTLRRIAHGADAVAARWDFDLLNGQGGWKSDGCHILYSDENITTIQCYSLSNYAVLMD

LTGSELYTQAASLLHPVVYTTAIILLLCLLAVIVSYIYHHSLIRISLKSWHMLVNLCFHIFLTCV

VFVGGITQTRNASICQAVGIILHYSTLATVLWVGVTARNIYKQVTKKAKRCQDPDEPPPPRP

MLRFYLIGGGIPIIVCGITAAANIKNYGSRPNAPYCWMAWEPSLGAFYGPASFITFVNCMYFL

SIFIQLKRHPERKYELKEPTEEQQRLAANENGEINHQDSMSLSLISTSALENEHTFHSQLLGAS

LTLLLYVALWMFGALAVSLYYPLDLVFSFVFGATSLSFSAFFVVHHCVNREDVRLAWIMTC

CPGRSSYSVQVNVQPPNSNGTNGEAPKCPNSSAESSCTNKSASSFKNSSQGCKLTNLQAAAA

QCHANSLPLNSTPQLDNSLTEHSMDNDIKMHVAPLEVQFRTNVHSSRHHKNRSKGHRASRL

TVLREYAYDVPTSVEGSVQNGLPKSRLGNNEGHSRSRRAYLAYRERQYNPPQQDSSDACST

LPKSSRNFEKPVSTTSKKDALRKPAVVELENQQKSYGLNLAIQNGPIKSNGQEGPLLGTDSTG

NVRTGLWKHETTV
```

>gi|61743940|ref|NP_722582.2|probable G-protein coupled receptor 110 isoform 1 {Homo sapiens} (SEQ ID NO: 1222)

```
MKVGVLWLISFFTFTDGHGGFLGKNDGIKTKKELIVNKKKHLGPVEEYQLLLQVTYRDSKE

KRDLRNFLKLLKPPLLWSHGLIRIIRAKATTDCNSLNGVLQCTCEDSYTWFPPSCLDPQNCYL
```

-continued

HTAGALPSCECHLNNLSQSVNFCERTKIWGTFKINERFTNDLLNSSSAIYSKYANGIEIQLKKA

YERIQGFESVQVTQFRNGSIVAGYEVVGSSSASELLSAIEHVAEKAKTALHKLFPLEDGSFRV

FGKAQCNDIVFGFGSKDDEYTLPCSSGYRGNITAKCESSGWQVIRETCVLSLLEELNKNFSMI

VGNATEAAVSSFVQNLSVIIRQNPSTTVGNLASVVSILSNISSLSLASHFRVSNSTMEDVISIAD

NILNSASVTNWTVLLREEKYASSRLLETLENISTLVPPTALPLNFSRKFIDWKGIPVNKSQLKR

GYSYQIKMCPQNTSIPIRGRVLIGSDQFQRSLPETIISMASLTLGNILPVSKNGNAQVNGPVIST

VIQNYSINEVFLFFSKIESNLSQPHCVFWDFSHLQWNDAGCHLVNETQDIVTCQCTHLTSFSIL

MSPFVPSTIFPVVKWITYVGLGISIGSLILCLIIEALFWKQIKKSQTSHTRRICMVNIALSLLIAD

VWFIVGATVDTTVNPSGVCTAAVFFTHFFYLSLFFWMLMLGILLAYRIILVFHHMAQHLMM

AVGFCLGYGCPLIISVITIAVTQPSNTYKRKDVCWLNWSNGSKPLLAFVVPALAIVAVNFVVV

LLVLTKLWRPTVGERLSRDDKATIIRVGKSLLILTPLLGLTWGFGIGTIVDSQNLAWHVIFALL

NAFQGFFILCFGILLDSKLRQLLFNKLSALSSWKQTEKQNSSDLSAKPKFSKPFNPLQNKGHY

AFSHTGDSSDNIMLTQFVSNE

>gi|62865887|ref|NP_115940.2|kiSS-1 receptor {Homo sapiens}                                                     (SEQ ID NO: 1223)

MHTVATSGPNASWGAPANASGCPGCGANASDGPVPSPRAVDAWLVPLFFAALMLLGLVGN

SLVIYVICRHKPMRTVTNFYIANLAATDVTFLLCCVPFTALLYPLPGWVLGDFMCKFVNYIQ

QVSVQATCATLTAMSVDRWYVTVFPLRALHRRTPRLALAVSLSIWVGSAAVSAPVLALHRL

SPGPRAYCSEAFPSRALERAFALYNLLALYLLPLLATCACYAAMLRHLGRVAVRPAPADSAL

QGQVLAERAGAVRAKVSRLVAAVVLLFAACWGPIQLFLVLQALGPAGSWHPRSYAAYALK

TWAHCMSYSNSALNPLLYAFLGSHFRQAFRRVCPCAPRRPRRPRRPGPSDPAAPHAELLRLG

SHPAPARAQKPGSSGLAARGLCVLGEDNAPL

>gi|62912472|ref|NP_067649.2|leucine-rich repeat-containing G
protein-coupled receptor 6 isoform 2 {Homo sapiens}                                                             (SEQ ID NO: 1224)

MGRPRLTLVCQVSIIISARDLSMNNLTELQPGLFHHLRFLEELRLSGNHLSHIPGQAFSGLYSL

KILMLQNNQLGGIPAEALWELPSLQSLRLDANLISLVPERSFEGLSSLRHLWLDDNALTEIPVR

ALNNLPALQAMTLALNRISHIPDYAFQNLTSLVVLHLHNNRIQHLGTHSFEGLHNLETLDLN

YNKLQEFPVAIRTLGRLQELGFHNNNIKAIPEKAFMGNPLLQTIHFYDNPIQFVGRSAFQYLPK

LHTLSLSNGAMDIQEFPDLKGTTSLEILTLTRAGIRLLPSGMCQQLPRLRVLELSHNQIEELPSL

HRCQKLEEIGLQHNRIWEIGADTFSQLSSLQALDLSWNAIRSIHPEAFSTLHSLVKLDLTDNQL

TTLPLAGLGGLMHLKLKGNLALSQAFSKDSFPKLRILEVPYAYQCCPYGMCASFFKASGQW

EAEDLHLDDEESSKRPLGLLARQAENHYDQDLDELQLEMEDSKPHPSVQCSPTPGPFKPCEY

LFESWGIRLAVWAIVLLSVLCNGLVLLTVFAGGPVPLPPVKFVVGAIAGANTLTGISCGLLAS

VDALTFGQFSEYGARWETGLGCRATGFLAVLGSEASVLLLTLAAVQCSVSVSCVRAYGKSP

SLGSVRAGVLGCLALAGLAAALPLASVGEYGASPLCLPYAPPEGQPAALGFTVALVMMNSF

CFLVVAGAYIKLYCDLPRGDFEAVWDCAMVRHVAWLIFADGLLYCPVAFLSFASMLGLFPV

TPEAVKSVLLVVLPLPACLNPLLYLLFNPHFRDDLRRLRPRAGDSGPLAYAAAGELEKSSCDS

TQALVAFSDVDLILEASEAGRPPGLETYGFPSVTLISCQQPGAPRLEGSHCVEPEGNHFGNPQP

SMDGELLLRAEGSTPAGGGLSGGGGFQPSGLAFASHV

>gi|63477962|ref|NP_000902.3|delta-type opioid
receptor {Homo sapiens}                                                                                         (SEQ ID NO: 1225)

MEPAPSAGAELQPPLFANASDAYPSACPSAGANASGPPGARSASSLALAIAITALYSAVCAVG

LLGNVLVMFGIVRYTKMKTATNIYIFNLALADALATSTLPFQSAKYLMETWPFGELLCKAVL

-continued

SIDYYNMFTSIFTLTMMSVDRYIAVCHPVKALDFRTPAKAKLINICIWVLASGVGVPIMVMA

VTRPRDGAVVCMLQFPSPSWYWDTVTKICVFLFAFVVPILIITVCYGLMLLRLRSVRLLSGSK

EKDRSLRRITRMVLVVVGAFVVCWAPIHIFVIVWTLVDIDRRDPLVVAALHLCIALGYANSSL

NPVLYAFLDENFKRCFRQLCRKPCGRPDPSSFSRAREATARERVTACTPSDGPGGGAAA

>gi|64085121|ref|NP_000360.2|thyroid stimulating hormone receptor isoform
1 precursor {Homo sapiens}
(SEQ ID NO: 1226)
MRPADLLQLVLLLDLPRDLGGMGCSSPPCECHQEEDFRVTCKDIQRIPSLPPSTQTLKLIETHL

RTIPSHAFSNLPNISRIYVSIDVTLQQLESHSFYNLSKVTHIEIRNTRNLTYIDPDALKELPLLKF

LGIFNTGLKMFPDLTKVYSTDIFFILEITDNPYMTSIPVNAFQGLCNETLTLKLYNNGFTSVQG

YAFNGTKLDAVYLNKNKYLTVIDKDAFGGVYSGPSLLDVSQTSVTALPSKGLEHLKELIARN

TWTLKKLPLSLSFLHLTRADLSYPSHCCAFKNQKKIRGILESLMCNESSMQSLRQRKSVNALN

SPLHQEYEENLGDSIVGYKEKSKFQDTHNNAHYYVFFEEQEDEIIGFGQELKNPQEETLQAFD

SHYDYTICGDSEDMVCTPKSDEFNPCEDIMGYKFLRIVVWFVSLLALLGNVFVLLILLTSHYK

LNVPRFLMCNLAFADFCMGMYLLLIASVDLYTHSEYYNHAIDWQTGPGCNTAGFFTVFASE

LSVYTLTVITLERWYAITFAMRLDRKIRLRHACAIMVGGWVCCFLLALLPLVGISSYAKVSIC

LPMDTETPLALAYIVFVLTLNIVAFVIVCCCYVKIYITVRNPQYNPGDKDTKIAKRMAVLIFTD

FICMAPISFYALSAILNKPLITVSNSKILLVLFYPLNSCANPFLYAIFTKAFQRDVFILLSKFGICK

RQAQAYRGQRVPPKNSTDIQVQKVTHEMRQGLHNMEDVYELIENSHLTPKKQGQISEEYMQ

TVL

>gi|66529100|ref|NP_000830.2|metabotropic glutamate receptor 2 isoform a precursor {Homo
sapiens}
(SEQ ID NO: 1227)
MGSLLALLALLLLWGAVAEGPAKKVLTLEGDLVLGGLFPVHQKGGPAEDCGPVNEHRGIQR

LEAMLFALDRINRDPHLLPGVRLGAHILDSCSKDTHALEQALDFVRASLSRGADGSRHICPDG

SYATHGDAPTAITGVIGGSYSDVSIQVANLLRLFQIPQISYASTSAKLSDKSRYDYFARTVPPD

FFQAKAMAEILRFFNWTYVSTVASEGDYGETGIEAFELEARARNICVATSEKVGRAMSRAAF

EGVVRALLQKPSARVAVLFTRSEDARELLAASQRLNASFTWVASDGWGALESVVAGSEGA

AEGAITIELASYPISDFASYFQSLDPWNNSRNPWFREFWEQRFRCSFRQRDCAAHSLRAVPFE

QESKIMFVVNAVYAMAHALHNMHRALCPNTTRLCDAMRPVNGRRLYKDFVLNVKFDAPFR

PADTHNEVRFDRFGDGIGRYNIFTYLRAGSGRYRYQKVGYWAEGLTLDTSLIPWASPSAGPL

PASRCSEPCLQNEVKSVQPGEVCCWLCIPCQPYEYRLDEFTCADCGLGYWPNASLTGCFELP

QEYIRWGDAWAVGPVTIACLGALATLFVLGVFVRHNATPVVKASGRELCYILLGGVFLCYC

MTFIFIAKPSTAVCTLRRLGLGTAFSVCYSALLTKTNRIARIFGGAREGAQRPRFISPASQVAIC

LALISGQLLIVVAWLVVEAPGTGKETAPERREVVTLRCNHRDASMLGSLAYNVLLIALCTLY

AFKTRKCPENFNEAKFIGFTMYTTCIIWLAFLPIFYVTSSDYRVQTTTMCVSVSLSGSVVLGCL

FAPKLHIILFQPQKNVVSHRAPTSRFGSAAARASSSLGQGSGSQFVPTVCNGREVVDSTTSSL

>gi|68215224|ref|NP_003956.2|C-C chemokine receptor-like 2 isoform 1 {Homo sapiens}
(SEQ ID NO: 1228)
MANYTLAPEDEYDVLIEGELESDEAEQCDKYDAQALSAQLVPSLCSAVFVIGVLDNLLVVLI

LVKYKGLKRVENIYLLNLAVSNLCFLLTLPFWAHAGGDPMCKILIGLYFVGLYSETFFNCLLT

VQRYLVFLHKGNFFSARRRVPCGIITSVLAWVTAILATLPEFVVYKPQMEDQKYKCAFSRTPF

LPADETFWKHFLTLKMNISVLVLPLFIFTFLYVQMRKTLRFREQRYSLFKLVFAIMVVFLLM

```
WAPYNIAFFLSTFKEHFSLSDCKSSYNLDKSVHITKLIATTHCCINPLLYAFLDGTFSKYLCRC

FHLRSNTPLQPRGQSAQGTSREEPDHSTEV
```

>gi|71773208|ref|NP_000674.2|alpha-2 C adrenergic receptor {Homo sapiens}  (SEQ ID NO: 1229)

```
MASPALAAALAVAAAAGPNASGAGERGSGGVANASGASWGPPRGQYSAGAVAGLAAVVG

FLIVFTVVGNVLVVIAVLTSRALRAPQNLFLVSLASADILVATLVMPFSLANELMAYWYFGQ

VWCGVYLALDVLFCTSSIVHLCAISLDRYWSVTQAVEYNLKRTPRRVKATIVAVWLISAVIS

FPPLVSLYRQPDGAAYPQCGLNDETWYILSSCIGSFFAPCLIMGLVYARIVRVAKLRTRTLSE

KRAPVGPDGASPTTENGLGAAAGAGENGHCAPPPADVEPDESSAAAERRRRRGALRRGGRR

RAGAEGGAGGADGQGAGPGAAESGALTASRSPGPGGRLSRASSRSVEFFLSRRRRARSSVCR

RKVAQAREKRFTFVLAVVMGVFVLCWFPFFFSYSLYGICREACQVPGPLFKFFFWIGYCNSS

LNPVIYTVFNQDFRRSFKHILFRRRRRGFRQ
```

>gi|71999131|ref|NP_055137.2|opsin-3 {Homo sapiens}  (SEQ ID NO: 1230)

```
MYSGNRSGGHGYWDGGGAAGAEGPAPAGTLSPAPLFSPGTYERLALLLGSIGLLGVGNNLL

VLVLYYKFQRLRTPTHLLLVNISLSDLLVSLFGVTFTFVSCLRNGWVWDTVGCVWDGFSGSL

FGIVSIATLTVLAYERYIRVVHARVINFSWAWRAITYIWLYSLAWAGAPLLGWNRYILDVHG

LGCTVDWKSKDANDSSFVLFLFLGCLVVPLGVIAHCYGHILYSIRMLRCVEDLQTIQVIKILK

YEKKLAKMCFLMIFTFLVCWMPYIVICFLVVNGHGHLVTPTISIVSYLFAKSNTVYNPVIYVF

MIRKFRRSLLQLLCLRLLRCQRPAKDLPAAGSEMQIRPIVMSQKDGDRPKKKVTFNSSSIIFIIT

SDESLSVDDSDKTNGSKVDVIQVRPL
```

>gi|74048357|ref|NP_065188.4|G-protein coupled receptor 126 alpha 1 precursor {Homo sapiens}  (SEQ ID NO: 1231)

```
MMFRSDRMWSCHWKWKPSPLLFLFALYIMCVPHSVWGCANCRVVLSNPSGTFTSPCYPND

YPNSQACMWTLRAPTGYIIQITFNDFDIEEAPNCIYDSLSLDNGESQTKFCGATAKGLSFNSSA

NEMHVSFSSDFSIQKKGFNASYIRVAVSLRNQKVILPQTSDAYQVSVAKSISIPELSAFTLCFE

ATKVGHEDSDWTAFSYSNASFTQLLSFGKAKSGYFLSISDSKCLLNNALPVKEKEDIFAESFE

QLCLVWNNSLGSIGVNFKRNYETVPCDSTISKVIPGNGKLLLGSNQNEIVSLKGDIYNFRLWN

FTMNAKILSNLSCNVKGNVVDWQNDFWNIPNLALKAESNLSCGSYLIPLPAAELASCADLGT

LCQATVNSPSTTPPTVTTNMPVTNRIDKQRNDGIIYRISVVIQNILRHPEVKVQSKVAEWLNST

FQNWNYTVYVVNISFHLSAGEDKIKVKRSLEDEPRLVLWALLVYNATNNTNLEGKIIQQKLL

KNNESLDEGLRLHTVNVRQLGHCLAMEEPKGYYWPSIQPSEYVLPCPDKPGFSASRICFYNA

TNPLVTYWGPVDISNCLKEANEVANQILNLTADGQNLTSANITNIVEQVKRIVNKEENIDITL

GSTLMNIFSNILSSSDSDLLESSSEALKTIDELAFKIDLNSTSHVNITTRNLALSVSSLLPGTNAIS

NFSIGLPSNNESYFQMDFESGQVDPLASVILPPNLLENLSPEDSVLRRAQFTFFNKTGLFQDV

GPQRKTLVSYVMACSIGNITIQNLKDPVQIKIKHTRTQEVHHPICAFWDLNKNKSFGGWNTS

GCVAHRDSDASETVCLCNHFTHFGVLMDLPRSASQLDARNTKVLTFISYIGCGISAIFSAATL

LTYVAFEKLRRDYPSKILMNLSTALLFLNLLFLLDGWITSFNVDGLCIAVAVLLHFFLLATFT

WMGLEAIHMYIALVKVFNTYIRRYILKFCIIGWGLPALVVSVVLASRNNNEVYGKESYGKEK

GDEFCWIQDPVIFYVTCAGYFGVMFFLNIAMFIVVMVQICGRNGKRSNRTLREEVLRNLRSV

VSLTFLLGMTWGFAFFAWGPLNIPFMYLFSIFNSLQGLFIFIFHCAMKENVQKQWRRHLCCG

RFRLADNSDWSKTATNIIKKSSDNLGKSLSSSSIGSNSTYLTSKSKSSSTTYFKRNSHTDNVSY

EHSFNKSGSLRQCFHGQVLVKTGPC
```

>gi|74275344|ref|NP_001028252.1|trace amine-associated receptor 2 isoform 1 {Homo sapiens}

(SEQ ID NO: 1232)

MAVSSEQHELSHFKRTQTKKEKFNCSEYGNRSCPENERSLGVRVAMYSFMAGSIFITIFGNLA

MIISISYFKQLHTPTNFLILSMAITDFLLGFTIMPYSMIRSVENCWYFGLTFCKIYYSFDLMLSIT

SIFHLCSVAIDRFYAICYPLLYSTKITIPVIKRLLLLCWSVPGAFAFGVVFSEAYADGIEGYDIL

VACSSSCPVMFNKLWGTTLFMAGFFTPGSMMVGIYGKIFAVSRKHAHAINNLRENQNNQVK

KDKKAAKTLGIVIGVFLLCWFPCFFTILLDPFLNFSTPVVLFDALTWFGYFNSTCNPLIYGFFY

PWFRRALKYILLGKIFSSCFHNTILCMQKESE

>gi|84662753|ref|NP_001033794.1|G protein-coupled receptor 149 {Homo sapiens}

(SEQ ID NO: 1233)

MSLFLSNLSTNDSSLWKENHNSTDLLNPPGTLNIYLFCLTCLMTFAALVGSIYSLISLLKMQN

RTVVSMLVASWSVDDLMSVLSVTIFMFLQWPNEVPGYFQFLCTTSALMYLCQGLSSNLKAT

LLVSYNFYTMHRGVGSQTASRRSGQVLGVVLTVWAASLLLSALPLCGWGAFVRTPWGCLV

DCSSSYVLFLSIVYALAFGLLVGLSVPLTHRLLCSEEPPRLHSNYQEISRGASIPGTPPTAGRVV

SLSPEDAPGPSLRRSGGCSPSSDTVFGPGAPAAAGAEACRRENRGTLYGTRSFTVSVAQKRFA

LILALTKVVLWLPMMMHMVVQNVVGFQSLPLETFSFLLTLLATTVTPVFVLSKRWTHLPCG

CIINCRQNAYAVASDGKKIKRKGFEFNLSFQKSYGIYKIAHEDYYDDDENSIFYHNLMNSECE

TTKDPQRDNRNIFNAIKVEISTTPSLDSSTQRGINKCTNTDITEAKQDSNNKKDAFSDKTGGDI

NYEETTFSEGPERRLSHEESQKPDLSDWEWCRSKSERTPRQRSGYALAIPLCAFQGTVSLHAP

TGKTLSLSTYEVSAEGQKITPASKKIEVYRSKSVGHEPNSEDSSSTFVDTSVKIHLEVLEICDNE

EALDTVSIISNISQSSTQVRSPSLRYSRKENRFVSCDLGETASYSLFLPTSNPDGDINISIPDTVE

AHRQNSKRQHQERDGYQEEIQLLNKAYRKREEESKGS

>gi|85986587|ref|NP_001034254.1|mas-related G-protein coupled receptor member E {Homo sapiens}

(SEQ ID NO: 1234)

MEPREAGQHVGAANGAQEDVAFNLIILSLTEGLGLGGLLGNGAVLWLLSSNVYRNPFAIYLL

DVACADLIFLGCHMVAIVPDLLQGRLDFPGFVQTSLATLRFFCYIVGLSLLAAVSVEQCLAAL

FPAWYSCRRPRHLTTCVCALTWALCLLLHLLLSGACTQFFGEPSRHLCRTLWLVAAVLLALL

CCTMCGASLMLLLRVERGPQRPPPRGFPGLILLTVLLFLFCGLPFGIYWLSRNLLWYIPHYFY

HFSFLMAAVHCAAKPVVYFCLGSAQGRRLPLRLVLQRALGDEAELGAVRETSRRGLVDIAA

>gi|85986601|ref|NP_067647.2|relaxin/insulin-like family peptide receptor 1 {Homo sapiens}

(SEQ ID NO: 1235)

MTSGSVFFYILIFGKYFSHGGGQDVKCSLGYFPCGNITKCLPQLLHCNGVDDCGNQADEDNC

GDNNGWSLQFDKYFASYYKMTSQYPFEAETPECLVGSVPVQCLCQGLELDCDETNLRAVPS

VSSNVTAMSLQWNLIRKLPPDCFKNYHDLQKLYLQNNKITSISIYAFRGLNSLTKLYLSHNRI

TFLKPGVFEDLHRLEWLIIEDNHLSRISPPTFYGLNSLILLVLMNNVLTRLPDKPLCQHMPRLH

WLDLEGNHIHNLRNLTFISCSNLTVLVMRKNKINHLNENTFAPLQKLDELDLGSNKIENLPPLI

FKDLKELSQLNLSYNPIQKIQANQFDYLVKLKSLSLEGIEISNIQQRMFRPLMNLSHIYFKKFQ

YCGYAPHVRSCKPNTDGISSLENLLASIIQRVFVWVVSAVTCFGNIFVICMRPYIRSENKLYA

MSIISLCCADCLMGIYLFVIGGFDLKFRGEYNKHAQLWMESTHCQLVGSLAILSTEVSVLLLT

FLTLEKYICIVYPFRCVRPGKCRTITVLILIWITGFIVAFIPLSNKEFFKNYYGTNGVCFPLHSED

TESIGAQIYSVAIFLGINLAAFIIIVFSYGSMFYSVHQSAITATEIRNQVKKEMILAKRFFFIVFTD

ALCWIPIFVVKFLSLLQVEIPGTITSWVVIFILPINSALNPILYTLTTRPFKEMIHRFWYNYRQRK

SMDSKGQKTYAPSFIWVEMWPLQEMPPELMKPDLFTYPCEMSLISQSTRLNSYS

-continued

>gi|88758590|ref|NP_005288.3|melanin-concentrating hormone receptor 1 {Homo sapiens}
(SEQ ID NO: 1236)

MSVGAMKKGVGRAVGLGGGSGCQATEEDPLPNCGACAPGQGGRRWRLPQPAWVEGSSAR

LWEQATGTGWMDLEASLLPTGPNASNTSDGPDNLTSAGSPPRTGSISYINIIMPSVFGTICLLG

IIGNSTVIFAVVKKSKLHWCNNVPDIFIINLSVVDLLFLLGMPFMIHQLMGNGVWHFGETMCT

LITAMDANSQFTSTYILTAMAIDRYLATVHPISSTKFRKPSVATLVICLLWALSFISITPVWLYA

RLIPFPGGAVGCGIRLPNPDTDLYWFTLYQFFLAFALPFVVITAAYVRILQRMTSSVAPASQRS

IRLRTKRVTRTAIAICLVFFVCWAPYYVLQLTQLSISRPTLTFVYLYNAAISLGYANSCLNPFV

YIVLCETFRKRLVLSVKPAAQGQLRAVSNAQTADEERTESKGT

>gi|89191861|ref|NP_000787.2|d(3) dopamine receptor isoform a {Homo sapiens}
(SEQ ID NO: 1237)

MASLSQLSGHLNYTCGAENSTGASQARPHAYYALSYCALILAIVFGNGLVCMAVLKERALQ

TTTNYLVVSLAVADLLVATLVMPWVVYLEVTGGVWNFSRICCDVFVTLDVMMCTASILNL

CAISIDRYTAVVMPVHYQHGTGQSSCRRVALMITAVWVLAFAVSCPLLFGFNTTGDPTVCSI

SNPDFVIYSSVVSFYLPFGVTVLVYARIYVVLKQRRRKRILTRQNSQCNSVRPGFPQQTLSPDP

AHLELKRYYSICQDTALGGPGFQERGGELKREEKTRNSLSPTIAPKLSLEVRKLSNGRLSTSL

KLGPLQPRGVPLREKKATQMVAIVLGAFIVCWLPFFLTHVLNTHCQTCHVSPELYSATTWLG

YVNSALNPVIYTTFNIEFRKAFLKILSC

>gi|89257346|ref|NP_005284.2|G-protein coupled receptor 20 {Homo sapiens}
(SEQ ID NO: 1238)

MPSVSPAGPSAGAVPNATAVTTVRTNASGLEVPLFHLFARLDEELHGTFPGLWLALMAVHG

AIFLAGLVLNGLALYVFCCRTRAKTPSVIYTINLVVTDLLVGLSLPTRFAVYYGARGCLRCAF

PHVLGYFLNMHCSILFLTCICVDRYLAIVRPEGSRRCRQPACARAVCAFVWLAAGAVTLSVL

GVTGSRPCCRVFALTVLEFLLPLLVISVFTGRIMCALSRPGLLHQGRQRRVRAMQLLLTVLIIF

LVCFTPFHARQVAVALWPDMPHHTSLVVYHVAVTLSSLNSCMDPIVYCFVTSGFQATVRGL

FGQHGEREPSSGDVVSMHRSSKGSGRHHILSAGPHALTQALANGPEA

>gi|89353783|ref|NP_003941.2|proteinase-activated receptor 4 precursor {Homo sapiens}
(SEQ ID NO: 1239)

MWGRLLLWPLVLGFSLSGGTQTPSVYDESGSTGGGDDSTPSILPAPRGYPGQVCANDSDTLE

LPDSSRALLLGWVPTRLVPALYGLVLVVGLPANGLALWVLATQAPRLPSTMLLMNLAAADL

LLALALPPRIAYHLRGQRWPFGEAACRLATAALYGHMYGSVLLLAAVSLDRYLALVHPLRA

RALRGRRLALGLCMAAWLMAAALALPLTLQRQTFRLARSDRVLCHDALPLDAQASHWQPA

FTCLALLGCFLPLLAMLLCYGATLHTLAASGRRYGHALRLTAVVLASAVAFFVPSNLLLLLH

YSDPSPSAWGNLYGAYVPSLALSTLNSCVDPFIYYYVSAEFRDKVRAGLFQRSPGDTVASKA

SAEGGSRGMGTHSSLLQ

>gi|91106202|ref|NP_005286.2|probable G-protein coupled receptor 22 {Homo sapiens}
(SEQ ID NO: 1240)

MCFSPILEINMQSESNITVRDDIDDINTNMYQPLSYPLSFQVSLTGFLMLEIVLGLGSNLTVLV

LYCMKSNLINSVSNIITMNLHVLDVIICVGCIPLTIVILLLSLESNTALICCFHEACVSFASVSTAI

NVFAITLDRYDISVKPANRILTMGRAVMLMISIWIFSFFSFLIPFIEVNFFSLQSGNTWENKTLL

CVSTNEYYTELGMYYHLLVQIPIFFFTVVVMLITYTKILQALNIRIGTRFSTGQKKARKKKTI

SLTTQHEATDMSQSSGGRNVVFGVRTSVSVIIALRRAVKRHRERRERQKRVFRMSLLIISTFL

LCWTPISVLNTTILCLGPSDLLVKLRLCFLVMAYGTTIFHPLLYAFTRQKFQKVLKSKMKKRV

VSIVEADPLPNNAVIHNSWIDPKRNKKITFEDSEIREKCLVPQVVTD

-continued

>gi|93204867|ref|NP_065803.2|probable G-protein coupled receptor
158 precursor {Homo sapiens}
(SEQ ID NO: 1241)

MGAMAYPLLLCLLLAQLGLGAVGASRDPQGRPDSPRERTPKGKPHAQQPGRASASDSSAPW

SRSTDGTILAQKLAEEVPMDVASYLYTGDSHQLKRANCSGRYELAGLPGKWPALASAHPSL

HRALDTLTHATNFLNVMLQSNKSREQNLQDDLDWYQALVWSLLEGEPSISRAAITFSTDSLS

APAPQVFLQATREESRILLQDLSSSAPHLANATLETEWFHGLRRKWRPHLHRRGPNQGPRGL

GHSWRRKDGLGGDKSHFKWSPPYLECENGSYKPGWLVTLSSAIYGLQPNLVPEFRGVMKV

DINLQKVDIDQCSSDGWFSGTHKCHLNNSECMPIKGLGFVLGAYECICKAGFYHPGVLPVNN

FRRRGPDQHISGSTKDVSEEAYVCLPCREGCPFCADDSPCFVQEDKYLRLAIISFQALCMLLD

FVSMLVVYHFRKAKSIRASGLILLETILFGSLLLYFPVVILYFEPSTFRCILLRWARLLGFATVY

GTVTLKLHRVLKVFLSRTAQRIPYMTGGRVMRMLAVILLVVFWFLIGWTSSVCQNLEKQISL

IGQGKTSDHLIFNMCLIDRWDYMTAVAEFLFLLWGVYLCYAVRTVPSAFHEPRYMAVAVH

NELIISAIFHTIRFVLASRLQSDWMLMLYFAHTHLTVTVTIGLLLIPKFSHSSNNPRDDIATEAY

EDELDMGRSGSYLNSSINSAWSEHSLDPEDIRDELKKLYAQLEIYKRKKMITNNPHLQKKRC

SKKGLGRSIMRRITEIPETVSRQCSKEDKEGADHGTAKGTALIRKNPPESSGNTGKSKEETLK

NRVFSLKKSHSTYDHVRDQTEESSSLPTESQEEETTENSTLESLSGKKLTQKLKEDSEAESTES

VPLVCKSASAHNLSSEKKTGHPRTSMLQKSLSVIASAKEKTLGLAGKTQTAGVEERTKSQKP

LPKDKETNRNHSNSDNTETKDPAPQNSNPAEEPRKPQKSGIMKQQRVNPTTANSDLNPGTTQ

MKDNFDIGEVCPWEVYDLTPGPVPSESKVQKHVSIVASEMEKNPTFSLKEKSHHKPKAAEVC

QQSNQKRIDKAEVCLWESQGQSILEDEKLLISKTPVLPERAKEENGGQPRAANVCAGQSEEL

PPKAVASKTENENLNQIGHQEKKTSSSEENVRGSYNSSNNFQQPLTSRAEVCPWEFETPAQPN

AGRSVALPASSALSANKIAGPRKEEIWDSFKV

>gi|93204873|ref|NP_079256.4|probable G-protein coupled receptor 157 {Homo sapiens}
(SEQ ID NO: 1242)

MQPSPPPTELVPSERAVVLLSCALSALGSGLLVATHALWPDLRSRARRLLLFLSLADLLSAAS

YFYGVLQNFAGPSWDCVLQGALSTFANTSSFFWTVAIALYLYLSIVRAARGPRTDRLLWAFH

VVSWGVPLVITVAAVALKKIGYDASDVSVGWCWIDLEAKDHVLWMLLTGKLWEMLAYVL

LPLLYLLVRKHINRAHTALSEYRPILSQEHRLLRHSSMADKKLVLIPLIFIGLRVWSTVRFVLT

LCGSPAVQTPVLVVLHGIGNTFQGGANCIMFVLCTRAVRTRLFSLCCCCCSSQPPTKSPAGTP

KAPAPSKPGESQESQGTPGELPST

>gi|93277083|ref|NP_001035269.1|melanin-concentrating hormone receptor 2 {Homo sapiens}
(SEQ ID NO: 1243)

MNPFHASCWNTSAELLNKSWNKEFAYQTASVVDTVILPSMIGIICSTGLVGNILIVFTIIRSRK

KTVPDIYICNLAVADLVHIVGMPFLIHQWARGGEWVFGGPLCTIITSLDTCNQFACSAIMTVM

SVDRYFALVQPFRLTRWRTRYKTIRINLGLWAASFILALPVWVYSKVIKFKDGVESCAFDLTS

PDDVLWYTLYLTITTFFFPLPLILVCYILILCYTWEMYQQNKDARCCNPSVPKQRVMKLTKM

VLVLVVVFILSAAPYHVIQLVNLQMEQPTLAFYVGYYLSICLSYASSSINPFLYILLSGNFQKR

LPQIQRRATEKEINNMGNTLKSHF

>gi|93352554|ref|NP_001004334.2|probable G-protein coupled receptor 179 precursor {Homo sapiens}
(SEQ ID NO: 1244)

MGTRGAVMPPPMWGLLGCCFVCAWALGGPRPIRSLPPLSSQVKPGSVPMQVPLEGAEAALA

YLYSGDAQQLSQVNCSERYEARGAGAMPGLPPSLQGAAGTLAQAANFLNMLLQANDIRESS

VEEDVEWYQALVRSVAEGDPRVYRALLTFNPPPGASHLQLALQATRTGEETILQDLSGNWV

-continued

QEENPPGDLDTPALKKRVLTNDLGSLGSPKWPQADGYVGDTQQVRLSPPFLECQEGRLRPG

WLITLSATFYGLKPDLSPEVRGQVQMDVDLQSVDINQCASGPGWYSNTHLCDLNSTQCVPL

ESQGFVLGRYLCRCRPGFYGASPSGGLEESDFQTTGQFGFPEGRSGRLLQCLPCPEGCTSCMD

ATPCLVEEAAVLRAAVLACQACCMLAIFLSMLVSYRCRRNKRIWASGVVLLETVLFGFLLLY

FPVFILYFKPSVFRCIALRWVRLLGFAIVYGTIILKLYRVLQLFLSRTAQRSALLSSGRLLRRLG

LLLLPVLGFLAVWTVGALERGIQHAPLVIRGHTPSGRHFYLCHHDRWDYIMVVAELLLLCW

GSFLCYATRAVLSAFHEPRYMGIALHNELLLSAAFHTARFVLVPSLHPDWTLLLFFFHTHSTV

TTTLALIFIPKFWKLGAPPREEMVDEVCEDELDLQHSGSYLGSSIASAWSEHSLDPGDIRDELK

KLYAQLEVHKTKEMAANNPHLPKKRGSSCQGLGRSFMRYLAEFPEALARQHSRDSGSPGHG

SLPGSSRRRLLSSSLQEPEGTPALHKSRSTYDQRREQDPPLLDSLLRRKLAKKASRTESRESVE

GPPALGFRSASAHNLTVGERLPRARPASLQKSLSVASSREKALLMASQAYLEETYRQAKERE

ERKKAKAAMASLVRRPSARRLERPRGAPLSAPPSPAKSSSVDSSHTSGRLHEEARRRLPHPPI

RHQVSTPILALSGGLGEPRMLSPTSTLAPALLPALAPTPAPALAPVPVSPQSPNLLTYICPWEN

AELPAKQENVPQEGPSGPERGHHSPAPARARLWRALSVAVEKSRAGENEMDAEDAHHQRE

ANDVDEDRPKIFPKSHSLKAPVQQGSMRSLGLAIKALTRSRSTYREKESVEESPEGQNSGTAG

ESMGAPSRSPRLGRPKAVSKQAALIPSDDKESLQNQQNAHTSRMLQVCQREGSREQEDRGR

RMTQGLGERKAERAGKTGLAMLRQVSRDKNIKQSKETPVGWQELPKAGLQSLGSADHRVA

EVCPWEVTESETRQPDSGNKAEICPWETSEGAPESRALRQDPGDSQKKRGEARGKSEPIDVV

PMMRKKPERLVREQEAVCPWESADRGGLSPGSAPQDPGRIRDKSEAGDSVEARKVEKPGWE

AAGPEAHTPDITKAEPCPWEASEGGEDGKPAQEAVKDLPQEKQKTRKATFWKEQKPGGDLE

SLCPWESTDFRGPSAVSIQAPGSSECSGSLGSGIAEVCLWEAGDAPAIQKAEICPWELDDNVM

GQEMLSLGTGRESLQEKEKASRKGSFGEMGEQTVKAVQKLSQQQESVCPRESTVPGHSSPCL

DNSSSKAGSQFLCNGGSRATQVCPQEDLRPEAQEATPAKTEICPWEVNERTREEWTSAQVPR

GGESQKDKEKMPGKSEIEDVTAWEKPEGQIQKQEAVGPWESVDPGSFSPQPRPQDTERPQTL

LQMSGSVGSKAADICPLDVEENLTAGKAEICPWEVGAGAGEERALGAEAIRKSPNDTGKVS

ADLGPRERAVTAPEKPQKPTPEWEVACPWGSVGPGACSQHPGTLDADGPKAGFQELDHMG

CRPGEVCPWEAQEAATSEKAKICPWEVSEGTTGKGLDQKAGSESAEQREKALEKGRLTSLG

EDVSKGMAKLCQQQETICIWENKDLRESPAQAPKISDLPSSMSSEVAEGHSLEATEKGDLRQ

DPKTGSFPEHITQEKAPAADTEEFTTEDGEKTSHELQSVCPWETTAPADSVSHLDRQRPDQPK

ASSQRLVSTGGRAADVCPWDVPDAGVYKSDSSAKAETCPWEVTERIPVKGVSRQDGKGDS

QEEKGRAPEKSEPKGVPVQKKPEMADFRQQEAVCPWESQDGKGLSPQPAPDASDRSRGSSE

AAGSVETRVAEVCLWEVVEAPSAKKAEICPWEAGGGAAEEGEQERESQGQGEMFLQKAGP

GGTEEHFSKAAAKPREQEAVCPGEGTGSGGLLPQSGALDPELKVSPKEAGSMGSRMAELCQ

WEITDPEGNKIKGTMADICPGEETGVPSEESGLLALTATRREFFPTAPEKPLCLLVHGPLDHFF

PESKIPCPKVSRPASTFTLEGVRELQGPSGLEPRTSLAPEPSLQEAESQSSSLTEDSGQVAFEAQ

YEEFTPPTVYPWDWE

>gi|106067657|ref|NP_000224.2|luteinizing hormone/choriogonadotropin receptor
precursor {Homo sapiens}
(SEQ ID NO: 1245)
MKQRFSALQLLKLLLLLQPPLPRALREALCPEPCNCVPDGALRCPGPTAGLTRLSLAYLPVKV

IPSQAFRGLNEVIKIEISQIDSLERIEANAFDNLLNSEILIQNTKNLRYIEPGAFINLPRLKYLSIC

NTGIRKFPDVTKVFSSESNFILEICDNLHITTIPGNAFQGMNNESVTLKLYGNGFEEVQSHAFN

-continued

GTTLTSLELKENVHLEKMHNGAFRGATGPKTLDISSTKLQALPSYGLESIQRLIATSSYSLKKL

PSRETFVNLLEATLTYPSHCCAFRNLPTKEQNFSHSISENFSKQCESTVRKVNNKTLYSSMLA

ESELSGWDYEYGFCLPKTPRCAPEPDAFNPCEDIMGYDFLRVLIWLINILAIMGNMTVLFVLL

TSRYKLTVPRFLMCNLSFADFCMGLYLLLIASVDSQTKGQYYNHAIDWQTGSGCSTAGFFTV

FASELSVYTLTVITLERWHTITYAIHLDQKLRLRHAILIMLGGWLFSSLIAMLPLVGVSNYMK

VSICFPMDVETTLSQVYILTILILNVVAFFIICACYIKIYFAVRNPELMATNKDTKIAKKMAILIF

TDFTCMAPISFFAISAAFKVPLITVTNSKVLLVLFYPINSCANPFLYAIFTKTFQRDFFLLLSKFG

CCKRRAELYRRKDFSAYTSNCKNGFTGSNKPSQSTLKLSTLHCQGTALLDKTRYTEC

>gi|110611176|ref|NP_000834.2|metabotropic glutamate receptor 6 precursor {Homo sapiens}
(SEQ ID NO: 1246)

MARPRRAREPLLVALLPLAWLAQAGLARAAGSVRLAGGLTLGGLFPVHARGAAGRACGQL

KKEQGVHRLEAMLYALDRVNADPELLPGVRLGARLLDTCSRDTYALEQALSFVQALIRGRG

DGDEVGVRCPGGVPPLRPAPPERVVAVVGASASSVSIMVANVLRLFAIPQISYASTAPELSDS

TRYDFFSRVVPPDSYQAQAMVDIVRALGWNYVSTLASEGNYGESGVEAFVQISREAGGVCI

AQSIKIPREPKPGEFSKVIRRLMETPNARGIIIFANEDDIRRVLEAARQANLTGHFLWVGSDSW

GAKTSPILSLEDVAVGAITILPKRASIDGFDQYFMTRSLENNRRNIWFAEFWEENFNCKLTSSG

TQSDDSTRKCTGEERIGRDSTYEQEGKVQFVIDAVYAIAHALHSMHQALCPGHTGLCPAMEP

TDGRMLLQYIRAVRFNGSAGTPVMFNENGDAPGRYDIFQYQATNGSASSGGYQAVGQWAE

TLRLDVEALQWSGDPHEVPSSLCSLPCGPGERKKMVKGVPCCWHCEACDGYRFQVDEFTCE

ACPGDMRPTPNHTGCRPTPVVRLSWSSPWAAPPLLLAVLGIVATTTVVATFVRYNNTPIVRA

SGRELSYVLLTGIFLIYAITFLMVAEPGAAVCAARRLFLGLGTTLSYSALLTKTNRIYRIFEQG

KRSVTPPPFISPTSQLVITFSLTSLQVVGMIAWLGARPPHSVIDYEEQRTVDPEQARGVLKCD

MSDLSLIGCLGYSLLLMVTCTVYAIKARGVPETFNEAKPIGFTMYTTCIIWLAFVPIFFGTAQS

AEKIYIQTTTLTVSLSLSASVSLGMLYVPKTYVILFHPEQNVQKRKRSLKATSTVAAPPKGED

AEAHK

>gi|110611243|ref|NP_002522.2|neurotensin receptor type 1 {Homo sapiens}
(SEQ ID NO: 1247)

MRLNSSAPGTPGTPAADPFQRAQAGLEEALLAPGFGNASGNASERVLAAPSSELDVNTDIYS

KVLVTAVYLALFVVGTVGNTVAFTLARKKSLQSLQSTVHYHLGSLALSDLLTLLLAMPVE

LYNFIWVHHPWAFGDAGCRGYYFLRDACTYATALNVASLSVERYLAICHPFKAKTLMSRSR

TKKFISAIWLASALLAVPMLFTMGEQNRSADGQHAGGLVCTPTIHTATVKVVIQVNTFMSFIF

PMVVISVLNTIIANKLTVMVRQAAEQGQVCTVGGEHSTFSMAIEPGRVQALRHGVRVLRAV

VIAFVVCWLPYHVRRLMFCYISDEQWTPFLYDFYHYFYMVTNALFYVSSTINPILYNLVSAN

FRHIFLATLACLCPVWRRRRKRPAFSRKADSVSSNHTLSSNATRETLY

>gi|110618256|ref|NP_778227.3|trace amine-associated receptor 9 {Homo sapiens}
(SEQ ID NO: 1248)

MVNNFSQAEAVELCYKNVNESCIKTPYSPGPRSILYAVLGFGAVLAAFGNLLVMIAILHFKQL

HTPTNFLIASLACADFLVGVTVMPFSTVRSVESCWYFGDSYCKFHTCFDTSFCFASLFHLCCIS

VDRYIAVTDPLTYPTKFTVSVSGICIVLSWFFSVTYSFSIFYTGANEEGIEELVVALTCVGGCQ

APLNQNWVLLCFLLFFIPNVAMVFIYSKIFLVAKHQARKIESTASQAQSSSESYKERVAKRER

KAAKTLGIAMAAFLVSWLPYLVDAVIDAYMNFITPPVYEILVWCVYYNSAMNPLIYAFFY

QWFGKAIKLIVSGKVLRTDSSTTNLFSEEVETD

>gi|111118992|ref|NP_000671.2|alpha-1A adrenergic receptor isoform 1 {Homo sapiens}
(SEQ ID NO: 1249)

MVFLSGNASDSSNCTQPPAPVNISKAILLGVILGGLILFGVLGNILVILSVACHRHLHSVTHYYI

VNLAVADLLLTSTVLPFSAIFEVLGYWAFGRVFCNIWAAVDVLCCTASIMGLCIISIDRYIGVS

YPLRYPTIVTQRRGLMALLCVWALSLVISIGPLFGWRQPAPEDETICQINEEPGYVLFSALGSF

YLPLAIILVMYCRVYVVAKRESRGLKSGLKTDKSDSEQVTLRIHRKNAPAGGSGMASAKTKT

HFSVRLLKFSREKKAAKTLGIVVGCFVLCWLPFFLVMPIGSFFPDFKPSETVFKIVFWLGYLNS

CINPIIYPCSSQEFKKAFQNVLRIQCLCRKQSSKHALGYTLHPPSQAVEGQHKDMVRIPVGSRE

TFYRISKTDGVCEWKFFSSMPRGSARITVSKDQSSCTTARVRSKSFLQVCCCVGPSTPSLDKN

HQVPTIKVHTISLSENGEEV

>gi|111118994|ref|NP_001693.2|brain-specific angiogenesis inhibitor
1 precursor {Homo sapiens}
(SEQ ID NO: 1250)

MRGQAAAPGPVWILAPLLLLLLLLGRRARAAAGADAGPGPEPCATLVQGKFFGYFSAAAVF

PANASRCSWTLRNPDPRRYTLYMKVAKAPVPCSGPGRVRTYQFDSFLESTRTYLGVESFDEV

LRLCDPSAPLAFLQASKQFLQMRRQQPPQHDGLRPRAGPPGPTDDFSVEYLVVGNRNPSRAA

CQMLCRWLDACLAGSRSSHPCGIMQTPCACLGGEAGGPAAGPLAPRGDVCLRDAVAGGPE

NCLTSLTQDRGGHGATGGWKLWSLWGECTRDCGGGLQTRTRTCLPAPGVEGGGCEGVLEE

GRQCNREACGPAGRTSSRSQSLRSTDARRREELGDELQQFGFPAPQTGDPAAEEWSPWSVCS

STCGEGWQTRTRFCVSSSYSTQCSGPLREQRLCNNSAVCPVHGAWDEWSPWSLCSSTCGRG

FRDRTRTCRPPQFGGNPCEGPEKQTKFCNIALCPGRAVDGNWNEWSSWSACSASCSQGRQQ

RTRECNGPSYGGAECQGHWVETRDCFLQQCPVDGKWQAWASWGSCSVTCGAGSQRRERV

CSGPFFGGAACQGPQDEYRQCGTQRCPEPHEICDEDNFGAVIWKETPAGEVAAVRCPRNAT

GLILRRCELDEEGIAYWEPPTYIRCVSIDYRNIQMMTREHLAKAQRGLPGEGVSEVIQTLVEIS

QDGTSYSGDLLSTIDVLRNMTEIFRRAYYSPTPGDVQNFVQILSNLLAEENRDKWEEAQLAG

PNAKELFRLVEDFVDVIGFRMKDLRDAYQVTDNLVLSIHKLPASGATDISFPMKGWRATGD

WAKVPEDRVTVSKSVFSTGLTEADEASVFVVGTVLYRNLGSFLALQRNTTVLNSKVISVTVK

PPPRSLRTPLEIEFAHMYNGTTNQTCILWDETDVPSSSAPPQLGPWSWRGCRTVPLDALRTRC

LCDRLSTFAILAQLSADANMEKATLPSVTLIVGCGVSSLTLLMLVIIYVSVWRYIRSERSVILIN

FCLSIISSNALILIGQTQTRNKVVCTLVAAFLHFFFLSSFCWVLTEAWQSYMAVTGHLRNRLIR

KRFLCLGWGLPALVVAISVGFTKAKGYSTMNYCWLSLEGGLLYAFVGPAAAVVLVNMVIGI

LVFNKLVSKDGITDKKLKERAGASLWSSCVVLPLLALTWMSAVLAVTDRRSALFQILFAVFD

SLEGFVIVMVHCILRREVQDAVKCRVVDRQEEGNGDSGGSFQNGHAQLMTDFEKDVDLAC

RSVLNKDIAACRTATITGTLKRPSLPEEEKLKLAHAKGPPTNFNSLPANVSKLHLHGSPRYPG

GPLPDFPNHSLTLKRDKAPKSSFVGDGDIFKKLDSELSRAQEKALDTSYVILPTATATLRPKPK

EEPKYSIHIDQMPQTRLIHLSTAPEASLPARSPPSRQPPSGGPPEAPPAQPPPPPPPPPPPQQPLP

PPPNLEPAPPSLGDPGEPAAHPGPSTGPSTKNENVATLSVSSLERRKSRYAELDFEKIMHTRKR

HQDMFQDLNRKLQHAAEKDKEVLGPDSKPEKQQTPNKRPWESLRKAHGTPTWVKKELEPL

QPSPLELRSVEWERSGATIPLVGQDIIDLQTEV

>gi|112807234|ref|NP_683766.2|G-protein coupled receptor family C group 6 member
A precursor {Homo sapiens}
(SEQ ID NO: 1251)

MAFLIILITCFVIILATSQPCQTPDDFVAATSPGHIIIGGLFAIHEKMLSSEDSPRRPQIQECVGFEI

SVFLQTLAMIHSIEMINNSTLLPGVKLGYEIYDTCTEVTVAMAATLRFLSKFNCSRETVEFKC

-continued

DYSSYMPRVKAVIGSGYSEITMAVSRMLNLQLMPQVGYESTAEILSDKIRFPSFLRTVPSDFH

QIKAMAHLIQKSGWNWIGIITTDDDYGRLALNTFIIQAEANNVCIAFKEVLPAFLSDNTIEVRI

NRTLKKIILEAQVNVIVVFLRQFHVFDLFNKAIEMNINKMWIASDNWSTATKITTIPNVKKIG

KVVGFAFRRGNISSFHSFLQNLHLLPSDSHKLLHEYAMHLSACAYVKDTDLSQCIFNHSQRTL

AYKANKAIERNFVMRNDFLWDYAEPGLIHSIQLAVFALGYAIRDLCQARDCQNPNAFQPWE

LLGVLKNVTFTDGWNSFHFDAHGDLNTGYDVVLWKEINGHMTVTKMAEYDLQNDVFIIPD

QETKNEFRNLKQIQSKCSKECSPGQMKKTTRSQHICCYECQNCPENHYTNQTDMPHCLLCN

NKTHWAPVRSTMCFEKEVEYLNWNDSLAILLLILSLLGIIFVLVVGIIFTRNLNTPVVKSSGGL

RVCYVILLCHFLNFASTSFFIGEPQDFTCKTRQTMFGVSFTLCISCILTKSLKILLAFSFDPKLQK

FLKCLYRPILIIFTCTGIQVVICTLWLIFAAPTVEVNVSLPRVIILECEEGSILAFGTMLGYIAILA

FICFIFAFKGKYENYNEAKFITFGMLIYFIAWITFIPIYATTFGKYVPAVEIIVILISNYGILYCTFI

PKCYVIICKQEINTKSAFLKMIYSYSSHSVSSIALSPASLDSMSGNVTMTNPSSSGKSATWQKS

KDLQAQAFAHICRENATSVSKTLPRKRMSSI

>gi|113722120|ref|NP_115495.3|G-protein coupled receptor 98 precursor {Homo sapiens}
(SEQ ID NO: 1252)

MSVFLGPGMPSASLLVNLLSALLILFVFGETEIRFTGQTEFVVNETSTTVIRLIIERIGEPANVTA

IVSLYGEDAGDFFDTYAAAFIPAGETNRTVYIAVCDDDLPEPDETFIFHLTLQKPSANVKLGW

PRTVTVTILSNDNAFGIISFNMLPSIAVSEPKGRNESMPLTLIREKGTYGMVMVTFEVEGGPNP

PDEDLSPVKGNITFPPGRATVIYNLTVLDDEVPENDEIFLIQLKSVEGGAEINTSRNSIEIIIKKN

DSPVRFLQSIYLVPEEDHILIIPVVRGKDNNGNLIGSDEYEVSISYAVTTGNSTAHAQQNLDFID

LQPNTTVVFPPFIHESHLKFQIVDDTIPEIAESFHIMLLKDTLQGDAVLISPSVVQVTIKPNDKP

YGVLSFNSVLFERTVIIDEDRISRYEEITVVRNGGTHGNVSANWVLTRNSTDPSPVTADIRPSS

GVLHFAQGQMLATIPLTVVDDDLPEEAEAYLLQILPHTIRGGAEVSEPAELLFYIQDSDDVYG

LITFFPMENQKIESSPGERYLSLSFTRLGGTKGDVRLLYSVLYIPAGAVDPLQAKEGILNISRRN

DLIFPEQKTQVTTKLPIRNDAFLQNGAHFLVQLETVELLNIIPLIPPISPRFGEICNISLLVTPAIA

NGEIGFLSNLPIIHEPEDFAAEVVYIPLHRDGTDGQATVYWSLKPSGFNSKAVTPDDIGPFNG

SVLFLSGQSDTTINITIKGDDIPEMNETVTLSLDRVNVENQVLKSGYTSRDLIILENDDPGGVF

EFSPASRGPYVIKEGESVELHIIRSRGSLVKQFLHYRVEPRDSNEFYGNTGVLEFKPGEREIVIT

LLARLDGIPELDEHYWVVLSSHGERESKLGSATIVNITILKNDDPHGIIEFVSDGLIVMINESKG

DAIYSAVYDVVRNRGNFGDVSVSWVVSPDFTQDVFPVQGTVVFGDQEFSKNITIYSLPDEIPE

EMEEFTVILLNGTGGAKVGNRTTATLRIRRNDDPIYFAEPRVVRVQEGETANFTVLRNGSVD

VTCMVQYATKDGKATARERDFIPVEKGETLIFEVGSRQQSISIFVNEDGIPETDEPPFYIILLNST

GDTVVYQYGVATVIIEANDDPNGIFSLEPIDKAVEEGKTNAFWILRHRGYFGSVSVSWQLFQ

NDSALQPGQEFYETSGTVNFMDGEEAKPIILHAFPDKIPEFNEFYFLKLVNISGGSPGPGGQLA

ETNLQVTVMVPFNDDPFGVFILDPECLEREVAEDVLSEDDMSYITNFTILRQQGVFGDVQLG

WEILSSEFPAGLPPMIDFLLVGIFPTTVHLQQHMRRHHSGTDALYFTGLEGAFGTVNPKYHPS

RNNTIANFTFSAWVMPNANTNGFIIAKDDGNGSIYYGVKIQTNESHVTLSLHYKTLGSNATYI

AKTTVMKYLEESVWLHLLIILEDGIIEFYLDGNAMPRGIKSLKGEAITDGPGILRIGAGINGND

RFTGLMQDVRSYERKLTLEEIYELHAMPAKSDLHPISGYLEFRQGETNKSFIISARDDNDEEG

EELFILKLVSVYGGARISEENTTARLTIQKSDNANGLFGFTGACIPEIAEEGSTISCVVERTRGA

LDYVHVFYTISQIETDGINYLVDDFANASGTITFLPWQRSEVLNIYVLDDDIPELNEYFRVTLV

SAIPGDGKLGSTPTSGASIDPEKETTDITIKASDHPYGLLQFSTGLPPQPKDAMTLPASSVPHIT

-continued

```
VEEEDGEIRLLVIRAQGLLGRVTAEFRTVSLTAFSPEDYQNVAGTLEFQPGERYKYIFINITDN
SIPELEKSFKVELLNLEGGVAELFRVDGSGSGDGDMEFFLPTIHKRASLGVASQILVTIAASDH
AHGVFEFSPESLFVSGTEPEDGYSTVTLNVIRHHGTLSPVTLHWNIDSDPDGDLAFTSGNITFE
IGQTSANITVEILPDEDPELDKAFSVSVLSVSSGSLGAHINATLTVLASDDPYGIFIFSEKNRPV
KVEEATQNITLSIIRLKGLMGKVLVSYATLDDMEKPPYFPPNLARATQGRDYIPASGFALFGA
NQSEATIAISILDDDEPERSESVFIELLNSTLVAKVQSRSIPNSPRLGPKVETIAQLIIIANDDAFG
TLQLSAPIVRVAENHVGPIINVTRTGGAFADVSVKFKAVPITAIAGEDYSIASSDVVLLEGETS
KAVPIYVINDIYPELEESFLVQLMNETTGGARLGALTEAVIIIEASDDPYGLFGFQITKLIVEEPE
FNSVKVNLPIIRNSGTLGNVTVQWVATINGQLATGDLRVVSGNVTFAPGETIQTLLLEVLAD
DVPEIEEVIQVQLTDASGGGTIGLDRIANIIIPANDDPYGTVAFAQMVYRVQEPLERSSCANIT
VRRSGGHFGRLLLFYSTSDIDVVALAMEEGQDLLSYYESPIQGVPDPLWRTWMNVSAVGEP
LYTCATLCLKEQACSAFSFFSASEGPQCFWMTSWISPAVNNSDFWTYRKNMTRVASLFSGQ
AVAGSDYEPVTRQWAIMQEGDEFANLTVSILPDDFPEMDESFLISLLEVHLMNISASLKNQPT
IGQPNISTVVIALNGDAFGVFVIYNISPNTSEDGLFVEVQEQPQTLVELMIHRTGGSLGQVAVE
WRVVGGTATEGLDFIGAGEILTFAEGETKKTVILTILDDSEPEDDESIIVSLVYTEGGSRILPSS
DTVRVNILANDNVAGIVSFQTASRSVIGHEGEILQFHVIRTFPGRGNVTVNWKIIGQNLELNFA
NFSGQLFFPEGSLNTTLFVHLLDDNIPEEKEVYQVILYDVRTQGVPPAGIALLDAQGYAAVLT
VEASDEPHGVLNFALSSRFVLLQEANITIQLFINREFGSLGAINVTYTTVPGMLSLKNQTVGNL
AEPEVDFVPIIGFLILEEGETAAAINITILEDDVPELEEYFLVNLTYVGLTMAASTSFPPRLDSEG
LTAQVIIDANDGARGVIEWQQSRFEVNETHGSLTLVAQRSREPLGHVSLFVYAQNLEAQVGL
DYIFTPMILHFADGERYKNVNIMILDDDIPEGDEKFQLILTNPSPGLELGKNTIALIIVLANDDG
PGVLSFNNSEHFFLREPTALYVQESVAVLYIVREPAQGLFGTVTVQFIVTEVNSSNESKDLTPS
KGYIVLEEGVRFKALQISAILDTEPEMDEYFVCTLFNPTGGARLGVHVQTLITVLQNQAPLGL
FSISAVENRATSIDIEEANRTVYLNVSRTNGIDLAVSVQWETVSETAFGMRGMDVVFSVFQSF
LDESASGWCFFTLENLIYGIMLRKSSVTVYRWQGIFIPVEDLNIENPKTCEAFNIGFSPYFVITH
EERNEEKPSLNSVFTFTSGFKLFLVQTIIILESSQVRYFTSDSQDYLIIASQRDDSELTQVFRWN
GGSFVLHQKLPVRGVLTVALFNKGGSVFLAISQANARLNSLLFRWSGSGFINFQEVPVSGTTE
VEALSSANDIYLIFAENVFLGDQNSIDIFIWEMGQSSFRYFQSVDFAAVNRIHSFTPASGIAHIL
LIGQDMSALYCWNSERNQFSFVLEVPSAYDVASVTVKSLNSSKNLIALVGAHSHIYELAYISS
HSDFIPSSGELIFEPGEREATIAVNILDDTVPEKEESFKVQLKNPKGGAEIGINDSVTITILSNDD
AYGIVAFAQNSLYKQVEEMEQDSLVTLNVERLKGTYGRITIAWEADGSISDIFPTSGVILFTEG
QVLSTITLTILADNIPELSEVVIVTLTRITTEGVEDSYKGATIDQDRSKSVITTLPNDSPFGLVG
WRAASVFIRVAEPKENTTTLQLQIARDKGLLGDIAIHLRAQPNFLLHVDNQATENEDYVLQE
TIIIMKENIKEAHAEVSILPDDLPELEEGFIVTITEVNLVNSDFSTGQPSVRRPGMEIAEIMIEEN
DDPRGIFMFHVTRGAGEVITAYEVPPPLNVLQVPVVRLAGSFGAVNVYWKASPDSAGLEDF
KPSHGILEFADKQVTAMIEITIIDDAEFELTETFNISLISVAGGGRLGDDVVVTVVIPQNDSPFG
VFGFEEKTVMIDESLSSDDPDSYVTLTVVRSPGGKGTVRLEWTIDEKAKHNLSPLNGTLHFD
ETESQKTIVLHTLQDTVLEEDRRFTIQLISIDEVEISPVKGSASIIIRGDKRASGEVGIAPSSRHILI
GEPSAKYNGTAIISLVRGPGILGEVTVFWRIFPPSVGEFAETSGKLTMRDEQSAVIVVIQALND
DIPEEKSFYEFQLTAVSEGGVLSESSSTANITVVASDSPYGRFAFSHEQLRVSEAQRVNITIIRSS
```

-continued

```
GDFGHVRLWYKTMSGTAEAGLDFVPAAGELLFEAGEMRKSLHVEILDDDYPEGPEEFSLTIT

KVELQGRGYDFTIQENGLQIDQPPEIGNISIVRIIIMKNDNAEGIIEFDPKYTAFEVEEDVGLIMI

PVVRLHGTYGYVTADFISQSSSASPGGVDYILHGSTVTFQHGQNLSFINISIIDDNESEFEEPIEI

LLTGATGGAVLGRHLVSRIIIAKSDSPFGVIRFLNQSKISIANPNSTMILSLVLERTGGLLGEIQV

NWETVGPNSQEALLPQNRDIADPVSGLFYFGEGEGGVRTIILTIYPHEEIEVEETFIIKLHLVKG

EAKLDSRAKDVTLTIQEFGDPNGVVQFAPETLSKKTYSEPLALEGPLLITFFVRRVKGTFGEIM

VYWELSSEFDITEDFLSTSGFFTIADGESEASFDVHLLPDEVPEIEEDYVIQLVSVEGGAELDLE

KSITWFSVYANDDPHGVFALYSDRQSILIGQNLIRSIQINITRLAGTFGDVAVGLRISSDHKEQP

IVTENAERQLVVKDGATYKVDVVPIKNQVFLSLGSNFTLQLVTVMLVGGRFYGMPTILQEA

KSAVLPVSEKAANSQVGFESTAFQLMNITAGTSHVMISRRGTYGALSVAWTTGYAPGLEIPE

FIVVGNMTPTLGSLSFSHGEQRKGVFLWTFPSPGWPEAFVLHLSGVQSSAPGGAQLRSGFIVA

EIEPMGVFQFSTSSRNIIVSEDTQMIRLHVQRLFGFHSDLIKVSYQTTAGSAKPLEDFEPVQNG

ELFFQKFQTEVDFEITIINDQLSEIEEFFYINLTSVEIRGLQKFDVNWSPRLNLDFSVAVITILDN

DDLAGMDISFPETTVAVAVDTTLIPVETESTTYLSTSKTTTILQPTNVVAIVTEATGVSAIPEKL

VTLHGTPAVSEKPDVATVTANVSIHGTFSLGPSIVYIEEEMKNGTFNTAEVLIRRTGGFTGNV

SITVKTFGERCAQMEPNALPFRGIYGISNLTWAVEEEDFEEQTLTLIFLDGERERKVSVQILDD

DEPEGQEFFYVFLTNPQGGAQIVEEKDDTGFAAFAMVIITGSDLHNGIIGFSEESQSGLELREG

AVMRRLHLIVTRQPNRAFEDVKVFWRVTLNKTVVVLQKDGVNLVEELQSVSGTTTCTMGQ

TKCFISIELKPEKVPQVEVYFFVELYEATAGAAINNSARFAQIKILESDESQSLVYFSVGSRLAV

AHKKATLISLQVARDSGTGLMMSVNFSTQELRSAETIGRTIISPAISGKDFVITEGTLVFEPGQR

STVLDVILTPETGSLNSFPKRFQIVLFDPKGGARIDKVYGTANITLVSDADSQAIWGLADQLH

QPVNDDILNRVLHTISMKVATENTDEQLSAMMHLIEKITTEGKIQAFSVASRTLFYEILCSLIN

PKRKDTRGFSHFAEVTENFAFSLLTNVTCGSPGEKSKTILDSCPYLSILALHWYPQQINGHKFE

GKEGDYIRIPERLLDVQDAEIMAGKSTCKLVQFTEYSSQQWFISGNNLPTLKNKVLSLSVKGQ

SSQLLTNDNEVLYRIYAAEPRIIPQTSLCLLWNQAAASWLSDSQFCKVVEETADYVECACSH

MSVYAVYARTDNLSSYNEAFFTSGFICISGLCLAVLSHIFCARYSMFAAKLLTHMMAASLGT

QILFLASAYASPQLAEESCSAMAAVTHYLYLCQFSWMLIQSVNFWYVLVMNDEHTERRYLL

FFLLSWGLPAFVVILLIVILKGIYHQSMSQIYGLIHGDLCFIPNVYAALFTAALVPLTCLVVVFV

VFIHAYQVKPQWKAYDDVFRGRTNAAEIPLILYLFALISVTWLWGGLHMAYRHFWMLVLF

VIFNSLQGLYVFMVYFILHNQMCCPMKASYTVEMNGHPGPSTAFFTPGSGMPPAGGEISKST

QNLIGAMEEVPPDWERASFQQGSQASPDLKPSPQNGATFPSSGGYGQGSLIADEESQEFDDLI

FALKTGAGLSVSDNESGQGSQEGGTLTDSQIVELRRIPIADTHL

>gi|114205383|ref|NP_002971.2|secretin receptor precursor {Homo sapiens}
                                                                        (SEQ ID NO: 1253)
MRPHLSPPLQQLLLPVLLACAAHSTGALPRLCDVLQVLWEEQDQCLQELSREQTGDLGTEQP

VPGCEGMWDNISCWPSSVPGRMVEVECPRFLRMLTSRNGSLFRNCTQDGWSETFPRPNLAC

GVNVNDSSNEKRHSYLLKLKVMYTVGYSSSLVMLLVALGILCAFRRLHCTRNYIHMHLFVS

FILRALSNFIKDAVLFSSDDVTYCDAHRAGCKLVMVLFQYCIMANYSWLLVEGLYLHTLLAI

SFFSERKYLQGFVAFGWGSPAIFVALWAIARHFLEDVGCWDINANASIWWIIRGPVILSILINFI

LFINILRILMRKLRTQETRGNEVSHYKRLARSTLLLIPLFGIHYIVFAFSPEDAMEIQLFFELALG

SFQGLVVAVLYCFLNGEVQLEVQKKWQQWHLREFPLHPVASFSNSTKASHLEQSQGTCRTSII
```

>gi|115387099|ref|NP_001694.2|brain-specific angiogenesis inhibitor 2 precursor {Homo sapiens}
(SEQ ID NO: 1254)

MENTGWMGKGHRMTPACPLLLSVILSLRLATAFDPAPSACSALASGVLYGAFSLQDLFPTIA

SGCSWTLENPDPTKYSLYLRFNRQEQVCAHFAPRLLPLDHYLVNFTCLRPSPEEAVAQAESE

VGRPEEEEAEAAAGLELCSGSGPFTFLHFDKNFVQLCLSAEPSEAPRLLAPAALAFRFVEVLLI

NNNNSSQFTCGVLCRWSEECGRAAGRACGFAQPGCSCPGEAGAGSTTTTSPGPPAAHTLSNA

LVPGGPAPPAEADLHSGSSNDLFTTEMRYGEEPEEEPKVKTQWPRSADEPGLYMAQTGDPA

AEEWSPWSVCSLTCGQGLQVRTRSCVSSPYGTLCSGPLRETRPCNNSATCPVHGVWEEWGS

WSLCSRSCGRGSRSRMRTCVPPQHGGKACEGPELQTKLCSMAACPVEGQWLEWGPWGPCS

TSCANGTQQRSRKCSVAGPAWATCTGALTDTRECSNLECPATDSKWGPWNAWSLCSKTCD

TGWQRRFRMCQATGTQGYPCEGTGEEVKPCSEKRCPAFHEMCRDEYVMLMTWKKAAAGE

IIYNKCPPNASGSASRRCLLSAQGVAYWGLPSFARCISHEYRYLYLSLREHLAKGQRMLAGE

GMSQVVRSLQELLARRTYYSGDLLFSVDILRNVTDTFKRATYVPSADDVQRFFQVVSFMVD

AENKEKWDDAQQVSPGSVHLLRVVEDFIHLVGDALKAFQSSLIVTDNLVISIQREPVSAVSSD

ITFPMRGRRGMKDWVRHSEDRLFLPKEVLSLSSPGKPATSGAAGSPGRGRGPGTVPPGPGHS

HQRLLPADPDESSYFVIGAVLYRTLGLILPPPRPPLAVTSRVMTVTVRPPTQPPAEPLITVELSY

IINGTTDPHCASWDYSRADASSGDWDTENCQTLETQAAHTRCQCQHLSTFAVLAQPPKDLTL

ELAGSPSVPLVIGCAVSCMALLTLLAIYAAFWRFIKSERSIILLNFCLSILASNILILVGQSRVLS

KGVCTMTAAFLHFFFLSSFCWVLTEAWQSYLAVIGRMRTRLVRKRFLCLGWGLPALVVAVS

VGFTRTKGYGTSSYCWLSLEGGLLYAFVGPAAVIVLVNMLIGIIVFNKLMARDGISDKSKKQ

RAGSERCPWASLLLPCSACGAVPSPLLSSASARNAMASLWSSCVVLPLLALTWMSAVLAMT

DRRSVLFQALFAVFNSAQGFVITAVHCFLRREVQDVVKCQMGVCRADESEDSPDSCKNGQL

QILSDFEKDVDLACQTVLFKEVNTCNPSTITGTLSRLSLDEDEEPKSCLVGPEGSLSFSPLPGNI

LVPMAASPGLGEPPPPQEANPVYMCGEGGLRQLDLTWLRPTEPGSEGDYMVLPRRTLSLQP

GGGGGGGEDAPRARPEGTPRRAAKTVAHTEGYPSFLSVDHSGLGLGPAYGSLQNPYGMTFQ

PPPPTPSARQVPEPGERSRTMPRTVPGSTMKMGSLERKKLRYSDLDFEKVMHTRKRHSELYH

ELNQKFHTFDRYRSQSTAKREKRWSVSSGGAAERSVCTDKPSPGERPSLSQHRRHQSWSTFK

SMTLGSLPPKPRERLTLHRAAAWEPTEPPDGDFQTEV

>gi|116063556|ref|NP_071332.2|probable G-protein coupled receptor 88 {Homo sapiens}
(SEQ ID NO: 1255)

MTNSSSTSTSSTTGGSLLLLCEEEESWAGRRIPVSLLYSGLAIGGTLANGMVIYLVSSFRKLQT

TSNAFIVNGCAADLSVCALWMPQEAVLGLLPTGSAEPPADWDGAGGSYRLLRGGLLGLGLT

VSLLSHCLVALNRYLLITRAPATYQALYQRRHTAGMLALSWALALGLVLLLPPWAPRPGAA

PPRVHYPALLAAAALLAQTALLLHCYLGIVRRVRVSVKRVSVLNFHLLHQLPGCAAAAAF

PGAQHAPGPGGAAHPAQAQPLPPALHPRRAQRRLSGLSVLLLCCVFLLATQPLVWVSLASGF

SLPVPWGVQAASWLLCCALSALNPLLYTWRNEEFRRSVRSVLPGVGDAAAAAVAATAVPA

VSQAQLGTRAAGQHW

>gi|116284382|ref|NP_001070662.1|G-protein coupled bile acid receptor 1 {Homo sapiens}
(SEQ ID NO: 1256)

MTPNSTGEVPSPIPKGALGLSLALASLIITANLLLALGIAWDRRLRSPPAGCFFLSLLLAGLLTG

LALPTLPGLWNQSRRGYWSCLLVYLAPNFSFLSLLANLLLVHGERYMAVLRPLQPPGSIRLA

LLLLTWAGPLLFASLPALGWNHWTPGANCSSQAIFPAPYLYLEVYGLLLPAVGAAAFLSVRVL

ATAHRQLQDICRLERAVCRDEPSALARALTWRQARAQAGAMLLFGLCWGPYVATLLLSVL

```
AYEQRPPLGPGTLLSLLSLGSASAAAVPVAMGLGDQRYTAPWRAAAQRCLQGLWGRASRD

SPGPSIAYHPSSQSSVDLDLN
```

>gi|116517328|ref|NP_722580.3|probable G-protein coupled receptor
115 precursor {Homo sapiens}

(SEQ ID NO: 1257)

```
MKMKSQATMICCLVFFLSTECSHYRSKIHLKAGDKLQSPEGKPKTGRIQEKCEGPCISSSNCS

QPCAKDFHGEIGFTCNQKKWQKSAETCTSLSVEKLFKDSTGASRLSVAAPSIPLHILDFRAPET

IESVAQGIRKNCPFDYACITDMVKSSETTSGNIAFIVELLKNISTDLSDNVTREKMKSYSEVAN

HILDTAAISNWAFIPNKNASSDLLQSVNLFARQLHIHNNSENIVNELFIQTKGFHINHNTSEKSL

NFSMSMNNTTEDILGMVQIPRQELRKLWPNASQAISIAFPTLGAILREAHLQNVSLPRQVNGL

VLSVVLPERLQEIILTFEKINKTRNARAQCVGWHSKKRRWDEKACQMMLDIRNEVKCRCNY

TSVVMSFSILMSSKSMTDKVLDYITCIGLSVSILSLVLCLIIEATVWSRVVVTEISYMRHVCIVN

IAVSLLTANVWFIIGSHFNIKAQDYNMCVAVTFFSHFFYLSLFFWMLFKALLIIYGILVIFRRM

MKSRMMVIGFAIGYGCPLIIAVTTVAITEPEKGYMRPEACWLNWDNTKALLAFAIPAFVIVA

VNLIVVLVVAVNTQRPSIGSSKSQDVVIIMRISKNVAILTPLLGLTWGFGIATLIEGTSLTFHIIF

ALLNAFQGFFILLFGTIMDHKIRDALRMRMSSLKGKSRAAENASLGPTNGSKLMNRQG
```

>gi|117940060|ref|NP_000905.3|opioid receptor, mu 1 isoform MOR-1 {Homo sapiens}

(SEQ ID NO: 1258)

```
MDSSAAPTNASNCTDALAYSSCSPAPSPGSWVNLSHLDGNLSDPCGPNRTDLGGRDSLCPPT

GSPSMITAITIMALYSIVCVVGLFGNFLVMYVIVRYTKMKTATNIYIFNLALADALATSTLPFQ

SVNYLMGTWPFGTILCKIVISIDYYNMFTSIFTLCTMSVDRYIAVCHPVKALDFRTPRNAKIIN

VCNWILSSAIGLPVMFMATTKYRQGSIDCTLTFSHPTWYWENLLKICVFIFAFIMPVLIITVCY

GLMILRLKSVRMLSGSKEKDRNLRRITRMVLVVVAVFIVCWTPIHIYVIIKALVTIPETTFQTV

SWHFCIALGYTNSCLNPVLYAFLDENFKRCFREFCIPTSSNIEQQNSTRIRQNTRDHPSTANTV

DRTNHQLENLEAETAPLP
```

>gi|119220588|ref|NP_115892.2|melanin-concentrating hormone receptor 2 {Homo sapiens}

```
MNPFHASCWNTSAELLNKSWNKEFAYQTASVVDTVILPSMIGIICSTGLVGNILIVFTIIRSRK

KTVPDIYICNLAVADLVHIVGMPFLIHQWARGGEWVFGGPLCTIITSLDTCNQFACSAIMTVM

SVDRYFALVQPFRLTRWRTRYKTIRINLGLWAASFILALPVWVYSKVIKFKDGVESCAFDLTS

PDDVLWYTLYLTITTFFFPLPLILVCYILILCYTWEMYQQNKDARCCNPSVPKQRVMKLTKM

VLVLVVVFILSAAPYHVIQLVNLQMEQPTLAFYVGYYLSICLSYASSSINPFLYILLSGNFQKR

LPQIQRRATEKEINNMGNTLKSHF
```

>gi|119508433|ref|NP_005903.2|melanocortin receptor 4 {Homo sapiens}

(SEQ ID NO: 1259)

```
MVNSTHRGMHTSLHLWNRSSYRLHSNASESLGKGYSDGGCYEQLFVSPEVFVTLGVISLLEN

ILVIVAIAKNKNLHSPMYFFICSLAVADMLVSVSNGSETIVITLLNSTDTDAQSFTVNIDNVIDS

VICSSLLASICSLLSIAVDRYFTIFYALQYHNIMTVKRVGIIISCIWAACTVSGILFIIYSDSSAVII

CLITMFFTMLALMASLYVHMFLMARLHIKRIAVLPGTGAIRQGANMKGAITLTILIGVFVVC

WAPFFLHLIFYISCPQNPYCVCFMSHFNLYLILIMCNSIIDPLIYALRSQELRKTFKEIICCYPLG

GLCDLSSRY
```

>gi|119943116|ref|NP_001073328.1|G-protein coupled receptor 64 isoform 2 {Homo sapiens}

(SEQ ID NO: 1260)

```
MVFSVRQCGHVGRTEEVLLTFKIFLVIICLHVVLVTSLEEDTDNSSLSPPPAKLSVVSFAPSSN

GTPEVETTSLNDVTLSLLPSNETGVKPQRNICNLSSICNDSAFFRGEIMFQYDKESTVPQNQHI

TNGTLTGVLSLSELKRSELNKTLQTLSETYFIMCATAEAQSTLNCTFTIKLNNTMNACAVIAA
```

-continued

LERVKIRPMEHCCCSVRIPCPSSPEELEKLQCDLQDPIVCLADHPRGPPFSSSQSIPVVPRATVL

SQVPKATSFAEPPDYSPVTHNVPSPIGEIQPLSPQPSAPIASSPAIDMPPQSETISSPMPQTHVSG

TPPPVKASFSSPTVSAPANVNTTSAPPVQTDIVNTSSISDLENQVLQMEKALSLGSLEPNLAGE

MINQVSRLLHSPPDMLAPLAQRLLKVVDDIGLQLNFSNTTISLTSPSLALAVIRVNASSFNTTT

FVAQDPANLQVSLETQAPENSIGTITLPSSLMNNLPAHDMELASRVQFNFFETPALFQDPSLE

NLSLISYVISSSVANLTVRNLTRNVTVTLKHINPSQDELTVRCVFWDLGRNGGRGGWSDNGC

SVKDRRLNETICTCSHLTSFGVLLDLSRTSVLPAQMMALTFITYIGCGLSSIFLSVTLVTYIAFE

KIRRDYPSKILIQLCAALLLLNLVFLLDSWIALYKMQGLCISVAVFLHYFLLVSFTWMGLEAF

HMYLALVKVFNTYIRKYILKFCIVGWGVPAVVVTIILTISPDNYGLGSYGKFPNGSPDDFCWI

NNNAVFYITVVGYFCVIFLLNVSMFIVVLVQLCRIKKKKQLGAQRKTSIQDLRSIAGLTFLLGI

TWGFAFFAWGPVNVTFMYLFAIFNTLQGFFIFIFYCVAKENVRKQWRRYLCCGKLRLAENSD

WSKTATNGLKKQTVNQGVSSSSNSLQSSSNSTNSTTLLVNNDCSVHASGNGNASTERNGVSF

SVQNGDVCLHDFTGKQHMFNEKEDSCNGKGRMALRRTSKRGSLHFIEQM

>gi|125625352|ref|NP_055694.3|P2Y14 receptor {Homo sapiens}

(SEQ ID NO: 1261)

MINSTSTQPPDESCSQNLLITQQIIPVLYCMVFIAGILLNGVSGWIFFYVPSSKSFIIYLKNIVIAD

FVMSLTFPFKILGDSGLGPWQLNVFVCRVSAVLFYVNMYVSIVFFGLISFDRYYKIVKPLWTS

FIQSVSYSKLLSVIVWMLMLLLAVPNIILTNQSVREVTQIKCIELKSELGRKWHKASNYIFVAI

FWIVFLLLIVFYTAITKKIFKSHLKSSRNSTSVKKKSSRNIFSIVFVFFVCFVPYHIARIPYTKSQT

EAHYSCQSKEILRYMKEFTLLLSAANVCLDPIIYFFLCQPFREILCKKLHIPLKAQNDLDISRIK

RGNTTLESTDTL

>gi|125660451|ref|NP_671732.3|MAS-related GPR, member X1 {Homo sapiens}

(SEQ ID NO: 1262)

MDPTISTLDTELTPINGTEETLCYKQTLSLTVLTCIVSLVGLTGNAVVLWLLGCRMRRNAFSI

YILNLAAADFLFLSGRLIYSLLSFISIPHTISKILYPVMMFSYFAGLSFLSAVSTERCLSVLWPIW

YRCHRPTHLSAVVCVLLWALSLLRSILEWMLCGFLFSGADSAWCQTSDFITVAWLIFLCVVL

CGSSLVLLIRILCGSRKIPLTRLYVTILLTVLVFLLCGLPFGIQFFLFLWIHVDREVLFCHVHLVS

IFLSALNSSANPIIYFFVGSFRQRQNRQNLKLVLQRALQDASEVDEGGGQLPEEILELSGSRLEQ

>gi|133930786|ref|NP_115960.2|EGF-like module-containing mucin-like hormone receptor-like 3 {Homo sapiens}

(SEQ ID NO: 1263)

MQGPLLLPGLCFLLSLFGAVTQKTKTSCAKCPPNASCVNNTHCTCNHGYTSGSGQKLFTFPL

ETCNDINECTPPYSVYCGFNAVCYNVEGSFYCQCVPGYRLHSGNEQFSNSNENTCQDTTSSK

TTEGRKELQKIVDKFESLLTNQTLWRTEGRQEISSTATTILRDVESKVLETALKDPEQKVLKIQ

NDSVAIETQAITDNCSEERKTFNLNVQMNSMDIRCSDIIQGDTQGPSAIAFISYSSLGNIINATF

FEEMDKKDQVYLNSQVVSAAIGPKRNVSLSKSVTLTFQHVKMTPSTKKVFCVYWKSTGQGS

QWSRDGCFLIHVNKSHTMCNCSHLSSFAVLMALTSQEEDPVLTVITYVGLSVSLLCLLLAAL

TFLLCKAIRNTSTSLHLQLSLCLFLAHLLFLVGIDRTEPKVLCSIIAGALHYLYLAAFTWMLLE

GVHLFLTARNLTVVNYSSINRLMKWIMFPVGYGVPAVTVAISAASWPHLYGTADRCWLHLD

QGFMWSFLGPVCAIFSANLVLFILVFWILKRKLSSLNSEVSTIQNTRMLAFKATAQLFILGCT

WCLGLLQVGPAAQVMAYLFTIINSLQGFFIFLVYCLLSQQVQKQYQKWFREIVKSKSESETY

TLSSKMGPDSKPSEGDVFPGQVKRKY

-continued

>gi|134244291|ref|NP_004758.3|endothelin B receptor-like protein 2 precursor
{Homo sapiens}
(SEQ ID NO: 1264)

MRWLWPLAVSLAVILAVGLSRVSGGAPLHLGRHRAETQEQQSRSKRGTEDEEAKGVQQYV

PEEWAEYPRPIHPAGLQPTKPLVATSPNPGKDGGTPDSGQELRGNLTGAPGQRLQIQNPLYPV

TESSYSAYAIMLLALVVFAVGIVGNLSVMCIVWHSYYLKSAWNSILASLALWDFLVLFFCLPI

VIFNEITKQRLLGDVSCRAVPFMEVSSLGVTTFSLCALGIDRFHVATSTLPKVRPIERCQSILAK

LAVIWVGSMTLAVPELLLWQLAQEPAPTMGTLDSCIMKPSASLPESLYSLVMTYQNARMW

WYFGCYFCLPILFTVTCQLVTWRVRGPPGRKSECRASKHEQCESQLNSTVVGLTVVYAFCTL

PENVCNIVVAYLSTELTRQTLDLLGLINQFSTFFKGAITPVLLLCICRPLGQAFLDCCCCCCE

ECGGASEASAANGSDNKLKTEVSSSIYFHKPRESPPLLPLGTPC

>gi|134244587|ref|NP_004221.3|endothelial differentiation, sphingolipid
G-protein-coupled receptor, 5 {Homo sapiens}
(SEQ ID NO: 1265)

MGSLYSEYLNPNKVQEHYNYTKETLETQETTSRQVASAFIVILCCAIVVENLLVLIAVARNSK

FHSAMYLFLGNLAASDLLAGVAFVANTLLSGSVTLRLTPVQWFAREGSAFITLSASVFSLLAI

AIERHVAIAKVKLYGSDKSCRMLLLIGASWLISLVLGGLPILGWNCLGHLEACSTVLPLYAKH

YVLCVVTIFSIILLAIVALYVRIYCVVRSSHADMAAPQTLALLKTVTIVLGVFIVCWLPAFSILL

LDYACPVHSCPILYKAHYFFAVSTLNSLLNPVIYTWRSRDLRREVLRPLQCWRPGVGVQGRR

RGGTPGHHLLPLRSSSSLERGMHMPTSPTFLEGNTVV

>gi|134288847|ref|NP_722581.4|probable G-protein coupled receptor 111 {Homo sapiens}
(SEQ ID NO: 1266)

MTHILLLYYLVFLLPTESCRTLYQAASKSKEKVPARPHGVCDGVCTDYSQCTQPCPPDTQGN

MGFSCRQKTWHKITDTCQTLNALNIFEEDSRLVQPFEDNIKISVYTGKSETITDMLLQKCPTD

LSCVIRNIQQSPWIPGNIAVIVQLLHNISTAIWTGVDEAKMQSYSTIANHILNSKSISNWTFIPD

RNSSYILLHSVNSFARRLFIDKHPVDISDVFIHTMGTTISGDNIGKNFTFSMRINDTSNEVTGRV

LISRDELRKVPSPSQVISIAFPTIGAILEASLLENVTVNGLVLSAILPKELKRISLIFEKISKSEERR

TQCVGWHSVENRWDQQACKMIQENSQQAVCKCRPSKLFTSFSILMSPHILESLILTYITYVGL

GISICSLILCLSIEVLVWSQVTKTEITYLRHVCIVNIAATLLMADVWFIVASFLSGPITHHKGCV

AATFFVHFFYLSVFFWMLAKALLILYGIMIVFHTLPKSVLVASLFSVGYGCPLAIAAITVAATE

PGKGYLRPEICWLNWDMTKALLAFVIPALAIVVVNLITVTLVIVKTQRAAIGNSMFQEVRAIV

RISKNIAILTPLLGLTWGFGVATVIDDRSLAFHIIFSLLNAFQGFFILVFGTILDPKIREALKG

>gi|141802362|ref|NP_722577.2|probable G-protein coupled receptor 113
isoform 3 {Homo sapiens}
(SEQ ID NO: 1267)

MTTRKLSAHSAATPGYKAVTHKHHTGWARMAKTGLPEKGQSQAGGESGSGQLLDQENGA

GESALVSVYVHLDFPDKTWPPELSRTLTLPAASASSSPRPLLTGLRLTTGEYMSCFEAQGFKW

NLYEVVRVPLKATDVARLPYQLSISCATSPGFQLSCCIPSTNLAYTAAWSPGEGSKASSFNES

GSQCFVLAVQRCPMADTTYACDLQSLGLAPLRVPISITIIQDGDITCPEDASVLTWNVTKAGH

VAQAPCPESKRGIVRRLCGADGVWGPVHSSCTDARLLALFTRTKLLQAGQGSPAEEVPQILA

QLPGQAAEASSPSDLLTLLSTMKYVAKVVAEARIQLDRRALKNLLIATDKVLDMDTRSLWT

LAQARKPWAGSTLLLAVETLACSLCPQDHPFAFSLPNVLLQSQLFGPTFPADYSISFPTRPPLQ

AQIPRHSLAPLVRNGTEISITSLVLRKLDHLLPSNYGQGLGDSLYATPGLVLVISIMAGDRAFS

QGEVIMDFGNTDGSPHCVFWDHSLFQGRGGWSKEGCQAQVASASPTAQCLCQHLTAFSVL

MSPHTVPEEPALALLTQVGLGASILALLVCLGVYWLVWRVVVRNKISYFRHAALLNMVFCL

LAADTCFLGAPFLSPGPRSPLCLAAAFLCHFLYLATFFWMLAQALVLAHQLLFVFHQLAKHR

```
VLPLMVLLGYLCPLGLAGVTLGLYLPQGQYLREGECWLDGKGGALYTFVGPVLAIIGVNGL

VLAMAMLKLLRPSLSEGPPAEKRQALLGVIKALLILTPIFGLTWGLGLATLLEEVSTVPHYIFT

ILNTLQGVFILLFGCLMDRKIQEALRKRFCRAQAPSSTISLATNEGCILEHSKGGSDTARKTDA

SE
```

>gi|144922665|ref|NP_001077378.1|probable G-protein coupled receptor 123 {Homo sapiens}

(SEQ ID NO: 1268)

```
MDLKTVLSLPRYPGEFLHPVVYACTAVMLLCLLASFVTYIVHQSAIRISRKGRHTLLNFCFHA

ALTFTVFAGGINRTKYPILCQAVGIVLHYSTLSTMLWIGVTARNIYKQVTKKAPLCLDTDQPP

YPRQPLLRFYLVSGGVPFIICGVTAATNIRNYGTEDEDTAYCWMAWEPSLGAFYGPAAIITLV

TCVYFLGTYVQLRRHPGRRYELRTQPEEQRRLATPEGGRGIRPGTPPAHDAPGASVLQNEHS

FQAQLRAAAFTLFLFTATWAFGALAVSQGHFLDMVFSCLYGAFCVTLGLFVLIHHCAKRED

VWQCWWACCPPRKDAHPALDANGAALGRAACLHSPGLGQPRGFAHPPGPCKMTNLQAAQ

GHASCLSPATPCCAKMHCEPLTADEAHVHLQEEGAFGHDPHLHGCLQGRTKPPYFSRHPAE

EPEYAYHIPSSLDGSPRSSRTDSPPSSLDGPAGTHTLACCTQGDPFPMVTQPEGSDGSPALYSC

PTQPGREAALGPGHLEMLRRTQSLPFGGPSQNGLPKGKLLEGLPFGTDGTGNIRTGPWKNET

TV
```

>gi|145309304|ref|NP_001398.2|cadherin EGF LAG seven-pass G-type receptor 3 precursor {Homo sapiens}

(SEQ ID NO: 1269)

```
MMARRPPWRGLGGRSTPILLLLLLSLFPLSQEELGGGHQGWDPGLAATTGPRAHIGGGALA

LCPESSGVREDGGPGLGVREPIFVGLRGRRQSARNSRGPPEQPNEELGIEHGVQPLGSRERET

GQGPGSVLYWRPEVSSCGRTGPLQRGSLSPGALSSGVPGSGNSSPLPSDFLIRHHGPKPVSSQ

RNAGTGSRKRVGTARCCGELWATGSKGQGERATTSGAERTAPRRNCLPGASGSGPELDSAP

RTARTAPASGSAPRESRTAPEPAPKRMRSRGLFRCRFLPQRPGPRPPGLPARPEARKVTSANR

ARFRRAANRHPQFPQYNYQTLVPENEAAGTAVLRVVAQDPDAGEAGRLVYSLAALMNSRS

LELFSIDPQSGLIRTAAALDRESMERHYLRVTAQDHGSPRLSATTMVAVTVADRNDHSPVFE

QAQYRETLRENVEEGYPILQLRATDGDAPPNANLRYRFVGPPAARAAAAAAFEIDPRSGLIST

SGRVDREHMESYELVVEASDQGQEPGPRSATVRVHITVLDENDNAPQFSEKRYVAQVREDV

RPHTVVLRVTATDRDKDANGLVHYNIISGNSRGHFAIDSLTGEIQVVAPLDFEAEREYALRIR

AQDAGRPPLSNNTGLASIQVVDINDHIPIFVSTPFQVSVLENAPLGHSVIHIQAVDADHGENAR

LEYSLTGVAPDTPFVINSATGWVSVSGPLDRESVEHYFFGVEARDHGSPPLSASASVTVTVLD

VNDNRPEFTMKEYHLRLNEDAAVGTSVVSVTAVDRDANSAISYQITGGNTRNRFAISTQGGV

GLVTLALPLDYKQERYFKLVLTASDRALHDHCYVHINITDANTHRPVFQSAHYSVSVNEDRP

MGSTIVVISASDDDVGENARITYLLEDNLPQFRIDADSGAITLQAPLDYEDQVTYTLAITARD

NGIPQKADTTYVEVMVNDVNDNAPQFVASHYTGLVSEDAPPFTSVLQISATDRDAHANGRV

QYTFQNGEDGDGDFTIEPTSGIVRTVRRLDREAVSVYELTAYAVDRGVPPLRTPVSIQVMVQ

DVNDNAPVFPAEEFEVRVKENSIVGSVVAQITAVDPDEGPNAHIMYQIVEGNIPELFQMDIFS

GELTALIDLDYEARQEYVIVVQATSAPLVSRATVHVRLVDQNDNSPVLNNFQILFNNYVSNR

SDTFPSGIIGRIPAYDPDVSDHLFYSFERGNELQLLVVNQTSGELRLSRKLDNNRPLVASMLVT

VTDGLHSVTAQCVLRVVIITEELLANSLTVRLENMWQERFLSPLLGRFLEGVAAVLATPAED

VFIFNIQNDTDVGGTVLNVSFSALAPRGAGAGAAGPWFSSEELQEQLYVRRAALAARSLLDV

LPFDDNVCLREPCENYMKCVSVLRFDSSAPFLASASTLFRPIQPIAGLRCRCPPGFTGDFCETE

LDLCYSNPCRNGGACARREGGYTCVCRPRFTGEDCELDTEAGRCVPGVCRNGGTCTDAPNG
```

```
GFRCQCPAGGAFEGPRCEVAARSFPPSSFVMFRGLRQRFHLTLSLSFATVQQSGLLFYNGRLN

EKHDFLALELVAGQVRLTYSTGESNTVVSPTVPGGLSDGQWHTVHLRYYNKPRTDALGGA

QGPSKDKVAVLSVDDCDVAVALQFGAEIGNYSCAAAGVQTSSKKSLDLTGPLLLGGVPNLP

ENFPVSHKDFIGCMRDLHIDGRRVDMAAFVANNGTMAGCQAKLHFCDSGPCKNSGFCSER

WGSFSCDCPVGFGGKDCQLTMAHPHHFRGNGTLSWNFGSDMAVSVPWYLGLAFRTRATQG

VLMQVQAGPHSTLLCQLDRGLLSVTVTRGSGRASHLLLDQVTVSDGRWHDLRLELQEEPGG

RRGHHVLMVSLDFSLFQDTMAVGSELQGLKVKQLHVGGLPPGSAEEAPQGLVGCIQGVWL

GSTPSGSPALLPPSHRVNAEPGCVVTNACASGPCPPHADCRDLWQTFSCTCQPGYYGPGCVD

ACLLNPCQNQGSCRHLPGAPHGYTCDCVGGYFGHHCEHRMDQQCPRGWWGSPTCGPCNC

DVHKGFDPNCNKTNGQCHCKEFHYRPRGSDSCLPCDCYPVGSTSRSCAPHSGQCPCRPGAL

GRQCNSCDSPFAEVTASGCRVLYDACPKSLRSGVWWPQTKFGVLATVPCPRGALGAAVRLC

DEAQGWLEPDLFNCTSPAFRELSLLLDGLELNKTALDTMEAKKLAQRLREVTGHTDHYFSQ

DVRVTARLLAHLLAFESHQQGFGLTATQDAHFNENLLWAGSALLAPETGDLWAALGQRAP

GGSPGSAGLVRHLEEYAATLARNMELTYLNPMGLVTPNIMLSIDRMEHPSSPRGARRYPRYH

SNLFRGQDAWDPHTHVLLPSQSPRPSPSEVLPTSSSIENSTTSSVVPPPAPPEPEPGISIIILLVYR

TLGGLLPAQFQAERRGARLPQNPVMNSPVVSVAVFHGRNFLRGILESPISLEFRLLQTANRSK

AICVQWDPPGLAEQHGVWTARDCELVHRNGSHARCRCSRTGTFGVLMDASPRERLEGDLEL

LAVFTHVVVAVSVAALVLTAAILLSLRSLKSNVRGIHANVAAALGVAELLFLLGIHRTHNQL

VCTAVAILLHYFFLSTFAWLFVQGLHLYRMQVEPRNVDRGAMRFYHALGWGVPAVLLGLA

VGLDPEGYGNPDFCWISVHEPLIWSFAGPVVLVIVMNGTMFLLAARTSCSTGQREAKKTSAL

TLRSSFLLLLLVSASWLFGLLAVNHSILAFHYLHAGLCGLQGLAVLLLFCVLNADARAAWM

PACLGRKAAPEEARPAPGLGPGAYNNTALFEESGLIRITLGASTVSSVSSARSGRTQDQDSQR

GRSYLRDNVLVRHGSAADHTDHSLQAHAGPTDLDVAMFHRDAGADSDSDSDLSLEEERSLS

IPSSESEDNGRTRGRFQRPLCRAAQSERLLTHPKDVDGNDLLSYWPALGECEAAPCALQTWG

SERRLGLDTSKDAANNNQPDPALTSGDETSLGRAQRQRKGILKNRLQYPLVPQTRGAPELSW

CRAATLGHRAVPAASYGRIYAGGGTGSLSQPASRYSSREQLDLLLRRQLSRERLEEAPAPVL

RPLSRPGSQECMDAAPGRLEPKDRGSTLPRRQPPRDYPGAMAGRFGSRDALDLGAPREWLS

TLPPPRRTRDLDPQPPPLPLSPQRQLSRDPLLPSRPLDSLSRSSNSREQLDQVPSRHPSREALGP

LPQLLRAREDSVSGPSHGPSTEQLDILSSILASFNSSALSSVQSSSTPLGPHTTATPSATASVLGP

STPRSATSHSISELSPDSEVPRSEGHS

>gi|145309315|ref|NP_543141.3|probable G-protein coupled receptor 62 {Homo sapiens}
                                                                    (SEQ ID NO: 1270)
MANSTGLNASEVAGSLGLILAAVVEVGALLGNGALLVVVLRTPGLRDALYAHLCVVDLLA

AASIMPLGLLAAPPPGLGRVRLGPAPCRAARFLSAALLPACTLGVAALGLARYRLIVHPLRPG

SRPPPVLVLTAVWAAAGLLGALSLLGTPPAPPPAPARCSVLAGGLGPFRPLWALLAFALPAL

LLLGAYGGIFVVARRAALRPPRPARGSRLHSDSLDSRLSILPPLRPRLPGGKAALAPALAVGQ

FAACWLPYGCACLAPAARAEAEAAVTWVAYSAFAAHPFLYGLLQRPVRLALGRLSRRAL

PGPVRACTPQAWHPRALLQCLQRPPEGPAVGPSEAPEQTPELAGGRSPAYQGPPESSLS

>gi|148664220|ref|NP_659452.3|mas-related G-protein coupled
receptor member F {Homo sapiens}
                                                                    (SEQ ID NO: 1271)
MAGNCSWEAHPGNRNKMCPGLSEAPELYSRGFLTIEQIAMLPPPAVMNYIFLLLCLCGLVGN

GLVLWFFGFSIKRNPFSIYFLHLASADVGYLFSKAVFSILNTGGFLGTFADYIRSVCRVLGLCM
```

```
FLTGVSLLPAVSAERCASVIFPAWYWRRRPKRLSAVVCALLWVLSLLVTCLHNYFCVFLGRG

APGAACRHMDIFLGILLFLLCCPLMVLPCLALILHVECRARRRQRSAKLNHVILAMVSVFLVS

SIYLGIDWFLFWVFQIPAPFPEYVTDLCICINSSAKPIVYFLAGRDKSQRLWEPLRVVFQRALR

DGAELGEAGGSTPNTVTMEMQCPPGNAS
```

>gi|148719673|ref|NP_056049.4|probable G-protein coupled receptor 116 precursor {Homo sapiens}

(SEQ ID NO: 1272)

```
MKSPRRTTLCLMFIVIYSSKAALNWNYESTIHPLSLHEHEPAGEEALRQKRAVATKSPTAEEY

TVNIEISFENASFLDPIKAYLNSLSFPIHGNNTDQITDILSINVTTVCRPAGNEIWCSCETGYGW

PRERCLHNLICQERDVFLPGHHCSCLKELPPNGPFCLLQEDVTLNMRVRLNVGFQEDLMNTS

SALYRSYKTDLETAFRKGYGILPGFKGVTVTGFKSGSVVVTYEVKTTPPSLELIHKANEQVV

QSLNQTYKMDYNSFQAVTINESNFFVTPEIIFEGDTVSLVCEKEVLSSNVSWRYEEQQLEIQN

SSRFSIYTALFNNMTSVSKLTIHNITPGDAGEYVCKLILDIFEYECKKKIDVMPIQILANEEMKV

MCDNNPVSLNCCSQGNVNWSKVEWKQEGKINIPGTPETDIDSSCSRYTLKADGTQCPSGSSG

TTVIYTCEFISAYGARGSANIKVTFISVANLTITPDPISVSEGQNFSIKCISDVSNYDEVYWNTS

AGIKIYQRFYTTRRYLDGAESVLTVKTSTREWNGTYHCIFRYKNSYSIATKDVIVHPLPLKLNI

MVDPLEATVSCSGSHHIKCCIEEDGDYKVTFHTGSSSLPAAKEVNKKQVCYKHNFNASSVS

WCSKTVDVCCHFTNAANNSVWSPSMKLNLVPGENITCQDPVIGVGEPGKVIQKLCRFSNVPS

SPESPIGGTITYKCVGSQWEEKRNDCISAPINSLLQMAKALIKSPSQDEMLPTYLKDLSISIDKA

EHEISSSPGSLGAIINILDLLSTVPTQVNSEMMTHVLSTVNVILGKPVLNTWKVLQQQWTNQS

SQLLHSVERFSQALQSGDSPPLSFSQTNVQMSSMVIKSSHPETYQQRFVFPYFDLWGNVVIDK

SYLENLQSDSSIVTMAFPTLQAILAQDIQENNFAESLVMTTTVSHNTTMPFRISMTFKNNSPSG

GETKCVFWNFRLANNTGGWDSSGCYVEEGDGDNVTCICDHLTSFSILMSPDSPDPSSLLGILL

DIISYVGVGFSILSLAACLVVEAVVWKSVTKNRTSYMRHTCIVNIAASLLVANTWFIVVAAIQ

DNRYILCKTACVAATFFIHFFYLSVFFWMLTLGLMLFYRLVFILHETSRSTQKAIAFCLGYGC

PLAISVITLGATQPREVYTRKNVCWLNWEDTKALLAFAIPALIIVVVNITITIVVITKILRPSIGD

KPCKQEKSSLFQISKSIGVLTPLLGLTWGFGLTTVFPGTNLVFHIIFAILNVFQGLFILLFGCLW

DLKVQEALLNKFSLSRWSSQHSKSTSLGSSTPVFSMSSPISRRFNNLFGKTGTYNVSTPEATSS

SLENSSSASSLLN
```

>gi|148806925|ref|NP_071442.2|EGF, latrophilin and seven transmembrane domain containing 1 precursor {Homo sapiens}

(SEQ ID NO: 1273)

```
MKRLPLLVVFSTLLNCSYTQNCTKTPCLPNAKCEIRNGIEACYCNMGFSGNGVTICEDDNEC

GNLTQSCGENANCTNTEGSYYCMCVPGFRSSSNQDRFITNDGTVCIENVNANCHLDNVCIAA

NINKTLTKIRSIKEPVALLQEVYRNSVTDLSPTDIITYIEILAESSSLLGYKNNTISAKDTLSNST

LTEFVKTVNNFVQRDTFVVWDKLSVNHRRTHLTKLMHTVEQATLRISQSFQKTTEFDTNSTD

IALKVFFFDSYNMKHIHPHMNMDGDYINIFPKRKAAYDSNGNVAVAFVYYKSIGPLLSSSDN

FLLKPQNYDNSEEEERVISSVISVSMSSNPPTLYELEKITFTLSHRKVTDRYRSLCAFWNYSPD

TMNGSWSSEGCELTYSNETHTSCRCNHLTHFAILMSSGPSIGIKDYNILTRITQLGIIISLICLAIC

IFTFWFFSEIQSTRTTIHKNLCCSLFLAELVFLVGINTNTNKLFCSIIAGLLHYFFLAAFAWMCIE

GIHLYLIVVGVIYNKGFLHKNFYIFGYLSPAVVVGFSAALGYRYYGTTKVCWLSTENNFIWSF

IGPACLIILVNLLAFGVIIYKVFRHTAGLKPEVSCFENIRSCARGALALLFLLGTTWIFGVLHVV

HASVVTAYLFTVSNAFQGMFIFLFLCVLSRKIQEEYYRLFKNVPCCFGCLR
```

-continued

\>gi|149944554|ref|NP_001043.2|somatostatin receptor type 4 {Homo sapiens}
(SEQ ID NO: 1274)

MSAPSTLPPGGEEGLGTAWPSAANASSAPAEAEEAVAGPGDARAAGMVAIQCIYALVCLVG

LVGNALVIFVILRYAKMKTATNIYLLNLAVADELFMLSVPFVASSAALRHWPFGSVLCRAVL

SVDGLNMFTSVFCLTVLSVDRYVAVVHPLRAATYRRPSVAKLINLGVWLASLLVTLPIAIFA

DTRPARGGQAVACNLQWPHPAWSAVFVVYTFLLGFLLPVLAIGLCYLLIVGKMRAVALRAG

WQQRRRSEKKITRLVLMVVVVFVLCWMPFYVVQLLNLFVTSLDATVNHVSLILSYANSCAN

PILYGFLSDNFRRFFQRVLCLRCCLLEGAGGAEEEPLDYYATALKSKGGAGCMCPPLPCQQE

ALQPEPGRKRIPLTRTTTF

\>gi|150170722|ref|NP_004215.2|G protein-coupled receptor 50 {Homo sapiens}
(SEQ ID NO: 1275)

MGPTLAVPTPYGCIGCKLPQPEYPPALIIFMFCAMVITIVVDLIGNSMVILAVTKNKKLRNSGN

IFVVSLSVADMLVAIYPYPLMLHAMSIGGWDLSQLQCQMVGFITGLSVVGSIFNIVAIAINRY

CYICHSLQYERIFSVRNTCIYLVITWIMTVLAVLPNMYIGTIEYDPRTYTCIFNYLNNPVFTVTI

VCIHFVLPLLIVGFCYVRIWTKVLAARDPAGQNPDNQLAEVRNFLTMFVIFLLFAVCWCPINV

LTVLVAVSPKEMAGKIPNWLYLAAYFIAYFNSCLNAVIYGLLNENFRREYWTIFHAMRHPIIF

FSGLISDIREMQEARTLARARAHARDQAREQDRAHACPAVEETPMNVRNVPLPGDAAAGHP

DRASGHPKPHSRSSSAYRKSASTHHKSVFSHSKAASGHLKPVSGHSKPASGHPKSATVYPKP

ASVHFKADSVHFKGDSVHFKPDSVHFKPASSNPKPITGHHVSAGSHSKSAFSAATSHPKPTTG

HIKPATSHAEPTTADYPKPATTSHPKPTAADNPELSASHCPEIPAIAHPVSDDSDLPESASSPAA

GPTKPAASQLESDTIADLPDPTVVTTSTNDYHDVVVIDVEDDPDEMAV

\>gi|153791424|ref|NP_004769.2|putative G-protein coupled receptor 44 {Homo sapiens}
(SEQ ID NO: 1276)

MSANATLKPLCPILEQMSRLQSHSNTSIRYIDHAAVLLHGLASLLGLVENGVILFVVGCRMRQ

TVVTTWVLHLALSDLLASASLPFFTYFLAVGHSWELGTTFCKLHSSIFFLNMFASGFLLSAISL

DRCLQVVRPVWAQNHRTVAAAHKVCLVLWALAVLNTVPYFVFRDTISRLDGRIMCYYNVL

LLNPGPDRDATCNSRQVALAVSKFLLAFLVPLAIIASSHAAVSLRLQHRGRRRPGRFVRLVAA

VVAAFALCWGPYHVFSLLEARAHANPGLRPLVWRGLPFVTSLAFFNSVANPVLYVLTCPDM

LRKLRRSLRTVLESVLVDDSELGGAGSSRRRRTSSTARSASPLALCSRPEEPRGPARLLGWLL

GSCAASPQTGPLNRALSSTSS

\>gi|153792268|ref|NP_005290.2|probable G-protein coupled receptor 31 {Homo sapiens}
(SEQ ID NO: 1277)

MPFPNCSAPSTVVATAVGVLLGLECGLGLLGNAVALWTFLFRVRVWKPYAVYLLNLALAD

LLLAACLPFLAAFYLSLQAWHLGRVGCWALHFLLDLSRSVGMAFLAAVALDRYLRVVHPR

LKVNLLSPQAALGVSGLVWLLMVALTCPGLLISEAAQNSTRCHSFYSRADGSFSIIWQEALSC

LQFVLPFGLIVFCNAGIIRALQKRLREPEKQPKLQRAQALVTLVVVLFALCFLPCFLARVLMHI

FQNLGSCRALCAVAHTSDVTGSLTYLHSVLNPVVYCFSSPTFRSSYRRVFHTLRGKGQAAEP

PDFNPRDSYS

\>gi|156104886|ref|NP_057686.2|C-C chemokine receptor type 10 {Homo sapiens}
(SEQ ID NO: 1278)

MGTEATEQVSWGHYSGDEEDAYSAEPLPELCYKADVQAFSRAFQPSVSLTVAALGLAGNGL

VLATHLAARRAARSPTSAHLLQLALADLLLALTLPFAAAGALQGWSLGSATCRTISGLYSAS

FHAGFLFLACISADRYVAIARALPAGPRPSTPGRAHLVSVIVWLLSLLLALPALLFSQDGQRE

GQRRCRLIFPEGLTQTVKGASAVAQVALGFALPLGVMVACYALLGRTLLAARGPERRRALR

VVVALVAAFVVLQLPYSLALLLDTADLLAARERSCPASKRKDVALLVTSGLALARCGLNPV

LYAFLGLRFRQDLRRLLRGGSCPSGPQPRRGCPRRPRLSSCSAPTETHSLSWDN

-continued

>gi|157364957|ref|NP_005963.3|neuropeptide Y receptor type 4 {Homo sapiens}
(SEQ ID NO: 1279)
MNTSHLLALLLPKSPQGENRSKPLGTPYNFSEHCQDSVDVMVFIVTSYSIETVVGVLGNLCL

MCVTVRQKEKANVTNLLIANLAFSDFLMCLLCQPLTAVYTIMDYWIFGETLCKMSAFIQCMS

VTVSILSLVLVALERHQLIINPTGWKPSISQAYLGIVLIWVIACVLSLPFLANSILENVFHKNHS

KALEFLADKVVCTESWPLAHHRTIYTTFLLLFQYCLPLGFILVCYARIYRRLQRQGRVFHKGT

YSLRAGHMKQVNVVLVVMVVAFAVLWLPLHVFNSLEDWHHEAIPICHGNLIFLVCHLLAM

ASTCVNPFIYGFLNTNFKKEIKALVLTCQQSAPLEESEHLPLSTVHTEVSKGSLRLSGRSNPI

>gi|157426873|ref|NP_001048.2|substance-K receptor {Homo sapiens}
(SEQ ID NO: 1280)
MGTCDIVTEANISSGPESNTTGITAFSMPSWQLALWATAYLALVLVAVTGNAIVIWIILAHRR

MRTVTNYFIVNLALADLCMAAFNAAFNFVYASHNIWYFGRAFCYFQNLFPITAMFVSIYSMT

AIAADRYMAIVHPFQPRLSAPSTKAVIAGIWLVALALASPQCFYSTVTMDQGATKCVVAWPE

DSGGKTLLLYHLVVIALIYFLPLAVMFVAYSVIGLTLWRRAVPGHQAHGANLRHLQAMKKF

VKTMVLVVLTFAICWLPYHLYFILGSFQEDIYCHKFIQQVYLALFWLAMSSTMYNPIIYCCLN

HRFRSGFRLAFRCCPWVTPTKEDKLELTPTTSLSTRVNRCHTKETLFMAGDTAPSEATSGEA

GRPQDGSGLWFGYGLLAPTKTHVEI

>gi|157671951|ref|NP_005061.2|anion exchange protein 3 isoform 1 {Homo sapiens}
(SEQ ID NO: 1281)
MANGVIPPPGGASPLPQVRVPLEEPPLSPDVEEEDDDLGKTLAVSRFGDLISKPPAWDPEKPS

RSYSERDFEFHRHTSHHTHHPLSARLPPPHKLRRLPPTSARHTRRKRKKEKTSAPPSEGTPPIQ

EEGGAGVDEEEEEEEEEEGESEAEPVEPPPSGTPQKAKFSIGSDEDDSPGLPGRAAVTKPLPSV

GPHTDKSPQHSSSSPSPRARASRLAGEKSRPWSPSASYDLRERLCPGSALGNPGGPEQQVPTD

EAEAQMLGSADLDDMKSHRLEDNPGVRRHLVKKPSRTQGGRGSPSGLAPILRRKKKKKKLD

RRPHEVFVELNELMLDRSQEPHWRETARWIKFEEDVEEETERWGKPHVASLSFRSLLELRRTI

AHGAALLDLEQTTLPGIAHLVVETMIVSDQIRPEDRASVLRTLLLKHSHPNDDKDSGFFPRNP

SSSSMNSVLGNHHPTPSHGPDGAVPTMADDLGEPAPLWPHDPDAKEKPLHMPGGDGHRGK

SLKLLEKIPEDAEATVVLVGCVPFLEQPAAAFVRLNEAVLLESVLEVPVPVRFLFVMLGPSHT

STDYHELGRSIATLMSDKLFHEAAYQADDRQDLLSAISEFLDGSIVIPPSEVEGRDLLRSVAAF

QRELLRKRREREQTKVEMTTRGGYTAPGKELSLELGGSEATPEDDPLLRTGSVFGGLVRDVR

RRYPHYPSDLRDALHSQCVAAVLFIYFAALSPAITFGGLLGEKTEGLMGVSELIVSTAVLGVL

FSLLGAQPLLVVGFSGPLLVFEEAFFKFCRAQDLEYLTGRVWVGLWLVVFVLALVAAEGSFL

VRYISPFTQEIFAFLISLIFIYETFYKLYKVFTEHPLLPFYPPEGALEGSLDAGLEPNGSALPPTE

GPPSPRNQPNTALLSLILMLGTFFIAFFLRKFRNSRFLGGKARRIIGDFGIPISILVMVLVDYSIT

DTYTQKLTVPTGLSVTSPDKRSWFIPPLGSARPFPPWMMVAAAVPALLVLILIFMETQITALIV

SQKARRLLKGSGFHLDLLLIGSLGGLCGLFGLPWLTAATVRSVTHVNALTVMRTAIAPGDKP

QIQEVREQRVTGVLIASLVGLSIVMGAVLRRIPLAVLFGIFLYMGVTSLSGIQLSQRLLLILMP

AKHHPEQPYVTKVKTWRMHLFTCIQLGCIALLWVVKSTAASLAFPFLLLLTVPLRHCLLPRL

FQDRELQALDSEDAEPNFDEDGQDEYNELHMPV

>gi|157694513|ref|NP_060960.2|leucine-rich repeat-containing G-protein
coupled receptor 4 precursor {Homo sapiens}
(SEQ ID NO: 1282)
MPGPLGLLCFLALGLLGSAGPSGAAPPLCAAPCSCDGDRRVDCSGKGLTAVPEGLSAFTQAL

DISMNNITQLPEDAFKNFPFLEELQLAGNDLSFIHPKALSGLKELKVLTLQNNQLKTVPSEAIR

GLSALQSLRLDANHITSVPEDSFEGLVQLRHLWLDDNSLTEVPVHPLSNLPTLQALTLALNKI

```
SSIPDFAFTNLSSLVVLHLHNNKIRSLSQHCFDGLDNLETLDLNYNNLGEFPQAIKALPSLKEL

GFHSNSISVIPDGAFDGNPLLRTIHLYDNPLSFVGNSAFHNLSDLHSLVIRGASMVQQFPNLTG

TVHLESLTLTGTKISSIPNNLCQEQKMLRTLDLSYNNIRDLPSFNGCHALEEISLQRNQIYQIKE

GTFQGLISLRILDLSRNLIHEIHSRAFATLGPITNLDVSFNELTSFPTEGLNGLNQLKLVGNFKL

KEALAAKDFVNLRSLSVPYAYQCCAFWGCDSYANLNTEDNSLQDHSVAQEKGTADAANVT

STLENEEHSQIIIHCTPSTGAFKPCEYLLGSWMIRLTVWFIFLVALFFNLLVILTTFASCTSLPSS

KLFIGLISVSNLFMGIYTGILTFLDAVSWGRFAEFGIWWETGSGCKVAGFLAVFSSESAIFLLM

LATVERSLSAKDIMKNGKSNHLKQFRVAALLAFLGATVAGCFPLFHRGEYSASPLCLPFPTG

ETPSLGFTVTLVLLNSLAFLLMAVIYTKLYCNLEKEDLSENSQSSMIKHVAWLIFTNCIFFCPV

AFFSFAPLITAISISPEIMKSVTLIFFPLPACLNPVLYVFFNPKFKEDWKLLKRRVTKKSGSVSVS

ISSQGGCLEQDFYYDCGMYSHLQGNLTVCDCCESFLLTKPVSCKHLIKSHSCPALAVASCQR

PEGYWSDCGTQSAHSDYADEEDSFVSDSSDQVQACGRACFYQSRGFPLVRYAYNLPRVKD
```

>gi|157738685|ref|NP_937822.2|G protein-coupled receptor 103 {Homo sapiens}
(SEQ ID NO: 1283)

```
MQALNITPEQFSRLLRDHNLTREQFIALYRLRPLVYTPELPGRAKLALVLTGVLIFALALFGN

ALVFYVVTRSKAMRTVTNIFICSLALSDLLITFFCIPVTMLQNISDNWLGGAFICKMVPFVQST

AVVTEILTMTCIAVERHQGLVHPFKMKWQYTNRRAFTMLGVVWLVAVIVGSPMWHVQQL

EIKYDFLYEKEHICCLEEWTSPVHQKIYTTFILVILFLLPLMVMLILYSKIGYELWIKKRVGDG

SVLRTIHGKEMSKIARKKKRAVIMMVTVVALFAVCWAPFHVVHMMIEYSNFEKEYDDVTIK

MIFAIVQIIGFSNSICNPIVYAFMNENFKKNVLSAVCYCIVNKTFSPAQRHGNSGITMMRKKA

KFSLRENPVEETKGEAFSDGNIEVKLCEQTEEKKKLKRHLALFRSELAENSPLDSGH
```

>gi|157738694|ref|NP_006009.2|G-protein coupled receptor 109B {Homo sapiens}
(SEQ ID NO: 1284)

```
MNRHHLQDHFLEIDKKNCCVFRDDFIAKVLPPVLGLEFIFGLLGNGLALWIFCFHLKSWKSSR

IFLFNLAVADFLLIICLPFVMDYYVRRSDWKFGDIPCRLVLFMFAMNRQGSIIFLTVVAVDRY

FRVVHPHHALNKISNWTAAIISCLLWGITVGLTVHLLKKKLLIQNGTANVCISFSICHTFRWH

EAMFLLEFFLPLGIILFCSARIIWSLRQRQMDRHAKIKRAITFIMVVAIVFVICFLPSVVVRIHIF

WLLHSGTQNCEVYRSVDLAFFITLSFTYMNSMLDPVVYYFSSPSFPNFFSTLINRCLQRKITG

EPDNNRSTSVELTGDPNKTRGAPEALIANSGEPWSPSYLGPTSNNHSKKGHCHQEPASLEKQ

LGCCIE
```

>gi|161484640|ref|NP_002502.2|neuromedin-B receptor {Homo sapiens}
(SEQ ID NO: 1285)

```
MPSKSLSNLSVTTGANESGSVPEGWERDFLPASDGTTTELVIRCVIPSLYLLIITVGLLGNIML

VKIFITNSAMRSVPNIFISNLAAGDLLLLLTCVPVDASRYFFDEWMFGKVGCKLIPVIQLTSVG

VSVFTLTALSADRYRAIVNPMDMQTSGALLRTCVKAMGIWVVSVLLAVPEAVFSEVARISSL

DNSSFTACIPYPQTDELHPKIHSVLIFLVYFLIPLAIISIYYYHIAKTLIKSAHNLPGEYNEHTKK

QMETRKRLAKIVLVFVGCFIFCWFPNHILYMYRSFNYNEIDPSLGHMIVTLVARVLSFGNSCV

NPFALYLLSESFRRHFNSQLCCGRKSYQERGTSYLLSSSAVRMTSLKSNAKNMVTNSVLLNG

HSMKQEMAL
```

>gi|163792198|ref|NP_056051.2|latrophilin-3 precursor {Homo sapiens}
(SEQ ID NO: 1286)

```
MWPSQLLIFMMLLAPIIHAFSRAPIPMAVVRRELSCESYPIELRCPGTDVIMIESANYGRTDDK

ICDSDPAQMENIRCYLPDAYKIMSQRCNNRTQCAVVAGPDVFPDPCPGTYKYLEVQYECVP

YKVEQKVFLCPGLLKGVYQSEHLFESDHQSGAWCKDPLQASDKIYYMPWTPYRTDTLTEYS
```

-continued

SKDDFIAGRPTTTYKLPHRVDGTGFVVYDGALFFNKERTRNIVKFDLRTRIKSGEAIIANANY

HDTSPYRWGGKSDIDLAVDENGLWVIYATEQNNGKIVISQLNPYTLRIEGTWDTAYDKRSAS

NAFMICGILYVVKSVYEDDDNEATGNKIDYIYNTDQSKDSLVDVPFPNSYQYIAAVDYNPRD

NLLYVWNNYHVVKYSLDFGPLDSRSGQAHHGQVSYISPPIHLDSELERPSVKDISTTGPLGM

GSTTTSTTLRTTTLSPGRSTTPSVSGRRNRSTSTPSPAVEVLDDMTTHLPSASSQIPALEESCEA

VEAREIMWFKTRQGQIAKQPCPAGTIGVSTYLCLAPDGIWDPQGPDLSNCSSPWVNHITQKL

KSGETAANIARELAEQTRNHLNAGDITYSVRAMDQLVGLLDVQLRNLTPGGKDSAARSLNK

LQKRERSCRAYVQAMVETVNNLLQPQALNAWRDLTTSDQLRAATMLLHTVEESAFVLADN

LLKTDIVRENTDNIKLEVARLSTEGNLEDLKFPENMGHGSTIQLSANTLKQNGRNGEIRVAFV

LYNNLGPYLSTENASMKLGTEALSTNHSVIVNSPVITAAINKEFSNKVYLADPVVFTVKHIKQ

SEENFNPNCSFWSYSKRTMTGYWSTQGCRLLTTNKTHTTCSCNHLTNFAVLMAHVEVKHSD

AVHDLLLDVITWVGILLSLVCLLICIFTFCFFRGLQSDRNTIHKNLCISLFVAELLFLIGINRTDQ

PIACAVFAALLHFFFLAAFTWMFLEGVQLYIMLVEVFESEHSRRKYFYLVGYGMPALIVAVS

AAVDYRSYGTDKVCWLRLDTYFIWSFIGPATLIIMLNVIFLGIALYKMFHHTAILKPESGCLD

NINYEDNRPFIKSWVIGAIALLCLLGLTWAFGLMYINESTVIMAYLFTIFNSLQGMFIFIFHCVL

QKKVRKEYGKCLRTHCCSGKSTESSIGSGKTSGSRTPGRYSTGSQSRIRRMWNDTVRKQSES

SFITGDINSSASLNREGLLNNARDTSVMDTLPLNGNHGNSYSIASGEYLSNCVQIIDRGYNHN

ETALEKKILKELTSNYIPSYLNNHERSSEQNRNLMNKLVNNLGSGREDDAIVLDDATSFNHEE

SLGLELIHEESDAPLLPPRVYSTENHQPHHYTRRRIPQDHSESFFPLLTNEHTEDLQSPHRDSL

YTSMPTLAGVAATESVTTSTQTEPPPAKCGDAEDVYYKSMPNLGSRNHVHQLHTYYQLGRG

SSDGFIVPPNKDGTPPEGSSKGPAHLVTSL

>gi|166362740|ref|NP_001983.2|proteinase-activated receptor 1 precursor {Homo sapiens}
(SEQ ID NO: 1287)

MGPRRLLLVAACFSLCGPLLSARTRARRPESKATNATLDPRSFLLRNPNDKYEPFWEDEEKN

ESGLTEYRLVSINKSSPLQKQLPAFISEDASGYLTSSWLTLFVPSVYTGVFVVSLPLNIMAIVVF

ILKMKVKKPAVVYMLHLATADVLFVSVLPFKISYYFSGSDWQFGSELCRFVTAAFYCNMYA

SILLMTVISIDRFLAVVYPMQSLSWRTLGRASFTCLAIWALAIAGVVPLLLKEQTIQVPGLNIT

TCHDVLNETLLEGYYAYYFSAFSAVFFFVPLIISTVCYVSIIRCLSSSAVANRSKKSRALFLSAA

VFCIFIICFGPTNVLLIAHYSFLSHTSTTEAAYFAYLLCVCVSSISCCIDPLIYYASSECQRYVY

SILCCKESSDPSSYNSSGQLMASKMDTCSSNLNNSIYKKLLT

>gi|166795283|ref|NP_002053.3|glucagon-like peptide 1 receptor precursor {Homo sapiens}
(SEQ ID NO: 1288)

MAGAPGPLRLALLLLGMVGRAGPRPQGATVSLWETVQKWREYRRQCQRSLTEDPPPATDLF

CNRTFDEYACWPDGEPGSFVNVSCPWYLPWASSVPQGHVYRFCTAEGLWLQKDNSSLPWR

DLSECEESKRGERSSPEEQLLFLYIIYTVGYALSFSALVIASAILLGFRHLHCTRNYIHLNLFASF

ILRALSVFIKDAALKWMYSTAAQQHQWDGLLSYQDSLSCRLVFLLMQYCVAANYYWLLVE

GVYLYTLLAFSVLSEQWIFRLYVSIGWGVPLLFVVPWGIVKYLYEDEGCWTRNSNMNYWLII

RLPILFAIGVNFLIFVRVICIVVSKLKANLMCKTDIKCRLAKSTLTLIPLLGTHEVIFAFVMDEH

ARGTLRFIKLFTELSFTSFQGLMVAILYCFVNNEVQLEFRKSWERWRLEHLHIQRDSSMKPLK

CPTSSLSSGATAGSSMYTATCQASCS

>gi|166999098|ref|NP_000829.2|metabotropic glutamate receptor 1 isoform alpha
precursor {Homo sapiens}
(SEQ ID NO: 1289)

MVGLLLFFFPAIFLEVSLLPRSPGRKVLLAGASSQRSVARMDGDVIIGALFSVHHQPPAEKVP

ERKCGEIREQYGIQRVEAMFHTLDKINADPVLLPNITLGSEIRDSCWHSSVALEQSIEFIRDSLI

SIRDEKDGINRCLPDGQSLPPGRTKKPIAGVIGPGSSSVAIQVQNLLQLFDIPQIAYSATSIDLSD

KTLYKYFLRVVPSDTLQARAMLDIVKRYNWTYVSAVHTEGNYGESGMDAFKELAAQEGLC

IAHSDKIYSNAGEKSFDRLLRKLRERLPKARVVVCFCEGMTVRGLLSAMRRLGVVGEFSLIG

SDGWADRDEVIEGYEVEANGGITIKLQSPEVRSFDDYFLKLRLDTNTRNPWFPEFWQHRFQC

RLPGHLLENPNFKRICTGNESLEENYVQDSKMGFVINAIYAMAHGLQNMHHALCPGHVGLC

DAMKPIDGSKLLDFLIKSSFIGVSGEEVWFDEKGDAPGRYDIMNLQYTEANRYDYVHVGTW

HEGVLNIDDYKIQMNKSGVVRSVCSEPCLKGQIKVIRKGEVSCCWICTACKENEYVQDEFTC

KACDLGWWPNADLTGCEPIPVRYLEWSNIESIIAIAFSCLGILVTLFVTLIFVLYRDTPVVKSSS

RELCYIILAGIFLGYVCPFTLIAKPTTTSCYLQRLLVGLSSAMCYSALVTKTNRIARILAGSKKK

ICTRKPRFMSAWAQVIIASILISVQLTLVVTLIIMEPPMPILSYPSIKEVYLICNTSNLGVVAPLG

YNGLLIMSCTYYAFKTRNVPANFNEAKYIAFTMYTTCIIWLAFVPIYFGSNYKIITTCFAVSLS

VTVALGCMFTPKMYIIIAKPERNVRSAFTTSDVVRMHVGDGKLPCRSNTFLNIFRRKKAGAG

NANSNGKSVSWSEPGGGQVPKGQHMWHRLSVHVKTNETACNQTAVIKPLTKSYQGSGKSL

TFSDTSTKTLYNVEEEEDAQPIRFSPPGSPSMVVHRRVPSAATTPPLPSHLTAEETPLFLAEPAL

PKGLPPPLQQQQQPPPQQKSLMDQLQGVVSNFSTAIPDFHAVLAGPGGPGNGLRSLYPPPPPP

QHLQMLPLQLSTFGEELVSPPADDDDDSERFKLLQEYVYEHEREGNTEEDELEEEEDLQAA

SKLTPDDSPALTPPSPFRDSVASGSSVPSSPVSESVLCTPPNVSYASVILRDYKQSSSTL

>gi|167000885|ref|NP_001471.2|galanin receptor type 1 {Homo sapiens}
(SEQ ID NO: 1290)

MELAVGNLSEGNASWPEPPAPEPGPLFGIGVENFVTLVVFGLIFALGVLGNSLVITVLARSKP

GKPRSTTNLFILNLSIADLAYLLFCIPFQATVYALPTWVLGAFICKFIHYFFTVSMLVSIFTLAA

MSVDRYVAIVHSRRSSSLRVSRNALLGVGCIWALSIAMASPVAYHQGLFHPRASNQTFCWE

QWPDPRHKKAYVVCTFVFGYLLPLLLICFCYAKVLNHLHKKLKNMSKKSEASKKKTAQTVL

VVVVVFGISWLPHHIIHLWAEFGVFPLTPASFLFRITAHCLAYSNSSVNPIIYAFLSENFRKAYK

QVFKCHIRKDSHLSDTKESKSRIDTPPSTNCTHV

>gi|170671732|ref|NP_063941.3|melanocortin receptor 3 {Homo sapiens}
(SEQ ID NO: 1291)

MNASCCLPSVQPTLPNGSEHLQAPFFSNQSSSAFCEQVFIKPEVFLSLGIVSLLENILVILAVVR

NGNLHSPMYFFLCSLAVADMLVSVSNALETIMIAIVHSDYLTFEDQFIQHMDNIFDSMICISLV

ASICNLLAIAVDRYVTIFYALRYHSIMTVRKALTLIVAIWVCCGVCGVVFIVYSESKMVIVCLI

TMFFAMMLLMGTLYVHMFLFARLHVKRIAALPPADGVAPQQHSCMKGAVTITILLGVFIFC

WAPFFLHLVLIITCPTNPYCICYTAHFNTYLVLIMCNSVIDPLIYAFRSLELRNTFREILCGCNG

MNLG

>gi|170932505|ref|NP_064552.3|neuromedin-U receptor 2 {Homo sapiens}
(SEQ ID NO: 1292)

MSGMEKLQNASWIYQQKLEDPFQKHLNSTEEYLAFLCGPRRSHFFLPVSVVYVPIFVVGVIG

NVLVCLVILQHQAMKTPTNYYLFSLAVSDLLVLLLGMPLEVYEMWRNYPFLFGPVGCYFKT

ALFETVCFASILSITTVSVERYVAILHPFRAKLQSTRRRALRILGIVWGFSVLFSLPNTSIHGIKF

HYFPNGSLVPGSATCTVIKPMWIYNFIIQVTSFLFYLLPMTVISVLYYLMALRLKKDKSLEAD

EGNANIQRPCRKSVNKMLFVLVLVFAICWAPFHIDRLFFSFVEEWSESLAAVFNLVHVVSGV

FFYLSSAVNPIIYNLLSRRFQAAFQNVISSFHKQWHSQHDPQLPPAQRNIFLTECHFVELTEDIG

PQFPCQSSMHNSHLPAALSSEQMSRTNYQSFHFNKT

>gi|183979980|ref|NP_001116513.2|C-C chemokine receptor type 2 isoform A {Homo sapiens}
(SEQ ID NO: 1293)

MLSTSRSRFIRNTNESGEEVTTFFDYDYGAPCHKFDVKQIGAQLLPPLYSLVFIFGFVGNMLV

VLILINCKKLKCLTDIYLLNLAISDLLFLITLPLWAHSAANEWVFGNAMCKLFTGLYHIGYFG

GIFFIILLTIDRYLAIVHAVFALKARTVTFGVVTSVITWLVAVFASVPGIIFTKCQKEDSVYVCG

PYFPRGWNNFHTIMRNILGLVLPLLIMVICYSGILKTLLRCRNEKKRHRAVRVIFTIMIVYFLF

WTPYNIVILLNTFQEFFGLSNCESTSQLDQATQVTETLGMTHCCINPIIYAFVGEKFRSLFHIAL

GCRIAPLQKPVCGGPGVRPGKNVKVTTQGLLDGRGKGKSIGRAPEASLQDKEGA

>gi|183979982|ref|NP_001116868.1|C-C chemokine receptor type 2 isoform B {Homo sapiens}
(SEQ ID NO: 1294)

MLSTSRSRFIRNTNESGEEVTTFFDYDYGAPCHKFDVKQIGAQLLPPLYSLVFIFGFVGNMLV

VLILINCKKLKCLTDIYLLNLAISDLLFLITLPLWAHSAANEWVFGNAMCKLFTGLYHIGYFG

GIFFIILLTIDRYLAIVHAVFALKARTVTFGVVTSVITWLVAVFASVPGIIFTKCQKEDSVYVCG

PYFPRGWNNFHTIMRNILGLVLPLLIMVICYSGILKTLLRCRNEKKRHRAVRVIFTIMIVYFLF

WTPYNIVILLNTFQEFFGLSNCESTSQLDQATQVTETLGMTHCCINPIIYAFVGEKFRRYLSVF

FRKHITKRFCKQCPVFYRETVDGVTSTNTPSTGEQEVSAGL

>gi|187960055|ref|NP_005675.3|probable G-protein coupled receptor 52 {Homo sapiens}
(SEQ ID NO: 1295)

MNESRWTEWRILNMSSGIVNVSERHSCPLGFGHYSVVDVCIFETVVIVLLTFLIIAGNLTVIFV

FHCAPLLHHYTTSYFIQTMAYADLFVGVSCLVPTLSLLHYSTGVHESLTCQVFGYIISVLKSVS

MACLACISVDRYLAITKPLSYNQLVTPCRLRICIILIWIYSCLIFLPSFFGWGKPGYHGDIFEWC

ATSWLTSAYFTGFIVCLLYAPAAFVVCFTYFHIFKICRQHTKEINDRRARFPSHEVDSSRETGH

SPDRRYAMVLFRITSVFYMLWLPYIIYFLLESSRVLDNPTLSFLTTWLAISNSFCNCVIYSLSNS

VFRLGLRRLSETMCTSCMCVKDQEAQEPKPRKRANSCSI

>gi|187960067|ref|NP_000836.2|metabotropic glutamate receptor 8 isoform a precursor {Homo sapiens}
(SEQ ID NO: 1296)

MVCEGKRSASCPCFFLLTAKFYWILTMMQRTHSQEYAHSIRVDGDIILGGLFPVHAKGERGV

PCGELKKEKGIHRLEAMLYAIDQINKDPDLLSNITLGVRILDTCSRDTYALEQSLTFVQALIEK

DASDVKCANGDPPIFTKPDKISGVIGAAASSVSIMVANILRLFKIPQISYASTAPELSDNTRYDF

FSRVVPPDSYQAQAMVDIVTALGWNYVSTLASEGNYGESGVEAFTQISREIGGVCIAQSQKIP

REPRPGEFEKIIKRLLETPNARAVIMFANEDDIRRILEAAKKLNQSGHFLWIGSDSWGSKIAPV

YQQEEIAEGAVTILPKRASIDGFDRYFRSRTLANNRRNVWFAEFWEENFGCKLGSHGKRNSH

IKKCTGLERIARDSSYEQEGKVQFVIDAVYSMAYALHNMHKDLCPGYIGLCPRMSTIDGKEL

LGYIRAVNFNGSAGTPVTFNENGDAPGRYDIFQYQITNKSTEYKVIGHWTNQLHLKVEDMQ

WAHREHTHPASVCSLPCKPGERKKTVKGVPCCWHCERCEGYNYQVDELSCELCPLDQRPN

MNRTGCQLIPIIKLEWHSPWAVVPVFVAILGIIATTFVIVTFVRYNDTPIVRASGRELSYVLLTG

IFLCYSITFLMIAAPDTIICSFRRVFLGLGMCFSYAALLTKTNRIHRIFEQGKKSVTAPKFISPAS

QLVITFSLISVQLLGVFVWFVVDPPHIIDYGEQRTLDPEKARGVLKCDISDLSLICSLGYSILL

MVTCTVYAIKTRGVPETFNEAKPIGFTMYTTCIIWLAFIPIFFGTAQSAEKMYIQTTTLTVSMS

LSASVSLGMLYMPKVYIIIFHPEQNVQKRKRSFKAVVTAATMQSKLIQKGNDRPNGEVKSEL

CESLETNTSSTKTTYISYSNHSI

```
>gi|188497623|ref|NP_006047.3|neuromedin-U receptor 1 {Homo sapiens}
                                                                          (SEQ ID NO: 1297)
MTPLCLNCSVLPGDLYPGGARNPMACNGSAARGHFDPEDLNLTDEALRLKYLGPQQTELFM

PICATYLLIFVVGAVGNGLTCLVILRHKAMRTPTNYYLFSLAVSDLLVLLVGLPLELYEMWH

NYPFLLGVGGCYFRTLLFEMVCLASVLNVTALSVERYVAVVHPLQARSMVTRAHVRRVLG

AVWGLAMLCSLPNTSLHGIRQLHVPCRGPVPDSAVCMLVRPRALYNMVVQTTALLFFCLPM

AIMSVLYLLIGLRLRRERLLLMQEAKGRGSAAARSRYTCRLQQHDRGRRQVTKMLFVLVVV

FGICWAPFHADRVMWSVVSQWTDGLHLAFQHVHVISGIFFYLGSAANPVLYSLMSSRFRETF

QEALCLGACCHRLRPRHSSHSLSRMTTGSTLCDVGSLGSWVHPLAGNDGPEAQQETDPS

>gi|193083134|ref|NP_002377.4|melanocyte-stimulating hormone receptor {Homo sapiens}
                                                                          (SEQ ID NO: 1298)
MAVQGSQRRLLGSLNSTPTAIPQLGLAANQTGARCLEVSISDGLFLSLGLVSLVENALVVATI

AKNRNLHSPMYCFICCLALSDLLVSGSNVLETAVILLLEAGALVARAAVLQQLDNVIDVITCS

SMLSSLCFLGAIAVDRYISIFYALRYHSIVTLPRARRAVAAIWVASVVFSTLFIAYYDHVAVLL

CLVVFFLAMLVLMAVLYVHMLARACQHAQGIARLHKRQRPVHQGFGLKGAVTLTILLGIFF

LCWGPFFLHLTLIVLCPEHPTCGCIFKNFNLFLALIICNAIIDPLIYAFHSQELRRTLKEVLTCSW

>gi|194018562|ref|NP_009163.2|histamine receptor H3 {Homo sapiens}
                                                                          (SEQ ID NO: 1299)
MERAPPDGPLNASGALAGEAAAAGGARGFSAAWTAVLAALMALLIVATVLGNALVMLAFV

ADSSLRTQNNFFLLNLAISDFLVGAFCIPLYVPYVLTGRWTFGRGLCKLWLVVDYLLCTSSAF

NIVLISYDRFLSVTRAVSYRAQQGDTRRAVRKMLLVWVLAFLLYGPAILSWEYLSGGSSIPEG

HCYAEFFYNWYFLITASTLEFFTPFLSVTFFNLSIYLNIQRRTRLRLDGAREAAGPEPPPEAQPS

PPPPPGCWGCWQKGHGEAMPLHRYGVGEAAVGAEAGEATLGGGGGGGSVASPTSSSGSSS

RGTERPRSLKRGSKPSASSASLEKRMKMVSQSFTQRFRLSRDRKVAKSLAVIVSIFGLCWAPY

TLLMIIRAACHGHCVPDYWYETSFWLLWANSAVNPVLYPLCHHSFRRAFTKLLCPQKLKIQP

HSSLEHCWK

>gi|194272183|ref|NP_116166.7|probable G-protein coupled receptor
124 precursor {Homo sapiens}
                                                                          (SEQ ID NO: 1300)
MGAGGRRMRGAPARLLLPLLPWLLLLLAPEARGAPGCPLSIRSCKCSGERPKGLSGGVPGPA

RRRVVCSGGDLPEPPEPGLLPNGTVTLLLSNNKITGLRNGSFLGLSLLEKLDLRNNIISTVQPG

AFLGLGELKRLDLSNNRIGCLTSETFQGLPRLLRLNISGNIFSSLQPGVFDELPALKVVDLGTE

FLTCDCHLRWLLPWAQNRSLQLSEHTLCAYPSALHAQALGSLQEAQLCCEGALELHTHHLIP

SLRQVVFQGDRLPFQCSASYLGNDTRIRWYHNRAPVEGDEQAGILLAESLIHDCTFITSELTLS

HIGVWASGEWECTVSMAQGNASKKVEIVVLETSASYCPAERVANNRGDFRWPRTLAGITAY

QSCLQYPFTSVPLGGGAPGTRASRRCDRAGRWEPGDYSHCLYTNDITRVLYTFVLMPINASN

ALTLAHQLRVYTAEAASFSDMMDVVYVAQMIQKFLGYVDQIKELVEVMVDMASNLMLVD

EHLLWLAQREDKACSRIVGALERIGGAALSPHAQHISVNARNVALEAYLIKPHSYVGLTCTA

FQRREGGVPGTRPGSPGQNPPPEPEPPADQQLRFRCTTGRPNVSLSSFHIKNSVALASIQLPPSL

FSSLPAALAPPVPPDCTLQLLVFRNGRLFHSHSNTSRPGAAGPGKRRGVATPVIFAGTSGCGV

GNLTEPVAVSLRHWAEGAEPVAAWWSQEGPGEAGGWTSEGCQLRSSQPNVSALHCQHLGN

VAVLMELSAFPREVGGAGAGLHPVVYPCTALLLLCLFATIITYILNHSSIRVSRKGWHMLLNL

CFHIAMTSAVFAGGITLTNYQMVCQAVGITLHYSSLSTLLWMGVKARVLHKELTWRAPPPQ

EGDPALPTPSPMLRFYLIAGGIPLIICGITAAVNIHNYRDHSPYCWLVWRPSLGAFYIPVALILL

ITWIYFLCAGLRLRGPLAQNPKAGNSRASLEAGEELRGSTRLRGSGPLLSDSGSLLATGSARV
```

```
GTPGPPEDGDSLYSPGVQLGALVTTHFLYLAMWACGALAVSQRWLPRVVCSCLYGVAASA

LGLFVFTHHCARRRDVRASWRACCPPASPAAPHAPPRALPAAAEDGSPVFGEGPPSLKSSPSG

SSGHPLALGPCKLTNLQLAQSQVCEAGAAAGGEGEPEPAGTRGNLAHRHPNNVHHGRRAH

KSRAKGHRAGEACGKNRLKALRGGAAGALELLSSESGSLHNSPTDSYLGSSRNSPGAGLQLE

GEPMLTPSEGSDTSAAPLSEAGRAGQRRSASRDSLKGGGALEKESHRRSYPLNAASLNGAPK

GGKYDDVTLMGAEVASGGCMKTGLWKSETTV
```

>gi|194294562|ref|NP_795713.2|P2Y purinoceptor 13 {Homo sapiens} (SEQ ID NO: 1301)

```
MTAAIRRQRELSILPKVTLEAMNTTVMQGFNRSERCPRDTRIVQLVFPALYTVVFLTGILLNT

LALWVFVHIPSSSTFIIYLKNTLVADLIMTLMLPFKILSDSHLAPWQLRAFVCRFSSVIFYETM

YVGIVLLGLIAFDRFLKIIRPLRNIFLKKPVFAKTVSIFIWFFLFFISLPNTILSNKEATPSSVKKC

ASLKGPLGLKWHQMVNNICQFIFWTVFILMLVFYVVIAKKVYDSYRKSKSKDRKNNKKLEG

KVFVVVAVFFVCFAPFHFARVPYTHSQTNNKTDCRLQNQLFIAKETTLFLAATNICMDPLIYI

FLCKKFTEKLPCMQGRKTTASSQENHSSQTDN

ITLG
```

>gi|194353970|ref|NP_000672.3|alpha-2A adrenergic receptor {Homo sapiens} (SEQ ID NO: 1302)

```
MFRQEQPLAEGSFAPMGSLQPDAGNASWNGTEAPGGGARATPYSLQVTLTLVCLAGLLMLL

TVFGNVLVIIAVFTSRALKAPQNLFLVSLASADILVATLVIPFSLANEVMGYWYFGKAWCEIY

LALDVLFCTSSIVHLCAISLDRYWSITQAIEYNLKRTPRRIKAIIITVWVISAVISFPPLISIEKKG

GGGGPQPAEPRCEINDQKWYVISSCIGSFFAPCLIMILVYVRIYQIAKRRTRVPPSRRGPDAVA

APPGGTERRPNGLGPERSAGPGGAEAEPLPTQLNGAPGEPAPAGPRDTDALDLEESSSSDHAE

RPPGPRRPERGPRGKGKARASQVKPGDSLPRRGPGATGIGTPAAGPGEERVGAAKASRWRG

RQNREKRFTFVLAVVIGVFVVCWFPFFFTYTLTAVGCSVPRTLFKFFFWFGYCNSSLNPVIYTI

FNHDFRRAFKKILCRGDRKRIV
```

>gi|222080049|ref|NP_000858.3|5-hydroxytryptamine receptor 2B {Homo sapiens} (SEQ ID NO: 1303)

```
MALSYRVSELQSTIPEHILQSTFVHVISSNWSGLQTESIPEEMKQIVEEQGNKLHWAALLILMV

IIPTIGGNTLVILAVSLEKKLQYATNYFLMSLAVADLLVGLFVMPIALLTIMFEAMWPLPLVL

CPAWLFLDVLFSTASIMHLCAISVDRYIAIKKPIQANQYNSRATAFIKITVVWLISIGIAIPVPIK

GIETDVDNPNNITCVLTKERFGDFMLFGSLAAFFTPLAIMIVTYFLTIHALQKKAYLVKNKPP

QRLTWLTVSTVFQRDETPCSSPEKVAMLDGSRKDKALPNSGDETLMRRTSTIGKKSVQTISN

EQRASKVLGIVFFLFLLMWCPFFITNITLVLCDSCNQTTLQMLLEIFVWIGYVSSGVNPLVYTL

FNKTFRDAFGRYITCNYRATKSVKTLRKRSSKIYFRNPMAENSKFFKKHGIRNGINPAMYQSP

MRLRSSTIQSSSIILLDTLLLTENEGDKTEEQVSYV
```

>gi|222080095|ref|NP_001516.2|orexin receptor type 1 {Homo sapiens} (SEQ ID NO: 1304)

```
MEPSATPGAQMGVPPGSREPSPVPPDYEDEFLRYLWRDYLYPKQYEWVLIAAYVAVFVVAL

VGNTLVCLAVWRNHHMRTVTNYFIVNLSLADVLVTAICLPASLLVDITESWLFGHALCKVIP

YLQAVSVSVAVLTLSFIALDRWYAICHPLLFKSTARRARGSILGIWAVSLAIMVPQAAVMECS

SVLPELANRTRLFSVCDERWADDLYPKIYHSCFFIVTYLAPLGLMAMAYFQIFRKLWGRQIP

GTTSALVRNWKRPSDQLGDLEQGLSGEPQPRARAFLAEVKQMRARRKTAKMLMVVLLVFA

LCYLPISVLNVLKRVFGMFRQASDREAVYACFTFSHWLVYANSAANPIIYNFLSGKFREQFK

AAFSCCLPGLGPCGSLKAPSPRSSASHKSLSLQSRCSISKISEHVVLTSVTTVLP
```

-continued

>gi|222080109|ref|NP_001517.2|orexin receptor type 2 {Homo sapiens}
(SEQ ID NO: 1305)

MSGTKLEDSPPCRNWSSASELNETQEPFLNPTDYDDEEFLRYLWREYLHPKEYEWVLIAGYII

VFVVALIGNVLVCVAVWKNHHMRTVTNYFIVNLSLADVLVTITCLPATLVVDITETWFFGQS

LCKVIPYLQTVSVSVSVLTLSCIALDRWYAICHPLMFKSTAKRARNSIVIIWIVSCIIMIPQAIV

MECSTVFPGLANKTTLFTVCDERWGGEIYPKMYHICFFLVTYMAPLCLMVLAYLQIFRKLW

CRQIPGTSSVVQRKWKPLQPVSQPRGPGQPTKSRMSAVAAEIKQIRARRKTARMLMIVLLVF

AICYLPISILNVLKRVFGMFAHTEDRETVYAWFTFSHWLVYANSAANPIIYNFLSGKFREEFK

AAFSCCCLGVHHRQEDRLTRGRTSTESRKSLTTQISNFDNISKLSEQVVLTSISTLPAANGAGP

LQNW

>gi|223633971|ref|NP_057624.3|probable G-protein coupled receptor 83 precursor {Homo sapiens}
(SEQ ID NO: 1306)

MVPHLLLLCLLPLVRATEPHEGRADEQSAEAALAVPNASHFFSWNNYTFSDWQNFVGRRRY

GAESQNPTVKALLIVAYSFIIVFSLFGNVLVCHVIFKNQRMHSATSLFIVNLAVADIMITLLNT

PFTLVRFVNSTWIFGKGMCHVSRFAQYCSLHVSALTLTAIAVDRHQVIMHPLKPRISITKGVI

YIAVIWTMATFFSLPHAICQKLFTFKYSEDIVRSLCLPDFPEPADLFWKYLDLATFILLYILPLLI

ISVAYARVAKKLWLCNMIGDVTTEQYFALRRKKKKTIKMLMLVVVLFALCWFPLNCYVLL

LSSKVIRTNNALYFAFHWFAMSSTCYNPFIYCWLNENFRIELKALLSMCQRPPKPQEDRPPSP

VPSFRVAWTEKNDGQRAPLANNLLPTSQLQSGKTDLSSVEPIVTMS

>gi|223633986|ref|NP_003958.2|trace amine-associated receptor 5 {Homo sapiens}
(SEQ ID NO: 1307)

MRAVFIQGAEEHPAAFCYQVNGSCPRTVHTLGIQLVIYLACAAGMLIIVLGNVFVAFAVSYF

KALHTPTNFLLLSLALADMFLGLLVLPLSTIRSVESCWFFGDFLCRLHTYLDTLFCLTSIFHLC

FISIDRHCAICDPLLYPSKFTVRVALRYILAGWGVPAAYTSLFLYTDVVETRLSQWLEEMPCV

GSCQLLLNKFWGWLNFPLFFVPCLIMISLYVKIFVVATRQAQQITTLSKSLAGAAKHERKAA

KTLGIAVGIYLLCWLPFTIDTMVDSLLHFITPPLVFDIFIWFAYFNSACNPIIYVFSYQWFRKAL

KLTLSQKVFSPQTRTVDLYQE

>gi|224586796|ref|NP_076404.3|G-protein coupled receptor 87 {Homo sapiens}
(SEQ ID NO: 1308)

MGFNLTLAKLPNNELHGQESHNSGNRSDGPGKNTTLHNEFDTIVLPVLYLIIFVASILLNGLA

VWIFFHIRNKTSFIFYLKNIVVADLIMTLTFPFRIVHDAGFGPWYFKFILCRYTSVLFYANMYT

SIVFLGLISIDRYLKVVKPFGDSRMYSITFTKVLSVCVWVIMAVLSLPNIILTNGQPTEDNIHDC

SKLKSPLGVKWHTAVTYVNSCLFVAVLVILIGCYIAISRYIHKSSRQFISQSSRKRKHNQSIRV

VVAVFFTCFLPYHLCRIPFTFSHLDRLLDESAQKILYYCKEITLFLSACNVCLDPIIYFFMCRSF

SRRLFKKSNIRTRSESIRSLQSVRRSEVRIYYDYTDV

>gi|229093087|ref|NP_740746.4|probable G-protein coupled receptor 97 precursor {Homo sapiens}
(SEQ ID NO: 1309)

MATPRGLGALLLLLLLPTSGQEKPTEGPRNTCLGSNNMYDIFNLNDKALCFTKCRQSGSDSC

NVENLQRYWLNYEAHLMKEGLTQKVNTPFLKALVQNLSTNTAEDFYFSLEPSQVPRQVMK

DEDKPPDRVRLPKSLFRSLPGNRSVVRLAVTILDIGPGTLFKGPRLGLGDGSGVLNNRLVGLS

VGQMHVTKLAEPLEIVFSHQRPPPNMTLTCVFWDVTKGTTGDWSSEGCSTEVRPEGTVCCC

DHLTFFALLLRPTLDQSTVHILTRISQAGCGVSMIFLAFTIILYAFLRLSRERFKSEDAPKIHVA

LGGSLFLLNLAFLVNVGSGSKGSDAACWARGAVFHYFLLCAFTWMGLEAFHLYLLAVRVF

NTYFGHYFLKLSLVGWGLPALMVIGTGSANSYGLYTIRDRENRTSLELCWFREGTTMYALYI

TVHGYFLITFLFGMVVLALVVWKIFTLSRATAVKERGKNRKKVLTLLGLSSLVGVTWGLAIF

TPLGLSTVYIFALFNSLQGVFICCWFTILYLPSQSTTVSSSTARLDQAHSASQE

>gi|238859647|ref|NP_116176.2|probable G-protein coupled receptor 128 precursor {Homo sapiens}

(SEQ ID NO: 1310)

MASCRAWNLRVLVAVVCGLLTGIILGLGIWRIVIRIQRGKSTSSSSTPTEFCRNGGTWENGRCI

CTEEWKGLRCTIANFCENSTYMGFTFARIPVGRYGPSLQTCGKDTPNAGNPMAVRLCSLSLY

GEIELQKVTIGNCNENLETLEKQVKDVTAPLNNISSEVQILTSDANKLTAENITSATRVVGQIF

NTSRNASPEAKKVAIVTVSQLLDASEDAFQRVAATANDDALTTLIEQMETYSLSLGNQSVVE

PNIAIQSANFSSENAVGPSNVRFSVQKGASSSLVSSSTFIHTNVDGLNPDAQTELQVLLNMTK

NYTKTCGFVVYQNDKLFQSKTFTAKSDFSQKIISSKTDENEQDQSASVDMVFSPKYNQKEFQ

LYSYACVYWNLSAKDWDTYGCQKDKGTDGFLRCRCNHTTNFAVLMTFKKDYQYPKSLDIL

SNVGCALSVTGLALTVIFQIVTRKVRKTSVTWVLVNLCISMLIFNLLFVFGIENSNKNLQTSD

GDINNIDFDNNDIPRTDTINIPNPMCTAIAALLHYFLLVTFTWNALSAAQLYYLLIRTMKPLPR

HFILFISLIGWGVPAIVVAITVGVIYSQNGNNPQWELDYRQEKICWLAIPEPNGVIKSPLLWSFI

VPVTIILISNVVMFITISIKVLWKNNQNLTSTKKVSSMKKIVSTLSVAVVFGITWILAYLMLVN

DDSIRIVFSYIFCLFNTTQGLQIFILYTVRTKVFQSEASKVLMLLSSIGRRKSLPSVTRPRLRVK

MYNFLRSLPTLHERFRLLETSPSTEEITLSESDNAKESI

>gi|239582753|ref|NP_473373.2|mas-related G-protein coupled receptor member X4 {Homo sapiens}

(SEQ ID NO: 1311)

MDPTVPVFGTKLTPINGREETPCYNQTLSFTVLTCIISLVGLTGNAVVLWLLGYRMRRNAVSI

YILNLAAADFLFLSFQIIRLPLRLINISHLIRKILVSVMTFPYFTGLSMLSAISTERCLSVLWPIW

YRCRRPTHLSAVVCVLLWGLSLLFSMLEWRFCDFLFSGADSSWCETSDFIPVAWLIFLCVVL

CVSSLVLLVRILCGSRKMPLTRLYVTILLTVLVFLLCGLPFGILGALIYRMHLNLEVLYCHVYL

VCMSLSSLNSSANPIIYFFVGSFRQRQNRQNLKLVLQRALQDKPEVDKGEGQLPEESLELSGS

RLGP

>gi|256418985|ref|NP_001157849.1|MAS-related GPR, member G {Homo sapiens}

(SEQ ID NO: 1312)

MFGLFGLWRTFDSVVFYLTLIVGLGGPVGNGLVLWNLGFRIKKGPFSIYLLHLAAADFLFLSC

RVGFSVAQAALGAQDTLYFVLTFLWFAVGLWLLAAFSVERCLSDLFPACYQGCRPRHASAV

LCALVWTPTLPAVPLPANACGLLRNSACPLVCPRYHVASVTWFLVLARVAWTAGVVLFVW

VTCCSTRPRPRLYGIVLGALLLLFFCGLPSVFYWSLQPLLNFLLPVFSPLATLLACVNSSSKPLI

YSGLGRQPGKREPLRSVLRRALGEGAELGARGQSLPMGLL

>gi|260763892|ref|NP_473372.3|mas-related G-protein coupled receptor member X3{Homo sapiens}

(SEQ ID NO: 1313)

MDSTIPVLGTELTPINGREETPCYKQTLSFTGLTCIVSLVALTGNAVVLWLLGCRMRRNAVSI

YILNLVAADFLFLSGHIICSPLRLINIRHPISKILSPVMTFPYFIGLSMLSAISTERCLSILWPIWYH

CRRPRYLSSVMCVLLWALSLLRSILEWMFCDFLFSGANSVWCETSDFITIAWLVFLCVVLCG

SSLVLLVRILCGSRKMPLTRLYVTILLTVLVFLLCGLPFGIQWALFSRIHLDWKVLFCHVHLVS

IFLSALNSSANPIIYFFVGSFRQRQNRQNLKLVLQRALQDTPEVDEGGGWLPQETLELSGSRLEQ

>gi|269973880|ref|NP_694547.2|probable G-protein coupled receptor 156 isoform 1 {Homo sapiens}

(SEQ ID NO: 1314)

MEPEINCSELCDSFPGQELDRRPLHDLCKTTITSSHHSSKTISSLSPVLLGIVWTFLSCGLLLILF

FLAFTIHCRKNRIVKMSSPNLNIVTLLGSCLTYSSAYLFGIQDVLVGSSMETLIQTRLSMLCIGT

-continued

SLVFGPILGKSWRLYKVFTQRVPDKRVIIKDLQLLGLVAALLMADVILLMTWVLTDPIQCLQI

LSVSMTVTGKDVSCTSTSTHFCASRYSDVWIALIWGCKGLLLLYGAYLAGLTGHVSSPPVNQ

SLTIMVGVNLLVLAAGLLFVVTRYLHSWPNLVFGLTSGGIFVCTTTINCFIFIPQLKQWKAFEE

ENQTIRRMAKYFSTPNKSFHTQYGEEENCHPRGEKSSMERLLTEKNAVIESLQEQVNNAKEK

IVRLMSAECTYDLPEGAAPPASSPNKDVQAVASVHTLAAAQGPSGHLSDFQNDPGMAARDS

QCTSGPSSYAQSLEGPGKDSSFSPGKEEKISDSKDFSDHLDSGCSQKPWTEQSLGPERGDQVP

MNPSQSLLPERGGSDPQRQRHLENSEEPPERRSRVSSVIREKLQEVLQDLGLGPEASLSTAPSC

HQQTWKNSAAFSPQKMPLSKELGFSPYMVRRRAAQRARSHFPGSAPSSVGHRANRTVPGA

HSRLHVQNGDSPSLAPQTTDSRVRRPSSRKPSLPSDPQDRPGTLEGSKQSQTEPEGARGSKAA

FLRQPSGSGRAPSPAAPCLSKASPDLPEQWQLWPPVPSGCASLSSQHSYFDTESSSSDEFFCRC

HRPYCEICFQSSSDSSDSGTSDTDPEPTGGLASWEKLWARSKPIVNFKDDLKPTLV

>gi|270265839|ref|NP_000264.2|G-protein coupled receptor 143 {Homo sapiens}
(SEQ ID NO: 1315)
MASPRLGTFCCPTRDAATQLVLSFQPRAFHALCLGSGGLRLALGLLQLLPGRRPAGPGSPATS

PPASVRILRAAAACDLLGCLGMVIRSTVWLGFPNFVDSVSDMNHTEIWPAAFCVGSAMWIQ

LLYSACFWWLFCYAVDAYLVIRRSAGLSTILLYHIMAWGLATLLCVEGAAMLYYPSVSRCE

RGLDHAIPHYVTMYLPLLLVLVANPILFQKTVTAVASLLKGRQGIYTENERRMGAVIKIRFFK

IMLVLIICWLSNIINESLLFYLEMQTDINGGSLKPVRTAAKTTWFIMGILNPAQGFLLSLAFYG

WTGCSLGFQSPRKEIQWESLTTSAAEGAHPSPLMPHENPASGKVSQVGGQTSDEALSMLSEG

SDASTIEIHTASESCNKNEGDPALPTHGDL

>gi|282403488|ref|NP_997253.2|probable G-protein coupled receptor 153 {Homo sapiens}
(SEQ ID NO: 1316)
MSDERRLPGSAVGWLVCGGLSLLANAWGILSVGAKQKKWKPLEFLLCTLAATHMLNVAVP

IATYSVVQLRRQRPDFEWNEGLCKVFVSTFYTLTLATCFSVTSLSYHRMWMVCWPVNYRLS

NAKKQAVHTVMGIWMVSFILSALPAVGWHDTSERFYTHGCRFIVAEIGLGFGVCFLLLVGGS

VAMGVICTAIALFQTLAVQVGRQADRRAFTVPTIVVEDAQGKRRSSIDGSEPAKTSLQTTGL

VTTIVFIYDCLMGFPVLVVSFSSLRADASAPWMALCVLWCSVAQALLLPVFLWACDRYRAD

LKAVREKCMALMANDEESDDETSLEGGISPDLVLERSLDYGYGGDFVALDRMAKYEISALE

GGLPQLYPLRPLQEDKMQYLQVPPTRRFSHDDADVWAAVPLPAFLPRWGSGEDLAALAHL

VLPAGPERRRASLLAFAEDAPPSRARRRSAESLLLSLRPSALDSGPRGARDSPPGSPRRRPGPGP

RSASASLLPDAFALTAFECEPQALRRPPGPFPAAPAAPDGADPGEAPTPPSSAQRSPGPRPSAH

SHAGSLRPGLSASWGEPGGLRAAGGGGSTSSFLSSPSESSGYATLHSDSLGSAS

>gi|284447291|ref|NP_997247.2|probable G-protein coupled receptor 148 {Homo sapiens}
(SEQ ID NO: 1317)
MGDELAPCPVGTTAWPALIQLISKTPCMPQAASNTSLGLGDLRVPSSMLYWLFLPSSLLAAA

TLAVSPLLLVTILRNQRLRQEPHYLLPANILLSDLAYILLHMLISSSSLGGWELGRMACGILTD

AVFAACTSTILSFTAIVLHTYLAVIHPLRYLSFMSHGAAWKAVALIWLVACCFPTFLIWLSKW

QDAQLEEQGASYILPPSMGTQPGCGLLVIVTYTSILCVLFLCTALIANCFWRIYAEAKTSGIWG

QGYSRARGTLLIHSVLITLYVSTGVVFSLDMVLTRYHHIDSGTHTWLLAANSEVLMMLPRA

MLTYLYLLRYRQLLGMVRGHLPSRRQAIFTIS

>gi|291042665|ref|NP_062813.2|leukotriene B4 receptor 2 {Homo sapiens}
(SEQ ID NO: 1318)
MSVCYRPPGNETLLSWKTSRATGTAFLLLAALLGLPGNGFVVWSLAGWRPARGRPLAATLV

LHLALADGAVLLLTPLFVAFLTRQAWPLGQAGCKAVYYVCALSMYASVLLTGLLSLQRCLA

-continued

```
VTRPFLAPRLRSPALARRLLLAVWLAALLLAVPAAVYRHLWRDRVCQLCHPSPVHAAAHLS

LETLTAFVLPFGLMLGCYSVTLARLRGARWGSGRHGARVGRLVSAIVLAFGLLWAPYHAVN

LLQAVAALAPPEGALAKLGGAGQAARAGTTALAFFSSSVNPVLYVFTAGDLLPRAGPRFLTR

LFEGSGEARGGGRSREGTMELRTTPQLKVVGQGRGNGDPGGGMEKDGPEWDL
```

>gi|4503825|ref|NP_003496.1|frizzled-1 precursor {Homo sapiens}   (SEQ ID NO: 1319)

```
MAEEEAPKKSRAAGGGASWELCAGALSARLAEEGSGDAGGRRRPPVDPRRLARQLLLLLW

LLEAPLLLGVRAQAAGQGPGQGPGPGQQPPPPPQQQQSGQQYNGERGISVPDHGYCQPISIPL

CTDIAYNQTIMPNLLGHTNQEDAGLEVHQFYPLVKVQCSAELKFFLCSMYAPVCTVLEQALP

PCRSLCERARQGCEALMNKFGFQWPDTLKCEKFPVHGAGELCVGQNTSDKGTPTPSLLPEF

WTSNPQHGGGGHRGGFPGGAGASERGKFSCPRALKVPSYLNYHFLGEKDCGAPCEPTKVYG

LMYFGPEELRFSRTWIGIWSVLCCASTLFTVLTYLVDMRRFSYPERPIIFLSGCYTAVAVAYIA

GFLLEDRVVCNDKFAEDGARTVAQGTKKEGCTILFMMLYFFSMASSIWWVILSLTWFLAAG

MKWGHEAIEANSQYFHLAAWAVPAIKTITILALGQVDGDVLSGVCFVGLNNVDALRGFVLA

PLFVYLFIGTSFLLAGFVSLFRIRTIMKHDGTKTEKLEKLMVRIGVFSVLYTVPATIVIACYFYE

QAFRDQWERSWVAQSCKSYAIPCPHLQAGGGAPPHPPMSPDFTVFMIKYLMTLIVGITSGFW

IWSGKTLNSWRKFYTRLTNSKQGETTV
```

>gi|4503827|ref|NP_001457.1|frizzled-2 precursor {Homo sapiens}   (SEQ ID NO: 1320)

```
MRPRSALPRLLLLPLLLLPAAGPAQFHGEKGISIPDHGFCQPISIPLCTDIAYNQTIMPNLLGHTN

QEDAGLEVHQFYPLVKVQCSPELRFFLCSMYAPVCTVLEQAIPPCRSICERARQGCEALMNK

FGFQWPERLRCEHFPRHGAEQICVGQNHSEDGAPALLTTAPPPGLQPGAGGTPGGPGGGAP

PRYATLEHPFHCPRVLKVPSYLSYKFLGERDCAAPCEPARPDGSMFFSQEETRFARLWILTWS

VLCCASTFFTVTTYLVDMQRFRYPERPIIFLSGCYTMVSVAYIAGFVLQERVVCNERFSEDGY

RTVVQGTKKEGCTILFMMLYFFSMASSIWWVILSLTWFLAAGMKWGHEAIEANSQYFHLAA

WAVPAVKTITILAMGQIDGDLLSGVCFVGLNSLDPLRGFVLAPLFVYLFIGTSFLLAGFVSLFR

IRTIMKHDGTKTEKLERLMVRIGVFSVLYTVPATIVIACYFYEQAFREHWERSWVSQHCKSL

AIPCPAHYTPRMSPDFTVYMIKYLMTLIVGITSGFWIWSGKTLHSWRKFYTRLTNSRHGETTV
```

>gi|4503833|ref|NP_003498.1|frizzled-7 precursor {Homo sapiens}   (SEQ ID NO: 1321)

```
MRDPGAAAPLSSLGLCALVLALLGALSAGAGAQPYHGEKGISVPDHGFCQPISIPLCTDIAYN

QTILPNLLGHTNQEDAGLEVHQFYPLVKVQCSPELRFFLCSMYAPVCTVLDQAIPPCRSLCER

ARQGCEALMNKFGFQWPERLRCENFPVHGAGEICVGQNTSDGSGGPGGGPTAYPTAPYLPD

LPFTALPPGASDGRGRPAFPFSCPRQLKVPPYLGYRFLGERDCGAPCEPGRANGLMYFKEEER

RFARLWVGVWSVLCCASTLFTVLTYLVDMRRFSYPERPIIFLSGCYFMVAVAHVAGFLLEDR

AVCVERFSDDGYRTVAQGTKKEGCTILFMVLYFFGMASSIWWVILSLTWFLAAGMKWGHE

AIEANSQYFHLAAWAVPAVKTITILAMGQVDGDLLSGVCYVGLSSVDALRGFVLAPLFVYLF

IGTSFLLAGFVSLFRIRTIMKHDGTKTEKLEKLMVRIGVFSVLYTVPATIVLACYFYEQAFREH

WERTWLLQTCKSYAVPCPPGHFPPMSPDFTVFMIKYLMTMIVGITTGFWIWSGKTLQSWRRF

YHRLSHSSKGETAV
```

>gi|4503835|ref|NP_003499.1|frizzled-9 precursor {Homo sapiens}   (SEQ ID NO: 1322)

```
MAVAPLRGALLLWQLLAAGGAALEIGRFDPERGRGAAPCQAVEIPMCRGIGYNLTRMPNLL

GHTSQGEAAAELAEFAPLVQYGCHSHLRFFLCSLYAPMCTDQVSTPIPACRPMCEQARLCA

PIMEQFNFGWPDSLDCARLPTRNDPHALCMEAPENATAGPAEPHKGLGMLPVAPRPARPPG
```

```
DLGPGAGGSGTCENPEKFQYVEKSRSCAPRCGPGVEVFWSRRDKDFALVWMAVWSALCFF

STAFTVLTFLLEPHRFQYPERPIIFLSMCYNVYSLAFLIRAVAGAQSVACDQEAGALYVIQEGL

ENTGCTLVFLLLYYFGMASSLWWVVLTLTWFLAAGKKWGHEMEAHGSYFHMAAWGLPA

LKTIVILTLRKVAGDELTGLCYVASTDAAALTGFVLVPLSGYLVLGSSFLLTGFVALFHIRKIM

KTGGTNTEKLEKLMVKIGVFSILYTVPATCVIVCYVYERLNMDFWRLRATEQPCAAAAGPG

GRRDCSLPGGSVPTVAVFMLKIFMSLVVGITSGVWVWSSKTFQTWQSLCYRKIAAGRARAK

ACRAPGSYGRGTHCHYKAPTVVLHMTKTDPSLENPTHL
```

>gi|5032099|ref|NP_005622.1|smoothened homolog precursor {Homo sapiens} (SEQ ID NO: 1323)

```
MAAARPARGPELPLLGLLLLLLGDPGRGAASSGNATGPGPRSAGGSARRSAAVTGPPPPLS

HCGRAAPCEPLRYNVCLGSVLPYGATSTLLAGDSDSQEEAHGKLVLWSGLRNAPRCWAVIQ

PLLCAVYMPKCENDRVELPSRTLCQATRGPCAIVERERGWPDFLRCTPDRFPEGCTNEVQNI

KFNSSGQCEVPLVRTDNPKSWYEDVEGCGIQCQNPLFTEAEHQDMHSYIAAFGAVTGLCTLF

TLATFVADWRNSNRYPAVILFYVNACFFVGSIGWLAQFMDGARREIVCRADGTMRLGEPTS

NETLSCVIIFVIVYYALMAGVVWFVVLTYAWHTSFKALGTTYQPLSGKTSYFHLLTWSLPFV

LTVAILAVAQVDGDSVSGICFVGYKNYRYRAGFVLAPIGLVLIVGGYFLIRGVMTLFSIKSNH

PGLLSEKAASKINETMLRLGIFGFLAFGFVLITFSCHFYDFFNQAEWERSFRDYVLCQANVTIG

LPTKQPIPDCEIKNRPSLLVEKINLFAMFGTGIAMSTWVWTKATLLIWRRTWCRLTGQSDDEP

KRIKKSKMIAKAFSKRHELLQNPGQELSFSMHTVSHDGPVAGLAFDLNEPSADVSSAWAQH

VTKMVARRGAILPQDISVTPVATPVPPEEQANLWLVEAEISPELQKRLGRKKKRRKRKKEVC

PLAPPPELHPPAPAPSTIPRLPQLPRQKCLVAAGAWGAGDSCRQGAWTLVSNPFCPEPSPPQD

PFLPSAPAPVAWAHGRRQGLGPIHSRTNLMDTELMDADSDF
```

>gi|6005762|ref|NP_009128.1|frizzled-10 precursor {Homo sapiens} (SEQ ID NO: 1324)

```
MQRPGPRLWLVLQVMGSCAAISSMDMERPGDGKCQPIEIPMCKDIGYNMTRMPNLMGHEN

QREAAIQLHEFAPLVEYGCHGHLRFFLCSLYAPMCTEQVSTPIPACRVMCEQARLKCSPIMEQ

FNFKWPDSLDCRKLPNKNDPNYLCMEAPNNGSDEPTRGSGLFPPLFRPQRPHSAQEHPLKDG

GPGRGGCDNPGKFHHVEKSASCAPLCTPGVDVYWSREDKRFAVVWLAIWAVLCFFSSAFTV

LTFLIDPARFRYPERPIIFLSMCYCVYSVGYLIRLFAGAESIACDRDSGQLYVIQEGLESTGCTL

VFLVLYYFGMASSLWWVVLTLTWFLAAGKKWGHEAIEANSSYFHLAAWAIPAVKTILILVM

RRVAGDELTGVCYVGSMDVNALTGFVLIPLACYLVIGTSFILSGFVALFHIRRVMKTGGENT

DKLEKLMVRIGLFSVLYTVPATCVIACYFYERLNMDYWKILAAQHKCKMNNQTKTLDCLM

AASIPAVEIFMVKIFMLLVVGITSGMWIWTSKTLQSWQQVCSRRLKKKSRRKPASVITSGGIY

KKAQHPQKTHHGKYEIPAQSPTCV
```

>gi|8393378|ref|NP_059108.1|frizzled-3 precursor {Homo sapiens} (SEQ ID NO: 1325)

```
MAMTWIVFSLWPLTVFMGHIGGHSLFSCEPITLRMCQDLPYNTTFMPNLLNHYDQQTAALA

MEPFHPMVNLDCSRDFRPFLCALYAPICMEYGRVTLPCRRLCQRAYSECSKLMEMFGVPWP

EDMECSRFPDCDEPYPRLVDLNLAGEPTEGAPVAVQRDYGFWCPRELKIDPDLGYSFLHVRD

CSPPCPNMYFRREELSFARYFIGLISIICLSATLFTFLTFLIDVTRFRYPERPIIFYAVCYMMVSLI

FFIGFLLEDRVACNASIPAQYKASTVTQGSHNKACTMLFMILYFFTMAGSVWWVILTITWFL

AAVPKWGSEAIEKKALLFHASAWGIPGTLTIILLAMNKIEGDNISGVCFVGLYDVDALRYFVL

APLCLYVVVGVSLLLAGIISLNRVRIEIPLEKENQDKLVKFMIRIGVFSILYLVPLLVVIGCYFY
```

-continued

EQAYRGIWETTWIQERCREYHIPCPYQVTQMSRPDLILFLMKYLMALIVGIPSVFWVGSKKT

CFEWASFFHGRRKKEIVNESRQVLQEPDFAQSLLRDPNTPIIRKSRGTSTQGTSTHASSTQLA

MVDDQRSKAGSIHSKVSSYHGSLHRSRDGRYTPCSYRGMEERLPHGSMSRLTDHSRHSSSHR

LNEQSRHSSIRDLSNNPMTHITHGTSMNRVIEEDGTSA

>gi|13994190|ref|NP_114072.1|frizzled-8 precursor {Homo sapiens} (SEQ ID NO: 1326)

MEWGYLLEVTSLLAALALLQRSSGAAAASAKELACQEITVPLCKGIGYNYTYMPNQFNHDT

QDEAGLEVHQFWPLVEIQCSPDLKFFLCSMYTPICLEDYKKPLPPCRSVCERAKAGCAPLMR

QYGFAWPDRMRCDRLPEQGNPDTLCMDYNRTDLTTAAPSPPRRLPPPPPGEQPPSGSGHGRP

PGARPPHRGGGRGGGGGDAAAPPARGGGGGGKARPPGGGAAPCEPGCQCRAPMVSVSSER

HPLYNRVKTGQIANCALPCHNPFFSQDERAFTVFWIGLWSVLCFVSTFATVSTFLIDMERFKY

PERPIIFLSACYLFVSVGYLVRLVAGHEKVACSGGAPGAGGAGGAGGAAAGAGAAGAGAG

GPGGRGEYEELGAVEQHVRYETTGPALCTVVFLLVYFFGMASSIWWVILSLTWFLAAGMK

WGNEAIAGYSQYFHLAAWLVPSVKSIAVLALSSVDGDPVAGICYVGNQSLDNLRGFVLAPL

VIYLFIGTMFLLAGFVSLFRIRSVIKQQDGPTKTHKLEKLMIRLGLFTVLYTVPAAVVVACLFY

EQHNRPRWEATHNCPCLRDLQPDQARRPDYAVFMLKYFMCLVVGITSGVWVWSGKTLES

WRSLCTRCCWASKGAAVGGGAGATAAGGGGGPGGGGGGPGGGGPGGGGSLYSDVST

GLTWRSGTASSVSYPKQMPLSQV

>gi|22547161|ref|NP_036325.2|frizzled-4 precursor {Homo sapiens} (SEQ ID NO: 1327)

MAWRGAGPSVPGAPGGVGLSLGLLLQLLLLLGPARGFGDEEERRCDPIRISMCQNLGYNVT

KMPNLVGHELQTDAELQLTTFTPLIQYGCSSQLQFFLCSVYVPMCTEKINIPIGPCGGMCLSV

KRRCEPVLKEFGFAWPESLNCSKFPPQNDHNHMCMEGPGDEEVPLPHKTPIQPGEECHSVGT

NSDQYIWVKRSLNCVLKCGYDAGLYSRSAKEFTDIWMAVWASLCFISTAFTVLTFLIDSSRFS

YPERPIIFLSMCYNIYSIAYIVRLTVGRERISCDFEEAAEPVLIQEGLKNTGCAIIFLLMYFFGMA

SSIWWVILTLTWFLAAGLKWGHEAIEMHSSYFHIAAWAIPAVKTIVILIMRLVDADELTGLCY

VGNQNLDALTGFVVAPLFTYLVIGTLFIAAGLVALFKIRSNLQKDGTKTDKLERLMVKIGVFS

VLYTVPATCVIACYFYEISNWALFRYSADDSNMAVEMLKIFMSLLVGITSGMWIWSAKTLHT

WQKCSNRLVNSGKVKREKRGNGWVKPGKGSETVV

>gi|27894385|ref|NP_003459.2|frizzled-5 precursor {Homo sapiens} (SEQ ID NO: 1328)

MARPDPSAPPSLLLLLLAQLVGRAAAASKAPVCQEITVPMCRGIGYNLTHMPNQFNHDTQDE

AGLEVHQFWPLVEIQCSPDLRFFLCSMYTPICLPDYHKPLPPCRSVCERAKAGCSPLMRQYGF

AWPERMSCDRLPVLGRDAEVLCMDYNRSEATTAPPRPFPAKPTLPGPPGAPASGGECPAGGP

FVCKCREPFVPILKESHPLYNKVRTGQVPNCAVPCYQPSFSADERTFATFWIGLWSVLCFISTS

TTVATFLIDMERFRYPERPIIFLSACYLCVSLGFLVRLVVGHASVACSREHNHIHYETTGPALC

TIVFLLVYFFGMASSIWWVILSLTWFLAAGMKWGNEAIAGYAQYFHLAAWLIPSVKSITALA

LSSVDGDPVAGICYVGNQNLNSLRGFVLGPLVLYLLVGTLFLLAGFVSLFRIRSVIKQGGTKT

DKLEKLMIRIGIFTLLYTVPASIVVACYLYEQHYRESWEAALTCACPGHDTGQPRAKPEYWV

LMLKYFMCLVVGITSGVWIWSGKTVESWRRFTSRCCCRPRRGHKSGGAMAAGDYPEASAA

LTGRTGPPGPAATYHKQVSLSHV

>gi|34734079|ref|NP_003497.2|frizzled-6 isoform a precursor {Homo sapiens} (SEQ ID NO: 1329)

MEMFTFLLTCIFLPLLRGHSLFTCEPITVPRCMKAYNMTFFPNLMGHYDQSIAAVEMEHFL

PLANLECSPNIETFLCKAFVPTCIEQIHVVPPCRKLCEKVYSDCKKLIDTFGIRWPEELECDRLQ

-continued

```
YCDETVPVTFDPHTEFLGPQKKTEQVQRDIGFWCPRHLKTSGGQGYKFLGIDQCAPPCPNMY

FKSDELEFAKSFIGTVSIFCLCATLFTFLTFLIDVRRFRYPERPIIYYSVCYSIVSLMYFIGFLLGD

STACNKADEKLELGDTVVLGSQNKACTVLFMLLYFFTMAGTVWWVILTITWFLAAGRKWS

CEAIEQKAVWFHAVAWGTPGFLTVMLLAMNKVEGDNISGVCFVGLYDLDASRYFVLLPLCL

CVFVGLSLLLAGIISLNHVRQVIQHDGRNQEKLKKFMIRIGVFSGLYLVPLVTLLGCYVYEQV

NRITWEITWVSDHCRQYHIPCPYQAKAKARPELALFMIKYLMTLIVGISAVFWVGSKKTCTE

WAGFFKRNRKRDPISESRRVLQESCEFFLKHNSKVHKKKHYKPSSHKLKVISKSMGTSTGA

TANHGTSAVAITSHDYLGQETLTEIQTSPETSMREVKADGASTPRLREQDCGEPASPAASISRL

SGEQVDGKGQAGSVSESARSEGRISPKSDITDTGLAQSNNLQVPSSSEPSSLKGSTSLLVHPVS

GVRKEQGGGCHSDT
```

For purposes of interpreting Table 4, please refer to the following legend:
Ac—Acylation
p-Cl-dF=para-Chlorine, D-Phenylalanine
4cl=Chlorinated Phenylalaine
$_dF$=para-Chlorine, D-Phenylalanine
$_dR$=D-Arginine
$_dY$=D-Tyrosine
dA=D-Alanine
$_hR$=homoarginine
pY=Phosphoroylated Tyrosine
pS=Phosphoroylated Serine
pE=Pyroglutamic acid
PEG=Polyetheythlene Glycol
PEG{number kD}=Polyetheythlene Glycol with a molecular weight near {number} in kilodaltons.
Nle=Noraleucine
$N_{le}$=Noraleucine
$Y_m$=methoxy-tyrosine.
$Y_M$=methoxy-tyrosine.
$K_m$=methalyated-lysine.
Aib=α-aminoisobutyric acid
Abu=ALPHA-AMINOBUTYRIC ACID
Gab=γ-aminobutyric acid;
Dip=β,β-diphenyl-L-alanine;
*=indicates cyclization between residues (lactam ring)
dHis=D-His
w=D-Tryptophan
Dnp=di-nitro-phenol
Mca=methoxycoumarin 4 acetic acid
Sar=sarcosine
Sta=statine
Ste=Stearyl
Pyr=pyroglutamic acid
Fam=carboxyfluoresceine
LC=—(NH$_2$—(CH$_2$)$_5$—C=O)—
TAMRA=carboxytetramethylrhodamine
T*=N-acetyl galactosamine labeled Thr
NH$_2$=amidation of carboxy terminus
Orn=ornithine
K(W)=Trp residue which is coupled to the side chain of a Lys
Y(OMe)=methylated Tyrosine
Cit=citrulline
C6=hexanoyl
Nva=Norvaline
In some embodiments, analogs of the present invention (including any polypeptide sequence identified in Tables 1, 2, 3, or 4) are either be N-terminal acylated or an N-terminal free-amine. In some embodiments, analogs of the present invention are either either a c-terminal amine or a c-terminal acid. These terminal groups do not preclude additional solubilization and/or stabilization attachments such a polyethylene glycol.

The following examples are provided to describe the invention in greater detail. They are intended to illustrate, not to limit, the invention. Various publications, including patents, published applications, technical articles and scholarly articles are cited throughout the specification. Each of these cited publications is incorporated by reference herein, in its entirety.

EXAMPLES

Example 1: Chemical Scheme to Synthesize Helical Polypeptides

This example describes how the polypeptide analogs may be designed prior to manufacture. The sequence of human vasoactive intestinal peptide (VIP) is given below, using the standard one-letter code for proteinogenic amino acid residues. For purposes of interpretation "position 1" of the sequence below is the N-terminal histidine. Each amino acid residue is numbered in sequence from the N-terminal end of the polypeptide to the C-terminal. Therefore, "position 28" of the sequence below is the C-terminal asparagine.

```
                                          (SEQ ID NO: 10)
        HSDAVFTDNYTRLRKQMAVKKYLNSILN
```

Design A.
A family of the following VIP analogues were synthesized each containing at least two alpha to β³ replacements per seven α-amino acid residues of VIP:

```
                                          (SEQ ID NO: 1342)
        HSDAV FTDNY TRLRK QLAVK KYLNA ILN (SEQ ID NO: 1342)
        HSDAV FTDNY TRLRK QLAVK KYLNA ILN (SEQ ID NO: 1342)
        HSDAV FTDNY TRLRK QLAVK KYLNA ILN (SEQ ID NO: 1342)
        HSDAV FTDNY TRLRK QLAVK KYLNA ILN
```

-continued

```
                                         (SEQ ID NO: 1343)
HSDAV FTDNY TRLZK QLXVK KYLNX ILN (SEQ ID NO: 1344)
HSDAV FTDNY TRLZK QLXVK ZYLNX ILN (SEQ ID NO: 1345)
HSDAV FTDNY XRLZK QLXVK KYLNX ILN (SEQ ID NO: 1346)
HSDAV FTDNY XRLZK QLXVK ZYLNX ILN (SEQ ID NO: 1347)
HSDAV FTDNY TRLRZ QLXVK KYLNX ILN (SEQ ID NO: 1348)
HSDAV FTDNY XRLRZ QLXVK KYLNX ILN (SEQ ID NO: 1349)
HSDAV FTDNY TRLZK QLAVK ZYLXA ILN (SEQ ID NO: 1350)
HSDAV FTDNY TRLZK QXAVK KYLXA ILN (SEQ ID NO: 1351)
HSDAV FTDNY TRLZK QXAVK ZYLXA ILN
```

In each of sequences above, at least one β-3 residue has been replaced by a cyclic or heterocyclic residue. In some embodiments, based upon the above sequences, X=ACPC, Z=APC; uncharged side chains replaced by ACPC, basic side chains replaced by APC, Protected β3-amino acids); the positions indicated with bold and underlined letters are those at which β-to-β3 replacement has occurred. Reagents for α/β-Peptide synthesis (Fmoc on the backbone nitrogen and appropriate protecting groups on side chains, when necessary) will be obtained from commercial suppliers or prepared via reported methods in Horne et. al. PNAS, September 1, 2009, vol. 106, no. 35, 14751-14756. Each β3-amino acid residue bore the side chain of the β-amino acid found at that site in the VIP sequence. Thus, for example, analogues that contain a β-residue at position 10 of the sequence had a 33-homotyrosine at this position, in place of the tyrosine at position 10 of VIP itself. The analogues shown above were synthesized manually by microwave-assisted Fmoc solid phase peptide synthesis on NovaSyn TGR resin. Coupling steps were carried out with a three-fold excess of the appropriate protected α- or β3-amino acid, using HBTU and HOBt to mediate amide bond formation. Piperidine was used for Fmoc deprotection steps. Each peptide was cleaved from resin by treatment with 94:2.5:2.5 TFA/H2O/triisopropylsilane, precipitated by addition of cold ethyl ether, and purified by reverse phase HPLC on a prep-C18 column using gradients between 0.1% TFA in water and 0.1% TFA in acetonitrile. The identity and purity of the HSDAVFTDNYXRLZKQLXVKZYLNXILN (Compound 8) was determined by MALDI-TOF-MS and analytical HPLC, respectively. Data from the MALDI-TOF-MS analysis showing the expected mass values is shown in FIG. 1. The sample was examined by MALDI-TOF to determine molecular weight. A 50:50 mixture of acetonitrile/water was used to dissolve alpha cyano-cinnamic acid matrix together with a 5 uM aliquot of sample. The sample was dried on an appropriate sample plate and examined in positive, reflectron mode with a 25 KV voltage, 100 mV electronic gain and a laser frequency of 60 Hz. The resulting spectra demonstrated an observed mass (mass/charge, m/z) of 3351.4 which compares favorably with the expected mass of 3350.79. In addition, the observed doubly charged species, (Z=2) of 1675.684 was also observed and compares favorably to the expected '+2' peak of 1675.395.

Design B (Prophetic).

A family of analogues will be prepared, each containing two alpha to β³ replacements per seven α-amino acid residues of VIP. Each β³-amino acid residue will bear the side chain of the α-amino acid found at that site in the VIP sequence. Thus, for example, analogues that contain a β-residue at position 4 of the sequence will have β³-homoalanine at this position, in place of the alanine at position 4 of VIP itself. The analogues to be prepared are shown below; the positions indicated with bold and underlined letters are those at which α-to-β³ replacement has occurred.

```
                                         (SEQ ID NO: 10)
HSDAVFTDNYTRLRKQMAVKKYLNSILN (SEQ ID NO: 10)
HSDAVFTDNYTRLRKQMAVKKYLNSILN (SEQ ID NO: 10)
HSDAVFTDNYTRLRKQMAVKKYLNSILN (SEQ ID NO: 10)
HSDAVFTDNYTRLRKQMAVKKYLNSILN (SEQ ID NO: 10)
HSDAVFTDNYTRLRKQMAVKKYLNSILN (SEQ ID NO: 10)
HSDAVFTDNYTRLRKQMAVKKYLNSILN (SEQ ID NO: 10)
HSDAVFTDNYTRLRKQMAVKKYLNSILN (SEQ ID NO: 10)
HSDAVFTDNYTRLRKQMAVKKYLNSILN (SEQ ID NO: 1342)
HSDAVFTDNYTRLRKQLAVKKYLNAILN (SEQ ID NO: 1342)
HSDAVFTDNYTRLRKQLAVKKYLNAILN (SEQ ID NO: 1342)
HSDAVFTDNYTRLRKQLAVKKYLNAILN (SEQ ID NO: 1344)
HSDAVFTDNYTRLZKQLXVKZYLNXILN (SEQ ID NO: 1345)
HSDAVFTDNYXRLZKQLXVKKYLNXILN (SEQ ID NO: 1346)
HSDAVFTDNYXRLZKQLXVKZYLNXILN (SEQ ID NO: 1349)
HSDAVFTDNYTRLZKQLAVKZYLXAILN (SEQ ID NO: 1350)
HSDAVFTDNYTRLZKQXAVKKYLXAILN (SEQ ID NO: 1351)
HSDAVFTDNYTRLZKQXAVKZYLXAILN (SEQ ID NO: 1367)
HSDAVFTDNYXRLRKQLAVKKYLNAILN (SEQ ID NO: 1368)
HSDAVFTDNYTRLZKQLAVKKYLNAILN (SEQ ID NO: 1369)
HSDAVFTDNYTRLRKQLXVKKYLNAILN (SEQ ID NO: 1370)
HSDAVFTDNYTRLRKQLAVKZYLNAILN (SEQ ID NO: 1371)
HSDAVFTDNYTRLRKQLAVKKYLNXILN
```

-continued (SEQ ID NO: 1346)
HSDAVFTDNYXRLZKQLXVKZYLNXILN (SEQ ID NO: 1372)
HSDAVFTDNYTRLRRQLAARRYLNAIKK

In each of sequences above, at least one β-3 residue has been replaced by a cyclic or heterocyclic residue. In some embodiments, based upon the above sequences, $\underline{X}$=ACPC, $\underline{Z}$=APC; uncharged side chains replaced by ACPC, basic side chains replaced by APC, Protected β³-amino acids). α/β-Peptide synthesis (Fmoc on the backbone nitrogen and appropriate protecting groups on side chains, when necessary) will be obtained from commercial suppliers or prepared via reported methods. Each β³-peptide will be prepared manually by microwave-assisted Fmoc solid phase peptide synthesis on NovaSyn TGR resin. Coupling steps will be carried out with a three-fold excess of the appropriate protected α- or β³-amino acid, using HBTU and HOBt to mediate amide bond formation. Piperidine will be used for Fmoc deprotection steps. Each peptide will be cleaved from resin by treatment with 94:2.5:2.5:1 TFA/H2O/ethanedithiol/triisopropylsilane, precipitated by addition of cold ethyl ether, and purified by reverse phase HPLC on a prep-C18 column using gradients between 0.1% TFA in water and 0.1% TFA in acetonitrile. The identity and purity of the final products will be determined by MALDI-TOF-MS and analytical HPLC, respectively.

Design and Synthesis of VPAC₁-Selective VIP Analogues.

Figure 6:
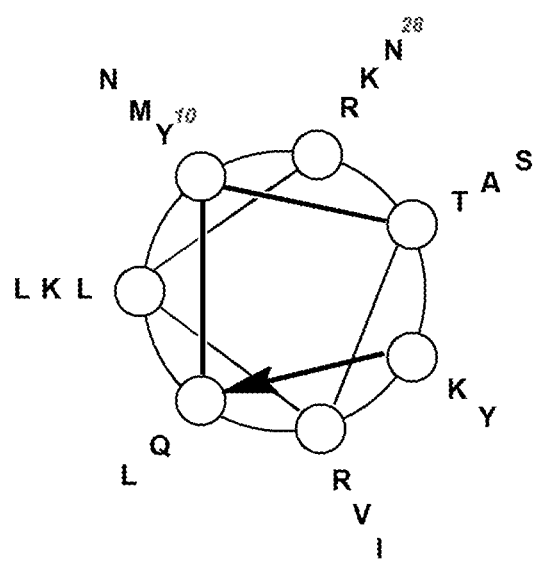
FIG. 6 illustrates a helical wheel diagram of the predicted α-helical portion of VIP polypeptide, positions 10-28.

VPAC₁-selective VIP analogues will be synthesized in accordance with the protocol outlined above. The predicted α-helical portion of VIP polypeptide is from positions 10-28 which are depicted in FIG. 6. The amino acid residues will be substituted with non-natural amino acid residues. β³-amino acid residue positions indicated in bold and underline, and, on the helical wheel diagrams shown in FIG. 7 (which correspond to the positions on the diagram depicted in FIG. 6), β³-amino acid residue positions indicated as solid dots. In some species, the non-polar β³-residues (e.g., β³-hAla, β³-hVal) will be replaced by (S,S)-trans-2-aminocyclopentanecarboxylic acid ((S,S)-ACPC), while basic β³-residues (such as β³-hLys or β³-hArg) will be replaced by APC:

(SEQ ID NO: 435)
HSDAV FTDNY ARLRK QMAVK KALNS ILA

(SEQ ID NO: 435)
HSDAV FTDNY ARLRK QMLVK KALNS ILA

(SEQ ID NO: 435)
HSDAV FTDNY ARLRK QMAVK KALNS ILA (SEQ ID NO: 435)
HSDAV FTDNY ARLRK QMAVK KALNS ILA

(SEQ ID NO: 435)
HSDAV FTDNY ARLRK QMAVK KALNS ILA

(SEQ ID NO: 435)
HSDAV FTDNY ARLRK QMAVK KALNS ILA (SEQ ID NO: 435)
HSDAV FTDNY ARLRK QMAVK KALNS ILA (SEQ ID NO: 434)
HADAV FTAAY ARLRK QMAAK KALNS ILA

α/β-Peptide analogues below will be synthesized:

(SEQ ID NO: 434)
HADAV FTAAY ARLRK QMAAK KALAA IAA

(SEQ ID NO: 434)
HADAV FTAAY ARLRK QMAAK KALAA IAA

(SEQ ID NO: 434)
HADAV FTAAY ARLRK QMAAK KALAA IAA

(SEQ ID NO: 434)
HADAV FTAAY ARLRK QMAAK KALAA IAA

(SEQ ID NO: 434)
HADAV FTAAY ARLRK QMAAK KALAA IAA (SEQ ID NO: 434)
HADAV FTAAY ARLRK QMAAK KALAA IAA (SEQ ID NO: 434)
HADAV FTAAY ARLRK QMAAK KALAA IAA

Designs Targeted Toward the VPAC₂ Receptor-Selective Analogues.

VPAC₁-selective VIP analogues will be synthesized in accordance with the protocol outlined above. α-helical portion of VIP polypeptide sequences will be substituted with non-natural amino acid residues where β³-amino acid residue positions indicated in bold and underlined. In some species, the non-polar β³-residues (e.g., β³-hAla, β³-hVal) will be replaced by (S,S)-trans-2-aminocyclopentanecarboxylic acid ((S,S)-ACPC), while basic β³-homo residues (such as β³-hLys or β³-hArg) will be replaced by the pyrrolidine analogue of (S,S)-ACPC, which is designated APC (Note: Ac=acetyl; $N^{le}$=norleucine; K*-D* indicates that the side chains of these two residues may be linked via an amide bond.)

a/b-Peptide analogues will be synthesized:

(SEQ ID NO: 1373)
Ac-HSDAV FTENY TKLRK QN$^{le}$AVK K*YLND* LKKGG T

(SEQ ID NO: 1373)
Ac-HSDAV FTENY TKLRK QN$^{le}$AVK K*YLND* LKKGG T

(SEQ ID NO: 1373)
Ac-HSDAV FTENY TKLRK QN$^{le}$AVK K*YLND* LKKGG T (SEQ ID NO: 1373)
Ac-HSDAV FTENY TKLRK QN$^{le}$AVK K*YLND* LKKGG T (SEQ ID NO: 1373)
Ac-HSDAV FTENY TKLRK QN$^{le}$AVK K*YLND* LKKGG T (SEQ ID NO: 1373)
Ac-HSDAV FTENY TKLRK QN$^{le}$AVK K*YLND* LKGG T (SEQ ID NO: 1373)
Ac-HSDAV FTENY TKLRK QN$^{le}$AVK K*YLND* LKKGG T (SEQ ID NO: 1373)
Ac-HSDAV FTENY TKLRK QN$^{le}$AVK K*YLND* LKKGG T (SEQ ID NO: 1374)
Ac-HSDAV FTENY TKLRK RN$^{le}$AAK N$^{le}$YLNN LKKGG T

(SEQ ID NO: 1374)
Ac-HSDAV FTENY TKLRK RN$^{le}$AAK N$^{le}$YLNN LKKGG T

(SEQ ID NO: 1374)
Ac-HSDAV FTENY TKLRK RN$^{le}$AAK N$^{le}$YLNN LKKGG T (SEQ ID NO: 1374)
Ac-HSDAV FTENY TKLRK RN$^{le}$AAK N$^{le}$YLNN LKKGG T (SEQ ID NO: 1374)
Ac-HSDAV FTENY TKLRK RN$^{le}$AAK N$^{le}$YLNN LKKGG T

```
                                             (SEQ ID NO: 1374)
Ac-HSDAV FTENY TKLRK RN^le AAK N^le YLNN LKKGG T (SEQ ID NO: 1374)
Ac-HSDAV FTENY TKLRK RN^le AAK N^le YLNN LKKGG T
``` wherein Ac=acetyl; N^le=norleucine; K*-D* indicates that the side chains of these two residues may be linked via an amide bond.

One purpose of this study will be to demonstrate that the analogs of the application may be designed to increase the half-life of the polypeptide as compared to the half-life of the naturally encoded protein by introducing non-natural amino acid analogs that are resistant to degradation and/or induce an equivalent or increased bioactivity as compared to the naturally encoded polypeptide sequence upon which the analog is based or derived through the possible incorporation of conformationally-constrained residues.

Example 2: Structural Analysis of Helical Polypeptides

Structural Analysis A

This example describes how a VIP analogue was characterized after chemical synthesis and and purification.

Figure 2:
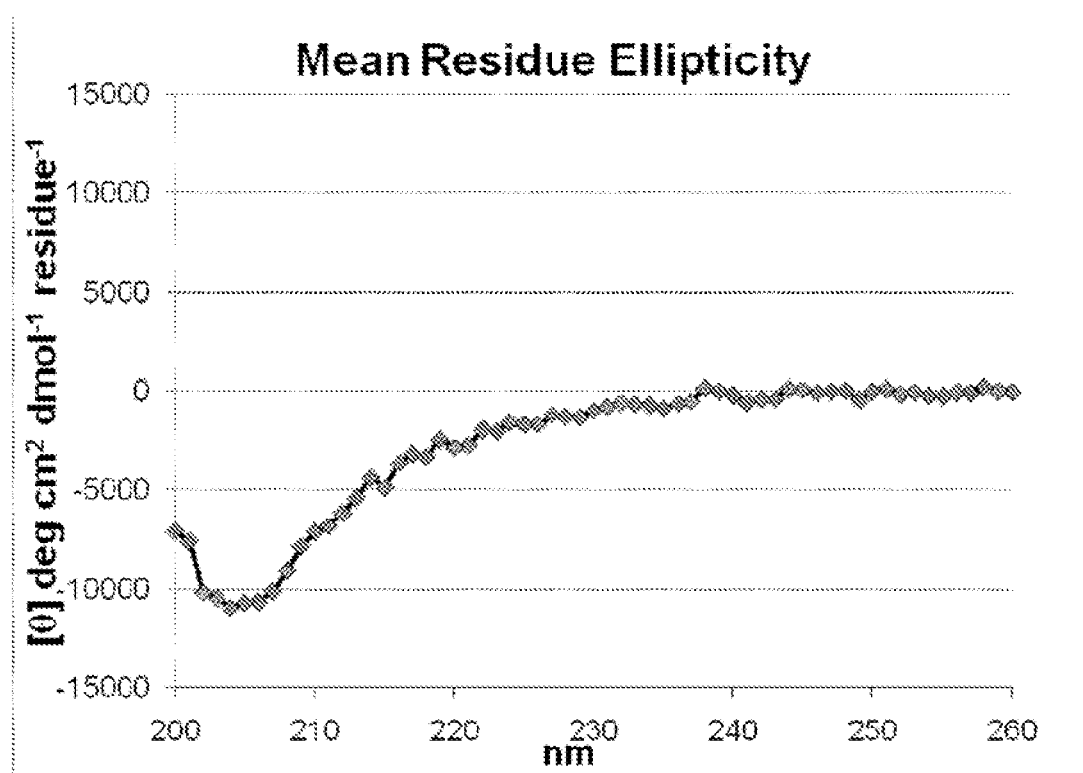
FIG. 2 presents circular dichroism data of a VIP analogue diluted in a 10 mM sodium phosphate buffer at pH of 7.5. The signal exhibited for the structure of the VIP analogue is similar to previously characterized α-amino acid/β amino acid peptides of similar backbone length and concentration, which indicates a substantial helical content (Home et. al., *J. Am. Chem. Soc.*, 2007, 129 (14), pp 4178-4180; Home et. al. PNAS, Sep. 1, 2009, vol. 106, no. 35, 14751-14756).

Circular Dichroism Spectroscopy. Circular dichroism measurements were carried out on a Aviv 202SF Circular Dichroism Spectrophotometer (FIG. 2). Samples of each peptide were prepared with a determined UV absorbance in the range of 0.1-1.0 at 280 nm in a phosphate-buffered solution at a pH of 7.5 for a final concentration of about 14 µM. The analogue was transferred a 0.1 cm path length cell for measurement. Wavelength scans were carried out with a 1 nm step and 8 sec averaging time, in quadruplicate at 23° C. All spectra were corrected against buffer measured in the same cell.

The data of FIG. 2 demonstrate the expected circular dichroism measurements of an alpha-beta hybrid polypeptide. The results are consistent with previously published data of an alpha-beta hybrid polypeptide that has similar backbone length and similar beta-amino acid percent and similar sample concentration.

Structural Analysis B (Prophetic)

This prophetic example describes how the polypeptide analogs of this invention may be characterized after manufacture through structural conformational assays such as circular dichrosim (CD) and Nuclear magnetic resonance (NMR).

Circular Dichroism Spectroscopy. Circular dichroism measurements will be carried out on an Aviv 202SF Circular Dichroism Spectrophotometer. Samples of each peptide will be prepared with a determined UV absorbance in the range of 0.1-1.0 at 280 nm in a pH buffered solution. Spectra will be recorded in a 1 mm cell with a step size of 1 nm and an averaging time of 5 sec. All spectra will be background corrected against buffer measured in the same cell. Thermal melts will be carried out in 1-degree increments with an equilibration time of 2 min between each temperature change. Thermal unfolding data will be fit to a simple two state folding model Shortle, D. Meeker, A. K. Freire, E. Biochemistry 1988, 27, 4761-4768) using GraphPad Prism.

Nuclear Magnetic Resonance: Structure elucidation of the proposed analogs can also be accomplished based on analyses of heteronuclear NMR experimental data. Global backbone structural information complementing the local structure information provided by backbone chemical-shift assignments can be obtained from nuclear Overhauser effect spectroscopy (NOESY) which yield atomic distance constraints together with residual dipolar coupling (RDC) experiments which provide orientation restraint information. Together, these techniques can be used to provide valuable structural information regarding the positioning and alignment of the amino acids within the polypeptide analog. Samples of each peptide or analog will be prepared with a determined UV absorbance in the range of 0.1-1.0 at 280 nm in an appropriate pH buffered solution. Each preparation will then be used to conduct NOESY and RDC experiments using standard NMR equipment (i.e. Bruker NMR) and data analysis software (i.e. Talos+). Further structural insight can be ascertained by comparing the results of NMR experiments in the presence and absence of the intended binding partner.

One purpose of this study is to evidence that the conformation of the analog is structurally constrained and that certain non-natural amino acids have been incorporated in the synthesized peptide in their predicted location along a longitudinal axis of the polypeptide.

Example 3: Stability Analysis of Helical Polypeptides in Solution (Prophetic)

This prophetic example describes how the solubility of the polypeptide analogs of this invention may be characterized after manufacture through assays such as a protease resistance assay.

In Vitro Stability Assay: Stock solutions of the both the naturally occurring peptides as well as peptide analogs will be prepared at a concentration of 25 µM (based on UV absorbance) in appropriate buffer. A solution of proteinase K in addition to other common animal proteases (i.e. Cathepsins and Trypsins) will be prepared at an appropriate concentration of 50 µg/mL (based on weight to volume) in appropriate buffer. For each proteolysis reaction, 40 µL of peptide stock will be mixed with 10 µL of protease stock. The reaction will be allowed to proceed at room temperature and quenched at the desired time point by addition of 100 µL of 1% TFA in water. 125 µL of the resulting quenched reaction will be injected onto an analytical reverse phase HPLC, and the amount of starting peptide present quantified by integration of the appropriate chromatogram peak via absorbance at either 220 or 280 nm. Duplicate reactions will be run for each time point. Half-lives will be determined by fitting time dependent peptide concentration to an exponential decay using GraphPad Prism. Samples for some time points will be analyzed by MALDI-MS, and the products observed will be used to identify amide bonds cleaved in the course of the reaction. The relative stability enhancement will be determined through the comparison of the various analogs with its naturally occurring peptide counterpart.

In Vivo Stability Assay: To investigate the in vivo stability of the analogs, both the naturally occurring peptide as well as the analogs will be administered to mice and/or rats by IV, IP, SC, PO and/or inhalation routes at concentrations ranging from 0.001 to 50 mg/kg and blood specimens withdrawn at 0 minutes, 5 minutes, 15 minutes, 30 minutes, 1 hr, 4 hrs, 8 hrs, 12 hrs, 24 hrs and 48 hrs post-injection. Levels of intact compound in 25 µL of fresh serum will then be injected onto an analytical reverse phase HPLC, and the amount of starting peptide present quantified by integration of the appropriate chromatogram peak via absorbance at either 220 or 280 nm or other means of measuring the presence or absence of fully intact analog as described herein. The expected molecular weights will be determined through either LC/MS or MALDI/TOF analysis. This analysis technique also allows the examination of the in-vivo metabolites by determination of fragment molecular weights. The relative stability enhancement will be determined through the comparison of the various analogs with its naturally occurring peptide counterpart.

Cassette Dosing and Serum Analysis for Determination of Bioavailability: The oral bioavailability will be screened by dosing rats with a cassette, i.e. mixture of 1-5 analogs per dosing solution. The cassette includes 1-5 test articles and a standard compound, for a total dose of 10 mg/kg. Each compound/test article will be converted to an appropriate salt form and dissolved in water at 2 mg/mL. The cassette will be prepared by mixing equal volumes of each of the two-six solutions. The cassette dosing solution should be mixed well and then the pH should be adjusted to 7.5-9. The dosing solution should be prepared the day before the study and stirred overnight at room temperature.

Male Sprague Dawley (SD) rats, 6-8 weeks old, will be used in this screen. Rats will be quarantined for at least one day and have continuous access to food and water. On the night before the administration of the cassette, the rats will be fasted for approximately 16 h.

Four SD rats will be assigned in each cassette. A single dose of the dosing solution will be administered orally to each rat. The dosing volume (5 mL/kg) and time will then be recorded and rats will be fed 2 h after dosing.

Blood samples will be collected via cardiac puncture at the following time points: 4 h, 8 h and 12 h. Immediately prior to blood collection, rats will be anesthetized with $CO_2$ gas within 10-20 seconds. After the 12-hour samples are collected, the rats will be euthanized via $CO_2$ asphyxiation followed by cervical dislocation.

Blood samples will be kept in heparinized microtainer tubes under subambient temperature (4° C.) before they are processed. Blood samples will be centrifuged (10,000 rpm for 5 minutes) and plasma samples should be removed and stored in a −20° C. freezer until analyzed for analog levels. Analog levels in the plasma will be analyzed using the following protocol for direct plasma precipitation.

The in vivo plasma samples will be prepared in a 1.5 mL 96-well plate, by adding, in order, 100 µL of the test plasma, 150 µl of methanol, followed by vortexing for 10-20 seconds. 150 µL of 0.05 ng/µL of an Internal Standard in acetonitrile shall be added and vortexed for 30 seconds.

The standard curve samples were prepared in a 1.5 mL 96-well plate, by adding, in order, 100 µL of control mouse plasma, followed by 150 µL of methanol and vortexing for 10-20 seconds. 150 µL of 0.05 ng/µL of an Internal Standard in acetonitrile shall be added and vortexed for 30 seconds. The samples will then be spiked with 0-200 ng (10 concentrations) of the compound of interest in 50% methanol to obtain a standard curve range of 0.5 ng/mL to 2,000 ng/mL. Again, the sample is vortexed for 30 seconds.

The samples should then be centrifuged for 20-30 minutes at 3,000 rpm in an Eppendorf microfuge before 80-90% of supernatant is transferred into a clean 96-well plate. The organic solvent will then be evaporated until the samples are dry (under $N_2$ at 40° C./30-60 min. (ZymarkTurbovap)).

The residue will then be dissolved in 200-600 L mobile phase (50% $CH_3OH$/0.1% TFA). LC/MS/MS will then be run using a mass spectrometer with pump. Data analysis and quantification accomplished using PE-Sciex Analyst (v 1.1). A 5-50 µl sample volume will be injected onto a reverse phase column (Keystone 2.0×20 mm, 5 µm, PN: 8823025-701) using a mobile phase of 25% $CH_3OH$, 0.1% TFA-100% $CH_3OH$, 0.1% TFA. The run time will be about 8 minutes at a flow rate of about 300 µL/minutes. The Area Under the Curve (AUC) will be calculated using the linear trapezoidal rule from t=0 to the last plasma concentration sampling time tx (see Handbook of Basic Pharmacokinetics, Wolfgang A. Ritschel and Gregory L. Kearns, 5th ed, 1999). $AUC^0$-tx=.SIGMA.$^0$-n$((C_n+C_n+1)/2))(t_n+1-t_n)$ {in (µg/mL)h}

In the case of the cassette dosing paradigm, samples at 4, 8 and 12 h post extravascular dosing, the AUC will be calculated from t=0 to t=12 h. Each of the analogs above when tested in this assay should provide for an AUC of at least 5 µgh/mL when normalized for administration at a 10 mg/kg dose.

One purpose of this study is to evidence that the analog is more resistant to peptidases as compared to the resistance of similarly-structured, naturally occurring polypeptides upon which the structure of the analog is based or derived. The results may show that, when treated with the same proteolytic enzymes, the analogs of the invention will resist degradation and have longer half-lives than similarly-structured, naturally occurring polypeptides upon which the structure of the analog is based or derived.

Example 4: Functional Analysis of Helical Polypeptides

This prophetic example describes the function of polypeptide analogs of this invention may be characterized after manufacture through assays that measure bioactivity of the analogs when exposed to tissue culture or when administered to an animal model of one of the following human disease states: COPD, pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis: Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small cell lung cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, elevated blood pressure levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction.

In Vitro Binding Assay 1: A VIP analogue (Compound 8) in appropriate phosphate buffer was at pH of 7.5 was exposed to a functional assay in parallel with wild-type VIP proteins. cAMP Hunter cell lines expressing VIPR1 and VIPR2 were expanded from freezer stocks in T25 flasks according to standard procedures and maintained in selective growth media prior to assay. Once it was established that the cells were healthy and growing normally, cells were passaged from flasks using cell dissociation reagent buffer and seeded into white walled clear bottom 384-well microplates for compound profiling. For profiling, cells were seeded at a density of 10,000 cells per well in a total volume of 20 µL and were allowed to adhere and recover overnight prior to compound addition. cAMP modulation was determined using the DiscoveRx HitHunter cAMP XS+ assay.

Figure 3:
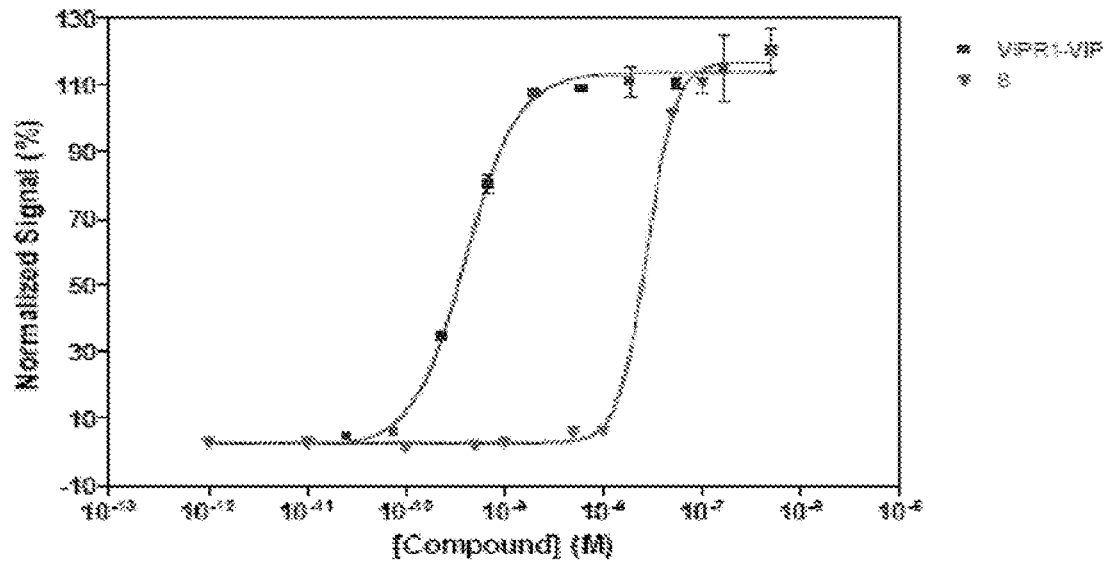
FIG. 3 illustrates in vitro functional $EC_{50}$ data of a VIP analogue tested in the presence of VIPR1 ($VPAC_1$) or VIPR2 (VPAC2) receptors as compared to the binding of wild-type VIP protein to the same receptors. The data show that the analogue achieves full activation of VIPR1 (~100%, relative to maximum activation), but has an $EC_{50}$ at a concentration higher than the $EC_{50}$ of wild-type VIP protein.
Figure 3:
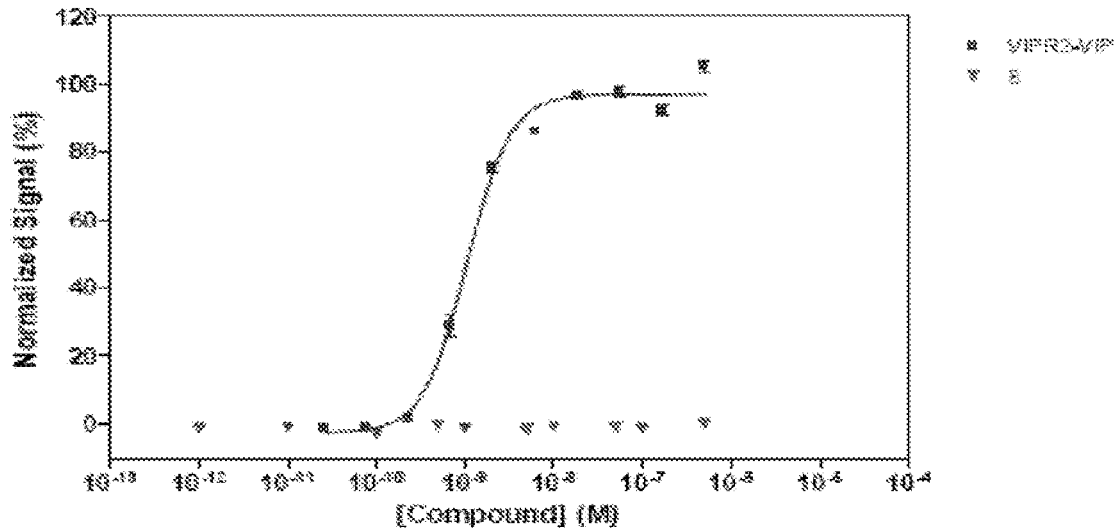

For profiling compound in agonist mode, the cells were incubated in the presence of compound at 37° C. for 30 minutes. Cells expressing both VIPR1 and VIPR2 were exposed to serial dilutions of wild-type VIP and separate samples of the same type of cells were exposed to serial dilutions of VIP analogue (Compound 8) to determine $EC_{50}$ values of the analogue as compared to wild-type VIP (FIG. 3). After appropriate compound incubation, assay signal was generated through incubation with DiscoverX lysis cocktail according to the manufacturers standard protocol. Dose curves were plotted using GraphPad Prism or Activity Base. Percentage activity is calculated using the following formula:

% Activity=100%×(mean RLU of test sample−mean RLU of vehicle control)/(mean RLU of MAX control−mean RLU of vehicle control).

Data from FIG. 3 demonstrates that Compound 8 was able to fully activate VIPR1, but not activate VIPR2. The following $EC_{50}$ values were measured (peptide concentration for 50% VIPR1 activation):

VIP: 0.4 nM
Compound 8: 28 nM

Compound 8 apparently does not interact substantially with VIPR2. Raw fluorescence data of measurements taken from the agonist binding experiments performed in triplicate appears below in Table 5.

TABLE 5

VIP Analogue Agonist $EC_{50}$ determination.

| [Compound] (M) | Mean RLU | SD | % CV | Readout cAMP Mode Agonist % Activity |
|---|---|---|---|---|
| Compound ID VIP [Starting] 0.50 µM Cell Line VIPR1 | | | | |
| 5.00E−07 M | 112760.0 | 7853.0 | 7.0% | 100.0% |
| 1.67E−07 M | 106220.0 | 12190.5 | 11.3% | 95.6% |
| 5.56E−08 M | 104420.0 | 2121.3 | 2.0% | 91.9% |
| 1.85E−08 M | 104460.0 | 5430.6 | 5.2% | 91.9% |
| 6.17E−09 M | 102840.0 | 396.0 | 0.4% | 90.4% |
| 2.06E−09 M | 101520.0 | 1301.1 | 1.3% | 89.1% |
| 5.66E−10 M | 78020.0 | 3422.4 | 4.4% | 66.2% |
| 2.29E−10 M | 38240.0 | 1414.2 | 3.7% | 27.5% |
| 7.62E−11 M | 13260.0 | 1216.2 | 9.2% | 3.2% |
| 2.54E−11 M | 11960.0 | 0.0 | 0.0% | 2.0% |
| 0.00E+00 M | 9920.0 | 843.5 | 5.5% | 0.0% |
| S/B | 11.4 | AvCV | 8.6% | |
| Compound ID 8 [Starting] 0.50 µM Cell Line VIPR1 | | | | |
| 5.00E−07 M | 112320.0 | 1640.5 | 1.5% | 99.6% |
| 1.00E−07 M | 104400.0 | 3733.5 | 3.6% | 91.7% |
| 5.00E−08 M | 95460.0 | 1612.2 | 1.7% | 83.8% |
| 1.00E−08 M | 13700.0 | 537.4 | 3.9% | 1.6% |
| 5.00E−09 M | 13200.0 | 339.4 | 2.6% | 1.2% |
| 1.00E−09 M | 10600.0 | 1074.8 | 10.1% | −1.4% |
| 5.00E−10 M | 9820.0 | 1555.6 | 15.8% | −2.2% |
| 1.00E−10 M | 9060.0 | 56.6 | 0.6% | −2.9% |
| 1.00E−11 M | 10500.0 | 424.3 | 4.0% | −1.5% |
| 1.00E−12 M | 10340.0 | 537.4 | 5.2% | −1.7% |
| 0.00E+00 M | 12040.0 | 396.0 | 3.3% | 0.0% |
| S/B | 9.3 | AvCV | 4.9% | |
| Compound ID 8 [Starting] 0.50 µM Cell Line VIPR2 | | | | |
| 5.00E−07 M | 10200.0 | 622.3 | 6.1% | 1.9% |
| 1.00E−07 M | 8920.0 | 1527.4 | 17.1% | 0.4% |
| 5.00E−08 M | 9200.0 | 1527.4 | 16.6% | 0.8% |
| 1.00E−08 M | 9560.0 | 64.9 | 0.9% | 1.2% |
| 5.00E−09 M | 8560.0 | 1329.4 | 15.4% | 0.1% |
| 1.00E−09 M | 8560.0 | 28.3 | 0.3% | 0.4% |

TABLE 5-continued

VIP Analogue Agonist $EC_{50}$ determination.

| [Compound] (M) | Mean RLU | SD | % CV | Readout cAMP Mode Agonist % Activity |
|---|---|---|---|---|
| 5.00E−10 M | 9820.0 | 676.8 | 8.9% | 1.5% |
| 1.00E−10 M | 7560.0 | 1414.2 | 18.7% | −1.1% |
| 1.00E−11 M | 9280.0 | 113.1 | 1.2% | 0.8% |
| 1.00E−12 M | 8300.0 | 594.0 | 6.7% | 0.4% |
| 0.00E+00 M | 8540.0 | 28.3 | 0.3% | 0.0% |
| S/B | 1.2 | AvCV | 7.7% | |

In Vitro Competition Assay 1: Antagonist Dose curves were calculated by first providing a VIP analogue (Compound 8) in appropriate phosphate buffer at pH of 7.5. Cells expressing both VIPR1 and VIPR2 were exposed to serial dilutions of VIP analogue (Compound 8) in combination with wild-type VIP to determine the level of inhibition of VIPR1 and VIPR2 (FIG. 4). cAMP Hunter cell lines expressing VIPR1 and VIPR2 were expanded from freezer stocks in T25 flasks according to standard procedures and maintained in selective growth media prior to assay. For profiling, cells were seeded according to manufacturer protocol using a cAMP modulation assay with the DiscoveRx HitHunter cAMP XS+ assay.

Before treatment of the cells, media was aspirated from cells and replaced with DiscoverX antibody solution according to their standard protocol. Agonist dose curves were performed to determine the EC80 value for the following antagonist testing with compounds. For antagonist determination, cells were pre incubated with Compound 8 followed by VIP challenge at the EC80 concentration of 2.2 nM. 5 µL of 4× Compound 8 was added to cells and incubated at 37° C. for 30 minutes. 5 µL of 4× EC80 VIP agonist was added to cells and incubated at 37° C. for 30 minutes.

Figure 4:
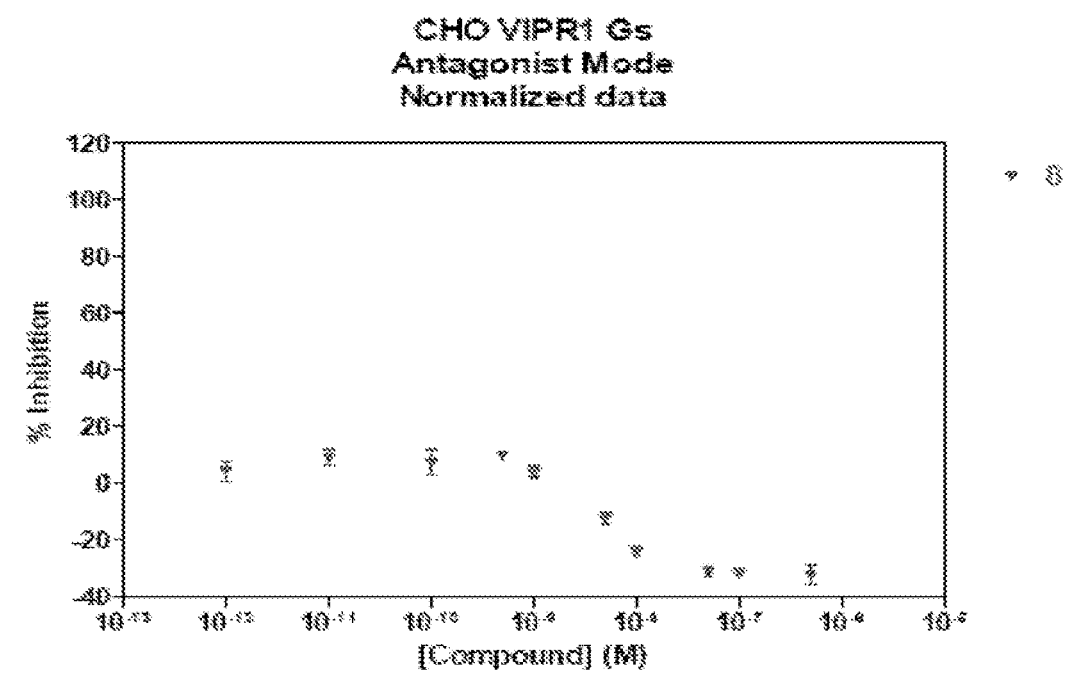
FIG. 4 illustrates data from an in vitro antagonist inhibition assay in which competition for VIPR1 ($VPAC_1$) or VIPR2 ($VPAC_2$) was measured by the amount of VIP analogue capable of inhibiting the association of wild-type VIP to its receptors.
Figure 4:
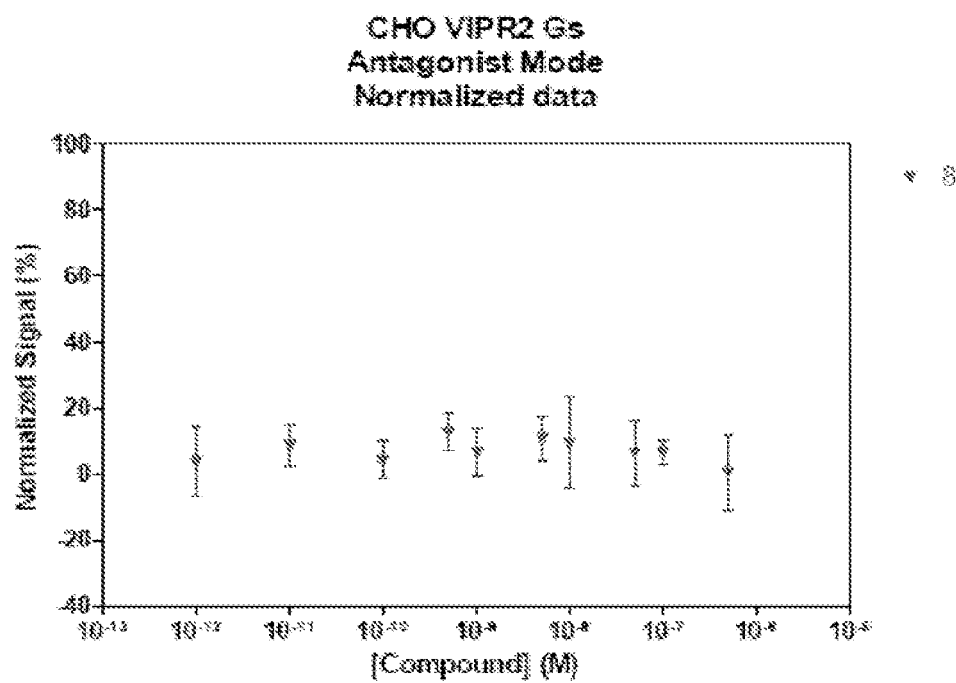

After appropriate compound incubation, assay signal was generated through incubation with DiscoverX lysis cocktail according to the manufacturers standard protocol. Dose curves were plotted using GraphPad Prism or Activity Base. Dose curves were plotted using GraphPad Prism or Activity Base. FIG. 4, Panel A, shows a percent inhibition of VIPR1 by Compound 8. For antagonist mode assays, percentage inhibition is calculated using the following formula:

% Inhibition=100%×(1−(mean RLU of test sample−mean RLU of vehicle control)/(mean RLU of EC80 control−mean RLU of vehicle control)).

Data shown in FIG. 4 was normalized to the maximal and minimal response observed in the presence of EC80 ligand and vehicle respectively. The decrease in inhbition observed in FIG. 4, Panel A, is related to agonist activity and receptor selectivity of VIPR1. FIG. 4, Panel B, shows a percent inhibition of VIPR2 by Compound 8. Raw fluorescence data from the binding experiments performed in duplicate appears below in Table 6.

TABLE 6

VIP Analogue Antagonist Activity

| [Compound] (M) | Mean RLU | SD | % CV | % Inhibition |
|---|---|---|---|---|
| Compound ID 5 [Starting] D.50 µM Cell Line VPR1 | | | Readcut cAMP Mode Antagonist | |
| Basal Activity | 9923.0 | 548.5 | 8.5% | 100.0% |
| 5.00E−07M | 124380.0 | 4497.2 | 3.6% | −30.5% |

TABLE 6-continued

VIP Analogue Antagonist Activity

| [Compound] (M) | Mean RLU | SD | % CV | % Inhibition |
|---|---|---|---|---|
| 1.00E−07M | 123523.0 | 198.0 | 0.2% | −29.5% |
| 5.00E−06M | 123150.0 | 2256.2 | 1.8% | −29.1% |
| 1.00E−06M | 117128.0 | 1527.4 | 1.3% | −22.2% |
| 5.00E−09M | 106740.0 | 3530.4 | 2.5% | −10.4% |
| 1.00E−09M | 52540.0 | 2573.9 | 2.8% | 5.6% |
| 5.00E−10M | 67923.0 | 0.0 | 0.0% | 11.1% |
| 1.00E−10M | 50150.0 | 5317.4 | 6.9% | 6.5% |
| 1.00E−11M | 68723.0 | 3224.4 | 3.5% | 10.2% |
| 1.08E−12M | 92720.0 | 4568.9 | 4.8% | 5.5% |
| 0.00E+00M | 97640.0 | 2149.6 | 2.2% | 0.0% |
| S/B | 9.6 | AvCV | 3.1% | |

| Compound ID 8 [Starting] D.50 µM Cell Line VPR2 | | | Readout cAMP Mode Antagonist | |
|---|---|---|---|---|
| Basal Activity | 9300.0 | 198.0 | 2.1% | 100.0% |
| 5.00E−07M | 64220.0 | 12077.4 | 14.3% | 0.4% |
| 1.00E−07M | 79550.0 | 3705.2 | 4.7% | 6.3% |
| 5.00E−06M | 79843.0 | 10634.9 | 13.3% | 6.2% |
| 1.00E−06M | 77450.0 | 14556.4 | 18.8% | 9.4% |
| 5.00E−09M | 76320.0 | 7071.1 | 9.3% | 10.9% |
| 1.00E−09M | 79520.0 | 7495.3 | 9.4% | 6.5% |
| 5.00E−10M | 74980.0 | 6081.1 | 8.1% | 12.7% |
| 1.00E−10M | 61340.0 | 6051.1 | 7.5% | 4.2% |
| 1.00E−11M | 78000.0 | 6618.5 | 8.5% | 5.7% |
| 1.00E−12M | 81720.0 | 11144.0 | 13.5% | 3.7% |
| 0.00E+00M | 84520.0 | 7523.5 | 6.9% | 0.0% |
| S/B | 9.1 | AvCV | 9.9% | |

In Vitro Binding Assay 2: The analogs of the present invention will be serially diluted into aqueous solutions with appropriate buffer. The various concentrations of analogs will be administered to a plurality of cells in culture that expresses relevant naturally occurring receptor family for the naturally occurring polypeptide upon which the analog is derived. In one method of detection, VPAC1 CHO-K1 Division Arrested (DA) cells or VPAC$_1$-CRE-β-lactamase CHO-K1 cells (10,000 cells/well) are plated in a 384-well format and incubated for 16-20 hours. Cells can then be stimulated with a dilution series of each Secretin analog in the presence of 0.5% DMOS for 5 hours. Cells can then be loaded with an engineered fluorescent substrate containing two fluoroprobes, coumarin and fluorescein (2 uM final concentration if CCF4AM and 1 mM solution D) for two hours. In the absence of β-lactamase expression, the substrate molecule remains intact. In this state, excitation of the coumarin results in fluorescence resonance energy transfer to the fluorescein moiety and emission of green light (530 nm). However, in the presence of β-lactamase expression, the substrate is cleaved, thereby separating the fluorophores, and disrupting energy transfer.

Excitation of the coumarin in the presence of enzyme β-lactamase activity results in a blue fluorescence signal (460 nm). Fluorescence emission values at 460 nm and 530 nm can be obtained using a standard fluorescence plate reader and plotted for each replicate against the concentration of analog present. The resulting blue:green ratio provides a normalized reporter response. The degree of β-lactamase expression is directly correlated to the stimulation of the specific receptor being interrogated. The particular receptor construct is covalently linked to a β-lactamase transcription factor, which is released upon receptor stimulation. Serially diluted analogs in the appropriate concentration of buffered solution (or medium alone as a control) will be added to individual wells together with cells expressing a specific receptor that is capable of β-lactamase production. A polypeptide that engages in competitive binding to the analog receptor, or medium only as a background control, will also be added to each well. After sufficient time, the wells will be inspected by light spectrometry to determine the relative light units, which serve a readout for receptor activation. Another mechanism for determining binding values is through the monitoring of a second messenger readout. For the intended receptor class, the detection of cAMP can be a direct indicator for receptor activation. Through the detection of cAMP (using known protocols) across a range of analog concentrations, the specific degree of receptor binding for each analog and concentration can be determined. The binding of the analog to receptor will be monitored by calculating the IC$_{50}$ values in media. The signal of test wells will be normalized to that of control wells without inhibitor after background subtraction from both. The percent inhibition of activity will be expressed as a function of the log 10 concentration of any competitive inhibitor added to the system. A four-parameter sigmoid function will be fitted to the data in Prism. The R$^2$ values for the fits will be determined. Finally, the means ±S.E.M. of the IC$_{50}$ values from the individual fits of the three repeat experiments will be calculated.

In Vitro Binding Assay 3: The analogs of the present invention will be serially diluted into aqueous solutions with appropriate buffer. The various concentrations of analogs will be administered to a plurality of cells in culture that expresses relevant naturally occurring receptor family for the naturally occurring polypeptide upon which the analog is derived. The analogs will be administered to the cAMP Hunter™ eXpress CHO-K1 VIPR2 (DisocveRx) cells according to the manufacturers suggested protocol. cAMP Hunter™ Detection Reagents will be used to detect the concentration of analog bound on the surface of the cells as a function of signal strength in the absence and presence of wild-type VIP provided as a control. Various EC$_{50}$ values for the VIP analogs will be calculated per the manufacturer's recommended instructions.

In Vitro Selectivity Binding Assay: Binding assays: Membranes prepared from a stable VPAC2 cell line (such as a CHO-S cell line stably expressing human VPAC2 receptor or from cells transiently transfected with human VPAC1 or PAC1) are used. A filter binding assay is performed using $^{125}$I-labeled VIP for VPAC1 and VPAC2 and $^{125}$I-labeled PACAP-27 for PAC as the tracers. For this assay, the solutions and equipment include:
Presoak solution: 0.5% Polyethyleneamine in Aqua dest
Buffer for flushing filter plates: 25 mM HEPES pH 7.4
Blocking buffer: 25 mM HEPES pH 7.4; 0.2% protease free BSA
Assay buffer: 25 mM HEPES pH 7.4; 0.5% protease free BSA
Dilution and assay plate: PS-Microplate, U form
Filtration Plate Multiscreen FB Opaque Plate; 1.0 mM Type B Glasfiber filter
In order to prepare the filter plates, the presoak solution will be aspirated by vacuum filtration. The plates will be flushed twice with 200 µL flush buffer. 200 µL blocking buffer will be added to the filter plate. The filter plate will then be incubated with 200 µL presoak solution for 1 hour at room temperature. The assay plate will be filled with 25 µL assay buffer, 25 µL membranes (2.5 µg) suspended in assay buffer, 25 µL agonist in assay buffer, and 25 µL tracer (about 40000 cpm) in assay buffer. The filled plate will be incubated for 1 hour with shaking. The transfer from assay plate to filter plate will be conducted. The blocking buffer will be aspirated by vacuum filtration and washed two times with flush buffer. 90 µL will be transferred from the assay plate to the filter plate. The 90 µL transferred from assay plate will be aspirated and washed three times with 200 µL flush buffer. The plastic support is removed. It is dried for 1 hour at 60° C. 30 µL Microscint will beadded. The count will be performed based upon analog affinity to VPAC1, VPAC2, or PAC1 receptors. $IC_{50}$ and $EC_{50}$ calculations will be performed based upon affinity scoring.

In Vivo Efficacy in Animal Models: To determine the activity of analogs of the invention in vivo as compared to the naturally occurring polypeptides upon which the analogs are derived, the analogs will be administered alone (IP, IV, SC, PO, by inhalation or nasal routes) or in combination with known active agent to monitor the above-mentioned disease states. Secretin family analogs alone or in combination with sub-optimal doses of relevant active agents for specific indications or disease states will be, for example, administered to an appropriate animal model mice (8-10 days after injection/day 1 of experiment) by tail vein or IP routes at doses ranging from 0.0001 mg/kg to 50 mg/kg for 1 to 21 days. Optionally, the mice will be assayed throughout the experiment with a selection marker relevant to the particular studies disease state every other day and survival monitored daily for the duration of the experiment. Expired mice will be optionally subjected to necropsy at the end of the experiment. These in vivo tests optionally generate preliminary pharmacokinetic, pharmacodynamic and toxicology data.

Adjuvant-Induced Arthritis in Rats: Adjuvant induced arthritis ("AIA") is an animal model useful in the study of rheumatoid arthritis ("RA"), which is induced by injecting *M. tuberculosis* in the base of the tail of Lewis rats. Between 10 and 15 days following injection, animals develop a severe, progressive arthritis.

Generally, analogs will be tested for their ability to alter hind paw swelling and bone damage resulting from adjuvant induced edema in rats. To quantitate the inhibition of hind paw swelling resulting from AIA, two phases of inflammation have been defined: (1) the primary and secondary injected hind paw, and (2) the secondary uninjected hind paw, which generally begins developing about eleven days from the induction of inflammation in the injected paw. Reduction of the latter type of inflammation is an indication of immunosuppressive activity. Cf. Chang, Arth. Rheum., 20, 1135-1141 (1977).

Using an animal model of RA, such as AIA, enables one to study the cellular events involved in the early stages of the disease. CD44 expression on macrophages and lymphocytes is up regulated during the early development of adjuvant arthritis, whereas LFA 1 expression is up regulated later in the development of the disease. Understanding the interactions between adhesion molecules and endothelium at the earliest stages of adjuvant arthritis could lead to significant advances in the methods used in the treatment of RA.

Collagen Induced Arthritis in Rats: To determine the efficacy of a representative analog of this invention administered by po bid dosing (Days (−1)-20) for inhibition of the inflammation, cartilage destruction and bone resorption that occurs in developing type II collagen arthritis in rats.

Animals: Female Lewis rats (Harlan), weighing 125-150 g on arrival. (inject subtotal of rats with collagen to get responders on days 10, 11, 12 for 6 groups of 10). The animals (a group for arthritis, a group for normal control), housed 4-5/cage, will be acclimated for 4-8 days. The animals will be dosed from about po1 mg/kg bid to po100 mg/kg bid.

Materials: Peptides or analogs in vehicle, Type II collagen, Freund's incomplete adjuvant, methotrexate (Sigma)

General Study Design: Dosing initiated on day minus 1. The acclimated animals will be anesthetized with isoflurane and given collagen injections (D0). On day 6 they will be anesthetized again for the second collagen injection. Collagen is prepared by making a 4 mg/mL solution in 0.01 N acetic acid. Equal volumes of collagen and Freund's incomplete adjuvant, will be emulsified by hand mixing until a bead of this material held its form when placed in water. Each animal will receive 300 uL of the mixture each time spread over 3 sites on back. Calipering of normal (pre-disease) right and left ankle joints are to be done approximately one ay prior to the expected days on onset of disease.

Rats will be weighed on days (−) 1, 6, 9, 10, 11, 12, 13, 14, 15, 16, 17, 18, 19, and 20 of the study and caliper measurements of ankles taken every day beginning on day 9. Final body weights will be taken on day 20. After final body weight measurement, animals are to be anesthetized for terminal plasma collection and then euthanization. Both hind paws and knees will be removed. Hind paws will be weighed, placed (with knees) in formalin and then processed for microscopy.

Processing of Joints: Following 1-2 days in fixative and then 4-5 days in decalcifier, the ankle joints will be cut in half longitudinally, knees will be cut in half in the frontal plane, processed, embedded, sectioned and stained with toluidine blue.

Induction of Colitis in HLA-B27 Rats: The efficacy of the analogs of the present invention in reversing colitis can be determined in HLA-B27 transgenic rats. HLA-B27 transgenic rats have been utilized as an animal model of Inflammatory Bowel Disease which mimics Crohn's Disease in humans. The rats overexpress the human MHC class I HLA-B27 heavy chain and beta-2 microglobulin proteins, which induces a variety of autoimmune diseases that include inflammation of the colon.

The therapeutic effect of the analogs described in this invention in terms of resolving colitis can be evaluated in HLA-B27 transgenic rats. Diseased rats will be dosed subcutaneously with 0.001-100 mg/kg of a single analog of this invention once or twice a day for 16 days or once per week for two weeks.

Disease Activity Index (DAI) scores will be used to determine the efficacy of each analog as compared to rats dosed with vehicle. In addition, fecal consistency and FOB scores for both rats dosed with analogs will be statistically compared to the vehicle group.

Induction of Colitis: 1-20 HLA-B27 (6-9 weeks old) transgenic rats will be acclimated in animal facility for 10 weeks. Animal bedding will be mixed from different cages once a week to control for a "dirty" environmental flora.

Treatments: Rats are to be enrolled and randomized into four groups (n=5) based on weight and DAI scores (FC.gtoreq.3, FOB.gtoreq.2). The experimental groups will be dosed subcutaneously with an analog 0.001-100 mg/kg once or twice a day for 16 days or once per week for two weeks and terminated at trough. The control groups include a vehicle-treated group and a GG5/3 (mouse anti-rat alpha-4 integrin antibody) positive control group dosed subcutaneously at 10 mg/kg (5 mL/kg) on d0, d3, and d6 and terminated at trough on d8. Fresh analog and vehicle treatments are to be formulated in advance of treatment.

Endpoint Read-outs: Disease Activity Index scores, Fecal Consistency test and Fecal Occult Blood test, are to be taken 4 times a week to generate in-life clinical scores. The primary read-out for the study is a histopathological analysis of cecum, proximal colon, mid-colon, and distal colon. An IBD scoring system was applied (Table H2). TABLE H2 IBD Scoring System Multiple Endpoints A Destruction of epithelium and glands B Dilatation of glandular crypts C Depletion and loss of goblet cells D Inflammatory cell infiltrates E Edema F Vascular congestion G Crypt Abscesses H Atrophia Primary Arterial Hypertension animal model: 36 adult male Sprague-Dawley rats (300-350 g in body weight were randomized for treatment 22 days after a s.c. injection of saline or 60 mg/kg MCT (Sigma-Aldrich) to induce pulmonary hypertension. In addition to a group of untreated rats, the experimental groups included rats that received either daily, weekly or monthly delivery of a secretin analog at an appropriate dose of (0.001-50 mg/kg or the delivery vehicle alone. On Day 22 a carotid/femoral artery will be accessed for arterial blood gases (systemic blood pressure can be monitored as well). Thoracotomy performed and right ventricle catheterized with a Millar catheter (or other appropriate catheter) which will be advanced to the pulmonary artery. Animals will have anesthesia induced and maintained on isoflurane through out the experiment. Rats will be intubated prior to surgical procedures. Hemodynamic measurements such as Pulmonary arterial pressure, systemic blood pressure (SAP, DAP, MAP) and heart rate are to be collected continuously via a Gould-Ponemah physiograph. Statistical analysis will be performed on all hemodynamic data. Arterial blood samples collected at protocol specified time points (up to 8 time points) for analysis of drug concentration and/or arterial blood gases. Animals euthanized after 30 minutes and lungs collected and snap frozen for shipment to the Sponsor. Lungs analyzed for levels of drug. Animals are to be clinically observed once daily with body weight measured weekly. While some embodiments of the invention have been illustrated and described, it will be appreciated that various changes can be made therein without departing from the spirit and scope of the invention.

Small Cell Lung Cancer Model: Female athymic BAL-Byc nude mice, 4-5 weeks old, will be housed in filter-top cages in a pathogenfree, temperature-controlled, laminar-flow, filtered-air, isolated room and will be exposed to light from 7:00 a.m. to 7:00 p.m. NCI-H69 cells will be injected subcutaneously into the right flank of each mouse. There were four experimental groups, of four mice each, three of which will receive VIP and/or an analog of VIP (1.0, 5.0, or 10 mg/day) in PBS; as a control, the fourth will receive only PBS. All solutions will be infused for 8 weeks, beginning 1 week after injection of the cells, and delivered by i.v., i.p., subc., i.m. injection or osmotic pumps placed aseptically under the skin of the back of the mice. The pump will release its contents at a rate of 0.5 ml/h for a duration of 2 weeks. The spent pumps will be removed every 2 weeks, and new pumps, containing fresh solutions, will be implanted with known techniques; this procedure will be repeated three times. After treatment, The tumors will be measured with calipers, and the mice will be weighed weekly for 8 weeks. Tumor volume will be calculated for an ellipsoid as (maximal length)×(maximal height)×(maximal width)×($\pi$/6). On the last day of the experiment, blood will be sampled from the retroorbital plexus into chilled heparin-containing tubes rinsed with 0.05% NaEDTA and containing three protease inhibitors, 10 mg/ml soybean trypsin inhibitor, 100 TIU/ml aprotinin, and 10 mg/ml phosphamidon), as well as 0.1 mM IBMX for measurement of plasma VIP and cAMP levels. The mice will then euthanized. The tumors will be excised, weighed, and frozen in liquid nitrogen for subsequent extraction (in methanol) and for measurement of protein content by known techniques; a portion of the tumor will be fixed in 10% neutral buffered formalin for morphologic examination.

One purpose of these studies is to evidence that the analogs are capable of producing the desired biological, biochemical, diagnostic, medicinal and/or therapeutic outcome in a living animal.

Example 5

DPPIV Protease Assay (Prophetic)

Digest buffer {100 mM Tris-HCl (pH 8)} containing 15 µM peptide and 1 µg porcine kidney DPPIV (Sigma-Aldrich) will be incubated at 37 C. The reaction will be terminated at the specifiedtime point by adding 10 µl 10% TFA, followed by reverse-phase HPLC on a Gemini C18 column (Phenomenex, Macclesfield, UK). The column will be eluted with a linear gradient of 27-31% AcN over 50 min at 1 ml/min. Peptides and their degradation products will be monitored by their absorbance at 214 nm. Percent degradation will be quantified by integration of peak areas related to undigested peptide peaks and corrected for degradation in the absence of enzyme.

Example 6

Method for Measuring Triglyceride Levels hApoA1 mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test polypeptide once daily for 8 days. The animals are then bled again by eye or tail vein, and serum triglyceride levels are determined. In each case, triglyceride levels are measured using a Technicon Axon Autoanalyzer (Bayer Corporation, Tarrytown, N.Y.).

Method for Measuring HDL-Cholesterol Levels

To determine plasma HDL-cholesteral levels, hApoA1 mice are bled and grouped with equivalent mean plasma HDL-cholesterol levels. The mice are orally dosed once daily with vehicle or test polypeptide for 7 days, and then bled again on day 8. Plasma is analyzed for HDL-cholesterol using the Synchron Clinical System (CX4) (Beckman Coulter, Fullerton, Calif.).

Method for Measuring Total Cholesterol, HDL-Cholesterol, Triglycerides, and Glucose Levels. In another in vivo assay, obese monkeys are bled, then orally dosed once daily with vehicle or test polypeptide for 4 weeks, and then bled again. Serum is analyzed for total cholesterol, HDL-cholesterol, triglycerides, and glucose using the Synchron Clinical System (CX4) (Beckman Coulter, Fullerton, Calif.). Lipoprotein subclass analysis is performed by NMR spectroscopy as described by Oliver, et al., (Proc. Natl. Aced. Sci. USA 98:5306-5311, 2001).

The following journal articles, which are herein incorporated by reference, disclose secretin family analogs contemplated to be a polypeptide backbone for the secretin family analogs of the invention. The journal articles also disclose a series of methods of administering secretin family analogs as part of pharmaceutical compositions:

1. Gozes, et. al., *Current Pharmaceutical Design,* 2003, Vol. 9, No. 6
2. Delgado, et. al., *Brain Behav Immun.* 2008 November; 22(8): 1146-1151. doi: 10.1016/j.bbi.2008.06.001.

3. L. Dickson, K. Finlayson/*Pharmacology & Therapeutics* 121 (2009) 294-316.
4. Gonzales-Rey, et. al., *TRENDS in Pharmacological Sciences* Vol. 28 No. 9.
5. Varela, et. al., *Expert Opin. Biol. Ther.* (2007) 7(4):461-478
6. Brenneman, Peptides 28 (2007) 1720-1726;
7. Onoue, et. al., Naunyn-Schmiedeberg's *Arch Pharmacol* (2008) 377:579-590

Any journal article, patent application, issued patent or other publication referenced in this application is herein incorporated by reference. The embodiments listed herein are not meant to be restrictive, but rather illustrative of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10772934B2). An electronic copy of the "Sequence Listing" will also be available from the USPTO upon request and payment of the fee set forth in 37 CFR 1.19(b)(3).

What is claimed is:

1. A composition comprising a peptide comprising the amino acid sequence HSDGIFTDSYSRYRKQMAVKKY-LAAVL (SEQ ID NO: 5) or a pharmaceutical salt thereof comprising at least one repetitive pattern of $\alpha$ and $\beta$ amino acids from the amino-terminus to the carboxy-terminus comprising $\beta\alpha\alpha\beta\alpha\alpha\alpha\beta\alpha\alpha$.

2. The composition of claim 1, wherein at least one $\beta$ amino acid is a cyclic $\beta$ amino acid.

3. The composition of claim 2, wherein the cyclic $\beta$ amino acid is APC or ACPC.

4. The composition of claim 1, further comprising at least one other active agent.

5. A kit comprising the composition of claim 1.

6. A method of manufacturing the composition of claim 1 or a pharmaceutical salt dervied therefrom comprising catalyzing a reaction between at least one $\alpha$-amino acid with at least one $\beta$-amino acid.

7. The kit of claim 6, wherein a first container comprises the compopsition and a second container comprise a vehicle for administration of the composition.

8. A composition comprising a peptide comprising the amino acid sequence HSDGIFTDSYSRYRKQMAVKKY-LAAVL (SEQ ID NO: 5) or a pharmaceutically acceptable salt thereof comprising at least one repetitive pattern of $\alpha$ and $\beta$ amino acids from the amino-terminus to the carboxy-terminus comprising $\beta\alpha\alpha\alpha\beta\alpha\alpha\alpha\beta$.

9. The composition of claim 8, wherein at least one $\beta$ amino acid is a cyclic $\beta$ amino acid; and wherein the cyclic $\beta$ amino acid is APC or ACPC.

10. The composition of claim 8, further comprising at least one other active agent.

11. A kit comprising the composition of claim 8.

12. A method of manufacturing the composition of claim 8 or a pharmaceutical salt derived therefrom comprising catalyzing a reaction between at least one $\alpha$-amino acid with at least one $\beta$-amino acid.

13. A composition comprising a peptide comprising the amino acid sequence HSDGIFTDSYSRYRKQMAVKKY-LAAVL (SEQ ID NO: 5) or a pharmaceutically acceptable salt thereof comprising at least one repetitive pattern of $\alpha$ and $\beta$ amino acids from the amino-terminus to the carboxy-terminus comprising $\beta\alpha\alpha\alpha\beta\alpha\alpha\beta\alpha\alpha\alpha\beta$.

14. The composition of claim 13, wherein at least one $\beta$ amino acid is a cyclic $\beta$ amino acid; and wherein the cyclic $\beta$ amino acid is APC or ACPC.

15. The composition of claim 13, further comprising at least one other active agent.

16. A kit comprising the composition of claim 13.

17. A method of manufacturing the composition of claim 13 or a pharmaceutical salt derived therefrom comprising catalyzing a reaction between at least one $\alpha$-amino acid with at least one $\beta$-amino acid.

* * * * *

UNITED STATES PATENT AND TRADEMARK OFFICE
CERTIFICATE OF CORRECTION

PATENT NO. : 10,772,934 B2
APPLICATION NO. : 15/691811
DATED : September 15, 2020
INVENTOR(S) : Shandler et al.

Page 1 of 1

It is certified that error appears in the above-identified patent and that said Letters Patent is hereby corrected as shown below:

On the Title Page

Under Related U.S. Application Data

Item (60) Line 4, reads:
61/364,659 filed on Jul. 14, 2010, provisional

Should be replaced with:
61/364,359 filed on Jul. 14, 2010, provisional

Signed and Sealed this
Twenty-seventh Day of October, 2020

Andrei Iancu
*Director of the United States Patent and Trademark Office*